United States Patent
Babaoglu et al.

(10) Patent No.: US 9,296,758 B2
(45) Date of Patent: Mar. 29, 2016

(54) 2-QUINOLINYL-ACETIC ACID DERIVATIVES AS HIV ANTIVIRAL COMPOUNDS

(75) Inventors: Kerim Babaoglu, Lansdale, PA (US); Kyla Bjornson, San Mateo, CA (US); Hongyan Guo, San Mateo, CA (US); Randall L. Halcomb, Foster City, CA (US); John O. Link, San Francisco, CA (US); Hongtao Liu, Cupertino, CA (US); Michael L. Mitchell, Hayward, CA (US); Jianyu Sun, Burnaby (CA); James Taylor, San Mateo, CA (US); Randall W. Vivian, San Mateo, CA (US); Lianhong Xu, Palo Alto, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 291 days.

(21) Appl. No.: 13/806,048

(22) PCT Filed: Jul. 1, 2011

(86) PCT No.: PCT/US2011/042881
§ 371 (c)(1),
(2), (4) Date: Apr. 26, 2013

(87) PCT Pub. No.: WO2012/003498
PCT Pub. Date: Jan. 5, 2012

(65) Prior Publication Data
US 2013/0210801 A1    Aug. 15, 2013

Related U.S. Application Data

(60) Provisional application No. 61/361,335, filed on Jul. 2, 2010.

(51) Int. Cl.
| | |
|---|---|
| *C07D 498/04* | (2006.01) |
| *C07D 215/06* | (2006.01) |
| *C07D 215/14* | (2006.01) |
| *C07D 215/18* | (2006.01) |
| *C07D 215/227* | (2006.01) |
| *C07D 215/38* | (2006.01) |
| *C07D 215/48* | (2006.01) |
| *C07D 401/04* | (2006.01) |
| *C07D 401/12* | (2006.01) |
| *C07D 405/04* | (2006.01) |
| *C07D 413/04* | (2006.01) |
| *C07D 417/04* | (2006.01) |
| *C07D 487/04* | (2006.01) |

(Continued)

(52) U.S. Cl.
CPC ............ *C07D 498/04* (2013.01); *C07D 215/06* (2013.01); *C07D 215/14* (2013.01); *C07D 215/18* (2013.01); *C07D 215/227* (2013.01); *C07D 215/38* (2013.01); *C07D 215/48* (2013.01); *C07D 401/04* (2013.01); *C07D 401/12* (2013.01); *C07D 405/04* (2013.01); *C07D 413/04* (2013.01); *C07D 417/04* (2013.01); *C07D 487/04* (2013.01); *C07D 491/052* (2013.01); *C07D 519/00* (2013.01); *C07D 215/20* (2013.01)

(58) Field of Classification Search
CPC .. C07D 215/06; C07D 215/14; C07D 215/18; C07D 215/227; C07D 215/38; C07D 215/48; C07D 215/58; C07D 401/04; C07D 401/12; C07D 405/04; C07D 413/04; C07D 417/04; C07D 487/04; C07D 491/052; C07D 498/04; C07D 519/00
See application file for complete search history.

(56) References Cited

U.S. PATENT DOCUMENTS

| | | |
|---|---|---|
| 3,895,028 A | 7/1975 | Wada et al. |
| 3,900,486 A | 8/1975 | Suzuki et al. |

(Continued)

FOREIGN PATENT DOCUMENTS

| | | |
|---|---|---|
| CA | 1144556 A1 | 4/1983 |
| CN | 1123275 A | 5/1996 |

(Continued)

OTHER PUBLICATIONS

De Luca, L. et al. (Feb. 2011; e-pub. Dec. 21, 2010). "HIV-1 integrase strand-transfer inhibitors: design, synthesis and molecular modeling investigation," *Eur. J. Med. Chem.* 46(2):756-764.

(Continued)

*Primary Examiner* — Sarah Pihonak
(74) *Attorney, Agent, or Firm* — Gilead Sciences, Inc.

(57) ABSTRACT

The invention provides compounds of formula (I): or a salt thereof as described herein. The invention also provides pharmaceutical compositions comprising a compound of formula (I), processes for preparing compounds of formula (I), intermediates useful for preparing compounds of formula I and therapeutic methods for treating the proliferation of the HIV virus, treating AIDS or delaying the onset of AIDS or ARC symptoms in a mammal using compounds of formula (I).

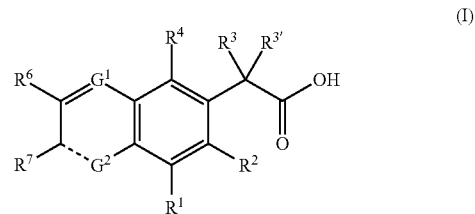

(I)

17 Claims, No Drawings

(51) Int. Cl.
   *C07D 519/00* (2006.01)
   *C07D 491/052* (2006.01)
   *C07D 215/20* (2006.01)

(56) References Cited

U.S. PATENT DOCUMENTS

| | | | |
|---|---|---|---|
| 4,816,570 | A | 3/1989 | Farquhar |
| 4,968,788 | A | 11/1990 | Farquhar |
| 5,434,188 | A | 7/1995 | Boschelli et al. |
| 5,663,159 | A | 9/1997 | Starrett, Jr. et al. |
| 5,733,906 | A | 3/1998 | Jungheim et al. |
| 5,738,985 | A | 4/1998 | Miles et al. |
| 5,792,756 | A | 8/1998 | Starrett, Jr. et al. |
| 5,798,365 | A | 8/1998 | Kirsch et al. |
| 7,514,233 | B2 | 4/2009 | Debyser et al. |
| 8,008,470 | B2 | 8/2011 | Debyser et al. |
| 2005/0165052 | A1 | 7/2005 | Fakhfakh et al. |
| 2005/0239819 | A1 | 10/2005 | Satoh et al. |
| 2005/0261336 | A1 | 11/2005 | Mousnier et al. |
| 2006/0035926 | A1 | 2/2006 | Lee et al. |
| 2006/0094755 | A1 | 5/2006 | Rajagopalan et al. |
| 2006/0275748 | A1 | 12/2006 | Debyser et al. |
| 2009/0197862 | A1 | 8/2009 | Steinig et al. |
| 2009/0203742 | A1 | 8/2009 | Surleraux et al. |
| 2010/0311735 | A1 | 12/2010 | Tsantrizos et al. |
| 2011/0223131 | A1 | 9/2011 | Jin et al. |
| 2013/0203727 | A1 | 8/2013 | Babaoglu et al. |
| 2013/0231331 | A1 | 9/2013 | Pendri et al. |
| 2013/0281433 | A1 | 10/2013 | Babaoglu et al. |
| 2013/0281434 | A1 | 10/2013 | Babaoglu et al. |
| 2014/0045818 | A1 | 2/2014 | Mitchell et al. |

FOREIGN PATENT DOCUMENTS

| | | | |
|---|---|---|---|
| CN | 1044117 | C | 7/1999 |
| CN | 1466576 | A | 1/2004 |
| DE | 24 03 682 | A1 | 7/1974 |
| EP | 0 017 543 | A1 | 10/1980 |
| EP | 1 441 228 | A1 | 7/2004 |
| EP | 1 541 558 | A1 | 6/2005 |
| EP | 1 565 471 | B1 | 10/2006 |
| EP | 1 873 238 | A1 | 1/2008 |
| EP | 1 873 238 | B1 | 1/2008 |
| GB | 2 154 583 | A | 9/1985 |
| JP | 3-287558 | A | 12/1991 |
| WO | WO-91/19721 | A1 | 12/1991 |
| WO | WO-94/23041 | A2 | 10/1994 |
| WO | WO-94/23041 | A3 | 10/1994 |
| WO | WO 9827974 | A1 * | 7/1998 |
| WO | WO-99/52850 | A1 | 10/1999 |
| WO | WO-00/63152 | A1 | 10/2000 |
| WO | WO-02/18341 | A2 | 3/2002 |
| WO | WO-02/18341 | A3 | 3/2002 |
| WO | WO-2004/014371 | A1 | 2/2004 |
| WO | WO-2004/046115 | A1 | 6/2004 |
| WO | WO-2004/087153 | A2 | 10/2004 |
| WO | WO-2004/087153 | A3 | 10/2004 |
| WO | WO-2005/120508 | A1 | 12/2005 |
| WO | WO-2006/001958 | A2 | 1/2006 |
| WO | WO-2006/001958 | A3 | 1/2006 |
| WO | WO-2006/002185 | A1 | 1/2006 |
| WO | WO-2006/116412 | A2 | 11/2006 |
| WO | WO-2006/116412 | A3 | 11/2006 |
| WO | WO-2006/124780 | A2 | 11/2006 |
| WO | WO-2006/124780 | A3 | 11/2006 |
| WO | WO-2007/016392 | A2 | 2/2007 |
| WO | WO-2007/016392 | A3 | 2/2007 |
| WO | WO 2007/131350 | A1 | 11/2007 |
| WO | WO 2007/138472 | A2 | 12/2007 |
| WO | WO-2007/147884 | A1 | 12/2007 |
| WO | WO-2008/053478 | A2 | 5/2008 |
| WO | WO-2008/053478 | A3 | 5/2008 |
| WO | WO-2008/071587 | A2 | 6/2008 |
| WO | WO-2008/071587 | A3 | 6/2008 |
| WO | WO 2009/062285 | A1 | 5/2009 |
| WO | WO-2009/062288 | A1 | 5/2009 |
| WO | WO 2009/062289 | A1 | 5/2009 |
| WO | WO-2009/062308 | A1 | 5/2009 |
| WO | WO-2009/095500 | A1 | 8/2009 |
| WO | WO-2010/059658 | A1 | 5/2010 |
| WO | WO-2010/130034 | A1 | 11/2010 |
| WO | WO-2010/130842 | A1 | 11/2010 |
| WO | WO-2011/002635 | A1 | 1/2011 |
| WO | WO-2011/015641 | A1 | 2/2011 |
| WO | WO-2011/047129 | A1 | 4/2011 |
| WO | WO-2011/076765 | A1 | 6/2011 |
| WO | WO-2011/106445 | A1 | 9/2011 |
| WO | WO-2011/149950 | A2 | 12/2011 |
| WO | WO-2011/149950 | A3 | 12/2011 |
| WO | WO 2012/003497 | A1 | 1/2012 |
| WO | WO-2012/003498 | A1 | 1/2012 |
| WO | WO-2012/033735 | A1 | 3/2012 |
| WO | WO-2012/065963 | A2 | 5/2012 |
| WO | WO-2012/065963 | A3 | 5/2012 |
| WO | WO-2012/066442 | A1 | 5/2012 |
| WO | WO-2012/088365 | A1 | 6/2012 |
| WO | WO-2012/102985 | A1 | 8/2012 |
| WO | WO 2012/137181 | A1 | 10/2012 |
| WO | WO-2012/138669 | A1 | 10/2012 |
| WO | WO-2012/138670 | A1 | 10/2012 |
| WO | WO 2012/140243 | A1 | 10/2012 |
| WO | WO 2012/145728 | A1 | 10/2012 |
| WO | WO-2013/002357 | A1 | 1/2013 |
| WO | WO-2013/025584 | A1 | 2/2013 |
| WO | WO-2013/043553 | A1 | 3/2013 |
| WO | WO-2013/058448 | A1 | 4/2013 |
| WO | WO-2013/062028 | A1 | 5/2013 |
| WO | WO-2013/103724 | A1 | 7/2013 |
| WO | WO-2013/103738 | A1 | 7/2013 |
| WO | WO-2013/106643 | A2 | 7/2013 |
| WO | WO-2013/106643 | A3 | 7/2013 |
| WO | WO-2013/123148 | A1 | 8/2013 |
| WO | WO-2013/134113 | A1 | 9/2013 |
| WO | WO-2013/134142 | A1 | 9/2013 |
| WO | WO-2013/157622 | A1 | 10/2013 |
| WO | WO-2013/159064 | A1 | 10/2013 |
| WO | WO-2014/009794 | A1 | 1/2014 |
| WO | WO-2014/028384 | A1 | 2/2014 |
| WO | WO-2014/055603 | A1 | 4/2014 |
| WO | WO-2014/055618 | A1 | 4/2014 |

OTHER PUBLICATIONS

Mekouar, K. et al. (Jul. 16, 1998; e-pub. Jun. 25, 1998). "Styrylquinoline Derivatives: A New Class of Potent HIV-1 Integrase Inhibitors That Block HIV-1 Replication in CEM Cells," *J. Med. Chem.* 41(15):2846-2857.

Wenhua, Z. et al. (2003). "Advances on Effects of Natural Products Against AIDS Virus," *Chinese Traditional Patent Medicine* 25(9):750-752 (with English Translation).

Restriction Requirement mailed on Apr. 24, 2014 for U.S. Appl. No. 14/112,473, filed Oct. 17, 2013, eight pages.

Non-Final Office Action mailed on May 23, 2014 for U.S. Appl. No. 13/866,997, filed Apr. 19, 2013, eight pages.

Chinese Office Action mailed on Mar. 25, 2014 for Chinese Patent Application No. 201180038443.4, filed on Jul. 1, 2011, eight pages.

Costa Rican Opposition filed Apr. 28, 2014 against Costa Rican Patent Application No. 201320102, filed Jul. 1, 2011, sixteen pages.

Eurasian Office Action mailed in Apr. 9, 2014, for Eurasian Patent Application No. 201291301, filed on Jul. 1, 2011, three pages.

Israeli Office Action mailed on Mar. 3, 2014 for Israeli Patent Application No. 223558, filed on Jul. 1, 2011, two pages.

New Zealand Office Action mailed on Aug. 22, 2013 for New Zealand Patent Application No. 604598, filed on Jul. 1, 2011, two pages.

Ecuadoran Opposition filed Apr. 23, 2014 against Ecuadoran Patent Application No. SP1312418, filed Jul. 1, 2011, ten pages.

Ecuadoran Opposition from Jun. of 2014, against Ecuadoran Patent Application No. SP1312417, filed Jul. 1, 2011, nine pages.

European Communication mailed on Feb. 15, 2013, for European Patent Application No. 11738339.8, filed on Jul. 1, 2011, two pages.

(56) References Cited

OTHER PUBLICATIONS

Mexican Office Action mailed on Mar. 13, 2014 for Mexican Patent Application No. MX/a/2012/015293, filed on Jul. 1, 2011, seven pages.
Columbian Office Action mailed on Jun. 12, 2014 for Columbian Patent Application No. 12236158, filed on Jul. 1, 2011, twelve pages.
Benzaria, S. et al. (Dec. 6, 1996). "Synthesis, In Vitro Antiviral Evaluation, and Stability Studies of Bis(S-Acyl-2-Thioethyl) Ester Derivatives of 9-[2-(Phosphonomethoxy)Ethyl]adenine (PMEA) as Potential PMEA Prodrugs with Improved Oral Bioavailability," *J. Med. Chem.* 39(25):4958-4965.
Bundgaard, H. (1991). "Design and Application of Prodrugs," Chapter 5 in *A Textbook of Drug Design and Development*, Krogsgaard-Larsen, P. et al. eds., Harwood Academic Publishers, Chur, Switzerland, pp. 113-191.
De Lombaert, S. et al. (Feb. 18, 1994). "N-Phosphonomethyl Dipeptides and Their Phosphonate Prodrugs, A New Generation of Neutral Endopeptidase (NEP, EC 3.4.24.11) Inhibitors," *J. Med. Chem.* 37(4):498-511.
Farquhar, D. et al. (Mar. 1983). "Biologically Reversible Phosphate-Protective Groups," *J. Pharm. Sci.* 72(3):324-325.
Khamnei, S. et al. (Sep. 27, 1996). "Neighboring Group Catalysis in the Design of Nucleotide Prodrugs," *J. Med. Chem.* 39(20):4109-4115.
Kocienski, P.J. (May 1994). "Protecting Groups: An Overview," Chapter 1 in *Protecting Groups*, Thieme Publishing Group: New York, NY, pp. 1-20.
Kocienski, P.J. (May 1994). "Hydroxyl Protecting Groups," Chapter 2 in *Protecting Groups*, Thieme Publishing Group: New York, NY, pp. 21-94.
Kocienski, P.J. (May 1994). "Diol Protecting Groups," Chapter 3 in *Protecting Groups*, Thieme Publishing Group: New York, NY, pp. 95-117.
Kocienski, P.J. (May 1994). "Carboxyl Protecting Groups," Chapter 4 in *Protecting Groups*, Thieme Publishing Group: New York, NY, pp. 118-154.
Kocienski, P.J. (May 1994). "Carbonyl Protecting Groups," Chapter 5 in *Protecting Groups*, Thieme Publishing Group: New York, NY, pp. 155-184.
McGinnity, D.F. et al. (Nov. 2004, e-pub. Jul. 30, 2004). "Evaluation of Fresh and Cryopreserved Hepatocytes as in Vitro Drug Metabolism Tools for the Prediction of Metabolic Clearance," *Drug Metab. Dispos.* 32(11):1247-1253.
Mitchell, A.G. et al. (1992). "Bioreversible Protection for the Phospho Group: Bioactivation of the Di(4-Acyloxybenzyl) and Mono(4-acyloxybenzyl) Phosphoesters of Methylphosphonate and Phosphonoacetate," *J. Chem. Soc. Perkin Trans. II* 2345-2353.
Obach, R.S. et al. (Oct. 1997). "The Prediction of Human Pharmacokinetic Parameters from Preclinical and In Vitro Metabolism Data," *J. Pharmacol. Exp. Ther.* 283(1):46-58.
Puech, F. et al. (Oct. 1993). "Intracellular Delivery of Nucleoside Monophosphates Through a Reductase-Mediated Activation Process," *Antiviral Res.* 22(2-3):155-174.
Spivey, A.C. et al. (1999, e-pub. Dec. 4, 1999). "Configurationally Stable Biaryl Analogues of 4-(Dimethylamino) Pyridine: A Novel Class of Chiral Nucleophilic Catalysts," *J. Org. Chem.* 64(26):9430-9443.
Restriction Requirement mailed on Nov. 8, 2013 for U.S. Appl. No. 13/866,997, filed Apr. 19, 2013, eight pages.
Australian Office Action mailed on Feb. 26, 2014, for Australian Patent Application No. 2011274323, filed on Jul. 1, 2011, three pages.
Bolivian Opposition submitted to the Bolivian Patent Office for Bolivian Patent Application No. SP-0194-2011, filed on Jul. 1, 2011, two pages.
Bolivian Opposition submitted to the Bolivian Patent Office for Bolivian Patent Application No. SP-0195-2011, filed on Jul. 1, 2011, two pages.
Columbian Office Action mailed on Mar. 11, 2014, for Columbian Patent Application No. 12236161 filed on Jul. 1, 2011, 10 pages.
Costa Rican Office Action mailed on Aug. 23, 2013 for Costa Rican Patent Application No. 20130045, filed on Jul. 1, 2011, three pages.
Costa Rican Opposition submitted to the Costa Rican Patent Office for Costa Rican Patent Application No. 20130043, filed on Jul. 1, 2011, three pages.
European Communication mailed on Feb. 8, 2013 for European Patent Application No. 11738878.5 filed on Jul. 1, 2011, two pages.
Pakistani Office Action mailed on Nov. 10, 2012 for Pakistani Patent Application No. 4932011, filed on Jul. 1, 2011, two pages.
Pakistani Office Action mailed on Nov. 10, 2012 for Pakistani Patent Application No. 4942011, filed on Jul. 1, 2011, two pages.
Taiwanese Office Action mailed on Nov. 5, 2013 for Taiwanese Patent Application No. 100123357, filed on Jul. 1, 2011, nine pages.
Australian Office Action mailed on Mar. 7, 2014, for Australian Patent Application No. 2011274322 filed on Jul. 1, 2011, three pages.
Chinese Office Action mailed on Mar. 3, 2014, for Chinese Patent Application No. 201180038442.X filed on Jul. 1, 2011, eight pages.
Eurasian Office Action mailed on Mar. 19, 2014, for Eurasian Patent Application No. 201291300 filed on Jul. 1, 2011, four pages.
European Communication mailed on Mar. 12, 2014 for European Patent Application No. 11738878.5 filed on Jul. 1, 2011, eight pages.
Written Opinion of the International Searching Authority mailed on Aug. 5, 2013, for PCT Patent Application No. PCT/US2013/037483 filed on Apr. 19, 2013, seven pages.
Philippines Office Action mailed on Mar. 14, 2014 for Philippine Patent Application No. 1/2013/500011, filed on Jul. 1, 2011, two pages.
Palella et al., "Declining Morbidity and Mortality Among Patients with Advanced Human Immunodeficiency Virus Infection", *N. Engl. J. Med.*, vol. 338, No. 13, 853-860 (1998).
Patent Cooperation Treaty, International Searching Authority, Search Report and Written Opinion for PCT/US2011/042881, 22 pages, Sep. 14, 2011.
Richman, "HIV chemotherapy", *Nature*, 410, 995-1001 (2001).
Willgerodt, Reports of the German Chemical Society, 33$^{rd}$ Issue, vol. III, 2927-2935 (1900) with English Translation.
Zouhiri et al., "HIV-1 replication inhibitors of the styrylquinoline class: incorporation of a masked diketo acid pharmacophore", *Tetrahedron Letters*, 42, 8189-8192 (2001).
Al-Mawsawi, L.Q. et al. (Feb. 7, 2011; e-pub. Jan. 12, 2011). "Allosteric inhibitor development targeting HIV-1 integrase," *ChemMedChem.* 6(2):228-241.
Balakrishnan, M. et al. (Sep. 9, 2013). "Non-catalytic site HIV-1 integrase inhibitors disrupt core maturation and induce a reverse transcription block in target cells," *PloS One* 8(9):e74163, 12 Total Pages.
Bartholomeeusen, K. et al. (Apr. 24, 2009; e-pub. Feb. 25, 2009). "Lens epithelium-derived growth factor/p75 interacts with the transposase-derived DDE domain of PogZ," *J. Biol. Chem.* 284(17):11467-11477.
Busschots, K. et al. (Feb. 2, 2007; e-pub. Nov. 3, 2006). "Identification of the LEDGF/p75 binding site in HIV-1 integrase," *J. Mol. Biol.* 365(5):1480-1492.
Busschots, K. et al. (Jan. 2009; e-pub. Oct. 16, 2008). "In search of small molecules blocking interactions between HIV proteins and intracellular cofactors," *Mol. Biosyst.* 5(1):21-31.
Chakraborty, A. et al. (Mar. 1, 2013; e-pub. Dec. 25, 2012). "Biochemical interactions between HIV-1 integrase and reverse transcriptase," *FEBS Letters* 587(5):425-429.
Cherepanov, P. et al. (Jun. 2005; e-pub. May 15, 2005). "Solution structure of the HIV-1 integrase-binding domain in LEDGF/p75," *Nat. Struct. Mol. Biol.* 12(6):526-532.
Cherepanov, P. et al. (Nov. 29, 2005; e-pub. Oct. 31, 2005). "Structural basis for the recognition between HIV-1 integrase and transcriptional coactivator p75," *PNAS* 102(48):17308-17313.
Christ, F. et al. (Aug. 2012; e-pub. Jun. 4, 2012). "Small-molecule inhibitors of the LEDGF/p75 binding site of integrase block HIV replication and modulate integrase multimerization," *Antimicrob. Agents Chemother.* 56(8):4365-4374.
Christ, F. et al. (Jun. 2010; e-pub. May 16, 2010). "Rational design of small-molecule inhibitors of the LEDGF/p75-integrase interaction and HIV replication," *Nat. Chem. Biol.*, 25 Total Pages.

(56) References Cited

OTHER PUBLICATIONS

De Luca, L. et al. (Jul. 2011). "Inhibition of the Interaction Between HIV-1 Integrase and its Cofactor LEDGF/p75: A Promising Approach in Anti-Retroviral Therapy," *Mini Rev. Med. Chem.* 11(8):714-727.

Desimmie, B.A. et al. (May 30, 2013). "LEDGINs inhibit late stage HIV-1 replication by modulating integrase multimerization in the virions," *Retrovirology* 10:57, 16 Total Pages.

Engelman, A. et al. (Mar. 28, 2008). "The lentiviral integrase binding protein LEDGF/p75 and HIV-1 replication," *PloS Pathog.* 4(3):e1000046, 9 Total Pages.

Graham, R.L.J. et al. (2011). "Proteomic Analysis of LEDGF/p75 Interactions with Nuclear Proteins," ASMS Poster, 1 page.

Hauser, F.M. et al. (1978). "Singlet Oxygen and Epoxidation from the Dehydration of Hydrogen Peroxide," *J. Org. Chem.* 43(1):180.

Hayouka, Z. et al. (2010). "Cyclic Peptide Inhibitors of HIV-1 Integrase Derived from the LEDGF/p75 Protein," *Bioorganic& Medicinal Chemistry* 18:8388-8395.

Hombrouck, A. et al. (Mar. 2007). "Virus Evolution Reveals an Exclusive Role for LEDGF/p75 in Chromosomal Tethering of HIV," *PloS* 3(3):e47, 13 Total Pages.

Huang, X. et al. (2007). "A Novel Multicomponent Reaction of Arynes, β-Keto Sulfones, and Michael-Type Acceptors: A Direct Synthesis of Polysubstituted Naphthols and Naphthalenes," *J. Org. Chem.* 72:3965-3968.

Johns, B.A. et al. (2013). "HIV Integrase Inhibitors," Chapter 6 *in Successful Strategies for the Discovery of Antiviral Drugs*, Desai, M.C. et al. eds., RSC Publishing, pp. 149-188.

Jurado, K.A. et al. (May 21, 2013). "Allosteric Integrase Inhibitor Potency is Determined through the Inhibition of HIV-1 Particle Maturation," *PNAS* 110(21):8690-8695.

Kessl, J.J. et al. (2011). "FRET Analysis Reveals Distinct Conformations of IN Tetramers in the Presence of Viral DNA or LEDGF/p75," *Nuc. Acids Res.*, pp. 1-14.

Llano, M. et al. (Sep. 2004). "LEDGF/p75 determines cellular trafficking of diverse lentiviral but not murine oncoretroviral integrase proteins and is a component of functional lentiviral preintegration complexes," *J. Virol.* 78(17):9524-9537.

Llano, M. et al. (Oct. 20, 2006; e-pub. Sep. 7, 2006). "An essential role for LEDGF/p75 in HIV integration," *Science* 314(5798):461-464.

Poeschla, E.M. et al. (2008). "Integrase, LEDGF/p75 and HIV Replication," *Cell. Mol. Life Sci.* 65:1403-1424.

Rain, J.C. et al. (2009). "Yeast-Two Hybrid Detection of Integrase-Host Factor Interactions," *Methods*, 7 Total Pages.

Rhodes, D.I. et al. (Oct. 17, 2011; e-pub. Aug. 17, 2011). "Crystal structures of novel allosteric peptide inhibitors of HIV integrase identify new interactions at the LEDGF binding site," *Chembiochem.* 12(15):2311-2315.

Shun, M.C. et al. (Jul. 15, 2007). "LEDGF/p75 functions downstream from preintegration complex formation to effect gene-specific HIV-1 integration," *Genes Dev.* 21(14):1767-1778.

Suzuki, Y. et al. (Mar. 2007). "The road to chromatin—nuclear entry of retroviruses," *Nat. Rev. Microbiol.* 5(3):187-196.

Tsiang, M. et al. (Jun. 15, 2012; e-pub. Apr. 25, 2012). "New class of HIV-1 integrase (IN) inhibitors with a dual mode of action," *J. Biol. Chem.* 287(25):21189-21203.

Vandekerckhove, L. et al. (Feb. 2006). "Transient and stable knockdown of the integrase cofactor LEDGF/p75 reveals its role in the replication cycle of human immunodeficiency virus," *J. Virol.* 80(4):1886-1896.

Walker, M.A. (2009). "New approaches for inhibiting HIV integrase: a journey beyond the active site," *Curr. Opin. Investig. Drugs* 10(2):129-136.

Notice of Allowance mailed on Aug. 15, 2014 for U.S. Appl. No. 14/112,473, filed Oct. 17, 2013, seven pages.

Philippine Office Action mailed on Aug. 1, 2014, for Philippine Patent Application No. 12013500011, filed on Jul. 1, 2011, two pages.

Written Opinion of the International Searching Authority mailed on Jul. 17, 2014, for PCT Patent Application No. PCT/US2013/020151 filed on Jan. 3, 2013, six pages.

Written Opinion of the International Searching Authority mailed on Jul. 17, 2014, for PCT Patent Application No. PCT/US2013/020172, filed on Jan. 3, 2013, seven pages.

Vietnamese Office Action mailed on Jul. 28, 2014, for Vietnamese Patent Application No. 1-201300326, filed on Jul. 1, 2011, two pages.

European Communication mailed on Oct. 15, 2013 for European Patent Application No. 11738878.5 filed on Jul. 1, 2011, four pages.

U.S. Appl. No. 14/112,473, filed Oct. 17, 2013, by Mitchell et al.

Office Action dated Apr. 13, 2015 for Japanese Patent Application 2013-518779.

Office Action dated Mar. 5, 2015 for Australian Patent Application 2011274323.

Chen, S. et al. (2009). "Design, Synthesis and Biological Evaluation of Novel Quinolone Derivatives as HIV-1 Tat-TAR Interaction Inhibitors," *Bioorganic & Medicinal Chem.* 17:1948-1956.

Pauwels, R. et al. (Jun. 1987). "Sensitive and Rapid Assay on MT-4 Cells for Detection of Antiviral Compounds Against The AIDS Virus," *J. Virol. Methods* 16(3):171-185.

Pendri, A. et al. (Aug. 2011, e-pub. May 20, 2011). "New First and Second Generation Inhibitors of Human Immunodeficiency Virus-1 Integrase," *Expert Opin. Ther. Pat.* 21(8):1173-1189.

Porto, S. et al. (2007). "Chiral Thiols: The Assignment of Their Absolute Configuration by $^1$H NMR," *Organic Letters* 9(24):5015-5018.

Sagar, K.S. et al. (Aug. 1, 2004). "Preparation and Anti-HIV Activities of Retrojusticidin B Analogs and Azalignans," *Bioorg. Med .Chem.* 12(15):4045-4054.

Wang, C.Y. et al. (Dec. 2004). "Pharmacokinetic And Metabolic Studies of Retrojusticidin B, A Potential Anti-Viral Lignan, in Rats," *Planta Medica* 70(12):1161-1165.

Zhan, P. et al. (2009). "Synthesis and Anti-HIV Activity Evaluation of 2-(4-(Naphthalen-2-yl)-1,2,3-thiadiazol-5-ylthio)-*N*-Acetamides as Novel Non-Nucleosides HIV-1 Reverse Transcriptase Inhibitors," *European Journal of Medicinal Chem.* 44:4648-4653.

International Search Report mailed on Feb. 21, 2013, for PCT Patent Application No. PCT/US2013/020172 filed on Jan. 3, 2013, four pages.

International Search Report mailed on Sep. 1, 2011, for PCT Patent Application No. PCT/US2011/042880 filed on Jul. 1, 2011, four pages.

International Search Report mailed on Mar. 26, 2013, for PCT Patent Application No. PCT/US2013/020151 filed on Jan. 3, 2013, five pages.

International Search Report mailed on Jul. 2, 2012, for PCT Patent Application No. PCT/US2012/034593 filed on Apr. 20, 2012, five pages.

International Search Report mailed on Aug. 5, 2013, for PCT Patent Application No. PCT/US2013/037483 filed on Apr. 19, 2013, three pages.

Written Opinion of the International Searching Authority mailed on Sep. 1, 2011, for PCT Patent Application No. PCT/US2011/042880 filed on Jul. 1, 2011, six pages.

Written Opinion of the International Searching Authority mailed on Jul. 2, 2012, for PCT Patent Application No. PCT/US2012/034593 filed on Apr. 20, 2012, six pages.

International Preliminary Report on Patentability mailed on Jan. 17, 2013, for PCT Patent Application No. PCT/US2011/042880 filed on Jul. 1, 2011, 7 pages.

\* cited by examiner

2-QUINOLINYL-ACETIC ACID DERIVATIVES AS HIV ANTIVIRAL COMPOUNDS

CROSS-REFERENCE TO RELATED APPLICATIONS

This application is a U.S. 371 of PCT/US2011/042881, which was filed on 1 Jul. 2011, and claims the benefit of priority of U.S. Ser. No. 61/361,335, which was filed on 2 Jul. 2010, the entirety of which are incorporated herein by reference.

BACKGROUND OF THE INVENTION

Human immunodeficiency virus (HIV) infection and related diseases are a major public health problem worldwide. Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al *N. Engl. J. Med.* (1998) 338:853-860; Richman, D. D. *Nature* (2001) 410:995-1001). Accordingly, there is a need for new agents that inhibit the replication of HIV. There is also a need for agents that are directed against alternate sites in the viral life cycle including agents that target the interaction of Lens Epithelial Derived Growth Factor (LEDGF/p75) and HIV-1 integrase.

SUMMARY OF THE INVENTION

In one embodiment, the invention provides a compound of the invention which is a compound of formula I:

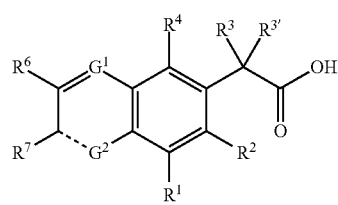

I wherein:
$G^1$ is N, $G^2$ is $CR^8$, and the dashed bond is a double bond; or
$G^1$ is $CR^5$, $G^2$ is N, and the dashed bond is a double bond; or
$G^1$ is $CR^5$, $G^2$ is $NR^{13}$, the dashed bond is a single bond, and $R^7$ is an oxo (=O) group; or
$G^1$ is $CR^5$, $G^2$ is $NR^{13}$, the dashed bond is a single bond, and $R^7$ and $R^{13}$ together with the atoms to which they are attached form a heteroaryl, wherein the heteroaryl is optionally substituted with one or more (e.g. 1, 2, 3, 4 or 5) $Z^1$ groups;
$R^1$ is $R^{1a}$ or $R^{1b}$;
$R^2$ is $R^{2a}$ or $R^{2b}$;
$R^3$ is $R^{3a}$ or $R^{3b}$;
$R^{3'}$ is $R^{3a'}$ or $R^{3b'}$;
$R^4$ is $R^{4a}$ or $R^{4b}$;
$R^5$ is $R^{5a}$ or $R^{5b}$;
$R^6$ is $R^{6a}$ or $R^{6b}$;
$R^7$ is $R^{7a}$ or $R^{7b}$;
$R^8$ is $R^{8a}$ or $R^{8b}$;
$R^{13}$ is $R^{13a}$ or $R^{13b}$;
$R^{1a}$ is selected from:
  a) H, halo, $(C_1-C_6)$alkyl and $(C_1-C_6)$haloalkyl;
  b) $(C_2-C_6)$alkenyl, $(C_2-C_6)$alkynyl, $(C_3-C_7)$cycloalkyl, nitro, cyano, aryl, heterocycle and heteroaryl;
  c) —C(=O)—$R^{11}$, —C(=O)—O—$R^{11}$, —O—$R''$, —S—$R''$, —S(O)—$R^{11}$, —SO$_2$—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R''$ and —$(C_1-C_6)$alkyl-SO$_2$—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl; and
  d) —N($R^9$)$R^{10}$, —C(=O)—N($R^9$)$R^{10}$, —O—C(=O)—N($R^9$)$R^{10}$, —SO$_2$—N($R^9$)$R^{10}$, —$(C_1-C_6)$alkyl-N($R^9$)$R^{10}$, —$(C_1-C_6)$alkyl-C(=O)—N($R^9$)$R^{10}$, —$(C_1-C_6)$alkyl-O—C(=O)—N($R^9$)$R^{10}$ and —$(C_1-C_6)$alkyl-SO$_2$—N($R^9$)$R^{10}$, wherein each $R^9$ is independently selected from H, $(C_1-C_6)$alkyl and $(C_3-C_7)$cycloalkyl, and each $R^{10}$ is independently selected from $R''$, —$(C_1-C_6)$alkyl-$R^{11}$, —SO$_2$—$R^{11}$, —C(=O)—$R^{11}$, —C(=O)O$R^{11}$ and —C(=O)N($R^9$)$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl,
and wherein any aryl, heterocycle or heteroaryl of $R^{1a}$ is optionally substituted with one or more (e.g. 1, 2 or 3) $Z^{10}$ groups;
$R^{1b}$ is selected from:
  a) —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkyl-S(O)—$(C_1-C_6)$alkyl-$(C_3-C_7)$carbocycle, —$(C_1-C_6)$alkyl-SO$_2$—$(C_1-C_6)$alkyl-$(C_3-C_7)$carbocycle, —$(C_1-C_6)$alkyl-SO$_2$—$(C_1-C_6)$alkyl-$Z^{13}$, —C(O)—$(C_1-C_6)$alkyl-$Z^{13}$, —O—$(C_1-C_6)$alkyl-$Z^{13}$, —S—$(C_1-C_6)$alkyl-$Z^{13}$, —S(O)—$(C_1-C_6)$alkyl-$Z^{13}$, —SO$_2$—$(C_1-C_6)$alkyl-$Z^{13}$, —$(C_1-C_6)$alkyl-$Z^{14}$, —$(C_1-C_6)$alkyl-C(O)—$(C_1-C_6)$alkyl-$Z^{13}$, —$(C_1-C_6)$alkyl-C(O)—O$(C_1-C_6)$alkyl-$Z^{13}$, —$(C_1-C_6)$alkyl-O—$(C_1-C_6)$alkyl-$Z^{13}$, —$(C_1-C_6)$alkyl-S—$(C_1-C_6)$alkyl-$Z^{13}$, —$(C_2-C_6)$alkenyl-$(C_1-C_6)$haloalkyl, —$(C_2-C_6)$alkynyl-$(C_1-C_6)$haloalkyl, —$(C_3-C_7)$halocarbocycle, —NR$_a$SO$_2$NR$_a$R$_d$, NR$_a$SO$_2$O$(C_3-C_7)$carbocycle, —NR$_a$SO$_2$Oaryl, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl —$(C_2-C_6)$alkynyl-heterocycle, —$(C_3-C_7)$carbocycle-$Z^1$ and -halo$(C_1-C_6)$alkyl-$Z^3$, wherein any $(C_1-C_6)$alkyl, $(C_1-C_6)$haloalkyl, $(C_3-C_7)$carbocycle, $(C_3-C_7)$halocarbocycle, $(C_2-C_6)$alkenyl, $(C_2-C_6)$alkynyl, aryl, heterocycle and heteroaryl, either alone or as part of a group, is optionally substituted with one or more (e.g. 1, 2, 3, 4 or 5) $Z^1$ groups;
  b) spiro-bicyclic carbocycle, fused-bicyclic carbocycle and bridged-bicyclic carbocycle, wherein any spiro-bicyclic carbocycle, fused-bicyclic carbocycle and bridged-bicyclic carbocycle is optionally substituted with one or more $Z^1$ groups (e.g. 1, 2, 3, 4 or 5), wherein two $Z^1$ groups together with the atom or atoms to which they are attached optionally form a $(C_3-C_7)$carbocycle or heterocycle, wherein the $(C_3-C_7)$carbocycle or heterocycle is optionally substituted with one or more (e.g. 1, 2, 3, 4 or 5) $Z^1$ groups;
  c) $(C_1-C_6)$alkyl, wherein $(C_1-C_6)$alkyl is substituted with one or more (e.g. 1, 2, 3, 4 or 5) $Z^2$ groups and optionally substituted with one or more (e.g. 1, 2, 3, 4 or 5) $Z^1$ groups;
  d) —X$(C_1-C_6)$alkyl, —X$(C_1-C_6)$haloalkyl, —X$(C_2-C_6)$alkenyl, —X$(C_2-C_6)$alkynyl and —X$(C_3-C_7)$carbocycle, wherein any —X$(C_1-C_6)$alkyl and —X$(C_1-C_6)$haloalkyl is substituted with one or more (e.g. 1, 2, 3, 4 or 5) $Z^3$ groups and optionally substituted with one or more (e.g. 1, 2, 3, 4 or 5) $Z^1$ groups, and wherein any $X(C_2-C_6)$alkenyl, —$X(C_2-C_6)$alkynyl and —$X(C_3-C_7)$carbocycle is substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle, wherein any aryl heteroaryl and heterocycle, either alone or as part of a group, is substituted with one or more (e.g. 1, 2, 3, 4 or 5) $Z^5$ groups and optionally substituted with one or more (e.g. 1, 2, 3, 4 or 5) $Z^1$ groups;

f) $(C_1-C_6)$haloalkyl, $(C_3-C_7)$carbocycle, $(C_2-C_6)$alkenyl, and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each substituted with one or more (e.g. 1, 2, 3, 4 or 5) $Z^6$ groups and optionally substituted with one or more (e.g. 1, 2, 3, 4 or 5) $Z^1$ groups; and g) —$NR_eR_f$, —$C(O)NR_eR_f$, —$OC(O)NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—C(O)—$NR_eR_f$ and —$(C_1-C_6)$alkyl-$SO_2NR_eR_f$ wherein any $(C_1-C_6)$alkyl, as a part of group, is optionally substituted with one or more (e.g. 1, 2, 3, 4 or 5) $Z^1$ groups;

$R^{2a}$ is selected from:

a) H, $(C_1-C_6)$alkyl and —$O(C_1-C_6)$alkyl;

b) $(C_2-C_6)$alkenyl, $(C_2-C_6)$alkynyl, $(C_1-C_6)$haloalkyl, $(C_3-C_7)$cycloalkyl, aryl, heterocycle, heteroaryl, halo, nitro and cyano;

c) $C(=O)$—$R^{11}$, —$C(=O)$—O—$R^{11}$, —S—$R^{11}$, —S(O)—$R^{11}$, —$SO_2$—$^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-$SO_2$—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl and heterocycle and heteroaryl, wherein aryl, heterocycle and heteroaryl are each optionally substituted with one or more (e.g. 1, 2 or 3) $Z^{11}$ groups; and d) —OH, —$O(C_2-C_6)$alkenyl, —$O(C_2-C_6)$alkynyl, —$O(C_1-C_6)$haloalkyl, —$O(C_3-C_7)$cycloalkyl, —Oaryl, —Oheterocycle and —Oheteroaryl;

e) —$N(R^9)R^{10}$, —$C(=O)$—$N(R^9)R^{10}$, —O—$C(=O)$—$N(R^9)R^{10}$, —$SO_2$—$N(R^9)R^{10}$, —$(C_1-C_6)$alkyl-$N(R^9)R^{10}$, —$(C_1-C_6)$alkyl-C(=O)—$N(R^9)R^{10}$, —$(C_1-C_6)$alkyl-O—C(=O)—$N(R^9)R^{10}$, and —$(C_1-C_6)$alkyl-$SO_2$—$N(R^9)R^{10}$, wherein each $R^9$ is independently selected from H, $(C_1-C_6)$alkyl and $(C_3-C_7)$cycloalkyl, and each $R^{10}$ is independently selected from $R^{11}$, —$(C_1-C_6)$alkyl-$R^{11}$, —$SO_2$—$R^{11}$, —$C(=O)$—$R^{11}$, —$C(=O)OR^{11}$ and —$C(=O)N(R^9)R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl;

$R^{2b}$ is selected from:

a) —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkyl-S(O)—$(C_1-C_6)$alkyl-$(C_3-C_7)$carbocycle, —$(C_1-C_6)$alkyl-$SO_2$—$(C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, —$(C_1-C_6)$alkyl-$SO_2$—$(C_1-C_6)$alkyl-$Z^{13}$, —$C(O)$—$(C_1-C_6)$alkyl-$Z^{13}$, —O—$(C_1-C_6)$alkyl-$Z^{13}$, —S—$(C_1-C_6)$alkyl-$Z^{13}$, —S(O)—$(C_1-C_6)$alkyl-$Z^{13}$, —$SO_2$—$(C_1-C_6)$alkyl-$Z^{13}$, —$(C_1-C_6)$alkyl-$Z^{14}$, —$(C_1-C_6)$alkyl-C(O)—$(C_1-C_6)$alkyl-$Z^{13}$, —$(C_1-C_6)$alkyl-C(O)—O$(C_1-C_6)$alkyl-$Z^{13}$, —$(C_1-C_6)$alkyl-O—$(C_1-C_6)$alkyl-$Z^{13}$, —$(C_1-C_6)$alkyl-S—$(C_1-C_6)$alkyl-$Z^{13}$, $(C_3-C_7)$halocarbocycle, —$NR_aSO_2NR_cR_d$, —$NR_aSO_2O(C_3-C_7)$carbocycle, —$NR_aSO_2Oaryl$, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$carbocycle-$Z^1$ and -halo$(C_1-C_6)$alkyl-$Z^3$, wherein any $(C_1-C_6)$alkyl, $(C_1-C_6)$haloalkyl, $(C_3-C_7)$halocarbocycle, $(C_3-C_7)$carbocycle, $(C_2-C_6)$alkenyl, $(C_2-C_6)$alkynyl, aryl, heterocycle and heteroaryl, either alone or as part of a group, is optionally substituted with one or more (e.g. 1, 2, 3, 4 or 5) $Z^1$ groups;

b) spiro-bicyclic carbocycle, fused-bicyclic carbocycle and bridged-bicyclic carbocycle, wherein any spiro-bicyclic carbocycle, fused-bicyclic carbocycle and bridged-bicyclic carbocycle is optionally substituted with one or more (e.g. 1, 2, 3, 4 or 5) $Z^1$ groups, and wherein two $Z^1$ groups together with the atom or atoms to which they are attached optionally form a $(C_3-C_7)$carbocycle or heterocycle, wherein the $(C_3-C_7)$carbocycle or heterocycle is optionally substituted with one or more (e.g. 1, 2, 3, 4 or 5) $Z^1$ groups;

c) $(C_1-C_6)$alkyl, wherein $(C_1-C_6)$alkyl is substituted with one or more (e.g. 1, 2, 3, 4 or 5) $Z^2$ groups and optionally substituted with one or more (e.g. 1, 2, 3, 4 or 5) $Z^1$ groups;

d) —$X(C_1-C_6)$alkyl, —$X(C_1-C_6)$haloalkyl, —$X(C_2-C_6)$alkenyl, —$X(C_2-C_6)$alkynyl and —$X(C_3-C_7)$carbocycle, wherein any —$X(C_1-C_6)$alkyl and —$X(C_1-C_6)$haloalkyl is substituted with one or more (e.g. 1, 2, 3, 4 or 5) $Z^3$ groups and optionally substituted with one or more (e.g. 1, 2, 3, 4 or 5) $Z^1$ groups, and wherein any —$X(C_2-C_6)$alkenyl, —$X(C_2-C_6)$alkynyl and —$X(C_3-C_7)$carbocycle is substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle; wherein any aryl, heteroaryl and heterocycle, either alone or as part of a group, is substituted with one or more (e.g. 1, 2, 3, 4 or 5) $Z^5$ groups and optionally substituted with one or more $Z^1$ groups;

f) $(C_1-C_6)$haloalkyl, $(C_3-C_7)$carbocycle, $(C_2-C_6)$alkenyl, and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each substituted with one or more (e.g. 1, 2, 3, 4 or 5) $Z^6$ groups and optionally substituted with one or more (e.g. 1, 2, 3, 4 or 5) $Z^1$ groups; and g) —$NR_eR_f$, —$C(O)NR_eR_f$, —$OC(O)NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—C(O)—$NR_eR_f$ and —$(C_1-C_6)$alkyl-$SO_2NR_eR_f$ wherein any $(C_1-C_6)$alkyl, as a part of group, is optionally substituted with one or more (e.g. 1, 2, 3, 4 or 5) $Z^1$ groups;

$R^{3a}$ is $(C_1-C_6)$alkyl, $(C_1-C_6)$haloalkyl, $(C_2-C_6)$alkenyl, $(C_2-C_6)$alkynyl, —$(C_1-C_6)$alkyl-$(C_3-C_7)$cycloalkyl, —$(C_1-C_6)$alkyl-aryl, —$(C_1-C_6)$alkyl-heterocycle, —$(C_1-C_6)$alkyl-heteroaryl, —$O(C_1-C_6)$alkyl, —$O(C_1-C_6)$haloalkyl, —$O(C_2-C_6)$alkenyl, —$O(C_2-C_6)$alkynyl, —$O(C_3-C_7)$cycloalkyl, —Oaryl, —$O(C_1-C_6)$alkyl-$(C_3-C_7)$cycloalkyl, —$O(C_1-C_6)$alkyl-aryl, —$O(C_1-C_6)$alkyl-heterocycle or —$O(C_1-C_6)$alkyl-heteroaryl, wherein any $(C_1-C_6)$alkyl, $(C_1-C_6)$haloalkyl, $(C_2-C_6)$alkenyl or $(C_2-C_6)$alkynyl of $R^{3a}$, either alone or as part of a group, is optionally substituted with one or more (e.g. 1, 2 or 3) groups selected from —$O(C_1-C_6)$alkyl, halo, oxo and —CN, and wherein any $(C_3-C_7)$cycloalkyl, aryl, heterocycle or heteroaryl of $R^{3a}$, either alone or as part of a group, is optionally substituted with one or more groups selected from $(C_1-C_6)$alkyl, —$O(C_1-C_6)$alkyl, halo, oxo and —CN; and $R^{3a'}$ is H;

$R^{3b}$ is —$(C_7-C_{14})$alkyl, $(C_3-C_7)$carbocycle, aryl, heteroaryl, heterocycle, —$(C_1-C_6)$alkylOH, —$(C_1-C_6)$alkyl-O—$(C_1-C_6)$alkyl-$Z^{12}$, —$(C_1-C_6)$alkyl-O—$(C_2-C_6)$alkenyl-$Z^{12}$, —$(C_2-C_6)$alkyl-O—$(C_2-C_6)$alkynyl-$Z^{12}$, —$(C_1-C_6)$ alkyl-S—$(C_1-C_6)$alkyl-$Z^{12}$, —$(C_1-C_6)$alkyl-S—$(C_2-C_6)$alkenyl-$Z^{12}$, —$(C_1-C_6)$alkyl-S—$(C_2-C_6)$alkynyl-$Z^{12}$, —$(C_1-C_6)$alkyl-S(O)—$(C_1-C_6)$alkyl-$Z^{12}$, —$(C_1-C_6)$alkyl-S(O)—$(C_2-C_6)$alkenyl-$Z^{12}$, —$(C_1-C_6)$alkyl-S(O)—$(C_2-C_6)$alkynyl-$Z^{12}$, —$(C_1-C_6)$alkyl-$SO_2$—$(C_1-C_6)$alkyl-$Z^{12}$, —$(C_1-C_6)$alkyl-$SO_2$—$(C_2-C_6)$alkenyl-$Z^{12}$, —$(C_1-C_6)$alkyl-$SO_2$—$(C_2-C_6)$alkynyl-$Z^{12}$, —$(C_1-C_6)$alkyl-$NR_aR_b$, —$(C_1-C_6)$alkylOC(O)—$NR_cR_d$, —$(C_1-C_6)$alkyl-$NR_a$—C(O)—$OR_6$, —$(C_1-C_6)$alkyl-$NR_a$—C(O)—$NR_aR_b$, —$(C_1-C_6)$alkyl-$SO_2(C_1-C_6)$alkyl, —$(C_1-C_6)$alkyl-$SO_2NR_cR_d$, —$(C_1-C_6)$alkyl-$NR_aSO_2NR_cR_d$, —$(C_1-C_6)$alkyl-$NR_aSO_2O(C_3-C_7)$carbocycle, —$(C_1-C_6)$alkyl-$NR_aSO_2$Oaryl, —$(C_1-C_6)$alkyl-$NR_a$—$SO_2$—$(C_1-C_6)$alkyl, —$(C_1-C_6)$alkyl-$NR_a$—$SO_2$-halo$(C_1-C_6)$alkyl, —$(C_1-C_6)$alkyl-$NR_a$—$SO_2$—$(C_2-C_6)$alkenyl, —$(C_1-C_6)$alkyl-$NR_a$—$SO_2$—$(C_2-C_6)$allynyl, —$(C_1-C_6)$alkyl-$NR_a$—$SO_2$—$(C_3-C_7)$carbocycle, —$(C_1-C_6)$alkyl-$NR_a$—$SO_2$-halo$(C_3-C_7)$carbocycle, —$(C_1-C_6)$alkyl-$NR_a$—$SO_2$-aryl, —$(C_1-C_6)$alkyl-$NR_a$—$SO_2$-heteroaryl, —$(C_1-C_6)$alkyl-$NR_a$—$SO_2$-heterocycle, —$O(C_7-C_{14})$alkyl, —$O(C_1-C_6)$alkyl-$NR_aR_b$, —$O(C_1-C_6)$alkylOC(O)—$NR_eR_a$, —$O(C_1-C_6)$alkyl-$NR_a$—C(O)—$OR_b$, —$O(C_1-C_6)$alkyl-$NR_a$—C(O)—$NR_aR_b$, —$O(C_1-C_6)$alkyl-$NR_a$—$SO_2$—$(C_1-C_6)$alkyl, —$O(C_1-C_6)$alkyl-$NR_a$—$SO_2$-halo$(C_1-C_6)$alkyl, —$O(C_1-C_6)$alkyl-$NR_a$—$SO_2$—$(C_2-C_6)$alkenyl, —$O(C_1-C_6)$alkyl-$NR_a$—$SO_2$—$(C_2-C_6)$alkynyl, —$O(C_1-C_6)$alkyl-$NR_a$—$SO_2$—$(C_3-C_7)$carbocycle, —$O(C_1-C_6)$alkyl-$NR_a$—$SO_2$-halo$(C_3-C_7)$carbocycle, —$O(C_1-C_6)$alkyl-$NR_a$—$SO_2$-aryl, —$O(C_1-C_6)$alkyl-$NR_a$—$SO_2$-heteroaryl, —$O(C_1-C_6)$alkyl-$NR_a$—$SO_2$-heterocycle, —$O(C_1-C_6)$alkyl-$NR_a$—$SO_2$—$NR_aR_6$, —$O(C_1-C_6)$alkyl-$NR_a$—$SO_2$—$(C_3-C_7)$carbocycle, —$O(C_1-C_6)$alkyl-$NR_a$—$SO_2$-halo$(C_3-C_7)$carbocycle, —$O(C_1-C_6)$alkyl-$NR_a$—$SO_2$-aryl, —$O(C_1-C_6)$alkyl-$NR_aSO_2NR_cR_d$, —$O(C_1-C_6)$alkyl-$NR_aSO_2O(C_3-C_7)$carbocycle, —$O(C_1-C_6)$alkyl-$NR_aSO_2$Oaryl, —Oheteroaryl, —Oheterocycle, —Sheteroaryl, —Sheterocycle, —S(O)heteroaryl, —S(O)heterocycle, —$SO_2$heteroaryl or —$SO_2$heterocycle, wherein any $(C_1-C_6)$alkyl, —$(C_7-C_{14})$alkyl, $(C_2-C_6)$alkenyl, $(C_2-C_6)$alkynyl, aryl, $(C_3-C_7)$carbocycle, heteroaryl or heterocycle of $R^{3b}$, either alone or as part of a group, is optionally substituted with one or more (e.g. 1, 2, 3, 4 or 5) $Z^1$ groups; and $R^{3b'}$ is H, $(C_1-C_6)$alkyl or —$O(C_1-C_6)$alkyl; or $R^{3b}$ and $R^{3b'}$ together with the carbon to which they are attached form a heterocycle or $(C_3-C_7)$carbocycle which heterocycle or $(C_3-C_7)$carbocycle of $R^3$ and $R^{3b'}$ together with the carbon to which they are attached is optionally substituted with one or more (e.g. 1, 2, 3, 4 or 5) $Z^1$ groups;

$R^{4a}$ is selected from aryl, heterocycle and heteroaryl, wherein any aryl, heterocycle and heteroaryl of $R^{4a}$ is optionally substituted with one or more (e.g. 1, 2, 3, 4 or 5) groups each independently selected from halo, $(C_1-C_6)$alkyl, $(C_2-C_6)$alkenyl, $(C_1-C_6)$haloalkyl, $(C_3-C_7)$cycloalkyl, —OH, —$O(C_1-C_6)$alkyl, —SH, —$S(C_1-C_6)$alkyl, —$NH_2$, —NH$(C_1-C_6)$alkyl and —$N((C_1-C_6)$alkyl$)_2$, wherein $(C_1-C_6)$alkyl is optionally substituted with hydroxy, —$O(C_1-C_6)$alkyl, cyano and oxo;

$R^{4b}$ is selected from;

a) $(C_1-C_6)$alkyl, $(C_2-C_6)$alkenyl and $(C_2-C_6)$alkynyl, wherein $(C_1-C_6)$alkyl, $(C_2-C_6)$alkenyl and $(C_2-C_6)$alkynyl are each optionally substituted with one or more (e.g. 1, 2, 3, 4 or 5) $Z^1$ groups;

b) $(C_3-C_{14})$carbocycle, wherein $(C_3-C_{14})$carbocycle is optionally substituted with one or more (e.g. 1, 2, 3, 4 or 5) $Z^1$ groups, wherein two $Z^1$ groups together with the atom or atoms to which they are attached optionally form a $(C_3-C_7)$ carbocycle or heterocycle;

c) spiro-heterocycle and bridged-heterocycle, wherein spiro-heterocycle and bridged-heterocycle are each optionally substituted with one or more (e.g. 1, 2, 3, 4 or 5) $Z^1$ groups, and wherein two $Z^1$ groups together with the atom or atoms to which they are attached optionally form a $(C_3-C_7)$ carbocycle or heterocycle; and d) aryl, heteroaryl, spiro-heterocycle, fused-heterocycle and bridged-heterocycle, wherein aryl, heteroaryl, spiro-heterocycle, fused-heterocycle and bridged-heterocycle are each independently substituted with one or more (e.g. 1, 2, 3, 4 or 5) $Z^7$ groups and optionally substituted with one or more (e.g. 1, 2, 3, 4 or 5) $Z^1$ groups; or $R^4$ and $R^3$ together with the atoms to which they are attached form a macroheterocycle or a macrocarbocycle wherein any macroheterocycle or macrocarbocycle of $R^4$ and $R^3$ together with the atoms to which they are attached may be optionally substituted with one or more (e.g. 1, 2, 3, 4 or 5) $Z^1$ groups; and $R^{3'}$ is H, $(C_1-C_6)$alkyl or —$O(C_1-C_6)$alkyl;

$R^{5a}$ is selected from:

a) halo, nitro and cyano;

b) $R^{11}$, —C(=O)—$R^{11}$, —C(=O)—O—$R^{11}$, —O—$R^{11}$, —S—$R^{11}$, —S(O)—$R^{11}$, —$SO_2$—$R^{11}$, —$(C_1-C_6)$alkyl-$R^{11}$, —$(C_1-C_6)$alkyl-C(=O)—$R^{11}$, $(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-$SO_2$—$R^{11}$, wherein each is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein aryl, heterocycle and heteroaryl are each optionally substituted with one or more (e.g. 1, 2 or 3) $Z^{11}$ groups; and c) —$N(R^9)R^{10}$, —C(=O)—$N(R^9)R^{10}$, —O—C(=O)—$N(R^9)R^{10}$, —$SO_2$—$N(R^9)R^{10}$, —$(C_1-C_6)$alkyl-$N(R^9)R^{10}$, —$(C_1-C_6)$alkyl-C(=O)—$N(R^9)R^{10}$, $C_6)$alkyl-O—C(=O)—$N(R^9)R^{10}$, and —$(C_1-C_6)$alkyl-$SO_2$—$N(R^9)R^{10}$, wherein each $R^9$ is independently selected from H, $(C_1-C_6)$alkyl and $(C_3-C_7)$cycloalkyl, and each $R^{10}$ is independently selected from $R^{11}$, —$(C_1-C_6)$alkyl-$R^{11}$, —$SO_2$—$R^{11}$, —C(=O)$R^{11}$, —C(=O)$OR^{11}$ and —C(=O)$N(R^9)R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl;

$R^{5b}$ is selected from:

a) —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkylS(O)—$(C_1-C_6)$alkyl-$(C_3-C_6)$carbocycle, —$(C_1-C_6)$alkylS O$_2(C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, —$(C_3-C_7)$halocarbocycle, —$NR_aSO_2NR_cR_d$, —$NR_aSO_2O(C_3-C_7)$carbocycle, —$NR_aSO_2$Oaryl, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$carbocycle-$Z^1$ and -halo$(C_1-C_6)$alkyl-$Z^3$, wherein any $(C_1-C_6)$alkyl, $(C_1-C_6)$haloalkyl, $(C_3-C_7)$halocarbocycle, $(C_3-C_7)$carbocycle, $(C_2-C_6)$alkenyl, $(C_2-C_6)$alkynyl, aryl, heterocycle and heteroaryl, either alone or as part of a group, is optionally substituted with one or more (e.g. 1, 2, 3, 4 or 5) $Z^1$ groups;

b) spiro-bicyclic carbocycle, fused-bicyclic carbocycle and bridged-bicyclic carbocycle, wherein any spiro-bicyclic carbocycle, fused-bicyclic carbocycle and bridged-bicyclic carbocycle is optionally substituted with one or more (e.g. 1, 2, 3, 4 or 5) $Z^1$ groups, wherein two $Z^1$ groups together with the atom or atoms to which they are attached optionally form a $(C_3-C_7)$carbocycle or heterocycle, wherein the $(C_3-C_7)$carbocycle or heterocycle is optionally substituted with one or more (e.g. 1, 2, 3, 4 or 5) $Z^1$ groups;

c) $(C_1-C_6)$alkyl, wherein $(C_1-C_6)$alkyl is substituted with one or more (e.g. 1, 2, 3, 4 or 5) $Z^2$ groups and optionally substituted with one or more (e.g. 1, 2, 3, 4 or 5) $Z^1$ groups;

d) —$X(C_1-C_6)$alkyl, —$X(C_1-C_6)$haloalkyl, —$X(C_2-C_6)$alkenyl, —$X(C_2-C_6)$alkynyl and —$X(C_3-C_7)$carbocycle, wherein any —$X(C_1-C_6)$alkyl and —$X(C_1-C_6)$haloalkyl is substituted with one or more (e.g. 1, 2, 3, 4 or 5) $Z^3$ groups and optionally substituted with one or more (e.g. 1, 2, 3, 4 or 5) $Z^1$ groups, and wherein any —$X(C_2-C_6)$alkenyl, —$X(C_2-C_6)$alkynyl and —$X(C_3-C_7)$carbocycle is substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle, wherein any aryl, heteroaryl and heterocycle, either alone or as part of a group, is substituted with one or more (e.g. 1, 2, 3, 4 or 5) $Z^5$ groups and optionally substituted with one or more (e.g. 1, 2, 3, 4 or 5) $Z^1$ groups;

f) $(C_1-C_6)$haloalkyl, $(C_3-C_7)$carbocycle, $(C_2-C_6)$alkenyl, and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each independently substituted with one or more (e.g. 1, 2, 3, 4 or 5) $Z^6$ groups and optionally substituted with one or more (e.g. 1, 2, 3, 4 or 5) $Z^1$ groups; and g) —$NR_eR_f$, —$C(O)NR_eR_f$, —$OC(O)NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—C(O)—$NR_eR_f$ and —$(C_1-C_6)$alkyl-$SO_2NR_eR_f$, wherein any $(C_1-C_6)$alkyl, as part of a group, is optionally substituted with one or more (e.g. 1, 2, 3, 4 or 5) $Z^1$ groups;

$R^{6a}$ is selected from:
a) H, halo, $(C_1-C_6)$alkyl, and $(C_1-C_6)$haloalkyl;
b) $(C_2-C_6)$alkenyl, $(C_2-C_6)$alkynyl, $(C_3-C_7)$cycloalkyl, nitro, cyano, aryl, heterocycle and heteroaryl;
c) —$C(=O)$—$R^{11}$, —$C(=O)$—O—$R^{11}$, —O—$R^{11}$, —S—$R^{11}$, —S(O)—$R^{11}$, —$SO_2$—$R^{11}$, —$(C_1-C_6)$alkyl-$R^{11}$, —$(C_1-C_6)$alkyl-$C(=O)$—$R^{11}$, —$(C_1-C_6)$alkyl-$C(=O)$—O—$R^{11}$, —$(C_1-C_6)$alkyl-S—$R^{11}$, —$(C_1-C_6)$alkyl-S(O)—$R^{11}$ and —$(C_1-C_6)$alkyl-$SO_2$—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl; and
d) —$N(R^9)R^{10}$, —$C(=O)$—$N(R^9)R^{10}$, —O—$C(=O)$—$N(R^9)R^{10}$, —$SO_2$—$N(R^9)R^{16}$, —$(C_1-C_6)$alkyl-$N(R^9)R^{10}$, —$(C_1-C_6)$alkyl-$C(=O)$—$N(R^9)R^{10}$, —$(C_1-C_6)$alkyl-O—C(=O)—$N(R^9)R^{10}$ and —$(C_1-C_6)$alkyl-$SO_2$—$N(R^9)R^{10}$, wherein each $R^9$ is independently selected from H, $(C_1-C_6)$alkyl and $(C_3-C_7)$cycloalkyl, and each $R^{10}$ is independently selected from $R^{11}$, —$(C_1-C_6)$alkyl-$R^{11}$, —$SO_2$—$R^{11}$, —$C(=O)$—$R^{11}$, —$C(=O)OR^{11}$ and —$C(=O)N(R^9)R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl;

and wherein any aryl, heterocycle or heteroaryl of $R^{6a}$ is optionally substituted with one or more (e.g. 1, 2 or 3) $Z^{10}$ groups;

$R^{6b}$ is selected from:
a) —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkyl-S(O)—$(C_1-C_6)$alkyl-$(C_3-C_7)$carbocycle, —$(C_1-C_6)$alkyl-$SO_2$—$(C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, halo$(C_3-C_7)$carbocycle, —$NR_aSO_2NR_cR_d$, —$NR_aSO_2O(C_3-C_7)$carbocycle, —$NR_aSO_2Oaryl$, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$carbocycle-$Z^1$ and -halo$(C_1-C_6)$alkyl-$Z^3$, wherein any $(C_1-C_6)$alkyl, $(C_1-C_6)$haloalkyl, $(C_3-C_7)$carbocycle, $(C_2-C_6)$alkenyl, $(C_2-C_6)$alkynyl, aryl, heterocycle and heteroaryl, either alone or as part of a group, is optionally substituted with one or more (e.g. 1, 2, 3, 4 or 5) $Z^1$ groups;

b) spiro-bicyclic carbocycle, fused-bicyclic carbocycle and bridged-bicyclic carbocycle, wherein any spiro-bicyclic carbocycle, fused-bicyclic carbocycle and bridged-bicyclic carbocycle is optionally substituted with one or more (e.g. 1, 2, 3, 4 or 5) $Z^1$ groups, wherein two $Z^1$ groups together with the atom or atoms to which they are attached optionally form a carbocycle or heterocycle wherein the carbocycle or heterocycle is optionally substituted with one or more (e.g. 1, 2, 3, 4 or 5) $Z^1$ groups;

c) $(C_1-C_6)$alkyl, wherein $(C_1-C_6)$alkyl is substituted with one or more (e.g. 1, 2, 3, 4 or 5) $Z^2$ groups and optionally substituted with one or more (e.g. 1, 2, 3, 4 or 5) $Z^1$ groups;

d) —$X(C_1-C_6)$alkyl, —$X(C_1-C_6)$haloalkyl, —$X(C_2-C_6)$alkenyl, —$X(C_2-C_6)$alkynyl and —$X(C_3-C_7)$carbocycle, wherein any —$X(C_1-C_6)$alkyl and —$X(C_1-C_6)$haloalkyl is substituted with one or more (e.g. 1, 2, 3, 4 or 5) $Z^3$ groups and optionally substituted with one or more (e.g. 1, 2, 3, 4 or 5) $Z^1$ groups, and wherein any —$X(C_2-C_6)$alkenyl, —$X(C_2-C_6)$alkynyl and —$X(C_3-C_7)$carbocycle is substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle, wherein any aryl, heteroaryl and heterocycle, either alone or as part of a group, is substituted with one or more (e.g. 1, 2, 3, 4 or 5) $Z^5$ groups and optionally substituted with one or more (e.g. 1, 2, 3, 4 or 5) $Z^1$ groups;

f) $(C_1-C_6)$haloalkyl, $(C_3-C_7)$carbocycle, $(C_2-C_6)$alkenyl, and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each independently substituted with one or more (e.g. 1, 2, 3, 4 or 5) $Z^6$ groups and optionally substituted with one or more (e.g. 1, 2, 3, 4 or 5) $Z1$ groups; and g) —$NR_eR_f$, —$C(O)NR_eR_f$, —$OC(O)NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—C(O)—$NR_eR_f$ and —$(C_1-C_6)$alkyl-$SO_2NR_eR_f$ wherein any $(C_1-C_6)$alkyl, as part of a group, is optionally substituted with one or more (e.g. 1, 2, 3, 4 or 5) $Z^1$ groups;

$R^{7a}$ is selected from:
a) H, halo, $(C_1-C_6)$alkyl and $(C_1-C_6)$haloalkyl;
b) $(C_2-C_6)$alkenyl, $(C_2-C_6)$alkynyl, $(C_3-C_7)$cycloalkyl, nitro, cyano, aryl, heterocycle and heteroaryl;
c) —$C(=O)$—$R^{11}$, —$C(=O)$—O—$R''$, —O—$R''$, —S—$R''$, —S(O)—$R''$, —$SO_2$—$R''$, —$(C_1-C_6)$alkyl-$R^{11}$, —$(C_1-C_6)$alkyl-$C(=O)$—$R''$, —$(C_1-C_6)$alkyl-$C(=O)$—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-$SO_2$—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl; and
d) —$N(R^9)R^{10}$, —$C(=O)$—$N(R^9)R^{10}$, —O—C(=O)—$N(R^9)R^{10}$, —$SO_2$—$N(R^9)R^{10}$, —$(C_1-C_6)$alkyl-$N(R^9)R^{10}$, —$(C_1-C_6)$alkyl-$C(=O)$—$N(R^9)R^{10}$, —$(C_1-C_6)$alkyl-O—C(=O)—$N(R^9)R^{10}$ and —$(C_1-C_6)$alkyl-$SO_2$—$N(R^9)R^{10}$, wherein each $R^9$ is independently selected from H, $(C_1-C_6)$alkyl and $(C_3-C_7)$cycloalkyl, and each $R^{10}$ is independently selected from $R^{11}$, —$(C_1-C_6)$alkyl-$R^{11}$, —$SO_2$—$R''$, —$C(=O)$—$R^{11}$, —$C(=O)OR^{11}$ and —$C(=O)N(R^9)R^{11}$, wherein each $R^{11}$ is independently selected from H, $(C_1-C_6)$ alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, and wherein any aryl, heterocycle or heteroaryl of $R^{7a}$ is optionally substituted with one or more (e.g. 1, 2 or 3) $Z^{10}$ groups;

$R^{7b}$ is selected from:

a) —$(C_1-C_6)$alkyl-$SO_2$—$(C_1-C_6)$alkyl-$Z^{13}$, —C(O)—$(C_1-C_6)$alkyl-$Z^{13}$, $C_6)$alkyl-$Z^{13}$, —S—$(C_1-C_6)$alkyl-$Z^{13}$, —S(O)—$(C_1-C_6)$alkyl-$Z^{13}$, —$SO_2$—$(C_1-C_6)$alkyl-$Z^{13}$, —$(C_1-C_6)$alkyl-$Z^{14}$, —$(C_1-C_6)$alkyl-C(O)—$(C_1-C_6)$alkyl-$Z^{13}$, —$(C_1-C_6)$alkyl-C(O)—O$(C_1-C_6)$alkyl-$Z^{13}$, —$(C_1-C_6)$alkyl-O—$(C_1-C_6)$alkyl-$Z^{13}$, —$(C_1-C_6)$alkyl-S—$(C_1-C_6)$alkyl-$Z^{13}$, —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkyl-S(O)—$(C_1-C_6)$alkyl-$(C_3-C_7)$carbocycle, —$(C_1-C_6)$alkyl-$SO_2$—$(C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, $(C_3-C_7)$halocarbocycle, —$NR_aSO_2NR_cR_d$, —$NR_aSO_2O(C_3-C_7)$carbocycle, —$NR_aSO_2$Oaryl, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$carbocycle-$Z^1$ and -halo$(C_1-C_6)$alkyl-$Z^3$, wherein any $(C_1-C_6)$alkyl, $(C_1-C_6)$haloalkyl, $(C_3-C_7)$carbocycle, $(C_3-C_7)$halocarbocycle, $(C_2-C_6)$alkenyl, $(C_2-C_6)$alkynyl, aryl, heterocycle and heteroaryl, either alone or as part of a group, is optionally substituted with one or more (e.g. 1, 2, 3, 4 or 5) $Z^1$ groups;

b) spiro-bicyclic carbocycle, fused-bicyclic carbocycle and bridged-bicyclic carbocycle, wherein any spiro-bicyclic carbocycle, fused-bicyclic carbocycle and bridged-bicyclic carbocycle is optionally substituted with one or more (e.g. 1, 2, 3, 4 or 5) $Z^1$ groups, wherein two $Z^1$ groups together with the atom or atoms to which they are attached optionally form a $(C_3-C_7)$carbocycle or heterocycle, wherein the $(C_3-C_7)$carbocycle or heterocycle is optionally substituted with one or more (e.g. 1, 2, 3, 4 or 5) $Z^1$ groups;

c) $(C_1-C_6)$alkyl, wherein $(C_1-C_6)$alkyl is substituted with one or more (e.g. 1, 2, 3, 4 or 5) $Z^2$ groups and optionally substituted with one or more (e.g. 1, 2, 3, 4 or 5) $Z^1$ groups;

d) —$X(C_1-C_6)$alkyl, —$X(C_1-C_6)$haloalkyl, —$X(C_2-C_6)$alkenyl, —$X(C_2-C_6)$alkynyl and —$X(C_3-C_7)$carbocycle, wherein any —$X(C_1-C_6)$alkyl and —$X(C_1-C_6)$haloalkyl is substituted with one or more (e.g. 1, 2, 3, 4 or 5) $Z^3$ groups and optionally substituted with one or more (e.g. 1, 2, 3, 4 or 5) $Z^1$ groups, and wherein any $X(C_2-C_6)$alkenyl, —$X(C_2-C_6)$alkynyl and —$X(C_3-C_7)$carbocycle is substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle, wherein any aryl, heteroaryl and heterocycle, either alone or as part of a group, is substituted with one or more (e.g. 1, 2, 3, 4 or 5) $Z^5$ groups and optionally substituted with one or more (e.g. 1, 2, 3, 4 or 5) $Z^1$ groups;

f) $(C_1-C_6)$haloalkyl, $(C_3-C_7)$carbocycle, $(C_2-C_6)$alkenyl and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each substituted with one or more (e.g. 1, 2, 3, 4 or 5) $Z^6$ groups and optionally substituted with one or more (e.g. 1, 2, 3, 4 or 5) $Z^1$ groups; and g) —$NR_eR_f$, —$C(O)NR_eR_f$, —$OC(O)NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—C(O)—$NR_eR_f$ and —$(C_1-C_6)$alkyl-$SO_2NR_eR_f$, wherein any $(C_1-C_6)$alkyl, as a part of group, is optionally substituted with one or more (e.g. 1, 2, 3, 4 or 5) $Z^1$ groups;

$R^{8a}$ is selected from:

a) halo, nitro and cyano;

b) $R^{11}$, —C(=O)—$R^{11}$, —C(=O)—O—$R^{11}$, —O—$R^{11}$, —S—$R^{11}$, —S(O)—$R^{11}$, —$SO_2$—$R^{11}$, —$(C_1-C_6)$algl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-$SO_2$—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein aryl, heterocycle and heteroaryl are each optionally substituted with one or more (e.g. 1, 2 or 3) $Z^{11}$ groups; and c) —$N(R^9)R^{10}$, —$C(=O)$—$N(R^9)R^{10}$, —O—C(=O)—$N(R^9)R^{10}$, —$SO_2$—$N(R^9)R^{10}$, —$(C_1-C_6)$alkyl-$N(R^9)R^{10}$, —$(C_1-C_6)$alkyl—$C(=O)$—$N(R^9)R^{10}$, —$(C_1-C_6)$alkyl-O—C(=O)—$N(R^9)R^{10}$ and —$(C_1-C_6)$alkyl-$SO_2$—$N(R^9)R^{10}$, wherein each $R^9$ is independently selected from H, $(C_1-C_6)$alkyl and $(C_3-C_7)$cycloalkyl, and each $R^{10}$ is independently selected from $R^{11}$, —$(C_1-C_6)$alkyl-$R^{11}$, —$SO_2$—$R^{11}$, —$C(=O)$—$R^{11}$, —$C(=O)OR^{11}$ and —$C(=O)N(R^9)R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein aryl, heterocycle and heteroaryl are each optionally substituted with one or more (e.g. 1, 2 or 3) $Z^{11}$ groups;

$R^{8b}$ is selected from:

a) —$(C_1-C_6)$alkyl-$SO_2$—$(C_1-C_6)$alkyl-$Z^{13}$, —C(O)—$(C_1-C_6)$alkyl-$Z^{13}$, —O—$(C_1-C_6)$alkyl-$Z^{13}$, —S—$(C_1-C_6)$alkyl-$Z^{13}$, —S(O)—$(C_1-C_6)$alkyl-$Z^{13}$, —$SO_2$—$(C_1-C_6)$alkyl-$Z^{13}$, —$(C_1-C_6)$alkyl-$Z^{14}$, —$(C_1-C_6)$alkyl-C(O)—$(C_1-C_6)$alkyl-$Z^{13}$, —$(C_1-C_6)$alkyl-C(O)—O$(C_1-C_6)$alkyl-$Z^{13}$, —$(C_1-C_6)$alkyl-O—$(C_1-C_6)$alkyl-$Z^{13}$, —$(C_1-C_6)$alkyl-S—$(C_1-C_6)$alkyl-$Z^{13}$, —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkyl-S(O)—$(C_1-C_6)$alkyl-$(C_3-C_7)$carbocycle, —$(C_1-C_6)$alkyl-$SO_2$—$(C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, halo$(C_3-C_7)$carbocycle, —$NR_aSO_2NR_cR_d$, —$NR_aSO_2O(C_3-C_7)$carbocycle, —$NR_aSO_2$Oaryl, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$carbocycle-$Z^1$ and -halo$(C_1-C_6)$alkyl-$Z^3$, wherein any $(C_1-C_6)$alkyl, $(C_1-C_6)$haloalkyl, $(C_3-C_7)$carbocycle, $(C_2-C_6)$alkenyl, $(C_2-C_6)$alkynyl, aryl, heterocycle and heteroaryl, either alone or as part of a group, is optionally substituted with one or more (e.g. 1, 2, 3, 4 or 5) $Z^1$ groups;

b) spiro-bicyclic carbocycle, fused-bicyclic carbocycle and bridged-bicyclic carbocycle, wherein any Spiro-bicyclic carbocycle, fused-bicyclic carbocycle and bridged-bicyclic carbocycle is optionally substituted with one or more (e.g. 1, 2, 3, 4 or 5) $Z^1$ groups, wherein two $Z^1$ groups together with the atom or atoms to which they are attached optionally form a $(C_3-C_7)$carbocycle or heterocycle wherein the $(C_3-C_7)$carbocycle or heterocycle is optionally substituted with one or more (e.g. 1, 2, 3, 4 or 5) $Z^1$ groups;

c) $(C_1-C_6)$alkyl, wherein $(C_1-C_6)$alkyl is substituted with one or more (e.g. 1, 2, 3, 4 or 5) $Z^2$ groups and optionally substituted with one or more (e.g. 1, 2, 3, 4 or 5) $Z^1$ groups;

d) —$X(C_1-C_6)$alkyl, —$X(C_1-C_6)$haloalkyl, —$X(C_2-C_6)$alkenyl, —$X(C_2-C_6)$alkynyl and —$X(C_3-C_7)$carbocycle, wherein any —$X(C_1-C_6)$alkyl and —$X(C_1-C_6)$haloalkyl is substituted with one or more (e.g. 1, 2, 3, 4 or 5) $Z^3$ groups and optionally substituted with one or more (e.g. 1, 2, 3, 4 or 5) $Z^1$ groups, and wherein any —X($C_2$-$C_6$)alkenyl, —X($C_2$-$C_6$)alkynyl and —X($C_3$-$C_7$)carbocycle is substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle, wherein any aryl, heteroaryl and heterocycle, either alone or as part of a group, is substituted with one or more (e.g. 1, 2, 3, 4 or 5) $Z^5$ groups and optionally substituted with one or more (e.g. 1, 2, 3, 4 or 5) $Z^1$ groups;

f) ($C_1$-$C_6$)haloalkyl, ($C_3$-$C_7$)carbocycle, ($C_2$-$C_6$)alkenyl and ($C_2$-$C_6$)alkynyl, wherein ($C_1$-$C_6$)haloalkyl, ($C_3$-$C_7$)carbocycle, ($C_2$-$C_6$)alkenyl and ($C_2$-$C_6$)alkynyl are each independently substituted with one or more (e.g. 1, 2, 3, 4 or 5) $Z^6$ groups and optionally substituted with one or more (e.g. 1, 2, 3, 4 or 5) $Z^1$ groups; and g) —$NR_eR_f$, —C(O)$NR_eR_f$, —OC(O)$NR_eR_f$, —$SO_2NR_eR_f$, —($C_1$-$C_6$)alkyl-$NR_eR_f$, —($C_1$-$C_6$)alkylC(O)—$NR_eR_f$, —($C_1$-$C_6$)alkyl-O—C(O)—$NR_eR_f$ and —($C_1$-$C_6$)alkyl-$SO_2NRA_f$, wherein any ($C_1$-$C_6$)alkyl, as part of a group, is optionally substituted with one or more (e.g. 1, 2, 3, 4 or 5) $Z^1$ groups;

$R^{13a}$ is selected from:

a) $R^{11}$, —C(=O)—$R^{11}$, —C(=O)—O—$R^{11}$, —O—$R^{11}$, —S—$R^{11}$, —S(O)—$R^{11}$, —$SO_2$—$R^{11}$, —($C_1$-$C_6$)alkyl-$R^{11}$, —($C_1$-$C_6$)alkyl-C(=)—$R^{11}$, —($C_1$-$C_6$)alkyl-C(=O)—$R^{11}$, —($C_1$-$C_6$)alkyl-C(=O)—O—$R^{11}$, —($C_1$-$C_6$)alkyl-O—$R^{11}$, —($C_1$-$C_6$)alkyl-S—$R^{11}$, —($C_1$-$C_6$)alkyl-S(O)—$R^{11}$ and —($C_1$-$C_6$)alkyl-$SO_2$—$R^{11}$, wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl, wherein aryl, heterocycle and heteroaryl are each optionally substituted with one or more (e.g. 1, 2 or 3) $Z^{11}$ groups; and b) —C(=O)—N($R^9$)$R^{10}$, —$SO_2$—N$R^9$)$R^{10}$, —($C_1$-$C_6$)alkyl-N($R^9$)$R^{10}$, —($C_1$-$C_6$)alkyl-C(=O)—N($R^9$)$R^{10}$, —($C_1$-$C_6$)alkyl-O—C(=O)—N($R^9$)$R^{10}$ and —($C_1$-$C_6$)alkyl-$SO_2$—N($R^9$)$R^{10}$, wherein each $R^9$ is independently selected from H, ($C_1$-$C_6$)alkyl and ($C_3$-$C_7$)cycloalkyl, and each $R^{10}$ is independently selected from $R^{11}$, —($C_1$-$C_6$)alkyl-$R^{11}$, —$SO_2$—$R^{11}$, —C(=O)—$R^{11}$, —C(=O)O$R^{11}$ and —C(=O)N($R^9$)$R^{11}$, wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, —($C_1$-$C_6$)alkylaryl, aryl, heterocycle and heteroaryl, wherein aryl, heterocycle and heteroaryl are each optionally substituted with one or more (e.g. 1, 2 or 3) $Z^{11}$ groups;

$R^{13b}$ is selected from:

a) —($C_1$-$C_6$)alkyl-$SO_2$—($C_1$-$C_6$)alkyl-$Z^{13}$, —C(O)—($C_1$-$C_6$)alkyl-$Z^{13}$, —O—($C_1$-$C_6$)alkyl-$Z^{13}$, —S—($C_1$-$C_6$)alkyl-$Z^{13}$, —S(O)—($C_1$-$C_6$)alkyl-$Z^{13}$, —$SO_2$—($C_1$-$C_6$)alkyl-$Z^{13}$, —($C_1$-$C_6$)alkyl-$Z^{14}$, —($C_1$-$C_6$)alkyl-C(O)—($C_1$-$C_6$)alkyl-$Z^{13}$, —($C_1$-$C_6$)alkyl-C(O)—O($C_1$-$C_6$)alkyl-$Z^{13}$, —($C_1$-$C_6$)alkyl-O—($C_1$-$C_6$)alkyl-$Z^{13}$, —($C_1$-$C_6$)alkyl-S—($C_1$-$C_6$)alkyl-$Z^{13}$, —($C_1$-$C_6$)alkyl-O—($C_1$-$C_6$)alkyl-($C_3$-$C_7$)carbocycle, —($C_1$-$C_6$)alkyl-S—($C_1$-$C_6$)alkyl-($C_3$-$C_7$)carbocycle, —($C_1$-$C_6$)alkyl-S(O)—($C_1$-$C_6$)alkyl-($C_3$-$C_7$)carbocycle, —($C_1$-$C_6$)alkyl-$SO_2$—($C_1$-$C_6$)alkyl-($C_3$-$C_7$)carbocycle, —($C_2$-$C_6$)alkenyl-($C_1$-$C_6$)haloalkyl, —($C_2$-$C_6$)alkynyl-($C_1$-$C_6$)haloalkyl, -halo($C_3$-$C_7$)carbocycle, —($C_2$-$C_6$)alkenyl-($C_3$-$C_7$)carbocycle, —($C_2$-$C_6$)alkenyl-aryl, —($C_2$-$C_6$)alkenyl-heteroaryl, —($C_2$-$C_6$)alkenyl-heterocycle, —($C_2$-$C_6$)alkynyl-($C_3$-$C_7$)carbocycle, —($C_2$-$C_6$)alkynyl-aryl, —($C_2$-$C_6$)alkynyl-heteroaryl, —($C_2$-$C_6$)alkynyl-heterocycle, —($C_3$-$C_7$)carbocycle-$Z^1$, -halo($C_1$-$C_6$)alkyl-$Z^3$, —$NR_aSO_2NR_cR_4$, —$NR_aSO_2O$($C_3$-$C_7$)carbocycle and —$NR_aSO_2O$aryl, wherein any ($C_1$-$C_6$)alkyl, ($C_1$-$C_6$)haloalkyl, ($C_3$-$C_7$)carbocycle, ($C_2$-$C_6$)alkenyl, ($C_2$-$C_6$)alkynyl, aryl, heterocycle and heteroaryl, either alone or as part of a group, is optionally substituted with one or more (e.g. 1, 2, 3, 4 or 5) $Z^1$ groups;

b) spiro-bicyclic carbocycle, fused-bicyclic carbocycle and bridged-bicyclic carbocycle, wherein spiro-bicyclic carbocycle, fused-bicyclic carbocycle and bridged-bicyclic carbocycle are optionally substituted with one or more (e.g. 1, 2, 3, 4 or 5) $Z^1$ groups, wherein two $Z^1$ groups together with the atom or atoms to which they are attached optionally form a ($C_3$-$C_7$)carbocycle or heterocycle wherein the ($C_3$-$C_7$)carbocycle or heterocycle is optionally substituted with one or more (e.g. 1, 2, 3, 4 or 5) $Z^1$ groups;

c) ($C_1$-$C_6$)alkyl, wherein ($C_1$-$C_6$)alkyl is substituted with one or more (e.g. 1, 2, 3, 4 or 5) $Z^2$ groups and optionally substituted with one or more (e.g. 1, 2, 3, 4 or 5) $Z^1$ groups;

d) —X($C_1$-$C_6$)alkyl, —X($C_1$-$C_6$)haloalkyl, —X($C_2$-$C_6$)alkenyl, —X($C_2$-$C_6$)alkynyl and —X($C_3$-$C_7$)carbocycle, wherein any —X($C_1$-$C_6$)alkyl, —X($C_1$-$C_6$)haloalkyl, is substituted with one or more (e.g. 1, 2, 3, 4 or 5) $Z^3$ groups and optionally substituted with one or more (e.g. 1, 2, 3, 4 or 5) $Z^1$ groups, and wherein any —X($C_2$-$C_6$)alkenyl, —X($C_2$-$C_6$)alkynyl and —X($C_3$-$C_7$)carbocycle, is substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle, wherein any aryl, heteroaryl and heterocycle, either alone or as part of a group, is substituted with one or more (e.g. 1, 2, 3, 4 or 5) $Z^5$ groups and optionally substituted with one or more (e.g. 1, 2, 3, 4 or 5) $Z^1$ groups;

f) ($C_1$-$C_6$)haloalkyl, ($C_3$-$C_7$)carbocycle, ($C_2$-$C_6$)alkenyl and ($C_2$-$C_6$)alkynyl, wherein ($C_1$-$C_6$)haloalkyl, ($C_3$-$C_7$)carbocycle, ($C_2$-$C_6$)alkenyl and ($C_2$-$C_6$)alkynyl are each independently substituted with one or more (e.g. 1, 2, 3, 4 or 5) $Z^6$ groups and optionally substituted with one or more (e.g. 1, 2, 3, 4 or 5) $Z^1$ groups; and g) —C(O)$NR_eR_f$, —$SO_2NR_eR_f$, —($C_1$-$C_6$)alkylC(O)—$NR_eR_f$, —($C_1$-$C_6$)alkyl-O—C(O)—$NR_eR_f$ and —($C_1$-$C_6$)alkyl-$SO_2NR_eR_f$, wherein any ($C_1$-$C_6$)alkyl, as part of a group, is optionally substituted with one or more (e.g. 1, 2, 3, 4 or 5) $Z^1$ groups;

or any of $R^{5a}$ and $R^{6a}$, $R^{6a}$ and $R^{7a}$, $R^{7a}$ and $R^{8a}$, $R^1$ and $R^8$, $R^1$ and $R^2$ or $R^1$ and $R^{13}$ together with the atoms to which they are attached form a 5 or 6-membered carbocycle or a 4, 5, 6 or 7-membered heterocycle, wherein the 5 or 6-membered carbocycle or the 4, 5, 6 or 7-membered heterocycle is optionally substituted with one or more (e.g. 1, 2 or 3) substituents each independently selected from halo, ($C_1$-$C_6$)alkyl, ($C_2$-$C_6$)alkenyl, ($C_1$-$C_6$)haloalkyl, ($C_3$-$C_7$)cycloalkyl, —OH, —O($C_1$-$C_6$)alkyl, —SH, —S($C_1$-$C_6$)alkyl, —$NH_2$, —NH($C_1$-$C_6$)alkyl and —N(($C_1$-$C_6$)alkyl)$_2$;

or any of $R^5$ and $R^6$, $R^6$ and $R^7$ or $R^7$ and $R^8$, together with the atoms to which they are attached form a 5 or 6-membered carbocycle or a 4, 5, 6 or 7-membered heterocycle, wherein the 5 or 6-membered carbocycle or the 4, 5, 6 or 7-membered heterocycle are each independently substituted with one or more (e.g. 1, 2 or 3) $Z^7$ or $Z^8$ groups, wherein when two $Z^7$ groups are on same atom the two $Z^7$ groups together with the atom to which they are attached optionally form a ($C_3$-$C_7$)carbocycle or 4, 5 or 6-membered heterocycle;

or any of $R^1$ and $R^8$, $R^1$ and $R^2$ or $R^1$ and $R^{13}$ together with the atoms to which they are attached form a 5 or 6-membered carbocycle or a 4, 5, 6 or 7-membered heterocycle, wherein the 5 or 6-membered carbocycle or the 4, 5, 6 or 7-membered heterocycle are each independently substituted with one or more (e.g. 1, 2 or 3) $Z^7$ or $Z^8$ groups; wherein when two $Z^7$ groups are on same atom the two $Z^7$ groups together with the atom to which they are attached optionally form a $(C_3-C_7)$ carbocycle or 4, 5 or 6-membered heterocycle;

X is independently selected from O, —C(O)—, —C(O)O—, —S—, —S(O)—, —SO$_2$—, —(C$_1$-C$_6$)alkylO—, —(C$_1$-C$_6$)alkylC(O)—, —(C$_1$-C$_6$)alkylC(O)O—, —(C$_1$-C$_6$)alkylS—, —(C$_1$-C$_6$)alkylS(O)— and —(C$_1$-C$_6$)alkylSO$_2$—;

each $Z^1$ is independently selected from halo, —NO$_2$, —OH, =NOR$_a$, —SH, —CN, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)carbocycle, (C$_3$-C$_7$)halocarbocycle, aryl, heteroaryl, heterocycle, —O(C$_1$-C$_6$)alkyl, —O(C$_2$-C$_6$)alkenyl, —O(C$_2$-C$_6$)alkynyl, —O(C$_1$-C$_6$)haloalkyl, —O(C$_3$-C$_7$)carbocycle, —O(C$_3$-C$_7$)halocarbocycle, —Oaryl, —Oheteroaryl, —Oheterocycle, —S(C$_1$-C$_6$)alkyl, —S(C$_2$-C$_6$)alkenyl, —S(C$_2$-C$_6$)alkynyl, —S(C$_1$-C$_6$)haloalkyl, —S(C$_3$-C$_7$)carbocycle, —S(C$_3$-C$_7$)halocarbocycle, —Saryl, —Sheteroaryl, —Sheterocycle, —S(O)(C$_1$-C$_6$)alkyl, —S(O)(C$_2$-C$_6$)alkenyl, —S(O)(C$_2$-C$_6$)alkynyl, —S(O)(C$_1$-C$_6$)haloalkyl, —S(O)(C$_3$-C$_7$)carbocycle, —S(O)(C$_3$-C$_7$)halocarbocycle, —SO$_2$(C$_1$-C$_6$)alkyl, —S(O)aryl, —S(O)carbocycle, —S(O)heterocycle, —S(O)heterocycle, —SO$_2$(C$_2$-C$_6$)alkenyl, —SO$_2$(C$_2$-C$_6$)alkynyl, —SO$_2$(C$_1$-C$_6$)haloalkyl, —SO$_2$(C$_3$-C$_7$)carbocycle, —SO$_2$(C$_3$-C$_7$)halocarbocycle, —SO$_2$aryl, —SO$_2$heteroaryl, —SO$_2$heterocycle, —SO$_2$NR$_c$R$_d$, —NR$_a$C(O)R$_a$, —NR$_a$C(O)OR$_a$, —NR$_a$C(O)NR$_c$R$_d$, —NR$_a$SO$_2$R$_b$, —NR$_a$SO$_2$NR$_c$R$_d$, —NR$_a$SO$_2$O(C$_3$-C$_7$)carbocycle, —NR$_a$SO$_2$Oaryl, —OS(O)$_2$R$_a$, —C(O)R$_a$, —C(O)OR$_b$, —C(O)NR$_c$R$_d$, and —OC(O)NR$_c$R$_d$, wherein any (C$_1$-C$_6$)alkyl, —(C$_1$-C$_6$)haloalkyl, (C$_2$-C$_6$)alkenyl, (C$_2$-C$_6$)alkynyl, (C$_3$-C$_7$)halocarbocycle, (C$_3$-C$_7$)carbocycle, (C$_3$-C$_7$)halocarbocycle, aryl, heteroaryl and heterocycle of Z, either alone or as part of a group, is optionally substituted with one or more (e.g. 1, 2, 3, 4 or 5) halogen, —OH, —OR$_b$, —CN, —NR$_a$C(O)$_2$R$_b$, -heteroaryl, -heterocycle, —Oheteroaryl, —Oheterocycle, —NHheteroaryl, —NHheterocycle or —S(O)$_2$NR$_c$R$_d$;

each $Z^2$ is independently selected from —NO$_2$, —CN, spiro-heterocycle, bridged-heterocycle, spiro-bicyclic carbocycle, bridged-bicyclic carbocycle, NR$_a$SO$_2$(C$_3$-C$_7$)carbocycle, —NR$_a$SO$_2$aryl, —NR$_a$SO$_2$heteroaryl, —NR$_a$SO$_2$NR$_c$R$_d$, —NR$_a$SO$_2$O(C$_3$-C$_7$)carbocycle and —NR$_a$SO$_2$Oaryl;

each $Z^3$ is independently selected from —NO$_2$, —CN, —OH, oxo, =NOR$_a$, thioxo, -aryl, -heterocycle, -heteroaryl, (C$_3$-C$_7$)carbocycle, (C$_3$-C$_7$)halocarbocycle, —O(C$_3$-C$_7$)carbocycle, —Ohalo(C$_3$-C$_7$)carbocycle, —Oaryl, —Oheterocycle, —Oheteroaryl, —S(C$_1$-C$_6$)alkyl, —S(C$_3$-C$_7$)carbocycle, —S(C$_3$-C$_7$)halocarbocycle, —Saryl, —Sheterocycle, —Sheteroaryl, —S(O)(C$_1$-C$_6$)alkyl, —S(O)(C$_3$-C$_7$)carbocycle, —S(O)(C$_3$-C$_7$)halocarbocycle, —S(O)aryl, —S(O)heterocycle, —S(O)heteroaryl, —SO$_2$(C$_1$-C$_6$)alkyl, —SO$_2$(C$_3$-C$_7$)carbocycle, —SO$_2$(C$_3$-C$_7$)halocarbocycle, SO$_2$aryl, —SO$_2$heterocycle, —SO$_2$heteroaryl, —NR$_a$R$_b$, —NR$_a$C(O)R$_b$, —C(O)NR$_c$R$_d$, —SO$_2$NR$_c$R$_d$, —NR$_a$SO$_2$NR$_c$R$_d$, —NR$_a$SO$_2$O(C$_3$-C$_7$)carbocycle and —NR$_a$SO$_2$Oaryl;

each $Z^4$ is independently selected from halogen, —(C$_1$-C$_6$)alkyl, (C$_3$-C$_7$)carbocycle, -halo(C$_1$-C$_6$)alkyl, —NO$_2$, —CN, —OH, oxo, =NOR$_a$, thioxo, -aryl, -heterocycle, -heteroaryl, (C$_3$-C$_7$)halocarbocycle, —O(C$_1$-C$_6$)alkyl, —O(C$_3$-C$_7$)carbocycle, —O(C$_3$-C$_7$)halocarbocycle, —Oaryl, —Oheterocycle, —Oheteroaryl, —S(C$_1$-C$_6$)alkyl, —S(C$_3$-C$_7$)carbocycle, —S(C$_3$-C$_7$)halocarbocycle, —Saryl, —Sheterocycle, —Sheteroaryl, —S(O)(C$_1$-C$_6$)alkyl, —S(O)(C$_3$-C$_7$)carbocycle, —S(O)(C$_3$-C$_7$)halocarbocycle, —S(O)aryl, —S(O)heterocycle, —S(O)heteroaryl, —SO$_2$(C$_1$-C$_6$)alkyl, —SO$_2$(C$_3$-C$_7$)carbocycle, —SO$_2$(C$_3$-C$_7$)halocarbocycle, SO$_2$aryl, —SO$_2$heterocycle, —SO$_2$heteroaryl, —NR$_a$R$_b$, —NR$_a$C(O)R$_a$, —C(O)NR$_c$R$_d$, —SO$_2$NR$_c$R$_d$, —NR$_a$SO$_2$NRA$_d$, —NR$_a$SO$_2$O(C$_3$-C$_7$)carbocycle and —NR$_a$SO$_2$Oaryl;

each $Z^5$ is independently selected from —NO$_2$, —CN, —NR$_a$SO$_2$NR$_c$R$_d$, —NR$_a$SO$_2$O(C$_3$-C$_7$)carbocycle, —NR$_a$SO$_2$Oaryl, —NR$_a$SO$_2$(C$_1$-C$_6$)alkyl, —NR$_a$SO$_2$(C$_2$-C$_6$)alkenyl, —NR$_a$SO$_2$(C$_2$-C$_6$)alkynyl, —NR$_a$SO$_2$(C$_3$-C$_7$)carbocycle, —NR$_a$SO$_2$(C$_3$-C$_7$)halocarbocycle, —NR$_a$SO$_2$aryl, —NR$_a$SO$_2$hetaryl, —NR$_a$SO$_2$heteroaryl, —NR$_a$SO$_2$heterocycle, —NR$_a$C(O)alkyl, —NR$_a$C(O)alkenyl, —NR$_a$C(O)alkynyl, —NR$_a$C(O)(C$_3$-C$_7$)carbocycle, —NR$_a$C(O)(C$_3$-C$_7$)halocarbocycle, —NR$_a$C(O)aryl, —NR$_a$C(O)heteroaryl, —NR$_a$C(O)heterocycle, NR$_a$C(O)NR$_c$R$_d$ and NR$_a$C(O)OR$_b$;

each $Z^6$ is independently selected from —NO$_2$, —CN, —NR$_a$R$_a$, NR$_a$C(O)R$_b$, —C(O)NIU$_d$, —(C$_3$-C$_7$)halocarbocycle, -aryl, -heteroaryl, -heterocycle, —Oaryl, -Oheteroaryl, —Oheterocycle, —O(C$_3$-C$_7$)halocarbocycle, —O(C$_1$-C$_6$)alkyl, —O(C$_1$-C$_6$)alkyl-O—(C$_1$-C$_6$)alkyl, —O(C$_3$-C$_7$)carbocycle, —Ohalo(C$_1$-C$_6$)alkyl, —Saryl, —Sheteroaryl, —Sheterocycle, —S(C$_3$-C$_7$)halocarbocycle, —S(C$_1$-C$_6$)alkyl, —S(C$_3$-C$_7$)carbocycle, —S(C$_1$-C$_6$)haloalkyl, —S(O)aryl, —S(O)heteroaryl, —S(O)heterocycle, —S(O)(C$_3$-C$_7$)halocarbocycle, —S(O)(C$_1$-C$_6$)alkyl, —S(O)(C$_3$-C$_7$)carbocycle, —S(O)halo(C$_1$-C$_6$)alkyl, —SO$_2$aryl, —SO$_2$heteroaryl, —SO$_2$heterocycle, —SO$_2$(C$_1$-C$_6$)alkyl, —SO$_2$halo(C$_1$-C$_6$)alkyl, —SO$_2$(C$_3$-C$_7$)carbocycle, —SO$_2$(C$_3$-C$_7$)halocarbocycle, —SO$_2$NR$_c$R$_d$, —NR$_a$SO$_2$(C$_3$-C$_7$)halocarbocycle, —NR$_a$SO$_2$aryl, —NR$_a$SO$_2$heteroaryl, —NR$_a$SO$_2$heterocycle, —NR$_a$SO$_2$NR$_c$R$_d$, —NR$_a$SO$_2$O(C$_3$-C$_7$)carbocycle and —NR$_a$SO$_2$Oaryl;

each $Z^7$ is independently selected from —NO$_2$, =NOR$_a$, —CN, —(C$_1$-C$_6$)alkyl-Z$^{12}$, —(C$_2$-C$_6$)alkenyl-Z$^{12}$, —(C$_2$-C$_6$)alkenylOH, —(C$_2$-C$_6$)alkynyl-Z$^{12}$, —(C$_2$-C$_6$)alkynylOH, —(C$_1$-C$_6$)haloalkyl-Z$^{12}$, —(C$_1$-C$_6$)haloalkylOH, —(C$_3$-C$_7$)carbocycle-Z$^{12}$, —(C$_3$-C$_7$)carbocycleOH, —(C$_3$-C$_7$)halocarbocycle, —(C$_1$-C$_6$)alkylNRA$_t$, —(C$_1$-C$_6$)alkylNR$_a$C(O)R$_a$, —(C$_1$-C$_6$)alkylNR$_a$SO$_2$R$_a$, -aryl, -heteroaryl, -heterocycle, —O(C$_1$-C$_6$)alkyl-Z$^{12}$, —O(C$_2$-C$_6$)alkenyl, —O(C$_2$-C$_6$)alkynyl, —O(C$_1$-C$_6$)haloalkyl, —O(C$_3$-C$_7$)carbocycle, —O(C$_3$-C$_7$)halocarbocycle, —Oaryl, —O(C$_1$-C$_6$)alkylNR$_c$R$_d$, —O(C$_1$-C$_6$)alkylNR$_a$C(O)R$_a$, —O(C$_1$-C$_6$)alkylNR$_a$SO$_2$R$_a$, —Oheteroaryl, —Oheterocycle, —S(C$_1$-C$_6$)alkyl-Z$^{12}$, —S(C$_2$-C$_6$)alkenyl, —S(C$_2$-C$_6$)alkynyl, —S(C$_1$-C$_6$)haloalkyl, —S(C$_3$-C$_7$)carbocycle, —S(C$_3$-C$_7$)halocarbocycle, —S(C$_1$-C$_6$)alkylNR$_c$R$_a$, —S(C$_1$-C$_6$)alkylNR$_a$C(O)R$_a$, —S(C$_1$-C$_6$)alkylNR$_a$SO$_2$R$_a$, —Saryl, —Sheteroaryl, —Sheterocycle, —S(O)(C$_1$-C$_6$)alkyl, —S(O)(C$_2$-C$_6$)alkenyl, —S(O)(C$_2$-C$_6$)alkynyl, —S(O)(C$_1$-C$_6$)haloalkyl, —S(O)(C$_3$-C$_7$)carbocycle, —S(O)(C$_3$-C$_7$)halocarbocycle, —SO$_2$(C$_1$-C$_6$)alkyl, —S(O)(C$_1$-C$_6$)alkylNRA$_t$, —S(O)(C$_1$-C$_6$)alkylNR$_a$C(O)R$_a$, —S(O)(C$_1$-C$_6$)alkylNR$_a$SO$_2$R$_a$, —S(O)aryl, —S(O)heteroaryl, —S(O)heterocycle, —SO$_2$(C$_1$-C$_6$)alkyl, —SO$_2$(C$_2$-C$_6$)alkenyl, —SO$_2$(C$_2$-C$_6$)alkynyl, —SO$_2$(C$_1$-C$_6$)haloalkyl, —SO$_2$(C$_3$-C$_7$)carbocycle, —SO$_2$(C$_3$-C$_7$)halocarbocycle, —SO$_2$aryl, —SO$_2$heteroaryl, —SO$_2$heterocycle, —SO$_2$(C$_1$-C$_6$)alkylNR$_e$R$_a$, —SO$_2$(C$_1$-C$_6$)alkylNR$_a$C(O)R$_a$, —SO$_2$(C$_1$-C$_6$)alkylNR$_a$SO$_2$R$_a$, —SO$_2$NR$_c$R$_d$, —NR$_a$C(O)OR$_b$, —NR$_a$C(O)NR$_c$R$_d$, —NR$_a$SO$_2$R$_b$, —NR$_a$SO$_2$NR$_c$R$_d$, —NR$_a$SO$_2$O(C$_3$-C$_7$)carbocycle, —NR$_a$SO$_2$Oaryl, —OS(O)$_2$R$_a$, —C(O)NR$_c$R$_d$, and —OC(O)NR$_c$R$_d$, wherein any (C$_1$-C$_6$)alkyl, (C$_1$-C$_6$)haloalkyl, (C$_2$-C$_6$)alkenyl, (C$_2$-C$_6$)alkynyl, (C$_3$-C$_7$)carbocycle, (C$_3$-C$_7$)halocarbocycle, aryl, heteroaryl and heterocycle of $Z^7$, either alone or as part of a group, is optionally substituted with one or more (e.g. 1, 2, 3, 4 or 5) halogen, —OH, —OR$_b$, —CN, —NR$_a$C(O)$_2$R$_b$, -heteroaryl, -heterocycle, —Oheteroaryl, -Oheterocycle, —NHheteroaryl, —NHheterocycle, or —S(O)$_2$NR$_c$R$_d$.

each $Z^8$ is independently selected from —NO$_2$ and —CN;

each $Z^9$ is independently selected from —(C$_1$-C$_6$)alkyl and —O(C$_1$-C$_6$)alkyl;

each $Z^{10}$ is independently selected from:
  i) halo, oxo, thioxo, (C$_2$-C$_6$)alkenyl, (C$_1$-C$_6$)haloalkyl, (C$_3$-C$_7$)cycloalkyl, (C$_3$-C$_7$)cycloalkyl-(C$_1$-C$_6$)alkyl-, —OH, —O(C$_1$-C$_6$)alkyl, —O(C$_1$-C$_6$)haloalkyl, —SH, —S(C$_1$-C$_6$)alkyl, —SO(C$_1$-C$_6$)alkyl, —SO$_2$(C$_1$-C$_6$)alkyl, —NH$_2$, —NH(C$_1$-C$_6$)alkyl and —N((C$_1$-C$_6$)alkyl)$_2$;
  ii) (C$_1$-C$_6$)alkyl optionally substituted with —OH, —O—(C$_1$-C$_6$)haloalkyl, or —O—(C$_1$-C$_6$)alkyl; and
  iii) aryl, heterocycle and heteroaryl, which aryl, heterocycle and heteroaryl is optionally substituted with halo, (C$_1$-C$_6$)alkyl or COOH;

each $Z^{11}$ is independently selected from $Z^{10}$, —C(=O)—NH$_2$, —C(=O)—NH(C$_1$-C$_4$)alkyl, —C(=O)—N((C$_1$-C$_4$)alkyl)$_2$, —C(=O)-aryl, —C(=O)-heterocycle and —C(=O)-heteroaryl;

each $Z^{12}$ is independently selected from —NO$_2$, =NOR$_a$, thioxo, -aryl, -heterocycle, -heteroaryl, —(C$_3$-C$_7$)halocarbocycle, —(C$_3$-C$_7$)carbocycle, —O(C$_3$-C$_7$)carbocycle, —Ohalo(C$_3$-C$_7$)carbocycle, —Oaryl, —Oheterocycle, —Oheteroaryl, —S(C$_1$-C$_6$)alkyl, —S(C$_3$-C$_7$)carbocycle, —Shalo(C$_3$-C$_7$)carbocycle, —Saryl, —Sheterocycle, —Sheteroaryl, —S(O)(C$_1$-C$_6$)alkyl, —S(O)(C$_3$-C$_7$)carbocycle, —S(O)halo(C$_3$-C$_7$)carbocycle, —S(O)aryl, —S(O)heterocycle, —S(O)heteroaryl, —SO$_2$(C$_1$-C$_6$)alkyl, —SO$_2$(C$_3$-C$_7$)carbocycle, —SO$_2$(C$_3$-C$_7$)halocarbocycle, SO$_2$aryl, —SO$_2$heterocycle, —SO$_2$heteroaryl, —NR$_a$R$_a$, —NR$_a$C(O)R$_b$, —C(O)NR$_c$R$_d$, —SO$_2$NR$_c$R$_d$, —NR$_a$SO$_2$NR-A$_d$, —NR$_a$SO$_2$O(C$_3$-C$_7$)carbocycle and —NR$_a$SO$_2$Oaryl;

each $Z^{13}$ is independently selected from —NO$_2$, —OH, =NOR$_a$, —SH, —CN, —(C$_3$-C$_7$)halocarbocycle, —O(C$_1$-C$_6$)alkyl, —O(C$_2$-C$_6$)alkenyl, —O(C$_2$-C$_6$)alkynyl, —O(C$_1$-C$_6$)haloalkyl, —O(C$_3$-C$_7$)carbocycle, —O(C$_3$-C$_7$)halocarbocycle, —Oaryl, —Oheteroaryl, -Oheterocycle, —S(C$_1$-C$_6$)alkyl, —S(C$_2$-C$_6$)alkenyl, —S(C$_2$-C$_6$)alkynyl, —S(C$_1$-C$_6$)haloalkyl, —S(C$_3$-C$_7$)carbocycle, —S(C$_3$-C$_7$)halocarbocycle, —Saryl, —Sheteroaryl, —Sheterocycle, —S(O)(C$_1$-C$_6$)alkyl, —S(O)(C$_2$-C$_6$)alkenyl, —S(O)(C$_2$-C$_6$)alkynyl, —S(O)(C$_1$-C$_6$)haloalkyl, —S(O)(C$_3$-C$_7$)carbocycle, —S(O)(C$_3$-C$_7$)halocarbocycle, —S(O)aryl, —S(O)heteroaryl, —S(O)heterocycle, —SO$_2$(C$_1$-C$_6$)alkyl, —SO$_2$(C$_2$-C$_6$)alkenyl, —SO$_2$(C$_2$-C$_6$)alkynyl, —SO$_2$(C$_1$-C$_6$)haloalkyl, —SO$_2$(C$_3$-C$_7$)carbocycle, —SO$_2$(C$_3$-C$_7$)halocarbocycle, —SO$_2$aryl, —SO$_2$heteroaryl, —SO$_2$heterocycle, —SO$_2$NR$_c$R$_d$, —NR$_c$R$_d$, —NR$_a$C(O)R$_a$, —NR$_a$C(O)OR$_b$, —NR$_a$C(O)NR$_c$R$_d$, —NR$_a$SO$_2$R$_b$, —NR$_a$SO$_2$NR$_c$R$_d$, —NR$_a$SO$_2$O(C$_3$-C$_7$)carbocycle, —NR$_a$SO$_2$Oaryl, —OS(O)$_2$R$_a$, —C(O)R$_a$, —C(O)OR$_b$, —C(O)NR$_c$R$_d$, and —OC(O)NR$_c$R$_d$, wherein any (C$_1$-C$_6$)alkyl, —(C$_1$-C$_6$)haloalkyl, (C$_2$-C$_6$)alkenyl, (C$_2$-C$_6$)alkynyl, —(C$_3$-C$_7$)halocarbocycle, (C$_3$-C$_7$)carbocycle, (C$_3$-C$_7$)halocarbocycle, aryl, heteroaryl and heterocycle of $Z^{13}$, either alone or as part of a group, is optionally substituted with one or more (e.g. 1, 2, 3, 4 or 5) halogen, —OH, —OR$_b$, —CN, —NR$_a$C(O)$_2$R$_b$, heteroaryl, heterocycle, —Oheteroaryl, —Oheterocycle, —NHheteroaryl, —NHheterocycle, or —S(O)$_2$NR$_c$R$_d$;

each $Z^{14}$ is independently selected from —NO$_2$, =NOR$_a$, —CN, —(C$_3$-C$_7$)halocarbocycle, —O(C$_3$-C$_7$)halocarbocycle, —S(C$_3$-C$_7$)halocarbocycle, —S(O)(C$_3$-C$_7$)halocarbocycle, —SO$_2$(C$_3$-C$_7$)halocarbocycle, —NR$_a$SO$_2$NR$_c$R$_d$, —NR$_a$SO$_2$O(C$_3$-C$_7$)halocarbocycle, —NR$_a$SO$_2$Oaryl and —OS(O)$_2$R$_a$, wherein any —(C$_3$-C$_7$)halocarbocycle of $Z^{14}$, either alone or as part of a group, is optionally substituted with one or more (e.g. 1, 2, 3, 4 or 5) halogen, —OH, —OR$_b$, —CN, —NR$_a$C(O)$_2$R$_b$, heteroaryl, heterocycle, -Oheteroaryl, —Oheterocycle, —NHheteroaryl, —NHheterocycle, or —S(O)$_2$NR$_c$R$_d$;

each R$_a$ is independently H, (C$_1$-C$_6$)alkyl, —(C$_2$-C$_6$)alkenyl, —(C$_2$-C$_6$)alkynyl, (C$_3$-C$_7$)carbocycle, heterocycle, aryl, aryl(C$_1$-C$_6$)alkyl-, heteroaryl or heteroaryl(C$_1$-C$_6$)alkyl-, wherein any (C$_1$-C$_6$)alkyl, (C$_2$-C$_6$)alkenyl, (C$_2$-C$_6$)alkynyl, (C$_3$-C$_7$)carbocycle, heterocycle, aryl or heteroaryl of R$_a$, either alone or as part of a group, is optionally substituted by one or more (e.g. 1, 2, 3, 4 or 5) halogen, OH and cyano;

each R$_b$ is independently —(C$_1$-C$_6$)alkyl, —(C$_2$-C$_6$)alkenyl, —(C$_2$-C$_6$)alkynyl, (C$_3$-C$_7$)carbocycle, heterocycle, aryl, aryl(C$_1$-C$_6$)alkyl-, heteroaryl or heteroaryl(C$_1$-C$_6$)alkyl-, wherein any (C$_1$-C$_6$)alkyl, —(C$_2$-C$_6$)alkenyl, —(C$_2$-C$_6$)alkynyl, (C$_3$-C$_7$)carbocycle, heterocycle, aryl or heteroaryl of R$_b$, either alone or as part of a group, is optionally substituted by one or more (e.g. 1, 2, 3, 4 or 5) halogen, OH and cyano;

R$_c$ and R$_d$ are each independently selected from H, (C$_1$-C$_6$)alkyl, (C$_2$-C$_6$)alkenyl, (C$_2$-C$_6$)alkynyl, (C$_3$-C$_7$)carbocycle, aryl, aryl(C$_1$-C$_6$)alkyl-, heterocycle, heteroaryl and heteroaryl(C$_1$-C$_6$)alkyl-, wherein any (C$_1$-C$_6$)alkyl, —(C$_2$-C$_6$)alkenyl, —(C$_2$-C$_6$)alkynyl, (C$_3$-C$_7$)carbocycle, heterocycle, aryl and heteroaryl of R$_c$ or R$_d$, either alone or as part of a group, is optionally substituted by one or more (e.g. 1, 2, 3, 4 or 5) halogen, OH and cyano; or R$_c$ and R$_d$ together with the nitrogen to which they are attached form a heterocycle, wherein any heterocycle of R$_c$ and R$_d$ together with the nitrogen to which they are attached is optionally substituted by one or more (e.g. 1, 2, 3, 4 or 5) halogen, OH or cyano;

each R$_e$ is independently selected from —OR$_a$, (C$_1$-C$_6$)alkyl and (C$_3$-C$_7$)carbocycle, wherein (C$_1$-C$_6$)alkyl and (C$_3$-C$_7$)carbocycle is substituted by one or more (e.g. 1, 2, 3, 4 or 5) $Z^6$ and optionally substituted with one or more (e.g. 1, 2, 3, 4 or 5) $Z^1$, —(C$_2$-C$_6$)haloalkyl, —(C$_2$-C$_6$)alkenyl and —(C$_2$-C$_6$)alkynyl, wherein any —(C$_2$-C$_6$)haloalkyl, —(C$_2$-C$_6$)alkenyl and —(C$_2$-C$_6$)alkynyl is optionally substituted with one or more (e.g. 1, 2, 3, 4 or 5) Z', and aryl, heterocycle and heteroaryl wherein aryl, heterocycle and heteroaryl is substituted by one or more (e.g. 1, 2, 3, 4 or 5) $Z^5$;

each R$_f$ is independently selected from —R$_g$, —OR$_a$, —(C$_1$-C$_6$)alkyl-$Z^6$, —SO$_2$R$_g$, —C(O)R$_g$, C(O)OR$_g$ and —C(O)NR$_e$R$_g$; and each R$_g$ is independently selected from H, —OR$_a$, (C$_1$-C$_6$)alkyl, (C$_3$-C$_7$)carbocycle, (C$_1$-C$_6$)haloalkyl, (C$_2$-C$_6$)alkenyl, (C$_2$-C$_6$)alkynyl, aryl, heterocycle and heteroaryl, wherein any (C$_1$-C$_6$)alkyl, (C$_3$-C$_7$)carbocycle, (C$_1$-C$_6$)haloalkyl, (C$_2$-C$_6$)alkenyl, (C$_2$-C$_6$)alkynyl, aryl, heterocycle and heteroaryl of R$_g$ is optionally substituted with one or more (e.g. 1, 2, 3, 4 or 5) $Z^1$ groups;

or a salt thereof.

The invention also provides a pharmaceutical composition comprising a compound of formula I or a pharmaceutically acceptable salt thereof, in combination with a pharmaceutically acceptable carrier.

The invention also provides method for treating (e.g. preventing, mediating or inhibiting) the proliferation of the HIV virus, treating AIDS or delaying the onset of AIDS or ARC symptoms in a mammal (e.g. a human), comprising administering a compound of formula I, or a pharmaceutically acceptable salt thereof, to the mammal.

The invention also provides a compound of formula I, or a pharmaceutically acceptable salt thereof for use in medical therapy (e.g. for use in treating (e.g. preventing, mediating or inhibiting) the proliferation of the HIV virus or AIDS or delaying the onset of AIDS or ARC symptoms in a mammal (e.g. a human)).

The invention also provides a compound of formula I, or a pharmaceutically acceptable salt thereof for use in the manufacture of a medicament for treating (e.g. preventing, mediating or inhibiting) the proliferation of the HIV virus or AIDS or delaying the onset of AIDS or ARC symptoms in a mammal (e.g. a human).

The invention also provides a compound of formula I, or a pharmaceutically acceptable salt thereof, for use in the prophylactic or therapeutic treatment (e.g. prevention, mediation or inhibiting) of the proliferation of the HIV virus or AIDS or for use in the therapeutic treatment of delaying the onset of AIDS or ARC symptoms.

The invention also provides processes and intermediates disclosed herein that are useful for preparing compounds of formula I or salts thereof.

DETAILED DESCRIPTION OF THE INVENTION

Definitions

Unless stated otherwise, the following terms and phrases as used herein are intended to have the following meanings:

When trade names are used herein, applicants intend to independently include the tradename product and the active pharmaceutical ingredient(s) of the tradename product.

"Alkyl" is hydrocarbon containing normal, secondary or tertiary atoms. For example, an alkyl group can have 1 to 20 carbon atoms (i.e, ($C_1$-$C_{20}$)alkyl), 1 to 10 carbon atoms (i.e., ($C_1$-$C_{10}$)alkyl), 1 to 8 carbon atoms (i.e., ($C_1$-$C_8$)alkyl)or 1 to 6 carbon atoms (i.e., ($C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$). "Alkyl" also refers to a saturated, branched or straight chain hydrocarbon radical having two monovalent radical centers derived by the removal of two hydrogen atoms from the same or two different carbon atoms of a parent alkane. For example, an alkyl group can have 1 to 10 carbon atoms (i.e., ($C_1$-$C_{10}$)alkyl), or 1 to 6 carbon atoms (i.e., ($C_1$-$C_6$)alkyl) or 1-3 carbon atoms (i.e., ($C_1$-$C_3$)alkyl). Typical alkyl radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

"Alkenyl" is a straight or branched hydrocarbon containing normal, secondary or tertiary carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 8 carbon atoms $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), alkyl (—$CH_2$CH=$CH_2$), cyclopentenyl (—$C_5H_7$), and 5-hexenyl (—$CH_2CH_2CH_2CH_2$CH=$CH_2$).

"Alkynyl" is a straight or branched hydrocarbon containing normal, secondary or tertiary carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

The term "halo" or "halogen" as used herein refers to fluoro, chloro, bromo and iodo.

The term "haloalkyl" as used herein refers to an alkyl as defined herein, wherein one or more hydrogen atoms are each replaced by a halo substituent. For example, a ($C_1$-$C_6$)haloalkyl is a ($C_1$-$C_6$)alkyl wherein one or more of the hydrogen atoms have been replaced by a halo substituent. Such a range includes one halo substituent on the alkyl group up to complete halogenation of the alkyl group.

The term "aryl" as used herein refers to a single aromatic ring or a bicyclic or multicyclic ring. For example, an aryl group can have 6 to 20 carbon atoms, 6 to 14 carbon atoms, or 6 to 12 carbon atoms. Aryl includes a phenyl radical or an ortho-fused bicyclic or multicyclic radical having about 9 to 14 atoms in which at least one ring is aromatic (e.g. an aryl fused to one or more aryl or carbocycle). Such bicyclic or multicyclic rings may be optionally substituted with one or more (e.g. 1, 2 or 3) oxo groups on any carbocycle portion of the bicyclic or multicyclic ring. It is to be understood that the point of attachment of a bicyclic or multicyclic radical, as defined above, can be at any position of the ring including an aryl or a carbocycle portion of the ring. Typical aryl groups include, but are not limited to, phenyl, indenyl, naphthyl, 1, 2, 3, 4-tetrahydronaphthyl, anthracenyl, and the like.

"Arylalkyl" refers to an alkyl radical as defined herein in which one of the hydrogen atoms bonded to a carbon atom is replaced with an aryl radical as described herein (i.e., an aryl-alkyl-moiety). The alkyl group of the "arylalkyl" is typically 1 to 6 carbon atoms (i.e. aryl($C_1$-$C_6$)alkyl). Arylalkyl groups include, but are not limited to, benzyl, 2-phenylethan-1-yl, 1-phenylpropan-1-yl, naphthylmethyl, 2-naphthylethan-1-yl and the like.

The term "heteroaryl" as used herein refers to a single aromatic ring or a multiple condensed ring. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2 or 3 rings) wherein a heteroaryl group, as defined above, can be fused with one or more heteroaryls (e.g. naphthyridinyl), carbocycles (e.g. 5,6,7,8-tetrahydroquinolyl) or aryls (e.g. indazolyl) to form a multiple condensed ring. Such multiple condensed rings may be optionally substituted with one or more (e.g. 1, 2 or 3) oxo groups on the carbocycle portions of the condensed ring. It is to be understood that the point of attachment of a heteroaryl multiple condensed ring, as defined above, can be at any position of the ring including a heteroaryl, aryl or a carbocycle portion of the ring. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thianaphthenyl.

The term "heterocyclyl" or "heterocycle" as used herein refers to a single saturated or partially unsaturated ring or a multiple condensed ring system. The term includes single saturated or partially unsaturated ring (e.g. 3, 4, 5, 6 or 7-membered ring) from about 1 to 6 carbon atoms and from about 1 to 3 heteroatoms selected from the group consisting of oxygen, nitrogen and sulfur in the ring. The ring may be substituted with one or more (e.g. 1, 2 or 3) oxo groups and the sulfur and nitrogen atoms may also be present in their oxidized forms. Such rings include but are not limited to azetidinyl, tetrahydrofuranyl or piperidinyl. The term also includes multiple condensed ring systems (e.g. ring systems comprising 2 or 3 rings) wherein a heterocycle group (as defined above) can be connected to two adjacent atoms (fused heterocycle) with one or more heterocycles (e.g. decahydronapthyridinyl), heteroaryls (e.g. 1,2,3,4-tetrahydronaphthyridinyl), carbocycles (e.g. decahydroquinolyl) or aryls. It is to be understood that the point of attachment of a heterocycle multiple condensed ring, as defined above, can be at any position of the ring including a heterocycle, heteroaryl, aryl or a carbocycle portion of the ring. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl and 1,4-benzodioxanyl.

The term "bridged-heterocycle" as used herein refers to a 4, 5, 6, 7 or 8-membered heterocycle as defined herein connected at two non-adjacent atoms of the 4, 5, 6, 7 or 8-membered heterocycle with one or more (e.g. 1 or 2) 3, 4, 5 or 6-membered heterocycles or a ($C_3$-$C_7$)carbocycles as defined herein. Such bridged-heterocycles include bicyclic and tricyclic ring systems (e.g. 2-azabicyclo[2.2.1]heptane and 4-azatricyclo[4.3.1.1$^{3,8}$]undecane).

The term "spiro-heterocycle" as used herein refers to a 3, 4, 5, 6, 7 or 8-membered heterocycle as defined herein connected to one or more (e.g. 1 or 2) single atoms of the 3, 4, 5, 6, 7 or 8-membered heterocycle with one or more (e.g. 1 or 2) 3, 4, 5, 6-membered heterocycles or a ($C_3$-$C_7$)carbocycles as defined herein. Such spiro-heterocycles include bicyclic and tricyclic ring systems (e.g. 1,4-dioxaspiro[4.5]dec-7-enyl).

The term "macroheterocycle" as used herein refers to a saturated or partially unsaturated 8, 9, 10, 11 or 12-membered ring comprising about 5 to 11 carbon atoms and about 1 to 3 heteroatoms selected from the group consisting of oxygen, nitrogen and sulfur in the ring which may be optionally fused at two adjacent atoms of the macroheterocycle to one or more (e.g. 1, 2 or 3) aryls, carbocycles, heteroaryls or heterocycles. The macroheterocycle may be substituted with one or more (e.g. 1, 2 or 3) oxo groups and the sulfur and nitrogen atoms may also be present in their oxidized forms.

"Heteroarylalkyl" refers to an alkyl radical as defined herein in which one of the hydrogen atoms bonded to a carbon atom is replaced with a heteroaryl radical as described herein (i.e., a heteroaryl-alkyl-moiety). The alkyl group of the "heteroarylalkyl" is typically 1 to 6 carbon atoms (i.e. heteroaryl ($C_1$-$C_6$)alkyl).

Heteroarylalkyl groups include, but are not limited to heteroaryl-$CH_2$—, heteroaryl-$CH(CH_3)$—, heteroaryl-$CH_2CH_2$—, 2-(heteroarypethan-1-yl, and the like, wherein the "heteroaryl" portion includes any of the heteroaryl groups described above. One skilled in the art will also understand that the heteroaryl group can be attached to the alkyl portion of the heteroarylalkyl by means of a carbon-carbon bond or a carbon-heteroatom bond, with the proviso that the resulting group is chemically stable. Examples of heteroarylalkyls include by way of example and not limitation 5-membered sulfur, oxygen, and/or nitrogen containing heteroaryls such as thiazolylmethyl, 2-thiazolylethan-1-yl, imidazolylmethyl, oxazolylmethyl, thiadiazolylmethyl, etc., 6-membered sulfur, oxygen, and/or nitrogen containing heteroaryls such pyridinylmethyl, pyridizylmethyl, pyrimidylmethyl, pyrazinylmethyl, etc.

"Heterocyclylalkyl" refers to an alkyl radical as defined herein in which one of the hydrogen atoms bonded to a carbon atom is replaced with a heterocyclyl radical as described herein (i.e., a heterocyclyl-alkyl-moiety). The alkyl group of the "heterocyclylalkyl" is typically 1 to 6 carbon atoms (i.e. heterocyclyl($C_1$-$C_6$)alkyl). Typical heterocyclylalkyl groups include, but are not limited to heterocyclyl-$CH_2$—, heterocyclyl-$CH(CH_3)$—, heterocyclyl-$CH_2CH_2$—, 2-(heterocyclypethari-1-yl, and the like, wherein the "heterocyclyl" portion includes any of the heterocyclyl groups described above. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. Examples of heterocyclylalkyls include by way of example and not limitation 5-membered sulfur, oxygen, and/or nitrogen containing heterocycles such tetrahydrofuranylmethyl and pyrroldinylmethyl, etc., and 6-membered sulfur, oxygen, and/or nitrogen containing heterocycles such as piperidinylmethyl, piperazinylmethyl, morpholinylmethyl, etc.

The term "carbocycle" or "carbocyclyl" refers to a saturated (i.e., cycloalkyl) or partially unsaturated (e.g. cycloalkenyl, cycloalkadienyl, etc.) ring having 3 to 7 carbon atoms as a monocycle or a multicyclic ring system. In one embodiment the carbocycle is a monocycle comprising 3-6 ring carbons (i.e. ($C_1$-$C_6$)carbocycle). Carbocycle includes multicyclic carbocycles have 7 to 12 carbon atoms as a bicycle, and up to about 20 carbon atoms as a polycycle provided that the largest single ring of a multicyclic carbocycle is 7 carbon atoms. The term "spiro-bicyclic carbocycle" refers to a carbocycle bicyclic ring system wherein the rings of the bicyclic ring system are connected to a single carbon atom (e.g. spiropentane, spiro[4,5]decane, spiro[4.5]decane, etc). The term "fused-bicyclic carbocycle" refers to a carbocycle bicyclic ring system wherein the rings of the bicyclic ring system are connected to two adjacent carbon atoms such as a bicyclo[4,5], [5,5], [5,6] or [6,6] system, or 9 or 10 ring atoms arranged as a bicyclo[5,6] or [6,6] system (e.g. decahydronaphthalene, norsabinane, norcarane). The term "bridged-bicyclic carbocycle" refers to a carbocycle bicyclic ring system wherein the rings of the bicyclic ring system are connected to two non-adjacent carbon atoms (e.g. norbornane, bicyclo[2.2.2] octane, etc). The "carbocycle" or "carbocyclyl" may be optionally substituted with one or more (e.g. 1, 2 or 3) oxo groups. Non-limiting examples of monocyclic carbocycles include cyclopropyl, cyclobutyl, cyclopentyl, 1-cyclopent-1- enyl, 1-cyclopent-2-enyl, 1-cyclopent-3-enyl, cyclohexyl, 1-cyclohex-1-enyl, 1-cyclohex-2-enyl and 1-cyclohex-3-enyl.

The term "halocarbocycle" as used herein refers to a carbocycle as defined herein, wherein one or more hydrogen atoms are each replaced by a halo substituent. For example, ($C_3$-$C_7$)halocarbocycle is a ($C_3$-$C_7$)carbocycle wherein one or more of the hydrogen atoms have been replaced by a halo substituent. Such a range includes one halo substituent on the carbocycle group to complete halogenation of the carbocycle group.

The term "macrocarbocycle" as used herein refers to a saturated or partially unsaturated 8, 9, 10, 11 or 12-membered ring comprising 8 to 12 carbon atoms which may be optionally fused at two adjacent atoms of the macrocarbocycle to one or more (e.g. 1, 2 or 3) aryls, carbocycles, heteroaryls or heterocycles. The macrocarbocycle may be substituted with one or more (e.g. 1, 2 or 3) oxo groups.

"Carbocyclylalkyl" refers to an alkyl radical as defined herein in which one of the hydrogen atoms bonded to a carbon atom is replaced with a carbocyclyl radical as described herein (i.e., a carbocyclyl-alkyl-moiety). The alkyl group of the "carbocyclylalkyl" is typically 1 to 6 carbon atoms (i.e. carbocyclyl($C_1$-$C_6$)alkyl). Typical carbocyclyl alkyl groups include, but are not limited to carbocyclyl-$CH_2$—, carbocyclyl-$CH(CH_3)$—, carbocyclyl-$CH_2CH_2$—, 2-(carbocyclyl)ethan-1-yl, and the like, wherein the "carbocyclyl" portion includes any of the carbocyclyl groups described above.

It is to be understood that when a variable is substituted, for example, as described by the phrase "($C_1$-$C_6$)alkyl, either alone or as part of a group, is optionally substituted", the phrase means that the variable ($C_1$-$C_6$)alkyl can be substituted when it is alone and that it can also be substituted when the variable "($C_1$-$C_6$)alkyl" is part of a larger group such as for example an aryl($C_1$-$C_6$)alkyl or a —($C_1$-$C_6$)alkyl-$SO_2$—($C_1$-$C_6$)alkyl-($C_3$-$C_7$)carbocycle group. Similarly, when stated, other variables (e.g. ($C_1$-$C_6$)alkenyl, ($C_1$-$C_6$)alkynyl, aryl, heteroaryl, heterocycle, etc....) can also be substituted "either alone or as part of a group."

It is to be understood that certain variables of formula I that connect two chemical groups may be oriented in either direction. Thus, for the X group of formula I (e.g. O, —C(O)—, —C(O)O—, —S—, —S(O)—, —$SO_2$—, —($C_1$-$C_6$)alkylO—, —($C_1$-$C_6$)alkylC(O)—, —($C_1$-$C_6$)alkylC(O)O—, —($C_1$-$C_6$)alkylS—, —($C_1$-$C_6$)alkylS(O)— and —($C_1$-$C_6$)alkyl$SO_2$—) certain values of X that are not symmetric can be oriented in either direction. For example, the —C(O)O—, can be oriented as either —C(O)O— or —OC(O)—, relative to the groups it connects.

It is to be understood that the nitrogen that is included in the core of the compound of formula I can be present in an oxidized form. For example, the quinoline nitrogen of either $G^1$ or $G^2$ of formula I can be an N-oxide. Accordingly, the invention includes a compound of formula I (as defined in the summary of the invention) or a salt or N-oxide thereof.

One skilled in the art will recognize that substituents and other moieties of the compounds of formula I should be selected in order to provide a compound which is sufficiently stable to provide a pharmaceutically useful compound which can be formulated into an acceptably stable pharmaceutical composition. Compounds of formula I which have such stability are contemplated as falling within the scope of the present invention.

The modifier "about" used in connection with a quantity is inclusive of the stated value and has the meaning dictated by the context (e.g., includes the degree of error associated with measurement of the particular quantity).

The term "chiral" refers to molecules which have the property of non-superimposability of the mirror image partner, while the term "achiral" refers to molecules which are superimposable on their mirror image partner. The term "stereoisomers" refers to compounds which have identical chemical constitution, but differ with regard to the arrangement of the atoms or groups in space.

"Diastereomer" refers to a stereoisomer with two or more centers or axes of chirality and whose molecules are not mirror images of one another. Diastereomers typically have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Certain compounds of the invention can exist as atropisomers. For example, it has been discovered that atropisomers exist for certain substituents at the $R^4$ position of formula I as marked by an asterisk in the formula below.

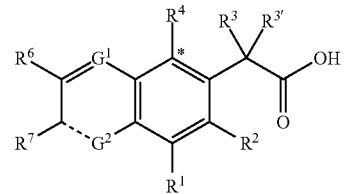

The chirality that results from the atropisomers at the asterisk position is a feature of certain compounds of the invention. Accordingly, the invention includes all atropisomers of compounds of the invention including mixtures of atropisomers and well as mixtures that are enriched in an atropisomer as well as single atropisomers, which mixtures or compounds possess the useful properties described herein.

In one embodiment, the compounds of the invention of formula I are at least 60% a single atropisomer for the $R^4$ substituent at the asterisk position. In another embodiment, the compounds of the invention of formula I are at least 70% a single atropisomer for the $R^4$ substituent at the asterisk position. In another embodiment, the compounds of the invention of formula I are at least 80% a single atropisomer for the $R^4$ substituent at the asterisk position. In another embodiment, the compounds of the invention of formula I are at least 90% a single atropisomer for the $R^4$ substituent at the asterisk position. In another embodiment, the compounds of the invention of formula I are at least 95% a single atropisomer for the $R^4$ substituent at the asterisk position. In one embodiment the stereochemistry for the $R^4$ substituent at the carbon marked with an asterisk as shown above for Formula I is the (R) stereochemistry. In another embodiment the stereochemistry for the $R^4$ substituent at the carbon marked with an asterisk as shown above for Formula I is the (S) stereochemistry.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

Many organic compounds exist in optically active forms, i.e., they have the ability to rotate the plane of plane-polarized light. In describing an optically active compound, the prefixes (D and L) or (R and S) are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. PGs do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free deprotected groups is dependent upon the intended direction of the synthesis and the reaction conditions to be encountered, and may occur in any order as determined by the artisan.

Various functional groups of the compounds of the invention may be protected. For example, protecting groups for OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether-nor ester-forming groups, as will be understood by those skilled in the art, and are included with amides, discussed below.

A very large number of hydroxylprotecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below.

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

Examples of pharmaceutically acceptable salts of the compounds of the invention include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a hydrogen atom or an amino group include for example salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, hydrobromic, sulfuric, phosphoric and sulfamic acids. Pharmaceutically acceptable salts of a compound of a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will typically be pharmaceutically acceptable, i.e. they will be salts derived from a physiologically acceptable acid or base. However, salts of acids or bases which are not pharmaceutically acceptable may also find use, for example, in the preparation or purification of a compound of formula I or another compound of the invention. All salts, whether or not derived from a physiologically acceptable acid or base, are within the scope of the present invention.

Metal salts typically are prepared by reacting the metal hydroxide with a compound of this invention. Examples of metal salts which are prepared in this way are salts containing $Li^+$, $Na^+$ and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the natural or unnatural amino acids are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Specific values listed below for radicals, substituents, and ranges in the embodiments of the invention are for illustration only; they do not exclude other defined values or other values within defined ranges for the radicals and substituents.

Isotopes

It is understood by one skilled in the art that this invention also includes any compound claimed that may be enriched at any or all atoms above naturally occurring isotopic ratios with one or more isotopes such as, but not limited to, deuterium ($^2H$ or D). As a non-limiting example, a —$CH_3$ group may be substituted with —$CD_3$.

Compounds of formula I.

A specific group of compounds of formula I are compounds of formula Ia.

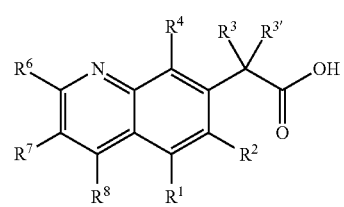

Ia

Another specific group of compounds of formula I are compounds of formula Ib.

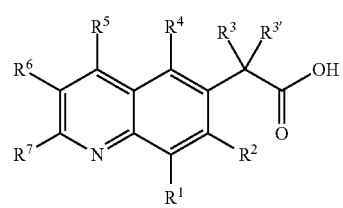

Ib

Another specific group of compounds of formula I are compounds of formula Ic.

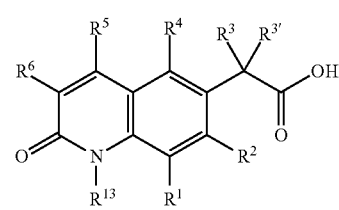

Ic

Another specific group of compounds of formula I are compounds of formula Id.

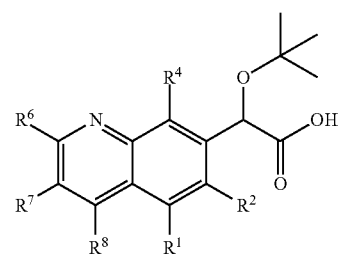

Id

Another specific group of compounds of formula I are compounds of formula Ie.

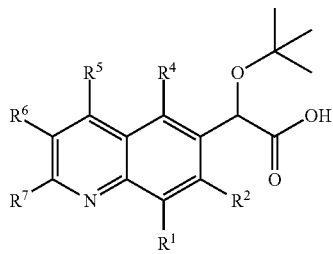

Ie

Another specific group of compounds of formula I are compounds of formula If.

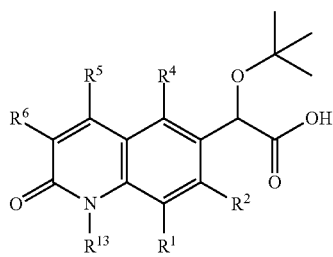

If

Another specific group of compounds of formula I are compounds of formula Ig.

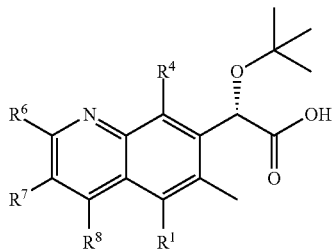

Ig

Another specific group of compounds of formula I are compounds of formula Ih.

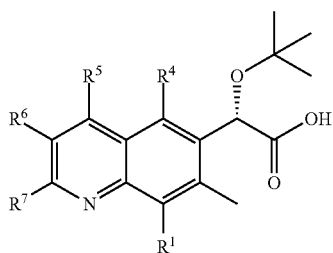

Ih

Another specific group of compounds of formula I are compounds of formula Ii.

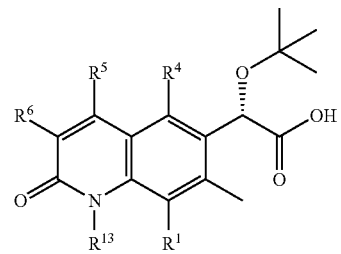

Ii

Another specific group of compounds of formula I are compounds of formula Ij.

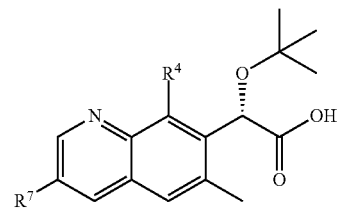

Ij

Another specific group of compounds of formula I are compounds of formula Ik.

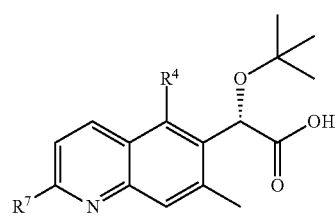

Ik

Another specific group of compounds of formula I are compounds of formula Im.

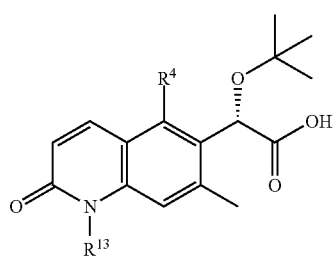

Im

Another specific group of compounds of formula I are compounds of formula In.

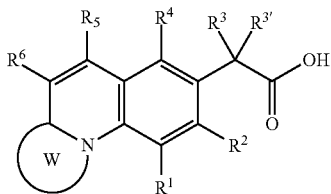

In wherein the ring W is heteroaryl optionally substituted with one or more (e.g. 1, 2, 3, 4 or 5) $Z^1$ groups.

Another specific group of compounds of formula I are compounds of formula In.

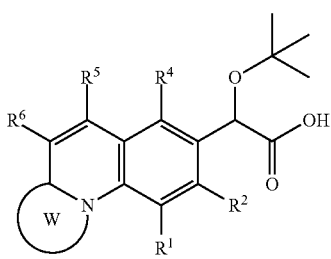

Io wherein the ring W is heteroaryl optionally substituted with one or more (e.g. 1, 2, 3, 4 or 5) $Z^1$ groups.

Another specific group of compounds of formula I are compounds of formula Ip.

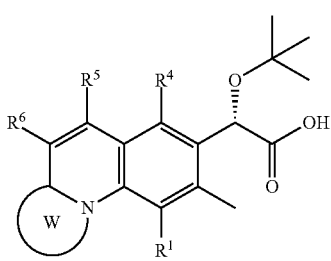

Ip wherein the ring W is heteroaryl optionally substituted with one or more (e.g. 1, 2, 3, 4 or 5) $Z^1$ groups.

Another specific group of compounds of formula I are compounds of formula Iq.

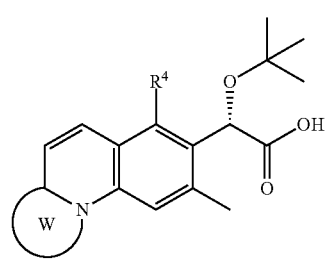

Iq wherein the ring W is heteroaryl optionally substituted with one or more (e.g. 1, 2, 3, 4 or 5) $Z^1$ groups.

Another specific group of compounds of formula I are compounds of formula Ir.

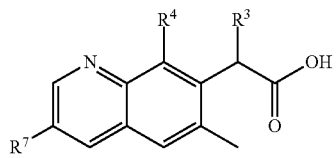

Ir

Another specific group of compounds of formula I are compounds of formula Is.

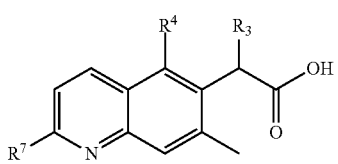

Is

Another specific group of compounds of formula I are compounds of formula It.

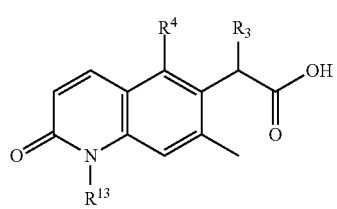

It

Another specific group of compounds of formula I are compounds of formula Iu.

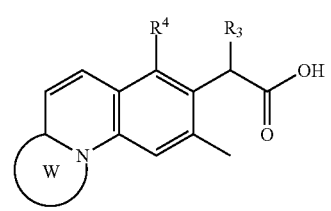

Iu wherein the ring W is heteroaryl optionally substituted with one or more (e.g. 1, 2, 3, 4 or 5) $Z^1$ groups.

Specific values listed below are values for compounds of formula I as well as the compounds of formula Ia, Ib, Ic, Id, Ie, If, Ig, Ih, Ii, Ij, Ik, Im, In, Io, Ip, Iq, Ir, Is, It and Iu.

A specific group of compounds of formula I are compounds wherein at least one of $R^1$, $R^2$, $R^3$, $R^{3'}$, $R^4$, $R^5$, $R^6$, $R^7$, $R^8$ or $R^{13}$ is selected from $R^{1b}$, $R^{2b}$, $R^{3b}$, $R^{3b'}$, $R^{4b}$, $R^{5b}$, $R^{6b}$, $R^{7b}$, $R^{8b}$ and $R^{13b}$.

Another specific group of compounds of formula I are compounds wherein at least two of $R^1$, $R^2$, $R^3$, $R^{3'}$, $R^4$, $R^5$, $R^6$, $R^7$, $R^8$ or $R^{13}$ is selected from $R^{1b}$, $R^{2b}$, $R^{3b}$, $R^{3b'}$, $R^{4b}$, $R^{5b}$, $R^{6b}$, $R^{7b}$, $R^{8b}$ or $R^{13b}$.

Another specific group of compounds of formula I are compounds wherein at least three of $R^1$, $R^2$, $R^3$, $R^{3'}$, $R^4$, $R^5$, $R^6$, $R^7$, $R^8$ or $R^{13}$ is selected from $R^{1b}$, $R^{2b}$, $R^{3b}$, $R^{3b'}$, $R^{4b}$, $R^{5b}$, $R^{6b}$, $R^{7b}$, $R^{8b}$ or $R^{13b}$.

Another specific group of compounds of formula I are compounds wherein at least four of $R^1$, $R^2$, $R^3$, $R^{3'}$, $R^4$, $R^5$, $R^6$, $R^7$, $R^8$ or $R^{13}$ is selected from $R^{1b}$, $R^{2b}$, $R^{3b}$, $R^{3b'}$, $R^{4b}$, $R^{5b}$, $R^{6b}$, $R^{7b}$, $R^{8b}$ or $R^{13b}$.

Another specific group of compounds of formula I are compounds wherein at least five of $R^1$, $R^2$, $R^3$, $R^{3'}$, $R^4$, $R^5$, $R^6$, $R^7$, $R^8$ or $R^{13}$ is selected from $R^{1b}$, $R^{2b}$, $R^{3b}$, $R^{3b'}$, $R^{4b}$, $R^{5b}$, $R^{6b}$, $R^{7b}$, $R^{8b}$ or $R^{13b}$.

Another specific group of compounds of formula I are compounds wherein at least six of $R^1$, $R^2$, $R^3$, $R^{3'}$, $R^4$, $R^5$, $R^6$, $R^7$, $R^8$ or $R^{13}$ is selected from $R^{1b}$, $R^{2b}$, $R^{3b}$, $R^{3b'}$, $R^{4b}$, $R^{5b}$, $R^{6b}$, $R^{7b}$, $R^{8b}$ or $R^{13b}$.

Another specific group of compounds of formula I are compounds wherein at least seven of $R^1$, $R^2$, $R^3$, $R^{3'}$, $R^4$, $R^5$, $R^6$, $R^7$, $R^8$ or $R^{13}$ is selected from $R^{1b}$, $R^{2b}$, $R^{3b}$, $R^{3b'}$, $R^{4b}$, $R^{5b}$, $R^{6b}$, $R^{7b}$, $R^{8b}$ or $R^{13b}$.

Another specific group of compounds of formula I are compounds wherein at least eight of $R^1$, $R^2$, $R^3$, $R^{3'}$, $R^4$, $R^5$, $R^6$, $R^7$, $R^8$ or $R^{13}$ is selected from $R^{1b}$, $R^{2b}$, $R^{3b}$, $R^{3b'}$, $R^{4b}$, $R^{5b}$, $R^{6b}$, $R^{7b}$, $R^{8b}$ or $R^{13b}$.

Another specific group of compounds of formula I are compounds wherein at least nine of $R^1$, $R^2$, $R^3$, $R^{3'}$, $R^4$, $R^5$, $R^6$, $R^7$, $R^8$ or $R^{13}$ is selected from $R^{1b}$, $R^{2b}$, $R^{3b}$, $R^{3b'}$, $R^{4b}$, $R^{5b}$, $R^{6b}$, $R^{7b}$, $R^{8b}$ or $R^{13b}$.

Another specific group of compounds of formula I are compounds wherein $R^1$, $R^2$, $R^3$, $R^{3'}$, $R^4$, $R^5$, $R^6$, $R^7$, $R^8$ and $R^{13}$ is selected from $R^{1b}$, $R^{2b}$, $R^{3b}$, $R^{3b'}$, $R^{4b}$, $R^{5b}$, $R^{6b}$, $R^7$, $R^{8b}$ and $R^{13b}$.

A specific value for $R^3$ is $R^{3b}$.

A specific value for $R^{3b}$ is —$OC(CH_3)_2CH_2OH$, —$OC(CH_3)_2CH_2OH$, —$O(C_1-C_6)alkyl-O—C(O)—NH_2$, —$O(C_1-C_6)alkyl-O—C(O)—N(CH_3)_2$ or —$O(C_1-C_6)alkyl-O—C(O)—NH(phenyl)$.

Another specific value for $R^{3b}$ is —$(C_1-C_6)alkylOH$ or —$O(C_1-C_6)alkyl-O—C(O)—NR_cIt_d$.

Another specific value for $R^3$ is $R^{3a}$.

A specific value for $R^{3a}$ is $(C_1-C_6)alkyl$, $(C_2-C_6)alkenyl$ or —$O(C_1-C_6)alkyl$, wherein any $(C_1-C_6)alkyl$ or $(C_2-C_6)alkenyl$ of $R^{3a}$ is optionally substituted with one or more groups selected from —$O(C_1-C_6)alkyl$, halo, oxo and —CN.

Another specific value for $R^{3a}$ is —$OC(CH_3)$.

A specific value for $R^{3'}$ is $R^{3b'}$.

A specific value for $R^{3b'}$ is $(C_1-C_6)alkyl$ or —$O(C_1-C_6)alkyl$.

A specific value for $R^{3'}$ is $R^{3a'}$.

A specific value for $R^{3a'}$ is H.

A specific group of compounds of formula I are compounds wherein $R^{3b}$ and $R^{3b'}$ together with the carbon to which they are attached form a $(C_3-C_7)$carbocycle or heterocycle, wherein the $(C_3-C_7)$carbocycle or heterocycle is optionally substituted with one or more $Z^1$ groups.

Another specific group of compounds of formula I are compounds wherein $R^{3b}$ and $R^{3b'}$ together with the carbon to which they are attached form a $(C_3-C_7)$carbocycle or a 4, 5 or 6-membered heterocycle, wherein the $(C_3-C_6)$carbocycle or the 4, 5 or 6-membered heterocycle is optionally substituted with one or more $Z^1$ groups.

Another specific group of compounds of formula I are compounds wherein Rab and $R^{3b'}$ together with the carbon to which they are attached form a $(C_4-C_6)$carbocycle or a 5 or 6-membered heterocycle, wherein the $(C_4-C_6)$carbocycle or the 5 or 6-membered heterocycle is optionally substituted with one or more $Z^1$ groups.

Another specific group of compounds of formula I are compounds wherein Rab and $R^{3b'}$ together with the carbon to which they are attached form a 5 or 6-membered heterocycle, wherein the 5 or 6-membered heterocycle is optionally substituted with one or more $Z^1$ groups.

Another specific group of compounds of formula I are compounds wherein $R^{3b}$ and $R^{3b'}$ together with the carbon to which they are attached form a tetrahydropyran or tetrahydrofuran optionally substituted with one or more $Z^1$ groups.

Another specific group of compounds of formula I are compounds wherein Rab and $R^{3b'}$ together with the carbon to which they are attached form:

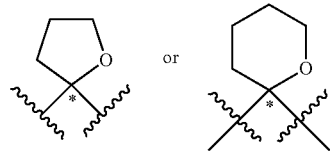 [SMILES: *C1(*)CCCO1 ; *C1(*)CCCCO1]

each of which is optionally substituted with one or more $Z^1$ groups, and wherein "*" denotes the point of attachment to the carbon of the compound of formula I.

A specific value for $R^4$ is $R^{4b}$.

A specific value for $R^{4b}$ is $(C_1-C_6)alkyl$, $(C_2-C_6)alkenyl$ or $(C_2-C_6)alkynyl$, wherein $(C_1-C_6)alkyl$, $(C_2-C_6)alkenyl$ or $(C_2-C_6)alkynyl$ are each optionally substituted with one or more $Z^1$ groups.

Another specific value for $R^{4b}$ is:

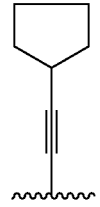 [SMILES: *C#CC1CCCC1]

optionally substituted with one or more $Z^1$ groups.

Another specific value for $R^{4b}$ is $(C_3-C_7)$carbocycle, wherein $(C_3-C_7)$carbocycle is optionally substituted with one or more $Z^1$ groups, or wherein two $Z^1$ groups together with the atom or atoms to which they are attached optionally form a $(C_3-C_6)$carbocycle or 5-6-membered heterocycle.

Another specific value for $R^{4b}$ is:

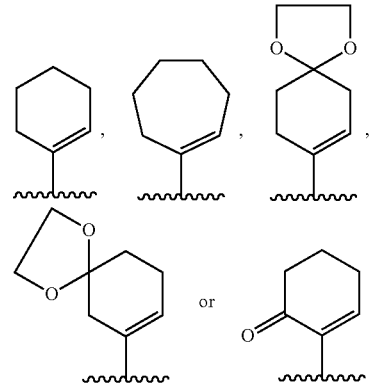

each of which is optionally substituted with one or more $Z^1$ groups.

Another specific value for $R^{4b}$ is aryl, heterocycle or heteroaryl, wherein aryl, heterocycle or heteroaryl are each independently substituted with one or more $Z^7$ groups and optionally substituted with one or more $Z^1$ groups.
Another specific value for $R^{4b}$ is:
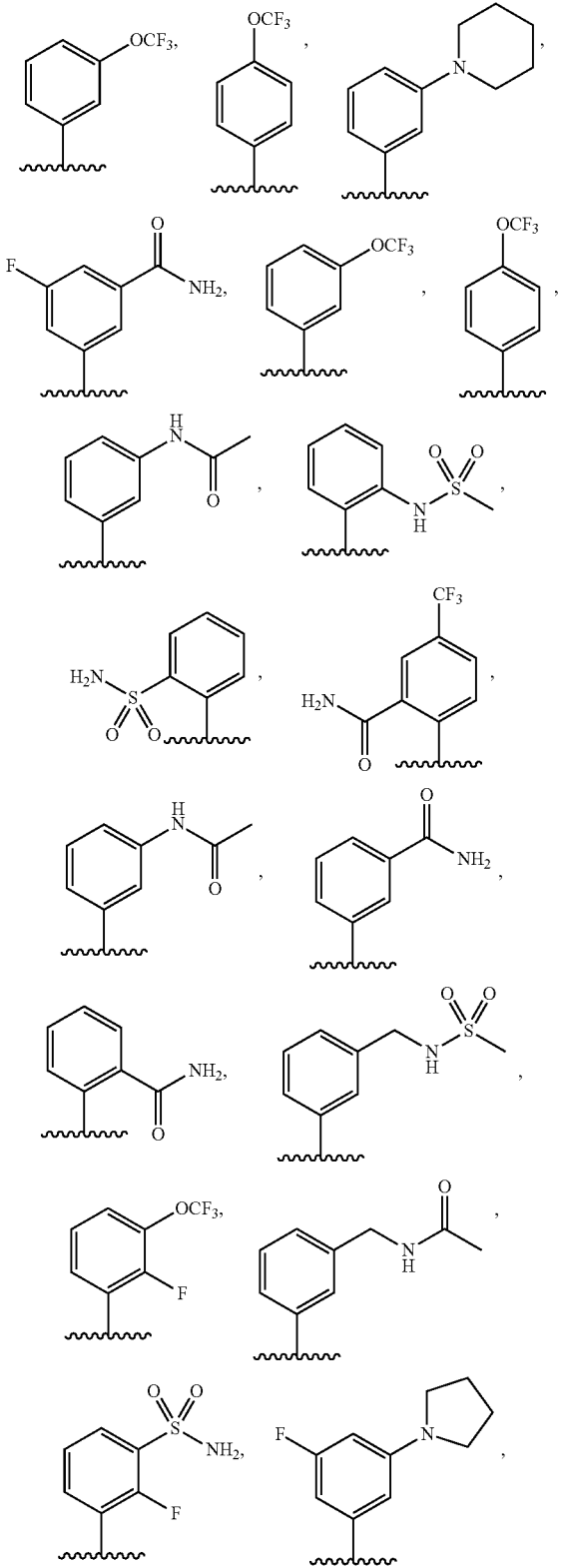
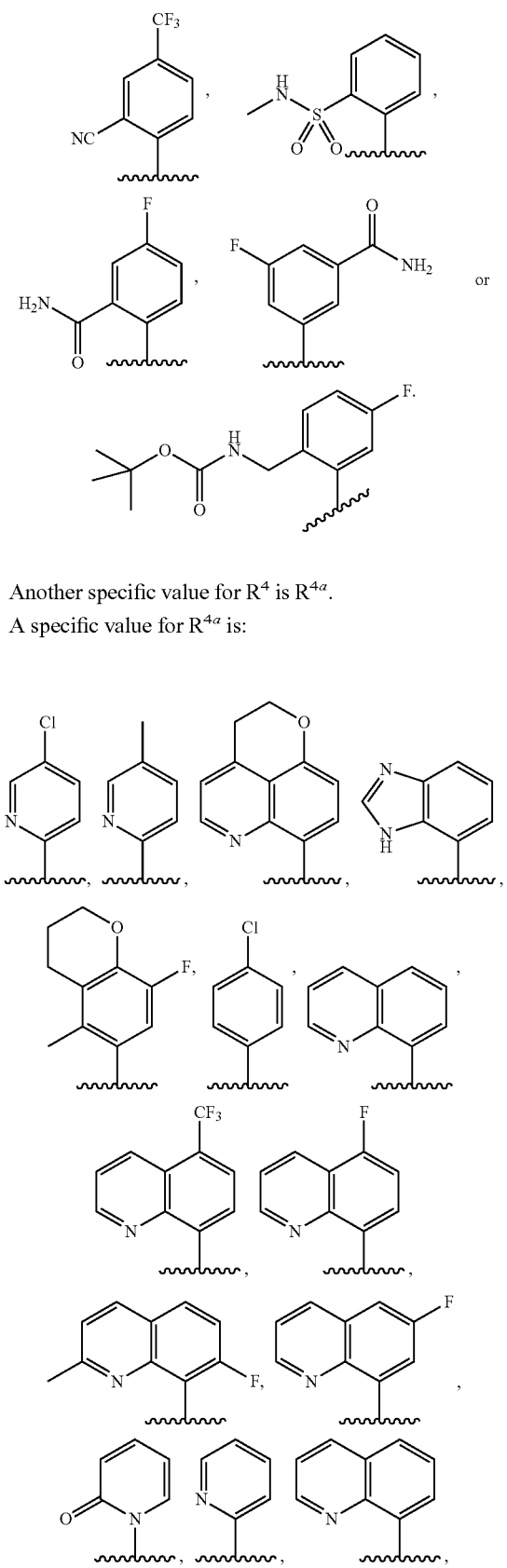
Another specific value for $R^4$ is $R^{4a}$.
A specific value for $R^{4a}$ is:

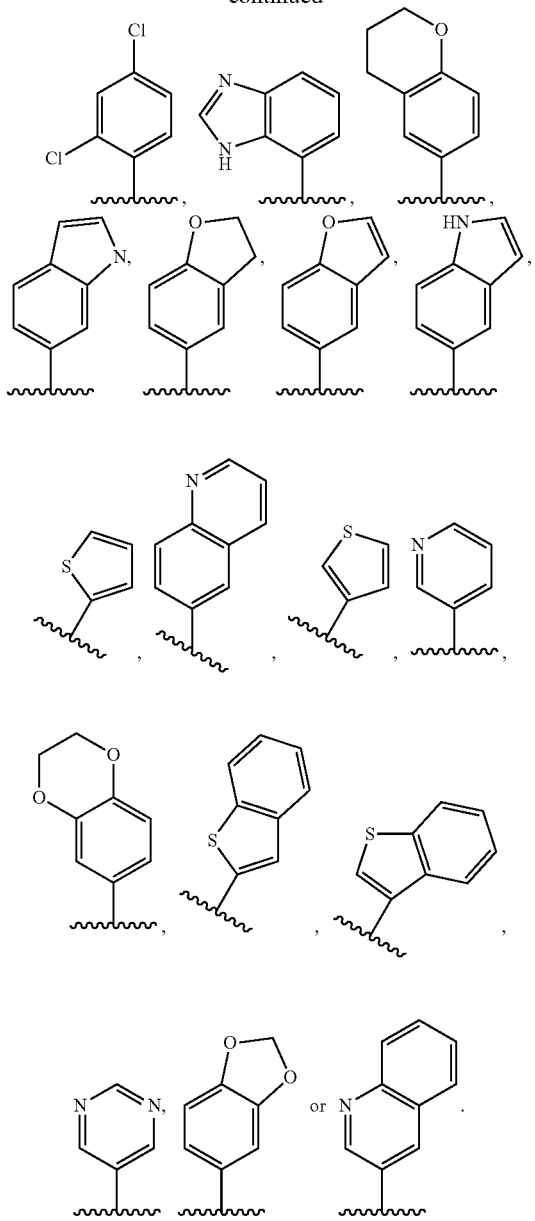

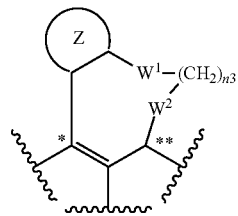

wherein:
Z is aryl, heteroaryl or $(C_3-C_6)$carbocycle;
n3 is 2, 3 or 4;
$W^1$ and $W^2$ are each independently O, NH or $CH_2$; and
wherein "*" denotes the $R^4$ point of attachment of the macroheterocycle or macrocarbocycle to the compound of formula I and "**" denotes the $R^3$ point of attachment of the macroheterocycle or macrocarbocycle to the compound of formula I, and wherein the macroheterocycle or a macrocarbocycle is optionally substituted with one or more $Z^1$ groups.

Another specific group of compounds of formula I are compounds wherein, $R^4$ and $R^3$ together with the atoms to which they are attached form the macroheterocycle:

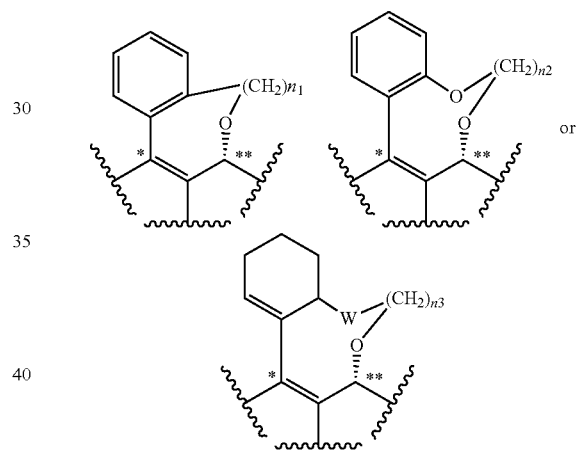

wherein:
n1 is 3 or 4; n2 is 2, 3 or 4; n3 is 2, 3 or 4; W is O, NH or $N(C_1-C_4)$alkyl; and wherein "*" denotes the $R^4$ point of attachment of the macroheterocycle to the compound of formula I and "**" denotes the $R^3$ point of attachment of the macroheterocycle to the compound of formula I; and wherein the macroheterocycle or a macrocarbocycle is optionally substituted with one or more $Z^1$ groups.

A specific value for $R^1$ is $R^{1b}$.
Another specific value $R^1$ is $R^{1a}$.
A specific value for $R^{1a}$ is H or halo.
A specific value for $R^2$ is $R^{2b}$.
Another specific value $R^2$ is $R^{2a}$.
A specific value for $R^{2a}$ is H, halo or —$CH_3$.
Another specific value for $R^{2a}$ is —Cl.
A specific value for $R^5$ is $R^{5b}$.
Another specific value for $R^5$ is $R^{5a}$.
A specific value for $R^{5a}$ is H.
A specific value for $R^6$ is $R^{6b}$.
Another specific value for $R^6$ is $R^{6a}$.
A specific value for $R^{6a}$ is H.
A specific value for $R^7$ is $R^{6b}$.
Another specific value for $R^7$ is $1e^a$.

A specific group of compounds of formula I are compounds wherein $R^4$ and $R^3$ together with the atoms to which they are attached form a macroheterocycle or a macrocarbocycle, wherein any macroheterocycle or macrocarbocycle of $R^4$ and $R^3$ together with the atoms to which they are attached may be optionally substituted with one or more $Z^1$ groups; and $R^{3'}$ is H, $(C_1-C_6)$alkyl or —$O(C_1-C_6)$alkyl.

Another specific group of compounds of formula I are compounds wherein $R^4$ and $R^3$ together with the atoms to which they are attached form a macroheterocycle or a macrocarbocycle, wherein any macroheterocycle or macrocarbocycle of $R^4$ and $R^3$ together with the atoms to which they are attached may be optionally substituted with one or more $Z^1$ groups; and $R^{3'}$ is H.

Another specific group of compounds of formula I are compounds wherein $R^4$ and $R^3$ together with the atoms to which they are attached form the macroheterocycle or a macrocarbocycle which is further fused to a Z group;

A specific value for $R^{7a}$ is H, —$CH_3$, $CF_3$ or halogen.
A specific value for $R^8$ is $R^{8b}$.
Another specific value for $R^8$ is $R^{8a}$.
Another specific value for $R^{8a}$ is H.
A specific group of compounds of formula I are compounds wherein $R^{ob}$ is selected from:
  a) $(C_1-C_6)$alkyl, $(C_2-C_6)$alkenyl and $(C_2-C_6)$alkynyl, wherein $(C_1-C_6)$alkyl, $(C_2-C_6)$alkenyl and $(C_2-C_6)$alkynyl are each optionally substituted with one or more (e.g. 1, 2, 3, 4 or 5) $Z^1$ groups;
  b) $(C_3-C_{14})$carbocycle, wherein $(C_3-C_{14})$carbocycle is optionally substituted with one or more (e.g. 1, 2, 3, 4 or 5) $Z^1$ groups;
  c) Spiro-heterocycle and bridged-heterocycle, wherein spiro-heterocycle and bridged-heterocycle is optionally substituted with one or more (e.g. 1, 2, 3, 4 or 5) $Z^1$ groups; and
  d) aryl, heterocycle and heteroaryl, wherein aryl, heterocycle and heteroaryl are each independently substituted with one or more $Z^7$ groups and optionally substituted with one or more (e.g. 1, 2, 3, 4 or 5) $Z^1$ groups.

Another specific group of compounds of formula I are compounds wherein Rob is selected from:
  a) $(C_1-C_6)$alkyl, $(C_2-C_6)$alkenyl and $(C_2-C_6)$alkynyl, wherein $(C_1-C_6)$alkyl, $(C_2-C_6)$alkenyl and $(C_2-C_6)$alkynyl are each optionally substituted with one or more (e.g. 1, 2, 3, 4 or 5) $Z^1$ groups;
  b) $(C_3-C_{14})$carbocycle, wherein $(C_3-C_{14})$carbocycle is optionally substituted with one or more (e.g. 1, 2, 3, 4 or 5) $Z^1$ groups, wherein two $Z^1$ groups together with the atom or atoms to which they are attached optionally form a $(C_3-C_7)$ carbocycle or heterocycle; and
  c) aryl, heterocycle and heteroaryl, wherein aryl, heterocycle and heteroaryl are each independently substituted with one or more $Z^7$ groups and optionally substituted with one or more (e.g. 1, 2, 3, 4 or 5) $Z^1$ groups.

Another specific group of compounds of formula I are compounds wherein Rob is selected from:
  a) $(C_1-C_6)$alkyl, $(C_2-C_6)$alkenyl and $(C_2-C_6)$alkynyl, wherein $(C_1-C_6)$alkyl, $(C_2-C_6)$alkenyl and $(C_2-C_6)$alkynyl are each optionally substituted with one or more (e.g. 1, 2, 3, 4 or 5) $Z^1$ groups;
  b) $(C_3-C_{14})$carbocycle, wherein $(C_3-C_{14})$carbocycle is optionally substituted with one or more (e.g. 1, 2, 3, 4 or 5) $Z^1$ groups; and
  c) aryl, heterocycle and heteroaryl, wherein aryl, heterocycle and heteroaryl are each independently substituted with one or more $Z^7$ groups and optionally substituted with one or more (e.g. 1, 2, 3, 4 or 5) $Z^1$ groups.

Another specific group of compounds of formula I are compounds wherein $R^3$ is $(C_1-C_6)$alkyl, $(C_2-C_6)$alkenyl or —$O(C_1-C_6)$alkyl, wherein any $(C_1-C_6)$alkyl or $(C_2-C_6)$alkenyl of $R^3$ is optionally substituted with one or more groups selected from —$O(C_1-C_6)$alkyl, halo, oxo and CN, and wherein $R^{3'}$ is H.

Another specific value for $R^3$ is —$O(C_1-C_6)$alkyl.
Another specific value for $R^3$ is —OtBu.
Another specific value for $R^{3'}$ is H.
Another specific value for $R^2$ is halo, H or —$CH_3$.
Another specific value for $R^2$ is chloro or —$CH_3$.
Another specific value for $R^2$ is —$CH_3$.
Another specific value for $R^1$ is H.
Another specific value for $R^6$ is H.
Another specific value for $R^5$ is H or $(C_1-C_6)$alkyl.
Another specific value for $R^5$ is H or —$CH_3$.
Another specific value for $R^5$ is H.
Another specific group of compounds of formula I are compounds wherein $R^4$ is selected from:
  a) aryl, heterocycle and heteroaryl, wherein aryl, heterocycle and heteroaryl are each optionally substituted with one or more groups each independently selected from halo, $(C_1-C_6)$alkyl, $(C_2-C_6)$alkenyl, $(C_1-C_6)$haloalkyl, $(C_3-C_7)$cycloalkyl, —OH, —$O(C_1-C_6)$alkyl, —SH, —$S(C_1-C_6)$alkyl, —$NH(C_1-C_6)$alkyl and —$N((C_1-C_6)alk_y1)_2$, wherein $(C_1-C_6)$alkyl is optionally substituted with hydroxy, —$O(C_1-C_6)$alkyl, cyano or oxo; and
  b) $(C_3-C_{14})$carbocycle, wherein $(C_3-C_{14})$carbocycle is optionally substituted with one or more $Z^1$ groups, wherein two $Z^1$ groups together with the atom or atoms to which they are attached optionally form a $(C_3-C_7)$carbocycle or heterocycle; and
  c) aryl, heteroaryl, spiro-heterocycle, fused-heterocycle and bridged-heterocycle, wherein aryl, heteroaryl, spiro-heterocycle, fused-heterocycle and bridged-heterocycle are each independently substituted with one or more $Z^7$ groups and optionally substituted with one or more $Z^1$ groups.

Another specific group of compounds of formula I are compounds wherein $R^4$ is selected from:
  a) aryl, heterocycle and heteroaryl, wherein aryl, heterocycle and heteroaryl are each optionally substituted with one or more groups each independently selected from halo, $(C_1-C_6)$alkyl, $(C_2-C_6)$alkenyl, $(C_1-C_6)$haloalkyl, $(C_3-C_7)$cycloalkyl, —OH, —$O(C_1-C_6)$alkyl, —SH, —$S(C_1-C_6)$alkyl, —$NH_2$, —$NH(C_1-C_6)$alkyl and —$N((C_1-C_6)alic_y1)_2$, wherein $(C_1-C_6)$alkyl is optionally substituted with hydroxy, —$O(C_1-C_6)$alkyl, cyano or oxo;
  b) aryl, heteroaryl, spiro-heterocycle, fused-heterocycle and bridged-heterocycle, wherein spiro-heterocycle, fused-heterocycle and bridged-heterocycle are each independently substituted with one or more $Z^7$ groups and optionally substituted with one or more $Z^1$ groups.

Another specific group of compounds of formula I are compounds wherein $R^4$ is selected from:
  a) aryl, heterocycle and heteroaryl, wherein aryl, heterocycle and heteroaryl are each optionally substituted with one or more groups each independently selected from halo, $(C_1-C_6)$alkyl, $(C_2-C_6)$alkenyl, $(C_1-C_6)$haloalkyl, $(C_3-C_7)$cycloalkyl, —OH, —$O(C_1-C_6)$alkyl, —SH, —$S(C_1-C_6)$alkyl, —$NH_2$, —$NH(C_1-C_6)$alkyl and —$N((C_1-C_6)$alkyl$)_2$, wherein $(C_1-C_6)$alkyl is optionally substituted with hydroxy, —$O(C_1-C_6)$alkyl, cyano or oxo; and
  b) aryl, heteroaryl and fused-heterocycle, wherein aryl, heteroaryl and fused-heterocycle are each independently substituted with one or more $Z^7$ groups and optionally substituted with one or more $Z^1$ groups.

Another specific group of compounds of formula I are compounds wherein $R^4$ is selected from:
  a) heterocycle, wherein heterocycle is optionally substituted with one or more groups each independently selected from halo, $(C_1-C_6)$alkyl, $(C_2-C_6)$alkenyl, $(C_r\,C_6)$haloalkyl, $(C_3-C_7)$cycloalkyl, —OH, —$O(C_1-C_6)$alkyl, —SH, —$S(C_1-C_6)$alkyl, —$NH_2$, —$NH(C_1-C_6)$alkyl and —$N((C_1-C_6)$alkyl$)_2$, wherein $(C_1-C_6)$alkyl is optionally substituted with hydroxy, —$O(C_1-C_6)$alkyl, cyano or oxo; and
  b) fused-heterocycle, wherein fused-heterocycle is substituted with one or more $Z^7$ groups and optionally substituted with one or more $Z^1$ groups.

Another specific group of compounds of formula I are compounds wherein $R^4$ is selected from:
  a) bicyclic aryl, tricyclic aryl, bicyclic heterocycle, tricyclic heterocycle, bicyclic heteroaryl and tricyclic heteroaryl, wherein bicyclic aryl, tricyclic aryl, bicyclic heterocycle, tricyclic heterocycle, bicyclic heteroaryl and tricyclic heteroaryl are each optionally substituted with one or more groups each independently selected from halo, $(C_1-C_6)$alkyl, ($C_2$-$C_6$)alkenyl, ($C_1$-$C_6$)haloalkyl, ($C_3$-$C_7$)cycloalkyl, —OH, —O($C_1$-$C_6$)alkyl, —SH, —S($C_1$-$C_6$)alkyl, —NH$_2$, —NH($C_1$-$C_6$)alkyl and —N(($C_1$-$C_6$)alkyl)$_2$, wherein ($C_1$-$C_6$)alkyl is optionally substituted with hydroxy, cyano or oxo; and b) bicyclic aryl, tricyclic aryl, bicyclic heteroaryl, tricyclic heteroaryl bicyclic fused-heterocycle, and tricyclic fused-heterocycle, wherein bicyclic aryl, tricyclic aryl, bicyclic heteroaryl, tricyclic heteroaryl bicyclic fused-heterocycle and tricyclic fused-heterocycle are each independently substituted with one or more $Z^7$ groups and optionally substituted with one or more $Z^1$ groups.

Another specific group of compounds of formula I are compounds wherein $R^4$ is selected from:

a) bicyclic heterocycle and tricyclic heterocycle, wherein bicyclic heterocycle and tricyclic heterocycle are each optionally substituted with one or more groups each independently selected from halo, ($C_1$-$C_6$)alkyl, ($C_2$-$C_6$)alkenyl, $C_6$)haloalkyl, ($C_3$-$C_7$)cycloalkyl, —OH, —O($C_1$-$C_6$)alkyl, —SH, —S($C_1$-$C_6$)alkyl, —NH$_2$, —NH($C_1$-$C_6$)alkyl and —N(($C_1$-$C_6$)alkyl)$_2$, wherein ($C_1$-$C_6$)alkyl is optionally substituted with hydroxy, —O($C_1$-$C_6$)alkyl, cyano or oxo; and b) bicyclic fused-heterocycle and tricyclic fused-heterocycle, wherein bicyclic fused-heterocycle and tricyclic fused-heterocycle are each substituted with one or more $Z^7$ groups and optionally substituted with one or more $Z^1$ groups.

Another specific group of compounds of formula I are compounds wherein $R^4$ is selected from:

a) bicyclic heterocycle, tricyclic heterocycle, bicyclic heteroaryl and tricyclic heteroaryl wherein bicyclic heterocycle, tricyclic heterocycle, bicyclic heteroaryl and tricyclic heteroaryl are each optionally substituted with one or more groups each independently selected from halo, ($C_1$-$C_6$)alkyl, ($C_2$-$C_6$)alkenyl, ($C_1$-$C_6$)haloalkyl, ($C_3$-$C_7$)cycloalkyl, —OH, —O($C_1$-$C_6$)alkyl, —SH, —S($C_1$-$C_6$)alkyl, —NH$_2$, —NH($C_1$-$C_6$)alkyl and —N(($C_1$-$C_6$)alkyl)$_2$, wherein ($C_1$-$C_6$)alkyl is optionally substituted with hydroxy, —O($C_1$-$C_6$)alkyl, cyano or oxo; and b) bicyclic fused-heterocycle and tricyclic fused-heterocycle, wherein bicyclic fused-heterocycle and tricyclic fused-heterocycle fused-heterocycle are each substituted with one or more $Z^7$ groups and optionally substituted with one or more $Z^1$ groups.

Another specific group of compounds of formula I are compounds wherein $R^4$ is selected from:

a) tricyclic heterocycle, wherein tricyclic heterocycle is optionally substituted with one or more groups each independently selected from halo, ($C_1$-$C_6$)alkyl, ($C_2$-$C_6$)alkenyl, ($C_1$-$C_6$)haloalkyl, ($C_3$-$C_7$)cycloalkyl, —OH, —O($C_1$-$C_6$)alkyl, —SH, —S($C_1$-$C_6$)alkyl, —NH$_2$, —NH($C_1$-$C_6$)alkyl and —N(($C_1$-$C_6$)alkyl)$_2$, wherein ($C_1$-$C_6$)alkyl is optionally substituted with hydroxy, —O($C_1$-$C_6$)alkyl, cyano or oxo; and b) tricyclic fused-heterocycle wherein tricyclic fused-heterocycle is substituted with one or more $Z^7$ groups and optionally substituted with one or more $Z^1$ groups.

Another specific group of compounds of formula I are compounds wherein $R^4$ is selected from:

a) ($C_3$-$C_{14}$)carbocycle, wherein ($C_3$-$C_{14}$)carbocycle is optionally substituted with one or more $Z^1$ groups, wherein two $Z^1$ groups together with the atom or atoms to which they are attached optionally form a ($C_3$-$C_7$)carbocycle or heterocycle; and b) aryl, heteroaryl, spiro-heterocycle, fused-heterocycle and bridged-heterocycle, wherein aryl, heteroaryl or spiro-heterocycle, fused-heterocycle and bridged-heterocycle are each independently substituted with one or more $Z^7$ groups and optionally substituted with one or more $Z^1$ groups.

Another specific group of compounds of formula I are compounds wherein $R^4$ is selected from aryl, heteroaryl, spiro-heterocycle, fused-heterocycle and bridged-heterocycle, wherein spiro-heterocycle, fused-heterocycle and bridged-heterocycle are each independently substituted with one or more $Z^7$ groups and optionally substituted with one or more $Z^1$ groups.

Another specific group of compounds of formula I are compounds wherein $R^4$ is selected from aryl, heteroaryl and fused-heterocycle, wherein aryl, heteroaryl and fused-heterocycle are each independently substituted with one or more $Z^7$ groups and optionally substituted with one or more $Z^1$ groups.

Another specific group of compounds of formula I are compounds wherein $R^4$ is fused-heterocycle, wherein fused-heterocycle is substituted with one or more $Z^7$ groups and optionally substituted with one or more $Z^1$ groups.

Another specific group of compounds of formula I are compounds wherein $R^4$ is selected from bicyclic aryl, tricyclic aryl, bicyclic heteroaryl, tricyclic heteroaryl bicyclic fused-heterocycle and tricyclic fused-heterocycle, wherein bicyclic aryl, tricyclic aryl, bicyclic heteroaryl, tricyclic heteroaryl bicyclic fused-heterocycle and tricyclic fused-heterocycle are each independently substituted with one or more $Z^7$ groups and optionally substituted with one or more $Z^1$ groups.

Another specific group of compounds of formula I are compounds wherein $R^4$ is selected from bicyclic fused-heterocycle and tricyclic fused-heterocycle, wherein bicyclic fused-heterocycle and tricyclic fused-heterocycle fused-heterocycle are each substituted with one or more $Z^7$ groups and optionally substituted with one or more $Z^1$ groups.

Another specific group of compounds of formula I are compounds wherein $R^4$ is tricyclic fused-heterocycle, wherein tricyclic fused-heterocycle fused-heterocycle is substituted with one or more $Z^7$ groups and optionally substituted with one or more $Z^1$ groups.

A specific value for $Z^{10}$ is:

i) halo, ($C_1$-$C_6$)haloalkyl; or ii) ($C_1$-$C_6$)alkyl optionally substituted with —OH, —O—($C_1$-$C_6$)haloalkyl.

Another specific value for $Z^{10}$ is halo.

Another specific value for $R^4$ is:

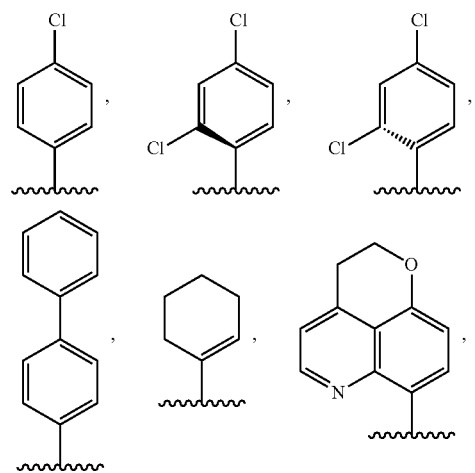

-continued
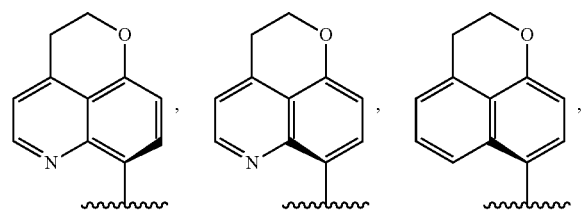
Another specific value for R⁴ is:
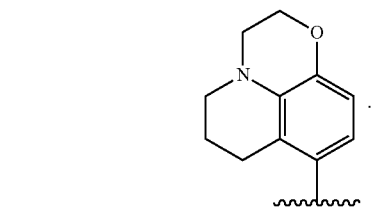
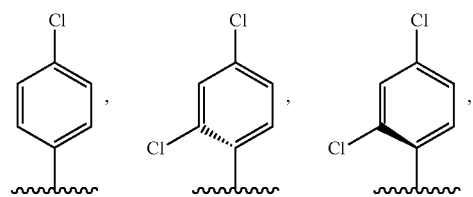
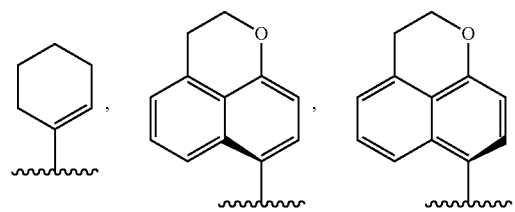
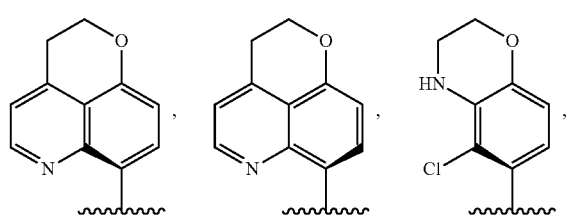
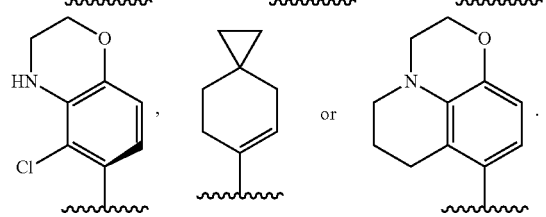
Another specific value for R⁴ is:
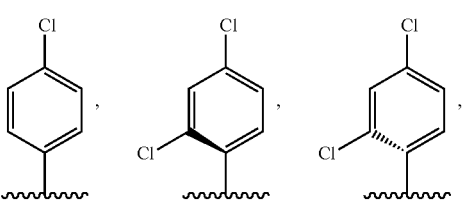
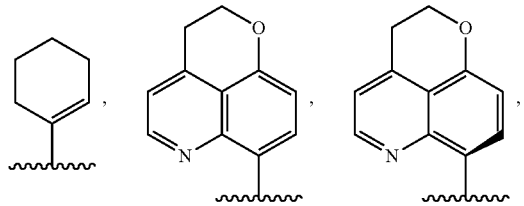
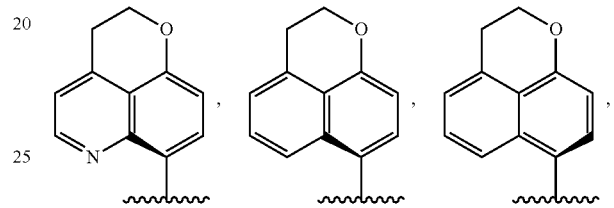
Another specific value for R⁴ is:
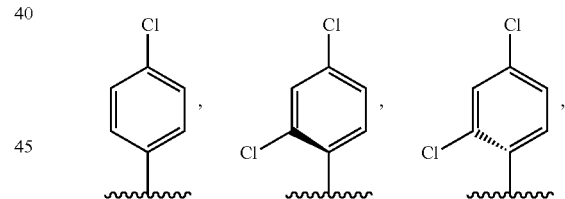
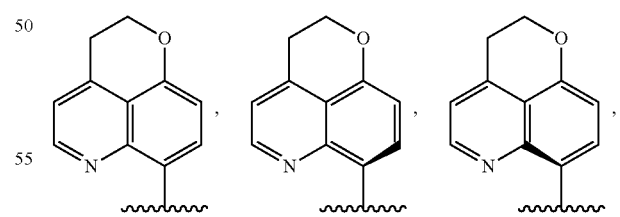
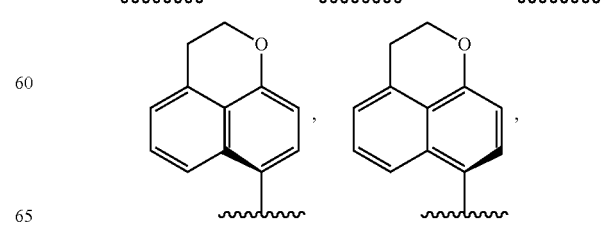

-continued
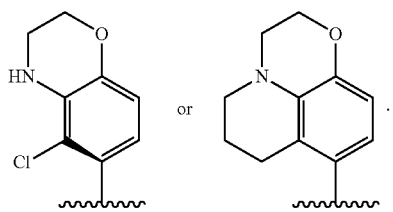
Another specific value for $R^4$ is:
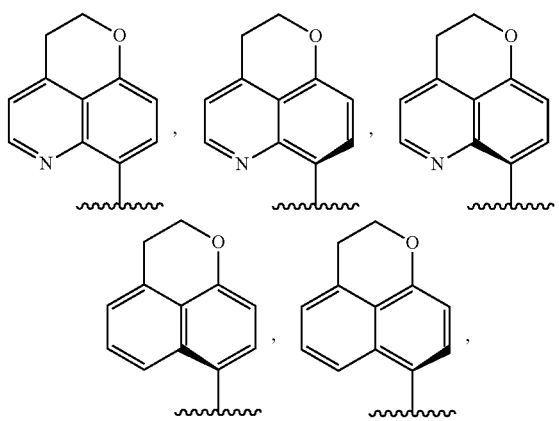
Another specific value for $R^4$ is:
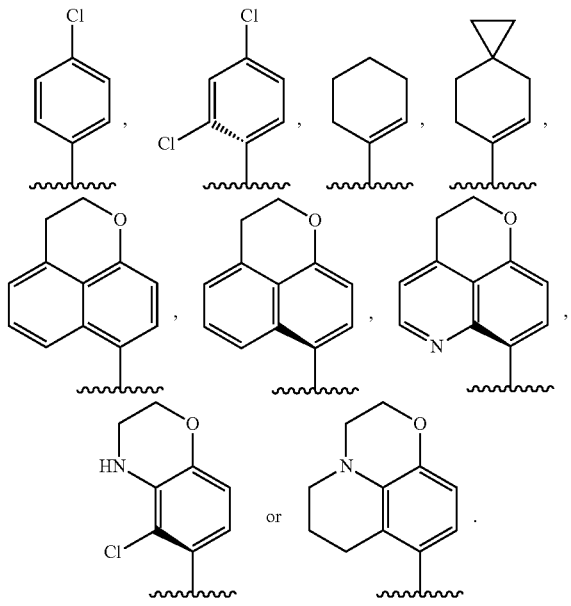
Another specific value for $R^4$ is:
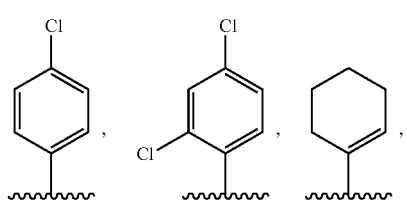
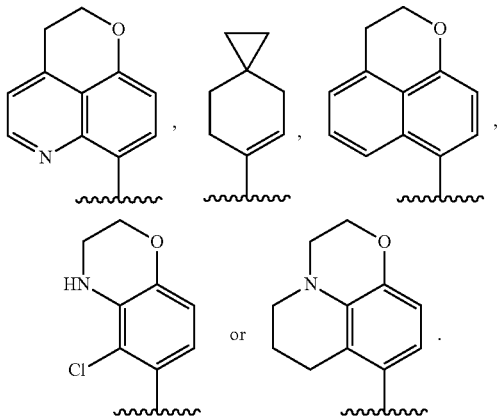
Another specific value for $R^4$ is:
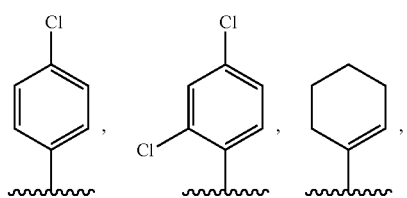
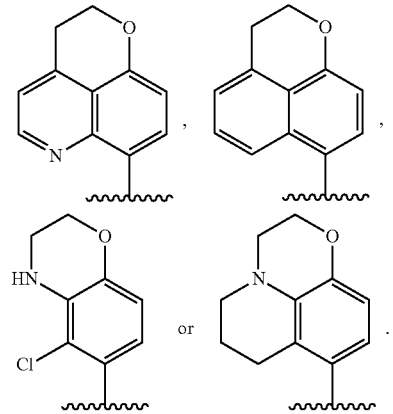
Another specific value for $R^4$ is:
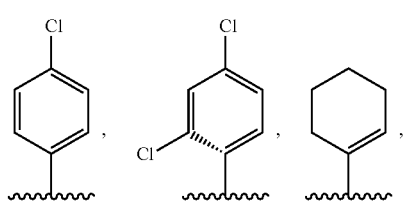

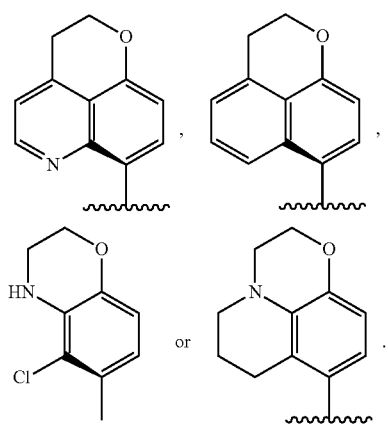
Another specific value for R⁴ is:
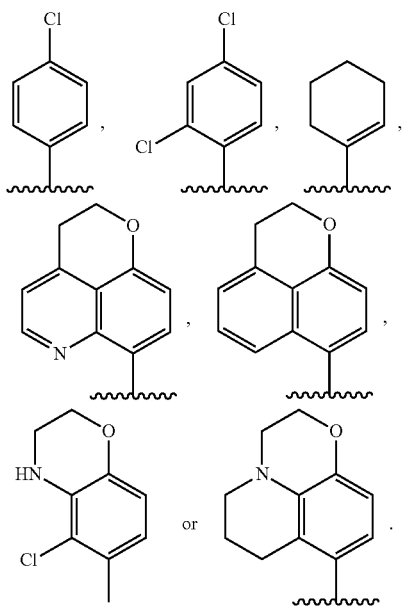
Another specific value for R⁴ is:
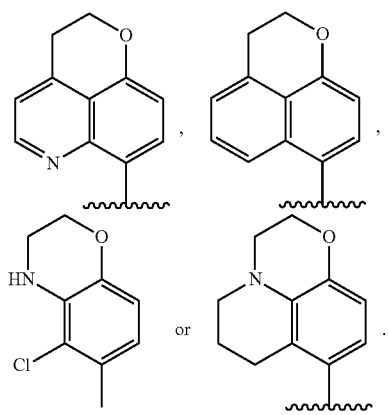
Another specific value for R⁴ is:
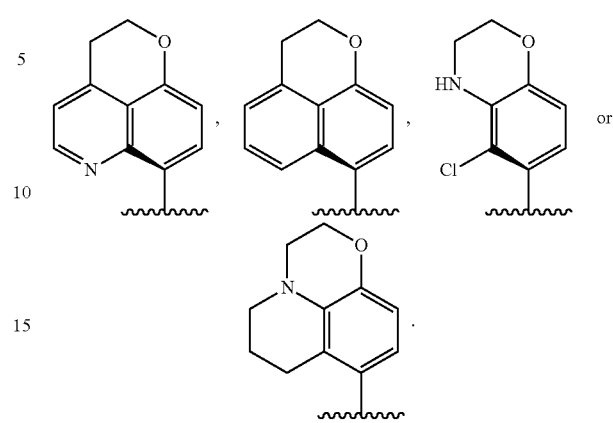
Another specific value for R⁴ is:

Another specific value for R⁴ is:
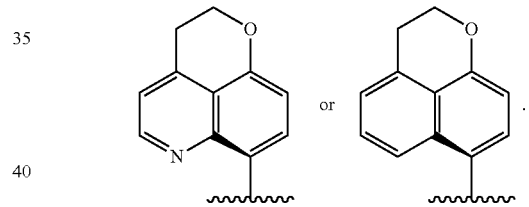
Another specific value for R⁴ is:
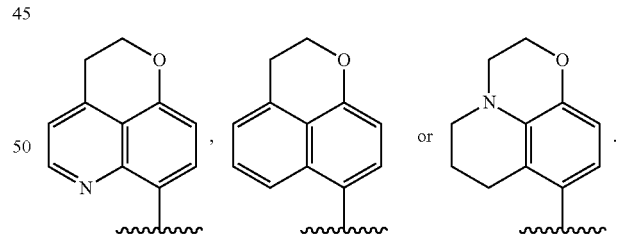
Another specific value for R⁴ is:
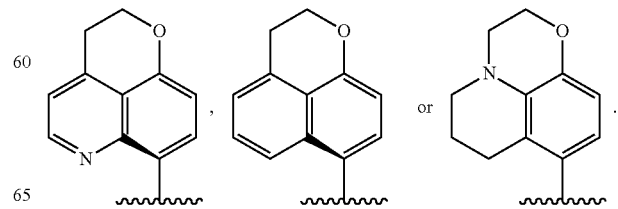

Another specific value for $R^4$ is:

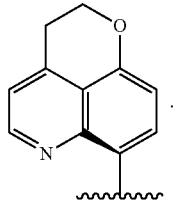

Another specific value for $R^4$ is:

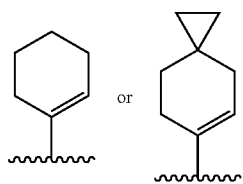

Another specific value for $R^4$ is:

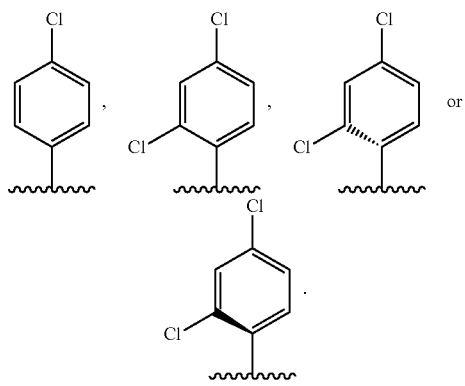

Another specific group of compounds of formula I are compounds wherein the stereochemistry of the $R^4$ substituent relative to the carbon of formula I to which it is attached is the (R) stereochemistry.

Another specific group of compounds of formula I are compounds wherein the stereochemistry of the $R^4$ substituent relative to the carbon of formula I to which it is attached is the (S) stereochemistry.

Another specific group of compounds of formula I are compounds wherein $R^7$ is selected from:

a) H, halo, $(C_1-C_6)$alkyl and $(C_1-C_6)$haloalkyl;

b) $(C_2-C_6)$alkenyl, $(C_2-C_6)$alkynyl, $(C_3-C_7)$cycloalkyl, nitro, cyano, aryl, heterocycle and heteroaryl, wherein any aryl, heterocycle or heteroaryl is optionally substituted with one or more $Z^{10}$ groups;

c) —C(=O)—$R^{11}$, —C(=O)—O—$R^{11}$, —O—$R^{11}$, —S(O)—$R^{11}$, —SO$_2$—$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-SO$_2$—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein any aryl, heterocycle or heteroaryl is optionally substituted with one or more $Z^{10}$ groups;

d) —N($R^9$)$R^{10}$; —C(=O)—N($R^9$)$R^{10}$, —O—C(=O)—N($R^9$)$R^{10}$, —SO$_2$—N($R^9$)$R^{10}$, —$(C_1-C_6)$alkyl-N($R^9$)$R^{10}$, —$(C_1-C_6)$alkyl-C(=O)—N($R^9$)$R^{10}$, —$(C_1-C_6)$alkyl-O—C(=O)—N($R^9$)$R^{10}$ and —$(C_1-C_6)$alkyl-SO$_2$—N($R^9$)$R^{10}$, wherein each $R^9$ is independently selected from H, $(C_1-C_6)$alkyl and $(C_3-C_7)$cycloalkyl, and each $R^{10}$ is independently selected from $R^{11}$, —$(C_1-C_6)$alkyl-$R^{11}$, —SO$_2$—$R^{11}$, —C(=O)—$R^{11}$, —C(=O)O$R^{11}$ and —C(=O)N($R^9$)$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein any aryl, heterocycle or heteroaryl is optionally substituted with one or more $Z^{10}$ groups;

e) —$(C_1-C_6)$alkyl-SO$_2$—$(C_1-C_6)$alkyl-$Z^{13}$, —C(O)—$(C_1-C_6)$alkyl-$Z^{13}$, —O—$(C_1-C_6)$alkyl-$Z^{13}$, —S—$(C_1-C_6)$alkyl-$Z^{13}$, —S(O)—$(C_1-C_6)$alkyl-$Z^{13}$, —SO$_2$—$(C_1-C_6)$alkyl-$Z^{13}$, —$(C_1-C_6)$alkyl-$Z^{14}$, $C_6)$alkyl-C(O)—$(C_1-C_6)$alkyl-$Z^{13}$, —$(C_1-C_6)$alkyl-C(O)—O$(C_1-C_6)$alkyl-$Z^{13}$, —$(C_1-C_6)$alkyl-O—$(C_1-C_6)$alkyl-$Z^{13}$, —$(C_1-C_6)$alkyl-S—$(C_1-C_6)$alkyl-$Z^{13}$, —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkyl-S(O)—$(C_1-C_6)$alkyl-$(C_3-C_7)$carbocycle, —$(C_1-C_6)$alkyl-SO$_2$—$(C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, —$(C_3-C_7)$halocarbocycle, —NR$_a$SO$_2$NR$_c$R$_d$, —NR$_a$SO$_2$O$(C_3-C_7)$carbocycle, —NR$_a$SO$_2$Oaryl, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$carbocycle-$Z^1$ and -halo$(C_1-C_6)$alkyl-$Z^3$, wherein any $(C_1-C_6)$alkyl, $(C_1-C_6)$haloalkyl, $(C_3-C_7)$carbocycle, $(C_2-C_6)$alkenyl, $(C_2-C_6)$alkynyl, aryl, heterocycle and heteroaryl, either alone or as part of a group, is optionally substituted with one or more $Z^1$ groups;

f) —X$(C_1-C_6)$alkyl, —X$(C_1-C_6)$haloalkyl, —X$(C_2-C_6)$alkenyl, —X$(C_2-C_6)$alkynyl and —X$(C_3-C_7)$carbocycle, wherein any —X$(C_1-C_6)$alkyl and —X$(C_1-C_6)$haloalkyl is substituted with one or more $Z^3$ groups and optionally substituted with one or more $Z^1$ groups, and wherein any —X$(C_2-C_6)$alkenyl, —X$(C_2-C_6)$alkynyl and —X$(C_3-C_7)$carbocycle is substituted with one or more $Z^4$ groups and optionally substituted with one or more $Z^1$ groups;

g) $(C_1-C_6)$alkyl, wherein $(C_1-C_6)$alkyl is substituted with one or more $Z^2$ groups and optionally substituted with one or more $Z^1$ groups;

h) aryl, heteroaryl, heterocycle, —Xaryl, —Xheteroaryl and —Xheterocycle, wherein any aryl, heteroaryl and heterocycle, either alone or as part of a group, is substituted with one or more $Z^5$ groups and optionally substituted with one or more $Z^1$ groups;

i) $(C_1-C_6)$haloalkyl, $(C_3-C_7)$carbocycle, $(C_2-C_6)$alkenyl and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each substituted with one or more $Z^6$ groups and optionally substituted with one or more $Z^1$ groups; and j) —NR$_e$R$_f$, —C(O)NR$_e$R$_f$, —OC(O)NR$_e$R$_f$, —SO$_2$NR$_e$R$_f$, —$(C_1-C_6)$alkyl-NR$_e$R$_f$, —$(C_1-C_6)$alkylC(O)—NR$_e$R$_f$, —$(C_1-C_6)$alkyl-O—C(O)—NR$_e$R$_f$ and —$(C_1-C_6)$alkyl-SO$_2$NR$_e$R$_f$ wherein each $(C_1-C_6)$alkyl is optionally substituted with one or more $Z^1$ groups.

Another specific group of compounds of formula I are compounds wherein $R^7$ is selected from:

a) H, $(C_1-C_6)$alkyl and $(C_1-C_6)$haloalkyl;
b) $(C_2-C_6)$alkenyl, $(C_2-C_6)$alkynyl, $(C_3-C_7)$cycloalkyl, aryl, heterocycle and heteroaryl, wherein any aryl, heterocycle or heteroaryl is optionally substituted with one or more $Z^{10}$ groups;
c) —C(=O)—O—$R^{11}$, —O—$R^{11}$, —$(C_1-C_6)$alkyl-$R^{11}$ and —$(C_1-C_6)$alkyl-O—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein any aryl, heterocycle or heteroaryl is optionally substituted with one or more $Z^{10}$ groups;
d) —N($R^9$)$R^{10}$, —C(=O)—N($R^9$)$R^{10}$, $(C_1-C_6)$alkyl-N($R^9$)$R^{10}$, wherein each $R^9$ is independently selected from H, $(C_1-C_6)$alkyl and $(C_3-C_7)$cycloalkyl, and each $R^{10}$ is independently selected from $R^{11}$, —$(C_1-C_6)$alkyl-$R^{11}$, —$SO_2$—$R^{11}$, —C(=O)—$R^{11}$, —C(=O)O$R^{11}$ and —C(=O)N($R^9$)$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein any aryl, heterocycle or heteroaryl is optionally substituted with one or more $Z^{10}$ groups;
e) —$(C_2-C_6)$alkynyl-$(C_3-C_7)$carbocycle and —$(C_2-C_6)$alkynyl-aryl, wherein —$(C_2-C_6)$alkynyl-$(C_3-C_7)$carbocycle and —$(C_2-C_6)$alkynyl-aryl are each optionally substituted with one or more $Z^1$ groups;
f) —X$(C_1-C_6)$alkyl, wherein —X$(C_1-C_6)$alkyl is substituted with one or more $Z^3$ groups and optionally substituted with one or more $Z^1$ groups, and wherein X is O;
g) $(C_1-C_6)$alkyl, wherein $(C_1-C_6)$alkyl is substituted with one or more $Z^2$ groups and optionally substituted with one or more $Z^1$ groups;
h) aryl, heteroaryl and heterocycle, wherein aryl, heteroaryl and heterocycle are each substituted with one or more $Z^5$ groups and optionally substituted with one or more $Z^1$ groups;
i) $(C_1-C_6)$haloalkyl, $(C_3-C_7)$carbocycle, $(C_2-C_6)$alkenyl and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each substituted with one or more $Z^6$ groups and optionally substituted with one or more $Z^1$ groups; and
j) —$NR_eR_f$, —C(O)$NR_eR_f$ and —$(C_1-C_6)$alkyl-$NR_eR_f$, wherein each $(C_1-C_6)$alkyl is optionally substituted with one or more $Z^1$ groups.

Another specific group of compounds of formula I are compounds wherein $R^7$ is selected from:

a) H, $(C_1-C_6)$alkyl and $(C_1-C_6)$haloalkyl;
b) $(C_2-C_6)$alkenyl, $(C_2-C_6)$alkynyl, $(C_3-C_7)$cycloalkyl, aryl, heterocycle and heteroaryl, wherein any aryl, heterocycle or heteroaryl is optionally substituted with one or more $Z^{10}$ groups;
c) —C(=O)—$R^{11}$, —C(=O)—O—$R^{11}$, —O—$R^{11}$, —$(C_1-C_6)$alkyl-$R^{11}$ and —$(C_1-C_6)$alkyl-O—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein any aryl, heterocycle or heteroaryl is optionally substituted with one or more $Z^{10}$ groups;
d) —N($R^9$)$R^{10}$, —C(=O)—N($R^9$)$R^{10}$, —$(C_1-C_6)$alkyl-N($R^9$)$R^{10}$, wherein each $R^9$ is independently selected from H, $(C_1-C_6)$alkyl and $(C_3-C_7)$cycloalkyl, and each $R^{10}$ is independently selected from $R^{11}$, —$(C_1-C_6)$alkyl-$R^{11}$, —$SO_2$—$R^{11}$, —C(=O)—$R^{11}$, —C(=O)O$R^{11}$ and —C(=O)N($R^9$)$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl, wherein any aryl, heterocycle or heteroaryl is optionally substituted with one or more $Z^{10}$ groups;
e) —$(C_2-C_6)$alkynyl-$(C_3-C_7)$carbocycle and —$(C_2-C_6)$alkynyl-aryl, wherein —$(C_2-C_6)$alkynyl-$(C_3-C_7)$carbocycle and —$(C_2-C_6)$alkynyl-aryl are each optionally substituted with one or more $Z^1$ groups;
f) —X$(C_1-C_6)$alkyl, wherein —X$(C_1-C_6)$alkyl is substituted with one or more $Z^3$ groups and optionally substituted with one or more $Z^1$ groups, and wherein X is O; and
g) —$NR_eR_f$.

Another specific group of compounds of formula I are compounds wherein $R^7$ is selected from:

a) $(C_1-C_6)$haloalkyl; and
b) $(C_1-C_6)$haloalkyl, wherein $(C_1-C_6)$haloalkyl is substituted with one or more $Z^6$ groups and optionally substituted with one or more $Z^1$ groups.

Another specific group of compounds of formula I are compounds wherein $R^7$ is selected from:

a) $(C_1-C_6)$alkyl and $(C_1-C_6)$haloalkyl;

b) $(C_2-C_6)$alkynyl, $(C_3-C_7)$cycloalkyl and aryl, wherein any aryl is optionally substituted with one or more $Z^{10}$ groups;

c) —$(C_1-C_6)$alkyl-$R^{11}$, wherein each $R''$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl and aryl, wherein aryl is optionally substituted with one or more $Z^{10}$ groups;

d) —$(C_2-C_6)$alkynyl-$(C_3-C_7)$carbocycle and —$(C_2-C_6)$alkynyl-aryl, wherein —$(C_2-C_6)$alkynyl-$(C_3-C_7)$carbocycle and —$(C_2-C_6)$alkynyl-aryl are each optionally substituted with one or more $Z^1$ groups;

e) $(C_1-C_6)$alkyl, wherein $(C_1-C_6)$alkyl is substituted with one or more $Z^2$ groups and optionally substituted with one or more $Z^1$ groups;

f) aryl, wherein aryl is substituted with one or more $Z^5$ groups and optionally substituted with one or more $Z^1$ groups; and g) $(C_1-C_6)$haloalkyl, $(C_3-C_7)$carbocycle and $(C_2-C_6)$alkynyl, wherein $(C_1-C_6)$haloalkyl, $(C_3-C_7)$carbocycle and $(C_2-C_6)$alkynyl are each substituted with one or more $Z^6$ groups and optionally substituted with one or more $Z^1$ groups.

Another specific group of compounds of formula I are compounds wherein $R^7$ is selected from:

a) $(C_1-C_6)$alkyl and $(C_1-C_6)$haloalkyl;

b) $(C_2-C_6)$alkynyl and aryl, wherein any aryl is optionally substituted with one or more $Z^{10}$ groups;

c) —$(C_1-C_6)$alkyl-$R''$, wherein each $R^{11}$ is independently selected from $(C_3-C_7)$cycloalkyl and aryl, wherein any aryl is optionally substituted with one or more $Z^{10}$ groups;

d) —$(C_2-C_6)$alkynyl-$(C_3-C_7)$carbocycle and —$(C_2-C_6)$alkynyl-aryl, wherein —$(C_2-C_6)$alkynyl-$(C_3-C_7)$carbocycle and —$(C_2-C_6)$alkynyl-aryl are each optionally substituted with one or more $Z^1$ groups;

e) $(C_1-C_6)$alkyl, wherein $(C_1-C_6)$alkyl is substituted with one or more $Z^2$ groups and optionally substituted with one or more $Z^1$ groups;

f) aryl, wherein aryl is substituted with one or more $Z^5$ groups and optionally substituted with one or more $Z^1$ groups; and g) $(C_1-C_6)$haloalkyl and $(C_2-C_6)$alkynyl, wherein $(C_1-C_6)$haloalkyl and $(C_2-C_6)$alkynyl are each substituted with one or more $Z^6$ groups and optionally substituted with one or more $Z^1$ groups.

Another specific group of compounds of formula I are compounds wherein $R^7$ is selected from:

a) $(C_1-C_6)$alkyl and $(C_1-C_6)$haloalkyl;

b) $(C_2-C_6)$alkynyl and aryl, wherein any aryl is optionally substituted with one or more $Z^{10}$ groups;

c) $(C_1-C_6)$alkyl, wherein $(C_1-C_6)$alkyl is substituted with one or more $Z^2$ groups and optionally substituted with one or more $Z^1$ groups; and d) aryl, wherein aryl is substituted with one or more $Z^5$ groups and optionally substituted with one or more $Z^1$ groups.

Another specific group of compounds of formula I are compounds wherein $R^7$ is selected from:

a) $(C_1-C_6)$alkyl and $(C_1-C_6)$haloalkyl; and b) $(C_2-C_6)$alkynyl and aryl, wherein any aryl is optionally substituted with one or more $(C_1-C_6)$alkyl groups.

Another specific group of compounds of formula I are compounds wherein $R^7$ is selected from $(C_1-C_6)$alkyl, $C_1-C_6)$haloalkyl and $(C_2-C_6)$alkynyl.

Another specific group of compounds of formula I are compounds wherein $R^7$ is selected from:

a) —$(C_1-C_6)$alkyl-$SO_2$—$(C_1-C_6)$alkyl-$Z^{13}$, —$C(O)$—$(C_1-C_6)$alkyl-$Z^{13}$, —$O$—$(C_1-C_6)$alkyl-$Z^{13}$, —$S$—$(C_1-C_6)$alkyl-$Z^{13}$, —$S(O)$—$(C_1-C_6)$alkyl-$Z^{13}$, —$SO_2$—$(C_1-C_6)$alkyl-$Z^{13}$, —$(C_1-C_6)$alkyl-$Z^{14}$, —$(C_1-C_6)$alkyl-$C(O)$—$(C_1-C_6)$alkyl-$Z^{13}$, —$(C_1-C_6)$alkyl-$C(O)$—$O(C_1-C_6)$alkyl-$Z^{13}$, —$(C_1-C_6)$alkyl-$O$—$(C_1-C_6)$alkyl-$Z^{13}$, —$(C_1-C_6)$alkyl-$S$—$(C_1-C_6)$alkyl-$Z^{13}$, —$(C_1-C_6)$alkyl-$O$—$(C_1-C_6)$alkyl-$(C_3-C_7)$carbocycle, —$(C_1-C_6)$alkyl-$S$—$(C_1-C_6)$alkyl-$(C_3-C_7)$carbocycle, —$(C_1-C_6)$alkyl-$S(O)$—$(C_1-C_6)$alkyl-$(C_3-C_7)$carbocycle, —$(C_1-C_6)$alkyl-$SO_2$—$(C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, —$(C_3-C_7)$halocarbocycle, —$NR_aSO_2NR_cR_a$, —$NR_aSO_2O(C_3-C_7)$carbocycle, —$NR_aSO_2Oaryl$, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$carbocycle-$Z^1$ and -halo$(C_1-C_6)$alkyl-$Z^3$, wherein any $(C_1-C_6)$alkyl, $(C_1-C_6)$haloalkyl, $(C_3-C_7)$carbocycle, $(C_2-C_6)$alkenyl, $(C_2-C_6)$alkynyl, aryl, heterocycle and heteroaryl, either alone or as part of a group, are each optionally substituted with one or more $Z^1$ groups;

b) —$X(C_1-C_6)$alkyl, —$X(C_1-C_6)$haloalkyl, —$X(C_2-C_6)$alkenyl, —$X(C_2-C_6)$alkynyl and —$X(C_3-C_7)$carbocycle, wherein —$X(C_1-C_6)$alkyl and —$X(C_1-C_6)$haloalkyl are each substituted with one or more $Z^3$ groups and optionally substituted with one or more $Z^1$ groups, and wherein —$X(C_2-C_6)$alkenyl, —$X(C_2-C_6)$alkynyl and —$X(C_3-C_7)$carbocycle are each substituted with one or more $Z^4$ groups and optionally substituted with one or more $Z^1$ groups;

c) $(C_1-C_6)$alkyl, wherein $(C_1-C_6)$alkyl is substituted with one or more $Z^2$ groups and optionally substituted with one or more $Z^1$ groups;

d) aryl, heteroaryl, heterocycle, —Xaryl, —Xheteroaryl and —Xheterocycle, wherein any aryl, heteroaryl and heterocycle, either alone or as part of a group, is substituted with one or more $Z^5$ groups and optionally substituted with one or more $Z^1$ groups;

e) $(C_1-C_6)$haloalkyl, $(C_3-C_7)$carbocycle, $(C_2-C_6)$alkenyl and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each substituted with one or more $Z^6$ groups and optionally substituted with one or more $Z^1$ groups; and f) —$NR_eR_f$, —$C(O)NR_eR_f$, —$OC(O)NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—$C(O)$—$NR_eR_f$ and —$(C_1-C_6)$alkyl-$SO_2NR_eR_f$, wherein each $(C_1-C_6)$alkyl is optionally substituted with one or more $Z^1$ groups.

Another specific group of compounds of formula I are compounds wherein $R^7$ is selected from:

a) —$(C_2-C_6)$alkynyl-$(C_3-C_7)$carbocycle and —$(C_2-C_6)$alkynyl-aryl, wherein —$(C_2-C_6)$alkynyl-$(C_3-C_7)$carbocycle and —$(C_2-C_6)$alkynyl-aryl are each optionally substituted with one or more $Z^1$ groups;

b) —$X(C_1-C_6)$alkyl, wherein —$X(C_1-C_6)$alkyl is substituted with one or more $Z^3$ groups and optionally substituted with one or more $Z^1$ groups, and wherein X is O;

c) $(C_1-C_6)$alkyl, wherein $(C_1-C_6)$alkyl is substituted with one or more $Z^2$ groups and optionally substituted with one or more $Z^1$ groups;

d) aryl, heteroaryl and heterocycle, wherein aryl, heteroaryl and heterocycle are each substituted with one or more $Z^5$ groups and optionally substituted with one or more $Z^1$ groups;

e) $(C_1-C_6)$haloalkyl, $(C_3-C_7)$carbocycle, $(C_2-C_6)$alkenyl and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each substituted with one or more $Z^6$ groups and optionally substituted with one or more $Z^1$ groups; and f) —NR$_e$R$_f$, —C(O)NR$_e$R$_f$, and —(C$_1$-C$_6$)alkyl-NR$_e$R$_f$, wherein (C$_1$-C$_6$)alkyl is optionally substituted with one or more Z$^1$ groups.

Another specific group of compounds of formula I are compounds wherein R$^7$ is (C$_1$-C$_6$)haloalkyl, wherein (C$_1$-C$_6$) haloalkyl is substituted with one or more Z$^6$ groups and optionally substituted with one or more Z$^1$ groups.

Another specific group of compounds of formula I are compounds wherein R$^7$ is selected from:

a) —(C$_2$-C$_6$)alkynyl-(C$_3$-C$_7$)carbocycle and —(C$_2$-C$_6$) alkynyl-aryl, wherein —(C$_2$-C$_6$)alkynyl-(C$_3$-C$_7$)carbocycle and —(C$_2$-C$_6$)alkynyl-aryl are each optionally substituted with one or more Z$^1$ groups;

b) (C$_1$-C$_6$)alkyl, wherein (C$_1$-C$_6$)alkyl is substituted with one or more Z$^2$ groups and optionally substituted with one or more Z$^1$ groups;

c) aryl, wherein aryl is substituted with one or more Z$^5$ groups and optionally substituted with one or more Z$^1$ groups; and d) (C$_1$-C$_6$)haloalkyl, (C$_3$-C$_7$)carbocycle and (C$_2$-C$_6$)alkynyl, wherein (C$_1$-C$_6$)haloalkyl, (C$_3$-C$_7$)carbocycle and (C$_2$-C$_6$)alkynyl are each substituted with one or more Z$^6$ groups and optionally substituted with one or more Z$^1$ groups.

Another specific group of compounds of formula I are compounds wherein R$^7$ is selected from:

a) —(C$_2$-C$_6$)alkynyl-(C$_3$-C$_7$)carbocycle and —(C$_2$-C$_6$) alkynyl-aryl, wherein —(C$_2$-C$_6$)alkynyl-(C$_3$-C$_7$)carbocycle and —(C$_2$-C$_6$)alkynyl-aryl are each optionally substituted with one or more Z$^1$ groups;

b) (C$_1$-C$_6$)alkyl, wherein (C$_1$-C$_6$)alkyl is substituted with one or more Z$^2$ groups and optionally substituted with one or more Z$^1$ groups;

c) aryl, wherein aryl is substituted with one or more Z$^5$ groups and optionally substituted with one or more Z$^1$ groups; and d) (C$_1$-C$_6$)haloalkyl and (C$_2$-C$_6$)alkynyl, wherein (C$_1$-C$_6$) haloalkyl and (C$_2$-C$_6$)alkynyl are each substituted with one or more Z$^6$ groups and optionally substituted with one or more Z$^1$ groups.

Another specific group of compounds of formula I are compounds wherein R$^7$ is selected from:

a) (C$_1$-C$_6$)alkyl, wherein (C$_1$-C$_6$)alkyl is substituted with one or more Z$^2$ groups and optionally substituted with one or more Z$^1$ groups; and b) aryl, wherein aryl is substituted with one or more Z$^5$ groups and optionally substituted with one or more Z$^1$ groups.

Another specific group of compounds of formula I are compounds wherein R$^{7a}$ is selected from:

a) H, halo, (C$_1$-C$_6$)alkyl and (C$_1$-C$_6$)haloalkyl;

b) (C$_2$-C$_6$)alkenyl, (C$_2$-C$_6$)alkynyl, (C$_3$-C$_7$)cycloalkyl, nitro, cyano, aryl, heterocycle and heteroaryl;

c) —C(=O)—R$^{11}$, —C(=O)—O—R$^{11}$, —O—R$^{11}$, —S—R$^{11}$, —S(O)—R$^{11}$, —SO$_2$—R$^{11}$, —(C$_1$-C$_6$)alkyl-R$^{11}$, —(C$_1$-C$_6$)alkyl-C(=O)—R$^{11}$, —(C$_1$-C$_6$)alkyl-C(=O)—O—R$^{11}$, —(C$_1$-C$_6$)alkyl-O—R$^{11}$, —(C$_1$-C$_6$)alkyl-S—R$^{11}$, —(C$_1$-C$_6$)alkyl-S(O)—R$^{11}$ and —(C$_1$-C$_6$)alkyl-SO$_2$—R$^{11}$, wherein each R$^{11}$ is independently selected from H, (C$_1$-C$_6$) alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl; and d) —N(R$^9$)R$^{10}$, —C(=O)—N(R$^9$)R$^{10}$, —O—C(=O)—N(R$^9$)R$^{10}$, —SO$_2$—N(R$^9$)R$^{10}$, —(C$_1$-C$_6$)alkyl-N(R$^9$)R$^{10}$, —(C$_1$-C$_6$)alkyl-C(=O)—N(R$^9$)R$^{10}$, —(C$_1$-C$_6$)alkyl-O—C (=O)—N(R$^9$)R$^{10}$ and —(C$_1$-C$_6$)alkyl-SO$_2$—N(R$^9$)R$^{10}$, wherein each R$^9$ is independently selected from H, (C$_1$-C$_6$) alkyl and (C$_3$-C$_7$)cycloalkyl, and each R$^{10}$ is independently selected from R$^{11}$, —(C$_1$-C$_6$)alkyl-R$^{11}$, —SO$_2$—R$^{11}$, —C(=O)—R$^{11}$, —C(=O)OR$^{11}$ and —C(=O)N(R$^9$)R$^{11}$, wherein each R$^{11}$ is independently selected from H, (C$_1$-C$_6$) alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl, and wherein any aryl, heterocycle or heteroaryl of R$^{7a}$ is optionally substituted with one or more (e.g. 1, 2 or 3) Z$^{10}$ groups, and wherein R$^{7a}$ is not OH.

Another specific group of compounds of formula I are compounds wherein R$^7$ has any of the above recited values for R$^7$ provided R$^7$ is not OH.

Another specific value for R$^7$ is:

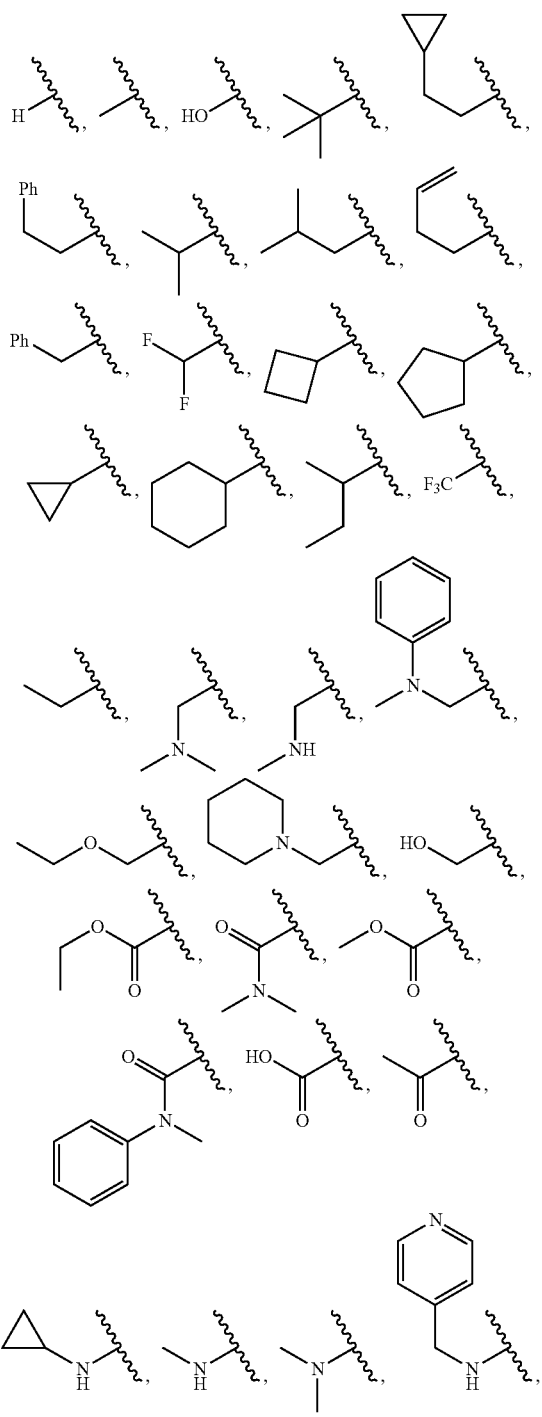

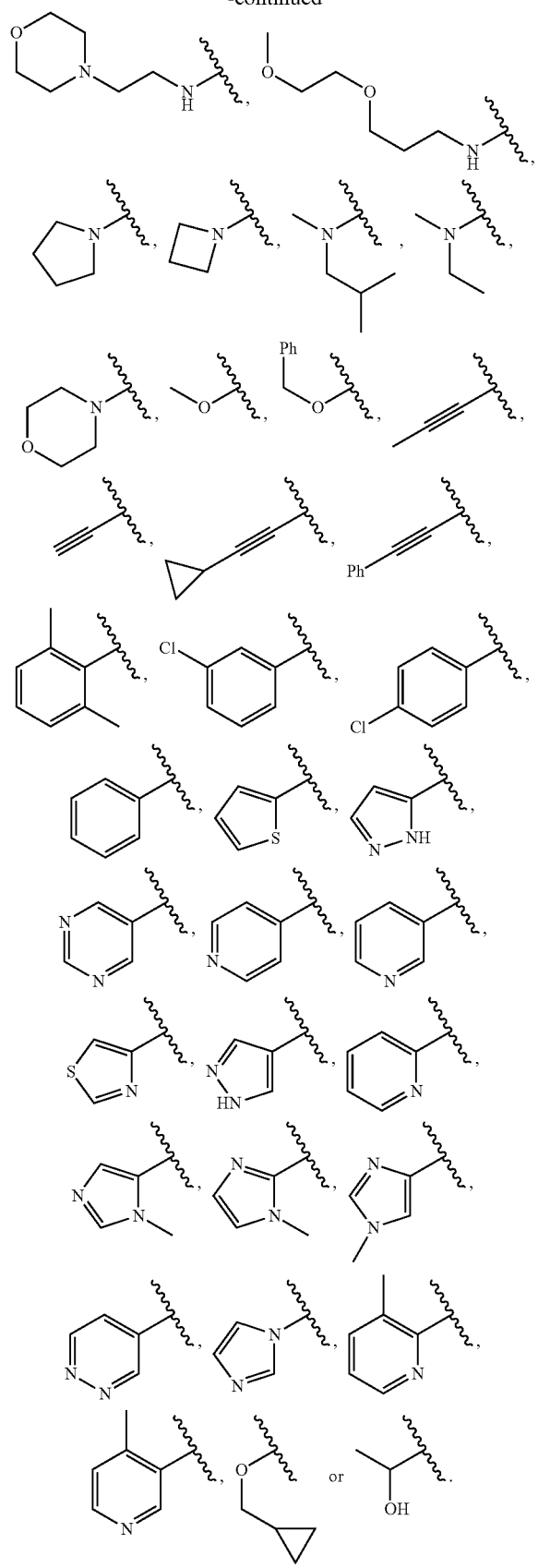
Another specific value for $R^7$ is:
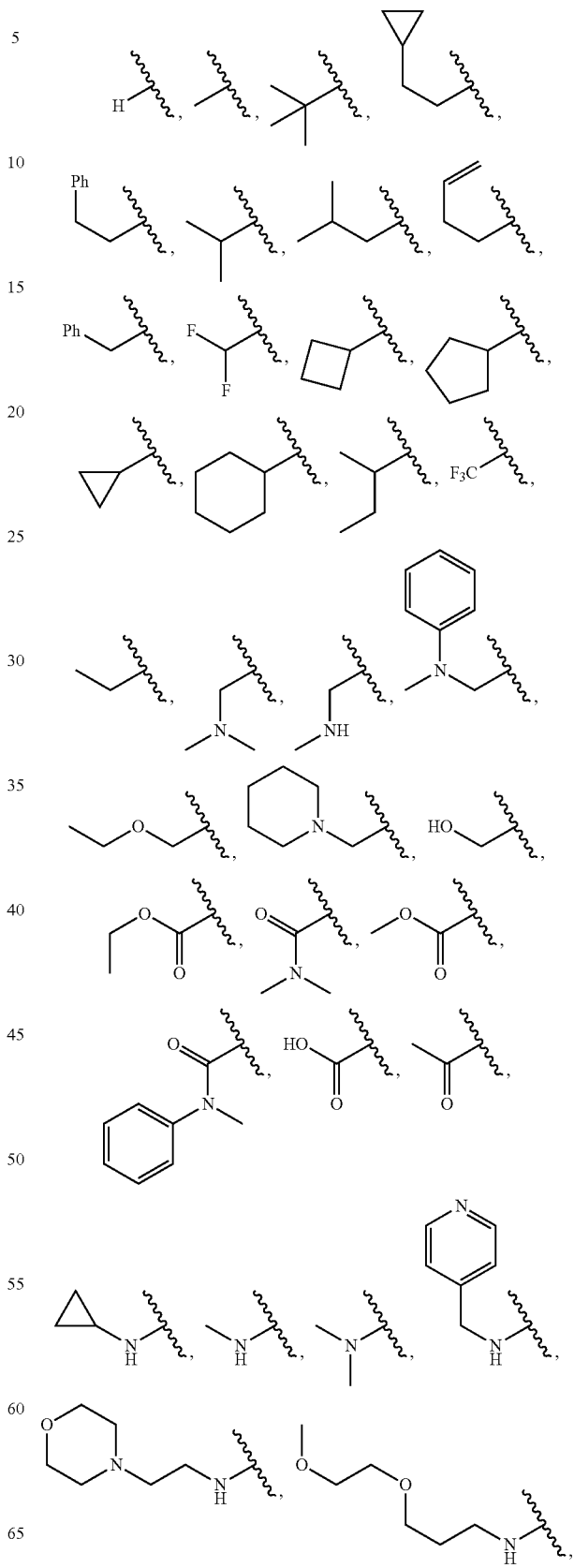

-continued

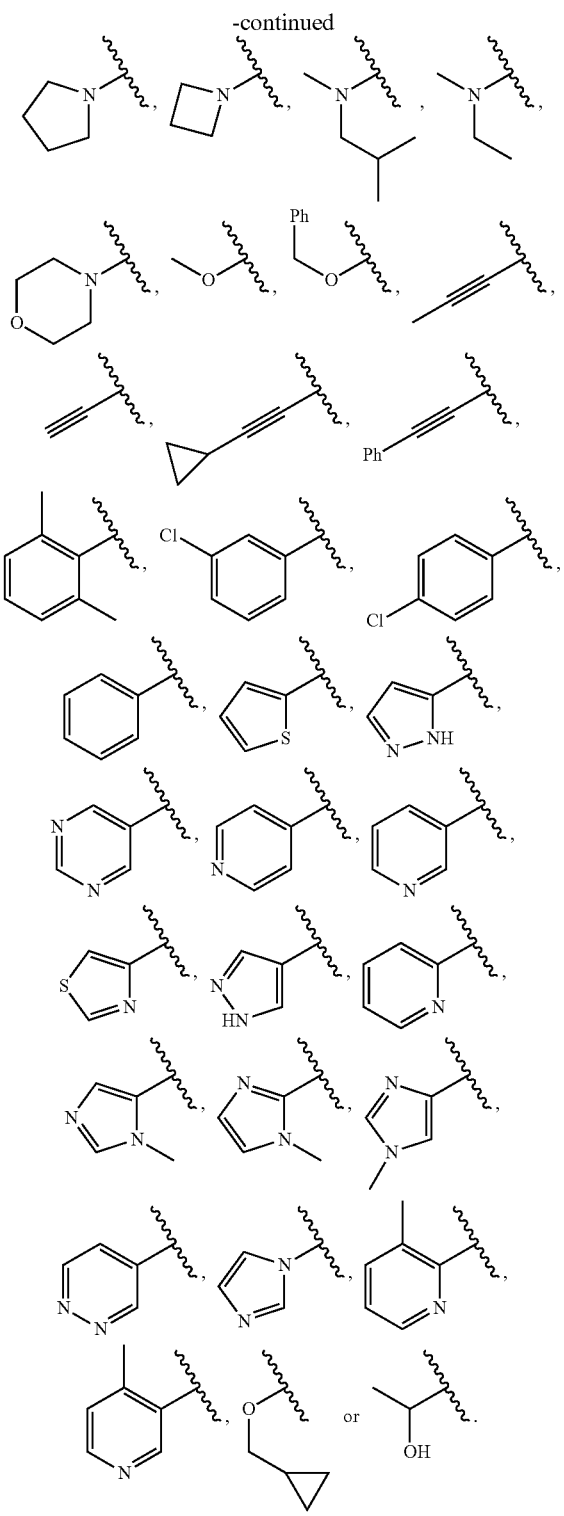

Another specific value for $R^7$ is:

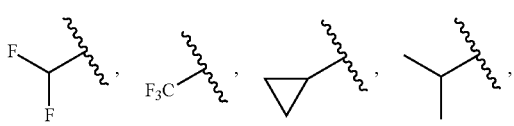

-continued

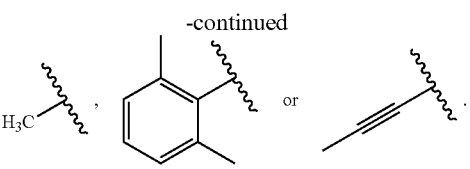

Another specific value for $R^7$ is:

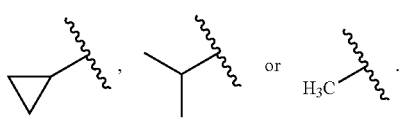

Another specific value for $R^7$ is:

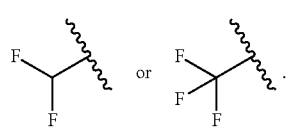

Another specific value for $R^7$ is:

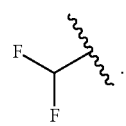

Another specific group of compounds of formula In, Io, Ip and Iq are compounds wherein W is a five-membered heteroaryl optionally substituted with one or more (e.g. 1, 2, 3, 4 or 5) $Z^1$ groups.

Another specific group of compounds of formula In, Io, Ip and Iq are compounds wherein W is imidazolyl, triazolyl, or tetrazolyl each optionally substituted with one or more (e.g. 1, 2, 3, 4 or 5) $Z^1$ groups.

A specific value for $Z^1$ is —($C_1$-$C_6$)alkyl or -aryl, wherein any ($C_1$-$C_6$)alkyl, or aryl of $Z^1$ is optionally substituted with one or more (e.g. 1, 2, 3, 4 or 5) halogen, —OH, —$OR_b$, —CN, —$NR_aC(O)_2R_b$, -heteroaryl, -heterocycle, —Oheteroaryl, —Oheterocycle, —NHheteroaryl, —NHheterocycle, or —$S(O)_2NR_cR_d$.

Another specific group of compounds of formula I are compounds wherein $R^{13a}$ is selected from:

a) $R^{11}$, —C(=O)—$R^{11}$, —S—$R^{11}$, —S(O)—$R^{11}$, —$SO_2$—$R^{11}$, —($C_1$-$C_6$)alkyl-$R^{11}$, —($C_1$-$C_6$)alkyl-C(=O)—$R^{11}$, —($C_1$-$C_6$)alkyl-C(=O)—O—$R^{11}$, —($C_1$-$C_6$)alkyl-O—$R^{11}$, —($C_1$-$C_6$)alkyl-S—R", —($C_1$-$C_6$)alkyl-S(O)—R" and —($C_1$-$C_6$)alkyl-$SO_2$—$R^{11}$, wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl, wherein aryl, heterocycle and heteroaryl are each optionally substituted with one or more (e.g. 1, 2 or 3) $Z^{11}$ groups; and b) —C(=O)—N($R^9$)$R^{10}$, —$SO_2$—N($R^9$)$R^{10}$, —($C_1$-$C_6$)alkyl-N($R^9$)$R^{10}$, —($C_1$-$C_6$)alkyl-C(=)—N($R^9$)$R^{10}$, —($C_1$-$C_6$)alkyl-O—C(=O)—N($R^9$)$R^{10}$ and —($C_1$-$C_6$)alkyl-$SO_2$—N($R^9$)$R^{10}$, wherein each $R^9$ is independently selected from H, ($C_1$-$C_6$)alkyl and ($C_3$-$C_7$)cycloalkyl, and each $R^{10}$ is independently selected from $R^{11}$, —($C_1$-$C_6$)alkyl-$R^{11}$, —$SO_2$—$R^{11}$, —C(=O)—$R^{11}$, —C(=O)O$R^{11}$ and —C(=O)N(R$^9$)R$^{11}$, wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl, wherein aryl, heterocycle and heteroaryl are each optionally substituted with one or more (e.g. 1, 2 or 3) Z$^{11}$ groups; provided R$^{13a}$ is not H.

Another specific group of compounds of formula I are compounds wherein R$^{13a}$ is selected from:

a) R$^{11}$, —C(=O)—R$^{11}$, —C(=O)—O—R$^{11}$, —O—R$^{11}$, —S(O)—R$^{11}$, —SO$_2$—R$^{11}$, —(C$_1$-C$_6$)alkyl-R$^{11}$, —(C$_1$-C$_6$)alkyl-C(=O)—R$^{11}$, —(C$_1$-C$_6$)alkyl-C(=O)—O—R$^{11}$, —(C$_1$-C$_6$)alkyl-O—R$^{11}$, —(C$_1$-C$_6$)alkyl-S—R$^{11}$, —(C$_1$-C$_6$)alkyl-S(O)—R$^{11}$ and —(C$_1$-C$_6$)alkyl-SO$_2$—R$^{11}$, wherein each R$^{11}$ is independently selected from (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl, wherein aryl, heterocycle and heteroaryl are each optionally substituted with one or more (e.g. 1, 2 or 3) Z$^{11}$ groups; and b) —C(=O)—N(R$^9$)R$^{10}$, —SO$_2$—N(R$^9$)R$^{10}$, —(C$_1$-C$_6$)alkyl-N(R$^9$)R$^{10}$, —(C$_1$-C$_6$)alkyl-C(=O)—N(R$^9$)R$^{10}$, —(C$_1$-C$_6$)allkl-O—C(=O)—N(R$^9$)R$^{10}$ and —(C$_1$-C$_6$)alkyl-SO$_2$—N(R$^9$)R$^{10}$, wherein each R$^9$ is independently selected from H, (C$_1$-C$_6$)alkyl and (C$_3$-C$_7$)cycloalkyl, and each R$^{10}$ is independently selected from R$^{11}$, —(C$_1$-C$_6$)alkyl-R$^{11}$, —SO$_2$—R$^{11}$, —C(=O)—R$^{11}$, —C(=O)OR$^{11}$ and —C(=O)N(R$^9$)R$^{11}$, wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl, wherein aryl, heterocycle and heteroaryl are each optionally substituted with one or more (e.g. 1, 2 or 3) Z$^{11}$ groups.

Another specific group of compounds of formula I are compounds wherein R$^{13}$ is selected from:

a) R$^{11}$ and —(C$_1$-C$_6$)alkyl-R$^{11}$, wherein each R$^{11}$ is independently selected from (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl, wherein aryl, heterocycle and heteroaryl are each optionally substituted with one or more (e.g. 1, 2 or 3) Z$^{11}$ groups;

b) —(C$_1$-C$_6$)alkyl-N(R$^9$)R$^{10}$, wherein each R$^9$ is independently selected from H, (C$_1$-C$_6$)alkyl and (C$_3$-C$_7$)cycloalkyl, and each R$^{10}$ is independently selected from R$^{11}$, —(C$_1$-C$_6$)alkyl-R$^{11}$, —SO$_2$—R$^{11}$, —C(=O)—R$^{11}$, —C(=O)OR$^{11}$ and —C(=O)N(R$^9$)R$^{11}$, wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl, wherein aryl, heterocycle and heteroaryl are each optionally substituted with one or more (e.g. 1, 2 or 3) Z$^{11}$ groups;

c) (C$_1$-C$_6$)alkyl, wherein (C$_1$-C$_6$)alkyl is substituted with one or more Z$^2$ groups and optionally substituted with one or more (e.g. 1, 2, 3, 4 or 5) Z' groups;

d) aryl, heteroaryl, heterocycle, wherein aryl heteroaryl and heterocycle are each independently substituted with one or more (e.g. 1, 2, 3, 4 or 5) Z$^5$ groups and optionally substituted with one or more (e.g. 1, 2, 3, 4 or 5) Z$^1$ groups;

e) (C$_1$-C$_6$)haloalkyl, (C$_3$-C$_7$)carbocycle, (C$_2$-C$_6$)alkenyl and (C$_2$-C$_6$)alkynyl, wherein (C$_1$-C$_6$)haloalkyl, (C$_3$-C$_7$)carbocycle, (C$_2$-C$_6$)alkenyl and (C$_2$-C$_6$)alkynyl are each independently substituted with one or more (e.g. 1, 2, 3, 4 or 5) Z$^6$ groups and optionally substituted with one or more (e.g. 1, 2, 3, 4 or 5) Z$^1$ groups; and f) —(C$_1$-C$_6$)alkyl-NR$_e$R$_f$, wherein —(C$_1$-C$_6$)alkyl-NR$_e$R$_f$ is optionally substituted with one or more (e.g. 1, 2, 3, 4 or 5) Z$^1$ groups.

Another specific group of compounds of formula I are compounds wherein R$^{13}$ is selected from:

a) R$^{11}$ and —(C$_1$-C$_6$)alkyl-R$^{11}$, wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl, wherein aryl, heterocycle and heteroaryl are each optionally substituted with one or more (e.g. 1, 2 or 3) Z$^H$ groups;

b) —(C$_1$-C$_6$)alkyl-N(R$^9$)R$^{10}$, wherein each R$^9$ is independently selected from H, (C$_1$-C$_6$)alkyl and (C$_3$-C$_7$)cycloalkyl, and each R$^{10}$ is independently selected from R$^{11}$, —(C$_1$-C$_6$)alkyl-R$^{11}$, —SO$_2$—R$^{11}$, —C(=O)—R$^{11}$, —C(=O)OR$^{11}$ and —C(=O)N(R$^9$)R$^{11}$, wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl, wherein aryl, heterocycle and heteroaryl are each optionally substituted with one or more (e.g. 1, 2 or 3) Z$^{11}$ groups;

c) (C$_1$-C$_6$)alkyl, wherein (C$_1$-C$_6$)alkyl is substituted with one or more Z$^2$ groups and optionally substituted with one or more (e.g. 1, 2, 3, 4 or 5) Z' groups;

d) aryl, heteroaryl, heterocycle, wherein aryl heteroaryl and heterocycle are each independently substituted with one or more (e.g. 1, 2, 3, 4 or 5) Z$^5$ groups and optionally substituted with one or more (e.g. 1, 2, 3, 4 or 5) Z$^1$ groups;

e) (C$_1$-C$_6$)haloalkyl, (C$_3$-C$_7$)carbocycle, (C$_2$-C$_6$)alkenyl and (C$_2$-C$_6$)alkynyl, wherein (C$_1$-C$_6$)haloalkyl, (C$_3$-C$_7$)carbocycle, (C$_2$-C$_6$)alkenyl and (C$_2$-C$_6$)alkynyl are each independently substituted with one or more (e.g. 1, 2, 3, 4 or 5) Z$^6$ groups and optionally substituted with one or more (e.g. 1, 2, 3, 4 or 5) Z$^1$ groups; and f) —(C$_1$-C$_6$)alkyl-NR$_e$R$_f$, wherein each (C$_1$-C$_6$)alkyl is optionally substituted with one or more (e.g. 1, 2, 3, 4 or 5) Z$^1$ groups.

Another specific group of compounds of formula I are compounds wherein R$^{13}$ is selected from:

a) R$^{11}$ and —(C$_1$-C$_6$)alkyl-R$^{11}$, wherein each R$^{11}$ is independently selected from (C$_1$-C$_6$)alkyl, aryl, heterocycle and heteroaryl, wherein aryl, heterocycle and heteroaryl are each optionally substituted with one or more (e.g. 1, 2 or 3) Z$^{11}$ groups; and b) —(C$_1$-C$_6$)alkyl-N(R$^9$)R$^{10}$, wherein each R$^9$ is independently selected from H and (C$_1$-C$_6$)alkyl, and each R$^{10}$ is independently selected from R$^{11}$, wherein each R$^{11}$ is independently selected from H, (C$_1$-C$_6$)alkyl and aryl, wherein aryl, is optionally substituted with one or more (e.g. 1, 2 or 3) Z$^{11}$ groups.

Another specific value for R$^{13}$ is H.
Another specific value for R$^{13}$ is:

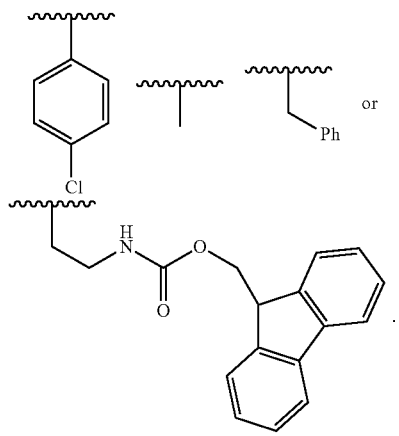

A specific group of compounds of formula I are compounds wherein $R_g$ is independently selected from —$OR_a$, $(C_1-C_6)$alkyl, $(C_3-C_7)$carbocycle $(C_1-C_6)$haloalkyl, $(C_2-C_6)$alkenyl, $(C_2-C_6)$alkynyl, aryl, heterocycle and heteroaryl, wherein any $(C_1-C_6)$alkyl, $(C_3-C_7)$carbocycle —$(C_1-C_6)$haloalkyl, $(C_2-C_6)$alkenyl, $(C_2-C_6)$alkynyl, aryl, heterocycle and heteroaryl of $R_g$ is optionally substituted with one or more (e.g. 1, 2, 3, 4 or 5) $Z^1$ groups.

In one embodiment, the invention provides a compound of the invention which is a compound of formula I:
wherein:
$G^1$ is N; $G^2$ is $CR^8$; and the dashed bond is a double bond;
or
$G^1$ is $CR^5$; $G^2$ is N; and the dashed bond is a double bond;
or
$G^1$ is $CR^5$; $G^2$ is $NR^{13}$; the dashed bond is a single bond; and $R^7$ is an oxo (=O) group;
$R^2$ is $R^{2a}$ or $R^{2b}$;
$R^3$ is $R^{3a}$ or $R^{3b}$;
$R^{3'}$ is $R^{3a'}$ or $R^{3b'}$;
$R^4$ is $R^{4a}$ or $R^{4b}$;
$R^5$ is $R^{5a}$ or $R^{5b}$;
$R^6$ is $R^{6a}$ or $R^{6b}$;
$R^7$ is $R^{7a}$ or $R^{7b}$;
$R^8$ is $R^{8a}$ or $R^{8b}$;
$R^{13}$ is $R^{13a}$ or $R^{13b}$;
$R^{1a}$ is selected from:
a) H, halo, $(C_1-C_6)$alkyl and $(C_1-C_6)$haloalkyl;
b) $(C_2-C_6)$alkenyl, $(C_2-C_6)$alkynyl, $(C_3-C_7)$cycloalkyl, nitro, cyano, aryl, heterocycle and heteroaryl;
c) —C(=O)—$R^{11}$, —C(=O)—O—$R^{11}$, —O—$R^{11}$, —S—$R^{11}$, —S(O)—$R^{11}$, —$SO_2$—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-$SO_2$—$R^{11}$; wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl; and
d) —N($R^9$)$R^{10}$, —C(=O)—N($R^9$)$R^{10}$, —O—C(=O)—N($R^9$)$R^{10}$, —$SO_2$—N($R^9$)$R^{10}$, —$(C_1-C_6)$alkyl-N($R^9$)$R^{10}$, —$(C_1-C_6)$alkyl-C(=O)—N($R^9$)$R^{10}$, —$(C_1-C_6)$alkyl-O—C(=O)—N($R^9$)$R^{10}$ and —$(C_1-C_6)$alkyl-$SO_2$—N($R^9$)$R^{10}$; wherein each $R^9$ is independently selected from H, $(C_1-C_6)$alkyl and $(C_3-C_7)$cycloalkyl; and
each $R^{10}$ is independently selected from $R^{11}$, —$(C_1-C_6)$alkyl-$R^{11}$, —$SO_2$—$R^{11}$, —C(=O)—$R^{11}$, —C(=O)$OR^{11}$ and —C(=O)N($R^9$)$R^{11}$; wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl; and
wherein any aryl, heterocycle or heteroaryl of $R^{1a}$ is optionally substituted with one or more (e.g. 1, 2 or 3) $Z^{10}$ groups;

$R^{1b}$ is selected from:
a) —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkyl-S(O)—$(C_1-C_6)$alkyl-$(C_3-C_7)$carbocycle, —$(C_1-C_6)$alkyl-$SO_2$—$(C_1-C_6)$alkyl-$(C_3-C_7)$carbocycle, —$(C_1-C_6)$alkyl-$SO_2$—$(C_1-C_6)$alkyl-$Z^{13}$, —C(O)—$(C_1-C_6)$alkyl-$Z^{13}$, —O—$(C_1-C_6)$alkyl-$Z^{13}$, —S—$(C_1-C_6)$alkyl-$Z^{13}$, —S(O)—$(C_1-C_6)$alkyl-$Z^{13}$, —$SO_2$—$(C_1-C_6)$alkyl-$Z^{13}$, —$(C_1-C_6)$alkyl-$Z^{14}$, —$(C_1-C_6)$alkyl-C(O)—$(C_1-C_6)$alkyl-$Z^{13}$, —$(C_1-C_6)$alkyl-C(O)—O—$(C_1-C_6)$alkyl-$Z^{13}$, —$(C_1-C_6)$alkyl-O—$(C_1-C_6)$alkyl-$Z^{13}$, —$(C_1-C_6)$alkyl-S—$(C_1-C_6)$alkyl-$Z^{13}$, —$(C_2-C_6)$alkenyl-$(C_1-C_6)$haloalkyl, —$(C_2-C_6)$alkynyl-$(C_1-C_6)$haloalkyl, —$(C_3-C_7)$halocarbocycle, —$NR_aSO_2NR_cR_d$, —$NR_aSO_2O(C_3-C_7)$carbocycle, —$NR_aSO_2O$aryl, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$allynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$carbocycle-$Z^1$ or -halo$(C_1-C_6)$alkyl-$Z^3$; wherein $(C_1-C_6)$alkyl, $(C_1-C_6)$haloalkyl, $(C_3-C_7)$carbocycle, $(C_2-C_6)$alkenyl, $(C_2-C_6)$alkynyl, aryl or heteroaryl are each optionally substituted with one or more (e.g. 1, 2, 3, 4 or 5) $Z^1$ groups;
b) spiro-bicyclic carbocycle, fused-bicyclic carbocycle and bridged-bicyclic carbocycle; wherein Spiro-bicyclic carbocycle, fused-bicyclic carbocycle or bridged-bicyclic carbocycle are optionally substituted with one or more (e.g. 1, 2, 3, 4 or 5) $Z^1$ groups; wherein two $Z^1$ groups together with the atom or atoms to which they are attached optionally form a carbocycle or heterocycle wherein the carbocycle or heterocycle is optionally substituted with one or more (e.g. 1, 2, 3, 4 or 5) $Z^1$ groups;
c) $(C_1-C_6)$alkyl; wherein $(C_1-C_6)$alkyl is substituted with one or more $Z^2$ groups and optionally substituted with one or more (e.g. 1, 2, 3, 4 or 5) $Z^1$ groups;
d) —X$(C_1-C_6)$alkyl, —X$(C_1-C_6)$haloalkyl, —X$(C_2-C_6)$alkenyl, —X$(C_2-C_6)$alkynyl and —X$(C_3-C_7)$carbocycle; wherein $(C_1-C_6)$alkyl and $(C_1-C_6)$haloalkyl are each substituted with one or more $Z^3$ groups and optionally substituted with one or more $Z^1$ groups; and wherein $(C_2-C_6)$alkenyl, $(C_2-C_6)$alkynyl and $(C_3-C_7)$carbocycle are each substituted with one or more (e.g. 1, 2, 3, 4 or 5) $Z^4$ groups and optionally substituted with one or more $Z^1$ groups;
e) aryl, heteroaryl, heterocycle, —Xaryl, —Xheteroaryl and —Xheterocycle; wherein aryl heteroaryl and heterocycle are each substituted with one or more (e.g. 1, 2, 3, 4 or 5) $Z^5$ groups and optionally substituted with one or more $Z^1$ groups;
f) $(C_1-C_6)$haloalkyl, $(C_3-C_7)$carbocycle, $(C_2-C_6)$alkenyl, and $(C_2-C_6)$alkynyl; wherein $(C_1-C_6)$haloalkyl, $(C_3-C_7)$carbocycle, $(C_2-C_6)$alkenyl and $(C_2-C_6)$alkynyl are each substituted with one or more (e.g. 1, 2, 3, 4 or 5) $Z^6$ groups and optionally substituted with one or more $Z^1$ groups; and
g) —$NR_eR_f$, —C(O)$NR_eR_f$, —OC(O)$NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—C(O)—$NR_eR_f$ and —$(C_1-C_6)$alkyl-$SO_2NR_eR_f$; wherein each $(C_1-C_6)$alkyl is substituted with one or more (e.g. 1, 2, 3, 4 or 5) $Z^6$ groups and optionally substituted with one or more $Z^1$ groups;

$R^{2a}$ is selected from:
a) H, $(C_1-C_6)$alkyl and —O$(C_1-C_6)$alkyl;
b) $(C_2-C_6)$alkenyl, $(C_2-C_6)$alkynyl, $(C_1-C_6)$haloalkyl, $(C_3-C_7)$cycloalkyl, aryl, heterocycle, heteroaryl, halo, nitro and cyano;
c) C(=O)—$R^{11}$, —C(=O)—O—$R^{11}$, —S—$R^{11}$, —S(O)—$R^{11}$, —$SO_2$—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-$SO_2$—$R^{11}$; wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl and heterocycle and heteroaryl; wherein aryl, heterocycle or heteroaryl are each optionally substituted with one or more (e.g. 1, 2 or 3) $Z^{11}$ groups;
d) —OH, —O$(C_2-C_6)$alkenyl, —O$(C_2-C_6)$alkynyl, —O$(C_1-C_6)$haloalkyl, —O$(C_3-C_7)$cycloalkyl, —Oaryl, —Oheterocycle and —Oheteroaryl; and
e) —N($R^9$)$R^{10}$, —C(=O)—N($R^9$)$R^{10}$, —O—C(=O)—N($R^9$)$R^{10}$, —$SO_2$—N($R^9$)$R^{10}$, —$(C_1-C_6)$alkyl-N($R^9$)$R^{10}$, —$(C_1-C_6)$alkyl-C(=O)—N($R^9$)$R^{10}$, —$(C_1-C_6)$alkyl-O—C(=O)—N($R^9$)$R^{10}$, and —$(C_1-C_6)$alkyl-$SO_2$—N($R^9$)$R^{10}$; wherein each $R^9$ is independently selected from H, $(C_1-C_6)$ alkyl and $(C_3-C_7)$cycloalkyl; and each $R^{10}$ is independently selected from $R^{11}$, $—(C_1-C_6)$alkyl-$R^{11}$, $—SO_2—R^{11}$, $—C(=O)—R^{11}$, $—C(=O)OR^{11}$ and $—C(=O)N(R^9)R^{11}$; wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl;

$R^{26}$ is selected from:

a) $—(C_1-C_6)$alkyl-O$—(C_1-C_6)$alkyl-$(C_3-C_7)$carbocycle, $—(C_1-C_6)$alkyl-S$—(C_1-C_6)$alkyl-$(C_3-C_7)$carbocycle, $—(C_1-C_6)$alkyl-S(O)$—(C_1-C_6)$alkyl-$(C_3-C_7)$carbocycle, $—(C_1-C_6)$alkyl-SO$_2$$—(C_1-C_6)$alkyl-$(C_3-C_7)$carbocycle, $—(C_2-C_6)$alkenyl-$(C_1-C_6)$haloalkyl, $—(C_2-C_6)$alkynyl-$(C_1-C_6)$haloalkyl, $—(C_1-C_6)$alkyl-SO$_2$$—(C_1-C_6)$alkyl-$Z^{13}$, $—C(O)—(C_1-C_6)$alkyl-$Z^{13}$, $—O—(C_1-C_6)$alkyl-$Z^{13}$, $—S—(C_1-C_6)$alkyl-$Z^{13}$, $—S(O)—(C_1-C_6)$alkyl-$Z^{13}$, $—SO_2—(C_1-C_6)$alkyl-$Z^{13}$, $—(C_1-C_6)$alkyl-$Z^{14}$, $—(C_1-C_6)$alkyl-C(O)—(C_1-C_6)$alkyl-$Z^{13}$, $—(C_1-C_6)$alkyl-C(O)—O(C_1-C_6)$alkyl-$Z^{13}$, $—(C_1-C_6)$alkyl-O—(C_1-C_6)$alkyl-$Z^{13}$, $—(C_1-C_6)$alkyl-S—(C_1-C_6)$alkyl-$Z^{13}$, $—(C_3-C_7)$halocarbocycle, $—NR_aSO_2NR_cR_d$, $—NR_aSO_2O(C_3-C_7)$carbocycle, $—NR_aSO_2Oaryl$, $—(C_2-C_6)$alkenyl-$(C_3-C_7)$carbocycle, $—(C_2-C_6)$alkenyl-aryl, $—(C_2-C_6)$alkenyl-heteroaryl, $—(C_2-C_6)$alkenyl-heterocycle, $—(C_2-C_6)$alkynyl-$(C_3-C_7)$carbocycle, $—(C_2-C_6)$alkynyl-aryl, $—(C_2-C_6)$alkynyl-heteroaryl, $—(C_2-C_6)$alkynyl-heterocycle, $—(C_3-C_7)$carbocycle-$Z^1$ or -halo$(C_1-C_6)$alkyl-$Z^3$; wherein $(C_1-C_6)$alkyl, $(C_1-C_6)$haloalkyl, $(C_3-C_7)$carbocycle, $(C_2-C_6)$alkenyl, $(C_2-C_6)$alkynyl, aryl or heteroaryl are each optionally substituted with one or more (e.g. 1, 2, 3, 4 or 5) $Z^1$ groups;

b) spiro-bicyclic carbocycle, fused-bicyclic carbocycle and bridged-bicyclic carbocycle; wherein spiro-bicyclic carbocycle, fused-bicyclic carbocycle or bridged-bicyclic carbocycle are optionally substituted with one or more (e.g. 1, 2, 3, 4 or 5) $Z^1$ groups; wherein two $Z^1$ groups together with the atom or atoms to which they are attached optionally form a $(C_3-C_7)$carbocycle or heterocycle wherein the $(C_3-C_6)$carbocycle or heterocycle is optionally substituted with one or more (e.g. 1, 2, 3, 4 or 5) $Z^1$ groups;

c) $(C_1-C_6)$alkyl; wherein $(C_1-C_6)$alkyl is substituted with one or more $Z^2$ groups and optionally substituted with one or more (e.g. 1, 2, 3, 4 or 5) $Z^1$ groups;

d) $—X(C_1-C_6)$alkyl, $X(C_1-C_6)$haloalkyl, $X(C_2-C_6)$alkenyl, $—X(C_2-C_6)$alkynyl and $—X(C_3-C_7)$carbocycle; wherein $(C_1-C_6)$alkyl and $(C_1-C_6)$haloalkyl are each substituted with one or more $Z^3$ groups and optionally substituted with one or more (e.g. 1, 2, 3, 4 or 5) $Z^1$ groups; and wherein $(C_2-C_6)$alkenyl, $(C_2-C_6)$alkynyl and $(C_3-C_7)$carbocycle are each substituted with one or more (e.g. 1, 2, 3, 4 or 5) $Z^4$ groups and optionally substituted with one or more $Z^1$ groups;

e) aryl, heteroaryl, heterocycle, $—Xaryl$, $—Xheteroaryl$ and $—Xheterocycle$; wherein aryl heteroaryl and heterocycle are each substituted with one or more (e.g. 1, 2, 3, 4 or 5) $Z^5$ groups and optionally substituted with one or more (e.g. 1, 2, 3, 4 or 5) $Z^1$ groups;

f) $(C_1-C_6)$haloalkyl, $(C_3-C_7)$carbocycle, $(C_2-C_6)$alkenyl, and $(C_2-C_6)$alkynyl; wherein $(C_1-C_6)$haloalkyl, $(C_3-C_7)$carbocycle, $(C_2-C_6)$alkenyl and $(C_2-C_6)$alkynyl are each substituted with one or more (e.g. 1, 2, 3, 4 or 5) $Z^6$ groups and optionally substituted with one or more (e.g. 1, 2, 3, 4 or 5) $Z^1$ groups; and g) $—NR_eR_f$, $—C(O)NR_eR_f$, $—OC(O)NR_eR_f$, $—SO_2NR_eR_f$, $—(C_1-C_6)$alkyl-$NR_eR_f$, $—(C_1-C_6)$alkylC(O)—NR_eR_f$, $—(C_1-C_6)$alkyl-O—C(O)—NR_eR_f$ and $—(C_1-C_6)$alkyl-SO$_2$NR$_e$R$_f$; wherein each $(C_1-C_6)$alkyl is substituted with one or more (e.g. 1, 2, 3, 4 or 5) $Z^6$ groups and optionally substituted with one or more (e.g. 1, 2, 3, 4 or 5) $Z^1$ groups;

$R^{3a}$ is $(C_1-C_6)$alkyl, $(C_1-C_6)$haloalkyl, $(C_2-C_6)$alkenyl, $(C_2-C_6)$alkynyl, $—(C_1-C_6)$alkyl-$(C_3-C_7)$cycloalkyl, $—(C_1-C_6)$alkyl-aryl, $—(C_1-C_6)$alkyl-heterocycle, $—(C_1-C_6)$alkyl-heteroaryl, $—O(C_1-C_6)$alkyl, $—O(C_1-C_6)$haloalkyl, $—O(C_2-C_6)$alkenyl, $—O(C_2-C_6)$alkynyl, $—O(C_3-C_7)$cycloalkyl, $—Oaryl$, $—O(C_1-C_6)$alkyl-$(C_3-C_7)$cycloalkyl, $—O(C_1-C_6)$alkyl-aryl, $—O(C_1-C_6)$alkyl-heterocycle and $—O(C_1-C_6)$alkyl-heteroaryl; wherein any $(C_1-C_6)$alkyl, $(C_1-C_6)$haloalkyl, $(C_2-C_6)$alkenyl or $(C_2-C_6)$alkynyl of $R^{3a}$ is optionally substituted with one or more (e.g. 1, 2 or 3) groups selected from $—O(C_1-C_6)$alkyl, halo, oxo and $—CN$; and wherein any $(C_3-C_7)$cycloalkyl, aryl, heterocycle, or heteroaryl of $R^{3a}$ is optionally substituted with one or more (e.g. 1, 2 or 3) groups selected from $(C_1-C_6)$alkyl, $—O(C_1-C_6)$alkyl, halo, oxo and $—CN$; and $R^{3a'}$ is H;

$R^{3b}$ is $—(C_3-C_7)$carbocycle, aryl, heteroaryl, heterocycle, $—(C_1-C_6)$alkylOH, $—(C_1-C_6)$alkyl-O—(C_1-C_6)$alkyl-$Z^{12}$, $—(C_1-C_6)$alkyl-O—(C_2-C_6)$alkenyl-$Z^{12}$, $—(C_2-C_6)$alkyl-O—(C_2-C_6)$alkynyl-$Z^{12}$, $—(C_1-C_6)$alkyl-S—(C_1-C_6)$alkyl-$Z^{12}$, $—(C_1-C_6)$alkyl-S—(C_2-C_6)$alkenyl-$Z^{12}$, $—(C_2-C_6)$alkyl-S—(C_2-C_6)$alkynyl-$Z^{12}$, $—(C_1-C_6)$alkyl-S(O)—(C_1-C_6)$alkyl-$Z^{12}$, $—(C_1-C_6)$alkyl-S(O)—(C_2-C_6)$alkenyl-$Z^{12}$, $—(C_2-C_6)$alkyl-S(O)—(C_2-C_6)$alkynyl-$Z^{12}$, $—(C_1-C_6)$alkyl-SO$_2$—(C_1-C_6)$alkyl-$Z^{12}$, $—(C_1-C_6)$alkyl-SO$_2$—(C_2-C_6)$alkenyl-$Z^{12}$, $—(C_2-C_6)$alkyl-SO$_2$—(C_2-C_6)$alkynyl-$Z^{12}$, $—(C_2-C_6)$alkyl-$NR_aR_b$, $—(C_2-C_6)$alkylOC(O)—$NR_cR_d$, $—(C_2-C_6)$alkyl-$NR_a—C(O)—OR_b$, $—(C_2-C_6)$alkyl-$NR_a—C(O)—NR_aR_b$, $—(C_1-C_6)$alkyl-SO$_2$($C_1-C_6$)alkyl, $—(C_1-C_6)$alkyl-SO$_2$NR$_c$R$_d$, $—(C_1-C_6)$alkyl-$NR_aSO_2NR_cR_d$, $—(C_1-C_6)$alkyl-$NR_aSO_2O(C_3-C_7)$carbocycle, $—(C_1-C_6)$alkyl-$NR_aSO_2Oaryl$, $—(C_1-C_6)$alkyl-$NR_a—SO_2—(C_1-C_6)$alkyl, $—(C_1-C_6)$alkyl-$NR_a—SO_2$-halo$(C_1-C_6)$alkyl, $—(C_1-C_6)$alkyl-$NR_a—SO_2—(C_2-C_6)$alkenyl, $—(C_1-C_6)$alkyl-$NR_a—SO_2—(C_2-C_6)$alkynyl, $—(C_1-C_6)$alkyl-$NR_a—SO_2—(C_3-C_7)$carbocycle, $—(C_1-C_6)$alkyl-$NR_a—SO_2$-halo$(C_3-C_7)$carbocycle, $—(C_1-C_6)$alkyl-$NR_a—SO_2$-aryl, $—(C_1-C_6)$alkyl-$NR_a—SO_2$-heteroaryl, $—(C_1-C_6)$alkyl-$NR_a—SO_2$-heterocycle, $—O(C_1-C_6)$alkyl-$NR_aR_b$, $—O(C_1-C_6)$alkylOC(O)—$NR_cIt_d$, $—O(C_1-C_6)$alkyl-$NR_a—C(O)—OR_b$, $—O(C_1-C_6)$alkyl-$NR_a—C(O)—NR_aR_b$, $—O(C_1-C_6)$alkyl-$NR_a—SO_2—(C_1-C_6)$alkyl, $—O(C_1-C_6)$alkyl-$NR_a—SO_2$-halo$(C_1-C_6)$alkyl, $—O(C_1-C_6)$alkyl-$NR_a—SO_2—(C_2-C_6)$alkenyl, $—O(C_1-C_6)$alkyl-$NR_a—SO_2—(C_2-C_6)$alkynyl, $—O(C_1-C_6)$alkyl-$NR_a—SO_2—(C_3-C_7)$carbocycle, $—O(C_1-C_6)$alkyl-$NR_a—SO_2$-halo$(C_3-C_7)$carbocycle, $—O(C_1-C_6)$alkyl-$NR_a—SO_2$-aryl, $—O(C_1-C_6)$alkyl-$NR_a—SO_2$-heteroaryl, $—O(C_1-C_6)$alkyl-$NR_a—SO_2$-heterocycle, $—O(C_1-C_6)$alkyl-$NR_a—SO_2—NR_aR_b$, $—O(C_1-C_6)$alkyl-$NR_a—SO_2—(C_3-C_7)$carbocycle, $—O(C_1-C_6)$alkyl-$NR_a—SO_2$-halo$(C_3-C_7)$carbocycle, $—O(C_1-C_6)$alkyl-$NR_a—SO_2$-aryl, $—O(C_1-C_6)$alkyl-$NR_aSO_2NR_cR_3$, $—O(C_1-C_6)$alkyl-$NR_aSO_2O(C_3-C_7)$carbocycle, $—O(C_1-C_6)$alkyl-$NR_aSO_2Oaryl$, $—Oheteroaryl$, $—Oheterocycle$, $—Sheteroaryl$, $—Sheterocycle$, $—S(O)heteroaryl$, $—S(O)heterocycle$, $—SO_2heteroaryl$ or $—SO_2heterocycle$; wherein any $(C_1-C_6)$alkyl, aryl, $(C_3-C_7)$carbocycle, heteroaryl or heterocycle of $R^{3b}$ is optionally substituted with one or more (e.g. 1, 2, 3, 4 or 5) $Z^1$ groups; and $R^{3b'}$ is H, $(C_1-C_6)$alkyl or $—O(C_1-C_6)$alkyl; or $R^{3b}$ and $R^{3b'}$ together with the carbon to which they are attached form a heterocycle or $(C_3-C_7)$carbocycle which heterocycle or $(C_3-C_7)$carbocycle of $R^{3b}$ and $R^{3b'}$ together with the carbon to which they are attached is optionally substituted with one or more (e.g. 1, 2, 3, 4 or 5) $Z^1$ groups;

$R^{4a}$ is selected from aryl, heterocycle and heteroaryl, wherein any aryl, heterocycle and heteroaryl of $R^{4a}$ is optionally substituted with one or more (e.g. 1, 2, 3, 4 or 5) groups each independently selected from halo, $(C_1-C_6)$alkyl, $(C_2-C_6)$alkenyl, $(C_1-C_6)$haloalkyl, $(C_3-C_7)$cycloalkyl, —OH, —O$(C_1-C_6)$alkyl, —SH, —S$(C_1-C_6)$alkyl, —NH$_2$, —NH$(C_1-C_6)$alkyl and —N$((C_1-C_6)$alkyl$)_2$; wherein $(C_1-C_6)$alkyl is optionally substituted with hydroxy, —O$(C_1-C_6)$alkyl, cyano or oxo;

$R^{4b}$ is selected from:

a) $(C_1-C_6)$alkyl, $(C_2-C_6)$alkenyl and $(C_2-C_6)$alkynyl; wherein $(C_1-C_6)$alkyl, $(C_2-C_6)$alkenyl or $(C_2-C_6)$alkynyl are each optionally substituted with one or more (e.g. 1, 2, 3, 4 or 5) $Z^1$ groups;

b) $(C_3-C_{14})$carbocycle; wherein $(C_3-C_{14})$carbocycle is optionally substituted with one or more (e.g. 1, 2, 3, 4 or 5) $Z^1$ groups; wherein two $Z^1$ groups together with the atom or atoms to which they are attached optionally form a $(C_3-C_7)$ carbocycle or heterocycle;

c) Spiro-heterocycle or bridged-heterocycle; wherein Spiro-heterocycle or bridged-heterocycle is optionally substituted with one or more (e.g. 1, 2, 3, 4 or 5) $Z^1$ groups; or wherein two $Z^1$ groups together with the atom or atoms to which they are attached optionally form a $(C_3-C_7)$carbocycle or heterocycle; and d) aryl, heteroaryl, spiro-, fused-, or bridged-heterocycle; wherein aryl, heteroaryl, or spiro-, fused-, or bridged-heterocycle are each independently substituted with one or more $Z^7$ groups and optionally substituted with one or more (e.g. 1, 2, 3, 4 or 5) $Z^1$ groups; or $R^4$ and $R^3$ together with the atoms to which they are attached form a macroheterocycle or a macrocarbocycle wherein any macroheterocycle or macrocarbocycle of $R^4$ and $R^3$ together with the atoms to which they are attached may be optionally substituted with one or more (e.g. 1, 2, 3, 4 or 5) $Z^1$ groups; and $R^{3b'}$ is H or $(C_1-C_6)$alkyl, —O$(C_1-C_6)$alkyl.

$R^{5a}$ is selected from:

a) halo, nitro and cyano;

b) $R^{11}$, —C(=O)—$R^{11}$, —C(=O)—O—$R^{11}$, —O—$R^{11}$, —S—$R^{11}$, —S(O)—$R^{11}$, —SO$_2$—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, O—$R^{11}$, —$(C_1-C_6)$alkyl-S—$R^{11}$, —$(C_1-C_6)$alkyl-S(O)—$R^{11}$ and —$(C_1-C_6)$alkyl-SO$_2$—$R^{11}$; wherein each $R^{11}$ is independently selected from H, $(C_1-C_6)$alkyl, $(C_2-C_6)$alkenyl, $(C_2-C_6)$allynyl, $(C_1-C_6)$haloalkyl, $(C_3-C_7)$cycloalkyl, aryl, heterocycle and heteroaryl; wherein aryl, heterocycle and heteroaryl are each optionally substituted with one or more (e.g. 1, 2 or 3) $Z^{11}$ groups;

c) —N$(R^9)R^{10}$, —C(=O)—N$(R^9)R^{10}$, —O—C(=O)—N$(R^9)R^{10}$, SO$_2$—N$(R^9)R^{10}$, —$(C_1-C_6)$alkyl-N$(R^9)R^{10}$, —$(C_1-C_6)$alkyl-C(=O)—N$(R^9)R^{10}$, —$(C_1-C_6)$alkyl-O—C(=O)—N$(R^9)R^{10}$, and —$(C_1-C_6)$alkyl-SO$_2$—N$(R^9)R^{10}$; wherein each $R^9$ is independently selected from H, $(C_1-C_6)$alkyl and $(C_3-C_7)$cycloalkyl; and each $R^{10}$ is independently selected from $R^{11}$, —$(C_1-C_6)$alkyl-$R^{11}$, —SO$_2$—$R^{11}$, —C(=O)—$R^{11}$, —C(=O)O$R^{11}$ and —C(=O)N$(R^9)R^{11}$; wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl;

$R^{5b}$ is selected from:

a) —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkylS(O)—$(C_1-C_6)$alkyl-$(C_3-C_6)$carbocycle, —$(C_1-C_6)$alkylSO$_2$$(C_1-C_6)$alkyl-$(C_3-C_7)$carbocycle, —$(C_2-C_6)$alkenyl-$(C_1-C_6)$haloalkyl, —$(C_2-C_6)$allynyl$(C_1-C_6)$haloalkyl, —$(C_3-C_7)$halocarbocycle, —NR$_a$SO$_2$NR$_c$R$_d$, NR$_a$SO$_2$O$(C_3-C_7)$carbocycle, —NR$_a$SO$_2$Oaryl, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$carbocycle-$Z^1$ or -halo$(C_1-C_6)$alkyl-$Z^3$; wherein $(C_1-C_6)$alkyl, $(C_1-C_6)$haloalkyl, $(C_3-C_7)$carbocycle, $(C_2-C_6)$alkenyl, $(C_2-C_6)$alkynyl, aryl or heteroaryl are each optionally substituted with one or more (e.g. 1, 2, 3, 4 or 5) $Z^1$ groups;

b) spiro-bicyclic carbocycle, fused-bicyclic carbocycle and bridged-bicyclic carbocycle; wherein spiro-bicyclic carbocycle, fused-bicyclic carbocycle or bridged-bicyclic carbocycle are optionally substituted with one or more (e.g. 1, 2, 3, 4 or 5) $Z^1$ groups; wherein two $Z^1$ groups together with the atom or atoms to which they are attached optionally form a $(C_3-C_7)$carbocycle or heterocycle wherein the $(C_3-C_7)$carbocycle or heterocycle is optionally substituted with one or more (e.g. 1, 2, 3, 4 or 5) $Z^1$ groups;

c) $(C_1-C_6)$alkyl; wherein $(C_1-C_6)$alkyl is substituted with one or more $Z^2$ groups and optionally substituted with one or more (e.g. 1, 2, 3, 4 or 5) $Z^1$ groups;

d) —X$(C_1-C_6)$alkyl, —X$(C_1-C_6)$haloalkyl, —X$(C_2-C_6)$alkenyl, —X$(C_2-C_6)$alkynyl and —X$(C_3-C_7)$carbocycle; wherein $(C_1-C_6)$alkyl or $(C_1-C_6)$haloalkyl are each substituted with one or more $Z^3$ groups and optionally substituted with one or more $Z^1$ groups; and wherein $(C_2-C_6)$alkenyl, $(C_2-C_6)$alkynyl and $(C_3-C_7)$carbocycle are each independently substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle; wherein aryl heteroaryl are heterocycle are each independently substituted with one or more (e.g. 1, 2, 3, 4 or 5) $Z^5$ groups and optionally substituted with one or more (e.g. 1, 2, 3, 4 or 5) $Z^1$ groups;

f) $(C_1-C_6)$haloalkyl, $(C_3-C_7)$carbocycle, $(C_2-C_6)$alkenyl, and $(C_2-C_6)$alkynyl; where $(C_1-C_6)$haloalkyl, $(C_3-C_7)$carbocycle, $(C_2-C_6)$alkenyl and $(C_2-C_6)$alkynyl are each independently substituted with one or more (e.g. 1, 2, 3, 4 or 5) $Z^6$ groups and optionally substituted with one or more (e.g. 1, 2, 3, 4 or 5) $Z^1$ groups; and g) —NR$_e$R$_f$, —C(O)NR$_e$R$_f$, —OC(O)NR$_e$R$_f$, —SO$_2$NR$_e$R$_f$, —$(C_1-C_6)$alkyl-NR$_e$R$_f$, —$(C_1-C_6)$alkylC(O)—NR$_e$R$_f$, —$(C_1-C_6)$alkyl-O—C(O)—NR$_e$R$_f$ and —$(C_1-C_6)$alkyl-SO$_2$NR$_e$R$_f$; wherein each $(C_1-C_6)$alkyl is independently substituted with one or more (e.g. 1, 2, 3, 4 or 5) $Z^6$ groups and optionally substituted with one or more (e.g. 1, 2, 3, 4 or 5) $Z^1$ groups;

$R^{6a}$ is selected from:

a) H, halo, $(C_1-C_6)$alkyl, and $(C_1-C_6)$haloalkyl b) $(C_2-C_6)$alkenyl, $(C_2-C_6)$alkynyl, $(C_3-C_7)$cycloalkyl, nitro, cyano, aryl, heterocycle or heteroaryl;

c) —C(=O)—$R^{11}$, —C(=O)—O—$R^{11}$, —O—$R^{11}$, —S—$R^{11}$, —S(O)—$R^{11}$, —SO$_2$—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-SO$_2$—$R^{11}$; wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl; and d) —N$(R^9)R^{10}$, —C(=O)—N$(R^9)R^{10}$, —O—C(=O)—N$(R^9)R^{10}$, —SO$_2$—N$(R^9)R^{10}$, —$(C_1-C_6)$alkyl-N$(R^9)R^{10}$, —$(C_1-C_6)$alkyl-C(=O)—N$(R^9)R^{16}$, —$(C_1-C_6)$alkyl-O—C(=O)—N$(R^9)R^{10}$ and —$(C_1-C_6)$alkyl-SO$_2$—N$(R^9)R^{16}$; wherein each $R^9$ is independently selected from H, $(C_1-C_6)$alkyl and $(C_3-C_7)$cycloalkyl; and each $R^{10}$ is independently selected from $R^{11}$, —($C_1$-$C_6$)alkyl-$R^{11}$, —$SO_2$—$R^{11}$, —C(=O)—$R^{11}$, —C(=O)O$R^{11}$ and —C(=O)N($R^9$)$R^{11}$; wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl; and wherein any aryl, heterocycle or heteroaryl of $R^{1a}$ is optionally substituted with one or more (e.g. 1, 2 or 3) $Z^{10}$ groups;

$R^{6b}$ is selected from:
  a) —($C_1$-$C_6$)alkyl-O—($C_1$-$C_6$)alkyl-($C_3$-$C_7$)carbocycle, —($C_1$-$C_6$)alkyl-S—(C $C_6$)alkyl-($C_3$-$C_7$)carbocycle, —($C_1$-$C_6$)alkyl-S(O)—($C_1$-$C_6$)alkyl-($C_3$-$C_7$)carbocycle, —($C_1$-$C_6$)alkyl-$SO_2$—($C_1$-$C_6$)alkyl-($C_3$-$C_7$)carbocycle, —($C_2$-$C_6$)alkenyl-($C_1$-$C_6$)haloalkyl, —($C_2$-$C_6$)alkynyl-($C_1$-$C_6$)haloalkyl, -halo($C_3$-$C_7$)carbocycle, —$NR_aSO_2NR_cR_d$, —$NR_aSO_2O$($C_3$-$C_7$)carbocycle, —$NR_aSO_2$Oaryl, —($C_2$-$C_6$)alkenyl-($C_3$-$C_7$)carbocycle, —($C_2$-$C_6$)alkenyl-aryl, —($C_2$-$C_6$)alkenyl-heteroaryl, —($C_2$-$C_6$)alkenyl-heterocycle, —($C_2$-$C_6$)alkynyl-($C_3$-$C_7$)carbocycle, —($C_2$-$C_6$)alkynyl-aryl, —($C_2$-$C_6$)alkynyl-heteroaryl, ($C_2$-$C_6$)alkynyl-heterocycle, —($C_3$-$C_7$)carbocycle-$Z^1$ or -halo($C_1$-$C_6$)alkyl-$Z^3$; wherein ($C_1$-$C_6$)alkyl, ($C_1$-$C_6$)haloalkyl, ($C_3$-$C_7$)carbocycle, ($C_2$-$C_6$)alkenyl, ($C_2$-$C_6$)alkynyl, aryl or heteroaryl are optionally substituted with one or more (e.g. 1, 2, 3, 4 or 5) $Z^1$ groups;
  b) spiro-bicyclic carbocycle, fused-bicyclic carbocycle and bridged-bicyclic carbocycle; wherein spiro-bicyclic carbocycle, fused-bicyclic carbocycle or bridged-bicyclic carbocycle are optionally substituted with one or more (e.g. 1, 2, 3, 4 or 5) $Z^1$ groups; wherein two $Z^1$ groups together with the atom or atoms to which they are attached optionally form a carbocycle or heterocycle wherein the carbocycle or heterocycle is optionally substituted with one or more $Z^1$ groups;
  c) ($C_1$-$C_6$)alkyl; wherein ($C_1$-$C_6$)alkyl is substituted with one or more (e.g. 1, 2, 3, 4 or 5) $Z^2$ groups and optionally substituted with one or more (e.g. 1, 2, 3, 4 or 5) $Z^1$ groups;
  d) —X($C_1$-$C_6$)alkyl, —X($C_1$-$C_6$)haloalkyl, —X($C_2$-$C_6$)alkenyl, —X($C_2$-$C_6$)alkynyl and —X($C_3$-$C_7$)carbocycle; wherein ($C_1$-$C_6$)alkyl or ($C_1$-$C_6$)haloalkyl are each independently substituted with one or more (e.g. 1, 2, 3, 4 or 5) $Z^3$ groups and optionally substituted with one or more $Z^1$ groups; and wherein ($C_2$-$C_6$)alkenyl, ($C_2$-$C_6$)alkynyl and ($C_3$-$C_7$)carbocycle are each independently substituted with one or more $Z^4$ groups and optionally substituted with one or more (e.g. 1, 2, 3, 4 or 5) $Z^1$ groups;
  e) aryl, heteroaryl, heterocycle, —Xaryl, —Xheteroaryl and —Xheterocycle wherein aryl heteroaryl and heterocycle are each independently substituted with one or more $Z^5$ groups and optionally substituted with one or more (e.g. 1, 2, 3, 4 or 5) $Z^1$ groups;
  f) ($C_1$-$C_6$)haloalkyl, ($C_3$-$C_7$)carbocycle, ($C_2$-$C_6$)alkenyl, and ($C_2$-$C_6$)alkynyl; wherein ($C_1$-$C_6$)haloalkyl, ($C_3$-$C_7$)carbocycle, ($C_2$-$C_6$)alkenyl and ($C_2$-$C_6$)alkynyl are each independently substituted with one or more (e.g. 1, 2, 3, 4 or 5) $Z^6$ groups and optionally substituted with one or more (e.g. 1, 2, 3, 4 or 5) $Z^1$ groups; and
  g) —$NR_eR_f$, —C(O)$NR_eR_f$, —OC(O)$NR_eR_f$, —$SO_2NR_eR_f$, —($C_1$-$C_6$)alkyl-$NR_eR_f$, —($C_1$-$C_6$)alkylC(O)—$NR_eR_f$, —($C_1$-$C_6$)alkyl-O—C(O)—$NR_eR_f$ and —($C_1$-$C_6$)alkyl-$SO_2NRA_f$; wherein each ($C_1$-$C_6$)alkyl is independently substituted with one or more (e.g. 1, 2, 3, 4 or 5) $Z^6$ groups and optionally substituted with one or more (e.g. 1, 2, 3, 4 or 5) $Z^1$ groups;

$R^{7a}$ is selected from:
  a) H, halo, ($C_1$-$C_6$)alkyl and ($C_1$-$C_6$)haloalkyl;
  b) ($C_2$-$C_6$)alkenyl, ($C_2$-$C_6$)alkynyl, ($C_3$-$C_7$)cycloalkyl, nitro, cyano, aryl, heterocycle and heteroaryl;
  c) —C(=O)—$R^{11}$, —C(=O)—O—$R^{11}$, —O—$R^{11}$, —S—$R^{11}$, —S(O)—$R^{11}$, —$SO_2$—$R^{11}$, —($C_1$-$C_6$)alkyl-$R^{11}$, —($C_1$-$C_6$)alkyl-C(=O)—$R^{11}$, —$C_6$)alkyl-C(=O)—O—$R^{11}$, —($C_1$-$C_6$)alkyl-O—$R^{11}$, —($C_1$-$C_6$)alkyl-S—$R^{11}$ —($C_1$-$C_6$)alkyl-S(O)—$R^{11}$ and —($C_1$-$C_6$)alkyl-$SO_2$—$R^{11}$; wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl; and
  d) —N($R^9$)$R^{10}$, —C(=O)—N($R^9$)$R^{10}$, —O—C(=O)—N($R^9$)$R^{10}$, —$SO_2$—N($R^9$)$R^{10}$, —($C_1$-$C_6$)alkyl-N($R^9$)$R^{10}$, —($C_1$-$C_6$)alkyl-C(=O)—N($R^9$)$R^{10}$, —($C_1$-$C_6$)alkyl-O—C(=O)—N($R^9$)$R^{10}$ and —($C_1$-$C_6$)alkyl-$SO_2$—N($R^9$)$R^{10}$; wherein each $R^9$ is independently selected from H, ($C_1$-$C_6$)alkyl and ($C_3$-$C_7$)cycloalkyl; and each $R^{10}$ is independently selected from $R^{11}$, —($C_1$-$C_6$)alkyl-$R^{11}$, —$SO_2$—$R^{11}$, —C(=O)—$R^{11}$, —C(=O)O$R^{11}$ and —C(=O)N($R^9$)$R^{11}$; wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl; and wherein any aryl, heterocycle or heteroaryl of $R^{1a}$ is optionally substituted with one or more (e.g. 1, 2 or 3) $Z^{19}$ groups;

$R^{7b}$ is selected from:
  a) —($C_1$-$C_6$)alkyl-$SO_2$—($C_1$-$C_6$)alkyl-$Z^{13}$, —C(O)—($C_1$-$C_6$)alkyl-$Z^{13}$, —O—($C_1$-$C_6$)alkyl-$Z^{13}$, —S—($C_1$-$C_6$)alkyl-$Z^{13}$, —S(O)—($C_1$-$C_6$)alkyl-$Z^{13}$, —$SO_2$—($C_1$-$C_6$)alkyl-$Z^{13}$, —($C_1$-$C_6$)alkyl-$Z^{14}$, —($C_1$-$C_6$)alkyl-C(O)—($C_1$-$C_6$)alkyl-$Z^{13}$, —($C_1$-$C_6$)alkyl-C(O)—O($C_1$-$C_6$)alkyl-$Z^{13}$, —($C_1$-$C_6$)alkyl-O—($C_1$-$C_6$)alkyl-$Z^{13}$, —($C_1$-$C_6$)alkyl-S—($C_1$-$C_6$)alkyl-$Z^{13}$, —($C_1$-$C_6$)alkyl-O—($C_1$-$C_6$)alkyl-($C_3$-$C_7$)carbocycle, —($C_1$-$C_6$)alkyl-S—($C_1$-$C_6$)alkyl-($C_3$-$C_7$)carbocycle, —($C_1$-$C_6$)alkyl-S(O)—($C_1$-$C_6$)alkyl-($C_3$-$C_7$)carbocycle, —($C_1$-$C_6$)alkyl-$SO_2$—($C_1$-$C_6$)alkyl-($C_3$-$C_7$)carbocycle, —($C_2$-$C_6$)alkenyl-($C_1$-$C_6$)haloalkyl, —($C_2$-$C_6$)alkynyl-($C_1$-$C_6$)haloalkyl, —($C_3$-$C_7$)halocarbocycle, —$NR_aSO_2NR_cR_d$, —$NR_aSO_2O$($C_3$-$C_7$)carbocycle, —$NR_aSO_2$Oaryl, —($C_2$-$C_6$)alkenyl-($C_3$-$C_7$)carbocycle, —($C_2$-$C_6$)alkenyl-aryl, —($C_2$-$C_6$)alkenyl-heteroaryl, —($C_2$-$C_6$)alkenyl-heterocycle, ($C_2$-$C_6$)alkynyl-($C_3$-$C_7$)carbocycle, —($C_2$-$C_6$)alkynyl-aryl, —($C_2$-$C_6$)alkynyl-heteroaryl, —($C_2$-$C_6$)alkynyl-heterocycle, —($C_3$-$C_7$)carbocycle-$Z^1$ or -halo($C_1$-$C_6$)alkyl-$Z^3$; wherein ($C_1$-$C_6$)alkyl, ($C_1$-$C_6$)haloalkyl, ($C_3$-$C_7$)carbocycle, ($C_2$-$C_6$)alkenyl, ($C_2$-$C_6$)alkynyl, aryl or heteroaryl are each optionally substituted with one or more (e.g. 1, 2, 3, 4 or 5) $Z^1$ groups;
  b) spiro-bicyclic carbocycle, fused-bicyclic carbocycle and bridged-bicyclic carbocycle; wherein spiro-bicyclic carbocycle, fused-bicyclic carbocycle or bridged-bicyclic carbocycle are optionally substituted with one or more (e.g. 1, 2, 3, 4 or 5) $Z^1$ groups; wherein two $Z^1$ groups together with the atom or atoms to which they are attached optionally form a ($C_3$-$C_7$)carbocycle or heterocycle wherein the ($C_3$-$C_6$)carbocycle or heterocycle is optionally substituted with one or more (e.g. 1, 2, 3, 4 or 5) $Z^1$ groups;
  c) ($C_1$-$C_6$)alkyl; wherein ($C_1$-$C_6$)alkyl is substituted with one or more $Z^2$ groups and optionally substituted with one or more (e.g. 1, 2, 3, 4 or 5) $Z^1$ groups;
  d) —X($C_1$-$C_6$)alkyl, X($C_1$-$C_6$)haloalkyl, X($C_2$-$C_6$)alkenyl, —X($C_2$-$C_6$)alkynyl and —X($C_3$-$C_7$)carbocycle; wherein ($C_1$-$C_6$)alkyl and ($C_1$-$C_6$)haloalkyl are each substituted with one or more $Z^3$ groups and optionally substituted with one or more $Z^1$ groups; and wherein ($C_2$-$C_6$)alkenyl, ($C_2$-$C_6$)alkynyl and ($C_3$-$C_7$)carbocycle are each substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle; wherein aryl, heteroaryl and heterocycle are each substituted with one or more $Z^5$ groups and optionally substituted with one or more (e.g. 1, 2, 3, 4 or 5) $Z^1$ groups;

f) ($C_1$-$C_6$)haloalkyl, ($C_3$-$C_7$)carbocycle, ($C_2$-$C_6$)alkenyl and ($C_2$-$C_6$)alkynyl; wherein ($C_1$-$C_6$)haloalkyl, ($C_3$-$C_7$)carbocycle, ($C_2$-$C_6$)alkenyl and ($C_2$-$C_6$)alkynyl are each substituted with one or more $Z^6$ groups and optionally substituted with one or more (e.g. 1, 2, 3, 4 or 5) $Z^1$ groups; and g) —$NR_eR_f$, —C(O)$NR_eR_f$, —OC(O)$NR_eR_f$, —$SO_2NRA_f$, —($C_1$-$C_6$)alkyl-$NR_eR_f$, —($C_1$-$C_6$)alkylC(O)—$NR_eR_f$, —($C_1$-$C_6$)alkyl-O—C(O)—$NR_eR_f$ and —($C_1$-$C_6$)alkyl-$SO_2NR_eR_f$; wherein each ($C_1$-$C_6$)alkyl is substituted with one or more (e.g. 1, 2, 3, 4 or 5) $Z^6$ groups and optionally substituted with one or more (e.g. 1, 2, 3, 4 or 5) $Z^1$ groups;

$R^{8a}$ is selected from:

a) halo, nitro and cyano;

b) $R^{11}$, —C(=O)—$R^{11}$, —C(=O)—O—$R^{11}$, —O—$R^{11}$, —S—$R^{11}$, —S(O)—$R^{11}$, —$SO_2$—$R^{11}$, —($C_1$-$C_6$)alkyl-$R^{11}$, —($C_1$-$C_6$)alkyl-C(=O)—$R^{11}$, —($C_1$-$C_6$)alkyl-C(=O)—O—$R^{11}$, O—$R^{11}$, —($C_1$-$C_6$)alkyl-S—$R^{11}$, —($C_1$-$C_6$)alkyl-S(O)—$R^{11}$ and —($C_1$-$C_6$)alkyl-$SO_2$—$R^{11}$; wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl; wherein aryl, heterocycle and heteroaryl are each optionally substituted with one or more (e.g. 1, 2 or 3) $Z^{11}$ groups;

c) —N($R^9$)$R^{10}$, —C(=O)—N($R^9$)$R^{10}$, —O—C(=O)—N($R^9$)$R^{10}$, —$SO_2$—N($R^9$)$R^{10}$, —($C_1$-$C_6$)alkyl-N($R^9$)$R^{10}$, —($C_1$-$C_6$)alkyl-C(=O)—N($R^9$)$R^{10}$, —($C_1$-$C_6$)alkyl-O—C(=O)—N($R^9$)$R^{10}$ and —($C_1$-$C_6$)alkyl-$SO_2$—N($R^9$)$R^{10}$; wherein each $R^9$ is independently selected from H, ($C_1$-$C_6$)alkyl and ($C_3$-$C_7$)cycloalkyl; and each $R^{10}$ is independently selected from $R^{11}$, —($C_1$-$C_6$)alkyl-$R^{11}$, —$SO_2$—$R^{11}$, —C(=O)—$R^{11}$, —C(=O)O$R^{11}$ and —C(=O)N($R^9$)$R^{11}$; wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl;

$R^{8b}$ is selected from:

a) —($C_1$-$C_6$)alkyl-$SO_2$—($C_1$-$C_6$)alkyl-$Z^{13}$, —C(O)—($C_1$-$C_6$)alkyl-$Z^{13}$, —O—($C_1$-$C_6$)alkyl-$Z^{13}$, —S—($C_1$-$C_6$)alkyl-$Z^{13}$, —S(O)—($C_1$-$C_6$)alkyl-$Z^{13}$, —$SO_2$—($C_1$-$C_6$)alkyl-$Z^{13}$, —($C_1$-$C_6$)alkyl-$Z^{14}$, —($C_1$-$C_6$)alkyl-C(O)—($C_1$-$C_6$)alkyl-$Z^{13}$, —($C_1$-$C_6$)alkyl-C(O)—O($C_1$-$C_6$)alkyl-$Z^{13}$, —($C_1$-$C_6$)alkyl-O—($C_1$-$C_6$)alkyl-$Z^{13}$, —($C_1$-$C_6$)alkyl-S—($C_1$-$C_6$)alkyl-$Z^{13}$, —($C_1$-$C_6$)alkyl-O—($C_1$-$C_6$)alkyl-($C_3$-$C_7$)carbocycle, —($C_1$-$C_6$)alkyl-S—($C_1$-$C_6$)alkyl-($C_3$-$C_7$)carbocycle, —($C_1$-$C_6$)alkyl-S(O)—($C_1$-$C_6$)alkyl-($C_3$-$C_7$)carbocycle, —($C_1$-$C_6$)alkyl-$SO_2$—($C_1$-$C_6$)alkyl-($C_3$-$C_7$)carbocycle, —($C_2$-$C_6$)alkenyl-($C_1$-$C_6$)haloalkyl, —($C_2$-$C_6$)alkynyl-($C_1$-$C_6$)haloalkyl, -halo($C_3$-$C_7$)carbocycle, —$NR_aSO_2NR_cR_d$, —$NR_aSO_2O$($C_3$-$C_7$)carbocycle, —$NR_aSO_2$Oaryl, —($C_2$-$C_6$)alkenyl-($C_3$-$C_7$)carbocycle, —($C_2$-$C_6$)alkenyl-aryl, —($C_2$-$C_6$)alkenyl-heteroaryl, —($C_2$-$C_6$)alkenyl-heterocycle, —($C_2$-$C_6$)alkynyl-($C_3$-$C_7$)carbocycle, —($C_2$-$C_6$)alkynyl-aryl, —($C_2$-$C_6$)alkynyl-heteroaryl, —($C_2$-$C_6$)alkynyl-heterocycle, —($C_3$-$C_7$)carbocycle-$Z^1$ or -halo($C_1$-$C_6$)alkyl-$Z^3$; wherein ($C_1$-$C_6$)alkyl, ($C_1$-$C_6$)haloalkyl, ($C_3$-$C_7$)carbocycle, ($C_2$-$C_6$)alkenyl, ($C_2$-$C_6$)alkynyl, aryl or heteroaryl are each optionally substituted with one or more (e.g. 1, 2, 3, 4 or 5) $Z^1$ groups;

b) spiro-bicyclic carbocycle, fused-bicyclic carbocycle and bridged-bicyclic carbocycle; wherein spiro-bicyclic carbocycle, fused-bicyclic carbocycle or bridged-bicyclic carbocycle are optionally substituted with one or more (e.g. 1, 2, 3, 4 or 5) $Z^1$ groups; wherein two $Z^1$ groups together with the atom or atoms to which they are attached optionally form a ($C_3$-$C_7$)carbocycle or heterocycle wherein the ($C_3$-$C_7$)carbocycle or heterocycle is optionally substituted with one or more (e.g. 1, 2, 3, 4 or 5) $Z^1$ groups;

c) ($C_1$-$C_6$)alkyl; wherein ($C_1$-$C_6$)alkyl is substituted with one or more $Z^2$ groups and optionally substituted with one or more (e.g. 1, 2, 3, 4 or 5) $Z^1$ groups;

d) —X($C_1$-$C_6$)alkyl, —X($C_1$-$C_6$)haloalkyl, —X($C_2$-$C_6$)alkenyl, —X($C_2$-$C_6$)alkynyl and —X($C_3$-$C_7$)carbocycle; wherein ($C_1$-$C_6$)alkyl and ($C_1$-$C_6$)haloalkyl are each independently substituted with one or more $Z^3$ groups and optionally substituted with one or more (e.g. 1, 2, 3, 4 or 5) $Z^1$ groups; and wherein any ($C_2$-$C_6$)alkenyl, ($C_2$-$C_6$)alkynyl and ($C_3$-$C_7$)carbocycle are each independently substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle wherein any aryl heteroaryl and heterocycle are each independently substituted with one or more (e.g. 1, 2, 3, 4 or 5) $Z^5$ groups and optionally substituted with one or more (e.g. 1, 2, 3, 4 or 5) $Z^1$ groups;

f) ($C_1$-$C_6$)haloalkyl, ($C_3$-$C_7$)carbocycle, ($C_2$-$C_6$)alkenyl and ($C_2$-$C_6$)alkynyl; wherein ($C_1$-$C_6$)haloalkyl, ($C_3$-$C_7$)carbocycle, ($C_2$-$C_6$)alkenyl and ($C_2$-$C_6$)alkynyl are each independently substituted with one or more (e.g. 1, 2, 3, 4 or 5) $Z^6$ groups and optionally substituted with one or more (e.g. 1, 2, 3, 4 or 5) $Z^1$ groups; and g) —$NR_eR_f$, —C(O)$NR_eR_f$, —OC(O)$NR_eR_f$, —$SO_2NR_eR_f$, —($C_1$-$C_6$)alkyl-$NR_eR_f$, —($C_1$-$C_6$)alkylC(O)—$NR_eR_f$, —($C_1$-$C_6$)alkyl-O—C(O)—$NR_eR_f$ and —($C_1$-$C_6$)alkyl-$SO_2NR_eR_f$; wherein each ($C_1$-$C_6$)alkyl is independently substituted with one or more (e.g. 1, 2, 3, 4 or 5) $Z^6$ groups and optionally substituted with one or more (e.g. 1, 2, 3, 4 or 5) $Z^1$ groups;

$R^{13a}$ is selected from:

a) $R^{11}$, —C(=O)—$R^{11}$, —C(=O)—O—$R^{11}$, —O—$R^{11}$, —S—$R^{11}$, —S(O)—$R^{11}$, —$SO_2$—$R^{11}$, —($C_1$-$C_6$)alkyl-$R^{11}$, —($C_1$-$C_6$)alkyl-C(=O)—$R^{11}$, —($C_1$-$C_6$)alkyl-C(=O)—O—$R^{11}$, —($C_1$-$C_6$)alkyl-O—$R^{11}$, —($C_1$-$C_6$)alkyl-S—$R^{11}$, —($C_1$-$C_6$)alkyl-S(O)—$R^{11}$ and —($C_1$-$C_6$)alkyl-$SO_2$—$R^{11}$; wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl; wherein aryl, heterocycle and heteroaryl are each optionally substituted with one or more (e.g. 1, 2 or 3) $Z^{11}$ groups; and b) —C(=O)—N($R^9$)$R^{10}$, —$SO_2$—N($R^9$)$R^{10}$, —($C_1$-$C_6$)alkyl-N($R^9$)$R^{10}$, —($C_1$-$C_6$)alkyl-C(=O)—N($R^9$)$R^{10}$, —($C_1$-$C_6$)alkyl-O—C(=O)—N($R^9$)$R^{10}$ and —($C_1$-$C_6$)alkyl-$SO_2$—N($R^9$)$R^{10}$; wherein each $R^9$ is independently selected from H, ($C_1$-$C_6$)alkyl and ($C_3$-$C_7$)cycloalkyl; and each $R^{10}$ is independently selected from $R^{11}$, —$SO_2$—$R^{11}$, —C(=O)—$R^{11}$, —C(=O)O$R^{11}$ and —C(=O)N($R^9$)$R^{11}$; wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl;

$R^{13b}$ is selected from:

a) —($C_1$-$C_6$)alkyl-$SO_2$—($C_1$-$C_6$)alkyl-$Z^{13}$, —C(O)—($C_1$-$C_6$)alkyl-$Z^{13}$, —O—($C_1$-$C_6$)alkyl-$Z^{13}$, —S—($C_1$-$C_6$)alkyl-$Z^{13}$, —S(O)—($C_1$-$C_6$)alkyl-$Z^{13}$, —$SO_2$—($C_1$-$C_6$)alkyl-$Z^{13}$, —($C_1$-$C_6$)alkyl-$Z^{14}$, —($C_1$-$C_6$)alkyl-C(O)—($C_1$-$C_6$)alkyl-$Z^{13}$, —($C_1$-$C_6$)alkyl-C(O)—O($C_1$-$C_6$)alkyl-$Z^{13}$, —($C_1$-$C_6$)alkyl-O—($C_1$-$C_6$)alkyl-$Z^{13}$, —($C_1$-$C_6$)alkyl-S—

$(C_1-C_6)$alkyl-$Z^{13}$, —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkyl-S(O)—$(C_1-C_6)$alkyl-$(C_3-C_7)$carbocycle, —$(C_1-C_6)$alkyl-$SO_2$—$(C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, -halo$(C_3-C_7)$carbocycle, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$carbocycle-$Z^1$ or -halo$(C_1-C_6)$alkyl-$Z^3$, —$NR_aSO_2NR_cR_d$, —$NR_aSO_2O(C_3-C_7)$carbocycle, —$NR_aSO_2$Oaryl; wherein $(C_1-C_6)$alkyl, $(C_1-C_6)$haloalkyl, $(C_3-C_7)$carbocycle, $(C_2-C_6)$alkenyl, $(C_2-C_6)$alkynyl, aryl or heteroaryl are each optionally substituted with one or more (e.g. 1, 2, 3, 4 or 5) $Z^1$ groups;

b) spiro-bicyclic carbocycle, fused-bicyclic carbocycle and bridged-bicyclic carbocycle; wherein spiro-bicyclic carbocycle, fused-bicyclic carbocycle or bridged-bicyclic carbocycle are optionally substituted with one or more (e.g. 1, 2, 3, 4 or 5) $Z^1$ groups; wherein two $Z^1$ groups together with the atom or atoms to which they are attached optionally form a $(C_3-C_7)$carbocycle or heterocycle wherein the $(C_3-C_7)$carbocycle or heterocycle is optionally substituted with one or more (e.g. 1, 2, 3, 4 or 5) $Z^1$ groups;

c) $(C_1-C_6)$alkyl; wherein $(C_1-C_6)$alkyl is substituted with one or more $Z^2$ groups and optionally substituted with one or more (e.g. 1, 2, 3, 4 or 5) $Z^1$ groups;

d) —X$(C_1-C_6)$alkyl, —X$(C_1-C_6)$haloalkyl, —X$(C_2-C_6)$alkenyl, —X$(C_2-C_6)$alkynyl and —X$(C_3-C_7)$carbocycle; wherein $(C_1-C_6)$alkyl and $(C_1-C_6)$haloalkyl are each independently substituted with one or more $Z^3$ groups and optionally substituted with one or more (e.g. 1, 2, 3, 4 or 5) $Z^1$ groups; and wherein any $(C_2-C_6)$alkenyl, $(C_2-C_6)$alkynyl and $(C_3-C_7)$carbocycle are each independently substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle wherein any aryl heteroaryl and heterocycle are each independently substituted with one or more (e.g. 1, 2, 3, 4 or 5) $Z^5$ groups and optionally substituted with one or more (e.g. 1, 2, 3, 4 or 5) $Z^1$ groups;

f) $(C_1-C_6)$haloalkyl, $(C_3-C_7)$carbocycle, $(C_2-C_6)$alkenyl and $(C_2-C_6)$alkynyl; wherein $(C_1-C_6)$haloalkyl, $(C_3-C_7)$carbocycle, $(C_2-C_6)$alkenyl and $(C_2-C_6)$alkynyl are each independently substituted with one or more (e.g. 1, 2, 3, 4 or 5) $Z^6$ groups and optionally substituted with one or more (e.g. 1, 2, 3, 4 or 5) $Z^1$ groups; and g) —C(O)$NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—C(O)—$NR_eR_f$ and —$(C_1-C_6)$alkyl-$SO_2NR_eR_f$; wherein each $(C_1-C_6)$alkyl is independently substituted with one or more (e.g. 1, 2, 3, 4 or 5) $Z^6$ groups and optionally substituted with one or more (e.g. 1, 2, 3, 4 or 5) $Z^1$ groups;

or any of $R^{5a}$ and $R^{6a}$, $R^{6a}$ and $R^{7a}$, $R^{7a}$ and $R^{8a}$, $R^1$ and $R^8$, $R^1$ and $R^2$ or $R^1$ and $R^{13}$ together with the atoms to which they are attached form a 5 or 6-membered carbocycle or a 4, 5, 6 or 7-membered heterocycle; wherein the 5 or 6-membered carbocycle or a 4, 5, 6 or 7-membered heterocycle is optionally substituted with one or more (e.g. 1, 2 or 3) substituents each independently selected from halo, $(C_1-C_6)$alkyl, $(C_2-C_6)$alkenyl, $(C_1-C_6)$haloalkyl, $(C_3-C_7)$cycloalkyl, —OH, —O$(C_1-C_6)$alkyl, —SH, —S$(C_1-C_6)$alkyl, —$NH_2$, —NH$(C_1-C_6)$alkyl and —N$((C_1-C_6)$alkyl$)_2$;

or any of $R^5$ and $R^6$, $R^6$ and $R^7$ or $R^7$ and $R^8$, together with the atoms to which they are attached form a 5 or 6-membered carbocycle or a 4, 5, 6 or 7-membered heterocycle; wherein the 5 or 6-membered carbocycle or a 4, 5, 6 or 7-membered heterocycle are each independently substituted with one or more (e.g. 1, 2 or 3) $Z^7$ or $Z^8$ groups; wherein when two $Z^7$ groups are on same atom the two $Z^7$ groups together with the atom to which they are attached optionally form a $(C_3-C_7)$ carbocycle or 4, 5 or 6-membered heterocycle;

or any of Wand $R^8$, $R^1$ and $R^2$ or $R^1$ and $R^{13}$ together with the atoms to which they are attached form a 5 or 6-membered carbocycle or a 4, 5, 6 or 7-membered heterocycle; wherein the 5 or 6-membered carbocycle or a 4, 5, 6 or 7-membered heterocycle are each independently substituted with one or more (e.g. 1, 2 or 3) $Z^7$ or $Z^8$ groups; wherein when two $Z^7$ groups are on same atom the two $Z^7$ groups together with the atom to which they are attached optionally form a $(C_3-C_7)$ carbocycle or 4, 5 or 6-membered heterocycle;

X is independently selected from O, —C(O)—, —C(O)O—, —S—, —S(O)—, —$SO_2$—, —$(C_1-C_6)$alkylO—, —$(C_1-C_6)$alkylC(O)—, —$(C_1-C_6)$alkylC(O)O—, —$(C_1-C_6)$alkylS—, —$(C_1-C_6)$alkylS(O)—, —$(C_1-C_6)$alkyl$SO_2$—;

each $Z^1$ is independently selected from halo, —$NO_2$, —OH, =$NOR_a$, —SH, —CN, —$(C_1-C_6)$alkyl, —$(C_2-C_6)$alkenyl, —$(C_2-C_6)$alkynyl, —$(C_1-C_6)$haloalkyl, $(C_3-C_7)$carbocycle, —$(C_3-C_7)$halocarbocycle, -aryl, -heteroaryl, -heterocycle, —O$(C_1-C_6)$alkyl, —O$(C_2-C_6)$alkenyl, —O$(C_2-C_6)$alkynyl, —O$(C_1-C_6)$haloalkyl, —O$(C_3-C_7)$carbocycle, —O$(C_3-C_7)$halocarbocycle, —Oaryl, —Oheteroaryl, —Oheterocycle, —S$(C_1-C_6)$alkyl, —S$(C_2-C_6)$alkenyl, —S$(C_2-C_6)$alkynyl, —S$(C_1-C_6)$haloalkyl, —S$(C_3-C_7)$carbocycle, —S$(C_3-C_7)$halocarbocycle, —Saryl, —Sheteroaryl, —Sheterocycle, —S(O)$(C_1-C_6)$alkyl, —S(O)$(C_2-C_6)$alkenyl, —S(O)$(C_2-C_6)$alkynyl, —S(O)$(C_1-C_6)$haloalkyl, —S(O) $(C_3-C_7)$carbocycle, —S(O)$(C_3-C_7)$halocarbocycle, —$SO_2(C_1-C_6)$alkyl, —S(O)aryl, —S(O)carbocycle, —S(O) heteroaryl, —S(O)heterocycle, —$SO_2(C_2-C_6)$alkenyl, —$SO_2(C_2-C_6)$alkynyl, —$SO_2(C_1-C_6)$haloalkyl, —$SO_2(C_3-C_7)$carbocycle, —$SO_2(C_3-C_7)$halocarbocycle, —$SO_2$aryl, —$SO_2$heteroaryl, —$SO_2$heterocycle, —$SO_2NR_cR_d$, —$NR_cR_d$, —$NR_aC(O)R_a$, —$NR_aC(O)OR_a$, —$NR_aC(O)NR_cR_d$—$NR_aSO_2R_b$, —$NR_aSO_2NR_cR_d$, —$NR_aSO_2O(C_3-C_7)$carbocycle, —$NR_aSO_2$Oaryl, —$OS(O)_2R_a$, —C(O)$R_a$, —C(O)$OR_b$, —C(O)$NR_cR_d$, and —OC(O)$NR_cR_d$, wherein any $(C_1-C_6)$alkyl, $(C_2-C_6)$alkenyl, $(C_2-C_6)$alkynyl, —$(C_3-C_7)$ halocarbocycle, $(C_3-C_7)$carbocycle, $(C_3-C_7)$halocarbocycle, aryl, heteroaryl or heterocycle of $Z^1$ is optionally substituted with one or more (e.g. 1, 2, 3, 4 or 5) halogen, —OH, —$OR_b$, —CN, —$NR_aC(O)_2R_b$, -heteroaryl, -heterocycle, —Oheteroaryl, —Oheterocycle, —NHheteroaryl, —NHheterocycle, or —S(O)$_2NR_cR_d$;

each $Z^2$ is independently selected from —$NO_2$, —CN, spiro-heterocycle, bridge-heterocycle, spiro-bicyclic carbocycle, bridged-bicyclic carbocycle, $NR_aSO_2(C_3-C_7)$carbocycle, —$NR_aSO_2$aryl, —$NR_aSO_2$heteroaryl, —$NR_aSO_2NR_cR_a$, —$NR_aSO_2O(C_3-C_7)$carbocycle and —$NR_aSO_2$Oaryl;

each $Z^3$ is independently selected from —$NO_2$, —CN, —OH, oxo, =$NOR_a$, thioxo, -aryl, -heterocycle, -heteroaryl, —$(C_3-C_7)$halocarbocycle, —O$(C_1-C_6)$alkyl, —O$(C_3-C_7)$carbocycle, —Ohalo$(C_3-C_7)$carbocycle, —Oaryl, —Oheterocycle, —Oheteroaryl, —S$(C_1-C_6)$alkyl, —S$(C_3-C_7)$carbocycle, —S$(C_3-C_7)$halocarbocycle, —Saryl, —Sheterocycle, —Sheteroaryl, —S(O)$(C_1-C_6)$alkyl, —S(O) $(C_3-C_7)$carbocycle, —S(O) $(C_3-C_7)$halocarbocycle, —S(O) aryl, —S(O)heterocycle, —S(O)heteroaryl, —$SO_2(C_1-C_6)$alkyl, —$SO_2(C_3-C_7)$carbocycle, —$SO_2(C_3-C_7)$halocarbocycle, $SO_2$aryl, —$SO_2$heterocycle, —$SO_2$heteroaryl, —$NR_aR_b$, —$NR_aC(O)R_b$, —C(O)$NR_cR_d$, —SO₂NR_cR_d, —NR_aSO₂NR_cR_d, —NR_aSO₂O(C₃-C₇)carbocycle and —NR_aSO₂Oaryl;

each Z⁴ is independently selected from halogen, —(C₁-C₆)alkyl, (C₃-C₇)carbocycle, -halo(C₁-C₆)alkyl, —NO₂, —CN, —OH, oxo, =NOR_a, thioxo, -aryl, -heterocycle, -heteroaryl, —(C₃-C₇)halocarbocycle, —O(C₁-C₆)alkyl, —O(C₃-C₇)carbocycle, —O(C₃-C₇)halocarbocycle, —Oaryl, —Oheterocycle, —Oheteroaryl, —S(C₁-C₆)alkyl, —S(C₃-C₇)carbocycle, —S(C₃-C₇)halocarbocycle, —Saryl, —Sheterocycle, —Sheteroaryl, —S(O)(C₁-C₆)alkyl, —S(O)(C₃-C₇)carbocycle, —S(O)(C₃-C₇)halocarbocycle, —S(O)aryl, —S(O)heterocycle, —S(O)heteroaryl, —SO₂(C₁-C₆)alkyl, —SO₂(C₃-C₇)carbocycle, —SO₂(C₃-C₇)halocarbocycle, SO₂aryl, —SO₂heterocycle, —SO₂heteroaryl, —NR_aR_b, —NR_aC(O)R_a, —C(O)NR_cR^d, —SO₂NR_cR_d, —NR_aSO₂NR_cR_d, —NR_aSO₂O(C₃-C₇)carbocycle and —NR_aSO₂Oaryl;

each Z⁵ is independently selected from —NO₂, —CN, —NR_aSO₂NR_cR_d, —NR_aSO₂O(C₃-C₇)carbocycle, —NR_aSO₂Oaryl, —NR_aSO₂(C₁-C₆)alkyl, —NR_aSO₂(C₂-C₆)alkenyl, —NR_aSO₂(C₂-C₆)alkynyl, —NR_aSO₂(C₃-C₇)carbocycle, —NR_aSO₂(C₃-C₇)halocarbocycle, —NR_aSO₂aryl, —NR_aSO₂heteraryl, —NR_aSO₂heteroaryl, —NR_aSO₂heterocycle, —NR_aC(O)alkyl, —NR_aC(O)alkenyl, —NR_aC(O)alkynyl, —NR_aC(O) (C₃-C₇)carbocycle, —NR_aC(O)(C₃-C₇)halocarbocycle, —NR_aC(O)aryl, —NR_aC(O)heteroaryl, —NR_aC(O)heterocycle, NR_aC(O)NR_cR_d and NR_aC(O)OR_b;

each Z⁶ is independently selected from —NO₂, —CN, —NR_aR_a, NR_aC(O)R_b, —C(O)NR_cR_d, —(C₃-C₇)halocarbocycle, -aryl, -heteroaryl, -heterocycle, —Oaryl, —Oheteroaryl, —Oheterocycle, —O(C₃-C₇)halocarbocycle, —O(C₁-C₆)alkyl, —O(C₃-C₇)carbocycle, —Ohalo(C₁-C₆)alkyl, —Saryl, —Sheteroaryl, —Sheterocycle, —S(C₃-C₇)halocarbocycle, —S(C₁-C₆)alkyl, —S(C₃-C₇)carbocycle, —S(C₁-C₆)haloalkyl, —S(O)aryl, —S(O)heteroaryl, —S(O)heterocycle, —S(O)(C₃-C₇)halocarbocycle, —S(O)(C₁-C₆)alkyl, —S(O)(C₃-C₇)carbocycle, —S(O)halo(C₁-C₆)alkyl, —SO₂aryl, —SO₂heteroaryl, —SO₂heterocycle, —SO₂(C₁-C₆)alkyl, —SO₂halo(C₁-C₆)alkyl, —SO₂(C₃-C₇)carbocycle, —SO₂(C₃-C₇)halocarbocycle, —SO₂NR_cR_d, —NR_aSO₂(C₃-C₇)halocarbocycle, —NR_aSO₂aryl, —NR_aSO₂heteraryl, —NR_aSO₂heteroaryl, —NR_aSO₂NR_cR_d, —NR_aSO₂O(C₃-C₇)carbocycle and —NR_aSO₂Oaryl;

each Z⁷ is independently selected from —NO₂, =NOR_a, —CN, —(C₁-C₆)alkyl-Z¹², —(C₂-C₆)alkenyl-Z¹², —(C₂-C₆)alkenylOH, —(C₂-C₆)alkynyl-Z¹², —(C₂-C₆)alkynyl-OH, —(C₁-C₆)haloalkyl-Z¹², —(C₁-C₆)haloalkylOH, —(C₃-C₇)carbocycle-Z¹², —(C₃-C₇)carbocycle, OH, —(C₃-C₇)halocarbocycle, —(C₁-C₆)alkylNR_cR_d, —(C₁-C₆)alkylNR_aC(O)R_a, —(C₁-C₆)alkylNR_aSO₂R_a, -aryl, -heteroaryl, -heterocycle, —O(C₁-C₆)alkyl-Z¹², —O(C₂-C₆)alkenyl, —O(C₂-C₆)alkynyl, —O(C₁-C₆)haloalkyl, —O(C₃-C₇)carbocycle, —O(C₃-C₇)halocarbocycle, —Oaryl, —O(C₁-C₆)alkylNR_cR_d, —O(C₁-C₆)alkylNR_aC(O)R_a, —O(C₁-C₆)alkylNR_aSO₂R_a, —Oheteroaryl, —Oheterocycle, —S(C₁-C₆)alkyl-Z¹², —S(C₂-C₆)alkenyl, —S(C₂-C₆)alkynyl, —S(C₁-C₆)haloalkyl, —S(C₃-C₇)carbocycle, —S(C₃-C₇)halocarbocycle, —S(C₁-C₆)alkylNR_cR_d, —S(C₁-C₆)alkylNR_aC(O)R_a, —S(C₁-C₆)alkylNR_aSO₂R_a, —Saryl, —Sheteroaryl, —Sheterocycle, —S(O)(C₁-C₆)alkyl, —S(O)(C₂-C₆)alkenyl, —S(O)(C₂-C₆)alkynyl, —S(O)(C₁-C₆)haloalkyl, —S(O)(C₃-C₇)carbocycle, —S(O)(C₃-C₇)halocarbocycle, —S(O)aryl, —S(O)heterocycle, —S(O)heteroaryl, —SO₂(C₁-C₆)alkyl, —SO₂(C₂-C₆)alkenyl, —SO₂(C₂-C₆)alkynyl, —SO₂(C₁-C₆)haloalkyl, —SO₂(C₃-C₇)carbocycle, —SO₂(C₃-C₇)halocarbocycle, —SO₂aryl, —SO₂heterocycle, —SO₂heteroaryl, —SO₂(C₁-C₆)alkylNR_cR_d, —SO₂(C₁-C₆)alkylNR_aSO₂R_a, —SO₂NR_cR_d, —NR_aC(O)OR_b, —NR_aC(O)NR_cR_d, —NR_aSO₂R_b, —NR_aSO₂NR_cR_d, —NR_aSO₂O(C₃-C₇)carbocycle, —NR_aSO₂Oaryl, —OS(O)₂R_a, —C(O)NR_cR_d, and —OC(O)NR_cR_d, wherein any (C₁-C₆)alkyl, (C₂-C₆)alkenyl, (C₂-C₆)alkynyl, (C₃-C₇)carbocycle, (C₃-C₇)halocarbocycle, aryl, heteroaryl or heterocycle of Z⁷ is optionally substituted with one or more (e.g. 1, 2, 3, 4 or 5) halogen, —OH, —OR_b, —CN, —NR_aC(O)₂R_b, -heteroaryl, -heterocycle, —Oheteroaryl, —Oheterocycle, —NHheteroaryl, —NHheterocycle, or —S(O)₂NR_cR_d;

each Z⁸ is independently selected from —NO₂ or —CN;
each Z⁹ is independently selected from —(C₁-C₆)alkyl, —O(C₁-C₆)alkyl;
each Z¹⁰ is independently selected from
i) halo, oxo, thioxo, (C₂-C₆)alkenyl, (C₁-C₆)haloalkyl, (C₃-C₇)cycloalkyl, (C₃-C₇)cycloalkyl-(C₁-C₆)alkyl-, —OH, —O(C₁-C₆)alkyl, —O(C₁-C₆)haloalkyl, —SH, —S(C₁-C₆)alkyl, —SO(C₁-C₆)alkyl, —SO₂(C₁-C₆)alkyl, —NH₂, —NH(C₁-C₆)alkyl and —N((C₁-C₆)alkyl)₂;
ii) (C₁-C₆)alkyl optionally substituted with —OH, —O—(C₁-C₆)haloalkyl, or —O—(C₁-C₆)alkyl; and
iii) aryl, heterocycle and heteroaryl, which aryl, heterocycle and heteroaryl is optionally substituted with halo, (C₁-C₆)alkyl or COOH;

each Z¹¹ is independently selected from Z¹⁰, —C(=O)—NH₂, —C(=O)—NH(C₁-C₄)alkyl, —C(=O)—N((C₁-C₄)alkyl)₂, —C(=O)-aryl, —C(=O)-heterocycle and —C(=O)-heteroaryl;

each Z¹² is independently selected from —NO₂, =NOR_a, thioxo, -aryl, -heterocycle, -heteroaryl, —(C₃-C₇)halocarbocycle, —(C₃-C₇)carbocycle, —O(C₃-C₇)carbocycle, —Ohalo(C₃-C₇)carbocycle, —Oaryl, —Oheterocycle, —Oheteroaryl, —S(C₁-C₆)alkyl, —S(C₃-C₇)carbocycle, —Shalo(C₃-C₇)carbocycle, —Saryl, —Sheterocycle, —Sheteroaryl, —S(O)(C₁-C₆)alkyl, —S(O)(C₃-C₇)carbocycle, —S(O)halo(C₃-C₇)carbocycle, —S(O)aryl, —S(O)heterocycle, —S(O)heteroaryl, —SO₂(C₁-C₆)alkyl, —SO₂(C₃-C₇)carbocycle, —SO₂(C₃-C₇)halocarbocycle, SO₂aryl, —SO₂heterocycle, —SO₂heteroaryl, —NR_aR_a, —NR_aC(O)R_b, —C(O)NR_cR_d, —SO₂NR_cR_d, —NR_aSO₂NR_cR_d, —NR_aSO₂O(C₃-C₇)carbocycle and —NR_aSO₂Oaryl;

each Z¹³ is independently selected from —NO₂, —OH, =NOR_a, —SH, —CN, —(C₃-C₇)halocarbocycle, —O(C₁-C₆)alkyl, —O(C₂-C₆)alkenyl, —O(C₂-C₆)alkynyl, —O(C₁-C₆)haloalkyl, —O(C₃-C₇)carbocycle, —O(C₃-C₇)halocarbocycle, —Oaryl, —Oheteroaryl, —Oheterocycle, —S(C₁-C₆)alkyl, —S(C₂-C₆)alkenyl, —S(C₂-C₆)alkynyl, —S(C₁-C₆)haloalkyl, —S(C₃-C₇)carbocycle, —S(C₃-C₇)halocarbocycle, —Saryl, —Sheteroaryl, —Sheterocycle, —S(O)(C₁-C₆)alkyl, —S(O)(C₂-C₆)alkenyl, —S(O)(C₂-C₆)alkynyl, —S(O)(C₁-C₆)haloalkyl, —S(O)(C₃-C₇)carbocycle, —S(O)(C₃-C₇)halocarbocycle, —S(O)aryl, —S(O)heteroaryl, —S(O)heterocycle, —SO₂(C₁-C₆)alkyl, —SO₂(C₂-C₆)alkenyl, —SO₂(C₂-C₆)alkynyl, —SO₂(C₁-C₆)haloalkyl, —SO₂(C₃-C₇)carbocycle, —SO₂(C₃-C₇)halocarbocycle, —SO₂aryl, —SO₂heterocycle, —SO₂heteroaryl, —SO₂NR_cR_d, —NR_cR_d, —NR_aC(O)R_a, —NR_aC(O)OR_b, —NR_aC(O)NR_cR_d, —NR_aSO₂R_b, —NR_aSO₂NR_cR_d, —NR_aSO₂O(C₃-C₇)carbocycle, —NR_aSO₂Oaryl, —OS(O)₂R_a, —C(O)R_a, —C(O)OR_b, —C(O)NR_cR_d, and —OC(O)NR_cR_d; wherein any (C₁-C₆)

alkyl, (C$_2$-C$_6$)alkenyl, (C$_2$-C$_6$)alkynyl, —(C$_3$-C$_7$)halocarbocycle, (C$_3$-C$_7$)carbocycle, (C$_3$-C$_7$)halocarbocycle, aryl, heteroaryl or heterocycle of Z$^{13}$ is optionally substituted with one or more (e.g. 1, 2, 3, 4 or 5) halogen, —OH, —OR$_b$, —CN, —NR$_a$C(O)$_2$R$_b$, -heteroaryl, -heterocycle, —Oheteroaryl, —Oheterocycle, —NHheteroaryl, —NHheterocycle, or —S(O)$_2$NR$_c$R$_d$;

each Z$^{14}$ is independently selected from —NO$_2$, =NOR$_a$, —CN, —(C$_3$-C$_7$)halocarbocycle, —O(C$_3$-C$_7$)halocarbocycle, —S(C$_3$-C$_7$)halocarbocycle, —S(O)(C$_3$-C$_7$)halocarbocycle, —SO$_2$(C$_3$-C$_7$)halocarbocycle, —NR$_a$SO$_2$NR$_c$R$_d$, —NR$_a$SO$_2$O(C$_3$-C$_7$)carbocycle, —NR$_a$SO$_2$Oaryl, —OS(O)$_2$R$_a$; wherein any —(C$_3$-C$_7$)halocarbocycle of Z$^{14}$ is optionally substituted with one or more (e.g. 1, 2, 3, 4 or 5) halogen, —OH, —OR$_b$, —CN, —NR$_a$C(O)$_2$R$_b$, -heteroaryl, -heterocycle, —Oheteroaryl, —Oheterocycle, —NHheteroaryl, —NHheterocycle, or —S(O)$_2$NR$_c$R$_d$;

each R$_a$ is independently H, (C$_1$-C$_6$)alkyl, —(C$_2$-C$_6$)alkenyl, —(C$_2$-C$_6$)alkynyl, (C$_3$-C$_7$)carbocycle, heterocycle, aryl, aryl(C$_1$-C$_6$)alkyl-, heteroaryl or heteroaryl(C$_1$-C$_6$)alkyl-; wherein any (C$_1$-C$_6$)alkyl, (C$_2$-C$_6$)alkenyl, (C$_2$-C$_6$)alkynyl, (C$_3$-C$_7$)carbocycle, heterocycle, aryl, or heteroaryl of R$_a$ is optionally substituted by halogen, OH and cyano;

each R$_b$ is independently —(C$_1$-C$_6$)alkyl, —(C$_2$-C$_6$)alkenyl, —(C$_2$-C$_6$)alkynyl, (C$_3$-C$_7$)carbocycle, heterocycle, aryl, aryl(C$_1$-C$_6$)alkyl-, heteroaryl or heteroaryl(C$_r$C$_6$)alkyl-; wherein any (C$_1$-C$_6$)alkyl, —(C$_2$-C$_6$)alkenyl, —(C$_2$-C$_6$)alkynyl, (C$_3$-C$_7$)carbocycle, heterocycle, aryl, or heteroaryl of R$_b$ is optionally substituted by halogen, OH and cyano;

R$_c$ and R$_d$ are each independently selected from H, (C$_1$-C$_6$)alkyl, (C$_2$-C$_6$)alkenyl, (C$_2$-C$_6$)alkynyl, (C$_3$-C$_7$)carbocycle, aryl, aryl(C$_1$-C$_6$)alkyl-, heterocycle, heteroaryl or heteroaryl (C$_1$-C$_6$)alkyl- wherein any (C$_1$-C$_6$)alkyl, —(C$_2$-C$_6$)alkenyl, —(C$_2$-C$_6$)alkynyl, (C$_3$-C$_7$)carbocycle, heterocycle, aryl, or heteroaryl of R$_c$ or R$_d$ is optionally substituted by halogen, OH and cyano; or R$_c$ and R$_d$ together with the nitrogen to which they are attached form a heterocycle; wherein any heterocycle of R$_c$ and R$_d$ together with the nitrogen to which they are attached is optionally substituted by halogen, OH or cyano;

each R$_e$ is independently selected from —OR$_a$, (C$_1$-C$_6$)alkyl or (C$_3$-C$_7$)carbocycle wherein (C$_1$-C$_6$)alkyl or (C$_3$-C$_7$)carbocycle is substituted by one or more Z$_d$ and optionally substituted with one or more Z$_1$; —(C$_2$-C$_6$)haloalkyl, —(C$_2$-C$_6$)alkenyl, or —(C$_2$-C$_6$)alkynyl wherein any haloalkyl, alkenyl or alkynyl is optionally substituted with one or more Z$_1$; aryl, heterocycle or heteroaryl wherein aryl, heterocycle or heteroaryl is substituted by one or more Z$_c$;

each R$_f$ is independently selected from —R$_g$, —OR$_a$, —(C$_1$-C$_6$)alkyl-Z$^6$, —SO$_2$R$_g$, —C(O)R$_g$, C(O)OR$_g$, or —C(O)NR$_e$R$_g$; and each R$_g$ is independently selected from —OR$_a$, (C$_1$-C$_6$) alkyl, (C$_3$-C$_7$)carbocycle (C$_1$-C$_6$)haloalkyl, (C$_2$-C$_6$)alkenyl, (C$_2$-C$_6$)alkynyl, aryl, heterocycle or heteroaryl wherein any (C$_1$-C$_6$)alkyl, (C$_3$-C$_7$)carbocycle —(C$_1$-C$_6$)haloalkyl, (C$_2$-C$_6$)alkenyl, (C$_2$-C$_6$)alkynyl, aryl, heterocycle or heteroaryl of R$_g$ is optionally substituted with one or more Z$_1$ groups;

or a salt thereof.

In one embodiment, the compounds of formula I include:

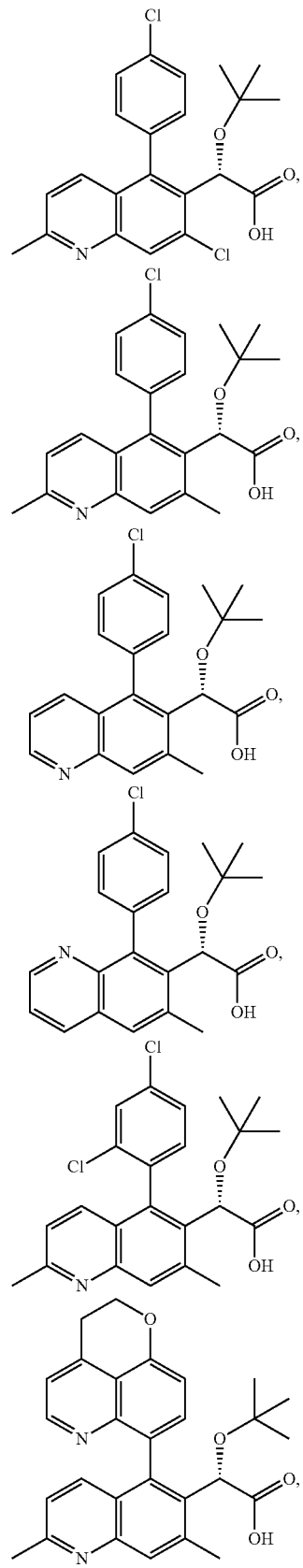

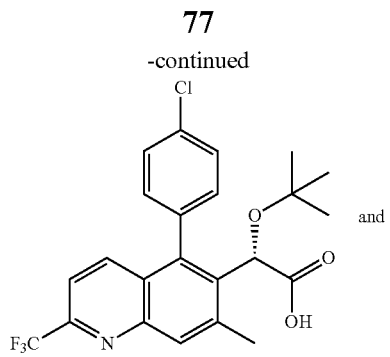
and
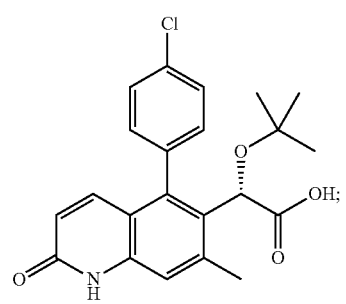
and salts thereof.
In another embodiment, the compounds of formula I include:
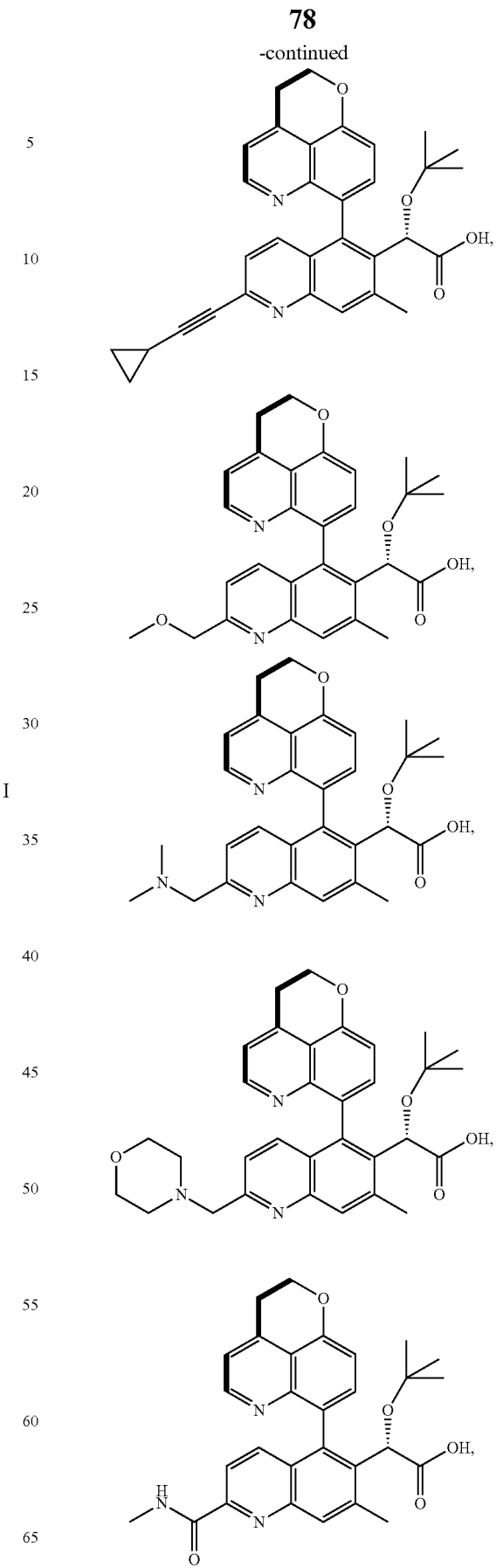

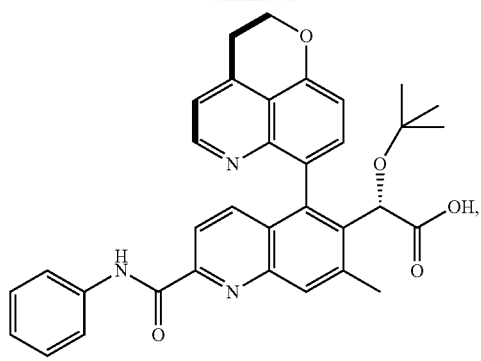
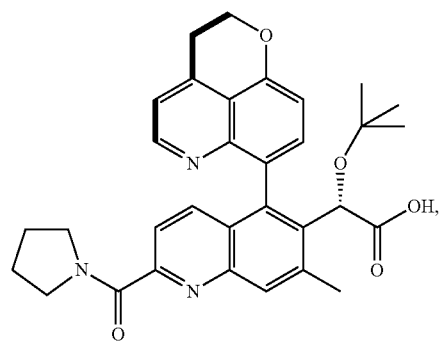
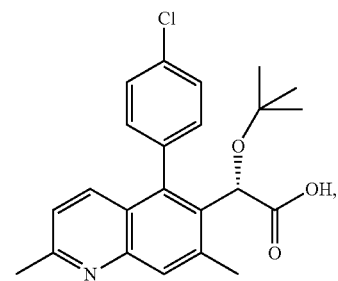
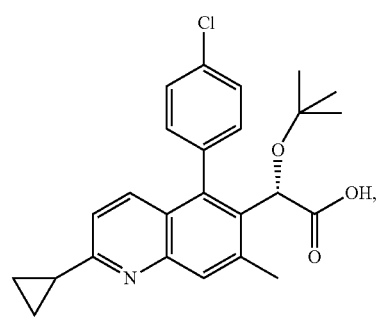
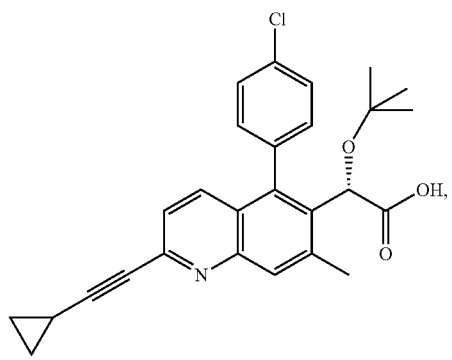
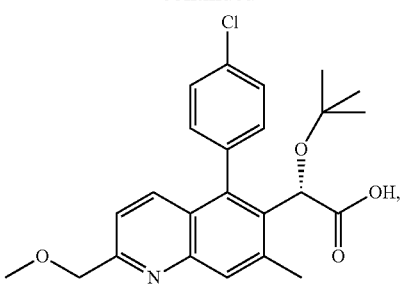
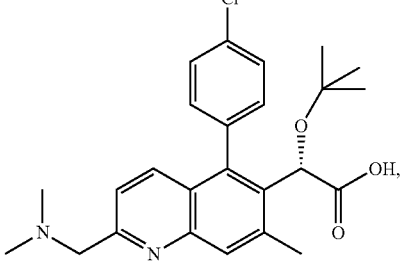
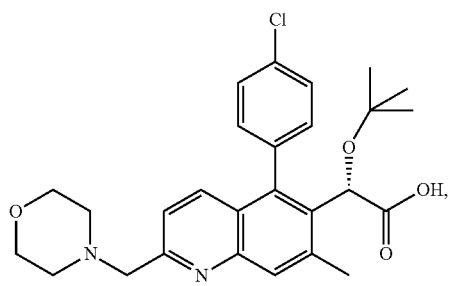
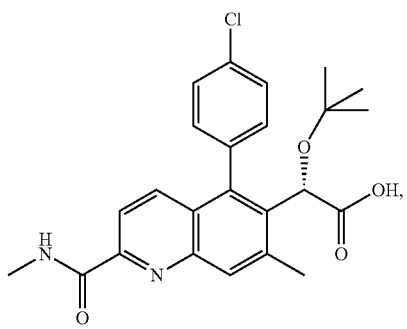
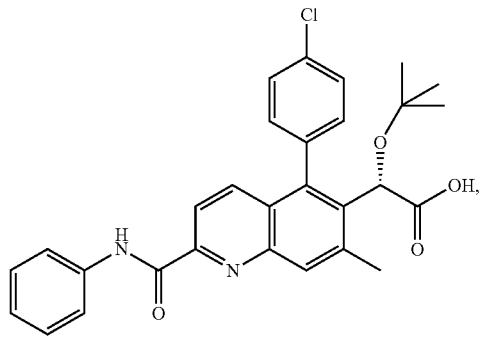

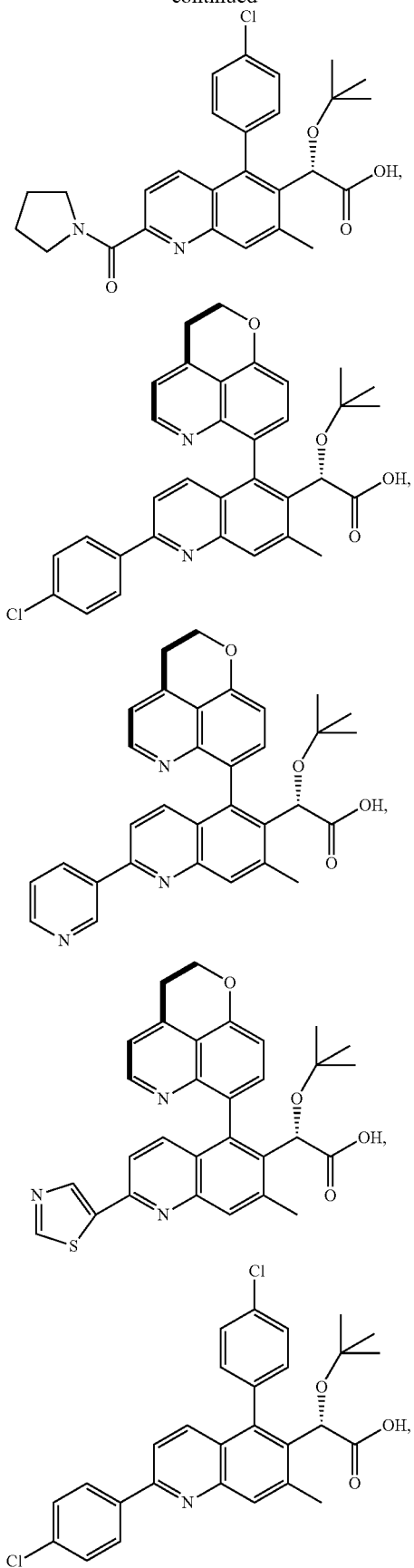
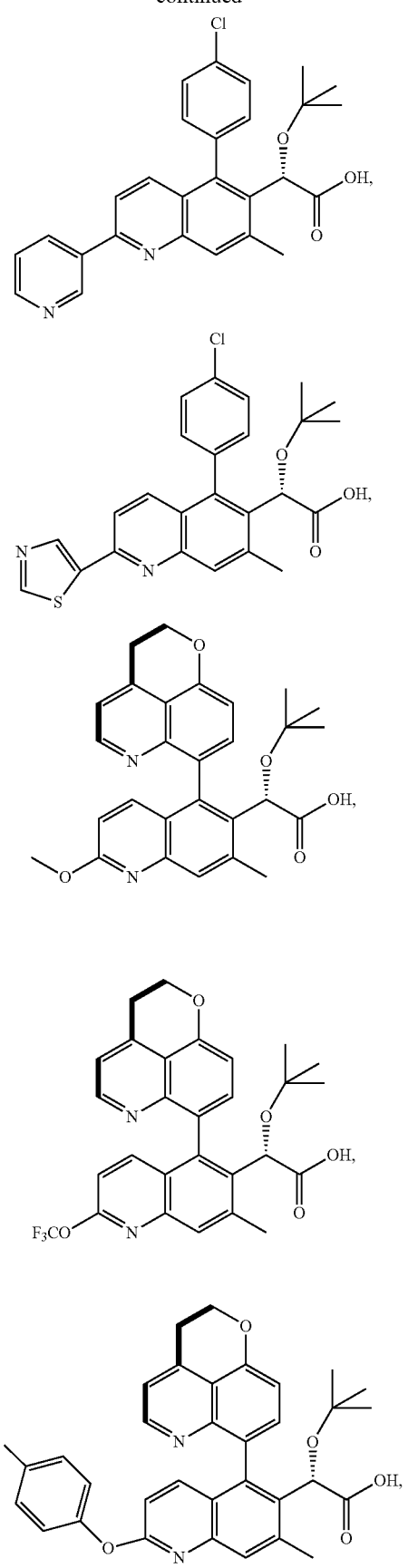

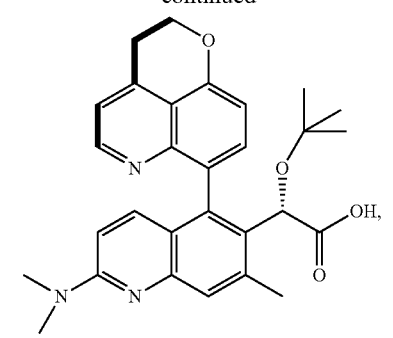
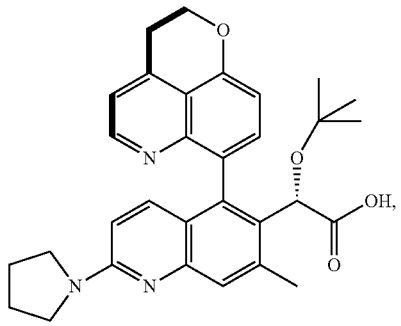
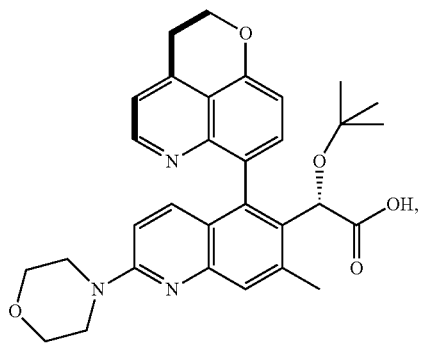
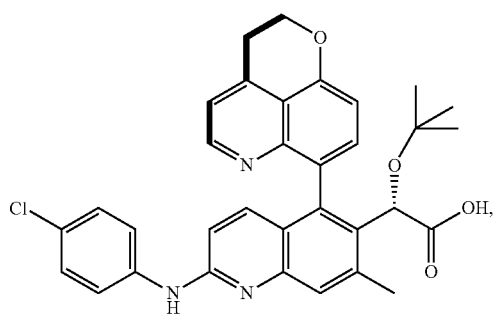
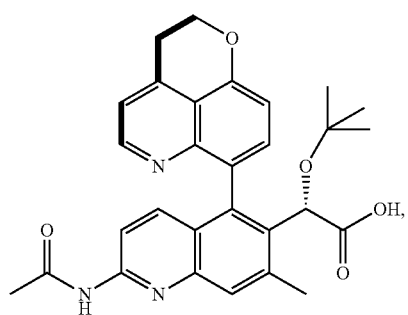
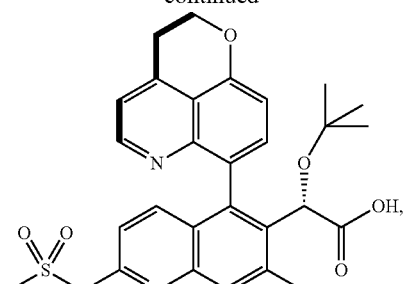
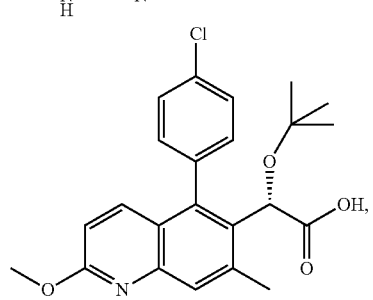
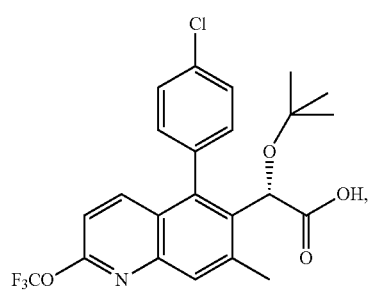
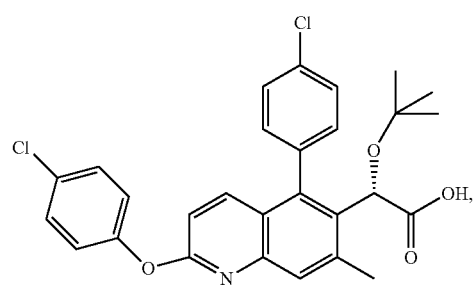
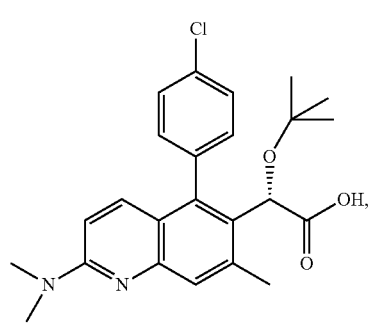

85
-continued
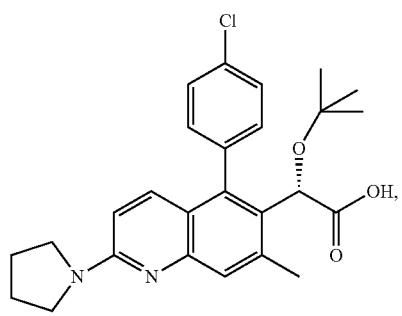
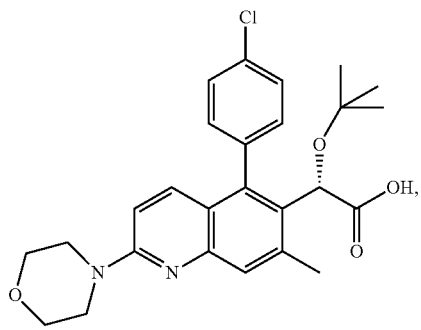
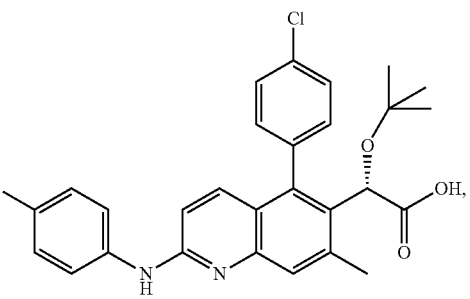
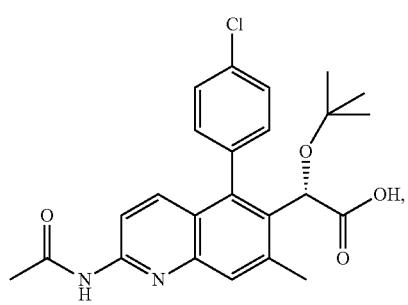
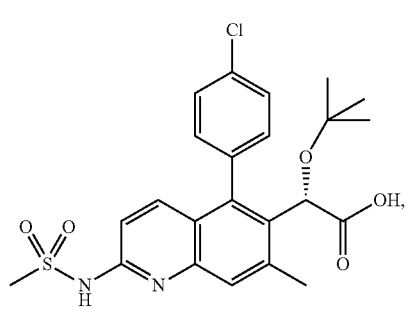
86
-continued
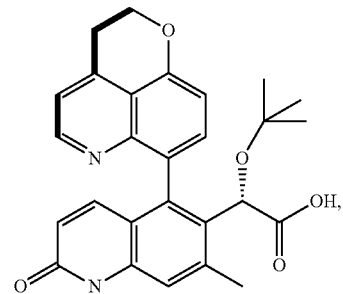
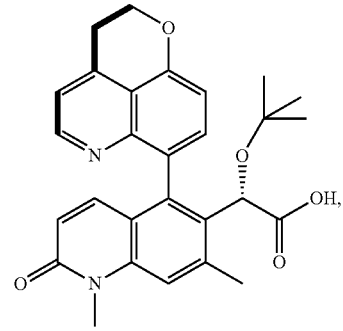
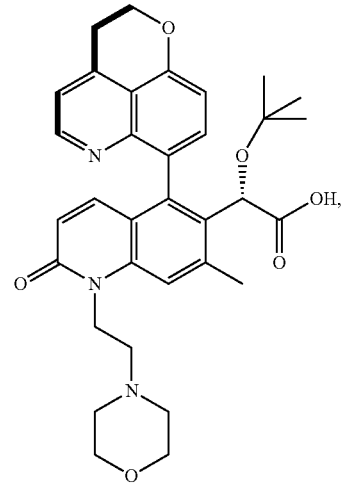
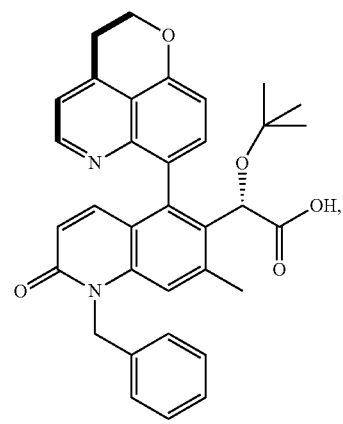

87
-continued
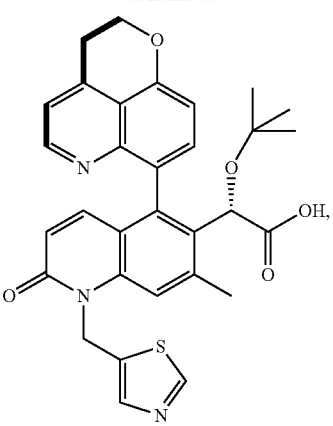
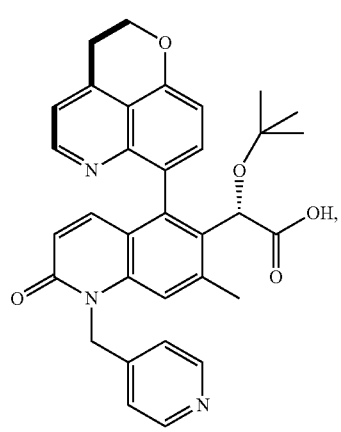
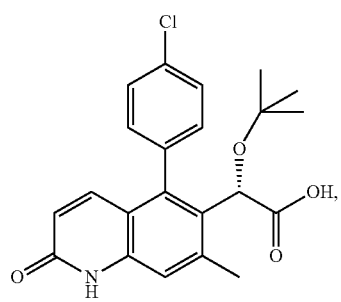
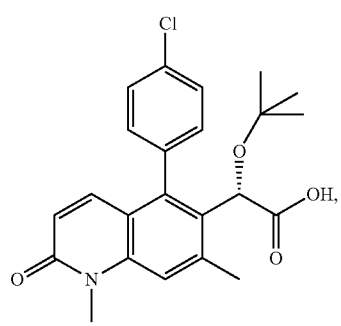
88
-continued
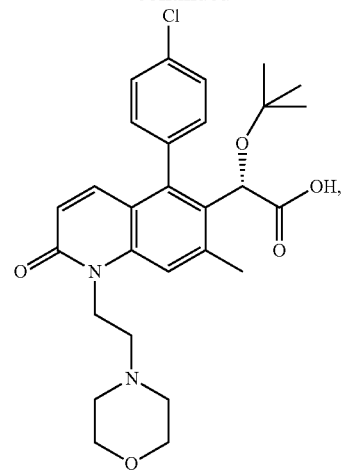
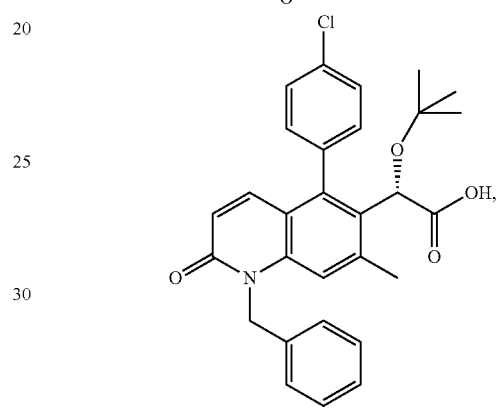
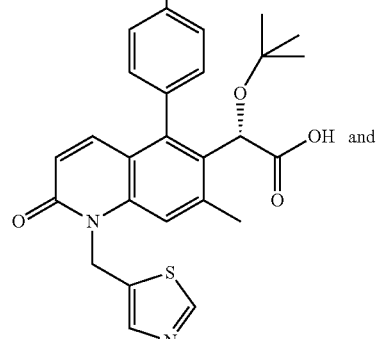 and
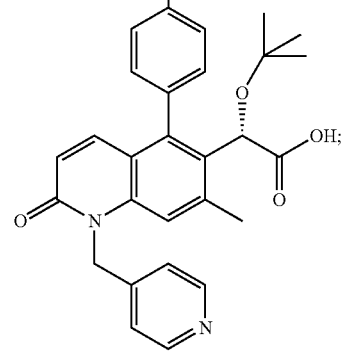
and salts thereof.

In one embodiment, the compounds of formula I include:
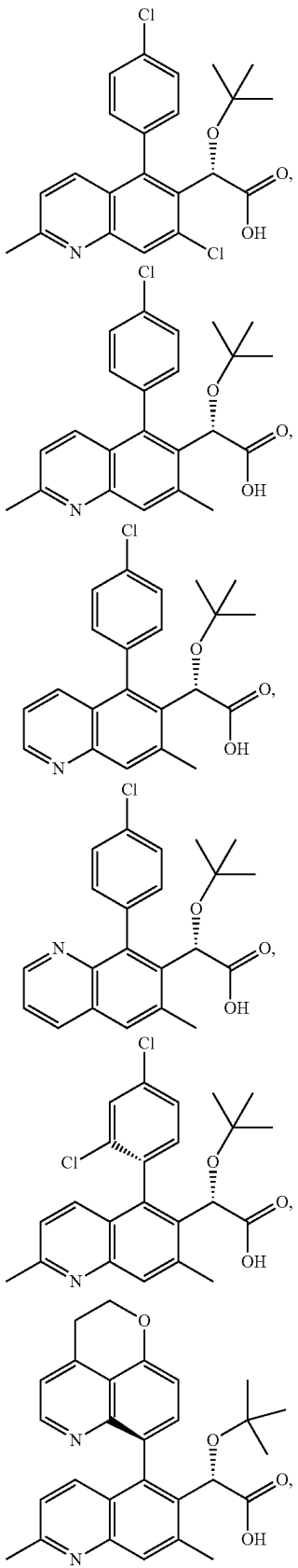
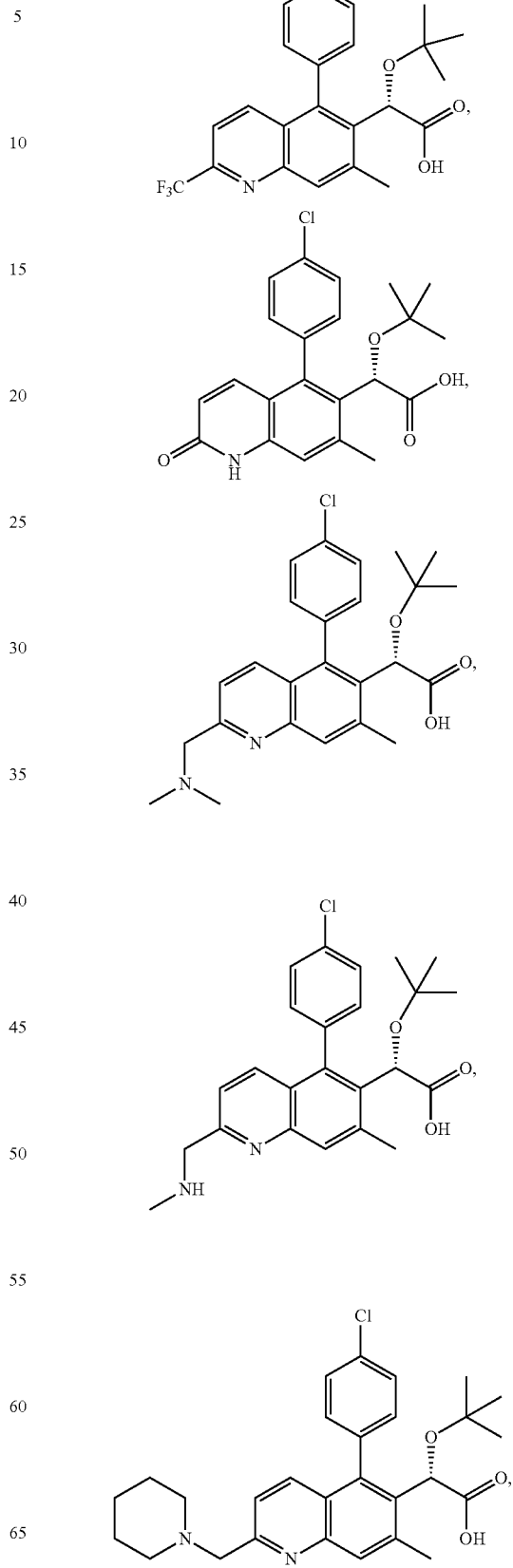

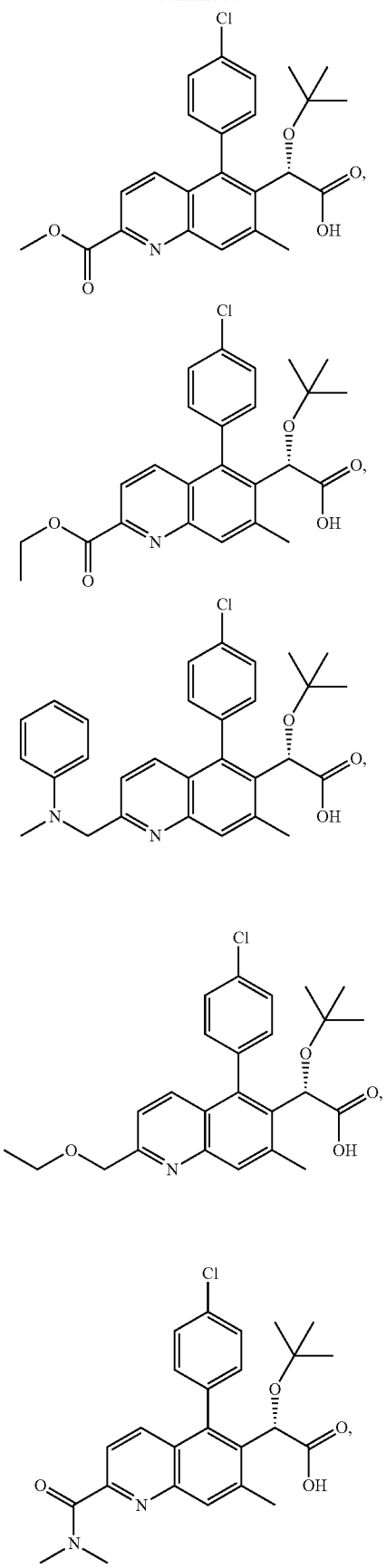
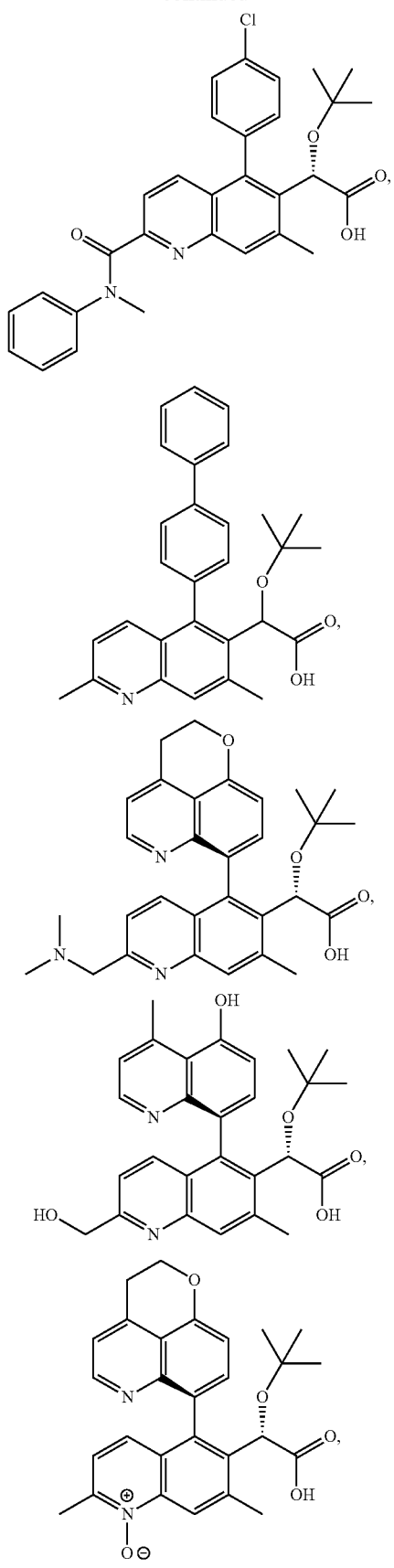

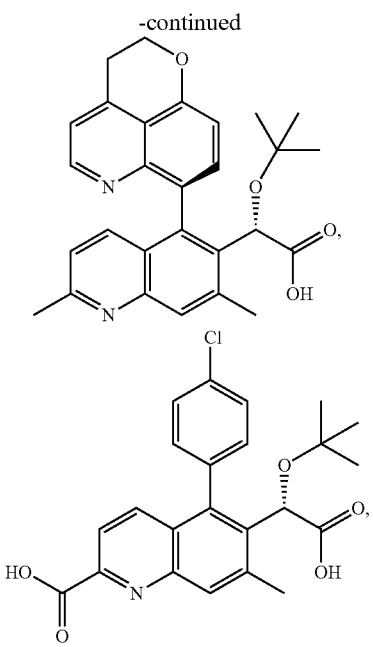
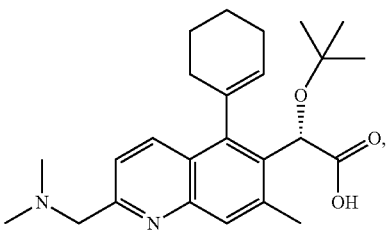
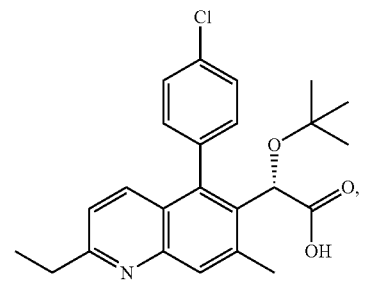
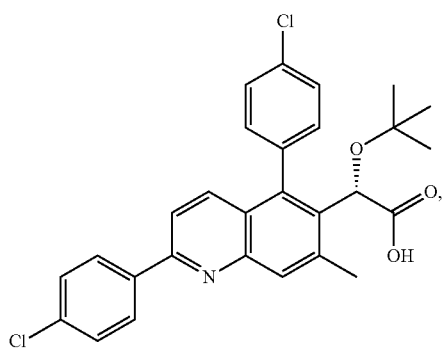
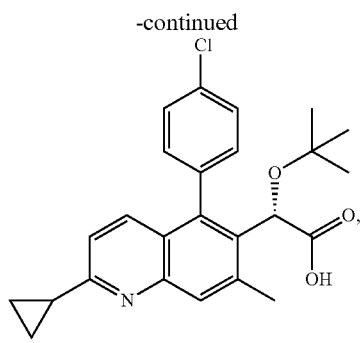
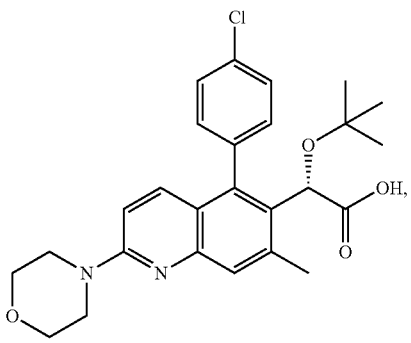
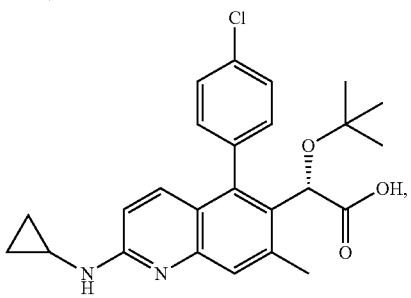
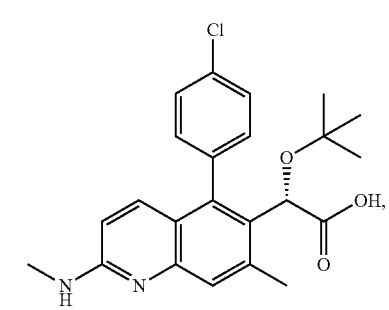
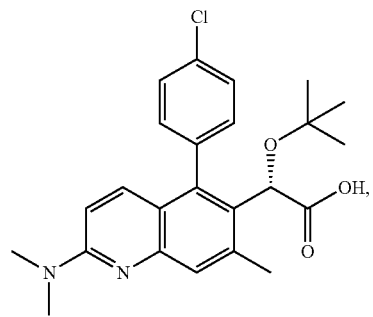

95
-continued
96
-continued
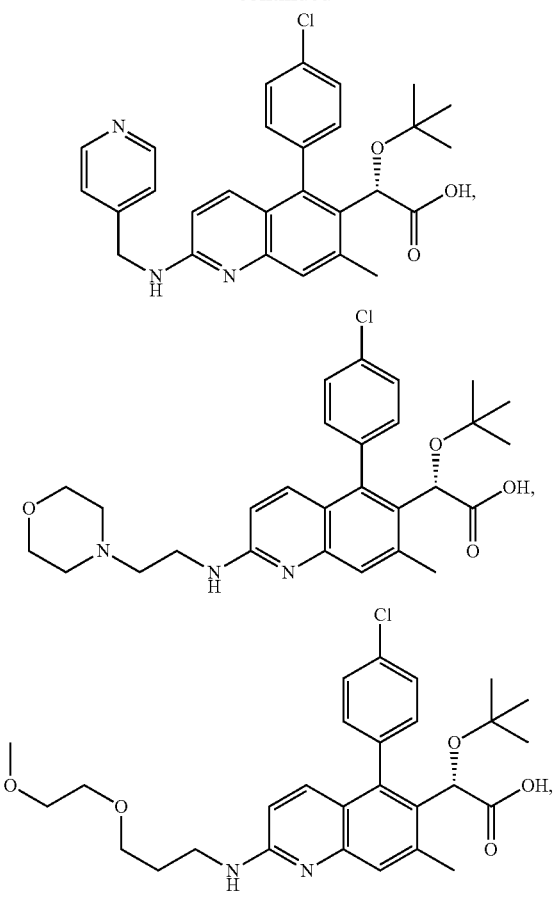
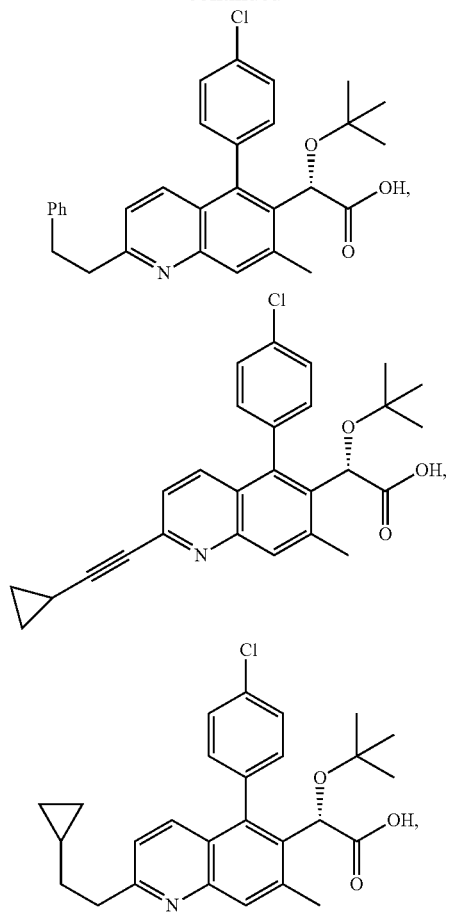
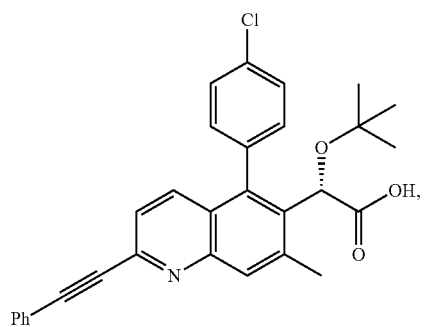
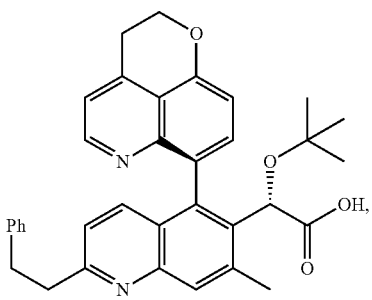

97
-continued
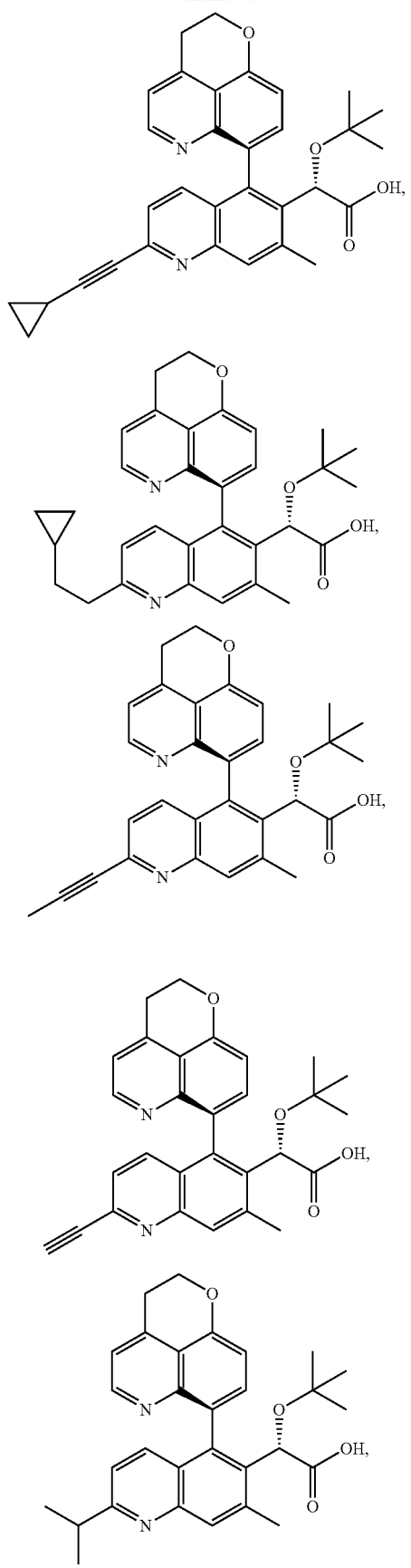
98
-continued
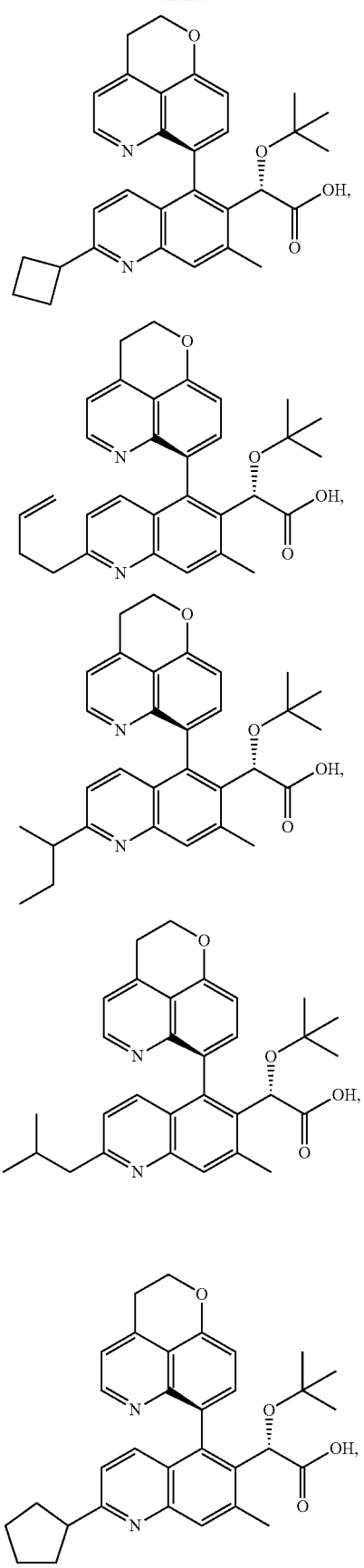

99
-continued
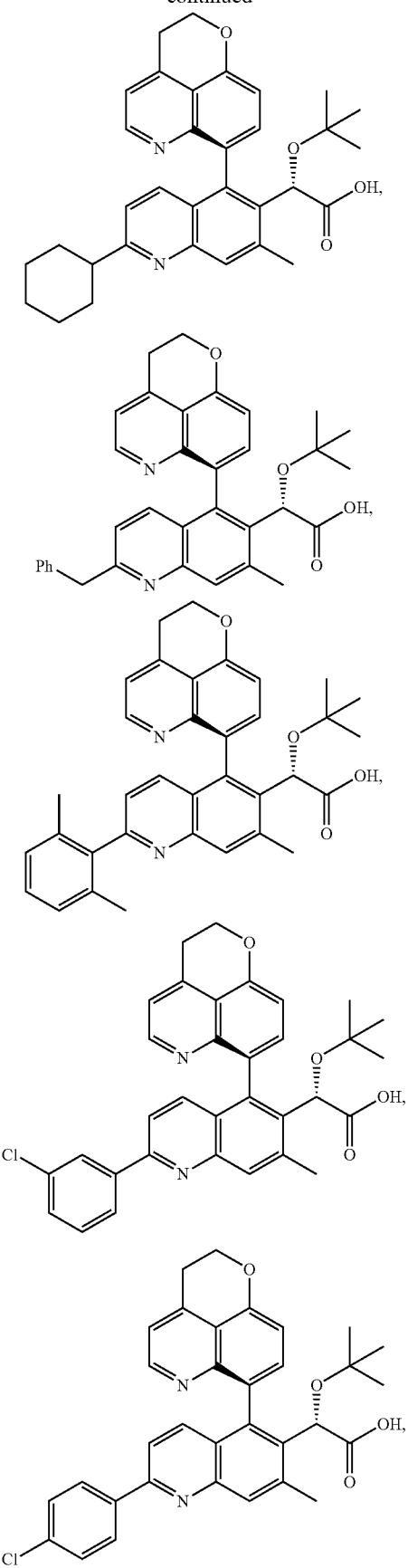
100
-continued
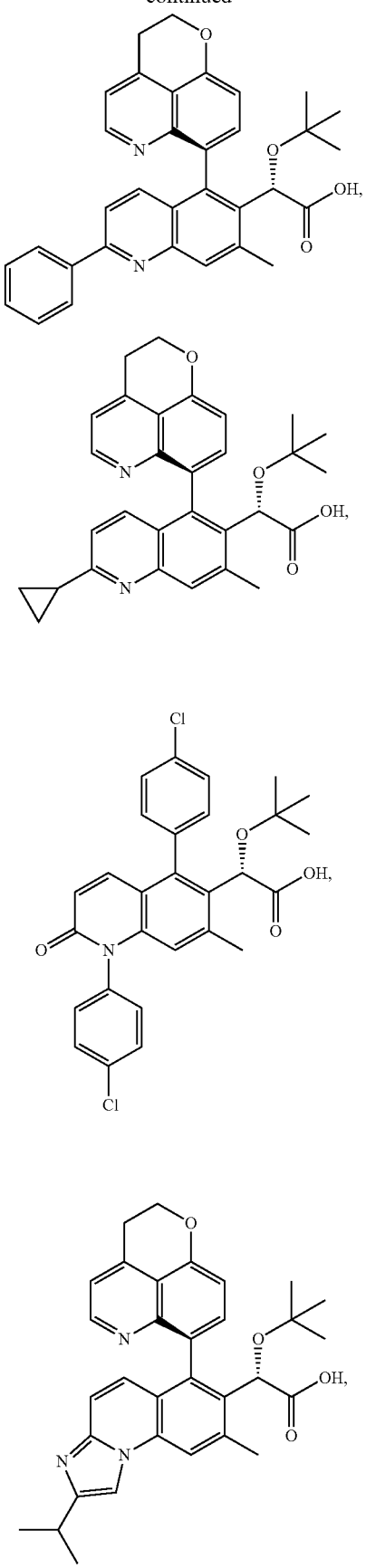

101
-continued
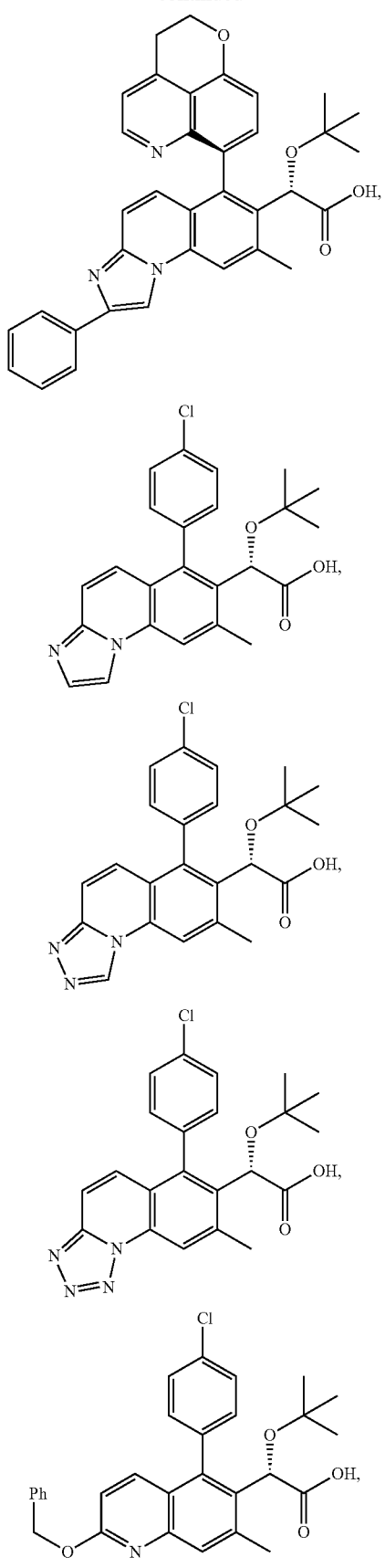
102
-continued
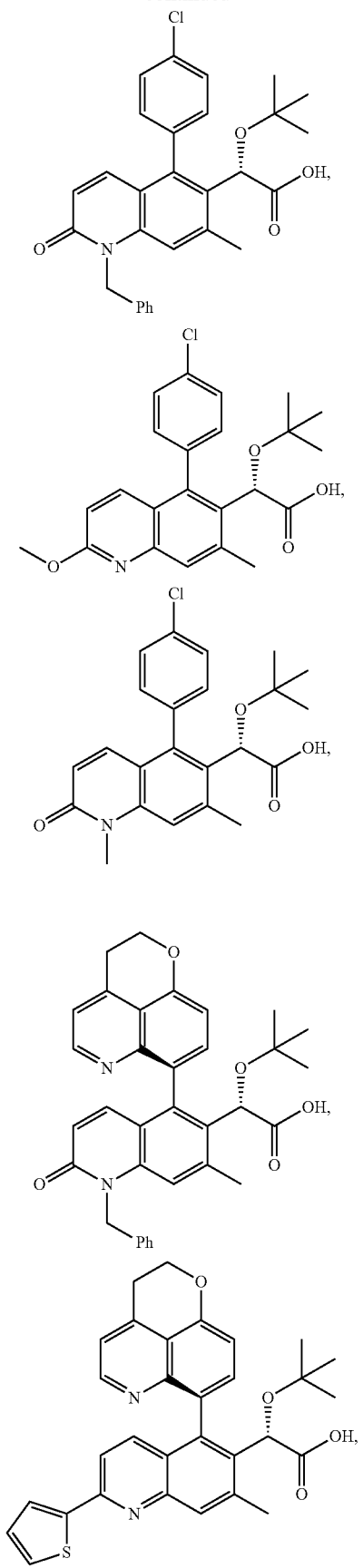

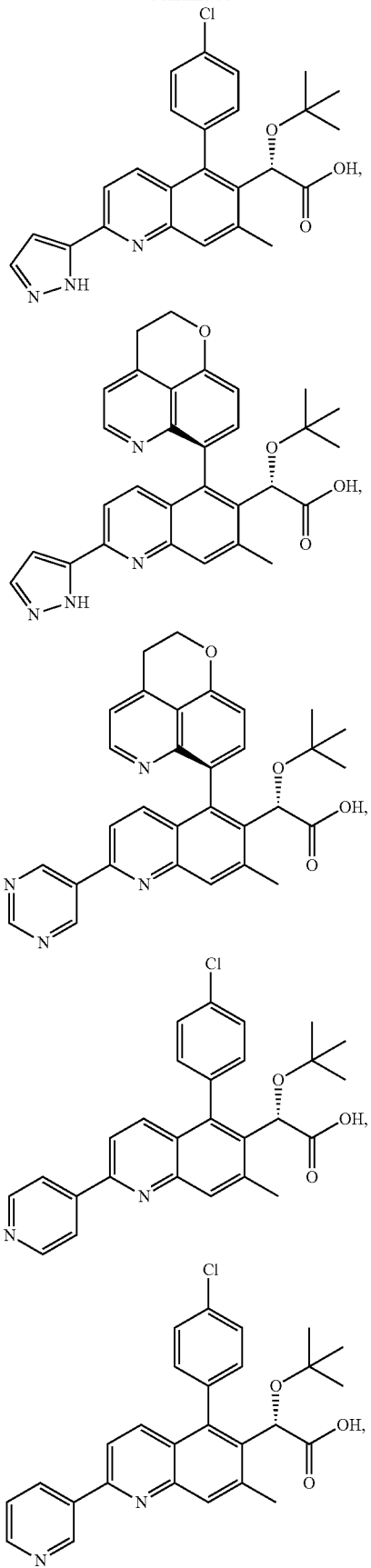
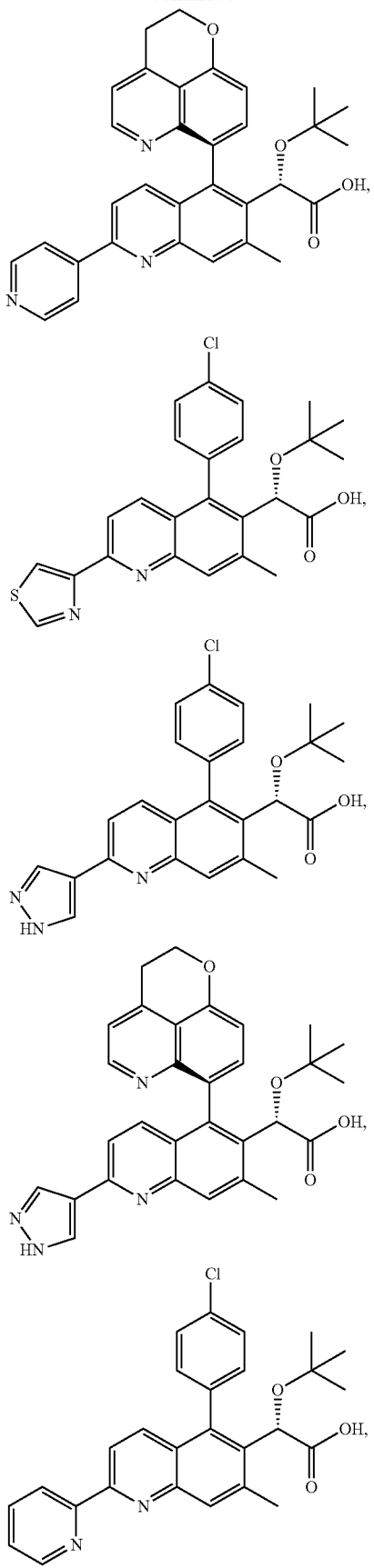

105
-continued
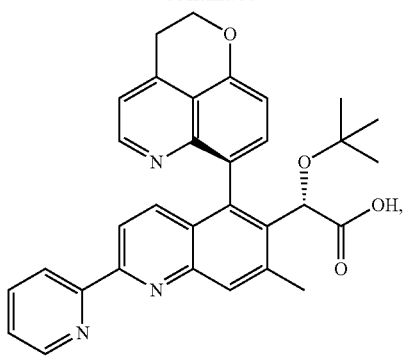
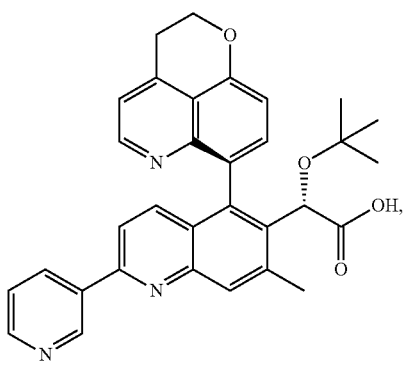
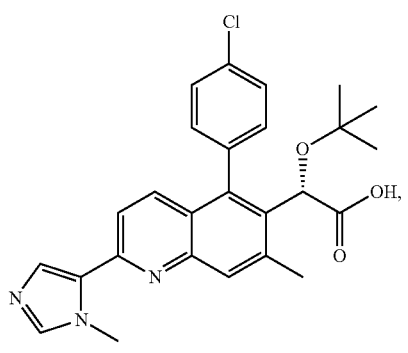
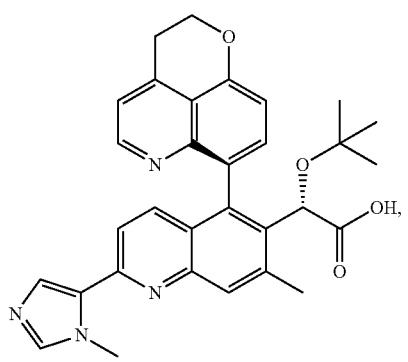
106
-continued
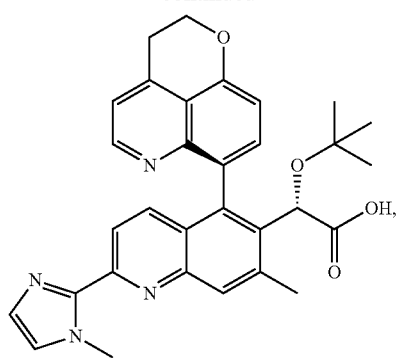
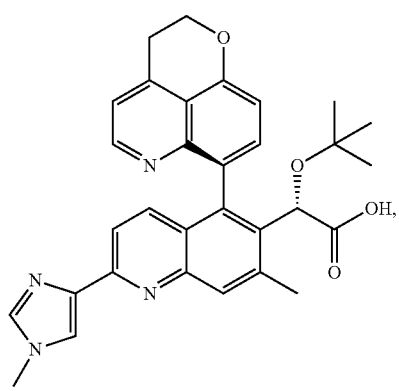
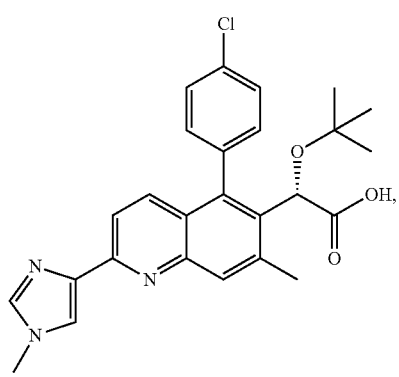
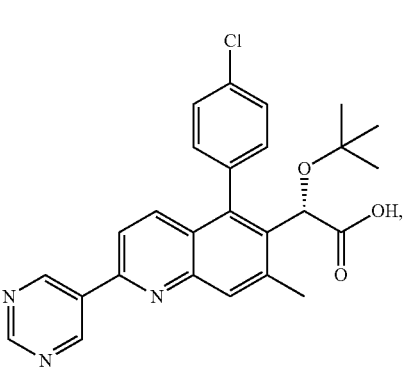

107
-continued
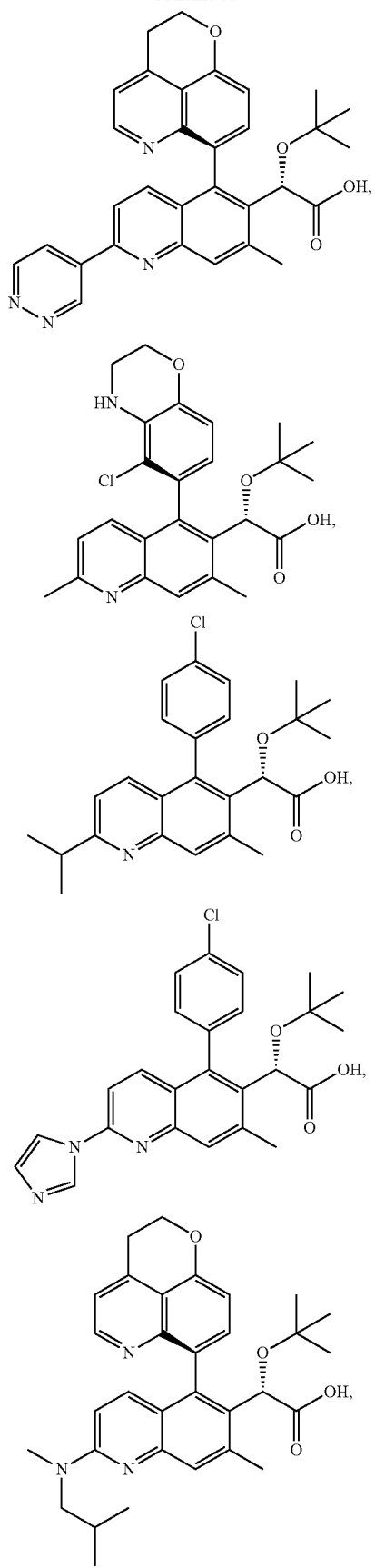
108
-continued
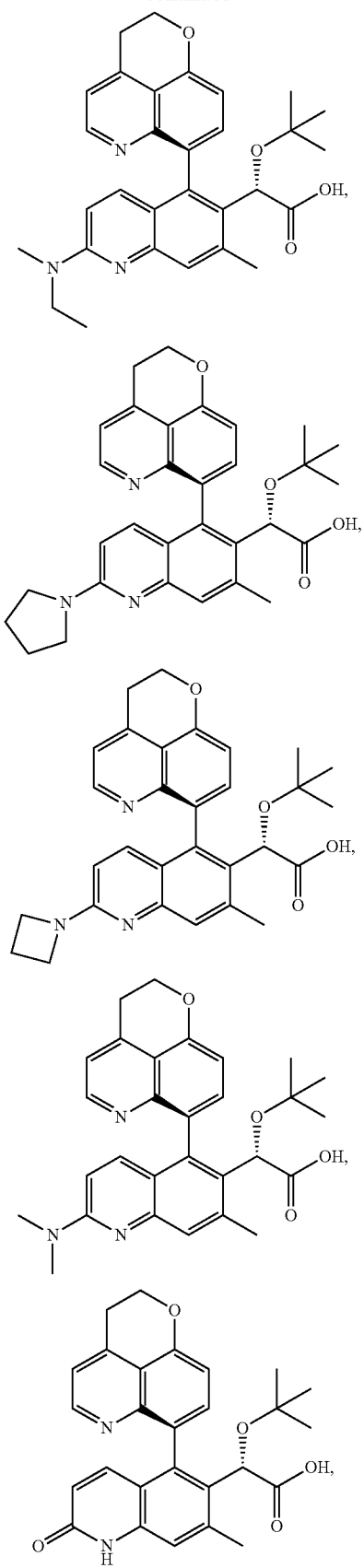

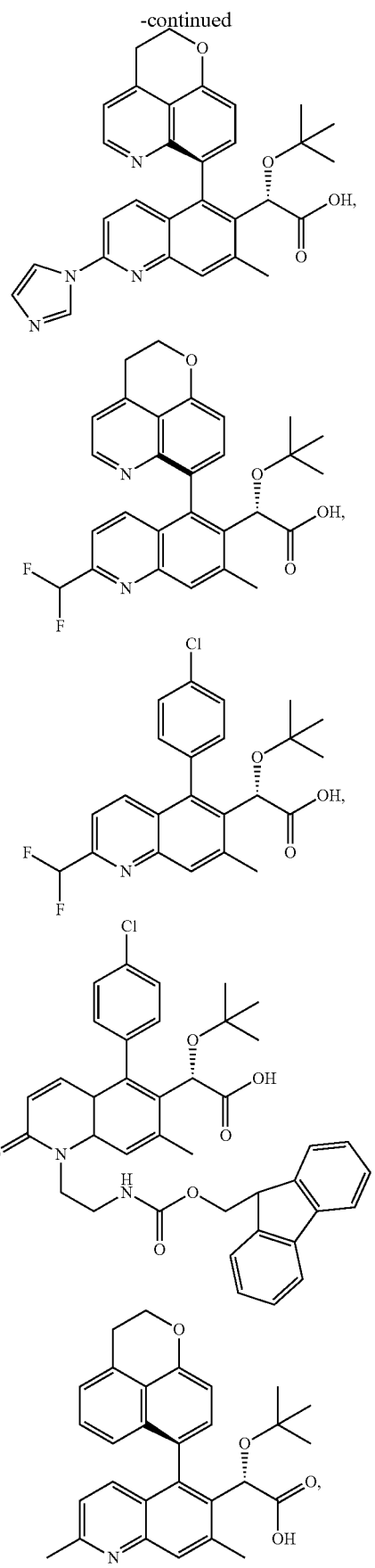
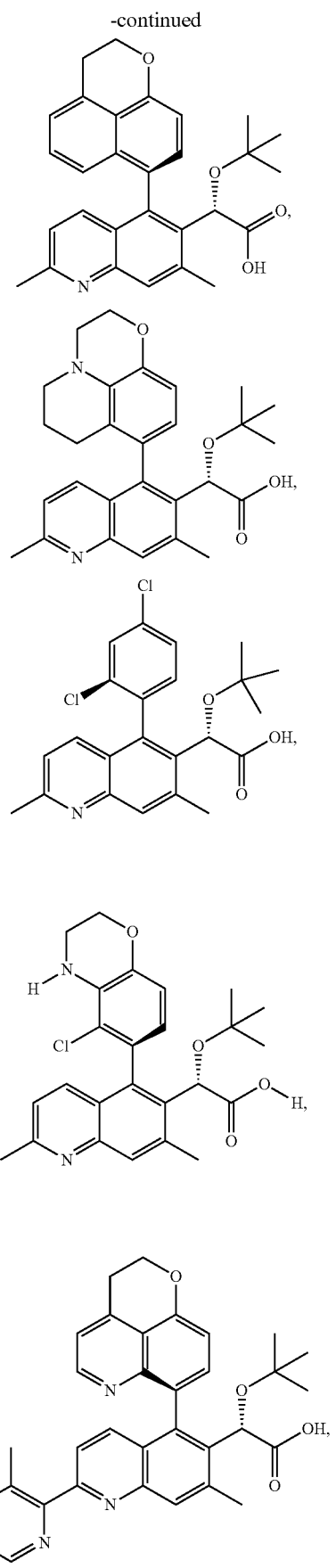

-continued
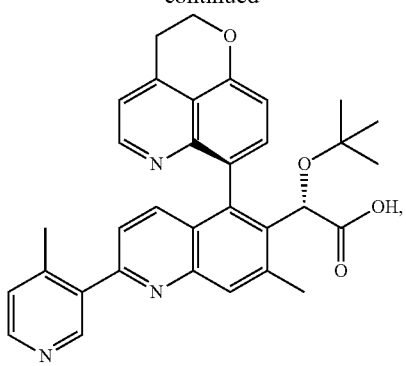
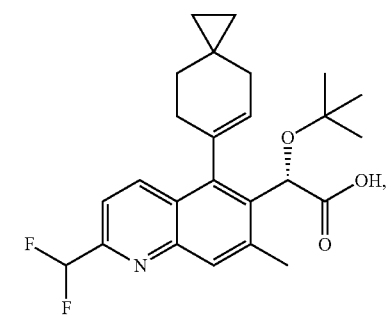
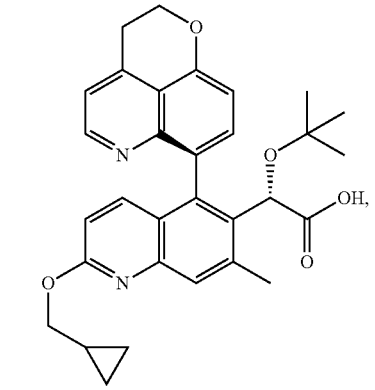
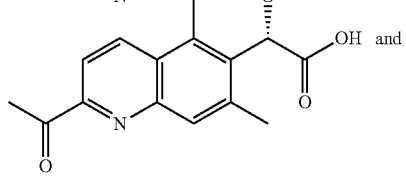
-continued
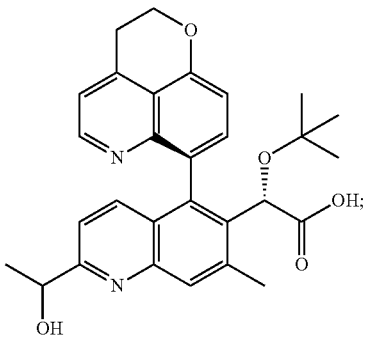
and salts thereof.
In one embodiment, the compounds of formula I include:
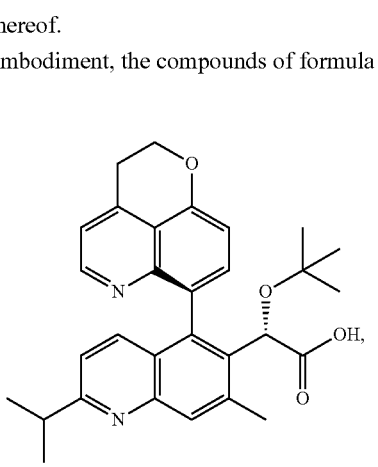
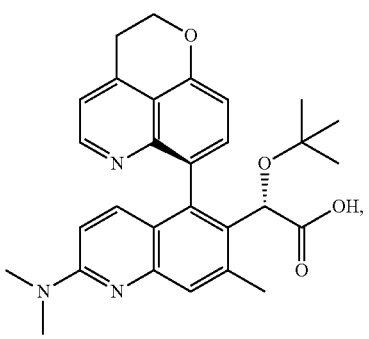
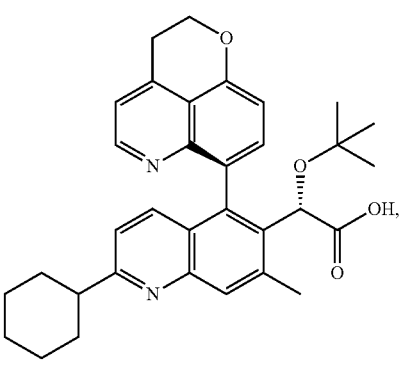

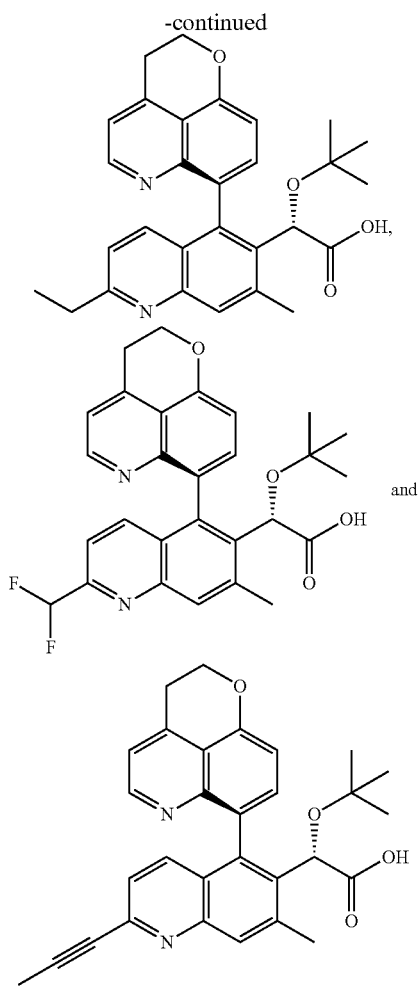
and salts thereof.
General Synthetic Procedures
Schemes 1, 2 and 3 are provided as further embodiments of the invention and illustrate general methods which were used to prepare compounds of formula I and which can be used to prepare additional compounds of formula I. Schemes 4-11 outline methods that were used or can be used to prepare compounds of formula I.
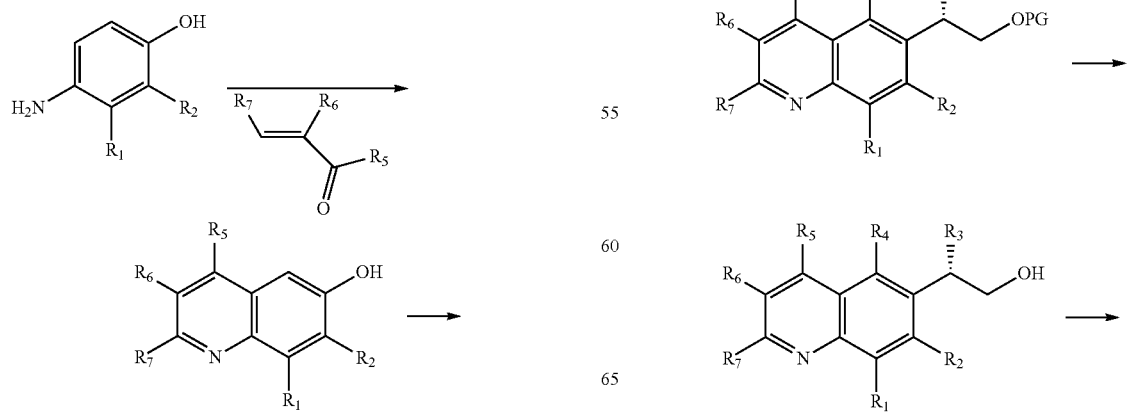
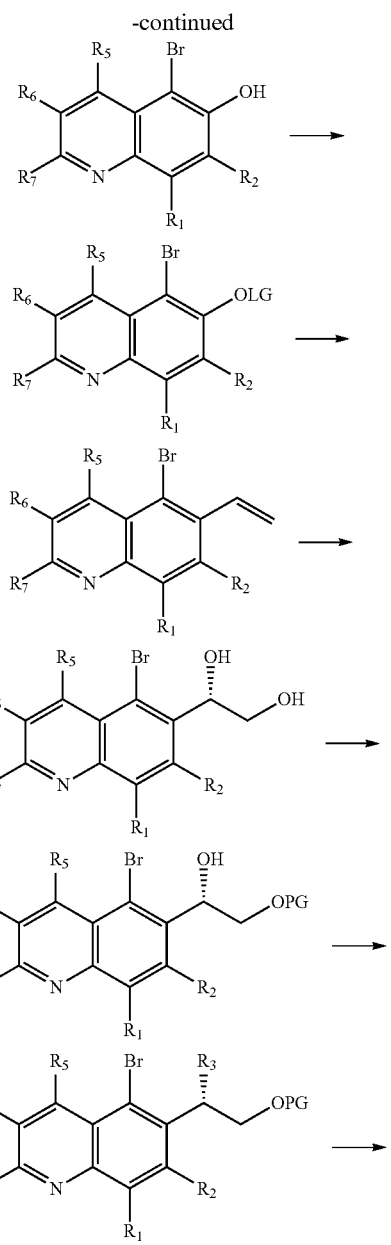

115
-continued

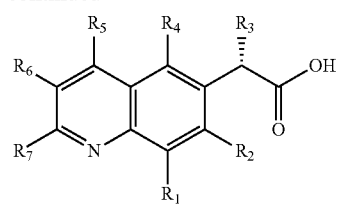

Cyclocondensation of a substituted hydroxyaniline with a substituted, unsaturated aldehyde leads to quinolinols. Bromination can be achieved using electrophilic sources of bromine such as NBS. The phenol can be activated by transforming to a leaving group such as trifluoromethanesulfonate by treatment with trifluoromethanesulfonic anhydride and an appropriate base such as 2,6-lutidine. Regioselective palladium catalysed cross-coupling reactions (e.g. Suzuki or Stille) can be used to alkylate the quinoline with a vinyl group which can then be asymmetrically di-hydroxylated using reagent mixtures such as AD-mix-α. Selective protection of the primary hydroxyl can be achieved with bulky protecting groups, such as pivaloyl chloride. Formation of the $R^3$ group can be achieved by alkylation of the secondary alcohol by various methods. Palladium catalysed cross coupling reactions (e.g. Suzuki or Stille) can be used to install the $R^4$ group. Following hydrolysis of the protecting group, the primary alcohol may then be oxidized to produce desired compounds.

Scheme 2

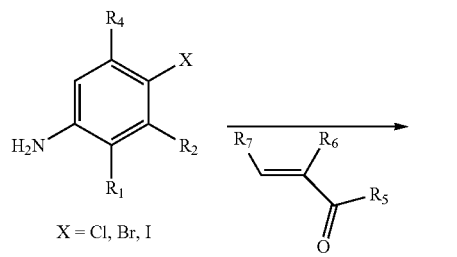

X = Cl, Br, I

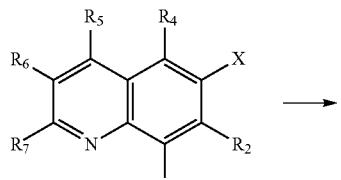

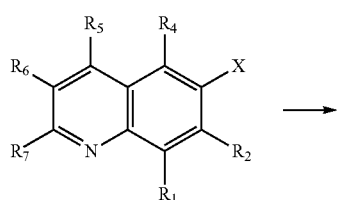

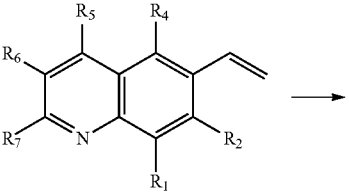

116
-continued


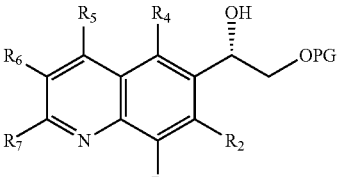

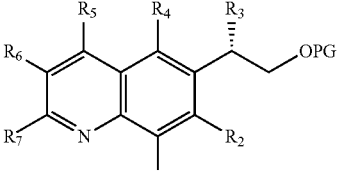

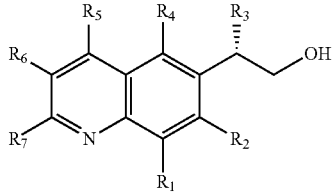

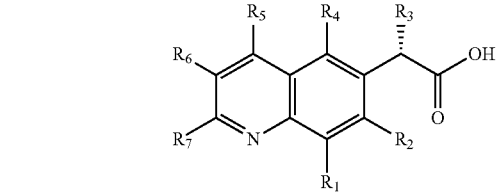

Alternatively, cyclocondensation of a halogenated aniline starting material that is substituted at $R^4$ can undergo cyclocondensation with a substituted, unsaturated aldehyde can deliver $R^4$ substituted, $R^3$ halogenated quinolines directly. These can be further elaborated similarly to the methods described for Scheme 1 to produce desired compounds.

Scheme 3

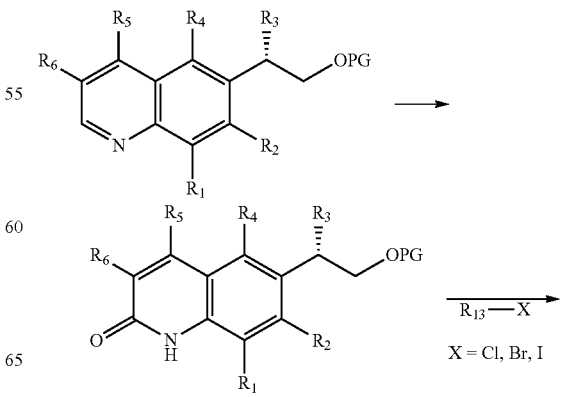

X = Cl, Br, I

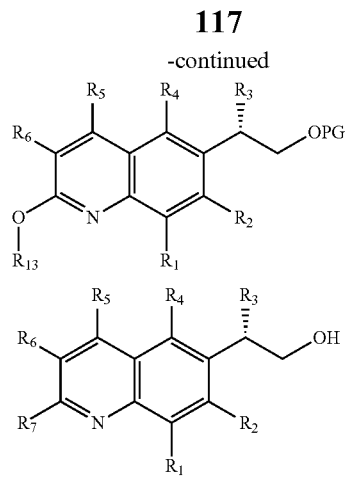

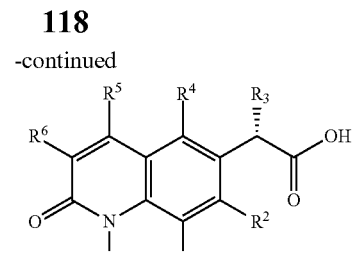

Deprotonation of the quinolinone followed by methods to favor N-alkylation when treated with an appropriate electrophile can yield desired alkylated quinolinone analogues with $R^{13}$ modifications. Subsequent hydrolysis and oxidation produces desired compounds.

Generation of a quinolinone intermediate is achieved by N-oxidation of the quinoline with a reagent such as mCPBA, followed by acylation, thermal rearrangement, and selective removal of the acetate. Deprotonation of the quinolinone followed by methods to favor O-alkylation when treated with an appropriate electrophile allow for substituents at $R^7$ to be produced wherein the $R^7$ group is an ether. Subsequent hydrolysis and oxidation can provide compounds of formula I with $R^7$ ether groups.

Scheme 4

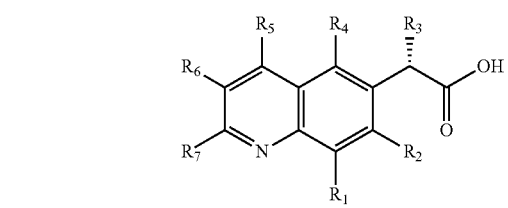

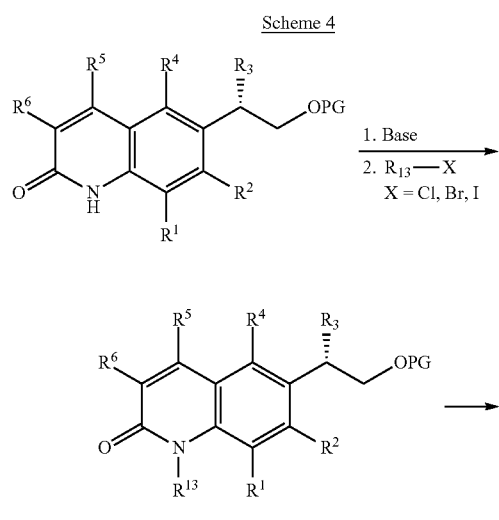

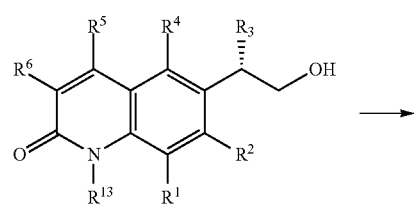

The quinolinyl triflate can be made from the quinolinone. Cross coupling reactions with the triflate (e.g. Suzuki and Sonagashira reaction) can introduce different $R^7$ moieties. Hydrolysis and oxidation can yield the desired compounds.

Scheme 6

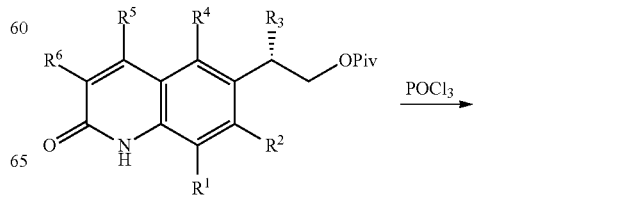

-continued

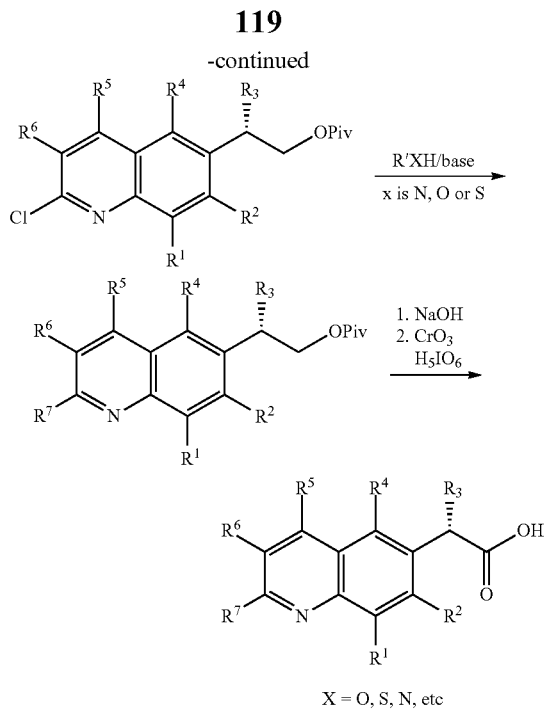

X = O, S, N, etc

The quinolinone can be converted to 2-chloroquinoline by treatment with reagents such as phosphorous oxychloride. Nucleophilic aromatic substitution can introduce different $R^7$ groups wherein the $R^7$ is linked through a heteroatom. Hydrolysis and oxidation can produce the desired analogs.

Scheme 7

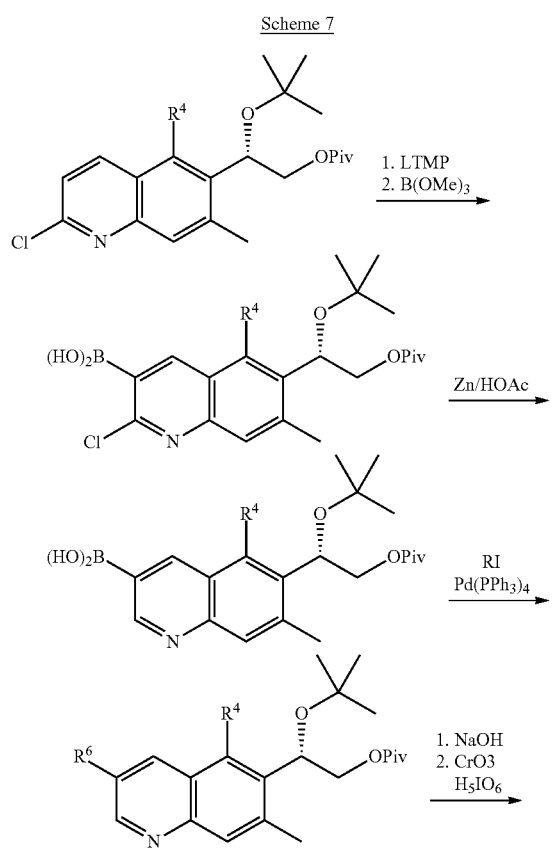

-continued

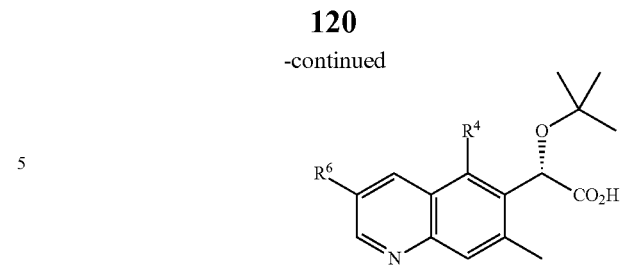

Deprotonation of 2-chloroquinoline, followed by reaction with trimethyl borate can generate the boronic acid. Zinc and acetic acid can be used to reduce the substituted chloroquinoline to the quinoline. Cross coupling and subsequent hydrolysis and oxidation can provide analogs with different $R^6$ moieties.

Scheme 8

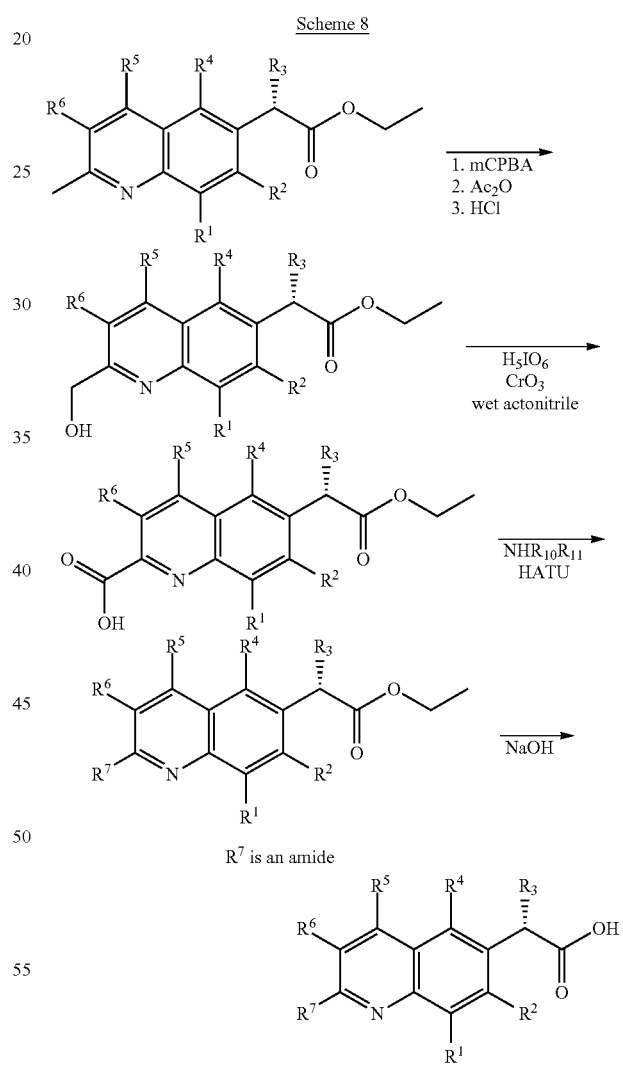

$R^7$ is an amide

The methylquinoline can be oxidized with mCPBA to give the N-oxide, which can react with acetic anhydride and rearrange to yield the hydroxymethylquinoline. Oxidation of the alcohol can provide the carboxylic acid. Coupling with different amines can provide $R^7$ amide moieties. Subsequent hydrolysis can generate compounds of formula I with $R^7$ amides.

Scheme 9

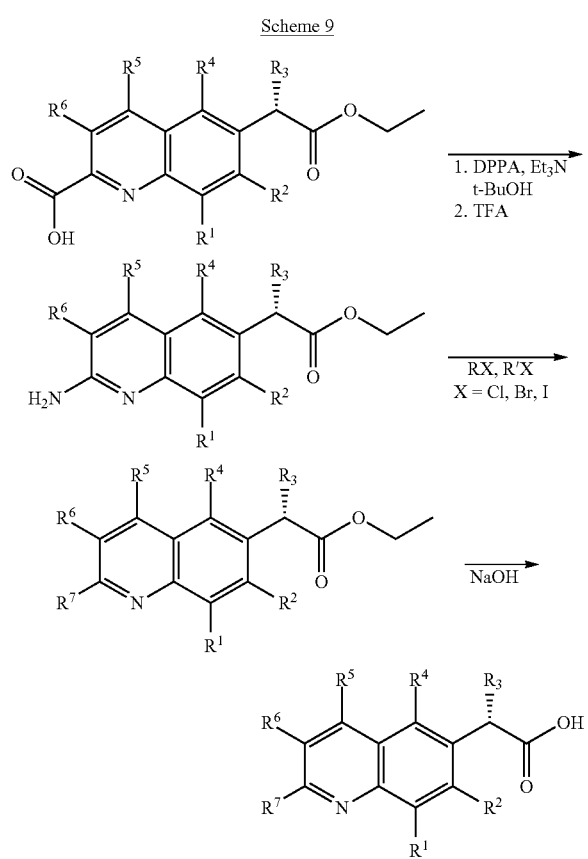

The quinoline carboxylic acid can be converted to a primary amine via a Curtius rearrangement which can be converted to additional R⁷ groups wherein the R⁷ group is an amine. Subsequent hydrolysis can provide compounds of formula 1 with R⁷ amine groups.

Scheme 10

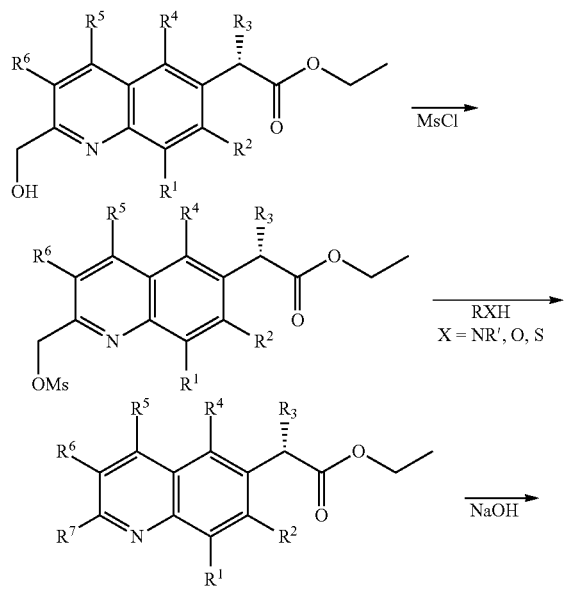

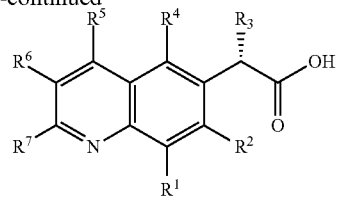

The hydroxymethylquinoline can be converted to mesylate, which can be reacted with different nucleophiles to provide R⁷ groups wherein the R⁷ group is represented by the general formula "—CH₂XR" wherein X is O, S or NR'. Subsequent hydrolysis can generate compounds of formula I.

Scheme 11

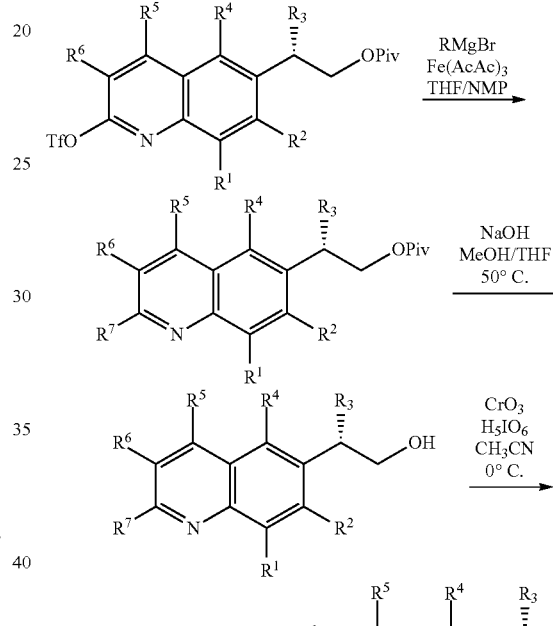

The quinolinyl triflate can react with Grignard or alkyllithium reagents in the presence of a catalyst such as Fe(AcAc)₃ to give the corresponding quinoline. Subsequent deprotection and oxidation can generate compounds of formula I.

Prodrugs

In one embodiment, the invention provides for a prodrug of a compound of the invention. The term "prodrug" as used herein refers to any compound that when administered to a biological system generates a compound of the invention that inhibits the replication of HIV ("the active inhibitory compound"). The compound may be formed from the prodrug as a result of: (i) spontaneous chemical reaction(s), (ii) enzyme catalyzed chemical reaction(s), (iii) photolysis, and/or (iv) metabolic chemical reaction(s).

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters $CH_2OC(=O)R^{99}$ and acyloxymethyl carbonates —$CH_2OC(=O)OR^{99}$ where $R^{99}$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2OC(=O)C(CH_3)_3$. An exemplary acyloxymethyl carbonate prodrug moiety is pivaloyloxymethylcarbonate (POC)—$CH_2OC(=O)OC(CH_3)_3$.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to a phosphate have also been described (Khamnei and Torrence, (1996) *J. Med. Chem.* 39:4109-4115). Benzyl esters are reported to generate parent phosphonic acids. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate phosphoric acid and a quinone methide intermediate. Examples of this class of prodrugs are described by Mitchell et al. (1992) *J. Chem. Soc. Perkin Trans.* II 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. De-esterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958).

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes.

The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provides compositions comprising one or more compounds of the invention formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

The antiviral properties of a compound of the invention may be determined using Test A described below.

Test A: Antiviral Assays in MT4 Cells

For the antiviral assay utilizing MT-4 cells, 0.4 μL of 189X test concentration of 3-fold serially diluted compound in DMSO was added to 40 μL of cell growth medium (RPMI 1640, 10% FBS, 1% penicillin/Streptomycin, 1% L-Glutamine, 1% HEPES) in each well of 384-well assay plates (10 concentrations) in quadruplicate.

1 mL aliquots of 2×10e6 MT-4 cells are pre-infected for 1 and 3 hrs respectively, @ 37° C. with 25 μL (MT4) or of either cell growth medium (mock-infected) or a fresh 1:250 dilution of an HIV-IIIb concentrated ABI stock (0.004 m.o.i. for MT4 cells). Infected and uninfected cells are diluted in cell growth medium and 35 uL of 2000 (for MT4) cells is added to each well of the assay plates.

Assay plates were then incubated in a 37° C. incubator. After 5 days of incubation, 25 μl of 2× concentrated CellTiter-Glo™ Reagent (catalog #G7573, Promega Biosciences, Inc., Madison, Wis.) was added to each well of the assay plate. Cell lysis was carried out by incubating at room temperature for 2-3 min and then chemiluminescence was read using the Envision reader (PerkinElmer).

Compounds of the present invention demonstrate antiviral activity in this assay (Test A) as depicted in the table below.

| Compound Number | EC50 (nM) |
| --- | --- |
| 1L | 170 |
| 2K | 55 |
| 3L | 1059 |
| 4J | 543 |
| 5J | 19 |
| 6D | 20 |
| 7J | 160 |
| 8L | 559 |
| 9 | 173 |
| 10 | 897 |
| 11 | 479 |
| 12 | 210 |
| 13 | 150 |
| 14 | 983 |
| 15 | 334 |
| 16 | 220 |
| 17 | 359 |
| 19 | 53000 |
| 20 | 1744 |
| 21 | 231 |
| 22 | 1075 |
| 23 | 26185 |
| 24 | 29783 |
| 25 | 346 |
| 26 | 45 |
| 27 | 23 |
| 28 | 43 |
| 29 | 939 |
| 30 | 153 |
| 31 | 105 |
| 32 | 108 |
| 33 | 95 |
| 34 | 266 |
| 35 | 157 |
| 36 | 20 |
| 37A | 36 |
| 37B | 46 |
| 38 | 68 |
| 39 | 11 |
| 40 | 51 |
| 41 | 26 |
| 42 | 46 |
| 43 | 27 |
| 44 | 18 |
| 45 | 29150 |
| 46 | 20 |
| 47 | 14 |
| 48 | 26 |
| 49 | 27 |
| 50 | 24 |
| 51 | 30 |
| 52 | 25 |
| 53 | 360 |
| 54 | 87 |
| 55 | 41 |
| 56 | 40 |
| 57 | 20 |
| 58 | 14 |
| 59 | 321 |
| 60 | 305 |
| 61 | 119 |
| 62 | 72 |
| 63 | 183 |
| 64 | 290 |
| 65A | 85 |
| 65B | 55 |
| 66 | 297 |
| 67 | 273 |
| 68 | 29150 |
| 69 | 82 |
| 70 | 206 |
| 71 | 118 |
| 72 | 194 |
| 73 | 247 |
| 74 | 92 |
| 75 | 38 |
| 76 | 267 |
| 77 | 135 |
| 78 | 163 |
| 79 | 86 |
| 80 | 52 |
| 81 | 69 |
| 82 | 171 |
| 83 | 42 |
| 84 | 330 |
| 85 | 131 |
| 86 | 78 |
| 87 | 175 |
| 88 | 514 |
| 89 | 42 |
| 90 | 67 |
| 91 | 73 |
| 92 | 300 |
| 93 | 94 |
| 94 | 149 |
| 95 | 54 |
| 96 | 37 |
| 97 | 898 |
| 98 | 251 |
| 99 | 12 |
| 100 | 75 |
| 101 | 367 |
| 102A | 13 |
| 102B | 110 |
| 103 | 25 |
| 104 | 720 |
| 105 | 105 |
| 106 | 25 |
| 107 | n.d. |
| 108 | n.d. |
| 109 | n.d |
| 110 | n.d. |
| 111 | 352 |
| 112 | n.d. | n.d. (not determined)

In certain embodiments, the compounds demonstrate an EC50 of <50 µM. In certain embodiments, the compounds demonstrate an EC50 of <30 µM. In certain embodiments, the compounds demonstrate an EC50 of <10 µM. In certain embodiments, the compounds demonstrate an EC50 of <1 µM.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

The invention has been described with reference to various specific and preferred embodiments and techniques. However, it should be understood that many variations and modifications may be made while remaining within the spirit and scope of the invention.

The invention will now be illustrated by the following non-limiting Examples.
EXAMPLE 1
Preparation of (S)-2-tert-butoxy-2-(7-chloro-5-(4-chlorophenyl)-2-methylquinolin-6-yl)acetic acid (1L)
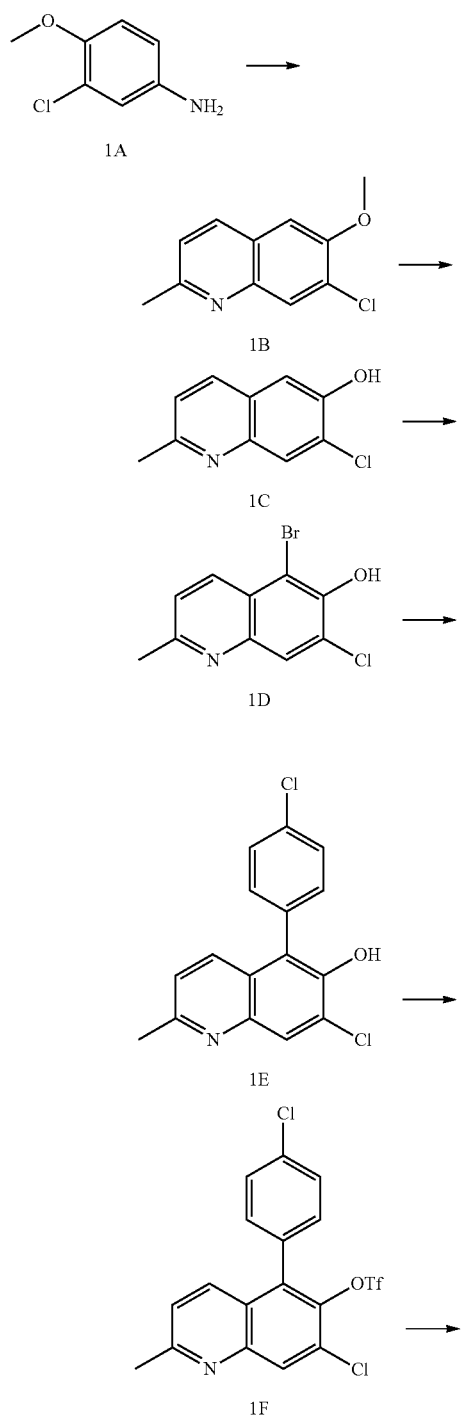

-continued

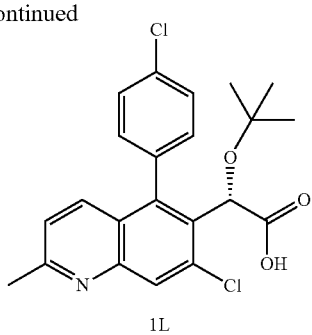

1L

A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% H₂O) to a volume of 114 mL. This stock solution (0.80 mL) was added to a solution of (S)-2-tert-butoxy-2-(7-chloro-5-(4-chlorophenyl)-2-methylquinolin-6-yl)ethanol (1K) (11 mg, 0.027 mmol) in wet acetonitrile (3.0 mL), 0.75% H₂O) at 0° C. The reaction mixture was stirred for 30 minutes at 0° C. and quenched with 1.5 M K₂HPO₄ solution. Ethyl acetate was added and the organic layer separated and washed with 1:1 brine/H₂O (2×) and saturated NaHSO₃/brine. The organic layer was dried (MgSO₄) and concentrated and purified by prep-HPLC to give 1L as a TFA salt (8 mg, 57%). ¹H-NMR 300 MHz, (CD₃OD) δ 8.19 (s, 1H), 8.17 (d, 1H), 7.70-7.52 (m, 4H), 7.40-7.30 (m, 1H), 2.89 (s, 3H), 1.01 (s, 9H); LCMS-ESI⁺ (m/z): [M-FH]⁺ calcd for C₂₂H₂₂Cl₂NO₃: 419.3. Found: 418.1, 420.1, 422.1.

Preparation of (S)-2-tert-butoxy-2-(7-chloro-5-(4-chlorophenyl)-2-methylquinolin-6-yl)ethanol (1K)

Step 1.
Preparation of 7-chloro-6-methoxy-2-methylquinoline (1B): To 3-chloro-4-methoxyaniline (1A) (5.0 g, 31.7 mmol) was added 6 M HCl (100 mL) and the reaction was heated to 100° C. with stirring. Toluene (30 mL) was added followed by the slow addition of crotonaldehyde (5.3 mL, 63.5 mmol) at 100° C. The mixture was stirred at 100° C. for 2 hours and cooled to room temperature. The water layer was separated and neutralized with 2 M NaOH solution to pH ~8. The solid that formed was filtered and collected. The crude product was purified by flash column chromatography to give 1B as white solid (3.3 g, 50%). LCMS-ESI⁺ (m/z): 208.2, 210.2 (M+H)⁺.
Step 2.
Preparation of 7-chloro-2-methylquinolin-6-ol (1C): To a stirred solution of 7-chloro-6-methoxy-2-methylquinoline (1B) (1.22 g, 5.9 mmol) in dichloromethane (15 mL) was added BBr₃ (23.6 mL 1 M DCM solution, 23.6 mmol) at 0° C. The mixture was stirred at 0° C. for 2 hours and quenched by the slow addition of a NaHCO₃ solution. The mixture was extracted with ethyl acetate. The organic layer was washed with brine, dried and concentrated. The residue was purified by column chromatography to give the pure product 1C (0.91 g, 80%). LCMS-ESI⁺ (m/z): 194.1, 196.1 (M+H)⁺.
Step 3.
Preparation of 5-bromo-7-chloro-2-methylquinolin-6-ol (1D): To a stirred solution of 7-chloro-2-methylquinolin-6-ol (1C) (450 mg, 2.3 mmol) in acetic acid (15 mL) was added Br₂ (0.13 mL, 2.4 mmol) at ambient temperature. The mixture was stirred at ambient temperature for 2 hours. The solid that formed was filtered and collected to give 1D as an off-white solid as the HBr salt (847 mg, 100%). LCMS-ESI⁺ (m/z): 281.1, 283.1 (M+H)⁺.
Step 4.
Preparation of 7-chloro-5-(4-chlorophenyl)-2-methylquinolin-6-ol (1E): Pd(PPh₃)₄ (120 mg, 0.1 mmol) was added to a mixture of 5-bromo-7-chloro-2-methylquinolin-6-ol (1D) (345 mg, 1.04 mmol), 4-chlorophenylboronic acid (326 mg, 2.09 mmol) and K₂CO₃ (2.3 mL 2 M in water, 4.7 mmol) in 1,2-dimethoxyethane (10 mL). The reaction mixture was flushed with nitrogen, heated at 80° C. for 16 hours, and then the volatile component was removed in vacuo. The residue was dissolved in ethyl acetate (100 mL), washed with a NaHCO₃ solution, water and brine, dried over Na₂SO₄, filtered and concentrated in vacuo. The obtained residue was purified by flash chromatography to provide 1E as a white solid (147 mg, 47%). LCMS-ESI⁺ (m/z): 304.2, 306.2 (M+H)⁺.
Step 5.
Preparation of 7-chloro-5-(4-chlorophenyl)-2-methylquinolin-6-yl trifluoromethanesulfonate (1F): To a stirred solution of 7-chloro-5-(4-chloro-phenyl)-2-methylquinolin-6-ol (1E) (138 mg, 0.46 mmol) in dichloromethane (4 mL) and pyridine (1.5 mL) was added Tf₂O (0.16 mL, 0.92 mmol) at 0° C. The mixture was stirred at room temperature for 2 hours and quenched by the slow addition of a NaHCO₃ solution. The mixture was extracted with ethyl acetate. The organic layer was washed with brine, dried and concentrated to get a brown solid (194 mg, 97%). LCMS-ESI⁺ (m/z): 436.0, 437.9 (M+H)⁺. The crude product 1F was used on next step reaction without further purification.
Step 6.
Preparation of 7-chloro-5-(4-chlorophenyl)-2-methyl-6-vinylquinoline (1G): Pd(PPh₃)₄ (52 mg, 0.045 mmol) and PdCl₂(PPh₃)₂ (32 mg, 0.045 mmol) were added to a mixture 7-chloro-5-(4-chlorophenyl)-2-methylquinolin-6-yl trifluoromethanesulfonate (1F) (194 mg, 0.45 mmol), tributyl(vinyl)stannane (0.17 mL, 0.58 mmol), lithium chloride (57 mg, 1.4 mmol) and 2,6-di-tert-butyl-4-methylphenol (cat. amount) in 1,4-dioxane (8 mL). The reaction mixture was flushed with nitrogen, heated at 80° C. for 16 hours, and then the volatile component was removed in vacuo. The residue was dissolved in ethyl acetate (100 mL), washed with a NaHCO₃ solution, water and brine, dried over Na₂SO₄, filtered and concentrated in vacuo. The obtained residue was purified by flash chromatography to provide the desired product 1G (50 mg, 35%). LCMS-ESI⁺ (m/z): 314.2, 316.2 (M+H)⁺.
Step 7.
Preparation of (S)-1-(7-chloro-5-(4-chlorophenyl)-2-methylquinolin-6-yl)ethane-1,2-diol (1H): AD-mix-α (1 g, excess) was added to a mixed solvent of t-butanol and water (4 mL/4 mL) and stirred at room temperature for 5 min and cooled to 0° C. The mixture was transferred to another flask containing 7-chloro-5-(4-chlorophenyl)-2-methyl-6-vinylquinoline (1G) (30 mg, 0.096 mmol) and stirred at 0° C. for 16 hours. The mixture was diluted with ethyl acetate, washed with NaHCO₃ solution, water and brine, dried over Na₂SO₄, filtered and concentrated in vacuo. The obtained residue was purified by flash chromatography to provide the desired product 1H (28 mg, 84%). LCMS-ESI⁺ (m/z): 348.2, 350.2 (M+H)⁺.
Step 8.
Preparation of (S)-2-(7-chloro-5-(4-chlorophenyl)-2-methylquinolin-6-yl)-2-hydroxyethyl pivalate (11): To a stirred solution of (S)-1-(7-chloro-5-(4-chlorophenyl)-2-methylquinolin-6-yl)ethane-1,2-diol (1H) (28 mg, 0.081 mmol) in dichloromethane (2 mL) and pyridine (0.5 mL) was added trimethyl acetylchloride (0.020 mL, 0.16 mmol) at 0° C. The mixture was stirred at room temperature for 2 hours and quenched by the slow addition of a NaHCO₃ solution. The mixture was extracted with ethyl acetate. The organic layer was washed with brine, dried and concentrated in vacuo. The obtained residue was purified by flash chromatography to provide the desired product 1I (25 mg, 72%). LCMS-ESI⁺ (m/z): 432.2, 434.2 (M+H)⁺.

Step 9.

Preparation of (S)-2-tert-butoxy-2-(7-chloro-5-(4-chlorophenyl)-2-methylquinolin-6-yl)ethyl pivalate (1J): To a stirred solution of (S)-2-(7-chloro-5-(4-chlorophenyl)-2-methylquinolin-6-yl)-2-hydroxyethyl pivalate (1I) (25 mg, 0.058 mmol) in t-butylacetate (3 mL) was added 70% perchloric acid (0.02 mL, 0.23 mmol) at 0° C. The mixture was stirred at room temperature for 2 hours and quenched by the slow addition of a NaHCO₃ solution. The mixture was extracted with ethyl acetate. The organic layer was washed with brine, dried and concentrated in vacuo. The obtained residue was purified by flash chromatography to provide the desired product 1J (22 mg, 78%). LCMS-ESI⁺ (m/z): 488.2, 490.2 (M+H)⁺.

Step 10.

Preparation of (S)-2-tert-butoxy-2-(7-chloro-5-(4-chlorophenyl)-2-methylquinolin-6-yl)ethanol (1K): To a stirred solution of (S)-2-tert-butoxy-2-(7-chloro-5-(4-chlorophenyl)-2-methylquinolin-6-yl)ethyl pivalate (1J) (22 mg, 0.045 mmol) in THF and methanol (3 mL/1 mL) was added 1 M NaOH solution (1 mL, excess) at 0° C. The mixture was stirred at room temperature for 16 hours and diluted with water. The mixture was extracted with ethyl acetate. The organic layer was washed with brine, dried and concentrated in vacuo. The obtained residue was purified by flash chromatography to provide the desired product 1K (11 mg, 61%). LCMS-ESI⁺ (m/z): 404.2, 406.2 (M+H)⁺.

EXAMPLE 2

Preparation of (S)-2-tert-butoxy-2-(5-(4-chlorophenyl)-2,7-dimethylquinolin-6-yl)acetic acid (2K)

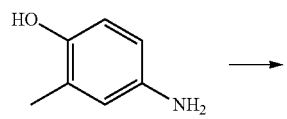

2A

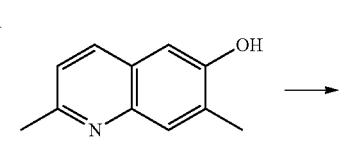

2B

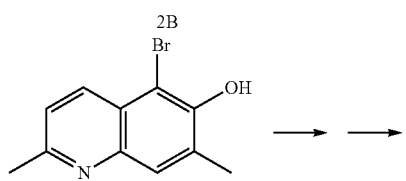

2C

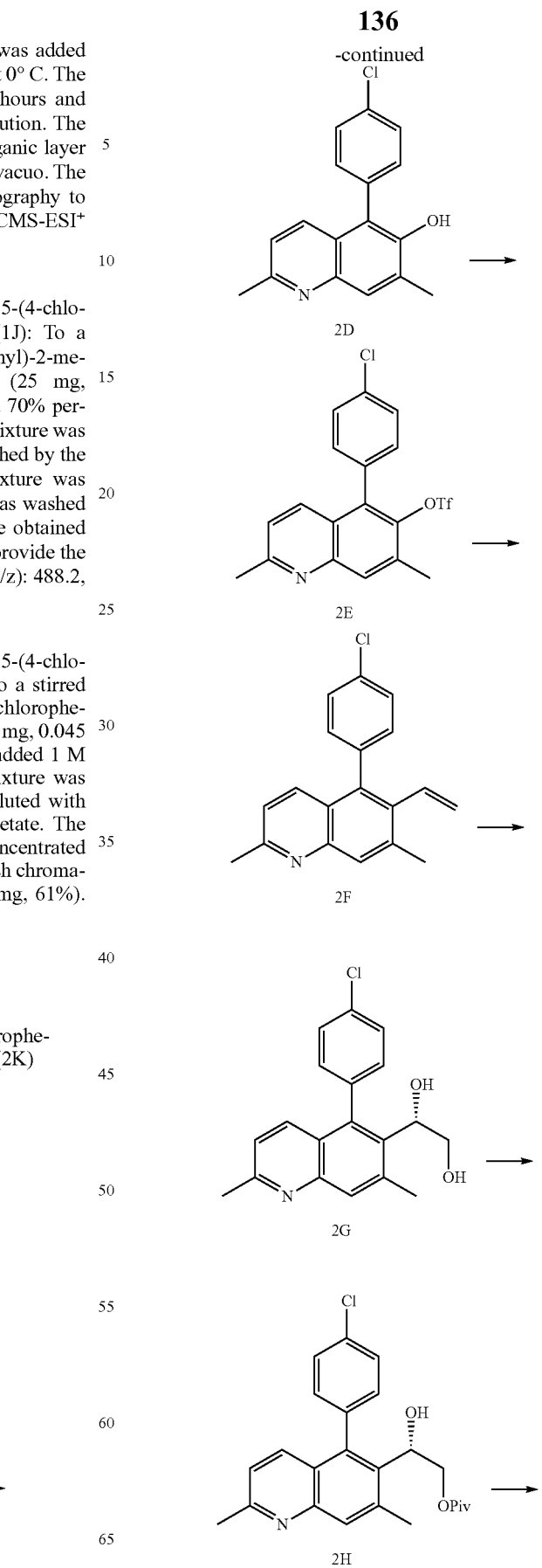

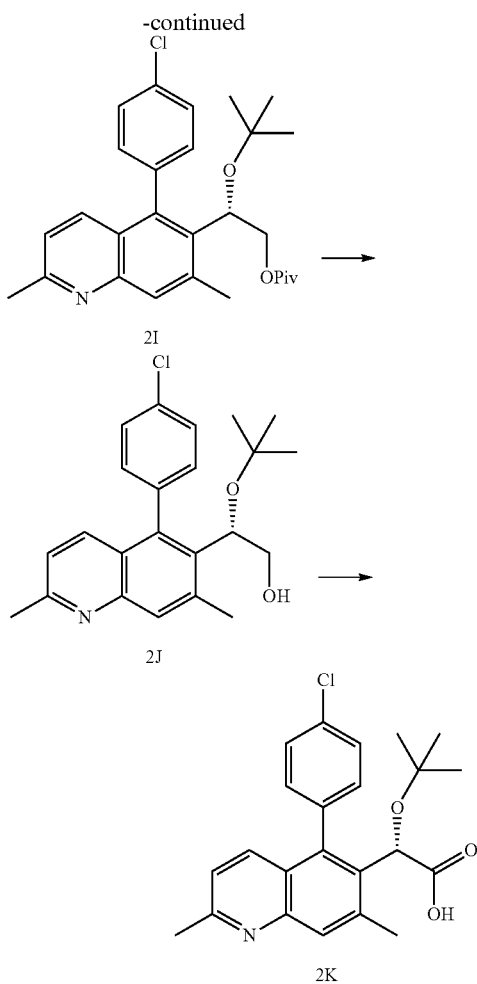

(S)-2-tert-butoxy-2-(5-(4-chlorophenyl)-2,7-dimethylquinolin-6-yl)acetic acid (2K) was prepared following the procedure used to prepare compound 1L of Example 1, except that (S)-2-tert-butoxy-2-(5-(4-chlorophenyl)-2,7-dimethylquinolin-6-yl)ethanol (2J) was used instead of compound 1K. $^1$H-NMR 300 MHz, (CD$_3$OD) δ 8.31 (d, 1H), 7.97 (s, 1H), 7.73 (d, 1H), 7.70-7.60 (m, 3H), 7.42-7.38 (m, 1H), 5.25 (s, 1H), 2.96 (s, 3H), 2.78 (s, 3H), 0.98 (s, 9H); LCMS-ESI$^+$ (m/z): [M+H]$^+$ calcd for C$_{23}$H$_{25}$ClNO$_3$: 398.9. Found: 398.2, 400.1.

Preparation of (S)-2-tert-butoxy-2-(5-(4-chlorophenyl)-2,7-dimethylquinolin-6-yl)ethanol (2J)

Step 1.

Preparation of 2,7-dimethylquinolin-6-ol (2B): Compound 2B was prepared following the procedure used to prepare compound 1B of Example 1, except that 4-amino-2-methylphenol (2A) was used instead of compound 1A. LCMS-ESI$^+$ (m/z): 174.2 (M+H)$^+$.

Step 2.

Preparation of 5-bromo-2,7-dimethylquinolin-6-ol (2C): Compound 2C was prepared following the procedure used to prepare compound 1D of Example 1, except that 2,7-dimethylquinolin-6-ol (2B) was used instead of compound 1C. LCMS-ESI$^+$ (m/z): 252.2, 254.2 (M+H)$^+$.

Step 3.

Preparation of 5-(4-chlorophenyl)-2,7-dimethylquinolin-6-ol (2D): Compound 2D was prepared following the procedure used to prepare compound 1E of Example 1, except that 5-bromo-2,7-dimethylquinolin-6-ol (2C) was used instead of compound 1D. LCMS-ESI$^+$ (m/z): 284.2, 286.2 (M+H)$^+$.

Step 4.

Preparation of 5-(4-chlorophenyl)-2,7-dimethylquinolin-6-yl trifluoromethanesulfonate (2E): Compound 2E was prepared following the procedure used to prepare compound 1F of Example 1, except that 5-(4-chlorophenyl)-2,7-dimethylquinolin-6-ol (2D) was used instead of compound 1E. LCMS-ESI$^+$ (m/z): 416.0, 418.0 (M+H)$^+$.

Step 5.

Preparation of 5-(4-chlorophenyl)-2,7-dimethyl-6-vinylquinoline (2F): Compound 2F was prepared following the procedure used to prepare compound 1G of Example 1, except that 5-(4-chlorophenyl)-2,7-dimethylquinolin-6-yl trifluoromethanesulfonate (2E) was used instead of compound 1F. LCMS-ESI$^+$ (m/z): 294.3, 296.3 (M+H)$^+$.

Step 6.

Preparation of (S)-1-(5-(4-chlorophenyl)-2,7-dimethylquinolin-6-yl)ethane-1,2-diol (2G): Compound 2G was prepared following the procedure used to prepare compound 1H of Example 1, except that 5-(4-chlorophenyl)-2,7-dimethyl-6-vinylquinoline (2F) was used instead of compound 1G. LCMS-ESI$^+$ (m/z): 328.2, 330.2 (M+H)$^+$.

Step 7.

Preparation of (S)-2-(5-(4-chlorophenyl)-2,7-dimethylquinolin-6-yl)-2-hydroxyethyl pivalate (2H): Compound 2H was prepared following the procedure used to prepare compound 1I of Example 1, except that (S)-1-(5-(4-chlorophenyl)-2,7-dimethylquinolin-6-yl)ethane-1,2-diol (2G) was used instead of compound 1H. LCMS-ESI$^+$ (m/z): 412.3, 414.3 (M+H)$^+$.

Step 8.

Preparation of (S)-2-tert-butoxy-2-(5-(4-chlorophenyl)-2,7-dimethylquinolin-6-yl)ethyl pivalate (2I): Compound 2I was prepared following the procedure used to prepare compound 1J of Example 1, except that (S)-2-(5-(4-chlorophenyl)-2,7-dimethylquinolin-6-yl)-2-hydroxyethyl pivalate (2H) was used instead of compound 1I. LCMS-ESI$^+$ (m/z): 468.3, 470.3 (M+H)$^+$.

Step 9.

Preparation of (S)-2-tert-butoxy-2-(5-(4-chlorophenyl)-2,7-dimethylquinolin-6-yl)ethanol (2J): Compound 2J was prepared following the procedure used to prepare compound 1K of Example 1, except that (S)-2-tert-butoxy-2-(5-(4-chlorophenyl)-2,7-dimethylquinolin-6-yl)ethyl pivalate (2I) was used instead of compound 1J. LCMS-ESI$^+$ (m/z): 384.2, 386.2 (M+H)$^+$.

EXAMPLE 3

Preparation of (S)-2-tert-butoxy-2-(5-(4-chlorophenyl)-7-methylquinolin-6-yl)acetic acid (3L)

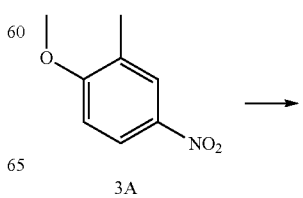

3A

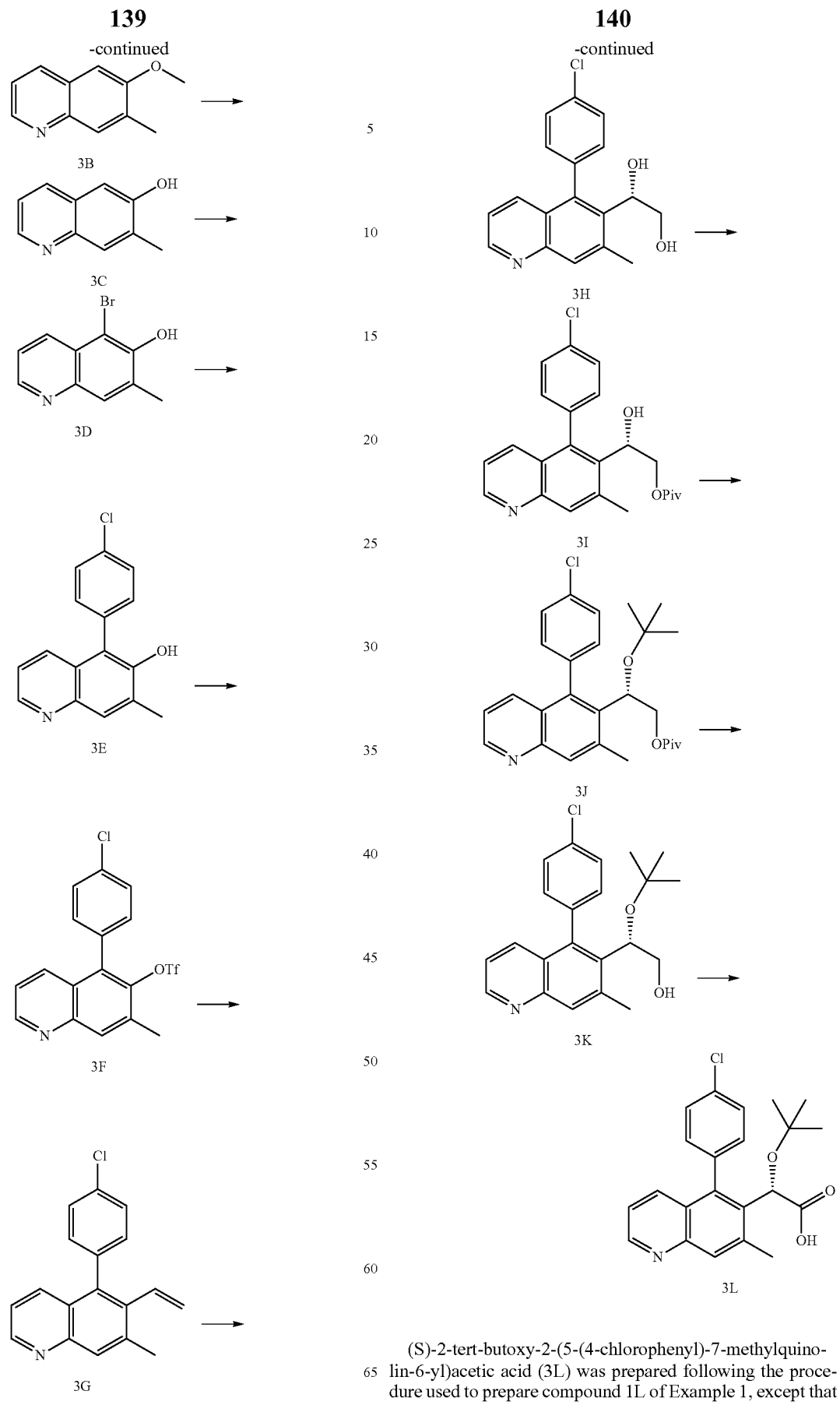
(S)-2-tert-butoxy-2-(5-(4-chlorophenyl)-7-methylquinolin-6-yl)acetic acid (3L) was prepared following the procedure used to prepare compound 1L of Example 1, except that (S)-2-tert-butoxy-2-(5-(4-chlorophenyl)-7-methylquinolin- 6-yl)ethanol (3K) was used instead of compound 1L. ¹H-NMR 300 MHz, (CDCl₃) δ 8.89-8.86 (m, 1H), 7.98 (s, 1H), 7.75-7.65 (m, 2H), 7.58-7.50 (m, 2H), 7.30-7.20 (m, 2H), 5.30 (s, 1H), 2.66 (s, 3H), 1.02 (s, 9H); LCMS-ESI⁺ (m/z): [M+H]⁺ calcd for $C_{22}H_{23}ClNO_3$: 384.9. Found:384.1, 386.1.

Preparation of (S)-2-tert-butoxy-2-(5-(4-chlorophenyl)-7-methylquinolin-6-yl)ethanol (3K)

Step 1.

Preparation of 6-methoxy-7-methylquinoline (3B): 1-methoxy-2-methyl-4-nitrobenzene (3A) (5 g, 30.0 mmol), 3-amino-1-propanol (0.57 mL, 7.5 mmol), isopropanol (3.43 mL, 4.5 mmol), ruthenium(III) chloride hydrate (156 mg, 0.75 mmol), triphenylphosphine (588 mg, 2.24 mmol), and tin(II) chloride dihydrate (1.69 g, 7.5 mmol) in dioxane/H₂O (67 mL/7 mL) were placed in a stainless steel pressure vessel. After the system was flushed with argon, the mixture was stirred at 180° C. for 20 hours. The reaction mixture was filtered through a short silica gel column (ethyl acetate/chloroform mixture) to eliminate inorganic compounds and concentrated under reduced pressure. The organic layer was poured into saturated brine, extracted with chloroform, dried over anhydrous sodium sulfate, and evaporated under reduced pressure. The residual oily material was separated by column chromatography to give the product 3B (200 mg, 15%). LCMS-ESI⁺ (m/z): 174.2 (M+H)⁺.

Step 2.

Preparation of 7-methylquinolin-6-ol (3C): Compound 3C was prepared following the procedure used to prepare compound 1C of Example 1, except that 6-methoxy-7-methylquinoline (3B) was used instead of compound 1B. LCMS-ESI⁺ (m/z): 160.2 (M+H)⁺.

Step 3.

Preparation of 5-bromo-7-methylquinolin-6-ol (3D): Compound 3D was prepared following the procedure used to prepare compound 1D of Example 1, except that 7-methylquinolin-6-ol (3C) was used instead of compound 1C. LCMS-ESI⁺ (m/z): 238.1, 240.1 (M+H)⁺.

Step 4.

Preparation of 5-(4-chlorophenyl)-7-methylquinolin-6-ol (3E): Compound 3E was prepared following the procedure used to prepare compound 1E of Example 1, except that 5-bromo-7-methylquinolin-6-ol (3D) was used instead of compound 1D.

LCMS-ESI⁺ (m/z): 270.2, 272.2 (M+H)⁺.

Step 5.

Preparation of 5-(4-chlorophenyl)-7-methylquinolin-6-yl trifluoromethanesulfonate (3F): Compound 3F was prepared following the procedure used to prepare compound 1F of Example 1, except that 5-(4-chloro-phenyl)-7-methylquinolin-6-ol (3E) was used instead of compound 1E. LCMS-ESI⁺ (m/z): 402.0, 404.0 (M+H)⁺.

Step 6.

Preparation of 5-(4-chlorophenyl)-7-methyl-6-vinylquinoline (3G): Compound 3G was prepared following the procedure used to prepare compound 1G of Example 1, except that 5-(4-chlorophenyl)-7-methylquinolin-6-yl trifluoromethanesulfonate (3F) was used instead of 1F. LCMS-ESI⁺ (m/z): 280.2, 282.2 (M+H)⁺.

Step 7.

Preparation of (S)-1-(5-(4-chlorophenyl)-7-methylquinolin-6-yl)ethane-1,2-diol (3H): Compound 3H was prepared following the procedure used to prepare compound 1H of Example 1, except that 5-(4-chlorophenyl)-7-methyl-6-vinyl-quinoline (3G) was used instead of compound 1G. LCMS-ESI⁺ (m/z): 314.2, 316.2 (M+H)⁺.

Step 8.

Preparation of (S)-2-(5-(4-chlorophenyl)-7-methylquinolin-6-yl)-2-hydroxyethyl pivalate (3I): Compound 3I was prepared following the procedure used to prepare compound 1I of Example 1, except that (S)-1-(5-(4-chlorophenyl)-7-methylquinolin-6-yl)ethane-1,2-diol (3H) was used instead of compound 1H. LCMS-ESI⁺ (m/z): 398.2, 400.2 (M+H)⁺.

Step 9.

Preparation of (S)-2-tert-butoxy-2-(5-(4-chlorophenyl)-7-methylquinolin-6-yl)ethyl pivalate (3J): Compound 3J was prepared following the procedure used to prepare compound 1J of Example 1, except that (S)-2-(5-(4-chlorophenyl)-7-methylquinolin-6-yl)-2-hydroxyethyl pivalate (3I) was used instead of compound 1I. LCMS-ESI⁺ (m/z): 454.3, 456.3 (M+H)⁺.

Step 10.

Preparation of (S)-2-tert-butoxy-2-(5-(4-chlorophenyl)-7-methylquinolin-6-yl)ethanol (3K): Compound 3K was prepared following the procedure used to prepare compound 1K of example 1, except that (S)-2-tert-butoxy-2-(5-(4-chlorophenyl)-7-methylquinolin-6-yl)ethyl pivalate (3J) was used instead of compound 1J. LCMS-ESI⁺ (m/z): 370.2, 372.2 (M+H)⁺.

EXAMPLE 4

Preparation of (S)-2-tert-butoxy-2-(8-(4-chlorophenyl)-6-methylquinolin-7-yl)acetic acid (4J)

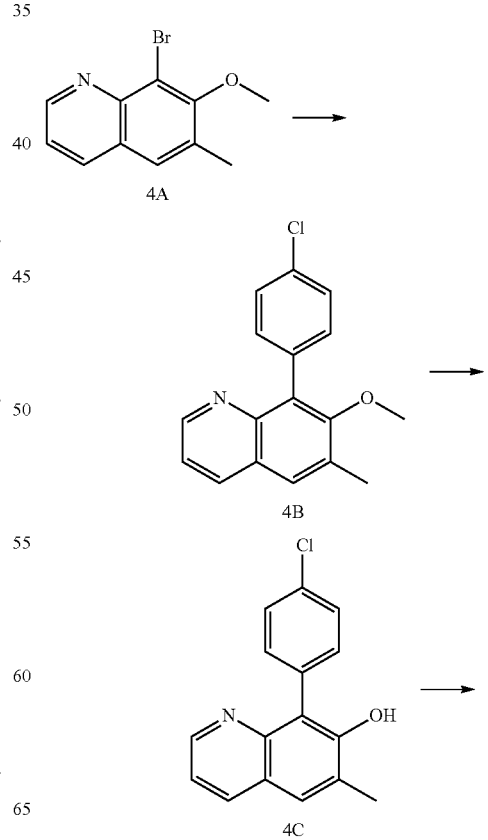

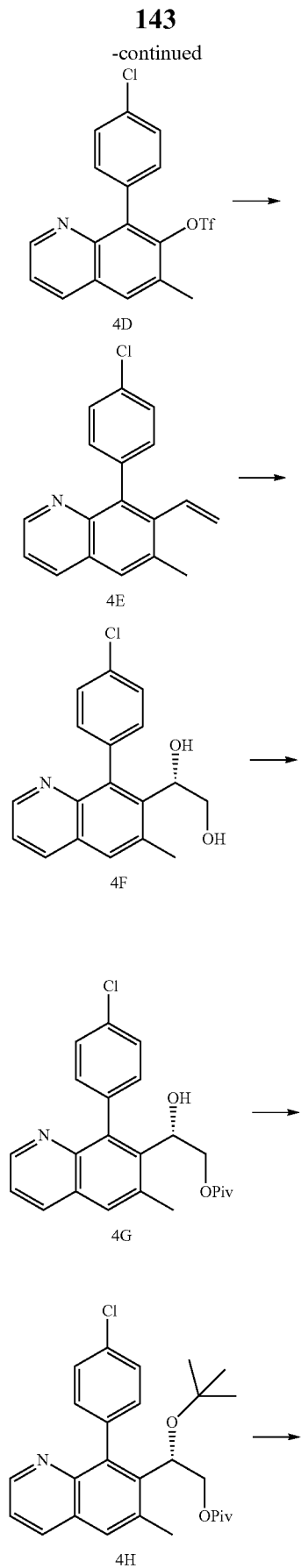

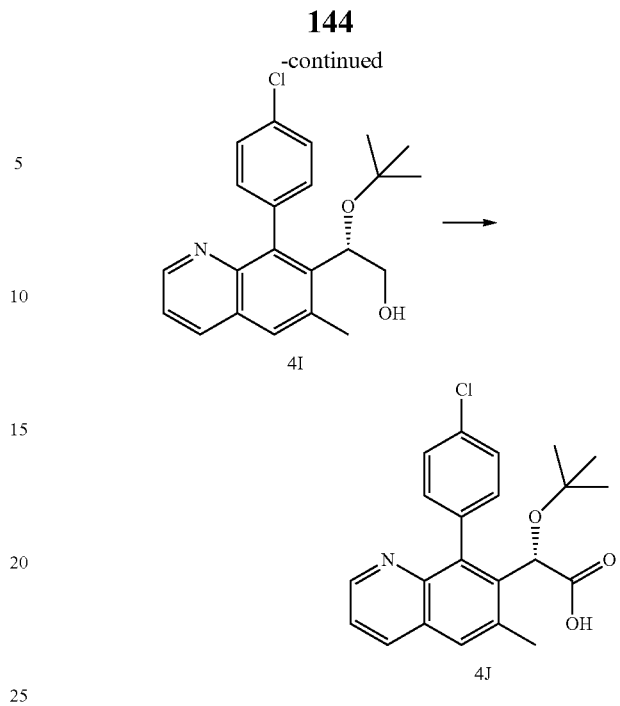

(S)-2-tert-butoxy-2-(8-(4-chlorophenyl)-6-methylquinolin-7-yl)acetic acid (4J) was prepared following the procedure used to prepare compound 1L of Example 1, except that (S)-2-tert-butoxy-2-(8-(4-chlorophenyl)-6-methylquinolin-7-yl)ethanol (4I) was used instead of compound 1K. $^1$H-NMR 300 MHz, (CD$_3$OD) δ 8.97-8.91 (m, 1H), 8.86-8.82 (m, 1H), 8.11 (s, 1H), 7.95-7.90 (m, 1H), 7.72-7.65 (m, 3H), 7.50-7.45 (m, 1H), 5.23 (s, 1H), 2.73 (s, 3H), 0.99 (s, 9H); LCMS-ESI$^+$ (m/z): [M+H]$^+$ calcd for C$_{22}$H$_{23}$ClNO$_3$: 384.9. Found: 384.1, 386.1.

Preparation of (S)-2-tert-butoxy-2-(8-(4-chlorophenyl)-6-methylquinolin-7-yl)ethanol (4I)

Step 1.

Preparation of 8-(4-chlorophenyl)-7-methoxy-6-methylquinoline (4B): Compound 4B was prepared following the procedure used to prepare compound 1E of Example 1, except that 8-bromo-7-methoxy-6-methylquinoline (4A) was used instead of compound 1D. LCMS-ESI$^+$ (m/z): 284.2, 286.2 (M+H)$^+$.

Step 2.

Preparation of 8-(4-chlorophenyl)-6-methylquinolin-7-ol (4C): Compound 4C was prepared following the procedure used to prepare compound 1C of Example 1, except that 8-(4-chlorophenyl)-7-methoxy-6-methylquinoline (4B) was used instead of compound 1B. LCMS-ESI$^+$ (m/z): 270.2, 272.2 (M+H)$^+$.

Step 3.

Preparation of 8-(4-chlorophenyl)-6-methylquinolin-7-yl trifluoromethanesulfonate (4D): Compound 4D was prepared following the procedure used to prepare compound 1F of example 1, except that 8-(4-chloro-phenyl)-6-methylquinolin-7-ol (4C) was used instead of compound 1E. LCMS-ESI$^+$ (m/z): 402.0, 403.9 (M+H)$^+$.

Step 4.

Preparation of 8-(4-chlorophenyl)-6-methyl-7-vinylquinoline (4E): Compound 4E was prepared following the procedure used to prepare compound 1G of Example 1, except that 8-(4-chlorophenyl)-6-methylquinolin-7-yl trifluoromethanesulfonate (4D) was used instead of compound 1F. LCMS-ESI$^+$ (m/z): 280.2, 282.2 (M+H)$^+$.

Step 5.

Preparation of (S)-1-(8-(4-chlorophenyl)-6-methylquinolin-7-yl)ethane-1,2-diol (4F): Compound 4F was prepared following the procedure used to prepare compound 1H of Example 1, except that 8-(4-chlorophenyl)-6-methyl-7-vinyl-quinoline (4E) was used instead of compound 1G. LCMS-ESI+ (m/z): 314.1, 316.1 (M+H)+.

Step 6.

Preparation of (S)-2-(8-(4-chlorophenyl)-6-methylquinolin-7-yl)-2-hydroxyethyl pivalate (4G): Compound 4G was prepared following the procedure used to prepare compound 1I of example 1, except that (S)-1-(8-(4-chlorophenyl)-6-methylquinolin-7-yl)ethane-1,2-diol (4F) was used instead of compound 1H. LCMS-ESI+ (m/z): 398.2, 400.2 (M+H)+.

Step 7.

Preparation of (S)-2-tert-butoxy-2-(8-(4-chlorophenyl)-6-methylquinolin-7-yl)ethyl pivalate (4H): Compound 4H was prepared following the procedure used to prepare compound 1J of example 1, except that (S)-2-(8-(4-chlorophenyl)-6-methylquinolin-7-yl)-2-hydroxyethyl pivalate (4G) was used instead of compound 1I. LCMS-ESI+ (m/z): 454.3, 456.3 (M+H)+.

Step 8.

Preparation of (S)-2-tert-butoxy-2-(8-(4-chlorophenyl)-6-methylquinolin-7-yl)ethanol (4I): Compound 4I was prepared following the procedure used to prepare compound 1K of Example 1, except that (S)-2-tert-butoxy-2-(8-(4-chlorophenyl)-6-methylquinolin-7-yl)ethyl pivalate (4H) was used instead of compound 1J. LCMS-ESI+ (m/z): 370.2, 372.1 (M+H)+.

EXAMPLE 5

Preparation of (S)-2-tert-butoxy-2-((S)-5-(2,4-dichlorophenyl)-2,7-dimethylquinolin-6-yl)acetic acid (5J)

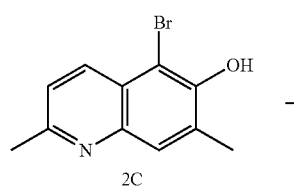
2C

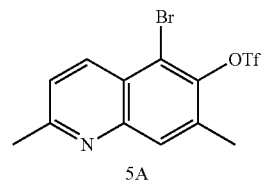
5A

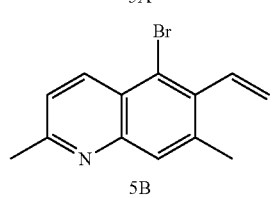
5B

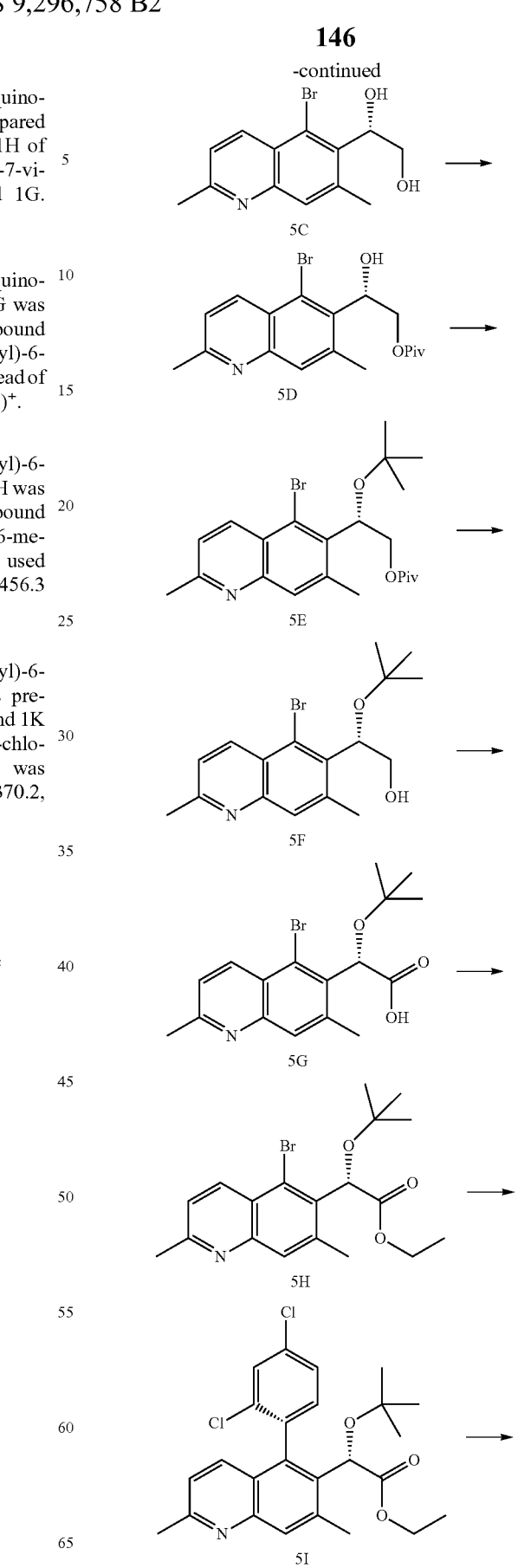

-continued

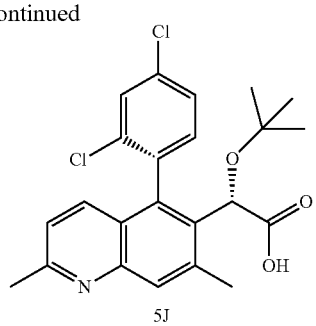

5J

To a stirred solution of (S)-ethyl 2-tert-butoxy-2-((S)-5-(2,4-dichlorophenyl)-2,7-dimethylquinolin-6-yl)acetate (5I) (15 mg as TFA salt, 0.027 mmol) in THF and methanol (3 mL/1 mL) was added 1 M NaOH solution (1 mL, excess) at 0° C. The mixture was stirred at 50° C. for 4 hours and diluted with water. The mixture was extracted with ethyl acetate. The organic layer was washed with brine, dried and concentrated in vacuo. The obtained residue was purified by Prep-HPLC to provide the desired isomer of 5J as a TFA salt (11 mg, 77%). $^1$H-NMR 300 MHz, (CD$_3$OD) δ 8.14 (d, 1H), 8.03 (s, 1H), 7.74 (d, 1H), 7.72 (d, 1H), 7.52 (dd, 1H), 7.25 (d, 1H), 5.36 (s, 1H), 2.96 (s, 3H), 2.90 (s, 3H), 1.11 (s, 9H); LCMS-ESI$^+$ (m/z): [M+H]$^+$ calcd for C$_{23}$H$_{24}$Cl$_2$NO$_3$: 433.3. Found: 432.1, 434.1.

The (S,R) isomer of 5J was obtained using the same procedure described above except that the (S,R) isomer of 5I was used in the reaction. $^1$H-NMR 300 MHz, (CD$_3$OD) δ 8.18 (d, 1H), 7.99 (s, 1H), 7.80 (d, 1H), 7.77 (d, 1H), 7.73 (d, 1H), 7.66-7.62 (m 1H), 5.17 (s, 1H), 2.95 (s, 3H), 2.80 (s, 3H), 1.05 (s, 9H); LCMS-ESI$^+$ (m/z): [M+H]$^+$ calcd for C$_{23}$H$_{24}$Cl$_2$NO$_3$: 433.3. Found: 432.1, 434.1

Preparation of (S)-ethyl 2-tert-butoxy-2-((S)-5-(2,4-dichlorophenyl)-2,7-dimethylquinolin-6-yl)acetate (5I)

Step 1.

Preparation of 5-bromo-2,7-dimethylquinolin-6-yl trifluoromethanesulfonate (5A): Compound 5A was prepared following the procedure used to prepare compound 1F of Example 1, except that 5-bromo-2,7-dimethylquinolin-6-ol (2C) was used instead of compound 1E. LCMS-ESI$^+$ (m/z): 383.9, 385.9 (M+14)$^+$.

Step 2.

Preparation of 5-bromo-2,7-dimethyl-6-vinylquinoline (5B): PdCl$_2$(PPh$_3$)$_2$ (207 mg, 0.30 mmol) was added to a mixture of 5-bromo-2,7-dimethylquinolin-6-yl trifluoromethanesulfonate (5A) (1.13 g, 2.95 mmol), tributyl(vinyl)stannane (0.95 mL, 3.25 mmol) and lithium chloride (375 mg, 8.85 mmol) in DMF (30 mL). The reaction mixture was flushed with argon, heated at 80° C. for 4 hours, and then the volatile component was removed in vacuo. The residue was dissolved in ethyl acetate (200 mL), washed with NaHCO$_3$ solution, water and brine, dried over Na$_2$SO$_4$, filtered and concentrated in vacuo. The obtained residue was purified by flash chromatography to provide 5B (678 mg, 88%). LCMS-ESI$^+$ (m/z): 262.1, 264.1 (M+H)$^+$.

Step 3.

Preparation of (S)-1-(5-bromo-2,7-dimethylquinolin-6-yl)ethane-1,2-diol (5C): Compound 5C was prepared following the procedure used to prepare compound 1H of Example 1, except that 5-bromo-2,7-dimethyl-6-vinylquinoline (5B) was used instead of compound 1G. LCMS-ESI$^+$ (m/z): 296.1, 298.1 (M+H)$^+$.

Step 4.

Preparation of (S)-2-(5-bromo-2,7-dimethylquinolin-6-yl)-2-hydroxyethyl pivalate (5D): Compound 5D was prepared following the procedure used to prepare compound 1I of Example 1, except that (S)-1-(5-bromo-2,7-dimethylquinolin-6-yl)ethane-1,2-diol (5C) was used instead of compound 1H. LCMS-ESI$^+$ (m/z): 380.2, 382.2 (M+H)$^+$.

Step 5.

Preparation of (S)-2-(5-bromo-2,7-dimethylquinolin-6-yl)-2-tert-butoxyethyl pivalate (5E): Compound 5E was prepared following the procedure used to prepare compound 1J of Example 1, except that (S)-2-(5-bromo-2,7-dimethylquinolin-6-yl)-2-hydroxyethyl pivalate (5D) was used instead compound 1I. LCMS-ESI$^+$ (m/z): 436.2, 438.2 (M+H)$^+$.

Step 6.

Preparation of (S)-2-(5-bromo-2,7-dimethylquinolin-6-yl)-2-tert-butoxyethanol (5F): Compound 5F was prepared following the procedure used to prepare compound 1K of Example 1, except that (S)-2-(5-bromo-2,7-dimethylquinolin-6-yl)-2-tert-butoxyethyl pivalate (5E) was used instead of compound 1J. LCMS-ESI$^+$ (m/z): 352.2, 354.2 (M+H)$^+$.

Step 7.

Preparation of (S)-2-(5-bromo-2,7-dimethylquinolin-6-yl)-2-tert-butoxyacetic acid (5G): Compound 5G was prepared following the procedure used to prepare compound 1L of Example 1, except that (S)-2-(5-bromo-2,7-dimethylquinolin-6-yl)-2-tert-butoxyethanol (5F) was used instead of compound 1K. LCMS-ESI$^+$ (m/z): 366.1, 368.1 (M+H)$^+$.

Step 8.

Preparation of (S)-ethyl 2-(5-bromo-2,7-dimethylquinolin-6-yl)-2-tert-butoxyacetate (5H): To a stirred solution of (S)-2-(5-bromo-2,7-dimethylquinolin-6-yl)-2-tert-butoxyacetic acid (5G) (180 mg, 0.49 mmol) in DMF (15 mL) was added cesium carbonate (321 mg, 0.98 mmol) at 0° C. After being stirred for 10 min iodoethane (0.059 mL, 0.74 mmol) was added. The mixture was stirred at room temperature for 2 hours and quenched by the slow addition of a NaHCO$_3$ solution. The mixture was extracted with ethyl acetate. The organic layer was washed with brine, dried and concentrated. The residue was purified by column chromatography to give the pure product 5H (168 mg, 87%). LCMS-ESI$^+$ (m/z): 394.1, 396.1 (M+H)$^+$.

Step 9.

Preparation of (S)-ethyl 2-tert-butoxy-2-((S)-5-(2,4-dichlorophenyl)-2,7-dimethylquinolin-6-yl)acetate (5I): Pd$_2$(dba)$_3$ (3.5 mg, 0.006 mmol) was added to a mixture of (S)-ethyl 2-(5-bromo-2,7-dimethylquinolin-6-yl)-2-tert-butoxyacetate (5H) (24 mg, 0.061 mmol), 2,4-dichlorophenylboronic acid (23 mg, 0.12 mmol), 2-dicyclohexylphosphino-2',6'-dimethoxybiphenyl ("Sphos", 5 mg, 0.012 mmol) and K$_3$PO$_4$ (39 mg, 0.18 mmol) in toluene (1.5 mL). The reaction mixture was flushed with argon, heated at 110° C. for 16 hours, and then the volatile component was removed in vacuo. The residue was dissolved in ethyl acetate (100 mL), washed with NaHCO$_3$ solution, water and brine, dried over Na$_2$SO$_4$, filtered and concentrated in vacuo. The obtained residue was purified by prep-HPLC to provide two isomers of 5 I as white solids. Each was obtained as a TFA salt (desired (S,R) enantiomer: 18 mg, 53%).

LCMS-ESI$^+$ (m/z): 460.2, 462.2 (M+H)$^+$.

EXAMPLE 6

Preparation of (S)-2-tert-butoxy-2-((R)-5-(2,3-dihydropyrano[4,3,2-de]quinolin-7-yl)-2,7-dimethylquinolin-6-yl)acetic acid (6D)

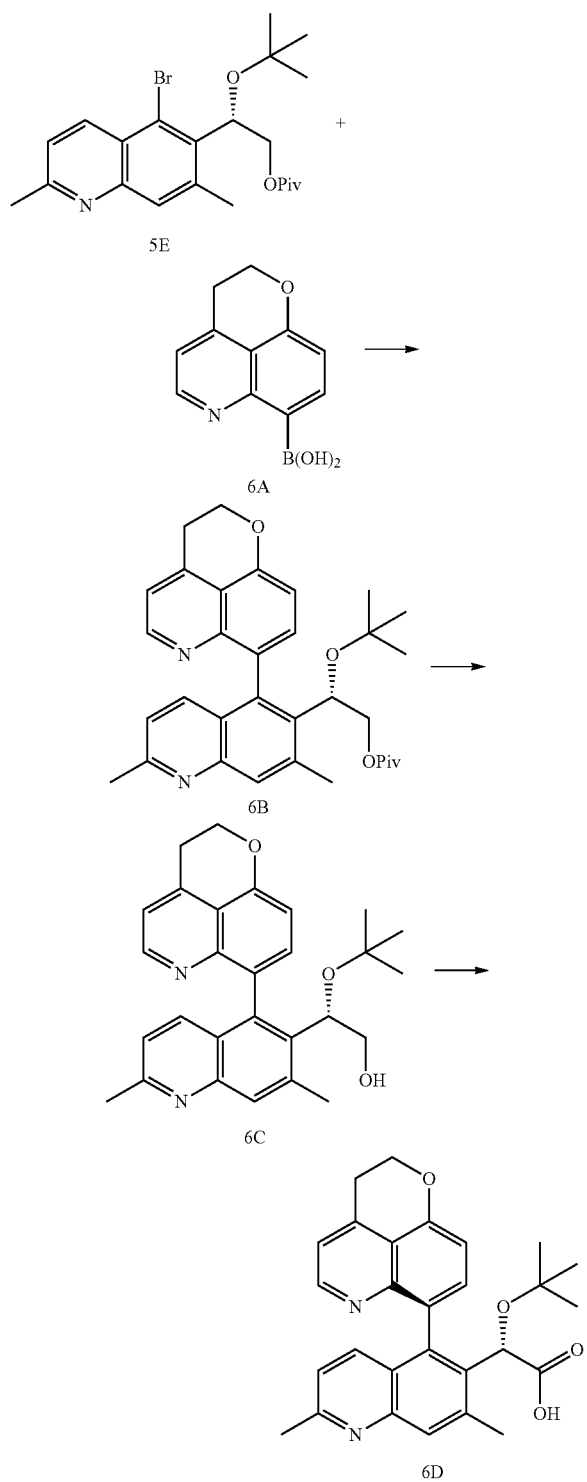

(S)-2-tert-butoxy-2-((R)-5-(2,3-dihydropyrano[4,3,2-de]quinolin-7-yl)-2,7-dimethylquinolin-6-yl)acetic acid (6D) was prepared following the procedure used to prepare compound 1L of Example 1 except that (2S)-2-tert-butoxy-2-(5-(2,3-dihydropyrano[4,3,2-de] quinolin-7-yl)-2,7-dimethylquinolin-6-yl)ethanol (6C) was used instead of compound 1K. $^1$H-NMR 300 MHz, (CD$_3$OD) δ 8.59 (d, 1H), 8.05 (s, 1H), 7.94 (d, 1H), 7.65 (d, 1H), 7.54 (d, 1H), 7.48 (d, 1H), 7.27 (d, 1H), 5.25 (s, 1H), 4.70-4.55 (m, 2H), 3.52-3.45 (m, 2H), 2.90 (s, 3H), 0.91 (s, 9H); LCMS-ESI$^+$ (m/z): [M+H]$^+$ calcd for C$_{28}$H$_{29}$N$_2$O$_4$: 457.5. Found: 457.1.

Preparation of (2S)-2-tert-butoxy-2-(5-(2,3-dihydropyrano[4,3,2-de] quinolin-7-yl)-2,7-dimethylquinolin-6-yl)ethanol (6C)

Step 1.

Preparation of (2S)-2-tert-butoxy-2-(5-(2,3-dihydropyrano[4,3,2-de]quinolin-7-yl)-2,7-dimethylquinolin-6-yl) ethyl pivalate (6B): Pd(PPh$_3$)$_4$ (4 mg, 0.0037 mmol) was added to a mixture (S)-2-(5-bromo-2,7-dimethylquinolin-6-yl)-2-tert-butoxyethyl pivalate (5E) (16 mg, 0.037 mmol), 2,3-dihydropyrano[4,3,2-de]quinolin-7-ylboronic acid hydrochloride (6A) (23 mg, 0.073 mmol) and K$_2$CO$_3$ (0.083 mL 2 M in water, 1.66 mmol) in 1,2-dimethoxyethane (2 mL). The reaction mixture was flushed with nitrogen, microwaved at 120° C. for 90 min and the volatile component was removed in vacuo. The residue was dissolved in ethyl acetate (50 mL), washed with NaHCO$_3$ solution, water and brine, dried over Na$_2$SO$_4$, filtered and concentrated in vacuo. The obtained residue was purified by prep-HPLC to provide 6B as a white solid (4 mg as TFA salt, 18%). LCMS-ESI$^+$ (m/z): 527.3 (M+H)$^+$.

Step 2.

Preparation of (2S)-2-tert-butoxy-2-(5-(2,3-dihydropyrano[4,3,2-de]quinolin-7-yl)-2,7-dimethylquinolin-6-yl) ethanol (6C): Compound 6C was prepared following the procedure used to prepare compound 1K of Example 1 except that (2S)-2-tert-butoxy-2-(5-(2,3-dihydropyrano[4,3,2-de] quinolin-7-yl)-2,7-dimethylquinolin-6-yl)ethyl pivalate (6B) was used instead of compound 1J. LCMS-ESI$^+$ (m/z): 433.3 (M+H)$^+$.

EXAMPLE 7

Preparation of (S)-2-tert-butoxy-2-(5-(4-chlorophenyl)-7-methyl-2-(trifluoromethyl)quinolin-6-yl)acetic acid (7J)

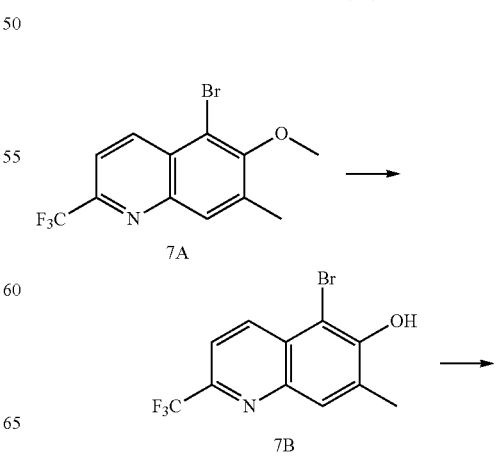

-continued

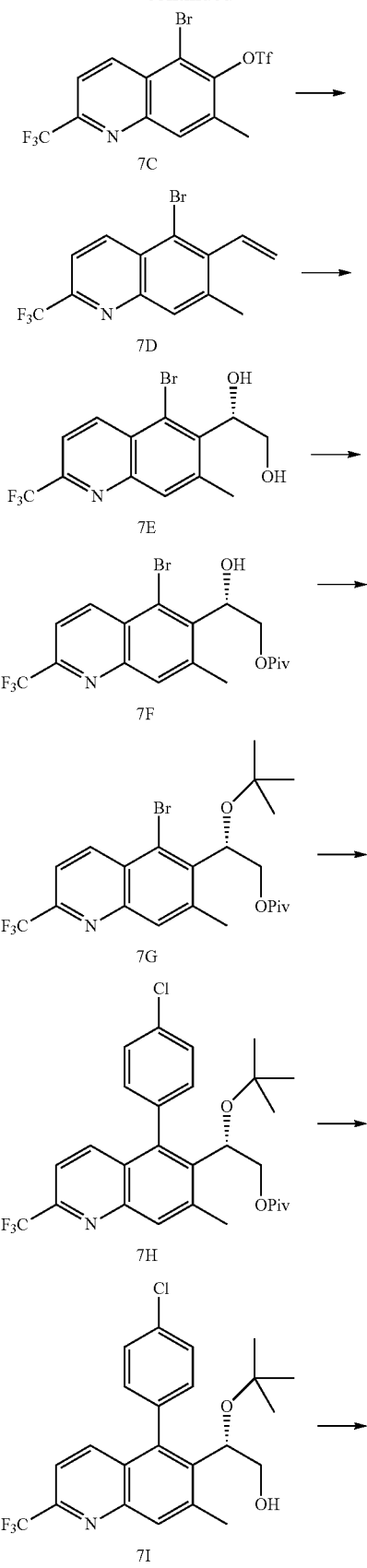

-continued

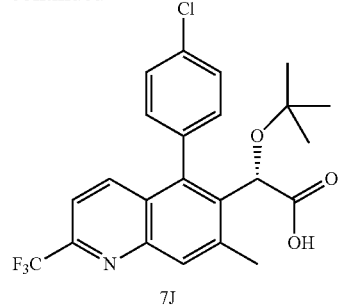

(S)-2-tert-Butoxy-2-(5-(4-chlorophenyl)-7-methyl-2-(trifluoromethyl)quinolin-6-yl)acetic acid (7J) was prepared following the procedure used to prepare compound 1L of Example 1 except that (S)-2-tert-butoxy-2-(5-(4-chlorophenyl)-7-methyl-2-(trifluoromethyl)quinolin-6-yl)ethanol (7I) was used instead of compound 1K. $^1$H-NMR 300 MHz, (CD$_3$OD) δ 8.01 (s, 1H), 7.95 (d, 1H), 7.71 (d, 1H), 7.65-7.55 (m, 2H), 7.35 (d, 1H), 5.24 (s, 1H), 2.71 (s, 3H), 0.99 (s, 9H); LCMS-ESI$^+$ (m/z): [M+H]$^+$ calcd for C$_{23}$H$_{22}$ClF$_3$NO$_3$: 452.9. Found: 452.1, 454.1.

Preparation of (S)-2-tert-butoxy-2-(5-(4-chlorophenyl)-7-methyl-2-(trifluoromethyl)quinolin-6-yl)ethanol (7I)

Step 1.

Preparation of 5-bromo-7-methyl-2-(trifluoromethyl)quinolin-6-ol (7B): Compound 7B was prepared following the procedure used to prepare compound 1C of Example 1, except that 5-bromo-6-methoxy-7-methyl-2-(trifluoromethyl)quinoline (7A) was used instead of compound 1B. LCMS-ESI$^+$ (m/z): 306.1, 308.1 (M+H)$^+$.

Step 2.

Preparation of 5-bromo-7-methyl-2-(trifluoromethyl)quinolin-6-yl trifluoromethanesulfonate (7C): Compound 7C was prepared following the procedure used to prepare compound 1F of Example 1 except that 5-bromo-7-methyl-2-(trifluoromethyl)quinolin-6-ol (7B) was used instead of compound 1E. LCMS-ESI$^+$ (m/z): 437.8, 439.8 (M+H)$^+$.

Step 3.

Preparation of 5-bromo-7-methyl-2-(trifluoromethyl)-6-vinylquinoline (7D): Compound 7D was prepared following the procedure used to prepare compound 5B of Example 5, except that 5-bromo-7-methyl-2-(trifluoromethyl)quinolin-6-yl trifluoromethanesulfonate (7C) was used instead of compound 5A. LCMS-ESI$^+$ (m/z): 316.1, 318.1 (M+H)$^+$.

Step 4.

Preparation of (S)-1-(5-bromo-7-methyl-2-(trifluoromethyl)quinolin-6-yl)ethane-1,2-diol (7E): Compound 7E was prepared following the procedure used to prepare compound 1H of Example 1, except that 5-bromo-7-methyl-2-(trifluoromethyl)-6-vinylquinoline (7D) was used instead 7 of compound 1G. LCMS-ESI$^+$ (m/z): 350.1, 352.1 (M+H)$^+$.

Step 5.

Preparation of (S)-2-(5-bromo-7-methyl-2-(trifluoromethyl)quinolin-6-yl)-2-hydroxyethyl pivalate (7F): Compound 7F was prepared following the procedure used to prepare compound 1I of Example 1 except that (S)-1-(5-bromo-7-methyl-2-(trifluoromethyl)quinolin-6-yl)ethane-1,2-diol (7E) was used instead of compound 1H.

Step 6.

Preparation of (S)-2-(5-bromo-7-methyl-2-(trifluoromethyl)quinolin-6-yl)-2-tert-butoxyethyl pivalate (7G): Compound 7G was prepared following the procedure used to prepare compound 1J of Example 1 except (S)-2-(5-bromo-7-methyl-2-(trifluoromethyl)quinolin-6-yl)-2-hydroxyethyl pivalate (7F) was used instead of compound 1I. LCMS-ESI$^+$ (m/z): 490.2, 492.2 (M+H)$^+$.

Step 7.

Preparation of (S)-2-tert-butoxy-2-(5-(4-chlorophenyl)-7-methyl-2-(trifluoromethyl)quinolin-6-yl)ethyl pivalate (7H): Compound 7H was prepared following the procedure used to prepare compound 1E of Example 1 except that (S)-2-(5-bromo-7-methyl-2-(trifluoromethyl)quinolin-6-yl)-2-tert-butoxyethyl pivalate (7G) was used instead of compound 1D. LCMS-ESI$^+$ (m/z): 522.2, 524.2 (M+H)$^+$.

Step 8.

Preparation of (S)-2-tert-butoxy-2-(5-(4-chlorophenyl)-7-methyl-2-(trifluoromethyl)quinolin-6-yl)ethanol (7I): Following the procedure used to prepare compound 1K of Example 1, except that (S)-2-tert-butoxy-2-(5-(4-chlorophenyl)-7-methyl-2-(trifluoromethyl)quinolin-6-yl)ethyl pivalate (7H) was used instead of compound 1J. LCMS-ESI$^+$ (m/z): 438.2, 440.2 (M+H)$^+$.

EXAMPLE 8

Preparation of (S)-2-tert-butoxy-2-(5-(4-chlorophenyl)-7-methyl-2-oxo-1,2-dihydroquinolin-6-yl)acetic acid (8L)

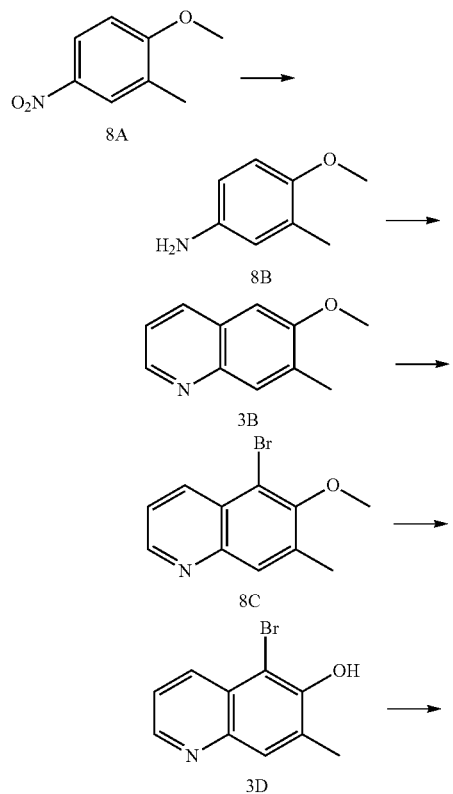

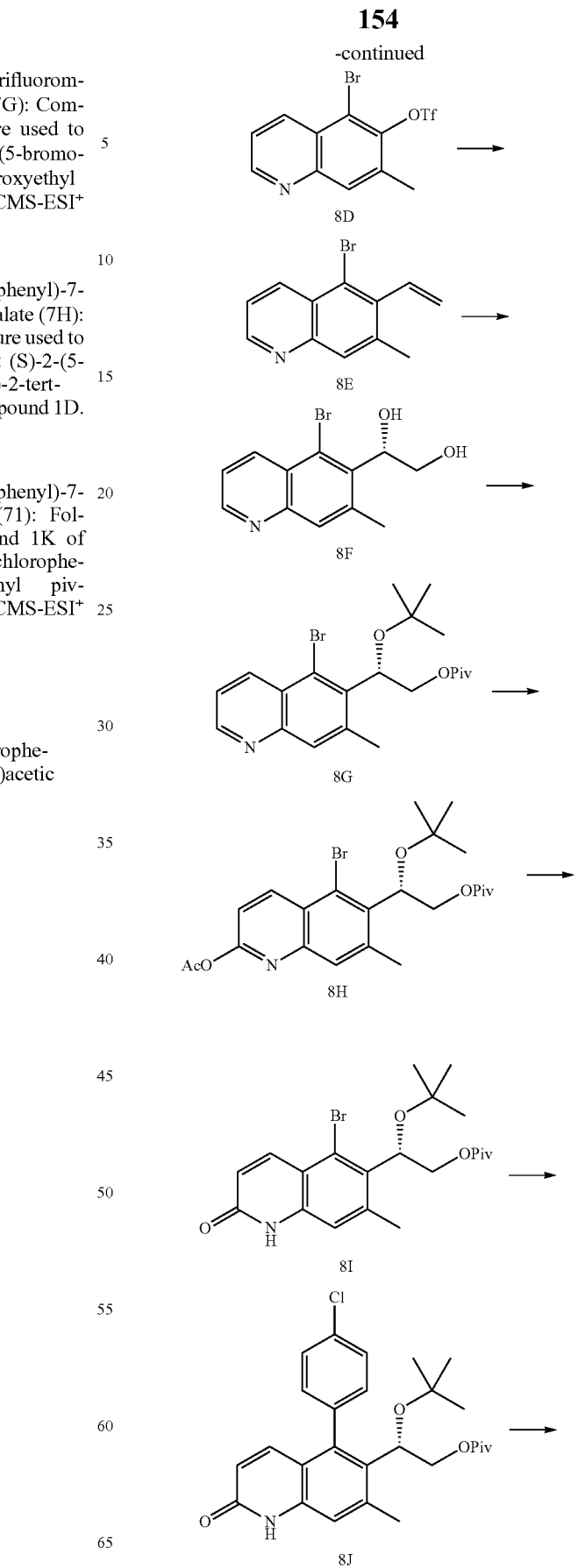

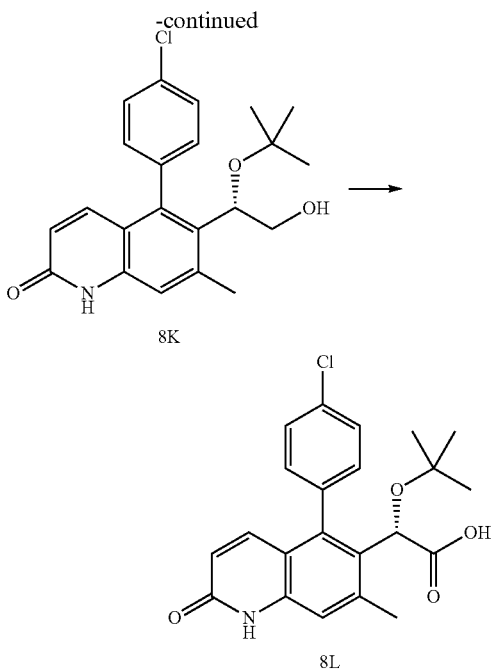

A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% $H_2O$) to a volume of 114 mL. This stock solution (0.40 mL) was added to a solution of (S)-6-(1-tert-butoxy-2-hydroxyethyl)-5-(4-chlorophenyl)-7-methylquinolin-2(1H)-one (8K, 4.4 mg) in wet acetonitrile (1.5 mL, 0.75% $H_2O$) at 0° C. After stirring for 60 min at 0° C., the reaction was quenched with 1.5 M $K_2HPO_4$ solution and extracted with ethyl acetate (2×). The combined organic layer was washed with 1:1 brine/$H_2O$ (2×), saturated $NaHSO_3$/brine, and was dried ($MgSO_4$). Concentration and purification by prep-HPLC gave (S)-2-tert-butoxy-2-(5-(4-chlorophenyl)-7-methyl-2-oxo-1,2-dihydroquinolin-6-yl)acetic acid (8L) (2 mg). $^1$H-NMR 300 MHz, ($CD_3OD$) 7.56-7.53 (3H, m), 7.35 (1H, d, J=9.7 Hz), 7.28 (1H, d, J=8.2 Hz), 7.22 (1H, s), 6.43 (1H, d, J=9.8 Hz), 5.06 (1H, s), 2.55 (3H, s), 0.95 (9H, s). LCMS-ESI$^+$ (m/z): [M+H]$^+$ calcd for $C_{22}H_{23}ClNO_4$: 400.9. Found: 400.2; LCMS-ESI$^-$ (m/z): [M−H]$^-$ calcd for $C_{22}H_{21}ClNO_4$: 398.9. Found: 397.9.

Preparation of (S)-6-(1-tert-butoxy-2-hydroxyethyl)-5-(4-chlorophenyl)-7-methylquinolin-2(1H)-one (8K)
Step 1.

Preparation of 4-methoxy-3-methylaniline (8B): To the solution of 1-methoxy-2-methyl-4-nitrobenzene (10 g, 60 mmol) in EtOH and EtOAc (250 mL, 3:2) was added 10% Pd/C (2 g). The mixture was stirred for 24 h under one atmosphere of hydrogen. Celite was added and the mixture was stirred for 10 min. The mixture was filtered through a pad of celite. Concentration under reduced pressure gave 4-methoxy-3-methylaniline (8B) (8.2 g). LCMS-ESI$^+$ (m/z): 138.2 (M+H)$^+$.
Step 2.

Preparation of 6-methoxy-7-methylquinoline (3B): To 4-methoxy-3-methylaniline (6.7 g) was added concentrated $H_2SO_4$ (12.4 mL), followed by glycerin (21.1 g), m-nitrobenzenesulfonic acid (6.53 g), $H_3BO_3$ (3.4 g) and $FeSO_4 \cdot 7H_2O$ (3.2 g). The mixture was stirred at 140° C. for 1 h. The reaction was cooled to 25° C., quenched with ice-water and neutralized with 30% KOH. The mixture was extracted with DCM (2×), and the combined extracts dried with $Na_2SO_4$ and concentrated in vacuo. The crude product was purified by column chromatography (EtOAc) to give 6-methoxy-7-methylquinoline (4.3 g) LCMS-ESI$^+$ (m/z): 174.1 (M+H)$^+$.
Step 3.

Preparation of 5-bromo-6-methoxy-7-methylquinoline (8C): To the solution of 6-methoxy-7-methylquinoline (4.28 g, 24.6 mmol) in 50 mL of concentrated $H_2SO_4$ was added NBS (4.41 g, 14.6 mmol) at 15° C., and the reaction was stirred at 15° C. for 3.5 hours. The reaction mixture was poured into ice-water (600 mL). The aqueous mixture was adjusted with a 50% KOH solution to pH ~10, and then extracted with DCM (3×). The combined extract was dried with sodium sulfate. Concentration under reduced pressure gave 5-bromo-6-methoxy-7-methylquinoline (6.3 g). LCMS-ESI$^+$ (m/z): 252.1, 254.1 (M+H)$^+$.
Step 4.

Preparation of 5-bromo-7-methylquinolin-6-ol (3D): To the solution of 5-bromo-6-methoxy-7-methylquinoline (6.5 g, 25.8 mmol) in DCM (150 mL) was added $BBr_3$ slowly (77.3 mL, 1.0 M in DCM, 77.3 mmol). The mixture was stirred for 3 hours and cooled to 0° C. Methanol (40 mL) was added slowly and the mixture was stirred for 20 minutes. The solvents were removed under reduced pressure. The solid was dissolved in methanol (100 mL) and was treated with 1.0 N sodium hydroxide solution (50 mL) (pH ~12). The mixture was stirred for 12 hours and acetic acid was added to adjust pH to between 4-5. The mixture was filtered and washed with water. The gray solid was dried under reduced pressure to give 5-bromo-7-methylquinolin-6-ol (5.0 g). LCMS-ESI$^+$ (m/z): 238.2, 240.1 (M+H)$^+$, 236.1, 238.0 (M−H).
Step 5.

Preparation of 5-bromo-7-methylquinolin-6-yl trifluoromethanesulfonate (8D): To the solution of 5-bromo-7-methylquinolin-6-ol (238 mg, 1.0 mmol) in dichloromethane (10 mL) and pyridine (2 mL) was added $Tf_2O$ (0.34 mL, 2.0 mmol) at −30° C. The mixture was stirred and warmed to 0° C. over a period of 2 hours. The reaction was quenched with slow addition of $NaHCO_3$ solution. The mixture was extracted with ethyl acetate. The organic layer was washed with brine, dried over sodium sulfate and concentrated to give 5-bromo-7-methylquinolin-6-yl trifluoromethanesulfonate. LCMS-ESI$^+$ (m/z): 369.9, 371.9 (M+H)$^+$.
Step 6.

Preparation of 5-bromo-7-methyl-6-vinylquinoline (8E): A mixture of 5-bromo-7-methylquinolin-6-yl trifluoromethanesulfonate (230 mg, 0.62 mmol), tributyl(vinyl)stannane (200 μL, 0.68 mmol), lithium chloride (78 mg, 1.86 mmol) and $PdCl_2(PPh_3)_2$ (43 mg) in DMF (10 mL) was heated at 80° C. for 16 hours, and then the volatile component was removed in vacuo. The residue was dissolved in ethyl acetate (100 mL), washed with $NaHCO_3$ solution, water and brine, dried over $Na_2SO_4$, filtered and concentrated in vacuo. The residue was purified by flash chromatography (hexanes/EtOAc) to provide 5-bromo-7-methyl-6-vinylquinoline (120 mg). LCMS-ESI$^+$ (m/z): 248.2, 250.2 (M+H)$^+$.
Step 7.

Preparation of (S)-1-(5-bromo-7-methylquinolin-6-yl)ethane-1,2-diol (8F): AD-mix-α (0.7 g) was added to a mixed solvent of t-butanol and water (2.5 mL/2.5 mL) and stirred at 25° C. for 5 min, cooled to 0° C. The mixture was transferred to another flask containing 5-bromo-7-methyl-6-vinylquinoline (120 mg) and stirred at 0° C. for 48 hours. The mixture was diluted with ethyl acetate, washed with $NaHCO_3$ solution, water and brine, dried over $Na_2SO_4$, filtered and concentrated in vacuo. The residue was purified by flash column chromatography (EtOAc) to provide (S)-1-(5-bromo-7-methylquinolin-6-yl)ethane-1,2-diol (118 mg). LCMS-ESI⁺ (m/z): 282.1, 284.1 (M+H)⁺.

Step 8.

Preparation of (S)-2-(5-bromo-7-methylquinolin-6-yl)-2-tert-butoxyethyl pivalate (8G): To a stirred solution of (S)-1-(5-bromo-7-methylquinolin-6-yl)ethane-1,2-diol (118 mg, 0.42 mmol) in dichloromethane (5 mL) and pyridine (1 mL) was added trimethylacetyl chloride (100 µL, 0.84 mmol) at 0° C. The mixture was stirred at room temperature for 12 hours, quenched with slow addition of NaHCO₃ solution. The mixture was extracted with ethyl acetate. The organic layer was washed with brine, dried over Na₂SO₄. Concentration gave the intermediate (124 mg) m/z 366.1, 368.1 (M+H)⁺. To the solution of above intermediate (124 mg, 0.34 mmol) in t-butylacetate (3 mL) was added 70% perchloric acid (67 uL, 1.1 mmol) at 25° C. The mixture was stirred at 25° C. for 2 hours, quenched with slow addition of NaHCO₃ solution. The mixture was extracted with ethyl acetate. The organic layer was washed with brine, dried and concentrated in vacuo. The residue was purified by flash chromatography (hexanes/EtOAc) to provide (S)-2-(5-bromo-7-methylquinolin-6-yl)-2-tert-butoxyethyl pivalate (133 mg). LCMS-ESI⁺ (m/z): 422.1, 424.2 (M+H)⁺.

Step 9.

Preparation of (S)-2-(2-acetoxy-5-bromo-7-methylquinolin-6-yl)-2-tert-butoxyethyl pivalate (8H): To the solution of (S)-2-(5-bromo-7-methylquinolin-6-yl)-2-tert-butoxyethyl pivalate (130 mg, 0.31 mmol) in DCM (2 mL) was added mCPBA (70%, 95 mg, 0.39 mmol). The mixture was stirred for 12 hours. The mixture was diluted with EtOAc, washed with saturated sodium bicarbonate solution, water and brine, and dried over sodium sulfate. Concentration under reduced pressure gave the intermediate N-oxide (147 mg). LCMS-ESI⁺ (m/z): 438.2, 440.2 (M+H)⁺. To the above intermediate was added acetic anhydride (5 mL). The mixture was heated at 140° C. for 10 hours. The excess reagents were removed under reduced pressure. The mixture was diluted with EtOAc, washed with saturated sodium bicarbonate solution, water and brine, and dried over sodium sulfate. Concentration gave (S)-2-(2-acetoxy-5-bromo-7-methylquinolin-6-yl)-2-tert-butoxyethyl pivalate (130 mg). LCMS-ESI⁺ (m/z): 480.0, 482.0 (M+H)⁺.

Step 10.

Preparation of (S)-2-(5-bromo-7-methyl-2-oxo-1,2-dihydroquinolin-6-yl)-2-tert-butoxyethyl pivalate (8I): To the solution of (S)-2-(2-acetoxy-5-bromo-7-methylquinolin-6-yl)-2-tert-butoxyethyl pivalate (130 mg) in ethanol (7.5 mL) was added aqueous methylamine solution (0.5 mL, 50%). The mixture was heated at 78° C. for 80 min. Concentration and purification gave (S)-2-(5-bromo-7-methyl-2-oxo-1,2-dihydroquinolin-6-yl)-2-tert-butoxyethyl pivalate (68 mg). LCMS-ESI⁺ (m/z): 438.2, 440.2 (M+H)⁺.

Step 11.

Preparation of (S)-2-tert-butoxy-2-(5-(4-chlorophenyl)-7-methyl-2-oxo-1,2-dihydroquinolin-6-yl)ethyl pivalate (8J): The mixture of (S)-2-(5-bromo-7-methyl-2-oxo-1,2-dihydroquinolin-6-yl)-2-tert-butoxyethyl pivalate (34 mg, 0.078 mmol), Pd(PPh₃)₄ (9 mg), 4-chlorophenylboronic acid (16 mg, 0.1 mmol), aqueous K₂CO₃ solution (0.15 mL, 2 M, 0.3 mmol) in 1,2-dimethoxyethane (2 mL) was heated at 100° C. for 90 minutes. The residue was diluted with ethyl acetate (100 mL), washed with NaHCO₃ solution, water and brine, dried over Na₂SO₄. Concentration and purification gave (S)-2-tert-butoxy-2-(5-(4-chlorophenyl)-7-methyl-2-oxo-1,2-dihydroquinolin-6-yl)ethyl pivalate (22 mg). LCMS-ESI⁺ (m/z): 470.3 (M+H)⁺.

Step 12.

Preparation of (S)-6-(1-tert-butoxy-2-hydroxyethyl)-5-(4-chlorophenyl)-7-methylquinolin-2(1H)-one (8K): To the solution of (S)-2-tert-butoxy-2-(5-(4-chlorophenyl)-7-methyl-2-oxo-1,2-dihydroquinolin-6-yl)ethyl pivalate (5.8 mg) in THF and methanol (1.5 mL/0.5 mL) was added 1 M NaOH solution (0.6 mL). The mixture was stirred at 25° C. for 16 hours, diluted with water. The mixture was extracted with ethyl acetate. The organic layer was washed with brine and dried over sodium sulfate. Concentration gave (S)-6-(1-tert-butoxy-2-hydroxyethyl)-5-(4-chlorophenyl)-7-methylquinolin-2(1H)-one (4.4 mg). LCMS-ESI⁺ (m/z): 386.2 (M+H)⁺.

EXAMPLE 9

(S)-2-tert-butoxy-2-(5-(4-chlorophenyl)-2-((dimethylamino)methyl)-7-methylquinolin-6-yl)acetic acid (9)

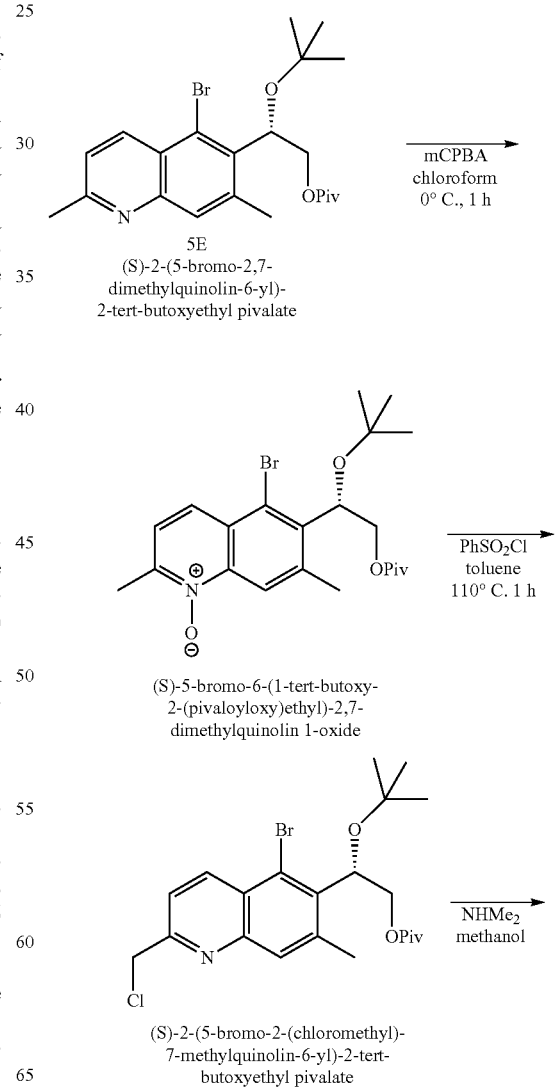

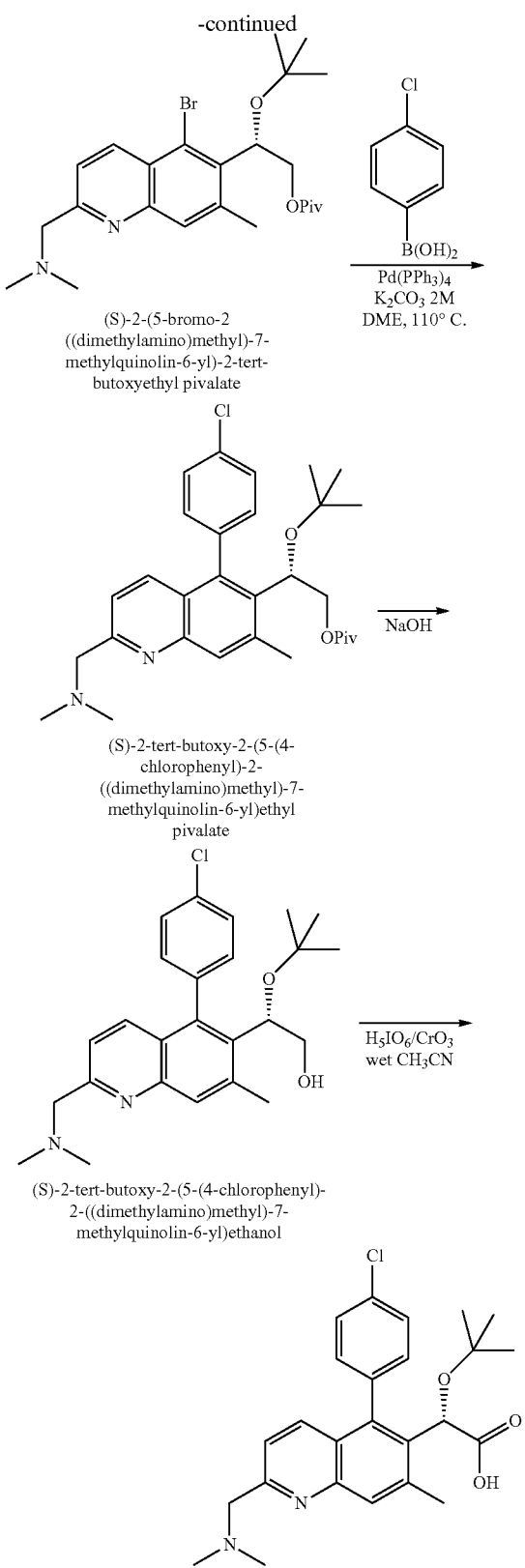

butoxyethyl pivalate (5E) (118 mg, 0.31 mmol) in chloroform (5 mL) was added mCPBA (209 mg, 77%, 0.93 mmol) at 0° C. The mixture was stirred at 0° C. for 1 hour before quenched with NaHCO$_3$ solution. The mixture was extracted with DCM (30 mL), washed with NaHCO$_3$ solution, water and brine, dried over Na$_2$SO$_4$, filtered and concentrated in vacuo. The obtained residue was purified by flash chromatography to provide the desired product (52 mg, 37%). LCMS-ESI$^+$ (m/z): 452.1, 454.1 (M+H)$^+$.

Preparation of (S)-2-(5-bromo-2-((dimethylamino)methyl)-7-methylquinolin-6-yl)-2-tert-butoxyethyl pivalate: To a stirred solution of (S)-5-bromo-6-(1-tert-butoxy-2-(pivaloyloxy)ethyl)-2,7-dimethylquinoline 1-oxide (25 mg, 0.055 mmol) in toluene (3 mL) was added benzenesulfonyl chloride (0.06 mL, 0.24 mmol). The mixture was stirred at 110° C. for 16 hours, then cooled to room temperature. Dimethylamine (2 mL 2 M solution in methanol, excess) was added. The mixture was stirred at room temperature for 16 h, then diluted in ethyl acetate (30 mL), washed with NaHCO$_3$ solution, water and brine, dried over Na$_2$SO$_4$, filtered and concentrated in vacuo. The obtained residue was purified by HPLC to provide the desired product as a white solid (11 mg, 42%). LCMS-ESI$^+$ (m/z): 479.3, 481.3 (M+H)$^+$.

Preparation of (S)-2-tert-butoxy-2-(5-(4-chlorophenyl)-2-((dimethylamino)methyl)-7-methylquinolin-6-Aethyl pivalate: Pd(PPh$_3$)$_4$ (2.5 mg, 0.002 mmol) was added to a mixture (S)-2-(5-bromo-2-((dimethylamino)methyl)-7-methylquinolin-6-yl)-2-tert-butoxyethyl pivalate (11 mg, 0.023 mmol), 4-chlorophenylboronic acid (7 mg, 0.046 mmol), K$_2$CO$_3$ (0.06 mL 2 M in water, 0.13 mmol) in 1,2-dimethoxyethane (1 mL). The reaction mixture was flushed with nitrogen, heated at 110° C. for 30 min under microwave, and then the volatile component was removed in vacuo. The residue was dissolved in ethyl acetate (100 mL), washed with NaHCO$_3$ solution, water and brine, dried over Na$_2$SO$_4$, filtered and concentrated in vacuo. The obtained residue was purified by HPLC to provide the desired product as a white solid (5.6 mg, 48%). LCMS-ESI$^+$ (m/z): 511.3, 513.3 (M+H)$^+$.

Preparation of (S)-2-tert-butoxy-2-(5-(4-chlorophenyl)-2-((dimethylamino)methyl)-7-methylquinolin-6-yl)ethanol:
To a stirred solution of (S)-2-tert-butoxy-2-(5-(4-chlorophenyl)-2-((dimethylamino)methyl)-7-methylquinolin-6-yl) ethyl pivalate (5.6 mg, 0.011 mmol) in THF and methanol (1.5 mL/0.5 mL) was added 2 M NaOH solution (0.5 mL, excess) at 0° C. The mixture was stirred at 50° C. for 3 hours, diluted with water and the resulting mixture was extracted with ethyl acetate. The organic layer was washed with brine, dried and concentrated in vacuo. The obtained residue was purified by prep-HPLC to provide the desired product (3.0 mg, 64%). LCMS-ESI$^+$ (m/z): 427.3, 429.2 (M+H)$^+$.

Preparation of (S)-2-tert-butoxy-2-(5-(4-chlorophenyl)-2-((dimethylamino)methyl)-7-methylquinolin-6-yl)acetic acid (9): A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% H$_2$O) to a volume of 114 mL. This stock solution (0.50 mL) was added to a solution of (S)-2-tert-butoxy-2-(5-(4-chlorophenyl)-2-((dimethylamino)methyl)-7-methylquinolin-6-yl)ethanol (3 mg, 0.007 mmol) in wet acetonitrile (2.0 mL, 0.75% H$_2$O) at 0° C. Reaction mixture was stirred for 30 minutes at 0° C. and quenched with NaHCO$_3$ solution. Ethyl acetate was added and organic layer separated and washed with 1:1 brine/H$_2$O (2×), then saturated NaHSO$_3$/brine. The organic layer was dried (MgSO$_4$), concentrated and purified by reverse phase HPLC to give the product as TFA salt (2.5 mg, 81%).

¹H-NMR 300 MHz, (CD₃OD) δ 7.97 (s, 1H), 7.78 (d, 1H), 7.65-7.55 (m, 3H), 7.40-7.30 (m, 2H), 5.22 (s, 1H), 4.65 (s, 2H), 3.04 (s, 6H), 2.68 (s, 3H), 0.98 (s, 9H); LCMS-ESI⁺ (m/z): [M+H]⁺ calcd for $C_{25}H_{29}ClN_2O_3$: 441.9. Found: 441.2, 443.3.

EXAMPLE 10

(S)-2-tert-Butoxy-2-(5-(4-chlorophenyl)-7-methyl-2-((methylamino)methyl)quinolin-6-yl)acetic acid (10)

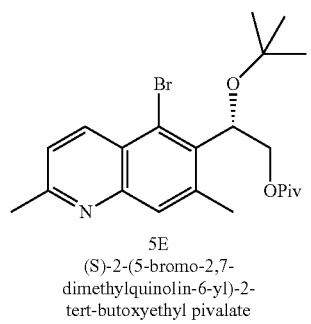
5E
(S)-2-(5-bromo-2,7-dimethylquinolin-6-yl)-2-tert-butoxyethyl pivalate

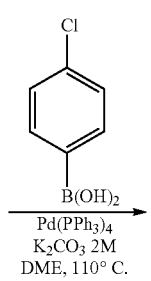
$\xrightarrow{\text{Pd(PPh}_3\text{)}_4 \\ \text{K}_2\text{CO}_3 \text{ 2M} \\ \text{DME, 110° C.}}$

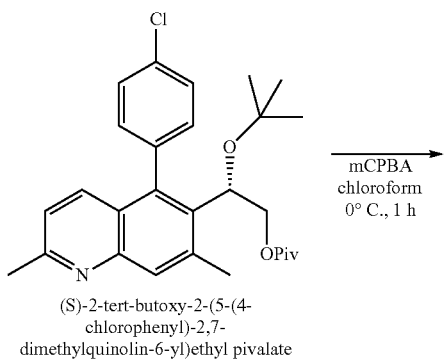
(S)-2-tert-butoxy-2-(5-(4-chlorophenyl)-2,7-dimethylquinolin-6-yl)ethyl pivalate $\xrightarrow{\text{mCPBA} \\ \text{chloroform} \\ \text{0° C., 1 h}}$

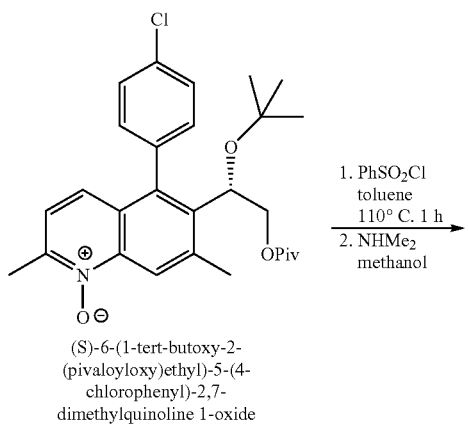
(S)-6-(1-tert-butoxy-2-(pivaloyloxy)ethyl)-5-(4-chlorophenyl)-2,7-dimethylquinoline 1-oxide $\xrightarrow{\text{1. PhSO}_2\text{Cl} \\ \text{toluene} \\ \text{110° C. 1 h} \\ \text{2. NHMe}_2 \\ \text{methanol}}$

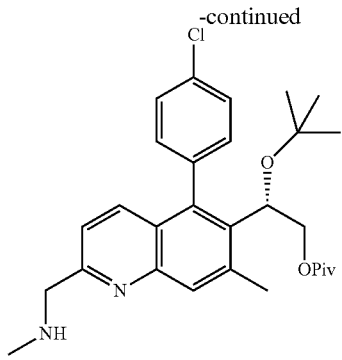
(S)-2-tert-butoxy-2-(5-(4-chlorophenyl)-7-methyl-2-((methylamino)methyl)quinolin-6-yl)ethyl pivalate $\xrightarrow{\text{2N NaOH} \\ \text{THF/MeOH}}$

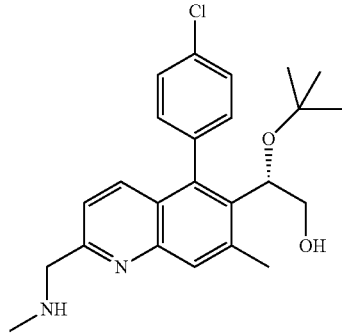
(S)-2-tert-butoxy-2-(5-(4-chlorophenyl)-7-methyl-2-((methylamino)methyl)quinolin-6-yl)ethanol $\xrightarrow{\text{H}_5\text{IO}_6/\text{CrO}_3 \\ \text{wet CH}_3\text{CN}}$

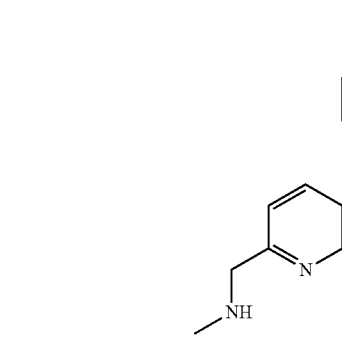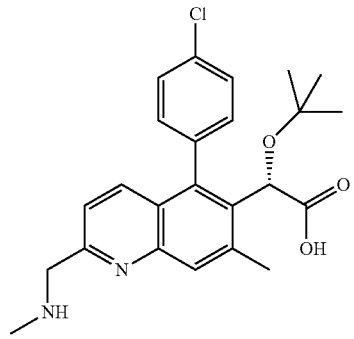
10
(S)-2-tert-butoxy-2-(5-(4-chlorophenyl)-7-methyl-2-((methylamino)methyl)quinolin-6-yl)acetic acid Preparation of (S)-2-tert-Butoxy-2-(5-(4-chlorophenyl)-2,7-dimethylquinolin-6-yl)ethyl pivalate: Pd(PPh₃)₄ (69 mg, 0.06 mmol) was added to a mixture (S)-2-(5-bromo-2,7-dimethylquinolin-6-yl)-2-tert-butoxyethyl pivalate (5E) (325 mg, 0.75 mmol), 4-chlorophenylboronic acid (175 mg, 1.1 mmol), K₂CO₃ (1.3 mL 2 M in water, 2.6 mmol) in 1,2-dimethoxyethane (10 mL). The reaction mixture was flushed with nitrogen, heated at 110° C. for 30 min under microwave, and then the volatile component was removed in vacuo. The residue was dissolved in ethyl acetate (100 mL), washed with NaHCO₃ solution, water and brine, dried over Na₂SO₄, filtered and concentrated in vacuo. The obtained residue was purified by flash chromatography to provide the desired product (256 mg, 73%). LCMS-ESI⁺ (m/z): 468.3, 469.3 (M+H)⁺.

Preparation of (S)-6-(1-tert-Butoxy-2-(pivaloyloxy)ethyl)-5-(4-chlorophenyl)-2,7-dimethylquinoline 1-oxide:

Following the procedure used to prepare compound (S)-5-bromo-6-(1-tert-butoxy-2-(pivaloyloxy)ethyl)-2,7-dimethylquinoline 1-oxide of Example 9, except that (S)-2-tert-butoxy-2-(5-(4-chlorophenyl)-2,7-dimethylquinolin-6-yl)ethyl pivalate was used instead of (S)-2-(5-bromo-2,7-dimethylquinolin-6-yl)-2-tert-butoxyethyl pivalate. LCMS-ESI⁺ (m/z): 484.3, 486.3 (M+H)⁺.

Preparation of (S)-2-tert-Butoxy-2-(5-(4-chlorophenyl)-7-methyl-2-((methylamino)methyl)quinolin-6-yl)ethyl pivalate: Following the procedure used to prepare compound (S)-2-(5-bromo-2-((dimethylamino)methyl)-7-methylquinolin-6-yl)-2-tert-butoxyethyl pivalate of Example 9, except that (S)-6-(1-tert-butoxy-2-(pivaloyloxy)ethyl)-5-(4-chlorophenyl)-2,7-dimethylquinoline 1-oxide was used instead of (S)-5-bromo-6-(1-tert-butoxy-2-(pivaloyloxy)ethyl)-2,7-dimethylquinoline 1-oxide, and methylamine solution was used instead of N,N-dimethylamine solution. LCMS-ESI⁺ (m/z): 497.3, 499.3 (M+H)⁺.

Preparation of (S)-2-tert-Butoxy-2-(5-(4-chlorophenyl)-7-methyl-2-((methylamino)methyl)quinolin-6-yl)ethanol: Following the procedure used to prepare compound (S)-2-tert-butoxy-2-(5-(4-chlorophenyl)-2-((dimethylamino)methyl)-7-methylquinolin-6-yl)ethanol of Example 9, except that (S)-2-tert-butoxy-2-(5-(4-chlorophenyl)-7-methyl-2-((methylamino)methyl)quinolin-6-yl)ethyl pivalate was used instead of (S)-2-tert-butoxy-2-(5-(4-chlorophenyl)-2-((dimethylamino)methyl)-7-methylquinolin-6-yl)ethyl pivalate. LCMS-ESI⁺ (m/z): 413.3, 415.3 (M+H)⁺.

Preparation of (S)-2-tert-Butoxy-2-(5-(4-chlorophenyl)-7-methyl-2-((methylamino)methyl)quinolin-6-yl)acetic acid (10): Following the procedure used to prepare compound (S)-2-tert-butoxy-2-(5-(4-chlorophenyl)-2-((dimethylamino)methyl)-7-methylquinolin-6-yl)acetic acid (9) of Example 9, except that (S)-2-tert-butoxy-2-(5-(4-chlorophenyl)-7-methyl-2-((methylamino)methyl)quinolin-6-yl)ethanol was used instead of (S)-2-tert-butoxy-2-(5-(4-chlorophenyl)-2-((dimethylamino)methyl)-7-methylquinolin-6-yl)ethanol. ¹H-NMR 300 MHz, (CD₃OD) δ7.95 (s, 1H), 7.74 (d, 1H), 7.65-7.55 (m, 3H), 7.35-7.28 (m, 2H), 5.22 (s, 1H), 4.51 (s, 2H), 2.88 (s, 3H), 2.67 (s, 3H), 0.98 (s, 9H); LCMS-ESI⁺ (m/z): [M+H]⁺ calcd for C₂₄H₂₇ClN₂O₃: 427.9. Found: 427.2, 429.2.

EXAMPLE 11

(S)-2-tert-Butoxy-2-(5-(4-chlorophenyl)-7-methyl-2-(piperidin-1-ylmethyl)quinolin-6-yl)acetic acid: (11)

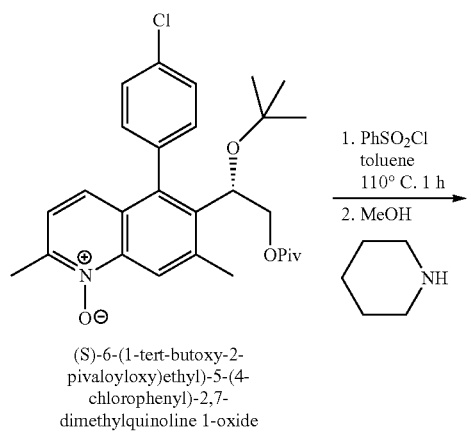

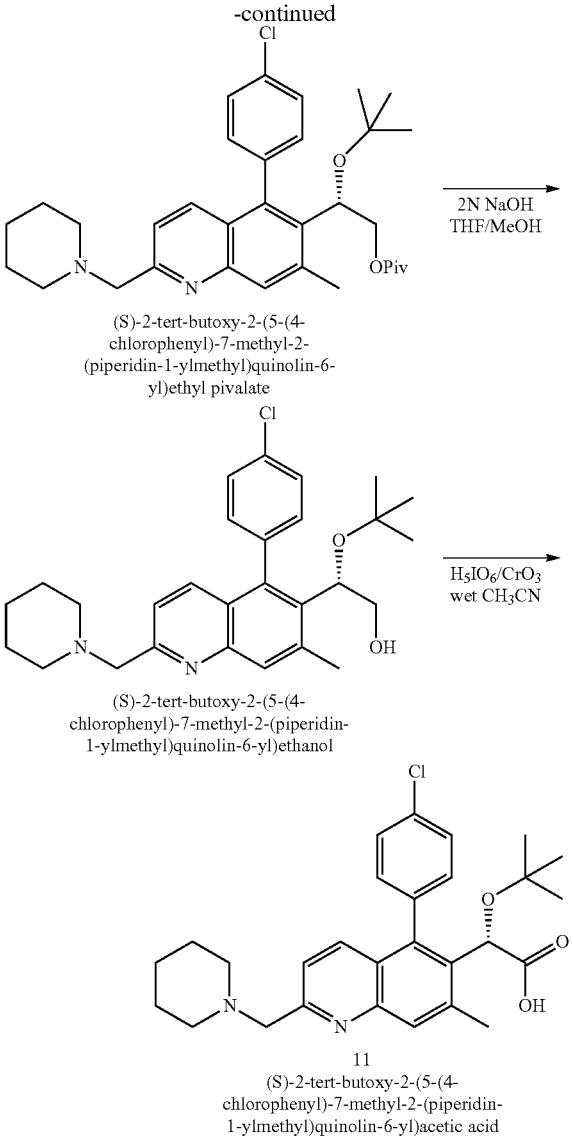

Preparation of (S)-2-tert-Butoxy-2-(5-(4-chlorophenyl)-7-methyl-2-(piperidin-1-ylmethyl)quinolin-6-yl)ethyl pivalate: (S)-2-tert-Butoxy-2-(5-(4-chlorophenyl)-7-methyl-2-(piperidin-1-ylmethyl)quinolin-6-yl)ethyl pivalate was prepared following the procedure used to prepare compound (S)-2-(5-bromo-2-((dimethylamino)methyl)-7-methylquinolin-6-yl)-2-tert-butoxyethyl pivalate of Example 9, except that (S)-6-(1-tert-butoxy-2-(pivaloyloxy)ethyl)-5-(4-chlorophenyl)-2,7-dimethylquinoline 1-oxide was used instead of (S)-5-bromo-6-(1-tert-butoxy-2-(pivaloyloxy)ethyl)-2,7-dimethylquinoline 1-oxide, and piperidine was used instead of N,N-dimethylamine solution. LCMS-ESI⁺ (m/z): 551.3, 553.3 (M+H)⁺.

Preparation of (S)-2-tert-butoxy-2-(5-(4-chlorophenyl)-7-methyl-2-(piperidin-1-ylmethyl)quinolin-6-yl)ethanol: (S)-2-tert-butoxy-2-(5-(4-chlorophenyl)-7-methyl-2-(piperidin-1-ylmethyl)quinolin-6-yl)ethanol was prepared following the procedure used to prepare compound (S)-2-tert-butoxy-2-(5-(4-chlorophenyl)-2-((dimethylamino)methyl)-7-methylquinolin-6-yl)ethanol of Example 9, except that (S)-2-tert-butoxy-2-(5-(4-chlorophenyl)-7-methyl-2-(piperidin-1-ylmethyl)quinolin-6-yl)ethyl pivalate was used instead of (S)-2-tert-butoxy-2-(5-(4-chlorophenyl)-2-((dimethylamino)methyl)-7-methylquinolin-6-yl)ethyl pivalate. LCMS-ESI⁺ (m/z): 467.4, 469.3 (M+H)⁺.

Preparation of (S)-2-tert-butoxy-2-(5-(4-chlorophenyl)-7-methyl-2-(piperidin-1-ylmethyl)quinolin-6-yl)acetic acid (11): (S)-2-tert-Butoxy-2-(5-(4-chlorophenyl)-7-methyl-2-(piperidin-1-ylmethyl)quinolin-6-yl)acetic acid was prepared following the procedure used to prepare compound (S)-2-tert-butoxy-2-(5-(4-chlorophenyl)-2-((dimethylamino)methyl)-7-methylquinolin-6-yl)acetic acid (9) of Example 9, except that (S)-2-tert-butoxy-2-(5-(4-chlorophenyl)-7-methyl-2-(piperidin-1-ylmethyl)quinolin-6-yl)ethanol was used instead of (S)-2-tert-butoxy-2-(5-(4-chlorophenyl)-2-((dimethylamino)methyl)-7-methylquinolin-6-yl)ethanol. $^{1}$H-NMR 300 MHz, (CD$_3$OD) δ 7.97 (s, 1H), 7.77 (d, 1H), 7.65-7.58 (m, 3H), 7.40-7.30 (m, 2H), 5.22 (s, 1H), 4.61 (s, 2H), 3.60-3.20 (m, 4H), 2.69 (s, 3H), 2.00-1.90 (m, 4H), 1.80-1.65 (m, 2H), 0.98 (s, 9H); LCMS-ESI⁺ (m/z): [M+H]⁺ calcd for C$_{28}$H$_{33}$ClN$_2$O$_3$: 482.0; Found: 481.3, 483.3.

EXAMPLE 12

(S)-2-tert-Butoxy-2-(5-(4-chlorophenyl)-2-(methoxycarbonyl)-7-methylquinolin-6-yl)acetic acid: (12)

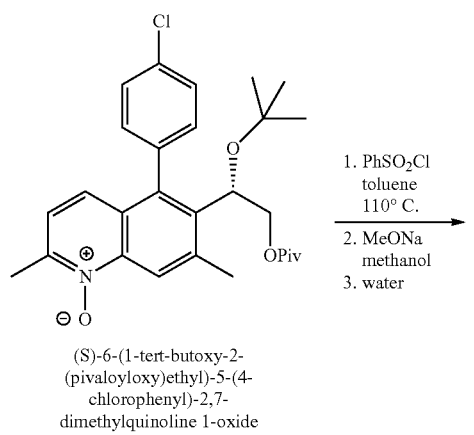

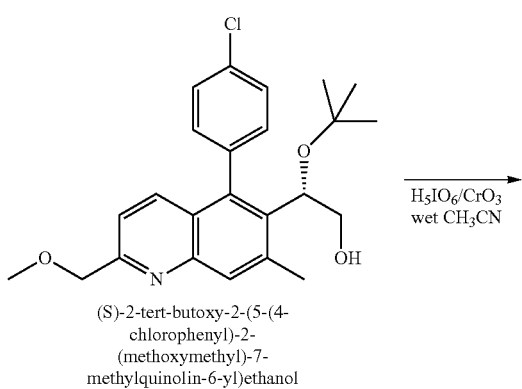

(S)-2-tert-butoxy-2-(5-(4-chlorophenyl)-2-(methoxymethyl)-7-methylquinolin-6-yl)ethanol

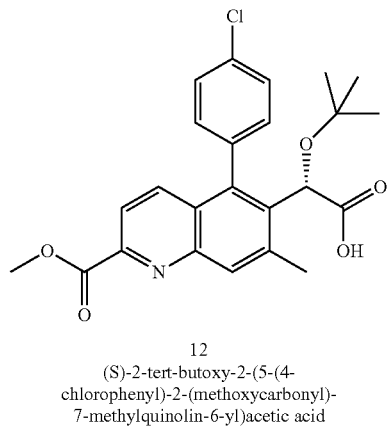

12
(S)-2-tert-butoxy-2-(5-(4-chlorophenyl)-2-(methoxycarbonyl)-7-methylquinolin-6-yl)acetic acid Preparation of (S)-2-tert-butoxy-2-(5-(4-chlorophenyl)-2-(methoxymethyl)-7-methylquinolin-6-yl)ethanol: To a stirred solution of (S)-6-(1-tert-butoxy-2-(pivaloyloxy)ethyl)-5-(4-chlorophenyl)-2,7-dimethylquinoline 1-oxide (compound of Example 10) (14 mg, 0.03 mmol) in toluene (2 mL) was added benzenesulfonyl chloride (0.04 mL, 0.29 mmol). The mixture was stirred at 110° C. for 16 hours, then cooled to room temperature. Sodium methoxide (1 mL 25% solution in methanol, excess) was added. The mixture was stirred at room temperature for 16 hours, then water (1 mL) was added. The mixture was stirred at 60° C. for 1 hour. The reaction mixture was diluted in ethyl acetate (30 mL), washed with NaHCO$_3$ solution, water and brine, dried over Na$_2$SO$_4$, filtered and concentrated in vacuo. The obtained residue was purified by HPLC to provide the desired product as TFA salt (4.8 mg, 33%). LCMS-ESI⁺ (m/z): 414.2, 416.2 (M+H)⁺.

Preparation of (S)-2-tert-butoxy-2-(5-(4-chlorophenyl)-2-(methoxycarbonyl)-7-methylquinolin-6-yl)acetic acid (12): A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% H$_2$O) to a volume of 114 mL. This stock solution (0.50 mL) was added to a solution of (S)-2-tert-butoxy-2-(5-(4-chlorophenyl)-2-(methoxymethyl)-7-methylquinolin-6-yl)ethanol (4.8 mg, 0.01 mmol) in wet acetonitrile (2.0 mL, 0.75% H$_2$O) at 0° C. The reaction mixture was stirred for 1 hour at 0° C. and quenched with NaHCO$_3$ solution. Ethyl acetate was added and the organic layer separated and washed with 1:1 brine/H$_2$O (2×), then saturated NaHSO$_3$/brine. The organic layer was dried (MgSO$_4$) and concentrated and purified by reverse phase HPLC to give the product as TFA salt (2.7 mg, 61%). $^{1}$H-NMR 300 MHz, (CD$_3$OD) δ 8.10-8.00 (m, 2H), 7.90 (d, 1H), 7.70-7.57 (m, 3H), 7.35 (d, 1H), 5.23 (s, 1H), 4.03 (s, 3H), 2.70 (s, 3H), 0.98 (s, 9H); LCMS-ESI⁺ (m/z): [M+H]⁺ calcd for $C_{24}H_{25}ClNO_5$: 442.9. Found: 442.2, 444.2.

EXAMPLE 13

(S)-2-tert-Butoxy-2-(5-(4-chlorophenyl)-2-(ethoxycarbonyl)-7-methylquinolin-6-yl)acetic acid (13)

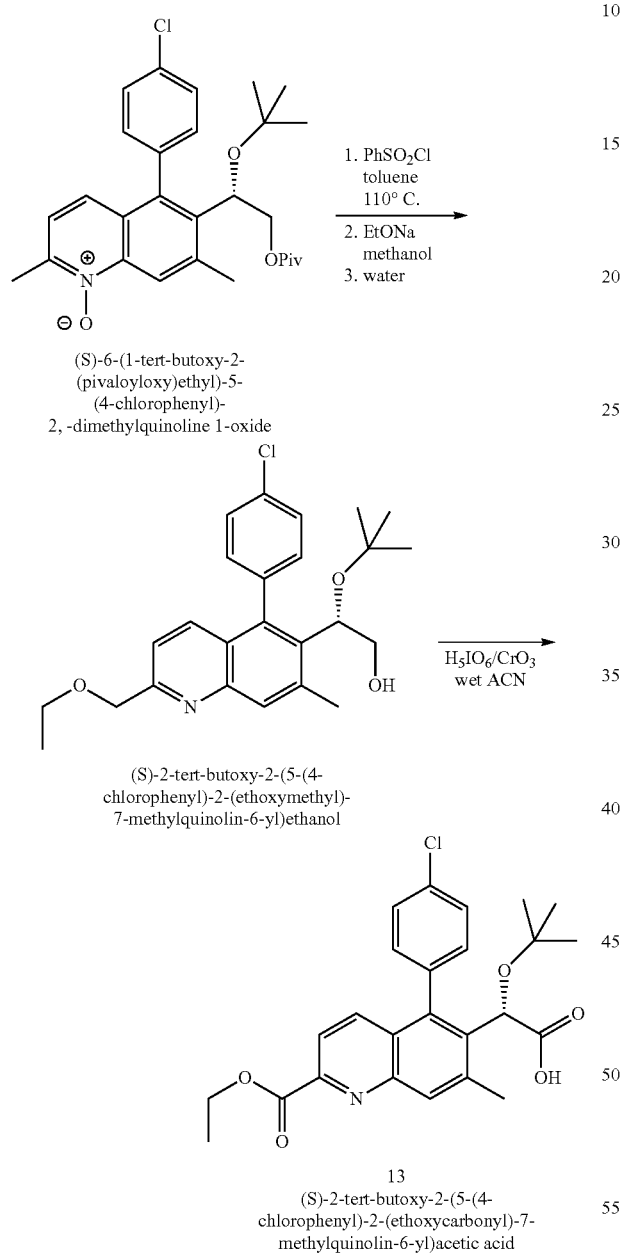

Preparation of (S)-2-tert-Butoxy-2-(5-(4-chlorophenyl)-2-(ethoxymethyl)-7-methylquinolin-6-yl)ethanol: (S)-2-tert-Butoxy-2-(5-(4-chlorophenyl)-2-(ethoxymethyl)-7-methylquinolin-6-yl)ethanol was prepared following the procedure used to prepare compound (S)-2-tert-butoxy-2-(5-(4-chlorophenyl)-2-(methoxymethyl)-7-methylquinolin-6-yl)ethanol of Example 12, except that sodium ethoxide in ethanol solution was used instead of sodium methoxide in methanol solution. LCMS-ESI⁺ (m/z): 428.2, 430.2 (M+H)⁺.

Preparation of (S)-2-tert-butoxy-2-(5-(4-chlorophenyl)-2-(ethoxycarbonyl)-7-methylquinolin-6-yl)acetic acid (13): (S)-2-tert-Butoxy-2-(5-(4-chlorophenyl)-2-(ethoxycarbonyl)-7-methylquinolin-6-yl)acetic acid was prepared following the procedure used to prepare compound (S)-2-tert-butoxy-2-(5-(4-chlorophenyl)-2-(methoxycarbonyl)-7-methylquinolin-6-yl)acetic acid of Example 12, except that (S)-2-tert-butoxy-2-(5-(4-chlorophenyl)-2-(ethoxymethyl)-7-methylquinolin-6-yl)ethanol was used instead of (S)-2-tert-butoxy-2-(5-(4-chlorophenyl)-2-(methoxymethyl)-7-methylquinolin-6-yl)ethanol. ¹H-NMR 300 MHz, (CD₃OD) δ8.10-8.00 (m, 2H), 7.90 (d, 1H), 7.70-7.57 (m, 3H), 7.35 (d, 1H), 5.23 (s, 1H), 4.50 (q, 2H), 2.70 (s, 3H), 1.46 (t, 3H) 0.98 (s, 9H); LCMS-ESI⁺ (m/z): [M+H]⁺ calcd for $C_{25}H_{26}ClNO_5$: 456.9. Found: 456.2, 458.2.

EXAMPLE 14

(S)-2-tert-Butoxy-2-(5-(4-chlorophenyl)-7-methyl-2-((methyl(phenyl)amino)methyl)quinolin-6-yl)acetic acid (14)

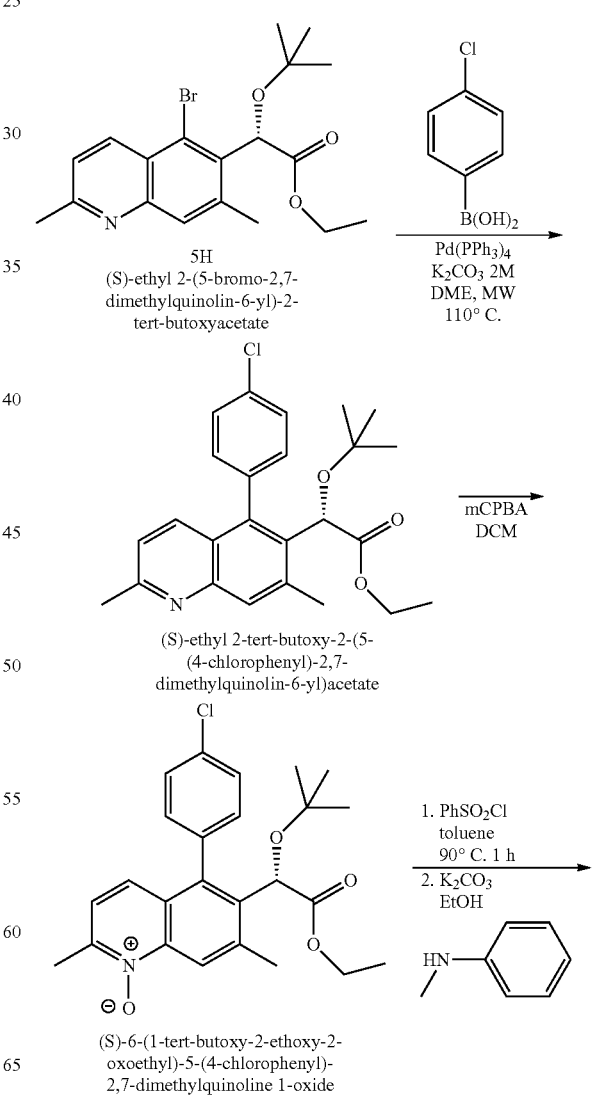

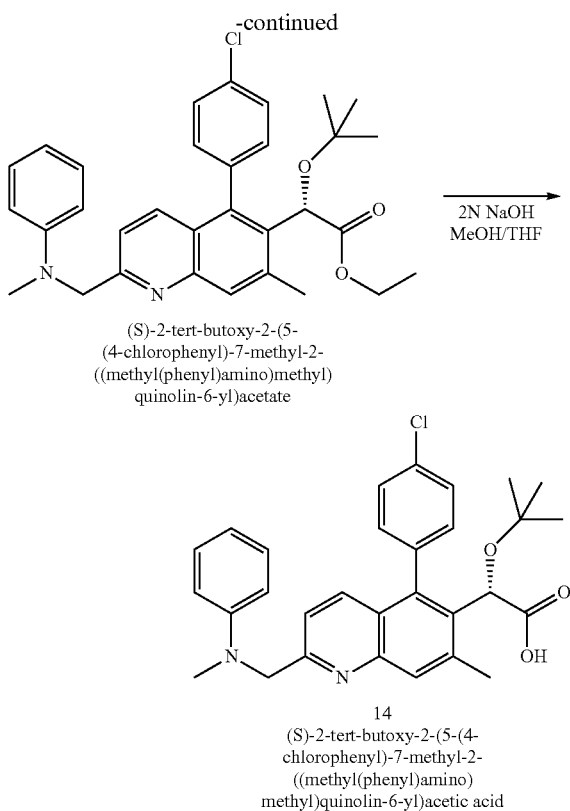

(S)-2-tert-butoxy-2-(5-(4-chlorophenyl)-7-methyl-2-((methyl(phenyl)amino)methyl)quinolin-6-yl)acetate 14
(S)-2-tert-butoxy-2-(5-(4-chlorophenyl)-7-methyl-2-((methyl(phenyl)amino)methyl)quinolin-6-yl)acetic acid Preparation of (S)-ethyl 2-tert-butoxy-2-(5-(4-chlorophenyl)-2,7-dimethylquinolin-6-yl)acetate: Pd(PPh$_3$)$_4$ (68 mg, 0.06 mmol) was added to a mixture of (S)-ethyl 2-(5-bromo-2,7-dimethylquinolin-6-yl)-2-tert-butoxyacetate (5H) (230 mg, 0.59 mmol) and 4-chlorophenylboronic acid (183 mg, 1.17 mmol), K$_2$CO$_3$ (1.0 mL 2 M in water, 2.06 mmol) in 1,2-dimethoxyethane (8 mL). The reaction mixture was flushed with nitrogen, heated at 110° C. for 30 min under microwave, and then the volatile component was removed in vacuo. The residue was dissolved in ethyl acetate (100 mL), washed with NaHCO$_3$ solution, water and brine, dried over Na$_2$SO$_4$, filtered and concentrated in vacuo. The obtained residue was purified by HPLC to provide the desired product (200 mg, 80%). LCMS-ESI$^+$ (m/z): 426.2, 428.2 (M+H)$^+$.

Preparation of (S)-6-(1-tert-butoxy-2-ethoxy-2-oxoethyl)-5-(4-chlorophenyl)-2,7-dimethylquinoline 1-oxide: To a stirred solution of (S)-ethyl 2-tert-butoxy-2-(5-(4-chlorophenyl)-2,7-dimethylquinolin-6-yl)acetate (100 mg, 0.25 mmol) in dichloromethane (5 mL) was added a solution of mCPBA (114 mg, 77%, 0.51 mmol) in DCM (2 mL) at 0° C. The mixture was stirred at 0° C. for 1 hour before quenched with NaHCO$_3$ solution. The mixture was extracted with DCM (30 mL), washed with NaHCO$_3$ solution, water and brine, dried over Na$_2$SO$_4$, filtered and concentrated in vacuo. The obtained residue was purified by flash chromatography to provide the desired product (104 mg, 94%). LCMS-ESI$^+$ (m/z): 442.2, 444.3 (M+H)$^+$.

Preparation of (S)-ethyl 2-tert-butoxy-2-(5-(4-chlorophenyl)-7-methyl-2-((methyl(phenyl) amino)methyl)quinolin-6-yl)acetate: To a stirred solution of (S)-6-(1-tert-butoxy-2-ethoxy-2-oxoethyl)-5-(4-chlorophenyl)-2,7-dimethylquinoline 1-oxide (13 mg, 0.029 mmol) in toluene (2 mL) was added benzenesulfonyl chloride (0.2 mL, excess). The mixture was stirred at 80° C. for 1 hour, then cooled to room temperature. N-methylaniline (0.2 mL, excess) and K$_2$CO$_3$ (250 mg, excess) were added. The mixture was stirred at 60° C. for 16 h, then diluted in ethyl acetate (30 mL), washed with NaHCO$_3$ solution, water and brine, dried over Na$_2$SO$_4$, filtered and concentrated in vacuo. The obtained residue was purified by flash chromatography to provide the desired product (12 mg, 78%). LCMS-ESI$^+$ (m/z): 531.3, 533.2 (M+H)$^+$.

Preparation of (S)-2-tert-Butoxy-2-(5-(4-chlorophenyl)-7-methyl-2-((methyl(phenyl)amino)methyl)quinolin-6-yl)acetic acid (14): To a stirred solution of (S)-ethyl 2-tert-butoxy-2-(5-(4-chlorophenyl)-7-methyl-2-((methyl(phenyl)amino) methyl)quinolin-6-yl)acetate (12 mg, 0.023 mmol) in THF and methanol (2 mL/1 mL) was added 2 M NaOH solution (0.5 mL, excess) at 0° C. The mixture was stirred at 50° C. for 3 hours, diluted with water. The mixture was extracted with ethyl acetate. The organic layer was washed with brine, dried and concentrated in vacuo. The obtained residue was purified by prep-HPLC to provide the desired product as TFA salt (9.0 mg, 65%). $^1$H-NMR 300 MHz, (CD$_3$OD). δ8.21 (d, 1H), 8.07 (s, 1H), 7.70-7.55 (m, 4H), 7.40-7.32 (m, 1H), 7.26-7.18 (m, 2H), 6.90-6.75 (m, 3H), 5.24 (s, 1H), 5.01 (s, 2H), 3.17 (s, 3H), 2.77 (s, 3H), 0.98 (s, 9H); LCMS-ESI$^+$ (m/z): [M+H]$^+$ calcd for C$_{30}$H$_{32}$ClN$_2$O$_3$: 504.0. Found: 503.3, 505.2.

EXAMPLE 15

(S)-2-tert-Butoxy-2-(5-(4-chlorophenyl)-7-methyl-2-((methyl(phenyl)amino)methyl)quinolin-6-yl)acetic acid (15)

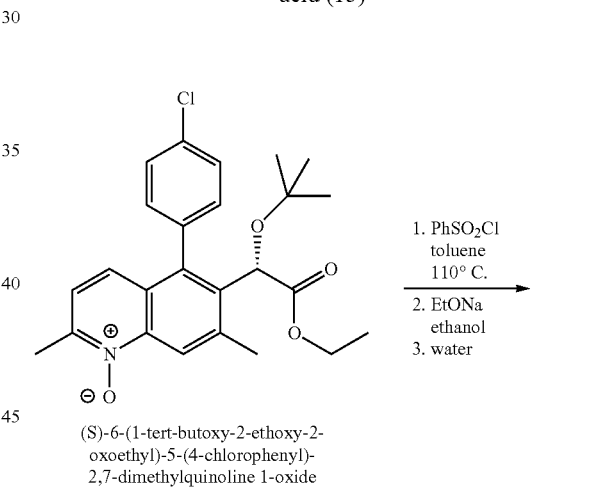

(S)-6-(1-tert-butoxy-2-ethoxy-2-oxoethyl)-5-(4-chlorophenyl)-2,7-dimethylquinoline 1-oxide

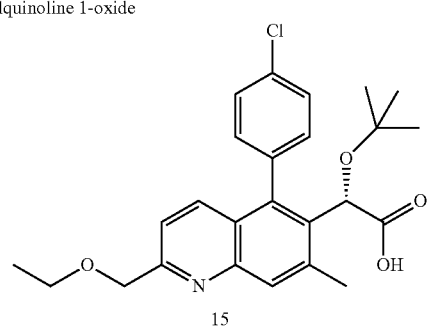

15
(S)-2-tert-butoxy-2-(5-(4-chlorophenyl)-2-(ethoxymethyl)-7-methylquinolin-6-yl)acetic acid Preparation of (S)-2-tert-butoxy-2-(5-(4-chlorophenyl)-2-(ethoxymethyl)-7-methylquinolin-6-yl)acetic acid (15): To a stirred solution of (S)-6-(1-tert-butoxy-2-ethoxy-2-oxoethyl)-5-(4-chlorophenyl)-2,7-dimethylquinoline 1-oxide (compound of Example 14) (12 mg, 0.027 mmol) in toluene (2 mL) was added benzenesulfonyl chloride (0.2 mL, excess). The mixture was stirred at 80° C. for 1 hour, then cooled to room temperature. Sodium ethoxide (0.5 mL 21% ethanol solution, excess) was added. The mixture was stirred at 60° C. for 16 h. Water (1 mL) was added, and the mixture was stirred at 60° C. for another 4 hours. The reaction mixture was diluted in ethyl acetate (30 mL), washed with NaHCO$_3$ solution, water and brine, dried over Na$_2$SO$_4$, filtered and concentrated in vacuo. The obtained residue was purified by prep-HPLC to provide the desired product as TFA salt (3.0 mg, 21%). $^1$H-NMR 300 MHz, (CD$_3$OD) δ 8.19 (d, 1H), 8.06 (s, 1H), 7.73 (d, 1H), 7.70-7.60 (m, 3H), 7.40-7.35 (m, 1H), 5.24 (s, 1H), 4.95 (s, 2H), 3.75 (q, 2H), 2.75 (s, 3H), 1.32 (t, 3H), 0.98 (s, 9H); LCMS-ESI$^+$ (m/z): [M+H]$^+$ calcd for C$_{25}$H$_{29}$ClNO$_4$: 442.9. Found: 442.2, 444.2.

EXAMPLE 16

(S)-2-tert-Butoxy-2-(5-(4-chlorophenyl)-2-(dimethylcarbamoyl)-7-methylquinolin-6-yl)acetic acid: (16)

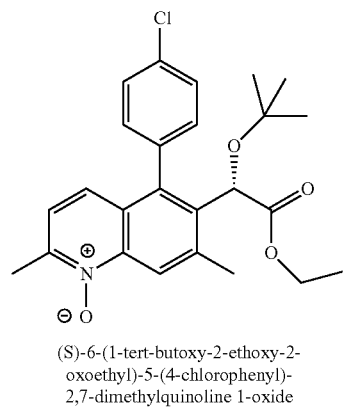

(S)-6-(1-tert-butoxy-2-ethoxy-2-oxoethyl)-5-(4-chlorophenyl)-2,7-dimethylquinoline 1-oxide

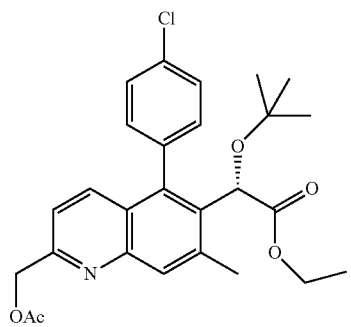

(S)-ethyl 2-(2-acetoxymethyl)-5-(4-chlorophenyl)-methylquinolin-6-yl)-2-tert-butoxyacetate

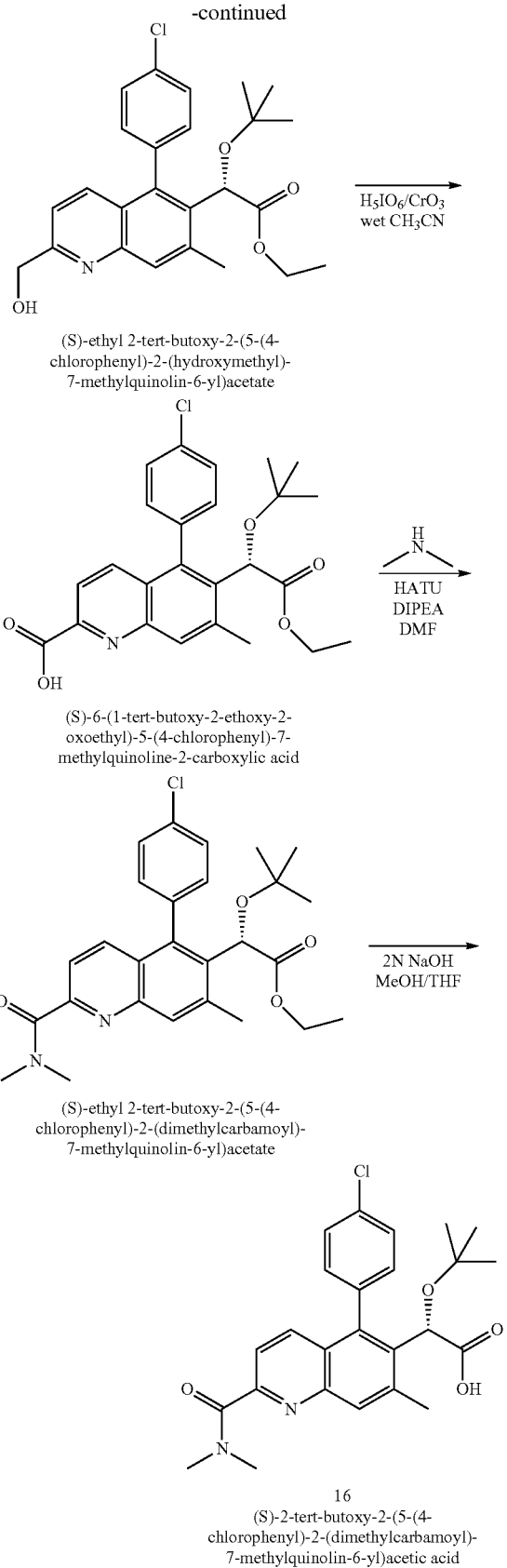

Preparation of (S)-ethyl 2-(2-(acetoxymethyl)-5-(4-chlorophenyl)-7-methylquinolin-6-yl)-2-tert-butoxyacetate:

Acetic anhydride was added to a flask containing (S)-6-(1-tert-butoxy-2-ethoxy-2-oxoethyl)-5-(4-chlorophenyl)-2,7-dimethylquinoline 1-oxide (compound of Example 14) (42 mg, 0.095 mmol). The mixture was stirred at 80° C. for 1 hour. Acetic anhydride was removed under vacuum. The residue was dissolved in ethyl acetate (50 mL). The organic layer was washed with NaHCO$_3$ solution and water, dried and concentrated in vacuo. The obtained residue was used for next step reaction without purification. LCMS-ESI$^+$ (m/z): 484.2, 486.2 (M+H)$^+$.

Preparation of (S)-ethyl 2-tert-butoxy-2-(5-(4-chlorophenyl)-2-(hydroxymethyl)-7-methylquinolin-6-yl)acetate: To a stirred solution of (S)-ethyl 2-(2-(acetoxymethyl)-5-(4-chlorophenyl)-7-methylquinolin-6-yl)-2-tert-butoxyacetate (0.095 mmol) in methanol (2 mL) was added 2 M K$_2$CO$_3$ (0.5 mL, excess) at room temperature. The mixture was stirred at room temperature for 1 hour, diluted with water. The mixture was extracted with ethyl acetate. The organic layer was washed with brine, dried and concentrated in vacuo. The obtained residue was purified by flash chromatography to provide the desired product (26 mg, 62%). LCMS-ESI$^+$ (m/z): 442.2, 444.2 (M+H)$^+$.

Preparation of (S)-6-(1-tert-butoxy-2-ethoxy-2-oxoethyl)-5-(4-chlorophenyl)-7-methylquinoline-2-carboxylic acid: (S)-6-(1-tert-Butoxy-2-ethoxy-2-oxoethyl)-5-(4-chlorophenyl)-7-methylquinoline-2-carboxylic acid was prepared following the procedure used to prepare compound (S)-2-tert-butoxy-2-(5-(4-chlorophenyl)-2-((dimethylamino)methyl)-7-methylquinolin-6-yl)acetic acid of Example 9, except that (S)-ethyl 2-tert-butoxy-2-(5-(4-chlorophenyl)-2-(hydroxymethyl)-7-methylquinolin-6-yl)acetate was used instead of (S)-2-tert-butoxy-2-(5-(4-chlorophenyl)-2-((dimethylamino)methyl)-7-methylquinolin-6-yl)ethanol. LCMS-ESI$^+$ (m/z): 456.2, 458.2 (M+H)$^+$.

Preparation of (S)-ethyl 2-tert-butoxy-2-(5-(4-chlorophenyl)-2-(dimethylcarbamoyl)-7-methylquinolin-6-yl)acetate: To a stirred solution of (S)-6-(1-tert-butoxy-2-ethoxy-2-oxoethyl)-5-(4-chlorophenyl)-7-methylquinoline-2-carboxylic acid (14 mg, 0.032 mmol), dimethylamine HCl salt (13 mg, 0.16 mmol) and DIPEA (0.056 mL, 0.32 mmol) in DMF (1 mL) was added HATU (61 mg, 0.16 mmol) at 0° C. The mixture was stirred for 2 hours at ambient temperature. The mixture was diluted with ethyl acetate (30 mL) and washed with water and brine, then dried over Na$_2$SO$_4$. Concentration and purification by column chromatography provided the product (7 mg, 45%). LCMS-ESI$^+$ (m/z): 483.2, 485.3 (M+H)$^+$.

Preparation of (S)-2-tert-Butoxy-2-(5-(4-chlorophenyl)-2-(dimethylcarbamoyl)-7-methylquinolin-6-yl)acetic acid (16): (S)-2-tert-Butoxy-2-(5-(4-chlorophenyl)-2-(dimethylcarbamoyl)-7-methylquinolin-6-yl)acetic acid was prepared following the procedure used to prepare compound (S)-2-tert-butoxy-2-(5-(4-chlorophenyl)-7-methyl-2-((methyl(phenyl)amino) methyl)quinolin-6-yl)acetic acid of Example 14, except that (S)-ethyl 2-tert-butoxy-2-(5-(4-chlorophenyl)-2-(dimethylcarbamoyl)-7-methylquinolin-6-yl)acetate was used instead of (S)-ethyl 2-tert-butoxy-2-(5-(4-chlorophenyl)-7-methyl-2-((methyl(phenyl)amino)methyl) quinolin-6-yl)acetate. $^1$H-NMR 300 MHz, (CD$_3$OD) δ 7.91 (s, 1H), 7.87 (d, 1H), 7.65-7.58 (m, 3H), 7.50 (d, 1H), 7.40-7.32 (m, 1H), 5.23 (s, 1H), 3.18 (s, 3H), 3.05 (s, 3H), 2.69 (s, 3H), 0.99 (s, 9H); LCMS-ESI$^+$ (m/z): [M+H]$^+$ calcd for C$_{25}$H$_{28}$ClN$_2$O$_4$: 455.9. Found: 455.2, 457.2.

EXAMPLE 17

(S)-2-tert-butoxy-2-(5-(4-chlorophenyl)-7-methyl-2-(methyl(phenyl)carbamoyl)quinolin-6-yl)acetic acid: (17)

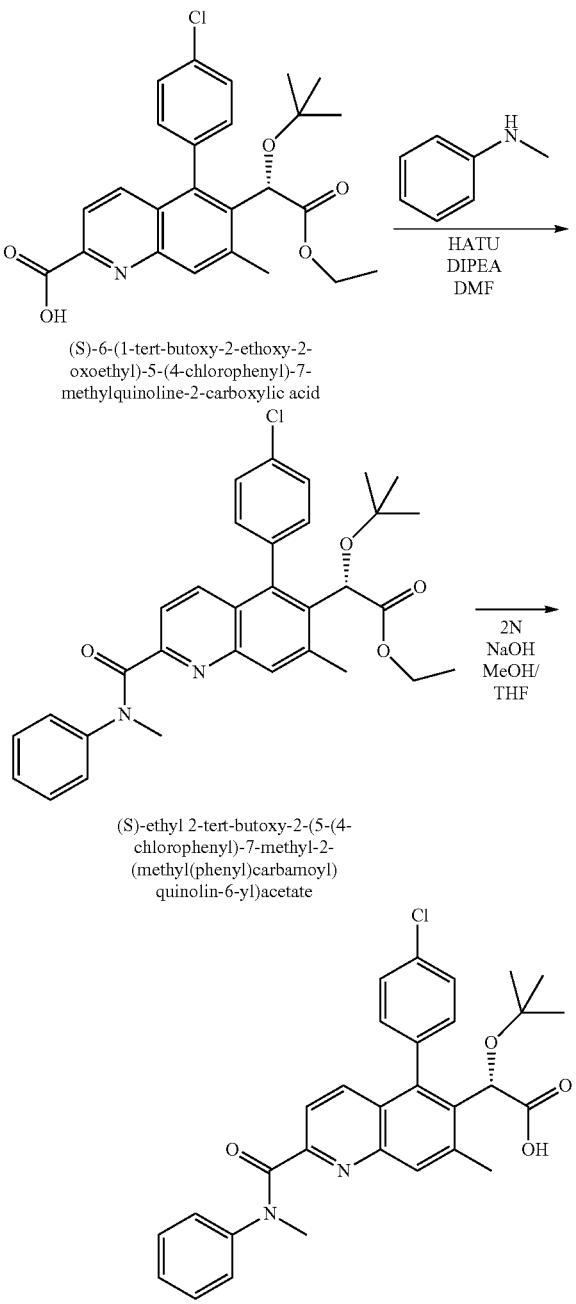

Preparation of (S)-ethyl 2-tert-butoxy-2-(5-(4-chlorophenyl)-7-methyl-2-(methyl(phenyl)carbamoyl) quinolin-6-yl)acetate: (S)-Ethyl 2-tert-butoxy-2-(5-(4-chlorophenyl)-7- methyl-2-(methyl(phenyl)carbamoyl) quinolin-6-yl)acetate was prepared following the procedure used to prepare compound (S)-ethyl 2-tert-butoxy-2-(5-(4-chlorophenyl)-2-(dimethylcarbamoyl)-7-methylquinolin-6-yl)acetate of Example 16, except that N-methylaniline was used instead of dimethylamine HCl salt. LCMS-ESI⁺ (m/z): 545.2, 547.2 (M+H)⁺.

Preparation of (S)-2-tert-butoxy-2-(5-(4-chlorophenyl)-7-methyl-2-(methyl(phenyl)carbamoyl)quinolin-6-yl)acetic acid (17): (S)-2-tert-butoxy-2-(5-(4-chlorophenyl)-7-methyl-2-(methyl(phenyl)carbamoyl)quinolin-6-yl)acetic acid was prepared following the procedure used to prepare compound (S)-2-tert-Butoxy-2-(5-(4-chlorophenyl)-7-methyl-2-((methyl(phenyl)amino)methyl)quinolin-6-yl)acetic acid of Example 14, except that (S)-ethyl 2-tert-butoxy-2-(5-(4-chlorophenyl)-7-methyl-2-(methyl(phenyl)carbamoyl) quinolin-6-yl)acetate was used instead of (S)-ethyl 2-tert-butoxy-2-(5-(4-chlorophenyl)-7-methyl-2-((methyl(phenyl)amino)methyl) quinolin-6-yl)acetate. $^1$H-NMR 300 MHz, (CD$_3$OD) δ 7.80-7.50 (m, 6H), 7.40-7.10 (m, 6H), 5.16 (s, 1H), 3.54 (s, 3H), 2.62 (s, 3H), 0.95 (s, 9H); LCMS-ESI⁺ (m/z): [M+H]⁺ calcd for C$_{30}$H$_{30}$ClN$_2$O$_4$: 518.0. Found: 517.2, 519.2.

EXAMPLE 19

2-(5-(Biphenyl-4-yl)-2,7-dimethylquinolin-6-yl)-2-tert-butoxyacetic acid (19)

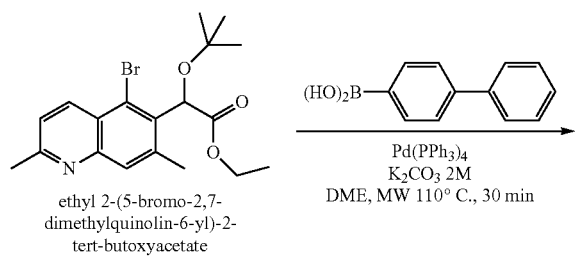

ethyl 2-(5-bromo-2,7-dimethylquinolin-6-yl)-2-tert-butoxyacetate

Pd(PPh$_3$)$_4$
K$_2$CO$_3$ 2M
DME, MW 110° C., 30 min

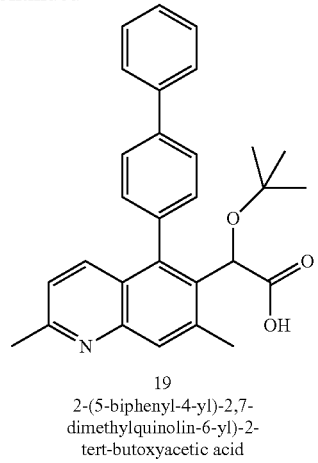

19
2-(5-biphenyl-4-yl)-2,7-dimethylquinolin-6-yl)-2-tert-butoxyacetic acid

Preparation of ethyl 2-(5-(biphenyl-4-yl)-2,7-dimethylquinolin-6-yl)-2-tert-butoxyacetate: Ethyl 2-(5-(biphenyl-4-yl)-2,7-dimethylquinolin-6-yl)-2-tert-butoxyacetate was prepared following the procedure used to prepare compound (S)-ethyl 2-tert-butoxy-2-(5-(4-chlorophenyl)-2,7-dimethylquinolin-6-yl)acetate of Example 14, except that biphenyl-4-ylboronic acid was used instead of 4-chlorophenylboronic acid. LCMS-ESI⁺ (m/z): 468.3 (M+H)⁺.

Preparation of 2-(5-(biphenyl-4-yl)-2,7-dimethylquinolin-6-yl)-2-tert-butoxyacetic acid (19): 2-(5-(Biphenyl-4-yl)-2,7-dimethylquinolin-6-yl)-2-tert-butoxyacetic acid was prepared following the procedure used to prepare compound (S)-2-tert-butoxy-2-(5-(4-chlorophenyl)-7-methyl-2-((methyl(phenyl)amino) methyl)quinolin-6-yl)acetic acid of Example 14, except that ethyl 2-(5-(biphenyl-4-yl)-2,7-dimethylquinolin-6-yl)-2-tert-butoxyacetate was used instead of (S)-ethyl 2-tert-butoxy-2-(5-(4-chlorophenyl)-7-methyl-2-(methyl(phenyl)amino)methyl)quinolin-6-yl)acetate. $^1$H-NMR 300 MHz, (CD$_3$OD) 8.40 (d, 1H), 7.96 (s, 1H), 7.95-7.90 (m, 2H), 7.70-7.60 (m, 4H), 7.55-7.40 (m, 4H), 5.39 (s, 1H), 2.96 (s, 3H), 2.80 (s, 3H), 0.98 (s, 9H); LCMS-ESI⁺ (m/z): [M+H]⁺ calcd for C$_{29}$H$_{30}$NO$_3$: 440.6. Found: 440.2.

EXAMPLE 20

(S)-2-tert-butoxy-2-((R)-5-(2,3-dihydropyrano[4,3,2-de]quinolin-7-yl)-2-((dimethylamino)methyl)-7-methylquinolin-6-yl)acetic acid (20)

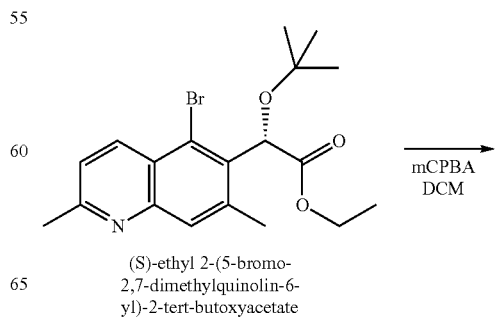

ethyl 2-(5-(biphenyl-4-yl)-2,7-dimethylquinolin-6-yl)-2-tert-butoxyacetate

2N NaOH
THF/MeOH (S)-ethyl 2-(5-bromo-2,7-dimethylquinolin-6-yl)-2-tert-butoxyacetate mCPBA
DCM

177

-continued

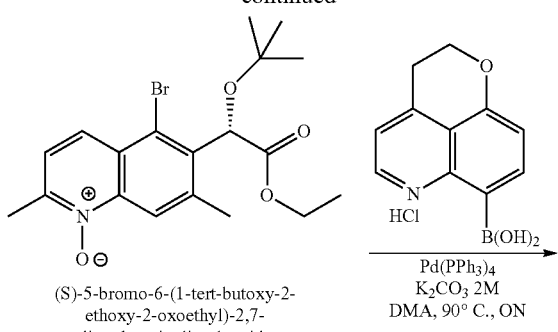

(S)-5-bromo-6-(1-tert-butoxy-2-
ethoxy-2-oxoethyl)-2,7-
dimethyquinoline 1-oxide

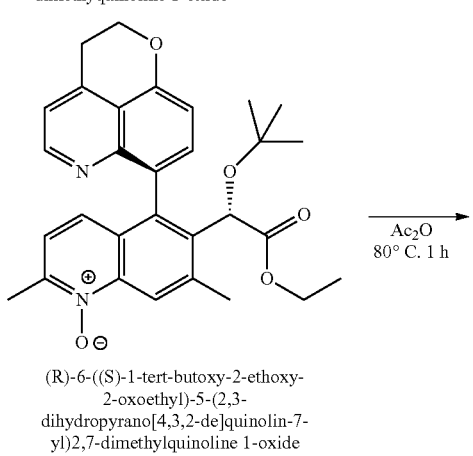

(R)-6-((S)-1-tert-butoxy-2-ethoxy-
2-oxoethyl)-5-(2,3-
dihydropyrano[4,3,2-de]quinolin-7-
yl)2,7-dimethylquinoline 1-oxide

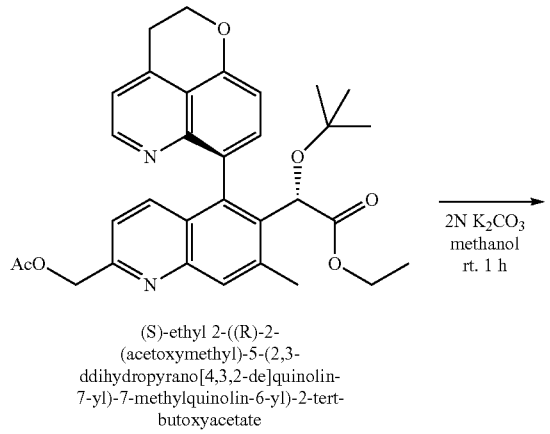

(S)-ethyl 2-((R)-2-
(acetoxymethyl)-5-(2,3-
ddihydropyrano[4,3,2-de]quinolin-
7-yl)-7-methylquinolin-6-yl)-2-tert-
butoxyacetate

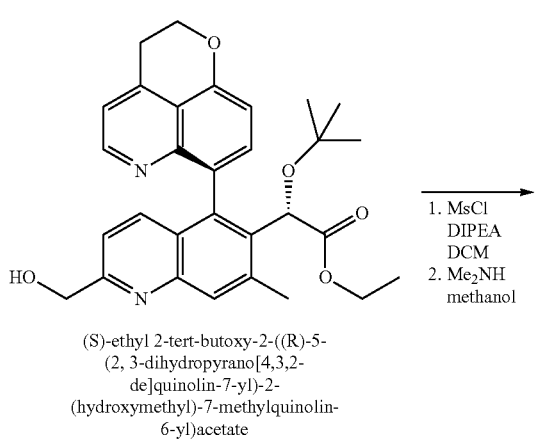

(S)-ethyl 2-tert-butoxy-2-((R)-5-
(2, 3-dihydropyrano[4,3,2-
de]quinolin-7-yl)-2-
(hydroxymethyl)-7-methylquinolin-
6-yl)acetate

178

-continued

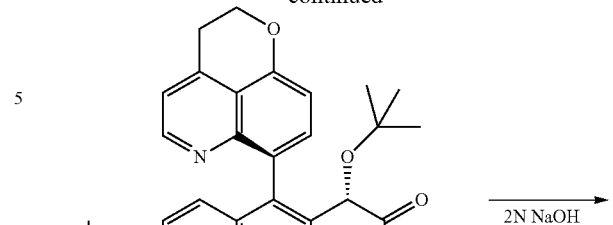

(S)-ethyl 2-tert-butoxy-2-((R)-5-(2,3-
dihydropyrano[4,3,2-de]quinolin-7-
yl)-2-((dimethylamino)methyl)-7-
methylquinolin-6-yl)acetate

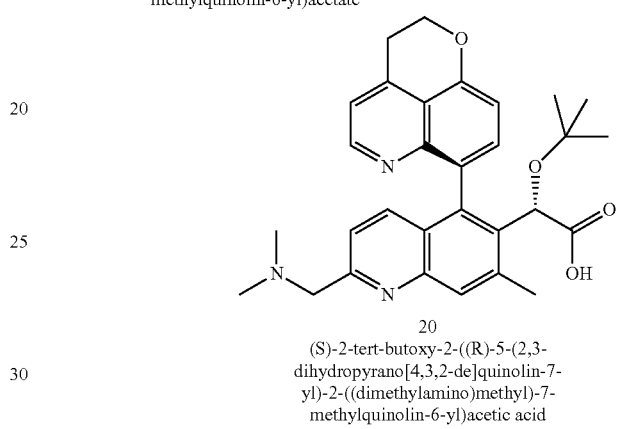

20
(S)-2-tert-butoxy-2-((R)-5-(2,3-
dihydropyrano[4,3,2-de]quinolin-7-
yl)-2-((dimethylamino)methyl)-7-
methylquinolin-6-yl)acetic acid Preparation of (S)-5-bromo-6-(1-tert-butoxy-2-ethoxy-2-oxoethyl)-2,7-dimethylquinoline 1-oxide: To a stirred solution of (S)-ethyl 2-(5-bromo-2,7-dimethylquinolin-6-yl)-2-tert-butoxyacetate (5H) (248 mg, 0.63 mmol) in dichloromethane (8 mL) was added a solution of mCPBA (283 mg, 77%, 1.26 mmol) in DCM (5 mL) at 0° C. The mixture was stirred at 0° C. for 1 hour before quenched with NaHCO$_3$ solution. The mixture was extracted with DCM (30 mL), washed with NaHCO$_3$ solution, water and brine, dried over Na$_2$SO$_4$, filtered and concentrated in vacuo. The obtained residue was purified by flash chromatography to provide the desired product (212 mg, 82%). LCMS-ESI$^+$ (m/z): 410.2, 412.2 (M+H)$^+$.

Preparation (R)-6-((S)-1-tert-butoxy-2-ethoxy-2-oxoethyl)-5-(2,3-dihydropyrano[4,3,2-de]quinolin-7-yl)-2,7-dimethylquinoline 1-oxide: Pd(PPh$_3$)$_4$ (36 mg, 0.03 mmol) was added to a mixture (S)-5-bromo-6-(1-tert-butoxy-2-ethoxy-2-oxoethyl)-2,7-dimethylquinoline 1-oxide (86 mg, 0.21 mmol), 2,3-dihydropyrano[4,3,2-de]quinolin-7-ylboronic acid hydrochloride (105 mg, 0.42 mmol), K$_2$CO$_3$ (0.47 mL 2 M in water, 0.95 mmol) in N,N-dimethylacetamide (3 mL). The reaction mixture was flushed with nitrogen, heated at 90° C. for 16 hours. The mixture was dissolved in ethyl acetate (50 mL), washed with NaHCO$_3$ solution, water and brine, dried over Na$_2$SO$_4$, filtered and concentrated in vacuo. The obtained residue was purified by HPLC to provide the desired product (87 mg, 69%). LCMS-ESI$^+$ (m/z): 501.2 (M+H)$^+$.

Preparation of (S)-ethyl 2-((R)-2-(acetoxymethyl)-5-(2,3-dihydropyrano[4,3,2-de]quinolin-7-yl)-7-methylquinolin-6-yl)-2-tert-butoxyacetate: (S)-Ethyl 2-((R)-2-(acetoxymethyl)-5-(2,3-dihydropyrano[4,3,2-de]quinolin-7-yl)-7-methylquinolin-6-yl)-2-tert-butoxyacetate was prepared following the procedure used to prepare compound (S)-ethyl 2-(2-(acetoxymethyl)-5-(4-chlorophenyl)-7-methylquinolin-6-yl)-2-tert-butoxyacetate of Example 16, except that (R)-6-((S)-1-tert-butoxy-2-ethoxy-2-oxoethyl)-5-(2,3-dihydropyrano[4,3,2-de]quinolin-7-yl)-2,7-dimethylquinoline 1-oxide was used instead of 2-ethoxy-2-oxoethyl)-5-(4-chlorophenyl)-2,7-dimethylquinoline 1-oxide. LCMS-ESI+ (m/z): 543.1 (M+H)+.

Preparation of (S)-ethyl 2-tert-butoxy-2-((R)-5-(2,3-dihydropyrano[4,3,2-de]quinolin-7-yl)-2-(hydroxymethyl)-7-methylquinolin-6-yl)acetate: (S)-Ethyl 2-tert-butoxy-2-((R)-5-(2,3-dihydropyrano[4,3,2-de]quinolin-7-yl)-2-(hydroxymethyl)-7-methylquinolin-6-yl)acetate was prepared following the procedure used to prepare compound (S)-ethyl 2-tert-butoxy-2-(5-(4-chlorophenyl)-2-(hydroxymethyl)-7-methylquinolin-6-yl)acetate of Example 16, except that (S)-ethyl 2-((R)-2-(acetoxymethyl)-5-(2,3-dihydropyrano[4,3,2-de]quinolin-7-yl)-7-methylquinolin-6-yl)-2-tert-butoxyacetate was used instead of (S)-ethyl 2-(2-(acetoxymethyl)-5-(4-chlorophenyl)-7-methylquinolin-6-yl)-2-tert-butoxyacetate. LCMS-ESI+ (m/z): 501.2 (M+H)+.

Preparation of (S)-ethyl 2-tert-butoxy-2-((R)-5-(2,3-dihydropyrano[4,3,2-de]quinolin-7-yl)-2-((dimethylamino)methyl)-7-methylquinolin-6-yl)acetate: To a stirred solution of (S)-ethyl 2-tert-butoxy-2-((R)-5-(2,3-dihydropyrano[4,3,2-de]quinolin-7-yl)-2-(hydroxymethyl)-7-methylquinolin-6-yl)acetate (15 mg, 0.03 mmol) and DIPEA (0.013 mL, 0.075 mmol) in dichloromethane (1 mL) was added methanesulfonyl chloride (6.8 mg, 0.06 mmol) at 0° C. The mixture was stirred at room temperature for 3 hours before the addition of N,N-dimethylamine in methanol (0.5 mL 2 M, excess). The mixture was stirred at room temperature for another 1 h, then diluted in ethyl acetate (30 mL), washed with NaHCO$_3$ solution, water and brine, dried over Na$_2$SO$_4$, filtered and concentrated in vacuo. The obtained residue was purified by HPLC to provide the desired product as TFA salt (18 mg, 97%). LCMS-ESI+ (m/z): 528.3 (M+H)+.

Preparation of (S)-2-tert-butoxy-2-((R)-5-(2,3-dihydropyrano[4,3,2-de]quinolin-7-yl)-2-((dimethylamino)methyl)-7-methylquinolin-6-yl)acetic acid (20): (S)-2-tert-Butoxy-2-((R)-5-(2,3-dihydropyrano[4,3,2-de]quinolin-7-yl)-2-((dimethylamino)methyl)-7-methylquinolin-6-yl)acetic acid was prepared following the procedure used to prepare compound (S)-2-tert-butoxy-2-(5-(4-chlorophenyl)-7-methyl-2-((methyl(phenyl)amino) methyl)quinolin-6-yl)acetic acid of Example 14, except that (S)-ethyl 2-tert-butoxy-2-((R)-5-(2,3-dihydropyrano[4,3,2-de]quinolin-7-yl)-2-((dimethylamino)methyl)-7-methylquinolin-6-yl)acetate was used instead of (S)-ethyl 2-tert-butoxy-2-(5-(4-chlorophenyl)-7-methyl-2-((methyl(phenyl)amino)methyl) quinolin-6-yl)acetate. $^1$H-NMR 300 MHz, (CD$_3$OD) δ 8.70 (d, 1H), 8.20 (s, 1H), 7.83-7.75 (m, 2H), 7.51 (d, 1H), 7.42 (d, 1H), 7.29 (d, 1H), 5.26 (s, 1H), 5.75-5.68 (m, 2H), 4.66 (s, 2H), 3.64 (t, 2H), 3.05 (s, 6H), 2.85 (s, 3H), 0.93 (s, 9H); LCMS-ESI+ (m/z): [M+14]+ calcd for C$_{30}$H$_{34}$N$_3$O$_4$: 500.6. Found: 500.2.

EXAMPLE 21

(S)-2-tert-Butoxy-2-((R)-5-(2,3-dihydropyrano[4,3,2-de]quinolin-7-yl)-2-(hydroxymethyl)-7-methylquinolin-6-yl)acetic acid (21)

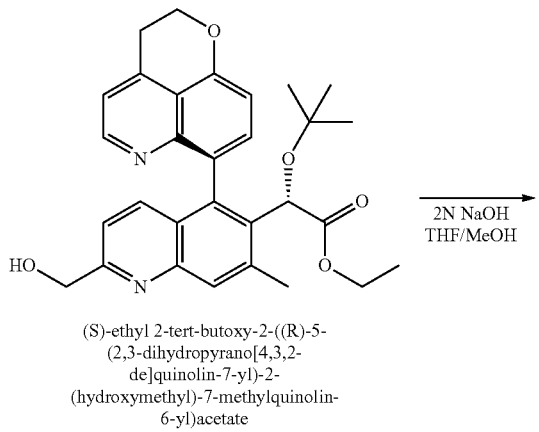

(S)-ethyl 2-tert-butoxy-2-((R)-5-(2,3-dihydropyrano[4,3,2-de]quinolin-7-yl)-2-(hydroxymethyl)-7-methylquinolin-6-yl)acetate 2N NaOH
THF/MeOH

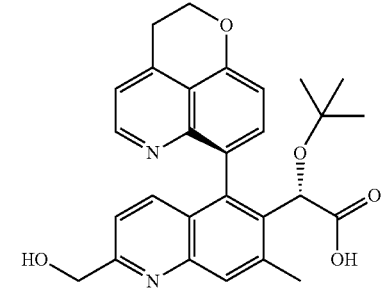

21

(S)-2-tert-butoxy-2-((R)-5-(2,3-dihydropyrano[4,3,2-de]quinolin-7-yl)-2-(hydroxymethyl)-7-methylquinolin-6-yl)acetic acid Preparation (S)-2-tert-butoxy-2-((R)-5-(2,3-dihydropyrano[4,3,2-de]quinolin-7-yl)-2-(hydroxymethyl)-7-methylquinolin-6-yl)acetic acid (21): To a stirred solution of (S)-ethyl 2-tert-butoxy-2-((R)-5-(2,3-dihydropyrano[4,3,2-de]quinolin-7-yl)-2-(hydroxymethyl)-7-methylquinolin-6-yl)acetate (compound of Example 20) (10 mg, 0.02 mmol) in THF and methanol (2 mL/1 mL) was added 2 M NaOH solution (0.5 mL, excess). The mixture was stirred at 50° C. for 3 hours, diluted with water. The mixture was extracted with ethyl acetate. The organic layer was washed with brine, dried and concentrated in vacuo. The obtained residue was purified by prep-HPLC to provide the desired product as TFA salt (9.0 mg, 79%). $^1$H-NMR 300 MHz, (CD$_3$OD) δ 8.66 (d, 1H), 8.27 (s, 1H), 7.94 (d, 1H), 7.67 (d, 1H), 7.70-7.60 (m, 2H), 7.37 (d, 1H), 5.26 (s, 1H), 5.06 (s, 2H), 4.75-4.65 (m, 2H), 3.57 (t, 2H), 2.90 (s, 3H), 0.93 (s, 9H-1); LCMS-ESI⁺ (m/z): [M+H]⁺ calcd for C₂₈H₂₉N₂O₄: 473.5. Found: 473.1.

EXAMPLE 22

(R)-6-((S)-tert-butoxy(carboxy)methyl)-5-(2,3-dihydropyrano[4,3,2-de]quinolin-7-yl)-2,7-dimethylquinoline 1-oxide (22)

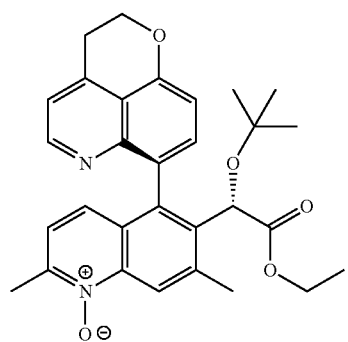

(R)6-((S)-1-tert-butoxy-2-ethoxy-2-oxoethyl)-5-(2,3-dihydropyrano[4,3,2-de]quinolin-7-yl)-2,7-dimethylquinoline 1-oxide

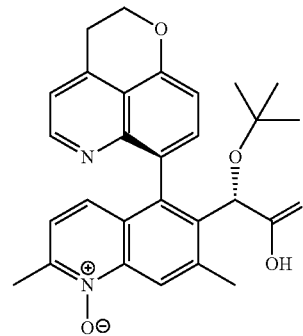

22

(R)6-((S)-tert-butoxy(carboxy)methyl)-5-(2,3-dihydropyrano[4,3,2-de]quinolin-7-yl)-2,7-dimethylquinoline 1-oxide (R)-6-((S)-tert-Butoxy(carboxy)methyl)-5-(2,3-dihydropyrano[4,3,2-de]quinolin-7-yl)-2,7-dimethylquinoline 1-oxide (22) was prepared following the procedure used to prepare compound (S)-2-tert-butoxy-2-((R)-5-(2,3-dihydropyrano[4,3,2-de]quinolin-7-yl)-2-(hydroxymethyl)-7-methylquinolin-6-yl)acetic acid of Example 21, except that (R)-6-((S)-1-tert-butoxy-2-ethoxy-2-oxoethyl)-5-(2,3-dihydropyrano[4,3,2-de]quinolin-7-yl)-2,7-dimethylquinoline 1-oxide was used instead of (S)-ethyl 2-tert-butoxy-2-((R)-5-(2,3-dihydropyrano[4,3,2-de]quinolin-7-yl)-2-(hydroxymethyl)-7-methylquinolin-6-yl)acetate. ¹H-NMR 300 MHz, (CD₃OD) δ 8.78-8.70 (m, 2H), 7.85 (d, 1H), 7.78 (d, Hi), 7.44 (d, 1H), 7.35 (d, 1H), 7.11 (d, 1H), 5.23 (s, 1H), 5.75-5.65 (m, 2H), 3.65 (t, 2H), 2.88 (s, 3H), 2.70 (s, 3H), 0.93 (s, 9H); LCMS-ESI⁺ (m/z): [M+H]⁺ calcd for C₂₈H₂₉N₂O₅: 473.5. Found: 473.2.

EXAMPLE 23

(S)-2-tert-Butoxy-2-((S)-5-(2,3-dihydropyrano[4,3,2-de]quinolin-7-yl)-2,7-dimethylquinolin-6-yl)acetic acid (23)

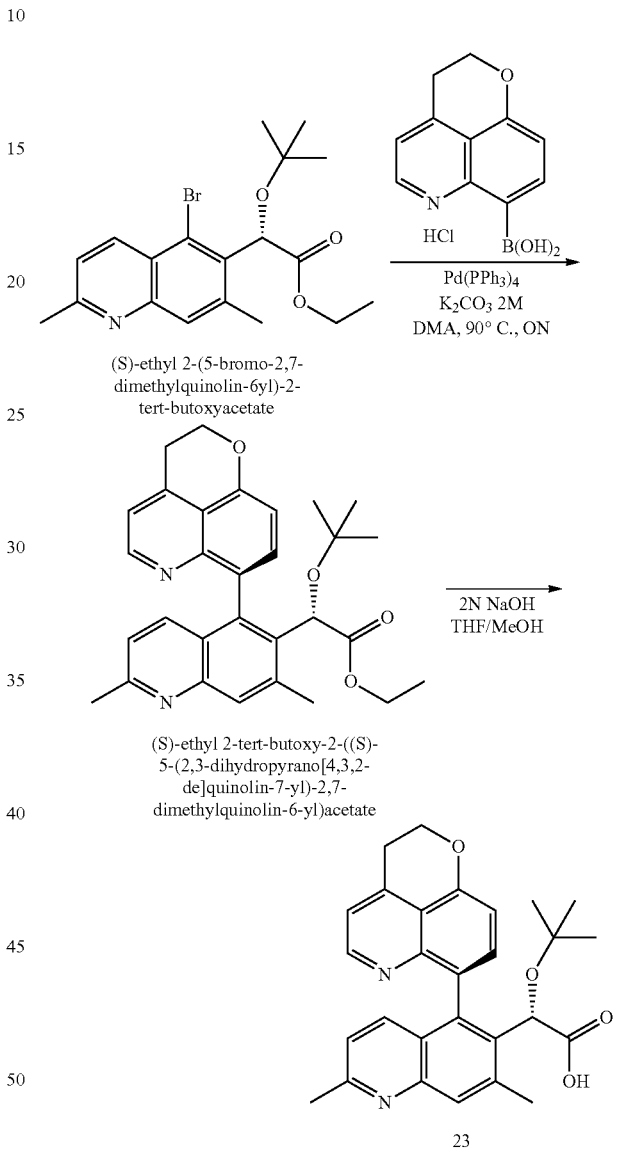

Preparation of (S)-ethyl 2-tert-butoxy-2-((S)-5-(2,3-dihydropyrano[4,3,2-de]quinolin-7-yl)-2,7-dimethylquinolin-6-yl)acetate: Pd(PPh₃)₄ (103 mg, 0.09 mmol) was added to a mixture (S)-ethyl 2-(5-bromo-2,7-dimethylquinolin-6-yl)-2-tert-butoxyacetate (5H) (350 mg, 0.89 mmol), 2,3-dihydropyrano[4,3,2-de]quinolin-7-ylboronic acid hydrochloride (447 mg, 1.78 mmol), K₂CO₃ (2.0 mL 2 M in water, 4.0 mmol) in N,N-dimethylacetamide (10 mL). The reaction mixture was flushed with nitrogen, heated at 90° C. for 16 h. The mixture was dissolved in ethyl acetate (150 mL), washed with NaHCO$_3$ solution, water and brine, dried over Na$_2$SO$_4$, filtered and concentrated in vacuo. The obtained residue was purified by HPLC to provide the desired product (407 mg, 43%). LCMS-ESI$^+$ (m/z): 485.2 (M+H)$^+$.

Preparation of (S)-2-tert-butoxy-2-((S)-5-(2,3-dihydropyrano[4,3,2-de]quinolin-7-yl)-2,7-dimethylquinolin-6-yl)acetic acid (23): (S)-2-tert-Butoxy-2-((S)-5-(2,3-dihydropyrano[4,3,2-de]quinolin-7-yl)-2,7-dimethylquinolin-6-yl)acetic acid was prepared following the procedure used to prepare compound (S)-2-tert-butoxy-2-((R)-5-(2,3-dihydropyrano[4,3,2-de]quinolin-7-yl)-2-(hydroxymethyl)-7-methylquinolin-6-yl)acetic acid of Example 21, except (S)-ethyl 2-tert-butoxy-2-((S)-5-(2,3-dihydropyrano[4,3,2-de] quinolin-7-yl)-2,7-dimethylquinolin-6-yl)acetate was used instead of (S)-ethyl 2-tert-butoxy-2-((R)-5-(2,3-dihydropyrano[4,3,2-de] quinolin-7-yl)-2-(hydroxymethyl)-7-methylquinolin-6-yl)acetate. $^1$H-NMR 300 MHz, (CD$_3$OD) δ 8.51 (d, 2H), 8.02-7.95 (m, 3H), 7.54 (d, 1H), 7.36 (d, 1H), 7.28 (d, 1H), 5.28 (s, 1H), 4.60 (t, 2H), 3.43 (t, 2H), 2.93 (s, 3H), 2.83 (s, 3H), 0.72 (s, 9H); LCMS-ESI$^+$ (m/z): [M+H]$^+$ calcd for C$_{28}$H$_{28}$N$_2$O$_4$: 457.5. Found: 457.1.

EXAMPLE 24

(S)-6-(tert-Butoxy(carboxy)methyl)-5-(4-chlorophenyl)-7-methylquinoline-2-carboxylic acid (24)

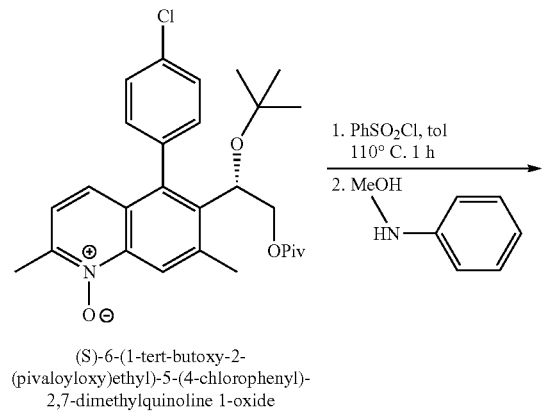

(S)-6-(1-tert-butoxy-2-(pivaloyloxy)ethyl)-5-(4-chlorophenyl)-2,7-dimethylquinoline 1-oxide

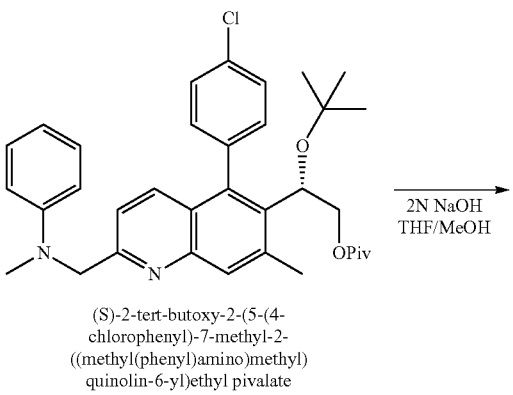

(S)-2-tert-butoxy-2-(5-(4-chlorophenyl)-7-methyl-2-((methyl(phenyl)amino)methyl)quinolin-6-yl)ethyl pivalate

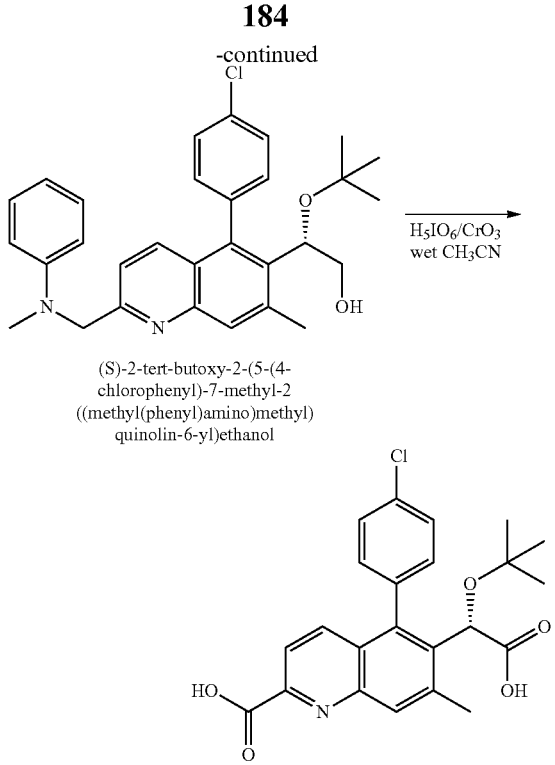

Preparation of (S)-2-tert-butoxy-2-(5-(4-chlorophenyl)-7-methyl-2-((methyl(phenyl)amino)methyl)quinolin-6-yl)ethyl pivalate: (S)-2-tert-Butoxy-2-(5-(4-chlorophenyl)-7-methyl-2-((methyl(phenyl)amino)methyl)quinolin-6-yl)ethyl pivalate was prepared following the procedure used to prepare compound (S)-ethyl 2-tert-butoxy-2-(5-(4-chlorophenyl)-7-methyl-2-((methyl(phenyl)amino)methyl)quinolin-6-yl)acetate of Example 14, except that (S)-6-(1-tert-butoxy-2-(pivaloyloxy)ethyl)-5-(4-chlorophenyl)-2,7-dimethylquinoline 1-oxide was used instead of (S)-6-(1-tert-butoxy-2-ethoxy-2-oxoethyl)-5-(4-chlorophenyl)-2,7-dimethylquinoline 1-oxide. LCMS-ESI$^+$ (m/z): 573.3, 575.4 (M+H)$^+$.

Preparation of (S)-2-tert-butoxy-2-(5-(4-chlorophenyl)-7-methyl-2-((methyl(phenyl)amino)methyl)quinolin-6-yl)ethanol: (S)-2-tert-Butoxy-2-(5-(4-chlorophenyl)-7-methyl-2-((methyl(phenyl)amino)methyl)quinolin-6-yl)ethanol was prepared following the procedure used to prepare compound S)-2-tert-butoxy-2-((R)-5-(2,3-dihydropyrano[4,3,2-de]quinolin-7-yl)-2-(hydroxymethyl)-7-methylquinolin-6-yl)acetic acid of Example 21, except that (S)-2-tert-butoxy-2-(5-(4-chlorophenyl)-7-methyl-2-((methyl(phenyl)amino)methyl)quinolin-6-yl)ethyl pivalate was used instead of (S)-ethyl 2-tert-butoxy-2-((R)-5-(2,3-dihydropyrano[4,3,2-de]quinolin-7-yl)-2-(hydroxymethyl)-7-methylquinolin-6-yl)acetate. LCMS-ESI$^+$ (m/z): 489.3, 491.3 (M+H)$^+$.

Preparation of (S)-6-(tert-butoxy(carboxy)methyl)-5-(4-chlorophenyl)-7-methylquinoline-2-carboxylic acid (24): (S)-6-(tert-Butoxy(carboxy)methyl)-5-(4-chlorophenyl)-7-methylquinoline-2-carboxylic acid was prepared following the procedure used to prepare compound (S)-2-tert-butoxy-2-(5-(4-chlorophenyl)-2-(methoxycarbonyl)-7-methylquinolin-6-yl)acetic acid of Example 12, except that (S)-2-tert-butoxy-2-(5-(4-chlorophenyl)-7-methyl-2-((methyl(phenyl)amino)methyl)quinolin-6-yl)ethanol was used instead of (S)-2-tert-butoxy-2-(5-(4-chlorophenyl)-2-(methoxymethyl)-7-methylquinolin-6-yl)ethanol. $^1$H-NMR 300 MHz, (CD$_3$OD). δ 8.15-8.05 (m, 2H), 7.93 (d, 1H), 7.70-7.60 (m, 3H), 7.40-7.35 (m, 1H), 5.24 (s, 1H), 2.70 (s, 3H), 0.99 (s, 9H); LCMS-ESI$^+$ (m/z): [M+H]$^+$ calcd for C$_{23}$H$_{23}$ClNO$_5$: 428.9. Found: 428.1, 430.1.

EXAMPLE 25

(S)-2-tert-butoxy-2-(5-cyclohexenyl-2-((dimethylamino)methyl)-7-methylquinolin-6-yl)acetic acid (25)

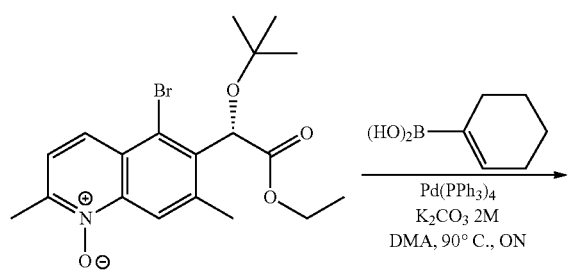

(S)-5-bromo-6-(1-tert-butoxy-2-ethoxy-2-oxoethyl)-2,7-dimethylquinoline 1-oxide

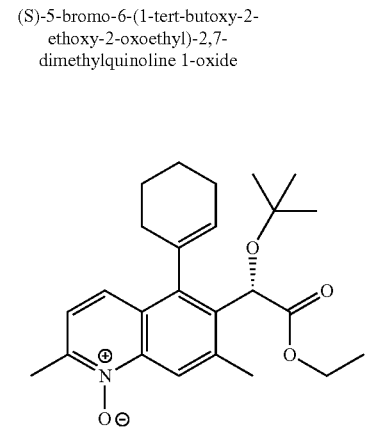

(S)-6-(1-tert-butoxy-2-ethoxy-2-oxoethyl)-5-cyclohexenyl-2,7-dimethylquinoline 1-oxide

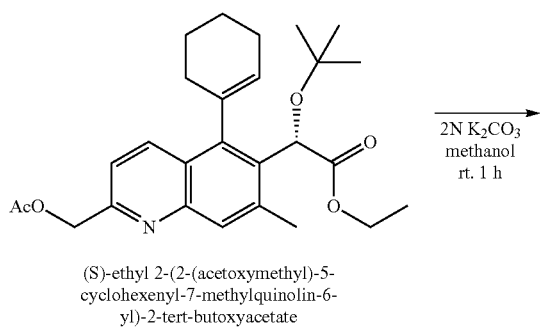

(S)-ethyl 2-(2-(acetoxymethyl)-5-cyclohexenyl-7-methylquinolin-6-yl)-2-tert-butoxyacetate

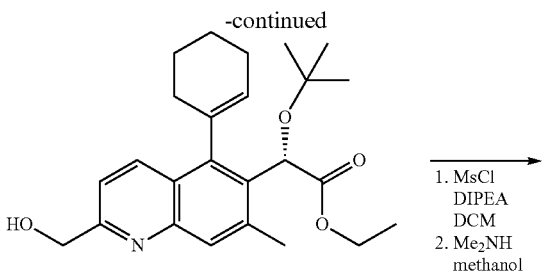

(S)-ethyl 2-tert-butoxy-2-(5-cyclohexenyl-2-(hydroxymethyl)-7-methylquinolin-6-yl)acetate

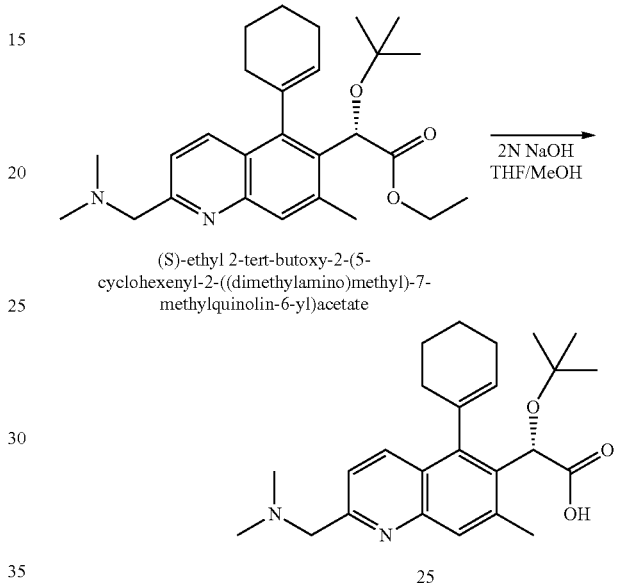

(S)-ethyl 2-tert-butoxy-2-(5-cyclohexenyl-2-((dimethylamino)methyl)-7-methylquinolin-6-yl)acetate (S)-2-tert-butoxy-2-(5-cyclohexenyl-2-((dimethylamino)methyl)-7-methylquinolin-6-yl)acetic acid Preparation of (S)-6-(1-tert-butoxy-2-ethoxy-2-oxoethyl)-5-cyclohexenyl-2,7-dimethylquinoline 1-oxide: Pd(PPh$_3$)$_4$ (6 mg, 0.006 mmol) was added to a mixture (S)-5-bromo-6-(1-tert-butoxy-2-ethoxy-2-oxoethyl)-2,7-dimethylquinoline 1-oxide (compound of Example 20) (20 mg, 0.05 mmol), cyclohexenylboronic acid (12 mg, 0.1 mmol), K$_2$CO$_3$ (0.09 mL 2 M in water, 0.17 mmol) in 1,2-dimethoxyethane (1 mL). The reaction mixture was flushed with nitrogen, heated at 85° C. for overnight, and then the volatile component was removed in vacuo. The residue was dissolved in ethyl acetate (30 mL), washed with NaHCO$_3$ solution, water and brine, dried over Na$_2$SO$_4$, filtered and concentrated in vacuo. The obtained residue was purified by HPLC to provide the desired product (17 mg, 68%). LCMS-ESI$^+$ (m/z): 412.3 (M+H)$^+$.

Preparation of (S)-ethyl 2-(2-(acetoxymethyl)-5-cyclohexenyl-7-methylquinolin-6-yl)-2-tert-butoxyacetate: (S)-Ethyl 2-(2-(acetoxymethyl)-5-cyclohexenyl-7-methylquinolin-6-yl)-2-tert-butoxyacetate was prepared following the procedure used to prepare compound (S)-ethyl 2-(2-(acetoxymethyl)-5-(4-chlorophenyl)-7-methylquinolin-6-yl)-2-tert-butoxyacetate of Example 16, except that (S)-6-(1-tert-butoxy-2-ethoxy-2-oxoethyl)-5-cyclohexenyl-2,7-dimethylquinoline 1-oxide was used instead of 2-ethoxy-2-oxoethyl)-5-(4-chlorophenyl)-2,7-dimethylquinoline 1-oxide. LCMS-ESI$^+$ (m/z): 454.3 (M+H)$^+$.

Preparation of (S)-ethyl 2-tert-butoxy-2-(5-cyclohexenyl-2-(hydroxymethyl)-7-methylquinolin-6-yl)acetate: (S)-

Ethyl 2-tert-butoxy-2-(5-cyclohexenyl-2-(hydroxymethyl)-7-methylquinolin-6-yl)acetate was prepared following the procedure used to prepare compound (S)-ethyl 2-tert-butoxy-2-(5-(4-chlorophenyl)-2-(hydroxymethyl)-7-methylquinolin-6-yl)acetate of Example 16, except that (S)-ethyl 2-(2-(acetoxymethyl)-5-cyclohexenyl-7-methylquinolin-6-yl)-2-tert-butoxyacetate was used instead of (S)-ethyl 2-(2-(acetoxymethyl)-5-(4-chlorophenyl)-7-methylquinolin-6-yl)-2-tert-butoxyacetate. LCMS-ESI$^+$ (m/z): 412.3 (M+H)$^+$.

Preparation of (S)-ethyl 2-tert-butoxy-2-(5-cyclohexenyl-2-((dimethylamino)methyl)-7-methylquinolin-6-yl)acetate: (S)-Ethyl 2-tert-Butoxy-2-(5-cyclohexenyl-2-((dimethylamino)methyl)-7-methylquinolin-6-yl)acetate was prepared following the procedure used to prepare compound (S)-ethyl 2-tert-butoxy-2-((R)-5-(2,3-dihydropyrano[4,3,2-de]quinolin-7-yl)-2-((dimethylamino)methyl)-7-methylquinolin-6-yl)acetate of Example 20 except that (S)-ethyl 2-tert-butoxy-2-(5-cyclohexenyl-2-(hydroxymethyl)-7-methylquinolin-6-yl)acetate was used instead of (S)-ethyl 2-tert-butoxy-2-((R)-5-(2,3-dihydropyrano[4,3,2-de]quinolin-7-yl)-2-(hydroxymethyl)-7-methylquinolin-6-yl)acetate. LCMS-ESI$^+$ (m/z): 439.4 (M+H)$^+$.

Preparation of (S)-2-tert-butoxy-2-(5-cyclohexenyl-2-((dimethylamino)methyl)-7-methylquinolin-6-yl)acetic acid (25): (S)-2-tert-Butoxy-2-(5-cyclohexenyl-2-((dimethylamino)methyl)-7-methylquinolin-6-yl)acetic acid was prepared following the procedure used to prepare compound (S)-2-tert-butoxy-2-(5-(4-chlorophenyl)-7-methyl-2-((methyl(phenyl)amino) methyl)quinolin-6-yl)acetic acid of Example 14, except that (S)-ethyl 2-tert-butoxy-2-(5-cyclohexenyl-2-((dimethylamino) methyl)-7-methylquinolin-6-yl)acetate was used instead of (S)-ethyl 2-tert-butoxy-2-(5-(4-chlorophenyl)-7-methyl-2-((methyl(phenyl)amino) methyl)quinolin-6-yl)acetate. $^1$H-NMR 300 MHz, (CD$_3$OD) 8.40-8.30 (m, 1H), 7.85-7.78 (m, 1H), 7.42 (d, 1H), 6.04, 5.70 (br, br, 1H), 5.80, 5.64 (s, s, 1H), 4.65 (s, 2H), 3.04 (s, 6H), 2.68-2.56 (m, 4H), 2.40-1.80 (m, 6H), 1.30-1.20 (m, 9H); LCMS-ESI$^+$ (m/z): [M-1-11]$^+$ calcd for C$_{25}$H$_{34}$N$_2$O$_3$: 411.6. Found: 411.3.

EXAMPLE 26

(S)-2-tert-butoxy-2-(5-(4-chlorophenyl)-2-ethyl-7-methylquinolin-6-yl)acetic acid (26)

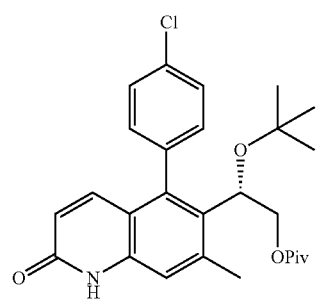

(S)-2-tert-butoxy-2-(5-(4-chlorophenyl)-7-methyl-2-oxo-1,2-dihydroquinolin-6-yl)ethyl pivalate Tf$_2$O
DCM/pyridine

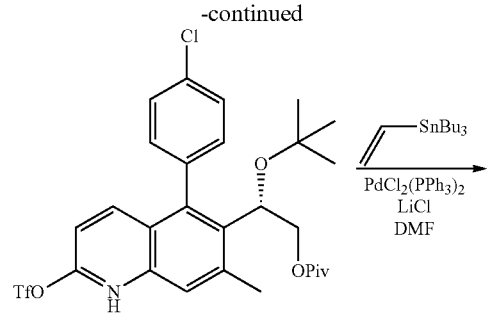

(S)-2-tert-butoxy-2-(5-(4-chlorophenyl)-7-methyl-2-(trifluoromethylsulfonyloxy)quinolin-6-yl)ethyl pivalate

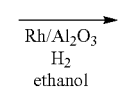—SnBu$_3$
PdCl$_2$(PPh$_3$)$_2$
LiCl
DMF

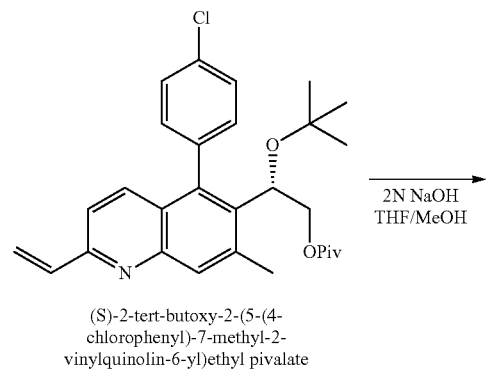

(S)-2-tert-butoxy-2-(5-(4-chlorophenyl)-7-methyl-2-vinylquinolin-6-yl)ethyl pivalate 2N NaOH
THF/MeOH

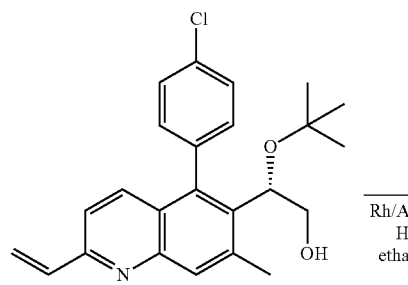

(S)-2-tert-butoxy-2-(5-(4-chlorophenyl)-7-methyl-2-vinylquinolin-6-yl)ethanol

Rh/Al$_2$O$_3$
H$_2$
ethanol

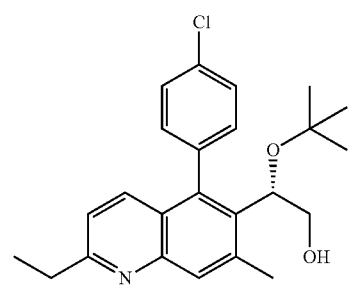

(S)-2-tert-butoxy-2-(5-(4-chlorophenyl)-2-ethyl-7-methylquinolin-6-yl)ethanol

H$_5$IO$_6$/CrO$_3$
wet CH$_3$CN

189
-continued

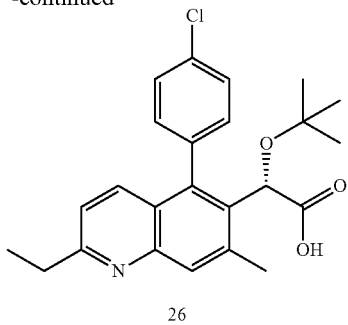

26

(S)-2-tert-butoxy-2-(5-(4-chlorophenyl)-2-ethyl-7-methylquinolin-6-yl)acetic acid Preparation of (S)-2-tert-butoxy-2-(5-(4-chlorophenyl)-7-methyl-2-(trifluoromethylsulfonyloxy)quinolin-6-yl)ethyl pivalate: To a stirred solution of (S)-2-tert-butoxy-2-(5-(4-chlorophenyl)-7-methyl-2-oxo-1,2-dihydroquinolin-6-yl)ethyl pivalate (8J) (200 mg, 0.43 mmol) in dichloromethane (10 mL) and pyridine (0.35 mL) was added Tf$_2$O (0.1 mL, 0.87 mmol) at −78° C. The temperature was slowly raised to 0° C. The mixture was stirred at 0° C. for 2 hours, quenched with slowly addition of NaHCO$_3$ solution. The mixture was extracted with ethyl acetate. The organic layer was washed with brine, dried and concentrated to provide a brown colored solid. The obtained residue was purified by flash chromatography to provide the desired product (200 mg, 77%). LCMS-ESI$^+$ (m/z): 602.0, 604.0 (M+H)$^+$.

Preparation of (S)-2-tert-butoxy-2-(5-(4-chlorophenyl)-7-methyl-2-vinylquinolin-6-yl)ethyl pivalate: PdCl$_2$(PPh$_3$)$_2$ (3 mg, 0.004 mmol) was added to (S)-2-tert-butoxy-2-(5-(4-chlorophenyl)-7-methyl-2-(trifluoromethylsulfonyloxy)quinolin-6-yl)ethyl pivalate (25 mg, 0.04 mmol), tributylvinyl-stannane (0.024 mL, 0.08 mmol) and lithium chloride (7 mg, 0.16 mmol) in DMF (2 mL). The reaction mixture was flushed with nitrogen, heated at 90° C. for 16 hours, and then the volatile component was removed in vacuo. The residue was dissolved in ethyl acetate (100 mL), washed with NaHCO$_3$ solution, water and brine, dried over Na$_2$SO$_4$, filtered and concentrated in vacuo. The obtained residue was purified by HPLC to provide the desired product as TFA salt (14 mg, 59%). LCMS-ESI$^+$ (m/z): 480.3, 482.3 (M+H)$^+$.

Preparation of (S)-2-tert-butoxy-2-(5-(4-chlorophenyl)-7-methyl-2-vinylquinolin-6-yl)ethanol: To a stirred solution of (S)-2-tert-butoxy-2-(5-(4-chlorophenyl)-7-methyl-2-vinylquinolin-6-yl)ethyl pivalate TFA salt (14 mg, 0.024 mmol) in THF and methanol (3 mL/1 mL) was added 1 M NaOH solution (0.5 mL, excess). The mixture was stirred at 0° C. for 6 hours and diluted with water. The resulting mixture was extracted with ethyl acetate. The organic layer was washed with brine, dried and concentrated in vacuo. The obtained residue was used in the next reaction without purification. LCMS-ESI$^+$ (m/z): 396.2, 398.2 (M+H)$^+$.

Preparation of (S)-2-tert-butoxy-2-(5-(4-chlorophenyl)-2-ethyl-7-methylquinolin-6-yl)ethanol: A balloon filled with hydrogen was connected to a degassed mixture of (S)-2-tert-butoxy-2-(5-(4-chlorophenyl)-7-methyl-2-vinylquinolin-6-yl)ethanol (9 mg, 0.024 mmol) and Rhodium on activated alumina (2 mg, cat.) in ethanol. The mixture was stirred at room temperature for 2 hours, filtered and concentrated to dry. The obtained residue was used on next step reaction without purification. LCMS-ESI$^+$ (m/z): 398.2, 400.2 (M+H)$^+$.

Preparation of (S)-2-tert-butoxy-2-(5-(4-chlorophenyl)-2-ethyl-7-methylquinolin-6-yl)acetic acid (26): (S)-2-tert-Butoxy-2-(5-(4-chlorophenyl)-2-ethyl-7-methylquinolin-6-yl)acetic acid was prepared following the procedure used to prepare compound tert-butoxy-[7-chloro-5-(4-chloro-phenyl)-2-methyl-quinolin-6-yl]-acetic acid of Example 1, except that (S)-2-tert-butoxy-2-(5-(4-chlorophenyl)-2-ethyl-7-methylquinolin-6-yl)ethanol was used instead 2-tert-butoxy-2-[7-chloro-5-(4-chloro-phenyl)-2-methyl-quinolin-6-yl]ethanol. $^1$H-NMR 300 MHz, (CD$_3$OD) δ 8.31 (d, 1H), 7.98 (s, 1H), 7.76 (d, 1H), 7.70-7.60 (m, 3H), 7.42-7.35 (m, 1H), 5.25 (s, 1H), 3.21 (q, 2H), 2.78 (s, 3H), 1.48 (t, 3H), 0.98 (s, 9H); LCMS-ESI$^+$ (m/z): [M+H]$^+$ calcd for C$_{24}$H$_{27}$ClNO$_3$: 412.9. Found: 412.2, 414.2.

EXAMPLE 27

(S)-2-(2,5-bis(4-chlorophenyl)-7-methylquinolin-6-yl)-2-tert-butoxyacetic acid (27)

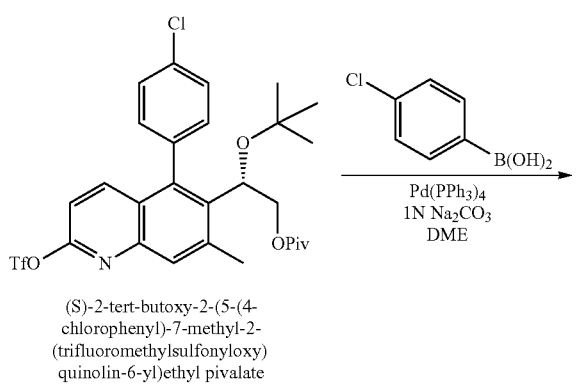

(S)-2-tert-butoxy-2-(5-(4-chlorophenyl)-7-methyl-2-(trifluoromethylsulfonyloxy)quinolin-6-yl)ethyl pivalate

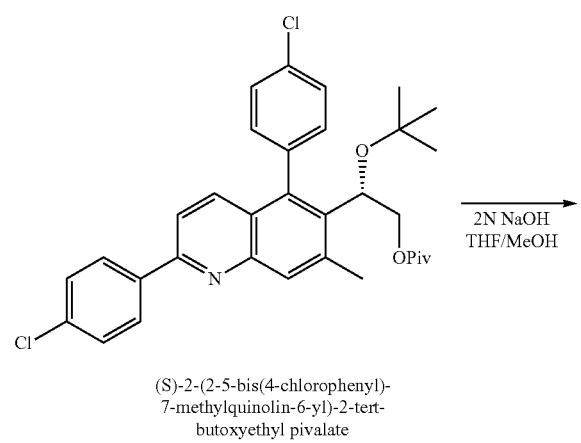

(S)-2-(2-5-bis(4-chlorophenyl)-7-methylquinolin-6-yl)-2-tert-butoxyethyl pivalate

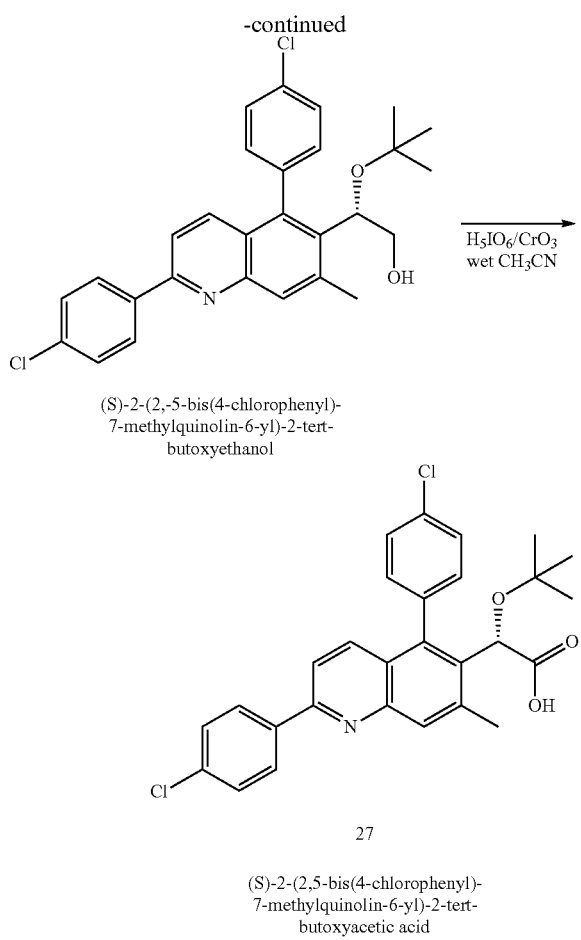

tic acid was prepared following the procedure used to prepare compound (S)-2-tert-butoxy-2-(5-(4-chlorophenyl)-2-ethyl-7-methylquinolin-6-yl)acetic acid (compound of Example 26), except that (S)-2-(2,5-bis(4-chlorophenyl)-7-methylquinolin-6-yl)-2-tert-butoxyethanol was used instead (S)-2-tert-butoxy-2-(5-(4-chlorophenyl)-2-ethyl-7-methylquinolin-6-yl)ethanol. $^1$H-NMR 300 MHz, (CD$_3$OD) δ 8.15-8.02 (m, 4H), 7.98 (d, 1H), 7.70-7.60 (m, 5H), 7.38 (d, 1H), 5.24 (s, 1H), 2.74 (s, 3H), 0.98 (s, 9H); LCMS-ESI$^+$ (m/z): [M+H]$^+$ calcd for C$_{28}$H$_{25}$Cl$_2$NO$_3$: 495.4. Found: 494.2, 496.2, 498.2.

EXAMPLE 28

(S)-2-tert-butoxy-2-(5-(4-chlorophenyl)-2-cyclopropyl-7-methylquinolin-6-yl)acetic acid (28).

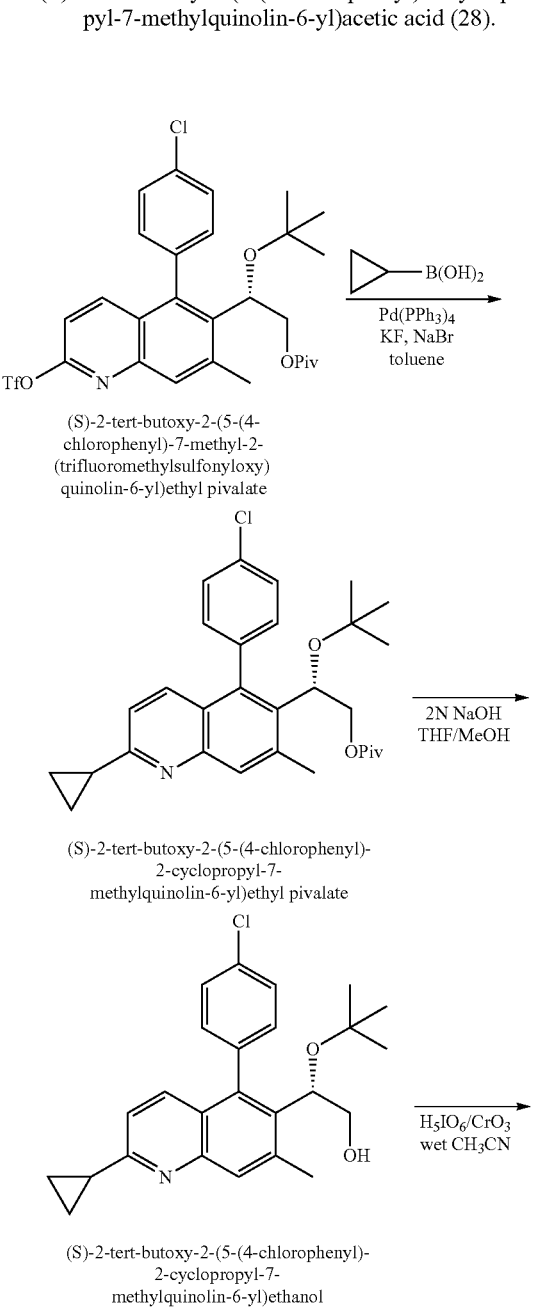

Preparation of (S)-2-(2,5-bis(4-chlorophenyl)-7-methylquinolin-6-yl)-2-tert-butoxyethyl pivalate: Pd(PPh$_3$)$_4$ (4.6 mg, 0.004 mmol) was added to a mixture (S)-2-tert-butoxy-2-(5-(4-chlorophenyl)-7-methyl-2-(trifluoromethylsulfonyloxy)quinolin-6-yl)ethyl pivalate (compound of Example 26) (25 mg, 0.04 mmol), 4-chlorophenylboronic acid (13 mg, 0.08 mmol), Na$_2$CO$_3$ (0.14 mL 1 M in water, 0.14 mmol) in 1,2-dimethoxyethane (2 mL). The reaction mixture was flushed with nitrogen, heated at 90° C. for 16 hours, and then the volatile component was removed in vacuo. The residue was dissolved in ethyl acetate (100 mL), washed with NaHCO$_3$ solution, water and brine, dried over Na$_2$SO$_4$, filtered and concentrated in vacuo. The obtained residue was purified by HPLC to provide the desired product as a TFA salt (15 mg, 55%). LCMS-ESI$^+$ (m/z): 564.3, 566.3, 568.3 (M+H)$^+$.

Preparation of (S)-2-(2,5-bis(4-chlorophenyl)-7-methylquinolin-6-yl)-2-tert-butoxyethanol: (S)-2-(2,5-Bis(4-chlorophenyl)-7-methylquinolin-6-yl)-2-tert-butoxyethanol was prepared following the procedure used to prepare compound (S)-2-tert-butoxy-2-(5-(4-chlorophenyl)-7-methyl-2-vinylquinolin-6-yl)ethanol (compound of Example 26), except that (S)-2-(2,5-bis(4-chlorophenyl)-7-methylquinolin-6-yl)-2-tert-butoxyethyl pivalate was used instead of (S)-2-tert-butoxy-2-(5-(4-chlorophenyl)-7-methyl-2-vinylquinolin-6-yl)ethyl pivalate. LCMS-ESI$^+$ (m/z): 480.2, 482.2, 484.2 (M+H)$^+$.

Preparation of (S)-2-(2,5-bis(4-chlorophenyl)-7-methylquinolin-6-yl)-2-tert-butoxyacetic acid (27): (S)-2-(2,5-Bis(4-chlorophenyl)-7-methylquinolin-6-yl)-2-tert-butoxyace-

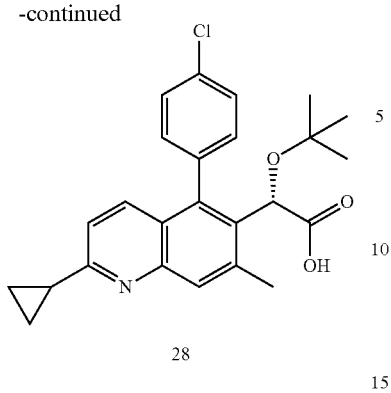

(S)-2-tert-butoxy-2-(5-(4-chlorophenyl)-
2-cyclopropyl-7-
methylquinolin-6-yl)acetic acid

28

Preparation of (S)-2-tert-butoxy-2-(5-(4-chlorophenyl)-2-cyclopropyl-7-methylquinolin-6-yl)ethyl pivalate: Pd(PPh₃)₄ (4.7 mg, 0.004 mmol) was added to a mixture (S)-2-tert-butoxy-2-(5-(4-chlorophenyl)-7-methyl-2-(trifluoromethylsulfonyloxy)quinolin-6-yl)ethyl pivalate (compound of Example 26) (25 mg, 0.04 mmol), cyclopropylboronic acid (7 mg, 0.08 mmol), KF (8 mg, 0.14) and NaBr (6 mg, 0.06 mmol) in toluene (2 mL) One drop of water was added to the mixture. The reaction mixture was flushed with nitrogen, heated at 90° C. for 16 hours, and then the volatile component was removed in vacuo. The residue was dissolved in ethyl acetate (100 mL), washed with NaHCO₃ solution, water and brine, dried over Na₂SO₄, filtered and concentrated in vacuo. The obtained residue was purified by HPLC to provide the desired product as a TFA salt (11 mg, 47%). LCMS-ESI⁺ (m/z): 494.3, 496.3 (M+H)⁺.

Preparation of (S)-2-tert-Butoxy-2-(5-(4-chlorophenyl)-2-cyclopropyl-7-methylquinolin-6-yl)ethanol: (S)-2-tert-Butoxy-2-(5-(4-chlorophenyl)-2-cyclopropyl-7-methylquinolin-6-yl)ethanol was prepared following the procedure used to prepare compound (S)-2-tert-butoxy-2-(5-(4-chlorophenyl)-7-methyl-2-vinylquinolin-6-yl)ethanol, (compound of Example 26) except that (S)-2-tert-butoxy-2-(5-(4-chlorophenyl)-2-cyclopropyl-7-methylquinolin-6-yl)ethyl pivalate was used instead of (S)-2-tert-butoxy-2-(5-(4-chlorophenyl)-7-methyl-2-vinylquinolin-6-yl)ethyl pivalate. LCMS-ESI⁺ (m/z): 410.3, 412.2 (M+H)⁺.

Preparation of (S)-2-tert-butoxy-2-(5-(4-chlorophenyl)-2-cyclopropyl-7-methylquinolin-6-yl)acetic acid (28): (S)-2-tert-butoxy-2-(5-(4-chlorophenyl)-2-cyclopropyl-7-methylquinolin-6-yl)acetic acid was prepared following the procedure used to prepare compound (S)-2-tert-butoxy-2-(5-(4-chlorophenyl)-2-ethyl-7-methylquinolin-6-yl)acetic acid (compound of Example 26) except that(S)-2-tert-butoxy-2-(5-(4-chlorophenyl)-2-cyclopropyl-7-methylquinolin-6-yl)ethanol was used instead (S)-2-tert-butoxy-2-(5-(4-chlorophenyl)-2-ethyl-7-methylquinolin-6-yl)ethanol. ¹H-NMR 300 MHz, (CD₃OD) δ 8.19 (d, 1H), 7.96 (s, 1H), 7.70-7.58 (m, 3H, 7.40-7.30 (m, 214), 5.23 (s, 1H), 2.77 (s, 3H), 2.58- 2.48 (m, 114), 1.65-1.55 (m, 2H), 1.42-1.36 (m, 2H), 0.98 (s, 9H); LCMS-ESI⁺ (m/z): [M+H]⁺ calcd for C₂₅H₂₆ClNO₃: 424.9. Found: 424.2, 426.2.

EXAMPLE 29

(S)-2-tert-Butoxy-2-(5-(4-chlorophenyl)-7-methyl-2-morpholinoquinolin-6-yl)acetic acid (29).

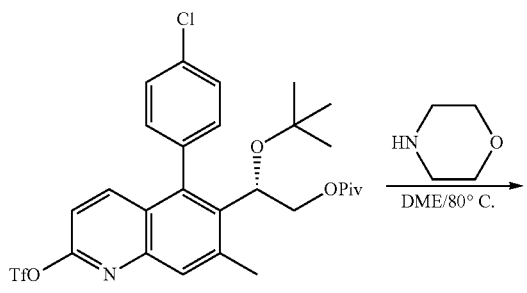

(S)-2-tert-butoxy-2-(5-(4-chlorophenyl)-7-methyl-2-(trifluoromethylsulfonyloxy)quinolin-6-yl)ethyl pivalate

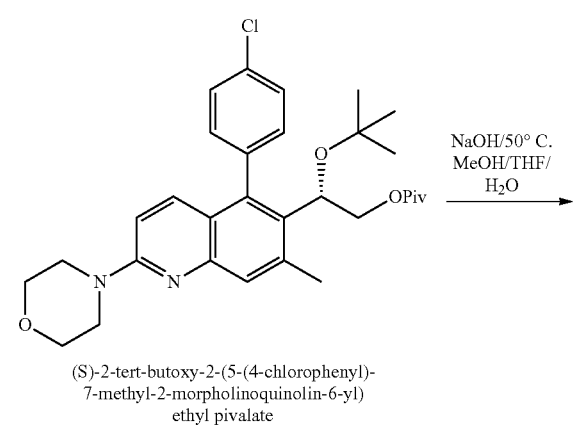

(S)-2-tert-butoxy-2-(5-(4-chlorophenyl)-7-methyl-2-morpholinoquinolin-6-yl) ethyl pivalate

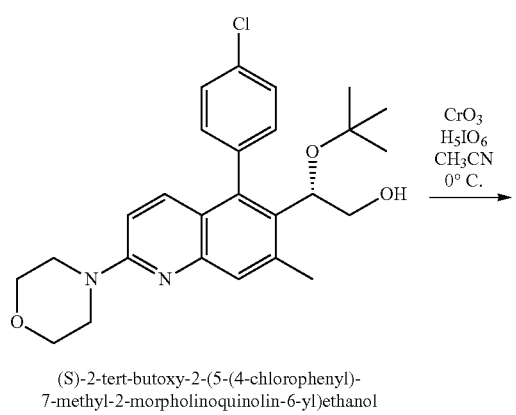

(S)-2-tert-butoxy-2-(5-(4-chlorophenyl)-7-methyl-2-morpholinoquinolin-6-yl)ethanol

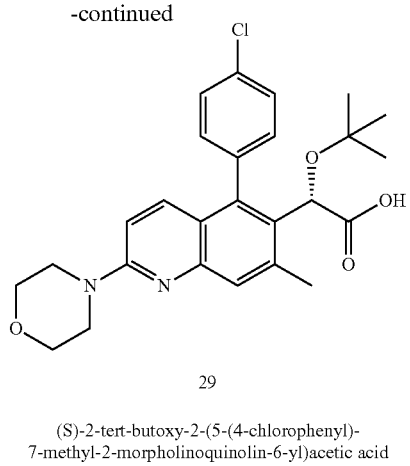

(S)-2-tert-butoxy-2-(5-(4-chlorophenyl)-
7-methyl-2-morpholinoquinolin-6-yl)acetic acid Preparation of (S)-2-tert-butoxy-2-(5-(4-chlorophenyl)-7-methyl-2-morpholinoquinolin-6-yl)ethyl pivalate: A mixture of (S)-2-tert-butoxy-2-(5-(4-chlorophenyl)-7-methyl-2-(trifluoromethylsulfonyloxy)quinolin-6-yl)ethyl pivalate (12 mg, prepared as in Example 26) and morpholine (0.2 mL) in DME was heated at 80° C. for 12 hours. Concentration in vacuo gave (S)-2-tert-butoxy-2-(5-(4-chlorophenyl)-7-methyl-2-morpholinoquinolin-6-yl)ethyl pivalate (15 mg). LCMS-ESI$^+$ (m/z): [M+H]$^+$ calcd for C$_{31}$H$_{40}$ClN$_2$O$_4$: 539.3. Found: 539.4

Preparation of (S)-2-tert-butoxy-2-(5-(4-chlorophenyl)-7-methyl-2-morpholinoquinolin-6-yl)ethanol: To the solution of (S)-2-tert-butoxy-2-(5-(4-chlorophenyl)-7-methyl-2-morpholinoquinolin-6-yl)ethyl pivalate (15 mg) in THF/MeOH (1 mL/1 mL) was added sodium hydroxide solution (1.0 N, 1 mL). The mixture was heated at 50° C. for 16 hours and was diluted with water. The aqueous was extracted with ethyl acetate, and the organic phase was washed with brine, and dried over sodium sulfate. Concentration under reduced pressure gave (S)-2-tert-butoxy-2-(5-(4-chlorophenyl)-7-methyl-2-morpholinoquinolin-6-yl)ethanol (10 mg). LCMS-ESI$^+$ (m/z): [M+H]$^+$ calcd for C$_{26}$H$_{32}$ClN$_2$O$_3$: 454.2. Found: 455.3.

Preparation of (S)-2-tert-butoxy-2-(5-(4-chlorophenyl)-7-methyl-2-morpholinoquinolin-6-yl)acetic acid (29): A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% H$_2$O) to a volume of 114 mL. This stock solution (0.40 mL) was added to a solution of (S)-2-tert-butoxy-2-(5-(4-chlorophenyl)-7-methyl-2-morpholinoquinolin-6-yl)ethanol (10 mg) in wet acetonitrile (1.5 mL, 0.75% H$_2$O) at 0° C. The reaction mixture was stirred for 30 minutes at 0° C. Filtration and purification by reverse phase HPLC (0.1% TFA/CH3CN-0.1% TFA/H2O) gave (S)-2-tert-butoxy-2-(5-(4-chlorophenyl)-7-methyl-2-morpholinoquinolin-6-yl)acetic acid (7.2 mg). $^1$H-NMR 400 MHz, (CD$_3$OD) δ 7.76 (m, 2 H), 7.62 (m, 3 H), 7.30 (m, 2 H), 5.14 (s, 1H), 3.89 (m, 8H), 2.66 (s, 3H), 0.97 (s, 9H); LCMS-ESI$^+$ (m/z): [M+H]$^+$ calcd for C$_{26}$H$_{30}$ClN$_2$O$_4$: 469.2. Found: 469.3; LCMS-ESI$^-$ (m/z): [M–H]$^-$ calcd for C$_{26}$H$_{28}$ClN$_2$O$_4$: 467.2 Found: 467.0.

EXAMPLE 30

(S)-2-tert-butoxy-2-(5-(4-chlorophenyl)-2-(cyclopropylamino)-7-methylquinolin-6-yl)acetic acid (30).

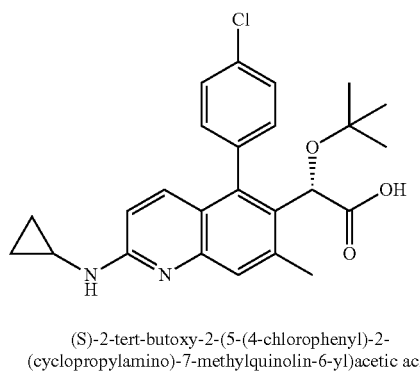

(S)-2-tert-butoxy-2-(5-(4-chlorophenyl)-2-
(cyclopropylamino)-7-methylquinolin-6-yl)acetic acid (S)-2-tert-Butoxy-2-(5-(4-chlorophenyl)-2-(cyclopropylamino)-7-methylquinolin-6-yl)acetic acid (30) was prepared in a similar manner as compound (S)-2-tert-butoxy-2-(5-(4-chlorophenyl)-7-methyl-2-morpholinoquinolin-6-yl)acetic acid of Example 29 except using cyclopropylamine instead of morpholine. $^1$H-NMR 400 MHz, (CD$_3$OD) δ 7.82 (m, 1 H), 7.61 (m, 4 H), 7.30 (d, J=7.6 Hz, 1H), 6.80 (m, 1 H), 5.12 (s, 1 H), 2.90 (m, 1 H), 2.67 (s, 3 H), 1.10 (m, 2 H), 0.97 (s, 9 H), 0.81 (m, 2H); LCMS-ESI$^+$ (m/z): [M+H]$^+$ calcd for C$_{25}$H$_{28}$ClN$_2$O$_3$: 439.2. Found: 439.2; LCMS-ESI$^-$ (m/z): [M–H]$^-$ calcd for C$_{25}$H$_{26}$ClN$_2$O$_3$: 437.2. Found: 437.0;

EXAMPLE 31

(S)-2-tert-butoxy-2-(5-(4-chlorophenyl)-7-methyl-2-(methylamino)quinolin-6-yl)acetic acid (31).

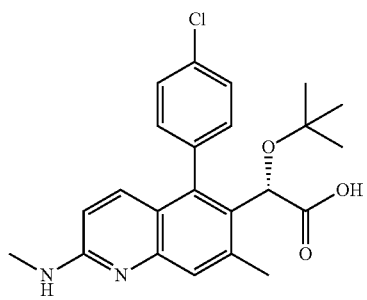

(S)-2-tert-butoxy-2-(5-(4-chlorophenyl)-
7-methyl-2-(methylamino)quinolin-6-yl)acetic acid (S)-2-tert-Butoxy-2-(5-(4-chlorophenyl)-7-methyl-2-(methylamino)quinolin-6-yl)acetic acid (31) was prepared in a similar manner as compound (S)-2-tert-butoxy-2-(5-(4-chlorophenyl)-7-methyl-2-morpholinoquinolin-6-yl)acetic acid of Example 29 except using methylamine instead of morpholine. ¹H-NMR 400 MHz, (CD₃OD) δ7.7 (m, 1 H), 7.58 (m, 4 H), 7.30 (d, J=8.4 Hz, 1 H), 6.82 (m, 1 H), 5.11 (s, 1 H), 3.19 (s, 3 H), 2.64 (s, 3 H), 0.97 (s, 9 H); LCMS-ESI⁺ (m/z): [M+H]⁺ calcd for $C_{23}H_{26}ClN_2O_3$: 413.2. Found: 413.2.

EXAMPLE 32

(S)-2-tert-Butoxy-2-(5-(4-chlorophenyl)-2-(dimethylamino)-7-methylquinolin-6-yl)acetic acid (32).

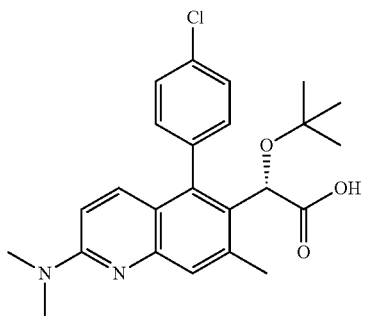

(S)-2-tert-butoxy-2-(5-(4-chlorophenyl)-2-(dimethylamino)-7-methylquinolin-6-yl)acetic acid (S)-2-tert-Butoxy-2-(5-(4-chlorophenyl)-2-(dimethylamino)-7-methylquinolin-6-yl)acetic acid (32) was prepared in a similar manner as compound (S)-2-tert-butoxy-2-(5-(4-chlorophenyl)-7-methyl-2-morpholinoquinolin-6-yl)acetic acid of Example 29 except using dimethylamine instead of morpholine. ¹H-NMR 400 MHz, (CD₃OD) δ 7.79 (s, 1 H), 7.71 (d, J=10 Hz, 1 H), 7.60 (m, 3 H), 7.31 (d, J=8 Hz, 1 H), 7.16 (d, J=10.4 Hz, 1 H), 5.13 (s, 1 H), 3.42 (s, 6 H), 2.66 (s, 3 H), 0.97 (s, 9H); LCMS-ESI⁺ (m/z): [M+H]⁺ calcd for $C_{24}H_{28}ClN_2O_3$: 427.2. Found: 427.2; LCMS-ESI (m/z): [M—H]⁻ calcd for $C_{24}H_{26}ClN_2O_3$: 425.2. Found: 425.0.

EXAMPLE 33

(S)-2-tert-Butoxy-2-(5-(4-chlorophenyl)-7-methyl-2-(pyridin-4-ylmethylamino)quinolin-6-yl)acetic acid (33).

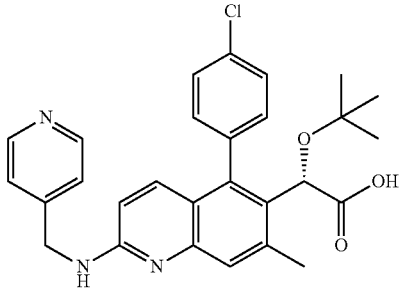

(S)-2-tert-butoxy-2-(5-(4-chlorophenyl)-7-methyl-2-(pyridin-4-ylmethylamino)quinolin-6-yl)acetic acid (S)-2-tert-Butoxy-2-(5-(4-chlorophenyl)-7-methyl-2-(pyridin-4-ylmethylamino)quinolin-6-yl)acetic acid (33) was prepared in a similar manner as compound (S)-2-tert-butoxy-2-(5-(4-chlorophenyl)-7-methyl-2-morpholinoquinolin-6-yl)acetic acid of Example 29 except using pyridin-4-ylmethanamime instead of morpholine. ¹H-NMR 400 MHz, (CD₃OD) δ 8.67 (m, 2 H), 7.72 (m, 3 H), 7.60 (m, 4H), 7.31 (d, J=8.4 Hz, 1 H), 6.97 (d, J=9.2 Hz, 1 H), 5.12 (s, 1 H), 5.0 (s, 2 H), 2.64 (s, 3 H), 0.96 (s, 9 H); LCMS-ESI⁺ (m/z): [M+H]⁺ calcd for $C_{28}H_{29}ClN_3O_3$: 490.2.

Found: 490.2; LCMS-ESI (m/z): [M–H]⁻ calcd for $C_{28}H_{27}ClN_3O_3$: 488.2. Found: 488.0.

EXAMPLE 34

(S)-2-tert-Butoxy-2-(5-(4-chlorophenyl)-7-methyl-2-(2-morpholinoethylamino) quinolin-6-yl)acetic acid (34).

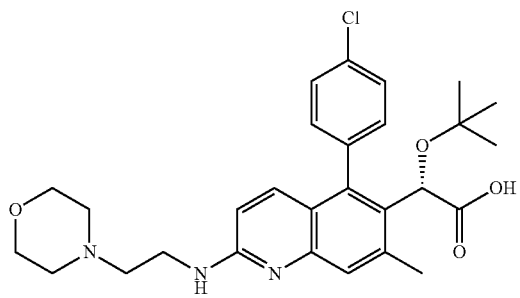

(S)-2-tert-butoxy-2-(5-(4-chlorophenyl)-7-methyl-2-(2-morpholinoethylamino)quinolin-6-yl)acetic acid (S)-2-tert-Butoxy-2-(5-(4-chlorophenyl)-7-methyl-2-(2-morpholinoethylamino)quinolin-6-yl)acetic acid (34) was prepared in a similar manner as compound (S)-2-tert-butoxy-2-(5-(4-chlorophenyl)-7-methyl-2-morpholinoquinolin-6-yl)acetic acid of Example 29 except using 2-morpholinoethanhanamine instead of morpholine. ¹H-NMR 400 MHz, (CD₃OD) δ 7.73-7.55 (m, 5 H), 7.29 (d, J=8 Hz, 1 H), 6.90 (m, 1 H), 5.12 (s, 1 H), 4.05-3.81 (m, 6 H), 3.45-3.35 (m, 6 H), 2.65 (s, 3 H), 0.97 (s, 9H); LCMS-ESI⁺ (m/z): [M+H]⁺ calcd for $C_{28}H_{35}ClN_3O_4$: 512.2. Found: 512.2; LCMS-ESI⁻ (m/z): [M–H]⁻ calcd for $C_{28}H_{33}ClN_3O_4$: 510.2. Found: 510.1.

EXAMPLE 35

(S)-2-tert-butoxy-2-(5-(4-chlorophenyl)-2-(3-(2-methoxyethoxy)propylamino)-7-methylquinolin-6-yl)acetic acid (35).

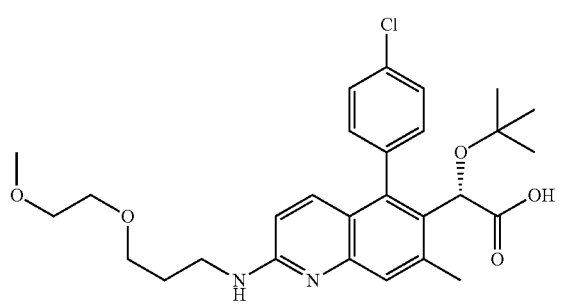

(S)-2-tert-butoxy-2-(5-(4-chlorophenyl)-2-(3-(2-methoxyethoxy)propylamino)-7-methylquinolin-6-yl)acetic acid ((S)-2-tert-Butoxy-2-(5-(4-chlorophenyl)-2-(3-(2-methoxyethoxy)propylamino)-7-methylquinolin-6-yl)acetic acid (35) was prepared in a similar manner as compound (S)-2-tert-butoxy-2-(5-(4-chlorophenyl)-7-methyl-2-morpholinoquinolin-6-yl)acetic acid of Example 29 except using 3-(2-methoxyethoxy)propan-1-amine instead of morpholine. ¹H-NMR 400 MHz, (CD₃OD) δ 7.7-7.55 (m, 5 H), 7.30 (d, J=8 Hz, 1 H), 6.85 (m, 1 H), 5.11 (s, 1 H), 3.7-3.5 (m, 8 H), 3.35 (s, 3 H), 2.65 (s, 3 H), 2.05 (m, 2 H), 0.97 (s, 9H); LCMS-ESI⁺ (m/z): [M+H]⁺ calcd for $C_{28}H_{36}ClN_2O_5$: 515.2. Found: 515.3; LCMS-ESI⁻ (m/z): [M–H]⁻ calcd for $C_{28}H_{34}ClN_2O_5$: 513.2. Found: 513.0.

EXAMPLE 36

(S)-2-tert-butoxy-2-((R)-2-tert-butyl-5-(2,3-dihydropyrano[4,3,2-de]quinolin-7-yl)-7-methylquinolin-6-yl)acetic acid (36).

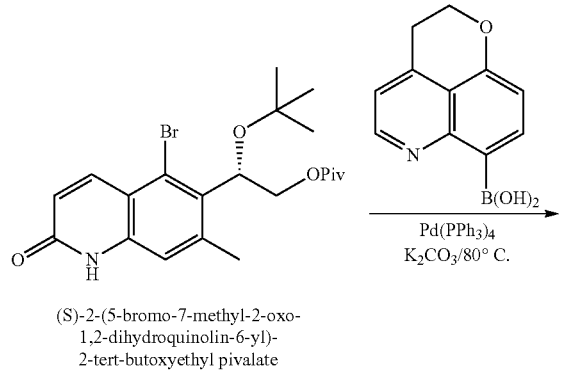

(S)-2-(5-bromo-7-methyl-2-oxo-1,2-dihydroquinolin-6-yl)-2-tert-butoxyethyl pivalate

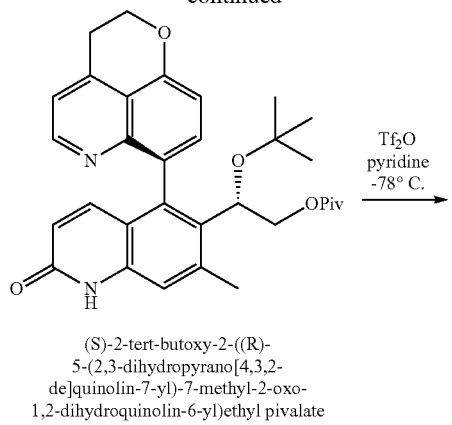

(S)-2-tert-butoxy-2-((R)-5-(2,3-dihydropyrano[4,3,2-de]quinolin-7-yl)-7-methyl-2-oxo-1,2-dihydroquinolin-6-yl)ethyl pivalate

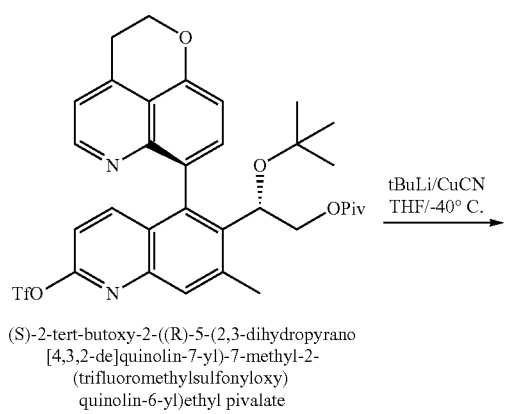

(S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate

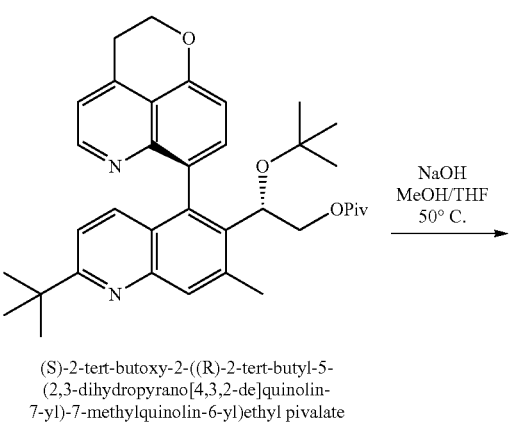

(S)-2-tert-butoxy-2-((R)-2-tert-butyl-5-(2,3-dihydropyrano[4,3,2-de]quinolin-7-yl)-7-methylquinolin-6-yl)ethyl pivalate

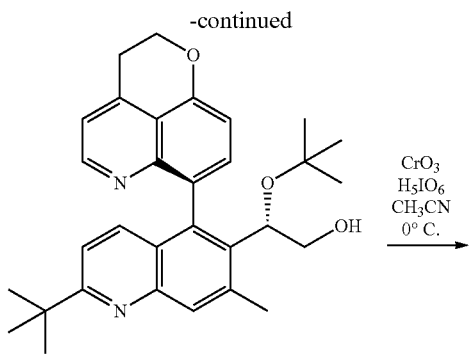

(S)-2-tert-butoxy-2-((R)-2-tert-butyl-5-
(2,3-dihydropyrano[4,3,2-de]quinolin-
7-yl)-7-methylquinolin-6-yl)ethanol

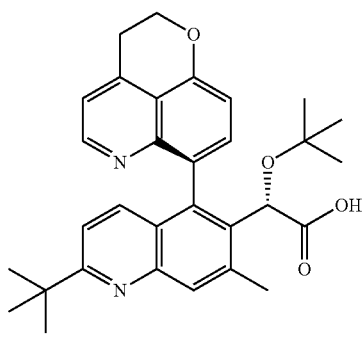

36

(S)-2-tert-butoxy-2-((R)-2-tert-butyl-5-
(2,3-dihydropyrano[4,3,2-de]quinolin-
7-yl)-7-methylquinolin-6-yl)acetic acid Preparation of (S)-2-tert-butoxy-2-((R)-5-(2,3-dihydropyrano[4,3,2-de]quinolin-7-yl)-7-methyl-2-oxo-1,2-dihydroquinolin-6-yl)ethyl pivalate: (S)-2-tert-Butoxy-2-((R)-5-(2,3-dihydropyrano[4,3,2-de]quinolin-7-yl)-7-methyl-2-oxo-1,2-dihydroquinolin-6-yl)ethyl pivalate (800 mg) was prepared in a similar manner as compound (S)-2-tert-butoxy-2-(5-(4-chlorophenyl)-7-methyl-2-oxo-1,2-dihydroquinolin-6-yl)ethyl pivalate of Example 29 except using 2,3-dihydropyrano[4,3,2-de]quinolin-7-ylboronic acid hydrochloride instead of 4-chlorophenylboronic acid. LCMS-ESI+ (m/z): [M+H]+ calcd for $C_{32}H_{37}N_2O_5$: 529.3. Found: 529.0.

Preparation of (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate: (S)-2-tert-Butoxy-2-((R)-5-(2,3-dihydropyrano[4,3,2-de]quinolin-7-yl)-7-methyl-2-(trifluoromethylsulfonyloxy)quinolin-6-yl)ethyl pivalate was prepared in a similar manner as compound (S)-2-tert-butoxy-2-(5-(4-chlorophenyl)-7-methyl-2-(trifluoromethylsulfonyloxy)quinolin-6-yl)ethyl pivalate of Example 29 except using (S)-2-tert-butoxy-2-((R)-5-(2,3-dihydropyrano[4,3,2-de]quinolin-7-yl)-7-methyl-2-oxo-1,2-dihydroquinolin-6-yl)ethyl pivalate instead of (S)-2-tert-butoxy-2-(5-(4-chlorophenyl)-7-methyl-2-oxo-1,2-dihydroquinolin-6-yl)ethyl pivalate LCMS-ESI+ (m/z): [M+H]+ calcd for $C_{33}H_{36}F_3N_2O_7S$: 661.2. Found: 661.0.

Preparation of (S)-2-tert-butoxy-2-((R)-2-tert-butyl-5-(2,3-dihydropyrano[4,3,2-de]quinolin-7-yl)-7-methylquinolin-6-yl)ethyl pivalate: To a suspension of copper(I) cyanide (40 mg, 0.44 mmol) in THF (1 mL) at −40° C. was added tert-butyllithium (0.48 mL, 1.7 N, 0.82 mmol) slowly. The mixture was stirred for 5 minutes, and a solution of (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate (40 mg, 0.06 mmol) in THF (0.5 mL) was added dropwise. The reaction mixture was kept at −45 to −35° C. for 4 hours, and warmed to 25° C. slowly and stirred for 12 hours. The reaction was quenched with water, and extracted with ethyl acetate. The organic layer was washed with brine, and dried with sodium sulfate. Concentration and purification by flash column chromatography (hexanes/EtOAc) gave (S)-2-tert-butoxy-2-((R)-2-tert-butyl-5-(2,3-dihydropyrano[4,3,2-de]quinolin-7-yl)-7-methylquinolin-6-yl)ethyl pivalate (14 mg). LCMS-ESI+ (m/z): [M+H]+ calcd for $C_{36}H_{45}N_2O_4$: 569.3. Found: 569.4.

Preparation of (S)-2-tert-butoxy-2-((R)-2-tert-butyl-5-(2,3-dihydropyrano[4,3,2-de]quinolin-7-yl)-7-methylquinolin-6-yl)ethanol: (S)-2-tert-Butoxy-2-((R)-2-tert-butyl-5-(2,3-dihydropyrano[4,3,2-de]quinolin-7-yl)-7-methylquinolin-6-yl)ethanol (13 mg) was prepared in a similar manner as compound ((S)-2-tert-butoxy-2-(5-(4-chlorophenyl)-7-methyl-2-morpholinoquinolin-6-yl)ethanol of Example 29, except using(S)-2-tert-butoxy-2-((R)-2-tert-butyl-5-(2,3-dihydropyrano[4,3,2-de]quinolin-7-yl)-7-methylquinolin-6-yl)ethyl pivalate instead of (S)-2-tert-butoxy-2-(5-(4-chlorophenyl)-7-methyl-2-morpholinoquinolin-6-yl)ethyl pivalate. LCMS-ESI+ (m/z): [M+H]+ calcd for $C_{31}H_{37}N_2O_3$: 485.2. Found: 485.1.

Preparation of (S)-2-tert-butoxy-2-((R)-2-tert-butyl-5-(2,3-dihydropyrano[4,3,2-de]quinolin-7-yl)-7-methylquinolin-6-yl)acetic acid (36): (S)-2-tert-Butoxy-2-((R)-2-tert-butyl-5-(2,3-dihydropyrano[4,3,2-de]quinolin-7-yl)-7-methylquinolin-6-yl)acetic acid (11.6 mg) was prepared in a similar manner as compound ((S)-2-tert-butoxy-2-(5-(4-chlorophenyl)-7-methyl-2-morpholinoquinolin-6-yl)acetic acid of Example 29, except using (S)-2-tert-butoxy-2-((R)-2-tert-butyl-5-(2,3-dihydropyrano[4,3,2-de]quinolin-7-yl)-7-methylquinolin-6-yl)ethanol instead of (S)-2-tert-butoxy-2-(5-(4-chlorophenyl)-7-methyl-2-morpholinoquinolin-6-yl)ethanol. 1H-NMR 400 MHz (CD3OD) δ 8.62 (d, J=4.8 Hz, 1 H), 8.27 (s, 1 H), 7.81 (d, J=8.4 Hz, 1 H), 7.71 (d, J=8 Hz, 1 H), 7.66 (d, J=8.8 Hz, 1 H), 7.59 (d, J=5.2 Hz, 1 H), 7.33 (d, J=7.6 Hz, 1 H), 5.26 (s, 1 H), 4.66 (m, 2 H), 3.55 (m, 2 H), 2.89 (s, 3H), 1.54 (s, 9 H), 0.92 (s, 9 H); LCMS-ESI+ (m/z): [M+H]+ calcd for $C_{31}H_{35}N_2O_4$: 499.2. Found: 499.2; LCMS-ESI− (m/z): [M−H]− calcd for $C_{31}H_{33}N_2O_4$: 497.2. Found: 497.2.

EXAMPLE 37

(S)-2-tert-butoxy-2-(5-(4-chlorophenyl)-7-methyl-2-(phenylethynyl)quinolin-6-yl)acetic acid (37A) and
(S)-2-tert-butoxy-2-(5-(4-chlorophenyl)-7-methyl-2-(phenylethynyl)quinolin-6-yl)acetic acid (37B).

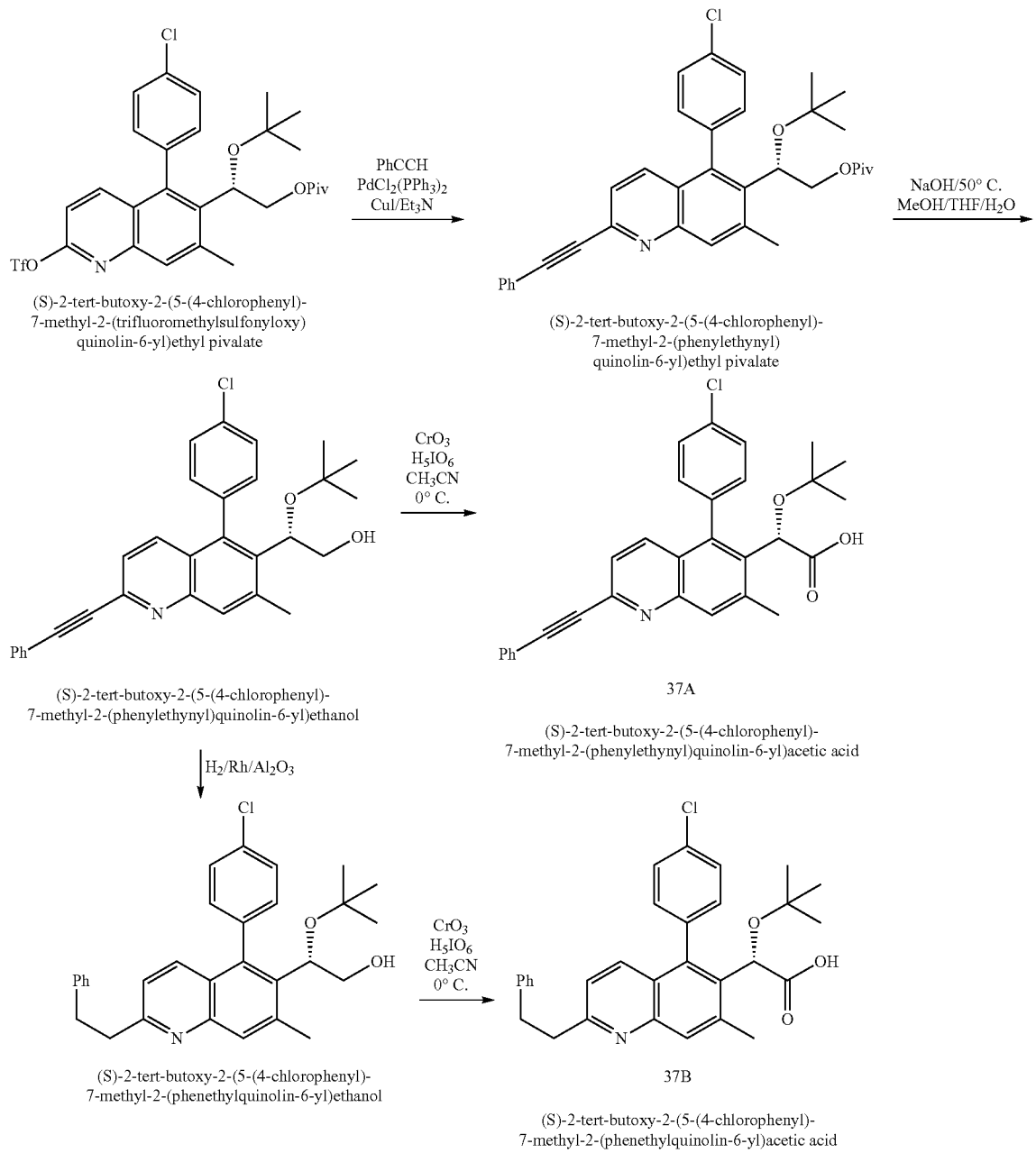

Preparation of (S)-2-tert-butoxy-2-(5-(4-chlorophenyl)-7-methyl-2-(phenylethynyl)quinolin-6-yl)ethyl pivalate: The solution of (S)-2-tert-butoxy-2-(5-(4-chlorophenyl)-7-methyl-2-(trifluoromethylsulfonyloxy)quinolin-6-yl)ethyl pivalate (compound of Example 26) (35 mg, 0.06 mmol), ethynylbenzene (8 µL, 0.08 mmol), and triethylamine (1 mL) in ethyl acetate (0.5 mL) was degassed with nitrogen. Copper(I) iodide (1 mg) and bis(triphenylphosphine)palladium (II) dichloride (7 mg) were added, and the mixture was stirred for 12 hours. The mixture was diluted with ethyl acetate, washed with water and brine, and dried with sodium sulfate. Concentration and purification by flash column chromatography (silica gel, ethyl acetate/hexanes) gave (S)-2-tert-butoxy-2-(5-(4-chlorophenyl)-7-methyl-2-(phenylethynyl)quinolin-6-yl)ethyl pivalate. LCMS-ESI$^+$ (m/z): [M+H]$^+$ calcd for $C_{35}H_{37}ClNO_3$: 554.2. Found: 554.3.

Preparation of (S)-2-tert-butoxy-2-(5-(4-chlorophenyl)-7-methyl-2-(phenylethynyl)quinolin-6-yl)ethanol: (S)-2-tert-Butoxy-2-(5-(4-chlorophenyl)-7-methyl-2-(phenylethynyl)quinolin-6-yl)ethanol (12 mg) was prepared in a similar manner as compound (S)-2-tert-butoxy-2-(5-(4-chlorophenyl)-7-methyl-2-morpholinoquinolin-6-yl)ethanol of Example 29 except using (S)-2-tert-butoxy-2-(5-(4-chlorophenyl)-7-methyl-2-(phenylethynyl)quinolin-6-yl)ethyl pivalate instead of (S)-2-tert-butoxy-2-(5-(4-chlorophenyl)-7-methyl-2-morpholinoquinolin-6-yl)ethyl pivalate. LCMS-ESI$^+$ (m/z): [M+H]$^+$ calcd for $C_{30}H_{29}ClNO_2$: 470.2. Found: 470.2.

Preparation of (S)-2-tert-butoxy-2-(5-(4-chlorophenyl)-7-methyl-2-(phenylethynyl)quinolin-6-yl)acetic acid (37A): (S)-2-tert-Butoxy-2-(5-(4-chlorophenyl)-7-methyl-2-(phenylethynyl)quinolin-6-yl)acetic acid (4.9 mg) was prepared in a similar manner as compound (S)-2-tert-butoxy-2-(5-(4-chlorophenyl)-7-methyl-2-morpholinoquinolin-6-yl)acetic acid of Example 29 except using (S)-2-tert-butoxy-2-(5-(4-chlorophenyl)-7-methyl-2-(phenylethynyl)quinolin-6-yl)ethanol instead of (S)-2-tert-butoxy-2-(5-(4-chlorophenyl)-7-methyl-2-morpholinoquinolin-6-yl)ethanol. $^1$H-NMR 400 MHz (CD$_3$OD) δ 7.95 (m, 1 H), 7.90 (s, 1 H), 7.7-7.6 (m, 6 H), 7.50 (m, 3 H), 7.37 (d, J=8.8 Hz, 1 H), 5.23 (s, 1 H), 2.72 (s, 3 H), 0.99 (s, 9 H); LCMS-ESI$^+$ (m/z): [M+H]$^+$ calcd for $C_{30}H_{27}ClNO_3$: 484.2. Found: 484.2. Preparation of (S)-2-tert-butoxy-2-(5-(4-chlorophenyl)-7-methyl-2-phenethylquinolin-6-yl)ethanol: The mixture of (S)-2-tert-butoxy-2-(5-(4-chlorophenyl)-7-methyl-2-(phenylethynyl)quinolin-6-yl)ethanol (6 mg) and rhodium on alumina (2 mg) in ethanol (1.5 mL) was stirred under 1 atm of hydrogen for 3 hours. Celite was added, and the mixture was filtered and washed with ethyl acetate. Concentration of the mother liquor under reduced pressure gave (S)-2-tert-butoxy-2-(5-(4-chlorophenyl)-7-methyl-2-phenethylquinolin-6-yl)ethanol (6.5 mg). LCMS-ESI$^+$ (m/z): [M+H]$^+$ calcd for $C_{30}H_{33}ClNO_2$: 474.2. Found: 474.3.

Preparation of (S)-2-tert-butoxy-2-(5-(4-chlorophenyl)-7-methyl-2-phenethylquinolin-6-yl)acetic acid (37B): (S)-2-tert-Butoxy-2-(5-(4-chlorophenyl)-7-methyl-2-phenethylquinolin-6-yl)acetic acid (4.8 mg) was prepared in a similar manner as compound (S)-2-tert-butoxy-2-(5-(4-chlorophenyl)-7-methyl-2-morpholinoquinolin-6-yl)acetic acid of Example 29 except using (S)-2-tert-butoxy-2-(5-(4-chlorophenyl)-7-methyl-2-phenethylquinolin-6-yl)ethanol instead of (S)-2-tert-butoxy-2-(5-(4-chlorophenyl)-7-methyl-2-morpholinoquinolin-6-yl)ethanol. $^1$H-NMR 400 MHz (CD$_3$OD) δ 8.21 (d, J=8 Hz, 1 H), 7.93 (s, 1 H), 7.7-7.6 (m, 4 H), 7.37 (d, J=8 Hz, 1 H), 7.3-7.15 (m, 5 H), 5.24 (s, 1 H), 3.46 (d, J=7.6 Hz, 2 H), 3.18 (d, J=7.6 Hz, 2 H), 2.76 (s, 3 H), 0.96 (s, 9 H); LCMS-ESI$^+$ (m/z): [M+H]$^+$ calcd for $C_{30}H_{31}ClNO_3$: 488.2. Found: 488.2.

EXAMPLE 38

(S)-2-tert-butoxy-2-(5-(4-chlorophenyl)-2-(cyclopropylethynyl)-7-methylquinolin-6-yl)acetic acid (38).

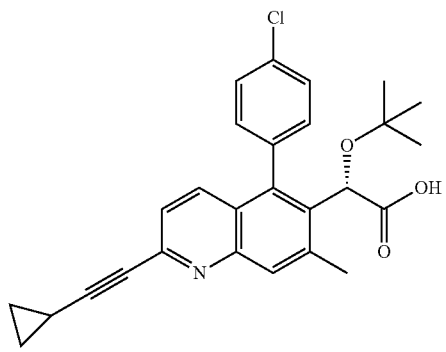

(S)-2-tert-butoxy-2-(5-(4-chlorophenyl)-2-(cyclopropylethynyl)-7-methylquinolin-6-yl)acetic acid (S)-2-tert-Butoxy-2-(5-(4-chlorophenyl)-2-(cyclopropylethynyl)-7-methylquinolin-6-yl)acetic acid (38) (5.5 mg) was prepared in a similar manner as compound (S)-2-tert-butoxy-2-(5-(4-chlorophenyl)-7-methyl-2-(phenylethynyl)quinolin-6-yl)acetic acid of Example 37 except using ethynylcyclopropane instead of ethynylbenzene. $^1$H-NMR 400 MHz (CD$_3$OD) 8.0 (m, 1 H), 7.84 (s, 1 H), 7.64-7.55 (4 H, m), 7.35 (d, J=7.6 Hz, 1H), 5.21 (s, 1 H), 2.72 (s, 3 H), 1.65 (m, 1 H), 1.13-1.02 (m, 4 H), 0.98 (s, 9 H); LCMS-ESI$^+$ (m/z): [M+H]$^+$ calcd for $C_{27}H_{27}ClNO_3$: 448.2. Found: 448.2.

EXAMPLE 39

(S)-2-tert-butoxy-2-(5-(4-chlorophenyl)-2-(2-cyclopropylethyl)-7-methylquinolin-6-yl)acetic acid (39).

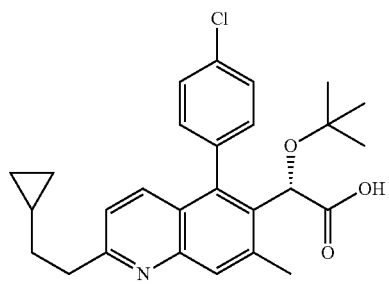

(S)-2-(tert-butoxy)-2-(5-(4-chlorophenyl)-2-(2-cyclopropylethyl)-7-methylquinolin-6-yl)acetic acid (S)-2-tert-Butoxy-2-(5-(4-chlorophenyl)-2-(2-cyclopropylethyl)-7-methylquinolin-6-yl)acetic acid (39) (5.7 mg) was prepared in a similar manner as compound (S)-2-tert-butoxy-2-(5-(4-chlorophenyl)-7-methyl-2-phenethylquinolin-6-yl)acetic acid of Example 37 except using ethynylcyclopropane instead of ethynylbenzene. $^1$H-NMR 400 MHz (CD$_3$OD) δ 8.17 (d, J=8.4 Hz, 1 H), 7.91 (s, 1 H), 7.66 (d, J=8.8 Hz, 1 H), 7.6-7.5 (m, 3 H), 7.31 (m, 1 H), 5.18 (s, 1 H), 3.21 (m, 2 H), 2.71 (s, 3 H), 1.72 (m, 2 H), 0.92 (s, 9 H), 0.75 (m, 1 H), 0.41 (m, 2 H), 0.02 (m, 2 H); LCMS-ESI$^+$ (m/z): [M+H]$^+$ calcd for $C_{27}H_{31}ClNO_3$: 452.2. Found: 452.2.

EXAMPLE 40

(S)-2-tert-butoxy-2-((R)-5-(2,3-dihydropyrano[4,3,2-de]quinolin-7-yl)-7-methyl-2-(phenylethynyl)quinolin-6-yl)acetic acid: (40).

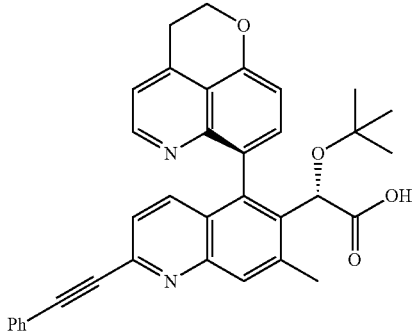

(S)-2-tert-butoxy-2-((R)-5-(2,3-dihydropyrano[4,3,2-de]quinolin-7-yl)-7-methyl-2-(phenylethynyl)quinolin-6-yl)acetic acid (S)-2-tert-Butoxy-2-((R)-5-(2,3-dihydropyrano[4,3,2-de]quinolin-7-yl)-7-methyl-2-(phenylethynyl)quinolin-6-yl)acetic acid (40) (4.9 mg) was prepared in a similar manner as compound (S)-2-tert-butoxy-2-(5-(4-chlorophenyl)-7-methyl-2-(phenylethynyl)quinolin-6-yl)acetic acid of Example 37 except using (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate instead of (S)-2-tert-butoxy-2-(5-(4-chlorophenyl)-7-methyl-2-(trifluoromethylsulfonyloxy)quinolin-6-yl)ethyl pivalate. $^1$H-NMR 400 MHz (CD$_3$OD) δ 8.71 (d, J=5.2 Hz, 1 H), 8.10 (s, 1 H), 7.9-7.8 (m, 2 H), 7.65 (m, 2 H), 7.58 (m, 2 H), 7.45 (m, 4 H), 5.26 (s, 1 H), 4.75 (m, 2 H), 3.64 (m, 2 H), 2.85 (s, 3 H), 0.94 (s, 9 H); LCMS-ESI$^+$ (m/z): [M+H]$^+$ calcd for C$_{35}$H$_{31}$N$_2$O$_4$: 543.2. Found: 543.1; LCMS-ESI$^-$ (m/z): [M–H]$^-$ calcd for C$_{35}$H$_{29}$N$_2$O$_4$: 541.2. Found: 541.0.

EXAMPLE 41

(S)-2-tert-butoxy-2-((R)-5-(2,3-dihydropyrano[4,3,2-de]quinolin-7-yl)-7-methyl-2-phenethylquinolin-6-yl)acetic acid: (41).

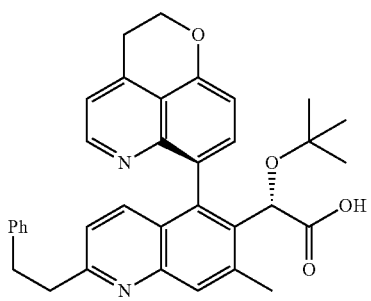

(S)-2-tert-butoxy-2-((R)-5-(2,3-dihydropyrano[4,3,2-de]quinolin-7-yl)-7-methyl-2-phenethylquinolin-6-yl)acetic acid (S)-2-tert-Butoxy-2-((R)-5-(2,3-dihydropyrano[4,3,2-de]quinolin-7-yl)-7-methyl-2-phenethylquinolin-6-yl)acetic acid (41) (5.2 mg) was prepared in a similar manner as compound (S)-2-tert-butoxy-2-(5-(4-chlorophenyl)-7-methyl-2-phenethylquinolin-6-yl)acetic acid of Example 37 except using (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate instead of (S)-2-tert-butoxy-2-(5-(4-chlorophenyl)-7-methyl-2-(trifluoromethylsulfonyloxy)quinolin-6-yl)ethyl pivalate. $^1$H-NMR 400 MHz (CD$_3$OD) δ 8.51 (d, J=5.7 Hz, 1 H), 7.96 (s, 1 H), 7.80 (d, J=8.8 Hz, 1 H), 7.59 (d, J=7.6 Hz, 1 H), 7.45 (m, 2 H), 7.2-7.05 (m, 6 H), 5.15 (s, 1H), 4.56 (m, 2 H), 3.35 (d, J=6.8 Hz, 2 H), 3.22 (m, 2 H), 3.07 (t, J=7.2 Hz, 2 H), 2.80 (s, 3 H), 0.82 (s, 9 H); LCMS-ESI$^+$ (m/z): [M+H]$^+$ calcd for C$_{35}$H$_{35}$N$_2$O$_4$: 547.2. Found: 547.2; LCMS-ESI$^-$ (m/z): [M–H]$^-$ calcd for C$_{35}$H$_{33}$N$_2$O$_4$: 545.2. Found: 545.1.

EXAMPLE 42

(S)-2-tert-butoxy-2-((R)-2-(cyclopropylethynyl)-5-(2,3-dihydropyrano[4,3,2-de]quinolin-7-yl)-7-methylquinolin-6-yl)acetic acid (42).

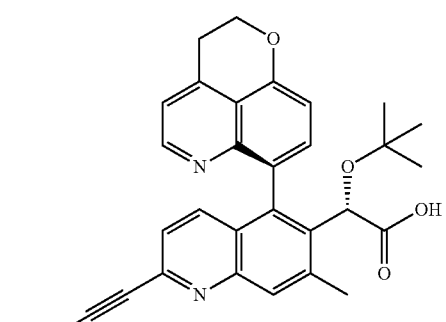

(S)-2-tert-butoxy-2-((R)-2-(cyclopropylethynyl)-5-(2,3-dihydropyrano[4,3,2-de]quinolin-7-yl)-7-methylquinolin-6-yl)acetic acid (S)-2-tert-butoxy-2-((R)-2-(cyclopropylethynyl)-5-(2,3-dihydropyrano[4,3,2-de]quinolin-7-yl)-7-methylquinolin-6-yl)acetic acid (42) (5.2 mg) was prepared in a similar manner as compound (S)-2-tert-butoxy-2-(5-(4-chlorophenyl)-7-methyl-2-(phenylethynyl)quinolin-6-yl)acetic acid of Example 37 except using (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate and ethynylcyclopropane instead of (S)-2-tert-butoxy-2-(5-(4-chlorophenyl)-7-methyl-2-(trifluoromethylsulfonyloxy)quinolin-6-yl)ethyl pivalate and ethynylbenzene. $^1$H-NMR 400 MHz (CD$_3$OD) δ 8.68 (d, J=5.6 Hz, 1 H), 8.0 (s, 1 H), 7.80 (d, J=7.6 Hz, 1 H), 7.74 (d, J=5.6 Hz, 1 H), 7.5 (d, J=8.4 Hz, 1 H), 7.41 (d, J=7.6 Hz, 1 H), 7.35 (d, J=8.8 Hz, 1 H), 5.23 (s, 1 H), 4.70 (m, 2 H), 3.62 (m, 2 H), 2.83 (s, 3 H), 1.60 (m, 1 H), 1.05-0.88 (m, 4 H), 0.93 (s, 9 H); LCMS-ESI$^+$ (m/z): [M+H]$^+$ calcd for C$_{32}$H$_{31}$N$_2$O$_4$: 507.2. Found: 507.1; LCMS-ESI$^+$ (m/z): [M+H]$^+$ calcd for C$_{32}$H$_{29}$N$_2$O$_4$: 505.2. Found: 505.1.

EXAMPLE 43

(S)-2-tert-Butoxy-2-((R)-2-(2-cyclopropylethyl)-5-(2,3-dihydropyrano[4,3,2-de]quinolin-7-yl)-7-methylquinolin-6-yl)acetic acid (43).

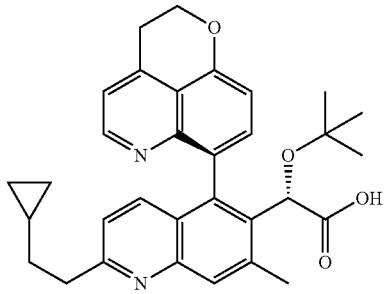

(S)-2-tert-butoxy-2-((R)-2-(2-cyclopropylethyl)-5-(2,3-dihydropyrano[4,3,2-de]quinolin-7-yl)-7-methylquinolin-6-yl)acetic acid (S)-2-tert-butoxy-2-((R)-2-(2-cyclopropylethyl)-5-(2,3-dihydropyrano[4,3,2-de]quinolin-7-yl)-7-methylquinolin-6-yl)acetic acid (43) (5.9 mg) was prepared in a similar manner as compound (S)-2-tert-butoxy-2-(5-(4-chlorophenyl)-7-methyl-2-phenethylquinolin-6-yl)acetic acid of Example 37 except using (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate and ethynylcyclopropane instead of (S)-2-tert-butoxy-2-(5-(4-chlorophenyl)-7-methyl-2-(trifluoromethylsulfonyloxy)quinolin-6-yl)ethyl pivalate and ethynylbenzene. $^1$H-NMR 400 MHz (CD$_3$OD) δ 8.55 (m, 1 H), 8.03 (s, 1 H), 7.92 (d, J=8.4 Hz, 1 H), 7.62-7.45 (m, 3 H), 7.23 (d, J=7.6 Hz, 1 H), 5.19 (s, 1 H), 4.78 (m, 2 H), 3.43 (m, 2 H), 3.20 (m, 2H), 2.84 (s, 3 H), 1.65 (m, 2 H), 0.84 (s, 9 H), 0.7 (m, 1 H), 0.4 (m, 2 H), 0.02 (m, 2H); LCMS-ESI$^+$ (m/z): [M+11]$^+$ calcd for C$_{32}$H$_{35}$N$_2$O$_4$: 511.2. Found: 511.2; LCMS-ESI$^-$ [M–H]$^-$ calcd for C$_{32}$H$_{33}$N$_2$O$_4$: 509.2. Found: 509.1.

EXAMPLE 44

(S)-2-tert-Butoxy-2-((R)-5-(2,3-dihydropyrano[4,3,2-de]quinolin-7-yl)-7-methyl-2-(prop-1-ynyl)quinolin-6-yl)acetic acid (44).

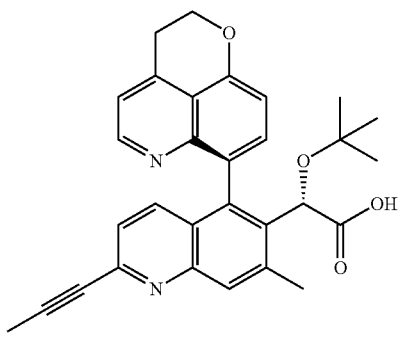

(S)-2-tert-butoxy-2-((R)-5-(2,3-dihydropyrano[4,3,2-de]quinolin-7-yl)-7-methyl-2-(prop-1-ynyl)quinolin-6-yl)acetic acid (S)-2-tert-butoxy-2-((R)-5-(2,3-dihydropyrano[4,3,2-de]quinolin-7-yl)-7-methyl-2-(prop-1-ynyl)quinolin-6-yl)acetic acid (44) (4.6 mg) was prepared in a similar manner as compound (S)-2-tert-butoxy-2-(5-(4-chlorophenyl)-7-methyl-2-(phenylethynyl)quinolin-6-yl)acetic acid of Example 37 except using (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate and prop-1-yne instead of (S)-2-tert-butoxy-2-(5-(4-chlorophenyl)-7-methyl-2-(trifluoromethylsulfonyloxy)quinolin-6-yl)ethyl pivalate and ethynylbenzene. $^1$H-NMR 400 MHz (CD$_3$OD). δ8.67 (d, J=5.6 Hz, 1 H), 8.02 (s, 1 H), 7.85-7.75 (m, 2 H), 7.5-7.4 (m, 1 H), 7.42 (d, J=8 Hz, 1 H), 7.35 (d, J=8.8 Hz, 1 H), 5.23 (s, 1 H), 4.70 (m, 2 H), 3.62 (m, 2 H), 2.83 (s, 3 H), 2.15 (s, 3 H), 0.93 (s, 9 H); LCMS-ESI$^+$ (m/z): [M+H]$^+$ calcd for C$_{30}$H$_{29}$N$_2$O$_4$: 481.2. Found: 481.4; LCMS-ESI$^+$ (m/z): [M+H]$^+$ calcd for C$_{30}$H$_{27}$N$_2$O$_4$: 479.2. Found: 479.1.

EXAMPLE 45

(S)-2-tert-butoxy-2-((R)-5-(2,3-dihydropyrano[4,3,2-de]quinolin-7-yl)-2-ethynyl-7-methylquinolin-6-yl)acetic acid (45).

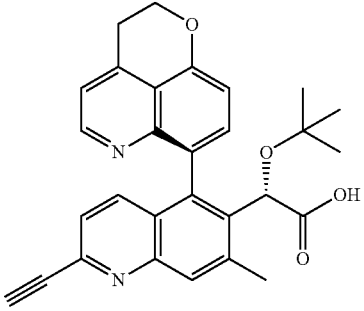

(S)-2-tert-butoxy-2-((R)-5-(2,3-dihydropyrano[4,3,2-de]quinolin-7-yl)-2-ethynyl-7-methylquinolin-6-yl)acetic acid (S)-2-tert-butoxy-2-((R)-5-(2,3-dihydropyrano[4,3,2-de]quinolin-7-yl)-2-ethynyl-7-methylquinolin-6-yl)acetic acid (45) (5 mg) was prepared in a similar manner as compound (S)-2-tert-butoxy-2-(5-(4-chlorophenyl)-7-methyl-2-(phenylethynyl)quinolin-6-yl)acetic acid of Example 37 except using (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate and ethynyltrimethylsilane instead of (S)-2-tert-butoxy-2-(5-(4-chlorophenyl)-7-methyl-2-(trifluoromethylsulfonyloxy)quinolin-6-yl)ethyl pivalate and ethynylbenzene. $^1$H-NMR 400 MHz (CD$_3$OD) δ 8.69 (d, J=5.6 Hz, 1 H), 8.07 (s, 1 H), 7.85-7.75 (m, 2 H), 7.5-7.4 (m, 3 H), 5.24 (s, 1 H), 4.75 (m, 2 H), 3.98 (s, 1 H), 3.65 (m, 2 H), 2.83 (s, 3 H), 0.93 (s, 9 H); LCMS-ESI$^+$ (m/z):

[M+H]+ calcd for C29H27N2O4: 467.2. Found: 467.1; LCMS-ESI− (m/z): [M−H]− calcd for C29H25N2O4: 465.2. Found: 465.0.

EXAMPLE 46

(S)-2-tert-Butoxy-2-((R)-5-(2,3-dihydropyrano[4,3,2-de]quinolin-7-yl)-2-isopropyl-7-methylquinolin-6-yl)acetic acid (46).

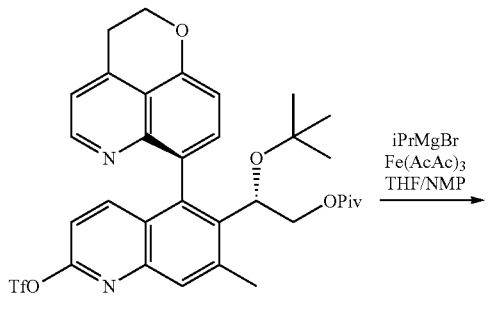

(S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate iPrMgBr
Fe(AcAc)3
THF/NMP

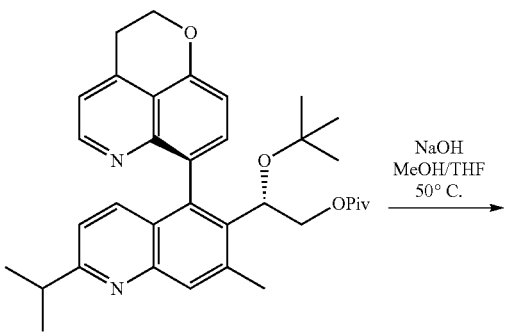

(S)-2-tert-butoxy-2-((R)-5-(2,3-dihydropyrano[4,3,2-de]quinolin-7-yl)-2-isopropyl-7-methylquinolin-6-yl)ethyl pivalate NaOH
MeOH/THF
50° C.

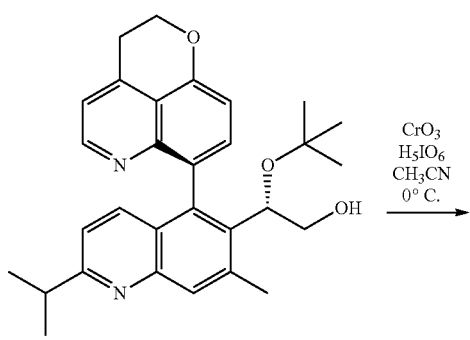

(S)-2-tert-butoxy-2-((R)-5-(2,3-dihydropyrano[4,3,2-de]quinolin-7-yl)-2-isopropyl-7-methylquinolin-6-yl)ethanol CrO3
H5IO6
CH3CN
0° C.

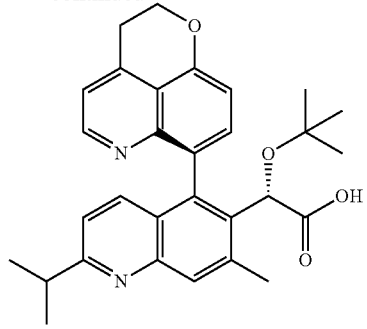

46

(S)-2-tert-butoxy-2-((R)-5-(2,3-dihydropyrano[4,3,2-de]quinolin-7-yl)2-isopropyl-7-methylquinolin-6-yl)acetic acid Preparation of (S)-2-tert-butoxy-2-((R)-5-(2,3-dihydropyrano[4,3,2-de]quinolin-7-yl)-2-isopropyl-7-methylquinolin-6-yl)ethyl pivalate: To a solution of (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate (compound of Example 36) (40 mg, 0.06 mmol) in THF/NMP (0.75 mL/75 μL) was added iron (III) acetylacetonate (2 mg), followed by isopropylmagnesium bromide (1.0 N, 0.14 mL, 0.14 mmol) slowly. The mixture was stirred for 30 minutes, and was quenched with water. Ethyl acetate was added, and the organic layer was separated, washed with brine and dried with sodium sulfate. Concentration and purification by flash column chromatography (hexanes/EtOAc) gave (S)-2-tert-butoxy-2-((R)-5-(2,3-dihydropyrano[4,3,2-de]quinolin-7-yl)-2-isopropyl-7-methylquinolin-6-yl)ethyl pivalate (11 mg). LCMS-ESI+ (m/z): [M+H]+ calcd for C35H43N2O4: 555.3. Found: 555.4.

Preparation of (S)-2-tert-butoxy-2-((R)-5-(2,3-dihydropyrano[4,3,2-de]quinolin-7-yl)-2-isopropyl-7-methylquinolin-6-yl)ethanol: (S)-2-tert-Butoxy-2-((R)-5-(2,3-dihydropyrano[4,3,2-de]quinolin-7-yl)-2-isopropyl-7-methylquinolin-6-yl)ethanol (8 mg) was prepared in a similar manner as compound (S)-2-tert-butoxy-2-(5-(4-chlorophenyl)-7-methyl-2-morpholinoquinolin-6-yl)ethanol of Example 29 except using (S)-2-tert-butoxy-2-((R)-5-(2,3-dihydropyrano[4,3,2-de]quinolin-7-yl)-2-isopropyl-7-methylquinolin-6-yl)ethyl pivalate instead of (S)-2-tert-butoxy-2-(5-(4-chlorophenyl)-7-methyl-2-morpholinoquinolin-6-yl)ethyl pivalate. LCMS-ESI+ (m/z): [M+H]+ calcd for C30H35N2O3: 471.3. Found: 471.3.

Preparation of (S)-2-tert-butoxy-2-((R)-5-(2,3-dihydropyrano[4,3,2-de]quinolin-7-yl)-2-isopropyl-7-methylquinolin-6-yl)acetic acid (46): (S)-2-tert-Butoxy-2-((R)-5-(2,3-dihydropyrano[4,3,2-de]quinolin-7-yl)-2-isopropyl-7-methylquinolin-6-yl)acetic acid (7 mg) was prepared in a similar manner as compound ((S)-2-tert-butoxy-2-(5-(4-chlorophenyl)-7-methyl-2-morpholinoquinolin-6-yl)acetic acid of Example 29 except using (S)-2-tert-butoxy-2-((R)-5-(2,3-dihydropyrano[4,3,2-de]quinolin-7-yl)-2-isopropyl-7-methylquinolin-6-yl)ethanol instead of (S)-2-tert-butoxy-2-(5-(4-chlorophenyl)-7-methyl-2-morpholinoquinolin-6-yl)ethanol. $^1$H-NMR 400 MHz (CD3OD) δ 8.60 (d, J=5.2 Hz, 1 H), 8.11 (s, 1 H), 7.98 (d, J=9.2 Hz, 1 H), 7.7-7.6 (m, 2 H), 7.51 (d, J=4.8 Hz, 1 H), 7.29 (d, J=8.4 Hz, 1 H), 5.26 (s, 1 H), 4.64 (m, 2H), 3.55-3.40 (m, 3 H), 2.90 (s, 3 H), 1.46 (m, 6 H), 0.91 (s, 9 H); LCMS-ESI+ (m/z): [M+H]+ calcd for $C_{30}H_{33}N_2O_4$: 485.2. Found: 485.2; LCMS-ESI (m/z): [M–H]$^-$ calcd for $C_{30}H_{31}N_2O_4$: 483.2. Found: 483.2.

EXAMPLE 47

(S)-2-tert-butoxy-2-((R)-2-cyclobutyl-5-(2,3-dihydropyrano[4,3,2-de]quinolin-7-yl)-7-methylquinolin-6-yl)acetic acid (47).

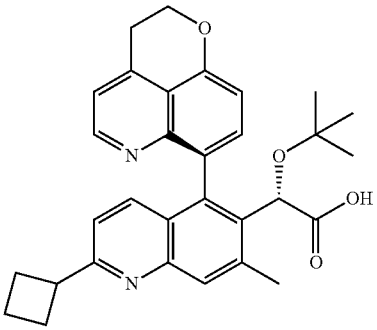

(S)-2-tert-butoxy-2-((R)-2-cyclobutyl-5-(2,3-dihydropyrano[4,3,2-de]quinolin-7-yl)-7-methylquinolin-6-yl)acetic acid (S)-2-tert-butoxy-2-((R)-2-cyclobutyl-5-(2,3-dihydropyrano[4,3,2-de] quinolin-7-yl)-7-methylquinolin-6-yl)acetic acid (47) (10 mg) was prepared in a similar manner as compound (S)-2-tert-butoxy-2-((R)-5-(2,3-dihydropyrano[4,3,2-de]quinolin-7-yl)-2-isopropyl-7-methylquinolin-6-yl)acetic acid of Example 46 except using cyclobutylmagnesium bromide instead of isopropylmagnesium bromide. $^1$H-NMR 400 MHz (CD$_3$OD) δ 8.60 (m, 1 H), 8.10 (m, 1 H), 7.95 (m, 1 H), 7.65 (m, 2 H), 7.45 (m, 1 H), 7.24 (m, 1 H), 5.25 (s, 1 H), 4.63 (m, 2 H), 3.5 (m, 2 H), 3.30 (m, 1 H), 2.90 (s, 3 H), 2.6-2.4 (m, 4 H), 2.3 (m, 1 H), 2.0 (m, 1 H), 0.91 (s, 9 H); LCMS-ESI$^+$ (m/z): [M+H]$^+$ calcd for $C_{31}H_{33}N_2O_4$: 497.2. Found: 497.2; LCMS-ESI (m/z): [M–H]$^-$ calcd for $C_{31}H_{31}N_2O_4$: 495.2. Found: 495.2.

EXAMPLE 48

(S)-2-((R)-2-(but-3-enyl)-5-(2,3-dihydropyrano[4,3,2-de]quinolin-7-yl)-7-methylquinolin-6-yl)-2-tert-butoxyacetic acid (48).

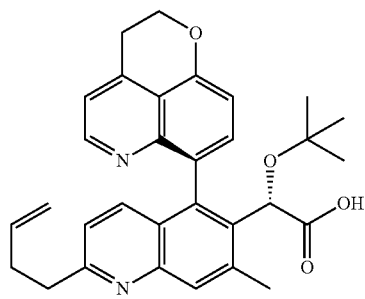

(S)-2-((R)-2-(but-3-enyl)-5-(2,3-dihydropyrano[4,3,2-de]quinolin-7-yl)-7-methylquinolin-6-yl)-2-tert-butoxyacetic acid (S)-2-((R)-2-(but-3-enyl)-5-(2,3-dihydropyrano[4,3,2-de]quinolin-7-yl)-7-methylquinolin-6-yl)-2-tert-butoxyacetic acid (48) (12 mg)) was prepared in a similar manner as compound (S)-2-tert-butoxy-2-((R)-5-(2,3-dihydropyrano[4,3,2-de]quinolin-7-yl)-2-isopropyl-7-methylquinolin-6-yl)acetic acid of Example 46 except using but-3-enylmagnesium bromide instead of isopropylmagnesium bromide. $^1$H-NMR 400 MHz (CD$_3$OD) δ 8.62 (m, 1 H), 8.09 (s, 1 H), 7.94 (m, 1 H), 7.68 (m, 1 H), 7.57 (m, 2 H), 7.32 (m, 1 H), 5.90 (m, 1 H), 5.25 (s, 1 H), 5.08 (m, 2 H), 4.64 (m, 2 H), 3.52 (m, 2 H), 3.25 (m, 2 H), 2.90 (s, 3 H), 2.62 (m, 2 H), 0.91 (s, 9 H); LCMS-ESI$^+$ (m/z): [M+H]$^+$ calcd for $C_{31}H_{33}N_2O_4$: 497.2. Found: 497.2; LCMS-ESI (m/z): [M–H]$^-$ calcd for $C_{31}H_{31}N_2O_4$: 495.2. Found: 495.1.

EXAMPLE 49

(2S)-2-tert-Butoxy-2-((5R)-2-sec-butyl-5-(2,3-dihydropyrano[4,3,2-de]quinolin-7-yl)-7-methylquinolin-6-yl)acetic acid (49).

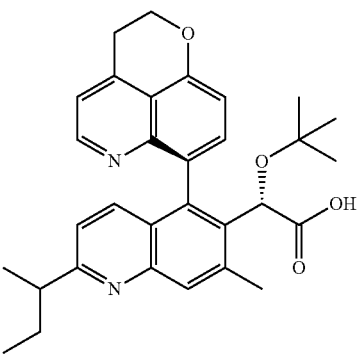

(2S)-2-tert-butoxy-2-((5R)-2-sec-butyl-5-(2,3-dihydropyrano[4,3,2-de]quinolin-7-yl)-7-methylquinolin-6-yl)acetic acid (2S)-2-tert-butoxy-2-((5R)-2-sec-butyl-5-(2,3-dihydropyrano[4,3,2-de]quinolin-7-yl)-7-methylquinolin-6-yl)acetic acid (49) (9.4 mg) was prepared in a similar manner as compound (S)-2-tert-butoxy-2-((R)-5-(2,3-dihydropyrano[4,3,2-de]quinolin-7-yl)-2-isopropyl-7-methylquinolin-6-yl)acetic acid of Example 46 except using sec-butylmagnesium bromide instead of isopropylmagnesium bromide. $^1$H-NMR 400 MHz (CD$_3$OD) 8.58 (d, J=4.4 Hz, 1 H), 8.10 (s, 1 H), 7.96 (m, 1 H), 7.67-7.58 (m, 2 H), 7.48 (m, 1 H), 7.26 (d, J=8 Hz, 1 H), 5.25 (s, 1 H), 4.62 (m, 2 H), 3.48 (m, 2H), 3.2 (m, 1 H), 2.90 (s, 3 H), 1.85 (m, 2 H), 1.44 (m, 3 H), 0.91 (m, 12 H); LCMS-ESI$^+$ (m/z): [M+H]$^+$ calcd for $C_{31}H_{35}N_2O_4$: 499.2.

Found: 499.2; LCMS-ESI (m/z): [M−H]⁻ calcd for $C_{31}H_{33}N_2O_4$: 497.2. Found: 497.2.

EXAMPLE 50

(S)-2-tert-butoxy-2-((R)-5-(2,3-dihydropyrano[4,3,2-de]quinolin-7-yl)-2-isobutyl-7-methylquinolin-6-yl)acetic acid (50).

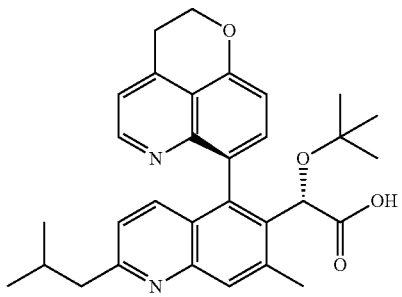

(S)-2-tert-butoxy-2-((R)-5-(2,3-dihydropyrano[4,3,2-de]quinolin-7-yl)-2-isobutyl-7-methylquinolin-6-yl)acetic acid (S)-2-tert-butoxy-2-((R)-5-(2,3-dihydropyrano[4,3,2-de]quinolin-7-yl)-2-isobutyl-7-methylquinolin-6-yl)acetic acid (50) (10 mg) was prepared in a similar manner as compound (S)-2-tert-butoxy-2-((R)-5-(2,3-dihydropyrano[4,3,2-de]quinolin-7-yl)-2-isopropyl-7-methylquinolin-6-yl)acetic acid of Example 46 except using isobutylmagnesium bromide instead of isopropylmagnesium bromide. ¹H-NMR 400 MHz (CD₃OD) δ 8.65 (d, J=5.2 Hz, 1 H), 8.12 (s, 1 H), 8.03 (d, J=9.2 Hz, 1 H), 7.72 (d, J=8 Hz, 1 H), 7.63-7.58 (m, 2 H), 7.33 (d, J=8 Hz, 1 H), 5.26 (s, 1 H), 4.65 (m, 2 H), 3.55 (m, 2 H), 3.05 (d, J=7.2 Hz, 2 H), 2.92 (s, 3 H), 2.2 (m, 1 H), 1.02 (d, J=6.8 Hz, 6 H), 0.92 (s, 9 H); LCMS-ESI⁺ (m/z): [M+H]⁺ calcd for $C_{31}H_{35}N_2O_4$: 499.2. Found: 499.2; LCMS-ESI⁻ (m/z): [M−H]⁻ calcd for $C_{31}H_{33}N_2O_4$: 497.2. Found: 497.2.

EXAMPLE 51

(S)-2-tert-Butoxy-2-((R)-2-cyclopentyl-5-(2,3-dihydropyrano[4,3,2-de]quinolin-7-yl)-7-methylquinolin-6-yl)acetic acid (51).

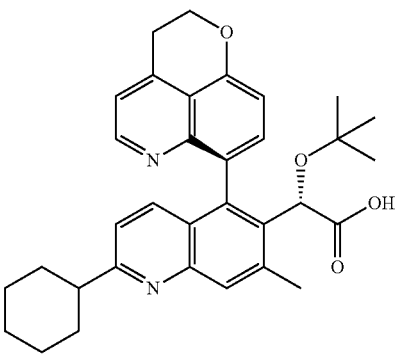

(S)-2-tert-butoxy-2-((R)-2-cyclopentyl-5-(2,3-dihydropyrano[4,3,2-de]quinolin-7-yl)-7-methylquinolin-6-yl)acetic acid (S)-2-tert-Butoxy-2-((R)-2-cyclopentyl-5-(2,3-dihydropyrano[4,3,2-de]quinolin-7-yl)-7-methylquinolin-6-yl)acetic acid (51) (8 mg) was prepared in a similar manner as compound (S)-2-tert-butoxy-2-((R)-5-(2,3-dihydropyrano[4,3,2-de]quinolin-7-yl)-2-isopropyl-7-methylquinolin-6-yl)acetic acid in of Example 46 except using cyclopentylmagnesium bromide instead of isopropylmagnesium bromide. ¹H-NMR 400 MHz (CD₃OD) δ 8.63 (m, 1 H), 8.12 (s, 1 H), 8.01 (d, J=7.2 Hz, 1 H), 7.65 (m, 2 H), 7.54 (m, 1 H), 7.32 (m, 1 H), 5.26 (s, 1 H), 4.65 (m, 2 H), 3.52 (m, 3 H), 2.91 (s, 3 H), 2.30 (m, 2 H), 2.0-1.8 (m, 6 H), 0.91 (s, 9 H); LCMS-ESI⁺ (m/z): [M+H]⁺ calcd for $C_{32}H_{35}N_2O_4$: 511.2. Found: 511.1; LCMS-ESI⁺ (m/z): [M+H]⁺ calcd for $C_{32}H_{33}N_2O_4$: 509.2 Found: 509.1.

EXAMPLE 52

(S)-2-tert-Butoxy-2-((R)-2-cyclohexyl-5-(2,3-dihydropyrano[4,3,2-de]quinolin-7-yl)-7-methylquinolin-6-yl)acetic acid (52).

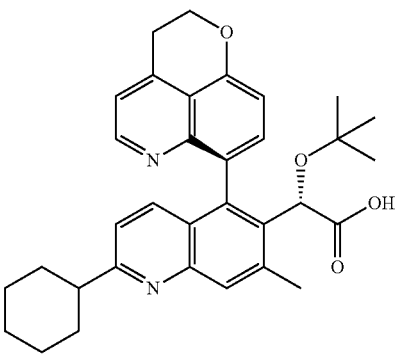

(S)-2-tert-butoxy-2-((R)-2-cyclohexyl-5-(2,3-dihydropyrano[4,3,2-de]quinolin-7-yl)-7-methylquinolin-6-yl)acetic acid (S)-2-tert-Butoxy-2-((R)-2-cyclohexyl-5-(2,3-dihydropyrano[4,3,2-de]quinolin-7-yl)-7-methylquinolin-6-yl)acetic acid (52) (11 mg) was prepared in a similar manner as compound (S)-2-tert-butoxy-2-((R)-5-(2,3-dihydropyrano[4,3,2-de]quinolin-7-yl)-2-isopropyl-7-methylquinolin-6-yl)acetic acid in of Example 46 except using cyclohexylmagnesium bromide instead of isopropylmagnesium bromide. ¹H-NMR 400 MHz (CD₃OD) δ 8.62 (m, 1 H), 8.13 (s, 1 H), 8.02 (d, J=8.4 Hz, 1 H), 7.65 (m, 2 H), 7.54 (m, 1 H), 7.30 (d, J=8 Hz, 1 H), 5.26 (s, 1 H), 4.65 (m, 2 H), 3.50 (m, 2 H), 3.15 (m, 1 H), 2.91 (s, 3 H), 2.1-1.35 (m, 10 H), 0.91 (s, 9 H); LCMS-ESI⁺

EXAMPLE 53

(S)-2-((R)-2-Benzyl-5-(2,3-dihydropyrano[4,3,2-de]quinolin-7-yl)-7-methylquinolin-6-yl)-2-tert-butoxyacetic acid: (53).

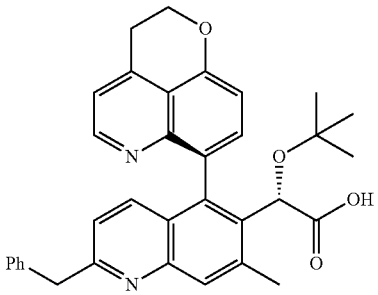

53

(S)-2-((R)-2-Benzyl-5-(2,3-dihydropyrano[4,3,2-de]quinolin-7-yl)-7-methylquinolin-6-yl)-2-tert-butoxyacetic acid (53) (8 mg) was prepared in a similar manner as compound (S)-2-tert-butoxy-2-((R)-5-(2,3-dihydropyrano[4,3,2-de]quinolin-7-yl)-2-isopropyl-7-methylquinolin-6-yl)acetic acid of Example 46 except using benzylmagnesium bromide instead of isopropylmagnesium bromide. $^1$H-NMR 400 MHz (CD$_3$OD) δ 8.61 (m, 1 H), 8.13 (s, 1 H), 7.82-7.70 (m, 2 H), 7.60 (m, 1 H), 7.4-7.2 (m, 7 H), 5.24 (s, 1 H), 4.65 (m, 2 H), 4.45 (s, 2 H), 3.55 (m, 2 H), 2.89 (s, 3 H), 0.91 (s, 9 H); LCMS-ESI$^+$ (m/z): [M+11]$^+$ calcd for C$_{34}$H$_{33}$N$_2$O$_4$: 533.3. Found: 533.2; LCMS-ESI$^-$ (m/z): [M–H]$^-$ calcd for C$_{34}$H$_{31}$N$_2$O$_4$: 531.3. Found: 531.1.

EXAMPLE 54

(S)-2-tert-Butoxy-2-((R)-5-(2,3-dihydropyrano[4,3,2-de]quinolin-7-yl)-2-(2,6-dimethylphenyl)-7-methylquinolin-6-yl)acetic acid (54).

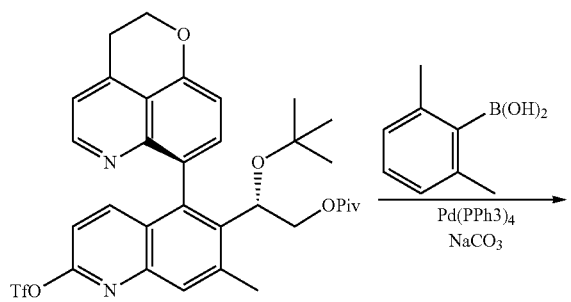

(S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate

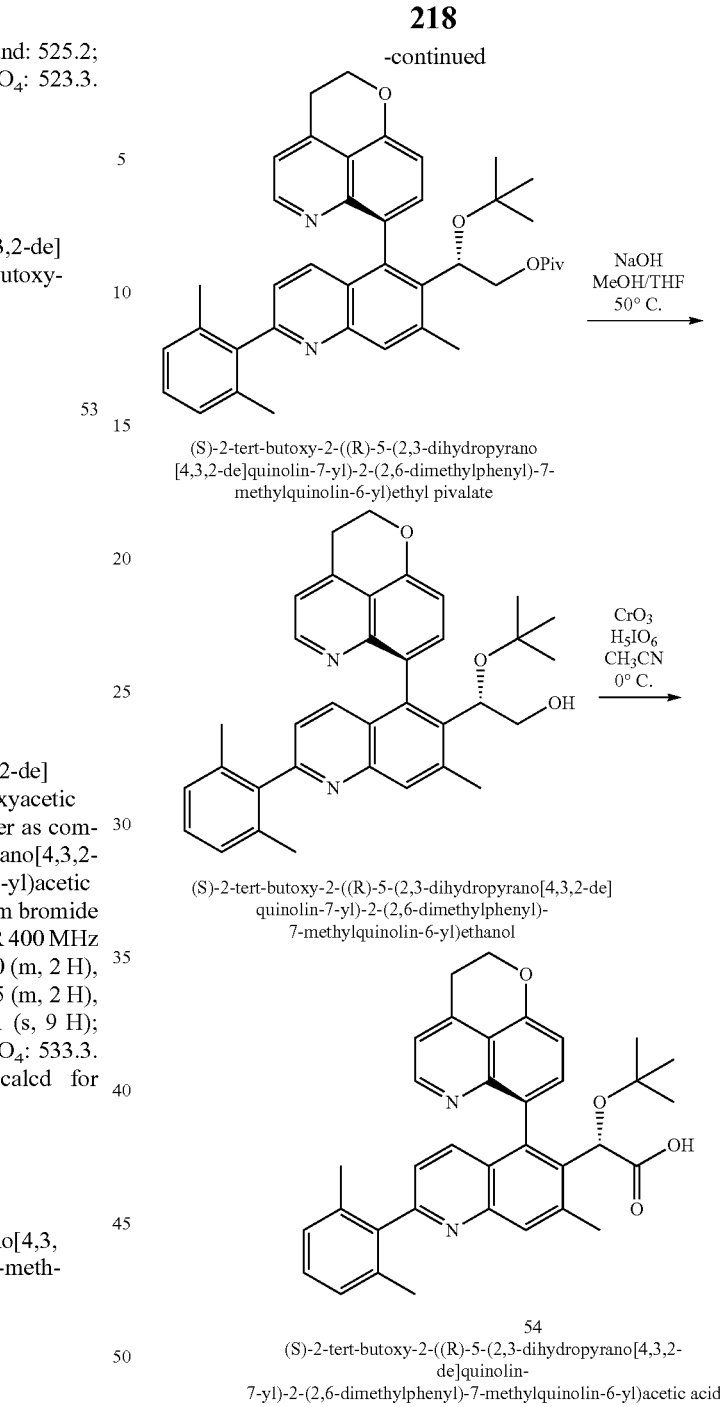

Preparation of (S)-2-tert-butoxy-2-((R)-5-(2,3-dihydropyrano[4,3,2-de]quinolin-7-yl)-2-(2,6-dimethylphenyl)-7-methylquinolin-6-yl)ethyl pivalate: (S)-2-tert-butoxy-2-((R)-5-(2,3-dihydropyrano[4,3,2-de]quinolin-7-yl)-2-(2,6-dimethylphenyl)-7-methylquinolin-6-yl)ethyl pivalate (7.5 mg) was prepared in a similar manner as compound (S)-2-tert-butoxy-2-(5-(4-chlorophenyl)-7-methyl-2-oxo-1,2-dihydroquinolin-6-yl)ethyl pivalate of Example 8 except using (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate and 2,6-dimethylphenylboronic acid instead of (S)-2-(5-bromo-7-methyl-2-oxo-1,2-dihydroquinolin-6-yl)-2-tert-butoxyethyl pivalate and 4-chlorophenylboronic acid. LCMS-ESI$^+$ (m/z): [M+H]$^+$ calcd for C$_{40}$H$_{45}$N$_2$O$_4$: 617.3. Found: 617.5.

Preparation of (S)-2-tert-butoxy-2-((R)-5-(2,3-dihydropyrano[4,3,2-de]quinolin-7-yl)-2-(2,6-dimethylphenyl)-7-methylquinolin-6-yl)ethanol: (S)-2-tert-butoxy-2-((R)-5-(2,3-dihydropyrano[4,3,2-de]quinolin-7-yl)-2-(2,6-dimethylphenyl)-7-methylquinolin-6-yl)ethanol (5.5 mg) was prepared in a similar manner as compound ((S)-2-tert-butoxy-2-(5-(4-chlorophenyl)-7-methyl-2-morpholinoquinolin-6-yl)ethanol of Example 29 except using (S)-2-tert-butoxy-2-((R)-5-(2,3-dihydropyrano[4,3,2-de]quinolin-7-yl)-2-(2,6-dimethylphenyl)-7-methylquinolin-6-yl)ethyl pivalate instead of (S)-2-tert-butoxy-2-(5-(4-chlorophenyl)-7-methyl-2-morpholinoquinolin-6-yl)ethyl pivalate. LCMS-ESI$^+$ (m/z): [M+H]$^+$ calcd for C$_{35}$H$_{37}$N$_2$O$_3$: 533.3. Found: 533.4.

Preparation of (S)-2-tert-butoxy-2-((R)-5-(2,3-dihydropyrano[4,3,2-de]quinolin-7-yl)-2-(2,6-dimethylphenyl)-7-methylquinolin-6-yl)acetic acid (54): (S)-2-tert-butoxy-2-((R)-5-(2,3-dihydropyrano[4,3,2-de]quinolin-7-yl)-2-(2,6-dimethylphenyl)-7-methylquinolin-6-yl)acetic acid (3.5 mg) was prepared in a similar manner as compound ((S)-2-tert-butoxy-2-(5-(4-chlorophenyl)-7-methyl-2-morpholinoquinolin-6-yl)acetic acid of Example 29 except using (S)-2-tert-butoxy-2-((R)-5-(2,3-dihydropyrano[4,3,2-de]quinolin-7-yl)-2-(2,6-dimethylphenyl)-7-methylquinolin-6-yl)ethanol instead of ((S)-2-tert-butoxy-2-(5-(4-chlorophenyl)-7-methyl-2-morpholinoquinolin-6-yl)ethanol. $^1$H-NMR 400 MHz (CD$_3$OD) δ 8.66 (m, 1H), 8.13 (m, 1 H), 7.95 (m, 1 H), 7.80 (m, 1 H), 7.64 (m, 1 H), 7.45 (m, 1 H), 7.4-7.25 (m, 2 H), 7.23 (m, 2 H), 5.29 (s, 1 H), 4.68 (m, 2 H), 3.57 (m, 2 H), 2.89 (s, 3 H), 2.06 (s, 6 H), 0.94 (s, 9 H); LCMS-ESI$^+$ (m/z): [M+H]$^+$ calcd for C$_{35}$H$_{35}$N$_2$O$_4$: 547.3. Found: 547.2; LCMS-ESI$^-$ (m/z): [M−H]$^-$ calcd for C$_{35}$H$_{33}$N$_2$O$_4$: 545.3. Found: 545.2.

EXAMPLE 55

(S)-2-tert-Butoxy-2-((R)-2-(3-chlorophenyl)-5-(2,3-dihydropyrano[4,3,2-de]quinolin-7-yl)-7-methylquinolin-6-yl)acetic acid (55).

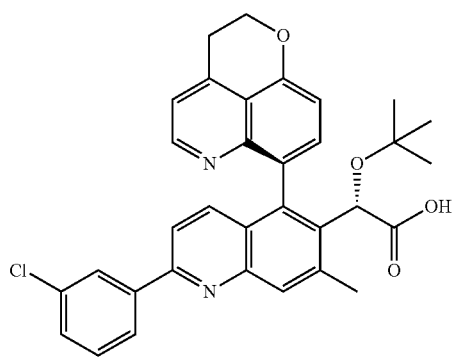

(S)-2-tert-butoxy-2-((R)-2-(3-chlorophenyl)-5-(2,3-dihydropyrano[4,3,2-de]quinolin-7-yl)-7-methylquinolin-6-yl)acetic acid (S)-2-tert-Butoxy-2-((R)-2-(3-chlorophenyl)-5-(2,3-dihydropyrano[4,3,2-de]quinolin-7-yl)-7-methylquinolin-6-yl)acetic acid (55) was prepared in a similar manner as compound (S)-2-tert-butoxy-2-((R)-5-(2,3-dihydropyrano[4,3,2-de]quinolin-7-yl)-2-(2,6-dimethylphenyl)-7-methylquinolin-6-yl)acetic acid (3.5 mg) of Example 54 except using 3-chlorophenylboronic acid instead of 2,6-dimethylphenylboronic acid. $^1$H-NMR 400 MHz (CD$_3$OD) δ 8.71 (d, J=5.6 Hz, 1 H), 8.23 (s, 1 H), 8.20 (s, 1 H), 8.04 (m, 1 H), 7.9-7.75 (m, 3 H), 7.6-7.4 (m, 4 H), 5.27 (s, 1 H), 4.74 (m, 2 H), 3.66 (m, 2H), 2.86 (s, 3 H), 0.95 (s, 9 H); LCMS-LCMS-ESI$^+$ (m/z): [M+H]$^+$ calcd for C$_{33}$H$_{30}$ClN$_2$O$_4$: 553.2. Found: 553.1; LCMS-ESI$^-$ (m/z): [M−H]$^-$ calcd for C$_{33}$H$_{28}$ClN$_2$O$_4$: 551.2. Found: 551.1.

EXAMPLE 56

(S)-2-tert-Butoxy-2-((R)-2-(4-chlorophenyl)-5-(2,3-dihydropyrano[4,3,2-de]quinolin-7-yl)-7-methylquinolin-6-yl)acetic acid (56).

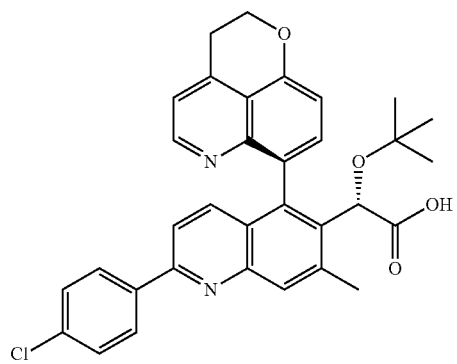

(S)-2-tert-Butoxy-2-((R)-2-(4-chlorophenyl)-5-(2,3-dihydropyrano[4,3,2-de]quinolin-7-yl)-7-methylquinolin-6-yl)acetic acid (56) was prepared in a similar manner as compound (S)-2-tert-butoxy-2-((R)-5-(2,3-dihydropyrano[4,3,2-de]quinolin-7-yl)-2-(2,6-dimethylphenyl)-7-methylquinolin-6-yl)acetic acid (3.5 mg) of Example 54 except using 4-chlorophenylboronic acid instead of 2,6-dimethylphenylboronic acid. $^1$H-NMR 400 MHz (CD$_3$OD) δ 8.70 (d, J=5.2 Hz, 1 H), 8.22 (s, 1 H), 8.13 (d, J=8.4 HZ, 2 H), 7.9-7.75 (m, 3 H), 7.6-7.5 (m, 2 H), 7.46 (d, J=8 Hz, 1 H), 7.35 (d, J=8.4 Hz, 1 H), 5.27 (s, 1 H), 4.75 (m, 2 H), 3.64 (m, 2 H), 2.86 (s, 3 H), 0.95 (s, 9 H). LCMS-ESI$^+$ (m/z): [M+H]$^+$ calcd for $C_{33}H_{30}ClN_2O_4$: 553.2. Found: 553.1; LCMS-ESI⁻ (m/z): [M–H]⁻ calcd for $C_{33}H_{28}ClN_2O_4$: 551.2. Found: 551.1.

EXAMPLE 57

(S)-2-tert-Butoxy-2-((R)-5-(2,3-dihydropyrano[4,3,2-de]quinolin-7-yl)-7-methyl-2-phenylquinolin-6-yl)acetic acid (57).

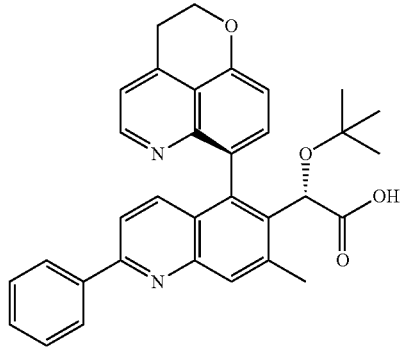

(S)-2-tert-Butoxy-2-((R)-5-(2,3-dihydropyrano[4,3,2-de]quinolin-7-yl)-7-methyl-2-phenylquinolin-6-yl)acetic acid (57) was prepared in a similar manner as compound (S)-2-tert-butoxy-2-((R)-5-(2,3-dihydropyrano[4,3,2-de]quinolin-7-yl)-2-(2,6-dimethylphenyl)-7-methylquinolin-6-yl)acetic acid (3.5 mg) of Example 54 except using phenylboronic acid instead of 2,6-dimethylphenylboronic acid. ¹H-NMR 400 MHz (CD₃OD) δ 8.71 (m, 1 H), 8.24 (m, 1 H), 8.12 (m, 2 H), 7.85 (m, 2 H), 7.75 (m, 2H), 7.60 (m, 3 H), 7.43 (d, J=8 Hz, 1 H), 5.28 (s, 1 H), 4.69 (m, 2 H), 3.63 (m, 2 H), 2.88 (s, 3 H), 0.95 (s, 9 H); LCMS-ESI⁺ (m/z): [M+H]⁺ calcd for $C_{33}H_{31}N_2O_4$: 519.2. Found: 519.1.

EXAMPLE 58

(S)-2-tert-Butoxy-2-((R)-2-cyclopropyl-5-(2,3-dihydropyrano[4,3,2-de]quinolin-7-yl)-7-methylquinolin-6-yl)acetic acid (58).

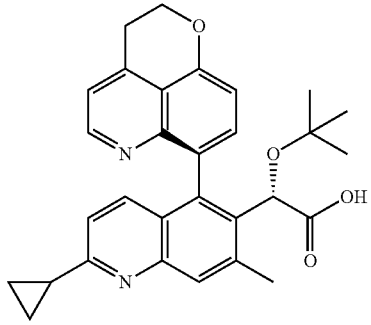

(S)-2-tert-Butoxy-2-((R)-2-cyclopropyl-5-(2,3-dihydropyrano[4,3,2-de]quinolin-7-yl)-7-methylquinolin-6-yl)acetic acid (58) was prepared in a similar manner as compound (S)-2-tert-butoxy-2-((R)-5-(2,3-dihydropyrano[4,3,2-de]quinolin-7-yl)-2-(2,6-dimethylphenyl)-7-methylquinolin-6-yl)acetic acid (3.5 mg) of Example 54 except using cyclopropylboronic acid instead of 2,6-dimethylphenylboronic acid. ¹H-NMR 400 MHz (CD₃OD) δ 8.65 (d, J=5.2 Hz, 1 H), 8.07 (s, 1 H), 7.86 (d, J=8.8 Hz, 1 H), 7.69 (d, J=8 Hz, 1 H), 7.56 (d, J=4.8 Hz, 1 H), 7.31 (d, J=8.4 Hz, 1 H), 7.18 (d, J=8.8 Hz, 1 H), 5.24 (s, 1 H), 4.65 (m, 2 H), 3.51 (m, 2 H), 2.90 (s, 3 H), 2.50 (m, 1 H), 1.54 (m, 2 H), 1.30 (m, 2 H), 0.92 (s, 9 H); LCMS-ESI⁺ (m/z): [M+H]⁺ calcd for $C_{30}H_{31}N_2O_4$: 483.2. Found: 483.2; LCMS-ESI (m/z): [M–H]⁻ calcd for $C_{30}H_{29}N_2O_4$: 481.2. Found: 481.2.

EXAMPLE 59

(S)-2-(1,5-Bis(4-chlorophenyl)-7-methyl-2-oxo-1,2-dihydroquinolin-6-yl)-2-tert-butoxyacetic acid: (59).

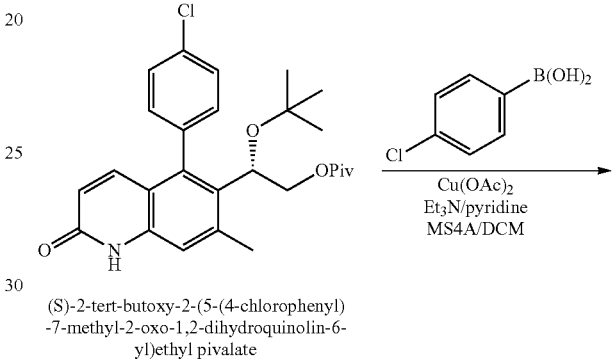

(S)-2-tert-butoxy-2-(5-(4-chlorophenyl)-7-methyl-2-oxo-1,2-dihydroquinolin-6-yl)ethyl pivalate

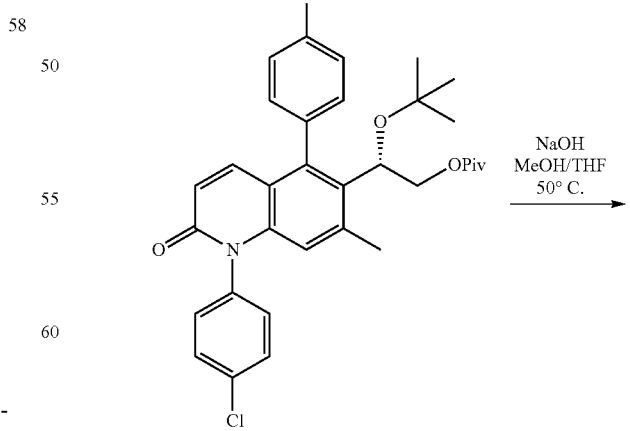

(S)-2-(1-bis(4-chlorophenyl)-7-methyl-2-oxo-1,2-dihydroquinolin-6-yl)-2-tert-butoxyethyl pivalate

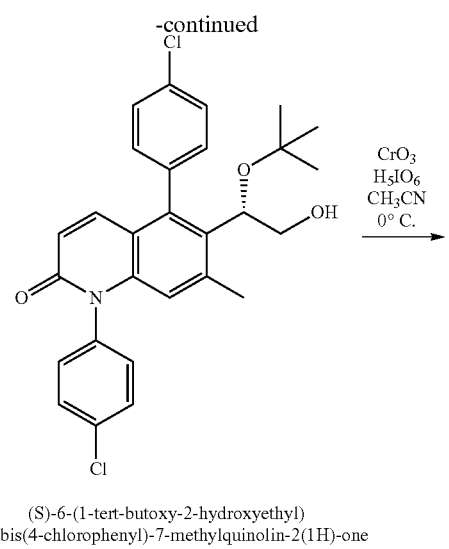

(S)-6-(1-tert-butoxy-2-hydroxyethyl)
-1,5-bis(4-chlorophenyl)-7-methylquinolin-2(1H)-one

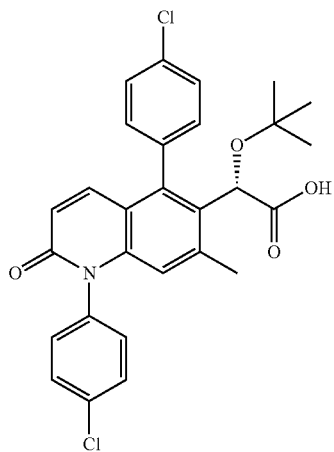

59

(S)-2-(1,5-bis(4-chlorophenyl)-7-methyl-2-oxo-1,2-
dihydroquinolin-6-yl)-2-tert-butoxyacetic acid Preparation of (S)-2-(1,5-bis(4-chlorophenyl)-7-methyl-2-oxo-1,2-dihydroquinolin-6-yl)-2-tert-butoxyethyl pivalate: To the solution of (S)-2-tert-butoxy-2-(5-(4-chlorophenyl)-7-methyl-2-oxo-1,2-dihydroquinolin-6-yl)ethyl pivalate (8J) (23 mg, 0.05 mmol) and 4-chlorophenylboronic acid (16 mg, 0.10 mmol) in dichloromethane (2 mL) was added copper (II) acetate (9 mg), followed by molecular sieve 4 Å and pyridine (82 µL). The mixture was stirred for 5 days, and filtered and washed with ethyl acetate. Concentration and purification by flash column chromatography (hexanes/EtOAc) gave (S)-2-(1,5-bis(4-chlorophenyl)-7-methyl-2-oxo-1,2-dihydroquinolin-6-yl)-2-tert-butoxyethyl pivalate (25 mg). LCMS-ESI⁺ (m/z): [M+H]⁺ calcd for $C_{33}H_{36}Cl_2NO_4$: 580.2. Found: 580.0.

Preparation of ((S)-6-(1-tert-butoxy-2-hydroxyethyl)-1,5-bis(4-chlorophenyl)-7-methylquinolin-2(1H)-one: (S)-6-(1-tert-butoxy-2-hydroxyethyl)-1,5-bis(4-chlorophenyl)-7-methylquinolin-2(1H)-one was prepared in a similar manner as compound ((S)-2-tert-butoxy-2-(5-(4-chlorophenyl)-7-methyl-2-morpholinoquinolin-6-yl)ethanol of Example 29 except using (S)-2-(1,5-bis(4-chlorophenyl)-7-methyl-2-oxo-1,2-dihydroquinolin-6-yl)-2-tert-butoxyethyl pivalate instead of (S)-2-tert-butoxy-2-(5-(4-chlorophenyl)-7-methyl-2-morpholinoquinolin-6-yl)ethyl pivalate. LCMS-ESI⁺ (m/z): [M+H]⁺ calcd for $C_{28}H_{28}Cl_2NO_3$: 496.1. Found: 496.3.

Preparation of ((S)-2-(1,5-bis(4-chlorophenyl)-7-methyl-2-oxo-1,2-dihydroquinolin-6-yl)-2-tert-butoxyacetic acid (59): (S)-2-(1,5-bis(4-chlorophenyl)-7-methyl-2-oxo-1,2-dihydroquinolin-6-yl)-2-tert-butoxyacetic acid was prepared in a similar manner as compound ((S)-2-tert-butoxy-2-(5-(4-chlorophenyl)-7-methyl-2-morpholinoquinolin-6-yl)acetic acid of Example 29 except using (S)-6-(1-tert-butoxy-2-hydroxyethyl)-1,5-bis(4-chlorophenyl)-7-methylquinolin-2(1H)-one instead of ((S)-2-tert-butoxy-2-(5-(4-chlorophenyl)-7-methyl-2-morpholinoquinolin-6-yl)ethanol.
¹H-NMR 400 MHz (CD₃OD) 7.51 (m, 3 H), 7.46 (m, 2 H), 7.25 (d, J=9.6 Hz, 1 H), 7.2-7.15 (m, 3 H), 6.52 (d, J=9.6 Hz, 1 H), 6.42 (s, 1 H), 5.05 (s, 1 H), 2.28 (s, 3 H), 0.93 (s, 9 H); LCMS-ESI⁺ (m/z): [M+H]⁺ calcd for $C_{28}H_{26}Cl_2NO_4$: 510.1. Found: 510.1.

EXAMPLE 60

(S)-2-tert-Butoxy-2-((R)-6-(2,3-dihydropyrano[4,3,2-de]quinolin-7-yl)-2-isopropyl-8-methylimidazo[1,2-a]quinolin-7-yl)acetic acid: (60).

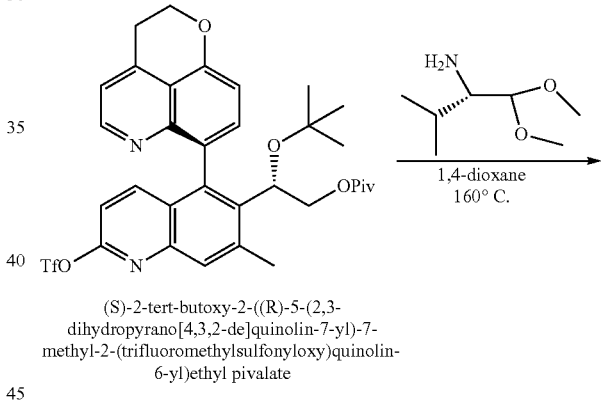

(S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate

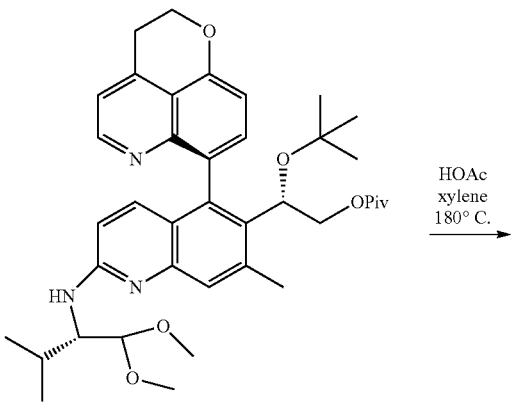

(S)-2-tert-butoxy-2-((R)-5-(2,3-dihydropyrano[4,3,2-de]quinolin-7-yl)-2-((S)-1,1-dimethoxy-3-methylbutan-2-ylamino)-7-methylquinolin-6-yl)ethyl pivalate

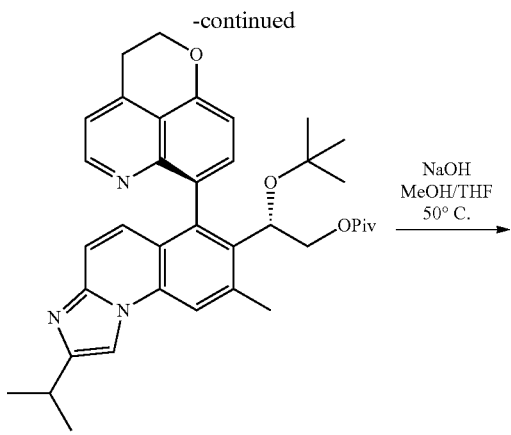

(S)-2-tert-butoxy-2-((R)-6-(2,3-dihydropyrano
[4,3,2-de]quinolin-7-yl)-2-isopropyl-8-methylimidazo[1,2-
a]quinolin-7-yl)ethyl pivalate

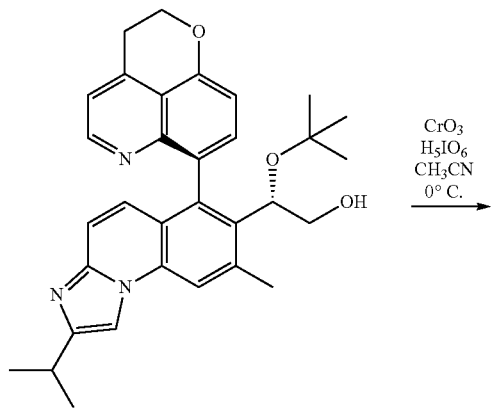

(S)-2-tert-butoxy-2-((R)-6-(2,3-dihydropyrano
[4,3,2-de]quinolin-7-yl)-2-isopropyl-8-methylimidazo
[1,2-a]quinolin-7-yl)ethyanol

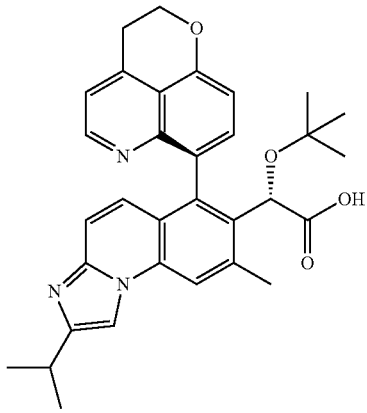

60

(S)-2-tert-butoxy-2-((R)-6-(2,3-
dihydropyrano[4,3,2-de]quinolin-7-yl)
-2-isopropyl-8-methylimidazo
[1,2-a]quinolin-7-yl)acetic acid Preparation of (S)-2-tert-butoxy-2-((R)-5-(2,3-dihydropyrano[4,3,2-de]quinolin-7-yl)-2-((S)-1,1-dimethoxy-3-methylbutan-2-ylamino)-7-methylquinolin-6-yl)ethyl pivalate: The mixture of (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate (compound of Example 36) (30 mg) and (S)-1,1-dimethoxy-3-methylbutan-2-amine (70 mg) in 1,4-dioxane (1 mL) was heated at 160° C. for 10 hours. The solution was diluted with ethyl acetate, and was washed with 1.0 N sodium hydroxide solution and brine, and dried with sodium sulfate. Concentration and purification by flash column chromatography (hexanes/EtOAc) gave (S)-2-tert-butoxy-2-((R)-5-(2,3-dihydropyrano[4,3,2-de]quinolin-7-yl)-2-((S)-1,1-dimethoxy-3-methylbutan-2-ylamino)-7-methylquinolin-6-yl)ethyl pivalate (22 mg). LCMS-ESI$^+$ (m/z): [M+H]$^+$ calcd for $C_{39}H_{52}N_3O_6$: 658.4. Found: 658.3.

Preparation of (S)-2-tert-butoxy-2-((R)-6-(2,3-dihydropyrano[4,3,2-de]quinolin-7-yl)-2-isopropyl-8-methylimidazo[1,2-a]quinolin-7-yl)ethyl pivalate: The mixture of (S)-2-tert-butoxy-2-((R)-5-(2,3-dihydropyrano[4,3,2-de]quinolin-7-yl)-2-((S)-1,1-dimethoxy-3-methylbutan-2-ylamino)-7-methylquinolin-6-yl)ethyl pivalate (22 mg) and acetic acid (0.1 mL) in xylene (2 mL) was heated at 180° C. for 90 minutes. The solution was diluted with ethyl acetate, and was washed with 1.0 N sodium hydroxide solution and brine, and dried with sodium sulfate. Concentration and purification by flash column chromatography (hexanes/EtOAc) gave (S)-2-tert-butoxy-2-((R)-6-(2,3-dihydropyrano[4,3,2-de]quinolin-7-yl)-2-isopropyl-8-methylimidazo[1,2-a]quinolin-7-yl) ethyl pivalate (8.7 mg). LCMS-ESI$^+$ (m/z): [M+H]$^+$ calcd for $C_{37}H_{44}N_3O_4$: 594.3; Found: 594.4.

Preparation of (S)-2-tert-butoxy-2-((R)-6-(2,3-dihydropyrano[4,3,2-de]quinolin-7-yl)-2-isopropyl-8-methylimidazo[1,2-a]quinolin-7-yl)ethanol: (S)-2-tert-butoxy-2-((R)-6-(2,3-dihydropyrano[4,3,2-de]quinolin-7-yl)-2-isopropyl-8-methylimidazo[1,2-a]quinolin-7-yl)ethanol was prepared in a similar manner as compound ((S)-2-tert-butoxy-2-(5-(4-chlorophenyl)-7-methyl-2-morpholinoquinolin-6-yl)ethanol of Example 29 except using (S)-2-tert-butoxy-2-((R)-6-(2,3-dihydropyrano[4,3,2-de]quinolin-7-yl)-2-isopropyl-8-methylimidazo[1,2-a]quinolin-7-yl)ethyl pivalate instead of (S)-2-tert-butoxy-2-(5-(4-chlorophenyl)-7-methyl-2-morpholinoquinolin-6-yl)ethyl pivalate. LCMS-ESI$^+$ (m/z): [M+H]$^+$ calcd for $C_{32}H_{36}N_3O_3$: 510.3. Found: 510.3.

Preparation of (S)-2-tert-butoxy-2-((R)-6-(2,3-dihydropyrano[4,3,2-de]quinolin-7-yl)-2-isopropyl-8-methylimidazo[1,2-a]quinolin-7-yl)acetic acid (60): (S)-2-tert-Butoxy-2-((R)-6-(2,3-dihydropyrano[4,3,2-de]quinolin-7-yl)-2-isopropyl-8-methylimidazo[1,2-a]quinolin-7-yl)acetic acid was prepared in a similar manner as compound ((S)-2-tert-butoxy-2-(5-(4-chlorophenyl)-7-methyl-2-morpholinoquinolin-6-yl)acetic acid of Example 29 except using (S)-2-tert-butoxy-2-((R)-6-(2,3-dihydropyrano[4,3,2-de]quinolin-7-yl)-2-isopropyl-8-methylimidazo[1,2-a]quinolin-7-yl) ethanol instead of ((S)-2-tert-butoxy-2-(5-(4-chlorophenyl)-7-methyl-2-morpholinoquinolin-6-yl)ethanol. $^1$H-NMR 400 MHz (CD$_3$OD) δ 8.8 (s, 1 H), 8.65 (d, J=5.2 Hz, 1 H), 8.58 (s, 1 H), 7.7 (m, 1 H), 7.6 (m, 1 H), 7.4-7.2 (m, 3 H), 5.23 (s, 1H), 4.65 (m, 2 H), 3.55 (m, 2 H), 3.3 (m, 1 H), 2.93 (s, 3 H), 1.50 (d, J=6.8 Hz, 6 H), 0.93 (s, 9 H); LCMS-ESI$^+$ (m/z): [M+H]$^+$ calcd for $C_{32}H_{34}N_3O_4$: 524.3. Found: 524.2; LCMS-ESI$^-$ (m/z): [M−H]$^-$ calcd for $C_{32}H_{32}N_3O_4$: 522.3. Found: 522.1.

EXAMPLE 61

(S)-2-tert-Butoxy-2-((R)-6-(2,3-dihydropyrano[4,3,2-de]quinolin-7-yl)-8-methyl-2-phenylimidazo[1,2-a]quinolin-7-yl)acetic acid (61).

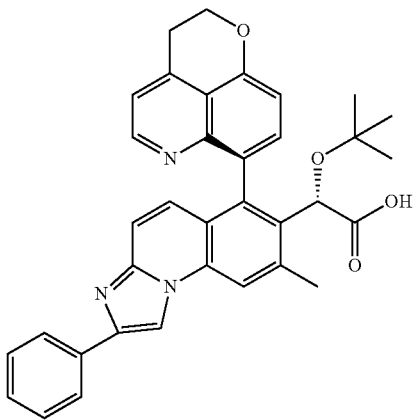

61

(S)-2-tert-butoxy-2-((R)-6-(2,3-dihydropyrano[4,3,2-de]quinolin-7-yl)-8-methyl-2-phenylimidazo[1,2-a]quinolin-7-yl)acetic acid (S)-2-tert-Butoxy-2-((R)-6-(2,3-dihydropyrano[4,3,2-de]quinolin-7-yl)-8-methyl-2-phenylimidazo[1,2-a]quinolin-7-yl)acetic acid (61) (2.9 mg) was prepared in a similar manner as compound (S)-2-tert-butoxy-2-((R)-6-(2,3-dihydropyrano[4,3,2-de]quinolin-7-yl)-2-isopropyl-8-methylimidazo[1,2-a]quinolin-7-yl)acetic acid of Example 60 except using 2,2-dimethoxy-1-phenylethanamine instead of (S)-1,1-dimethoxy-3-methylbutan-2-amine. $^1$H-NMR 400 MHz (CD$_3$OD) δ 9.34 (s, 1 H), 8.67 (m, 1 H), 8.60 (m, 1 H), 7.98 (m, 2 H), 7.7 (m, 1 H), 7.6-7.4 (m, 5 H), 7.3 (m, 2 H), 5.25 (s, 1 H), 4.66 (m, 2 H), 3.54 (m, 2 H), 2.95 (s, 3 H), 0.95 (s, 9 H); LCMS-ESI$^+$ (m/z): [M+H]$^+$ calcd for C$_{35}$H$_{32}$N$_3$O$_4$: 558.2. Found: 558.2; Lcms-ESI$^-$ (m/z): [m-H]$^-$ calcd for C$_{35}$H$_{30}$N$_3$O$_4$: 556.2. Found: 556.1.

EXAMPLE 62

(S)-2-tert-Butoxy-2-(6-(4-chlorophenyl)-8-methylimidazo[1,2-a]quinolin-7-yl)acetic acid (62).

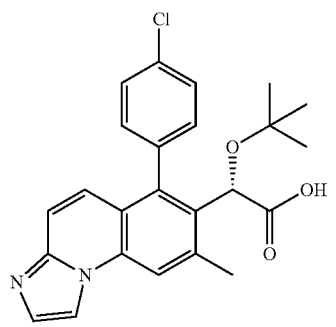

62

(S)-2-tert-butoxy-2-(6-(4-chlorophenyl)-8-methylimidazo[1,2-a]quinolin-7-yl)acetic acid (S)-2-tert-Butoxy-2-(6-(4-chlorophenyl)-8-methylimidazo[1,2-a]quinolin-7-yl)acetic acid (62) was prepared in a similar manner as compound (S)-2-tert-butoxy-2-((R)-6-(2,3-dihydropyrano[4,3,2-de]quinolin-7-yl)-2-isopropyl-8-methylimidazo[1,2-a]quinolin-7-yl)acetic acid of Example 60 except using (S)-2-tert-butoxy-2-(5-(4-chlorophenyl)-7-methyl-2-(trifluoromethylsulfonyloxy)quinolin-6-yl)ethyl pivalate and 2,2-dimethoxyethanamine instead of (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate and (S)-1,1-dimethoxy-3-methylbutan-2-amine. $^1$H-NMR 400 MHz (CD$_3$OD) δ 8.92 (m, 1 H), 8.45 (m, 1 H), 8.10 (m, 1 H), 7.7-7.6 (m, 5 H), 7.38 (m, 1 H), 5.21 (s, 1 H), 2.80 (s, 3 H), 0.99 (s, 9 H); LCMS-ESI$^+$ (m/z): [M+H]$^+$ calcd for C$_{24}$H$_{24}$ClN$_2$O$_3$: 423. Found: 423.2; LCMS-ESI$^+$ (m/z): [M+H]$^+$ calcd for C$_{24}$H$_{22}$ClN$_2$O$_3$: 421.1. Found: 421.0.

EXAMPLE 63

(S)-2-tert-butoxy-2-(6-(4-chlorophenyl)-8-methyl-[1,2,4]triazolo[4,3-a]quinolin-7-yl)acetic acid (63).

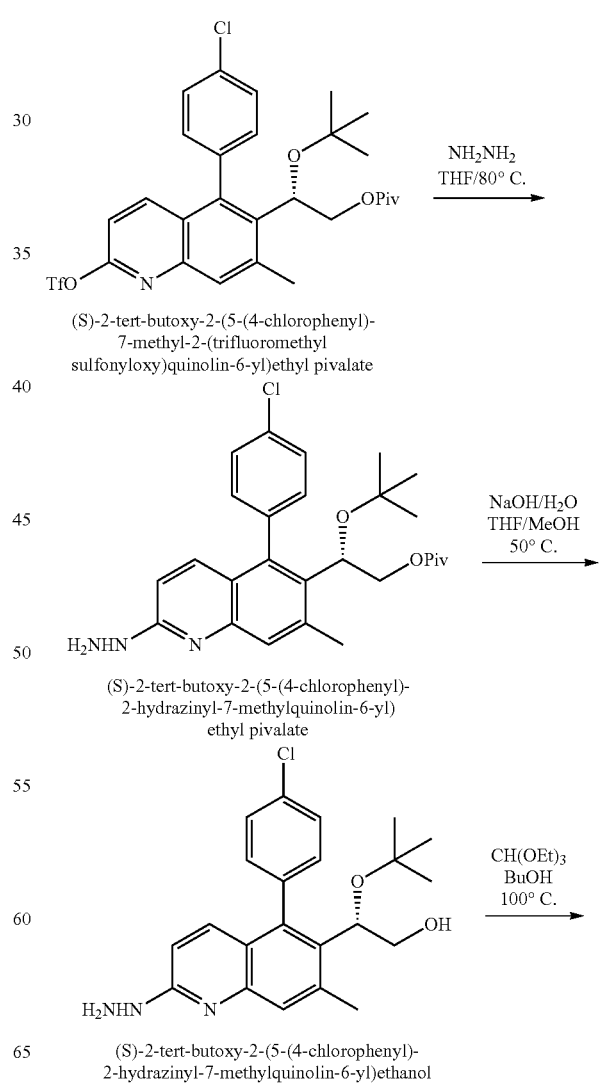

229

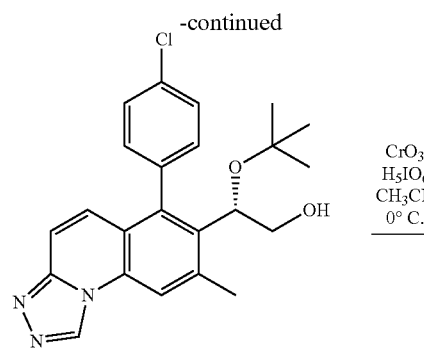

(S)-2-tert-butoxy-2-(6-(4-chlorophenyl)-
8-methyl-[1,2,4]triazolo[4,3-a]quinolin-7-yl)
ethanol

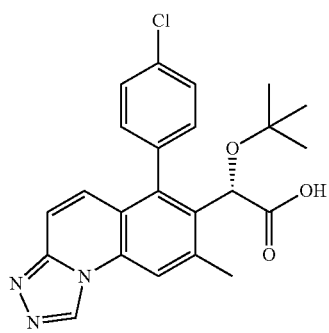

63

(S)-2-tert-butoxy-2-(6-(4-chlorophenyl)-
8-methyl-[1,2,4]triazolo[4,3-a]quinolin-7-yl)
acetic acid Preparation of (S)-2-tert-butoxy-2-(5-(4-chlorophenyl)-2-hydrazinyl-7-methylquinolin-6-yl)ethyl pivalate: The mixture of (S)-2-tert-butoxy-2-(5-(4-chlorophenyl)-7-methyl-2-(trifluoromethylsulfonyloxy)quinolin-6-yl)ethyl pivalate (compound of Example 26) (10 mg) and hydrazine in THF (1.0 N, 1 mL, 1 mmol) was heated at 80° C. for 12 hours. Concentration under reduced pressure gave (S)-2-tert-butoxy-2-(5-(4-chlorophenyl)-2-hydrazinyl-7-methylquinolin-6-yl)ethyl pivalate, which was used for next step without purification. LCMS-ESI$^+$ (m/z): [M+H]$^+$ calcd for $C_{27}H_{35}ClN_3O_3$: 484.2. Found: 484.3.

Preparation of (S)-2-tert-butoxy-2-(5-(4-chlorophenyl)-2-hydrazinyl-7-methylquinolin-6-yl)ethanol: (S)-2-tert-butoxy-2-(5-(4-chlorophenyl)-2-hydrazinyl-7-methylquinolin-6-yl)ethanol was prepared in a similar manner as compound ((S)-2-tert-butoxy-2-(5-(4-chlorophenyl)-7-methyl-2-morpholinoquinolin-6-yl)ethanol of Example 29 except using (S)-2-tert-butoxy-2-(5-(4-chlorophenyl)-2-hydrazinyl-7-methylquinolin-6-yl)ethyl pivalate instead of (S)-2-tert-butoxy-2-(5-(4-chlorophenyl)-7-methyl-2-morpholinoquinolin-6-yl)ethyl pivalate. LCMS-ESI$^+$ (m/z): [M+H]$^+$ calcd for $C_{22}H_{27}ClN_3O_2$: 400.2. Found: 400.2.

Preparation of (S)-2-tert-butoxy-2-(6-(4-chlorophenyl)-8-methyl-[1,2,4]triazolo[4,3-a]quinolin-7-yl)ethanol: The mixture of (S)-2-tert-butoxy-2-(5-(4-chlorophenyl)-2-hydrazinyl-7-methylquinolin-6-yl)ethanol and triethyl orthoformate (0.5 mL) in butanol (5 mL) was heated at 100° C. for 12 hours. The solution was diluted with ethyl acetate, and was washed with 1.0 N sodium hydroxide solution and brine, and dried with sodium sulfate. Concentration and purification by flash column chromatography (hexanes/EtOAc) gave (S)-2-tert-butoxy-2-(6-(4-chlorophenyl)-8-methyl-[1,2,4]triazolo

230

[4,3-a]quinolin-7-yl)ethanol (3.3 mg). LCMS-ESI$^+$ (m/z): [M+H]$^+$ calcd for $C_{23}H_{25}ClN_3O_2$: 410.2. Found: 410.2.

Preparation of (S)-2-tert-butoxy-2-(6-(4-chlorophenyl)-8-methyl-[1,2,4]triazolo[4,3-a]quinolin-7-yl)acetic acid (63): (S)-2-tert-butoxy-2-(6-(4-chlorophenyl)-8-methyl-[1,2,4]triazolo[4,3-a]quinolin-7-yl)acetic acid was prepared in a similar manner as compound ((S)-2-tert-butoxy-2-(5-(4-chlorophenyl)-7-methyl-2-morpholinoquinolin-6-yl)acetic acid of Example 29 except using (S)-2-tert-butoxy-2-(6-(4-chlorophenyl)-8-methyl-[1,2,4]triazolo[4,3-a]quinolin-7-yl)ethanol instead of ((S)-2-tert-butoxy-2-(5-(4-chlorophenyl)-7-methyl-2-morpholinoquinolin-6-yl)ethanol. $^1$H-NMR 400 MHz (CD$_3$OD) δ 9.95 (s, 1 H), 8.34 (s, 1 H), 7.6 (m, 3 H), 7.54 (m, 1 H), 7.35 (m, 2 H), 5.17 (s, 1 H), 2.75 (s, 3 H), 0.99 (s, 9 H); LCMS-ESI$^+$ (m/z): [M+H]$^+$ calcd for $C_{23}H_{23}ClN_3O_3$: 424.1. Found: 424.2; LCMS-EST (m/z): [M−H]$^−$ calcd for $C_{23}H_{21}ClN_3O_3$: 422.1 Found: 421.9.

EXAMPLE 64

(S)-2-tert-butoxy-2-(6-(4-chlorophenyl)-8-methyltetrazolo[1,5-a]quinolin-7-yl)acetic acid (64).

Scheme 9

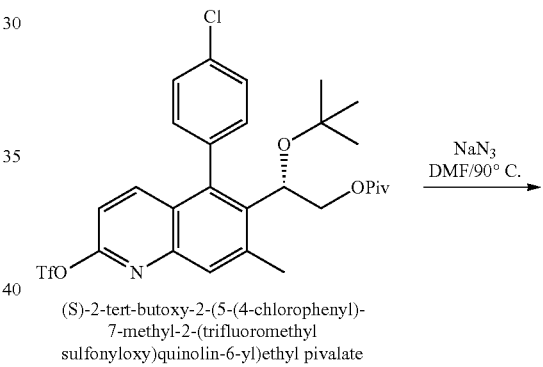

(S)-2-tert-butoxy-2-(5-(4-chlorophenyl)-
7-methyl-2-(trifluoromethyl
sulfonyloxy)quinolin-6-yl)ethyl pivalate

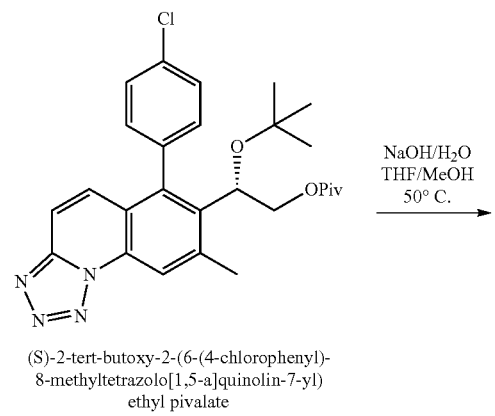

(S)-2-tert-butoxy-2-(6-(4-chlorophenyl)-
8-methyltetrazolo[1,5-a]quinolin-7-yl)
ethyl pivalate

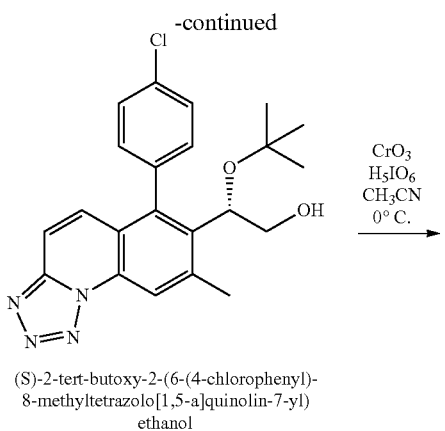

(S)-2-tert-butoxy-2-(6-(4-chlorophenyl)-
8-methyltetrazolo[1,5-a]quinolin-7-yl)
ethanol

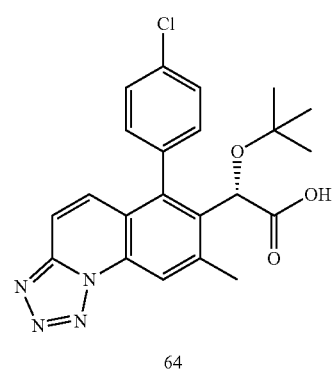

64

(S)-2-tert-butoxy-2-(6-(4-chlorophenyl)-
8-methyltetrazolo[1,5-a]quinolin-7-yl)
acetic acid Preparation of (S)-2-tert-butoxy-2-(6-(4-chlorophenyl)-8-methyltetrazolo[1,5-a]quinolin-7-yl)ethyl pivalate: The mixture of (S)-2-tert-butoxy-2-(5-(4-chlorophenyl)-7-methyl-2-(trifluoromethylsulfonyloxy)quinolin-6-yl)ethyl pivalate (compound of Example 26)(30 mg) and sodium azide (32 mg) in DMF (1 mL) was heated at 90° C. for 4 hours. The mixture was diluted with ethyl acetate, and washed with water and brine, and dried with sodium sulfate. Concentration and purification by flash column chromatography (hexanes/EtOAc) gave (S)-2-tert-butoxy-2-(6-(4-chlorophenyl)-8-methyltetrazolo[1,5-a]quinolin-7-yl)ethyl pivalate (5.9 mg). LCMS-ESI+ (m/z): [M+H]+ calcd for $C_{27}H_{32}ClN_4O_3$: 495.2. Found: 495.2.

Preparation of (S)-2-tert-butoxy-2-(6-(4-chlorophenyl)-8-methyltetrazolo[1,5-a]quinolin-7-yl)ethanol: (S)-2-tert-butoxy-2-(6-(4-chlorophenyl)-8-methyltetrazolo[1,5-a]quinolin-7-yl)ethanol (5 mg) was prepared in a similar manner as compound ((S)-2-tert-butoxy-2-(5-(4-chlorophenyl)-7-methyl-2-morpholinoquinolin-6-yl)ethanol of Example 29 except using (S)-2-tert-butoxy-2-(6-(4-chlorophenyl)-8-methyltetrazolo[1,5-a]quinolin-7-yl)ethyl pivalate instead of (S)-2-tert-butoxy-2-(5-(4-chlorophenyl)-7-methyl-2-morpholinoquinolin-6-yl)ethyl pivalate. LCMS-ESI+ (m/z): [M+H]+ calcd for $C_{22}H_{24}ClN_4O_2$: 411.2. Found: 411.1.

Preparation of (S)-2-tert-butoxy-2-(6-(4-chlorophenyl)-8-methyltetrazolo[1,5-a]quinolin-7-yl)acetic acid (64): (S)-2-tert-butoxy-2-(6-(4-chlorophenyl)-8-methyltetrazolo[1,5-a]quinolin-7-yl)acetic acid (4.9 mg) was prepared in a similar manner as compound ((S)-2-tert-butoxy-2-(5-(4-chlorophenyl)-7-methyl-2-morpholinoquinolin-6-yl)acetic acid of Example 29 except using (S)-2-tert-butoxy-2-(6-(4-chlorophenyl)-8-methyltetrazolo[1,5-a]quinolin-7-yl)ethanol instead of ((S)-2-tert-butoxy-2-(5-(4-chlorophenyl)-7-methyl-2-morpholinoquinolin-6-yl)ethanol. $^1$H-NMR 400 MHz (CD$_3$OD) 8.61 (s, 1 H), 7.75 (d, J=9.6 Hz, 1 H), 7.67-7.55 (m, 4 H), 7.39 (d, J=9.2 HZ, 1 H), 5.2 (s, 1 H), 2.79 (s, 3 H), 1.00 (s, 9 H); LCMS-ESI+ (m/z): [M+H]+ calcd for $C_{22}H_{22}ClN_4O_3$: 425.1. Found: 425.1.

EXAMPLE 65

(S)-2-(2-(benzyloxy)-5-(4-chlorophenyl)-7-methylquinolin-6-yl)-2-tert-butoxyacetic acid (65A) and
(S)-2-(1-benzyl-5-(4-chlorophenyl)-7-methyl-2-oxo-1,2-dihydroquinolin-6-yl)-2-tert-butoxyacetic acid (65B)

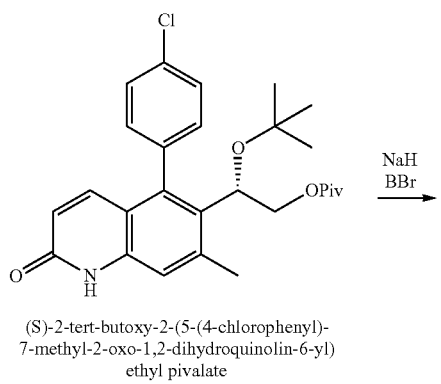

(S)-2-tert-butoxy-2-(5-(4-chlorophenyl)-
7-methyl-2-oxo-1,2-dihydroquinolin-6-yl)
ethyl pivalate

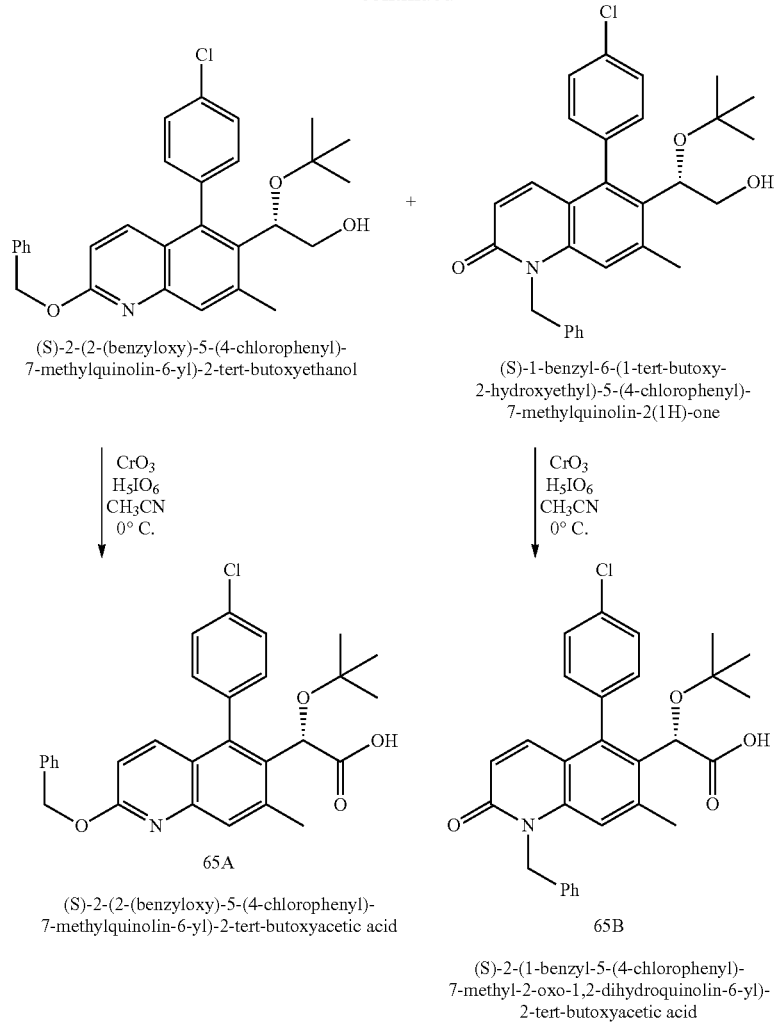

(S)-2-(2-(benzyloxy)-5-(4-chlorophenyl)-
7-methylquinolin-6-yl)-2-tert-butoxyethanol (S)-1-benzyl-6-(1-tert-butoxy-
2-hydroxyethyl)-5-(4-chlorophenyl)-
7-methylquinolin-2(1H)-one 65A
(S)-2-(2-(benzyloxy)-5-(4-chlorophenyl)-
7-methylquinolin-6-yl)-2-tert-butoxyacetic acid 65B
(S)-2-(1-benzyl-5-(4-chlorophenyl)-
7-methyl-2-oxo-1,2-dihydroquinolin-6-yl)-
2-tert-butoxyacetic acid Preparation of (S)-2-(2-(benzyloxy)-5-(4-chlorophenyl)-7-methylquinolin-6-yl)-2-tert-butoxyethanol and (S)-1-benzyl-6-(1-tert-butoxy-2-hydroxyethyl)-5-(4-chlorophenyl)-7-methylquinolin-2(1H)-one: To the solution of (S)-2-tert-butoxy-2-(5-(4-chlorophenyl)-7-methyl-2-oxo-1,2-dihydroquinolin-6-yl)ethyl pivalate (8J) (16 mg, 0.03 mmol) in DMF (1 mL) was added sodium hydride (7 mg, 60% oil, 0.17 mmol). The mixture was stirred for 30 minutes, and benzyl bromide (64, 0.05 mmol) was added. The mixture was stirred another 90 minutes, and was quenched with water, and left for 12 hours. The mixture was extracted with ethyl acetate, and the organic layer was washed with water and brine, and dried over sodium sulfate. Concentration and purification by flash column chromatography (hexanes/EtOAc) gave (S)-2-(2-(benzyloxy)-5-(4-chlorophenyl)-7-methylquinolin-6-yl)-2-tert-butoxyethanol (3.1 mg). LCMS-ESI$^+$ (m/z): [M-FH]$^+$ calcd for $C_{29}H_{30}ClNO_3$: 476.2. Found: 476.1. (S)-1-Benzyl-6-(1-tert-butoxy-2-hydroxyethyl)-5-(4-chlorophenyl)-7-methylquinolin-2(1H)-one was also isolated 6.1 mg LCMS-ESI$^+$ (m/z): [M+H]$^+$ calcd for LCMS-ESI$^+$ (m/z): [M+H]$^+$ calcd for $C_{29}H_{31}ClNO_3$: 476.2. Found: 476.2.

Preparation of (S)-2-(2-(benzyloxy)-5-(4-chlorophenyl)-7-methylquinolin-6-yl)-2-tert-butoxyacetic acid: (S)-2-(2-(Benzyloxy)-5-(4-chlorophenyl)-7-methylquinolin-6-yl)-2-tert-butoxyacetic acid (65A) (3.3 mg) was prepared in a similar manner as compound ((S)-2-tert-butoxy-2-(5-(4-chlorophenyl)-7-methyl-2-morpholinoquinolin-6-yl)acetic acid of Example 29 except using (S)-2-(2-(benzyloxy)-5-(4-chlorophenyl)-7-methylquinolin-6-yl)-2-tert-butoxyethanol instead of ((S)-2-tert-butoxy-2-(5-(4-chlorophenyl)-7-methyl-2-morpholinoquinolin-6-yl)ethanol. $^1$H-NMR 400 MHz (CD$_3$OD) δ 7.82 (d, J=9.6 Hz, 1 H), 7.71 (s, 1 H), 7.80 (m, 3 H), 7.51 (m, 2 H), 7.41-7.10 (m, 4 H), 7.12 (d, J=9.6 Hz, 1 H), 5.58 (s, 2 H), 5.18 (s, 1 H), 2.66 (s, 3 H), 0.97 (s, 9 H); LCMS-ESI$^+$ (m/z): [M+H]$^+$ calcd for $C_{29}H_{29}ClNO_4$: 490.2. Found: 490.2.

Preparation of (S)-2-(1-benzyl-5-(4-chlorophenyl)-7-methyl-2-oxo-1,2-dihydroquinolin-6-yl)-2-tert-butoxyacetic acid: (S)-2-(1-Benzyl-5-(4-chlorophenyl)-7-methyl-2-oxo-1,2-dihydroquinolin-6-yl)-2-tert-butoxyacetic acid (65B) (5.4 mg) was prepared in a similar manner as compound ((S)-2-tert-butoxy-2-(5-(4-chlorophenyl)-7-methyl-2-morpholinoquinolin-6-yl)acetic acid of Example 29 except using (S)-1-benzyl-6-(1-tert-butoxy-2-hydroxyethyl)-5-(4-chlorophenyl)-7-methylquinolin-2(1H)-one instead of ((S)-2-tert-butoxy-2-(5-(4-chlorophenyl)-7-methyl-2-morpholinoquinolin-6-yl)ethanol. $^1$H-NMR 400 MHz (CD$_3$OD) δ 7.6-7.5 (m, 3 H), 7.4-7.2 (m, 8 H), 6.59 (d, J=9.6 Hz, 1 H), 5.64 (s, 2 H), 5.02 (s, 1 H), 2.47 (s, 3 H), 0.94 (s, 9 H); LCMS-ESI$^+$ (m/z): [M+H]+ calcd for C29H29ClNO4: 490.2. Found: 490.2; LCMS-ESI+ (m/z): [M+H]+ calcd for C29H27ClNO4: 488.2. Found: 488.0.

EXAMPLE 66

(S)-2-tert-butoxy-2-(5-(4-chlorophenyl)-2-methoxy-7-methylquinolin-6-yl)acetic acid: (66).

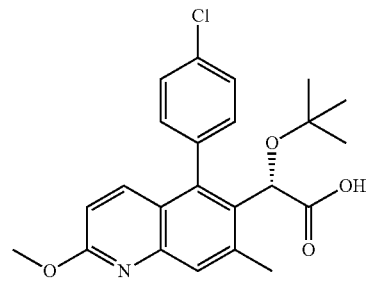

(S)-2-tert-butoxy-2-(5-(4-chlorophenyl)-2-methoxy-7-methylquinolin-6-yl)acetic acid (S)-2-tert-Butoxy-2-(5-(4-chlorophenyl)-2-methoxy-7-methylquinolin-6-yl)acetic acid (66) (2.3 mg) was prepared in a similar manner as compound (S)-2-(2-(benzyloxy)-5-(4-chlorophenyl)-7-methylquinolin-6-yl)-2-tert-butoxyacetic acid of Example 65 except using iodomethane instead of benzyl bromide. $^1$H-NMR 400 MHz (CD3OD) δ 7.68 (s, 1 H), 7.6-7.5 (m, 4 H), 7.30 (d, J=8 Hz, 1 H), 6.87 (d, J=9.6 Hz, 1H), 5.16 (s, 1 H), 4.08 (s, 3 H), 2.62 (s, 3 H), 0.97 (s, 9 H); LCMS-ESI+ (m/z): [M+H]+ calcd for C23H25ClNO4: 414.1. Found: 414.2; LCMS-ESI+ (m/z): [M+H]+ calcd for C23H23ClNO4: 412.1. Found: 412.0.

EXAMPLE 67

(S)-2-tert-butoxy-2-(5-(4-chlorophenyl)-1,7-dimethyl-2-oxo-1,2-dihydroquinolin-6-yl)acetic acid (67).

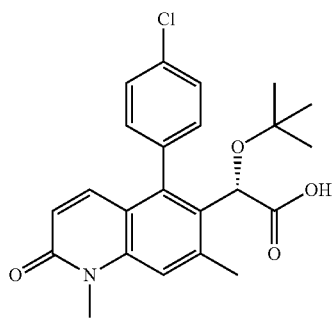

(S)-2-tert-butoxy-2-(5-(4-chlorophenyl)-1,7-dimethyl-2-oxo-1,2-dihydroquinolin-6-yl)acetic acid (S)-2-tert-Butoxy-2-(5-(4-chlorophenyl)-1,7-dimethyl-2-oxo-1,2-dihydroquinolin-6-yl)acetic acid (67) (2.0 mg) was prepared in a similar manner as compound (S)-2-(1-benzyl-5-(4-chlorophenyl)-7-methyl-2-oxo-1,2-dihydroquinolin-6-yl)-2-tert-butoxyacetic acid of Example 65 except using iodomethane instead of benzyl bromide. $^1$H-NMR 400 MHz (CD3OD) δ 7.6-7.5 (m, 4 H), 7.3-7.26 (m, 2 H), 6.49 (d, J=10 Hz, 1 H), 5.06 (s, 1 H), 3.78 (s, 3 H), 2.64 (s, 3 H), 0.97 (s, 9 H); LCMS-ESI+ (m/z): [M+H]+ calcd for C23H25ClNO4: 414.1. Found: 414.2; LCMS-ESI− (m/z): [M−H]− calcd for C23H23ClNO4: 412.1. Found: 412.0.

EXAMPLE 68

(S)-2-((R)-1-benzyl-5-(2,3-dihydropyrano[4,3,2-de]quinolin-7-yl)-7-methyl-2-oxo-1,2-dihydroquinolin-6-yl)-2-tert-butoxyacetic acid (68).

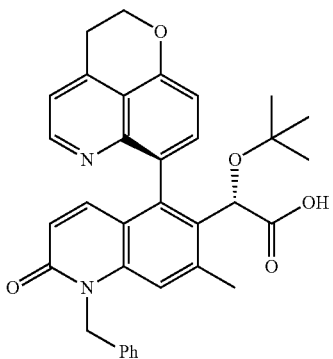

(S)-2-((R)-1-benzyl-5-(2,3-dihydropyrano[4,3,2-de]quinolin-7-yl)-7-methyl-2-oxo-1,2-dihydroquinolin-6-yl)-2-tert-butoxyacetic acid (S)-2-((R)-1-Benzyl-5-(2,3-dihydropyrano[4,3,2-de]quinolin-7-yl)-7-methyl-2-oxo-1,2-dihydroquinolin-6-yl)-2-tert-butoxyacetic acid (68) (1.0 mg) was prepared in a similar manner as compound (S)-2-(1-benzyl-5-(4-chlorophenyl)-7-methyl-2-oxo-1,2-dihydroquinolin-6-yl)-2-tert-butoxyacetic acid of Example 65 except using (S)-2-tert-butoxy-2-((R)-5-(2,3-dihydropyrano[4,3,2-de] quinolin-7-yl)-7-methyl-2-oxo-1,2-dihydroquinolin-6-yl)ethyl pivalate instead of (S)-2-tert-butoxy-2-(5-(4-chlorophenyl)-7-methyl-2-oxo-1,2-dihydroquinolin-6-yl)ethyl pivalate. $^1$H-NMR 400 MHz (CD3OD) δ 8.68 (m, 1 H), 7.9 (m, 1 H), 7.75 (m, 1 H), 7.6 (m, 3 H), 7.43 (m, 4 H), 7.06 (d, J=9.2 Hz, 1 H), 6.37 (d, J=9.6 Hz, 1 H), 5.49 (s, 2 H), 5.07 (s, 1 H), 4.83 (m, 2 H), 3.50 (m, 2 H), 2.72 (s, 3 H), 0.90 (s, 9 H); LCMS- ESI+ (m/z): [M+H]+ calcd for $C_{34}H_{33}N_2O_5$: 549.2. Found: 549.1; LCMS-ESI− (m/z): [M−H]− calcd for $C_{34}H_{31}N_2O_5$: 547.22. Found: 547.1.

EXAMPLE 69

(S)-2-tert-butoxy-2-((R)-5-(2,3-dihydropyrano[4,3,2-de]quinolin-7-yl)-7-methyl-2-(thiophen-2-yl)quinolin-6-yl)acetic acid (69).

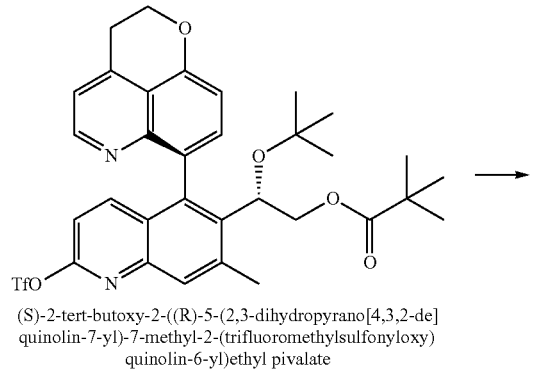

(S)-2-tert-butoxy-2-((R)-5-(2,3-dihydropyrano[4,3,2-de] quinolin-7-yl)-7-methyl-2-(trifluoromethylsulfonyloxy) quinolin-6-yl)ethyl pivalate

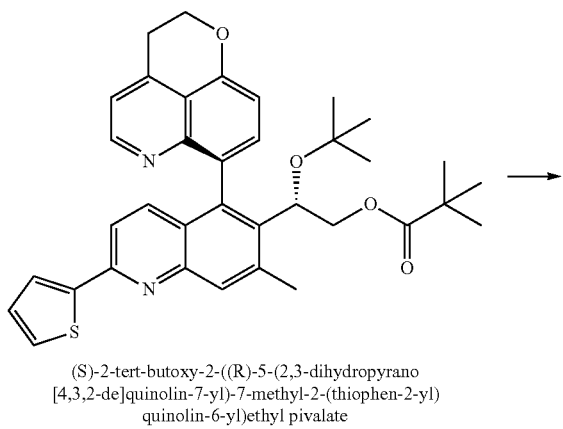

(S)-2-tert-butoxy-2-((R)-5-(2,3-dihydropyrano [4,3,2-de]quinolin-7-yl)-7-methyl-2-(thiophen-2-yl) quinolin-6-yl)ethyl pivalate

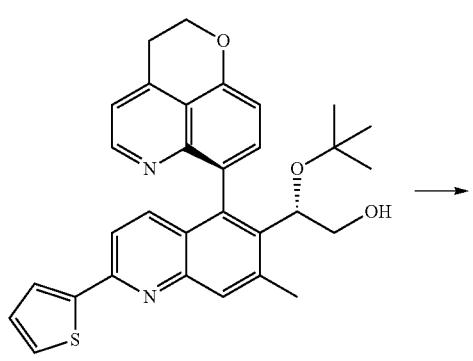

(S)-2-tert-butoxy-2-((R)-5-(2,3-dihydropyrano [4,3,2-de]quinolin-7-yl)-7-methyl-2-(thiophen-2-yl)quinolin-6-yl)ethanol -continued

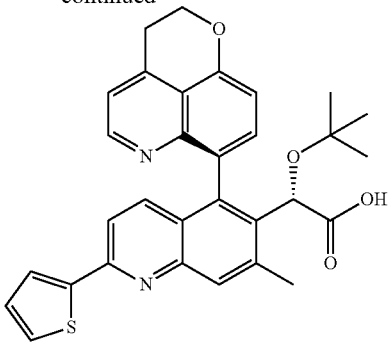

69
(S)-2-tert-butoxy-2-((R)-5-(2,3-dihydropyrano [4,3,2-de]quinolin-7-yl)-7-methyl-2-(thiophen-2-yl) quinolin-6-yl)acetic acid Preparation of (S)-2-tert-butoxy-2-((R)-5-(2,3-dihydropyrano[4,3,2-de]quinolin-7-yl)-7-methyl-2-(thiophen-2-yl) quinolin-6-yl)ethyl pivalate: To a solution of (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate (compound of Example 36) (50 mg, 0.08 mmol) in 1,2-dimethoxyethane was added thiophen-2-ylboronic acid (15 mg, 0.114 mmol), 2 M potassium carbonate (0.15 mL, 0.30 mmol) and Pd(PPh$_3$)$_4$ (9 mg, 0.008 mmol) and the resulting solution was degassed 5 minutes with argon. The mixture was then heated for 20 minutes at 110° C. in a microwave reactor. The crude reaction was absorbed onto silica gel and purified by flash column chromatography (silica gel, ethyl acetate/hexanes) to give a brown film (23.2 mg). LCMS-ESI+ (m/z): [M+H]+ calcd for $C_{36}H_{39}N_2O_4S$: 595.26. found: 595.48.

Preparation of (S)-2-tert-butoxy-2-((R)-5-(2,3-dihydropyrano[4,3,2-de]quinolin-7-yl)-7-methyl-2-(thiophen-2-yl) quinolin-6-yl)ethanol: To a solution of (S)-2-tert-butoxy-2-((R)-5-(2,3-dihydropyrano[4,3,2-de]quinolin-7-yl)-7-methyl-2-(thiophen-2-yl)quinolin-6-yl)ethyl pivalate (23 mg, 0.039 mmol) in tetrahydrofuran and methanol (5:1, 3 mL) was added 1 M sodium hydroxide (2 mL) and the reaction was heated to 45° C. overnight. An additional 2 mL of 1 M sodium hydroxide was added and the reaction was stirred at room temperature over the weekend. The reaction was diluted with water and extracted with ethyl acetate. The organic layer was washed with brine and then dried over sodium sulfate and concentrated to give a yellow film (14 mg). LCMS-ESI+ (m/z): [M+H]+ calcd for $C_{31}H_{31}N_2O_3S$: 511.20. found: 511.40.

Preparation of (S)-2-tert-butoxy-2-((R)-5-(2,3-dihydropyrano[4,3,2-de]quinolin-7-yl)-7-methyl-2-(thiophen-2-yl) quinolin-6-yl)acetic acid (69): To a solution of (S)-2-tert-butoxy-2-((R)-5-(2,3-dihydropyrano[4,3,2-de]quinolin-7-yl)-7-methyl-2-(thiophen-2-yl)quinolin-6-yl)ethanol in wet acetonitrile at 0° C. was added 0.4 M CrO$_3$/H$_5$IO$_6$ (0.206 mL, 0.082 mmol). The solution was stirred at 0° C. for 3 hours, and an additional 0.082 mmol of 0.4 M CrO$_3$/H$_5$IO$_6$ was added. The reaction was quenched with 1 M NaH$_2$PO$_4$·2H$_2$O and extracted with ethyl acetate. The organic layer was concentrated and purified by reverse phase HPLC (Gemini, 10-55% ACN/H$_2$O+0.1% TFA). Product lyophilized to give a yellow powder (4 mg). $^1$H-NMR: 400 MHz, (CD$_3$CN) δ: 8.62 (d, J=5.2 Hz, 1 H), 7.96 (s, 1 H), 7.76 (d, J=3.2 Hz, 1 H), 7.70 (d, J=7.6 Hz, 1 H), 7.67 (d, J=9.2 Hz, 1 H), 7.58 (d, J=4.4 Hz, 1 H), 7.51 (d, J=5.2 Hz, 1 H), 7.29 (d, J=8 Hz, 2 H), 7.17 (t, J=3.2 Hz, 1 H), 5.19 (s, 1 H), 4.62 (m, 2 H), 3.48 (t, J=6.0, 2H), 2.72 (s, 3 H), 0.92 (s, 9 H).

LCMS-ESI+ (m/z): [M+H]+ calcd for $C_{31}H_{29}N_2O_4S$: 425.18. found: 425.25.

EXAMPLE 70

(S)-2-tert-Butoxy-2-(5-(4-chlorophenyl)-7-methyl-2-(1H-pyrazol-5-yl)quinolin-6-yl)acetic acid (70).

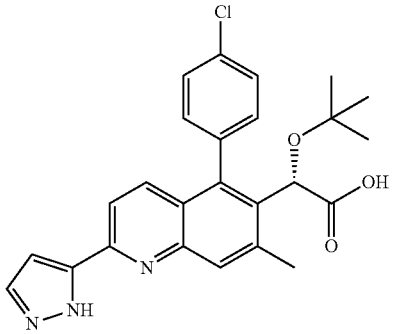

(S)-2-tert-butoxy-2-(5-(4-chlorophenyl)-7-methyl-2-(1H-pyrazol-5-yl)quinolin-6-yl)acetic acid (S)-2-tert-Butoxy-2-(5-(4-chlorophenyl)-7-methyl-2-(1H-pyrazol-5-yl)quinolin-6-yl)acetic acid (70) was prepared using the procedure to prepare (S)-2-tert-butoxy-2-((R)-5-(2,3-dihydropyrano[4,3,2-de]quinolin-7-yl)-7-methyl-2-(thiophen-2-yl)quinolin-6-yl)acetic acid of Example 69 except that (S)-2-tert-butoxy-2-(5-(4-chlorophenyl)-7-methyl-2-(trifluoromethylsulfonyloxy)quinolin-6-yl)ethyl pivalate was used instead of (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate and 1H-pyrazol-5-ylboronic acid was used instead of thiophen-2-ylboronic acid. Additionally, in the second step the crude extract was co-evaporated two times with acetonitrile and in the final step the $CrO_3/H_5IO_6$ was added in one portion and stirred 2 hours. $^1$H-NMR: 400 MHz, ($CD_3CN$) δ: 8.06 (s, 1 H), 7.98 ($AB_q$, J=22.4, 8.8 Hz, 2 H), 7.78 (s, 1 H), 7.74 (d, J=8.4 Hz, 1 H), 7.58 (m, 2 H), 7.37 (d, J=8.4 Hz, 1 H), 7.33 (d, J=7.2 Hz, 1 H), 7.20 (s, 1 H), 5.23 (s, 1 H), 2.64 (s, 3 H), 097 (s, 9 H). LCMS-ESI$^+$ (m/z): [M+H]$^+$ calcd for $C_{25}H_{25}ClN_3O_3$: 450.15. found: 450.62.

EXAMPLE 71

(S)-2-tert-butoxy-2-((R)-5-(2,3-dihydropyrano[4,3,2-de]quinolin-7-yl)-7-methyl-2-(1H-pyrazol-5-yl)quinolin-6-yl)acetic acid (71).

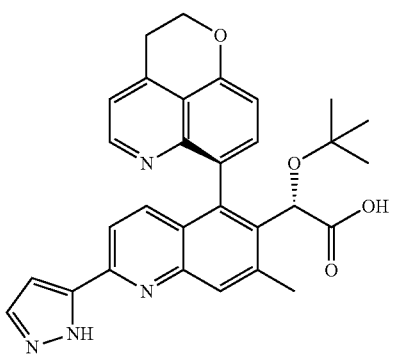

(S)-2-tert-butoxy-2-((R)-5-(2,3-dihydropyrano[4,3,2-de]quinolin-7-yl)-7-methyl-2-(1H-pyrazol-5-yl)quinolin-6-yl)acetic acid (S)-2-tert-Butoxy-2-((R)-5-(2,3-dihydropyrano[4,3,2-de]quinolin-7-yl)-7-methyl-2-(1H-pyrazol-5-yl)quinolin-6-yl)acetic acid (71) was prepared using the procedure to prepare (S)-2-tert-butoxy-2-((R)-5-(2,3-dihydropyrano[4,3,2-de]quinolin-7-yl)-7-methyl-2-(thiophen-2-yl)quinolin-6-yl)acetic acid of Example 69 except that 1H-pyrazol-5-ylboronic acid was used instead of thiophen-2-ylboronic acid, in the second step the crude extract was co-evaporated two times with acetonitrile and in the final step the $CrO_3/H_5IO_6$ was added in one portion and stirred for 2 hours. $^1$H-NMR: 400 MHz, ($CD_3CN$) δ: 8.64 (d, J=4.8 Hz, 1 H), 8.07 (s, 1 H), 7.80 (d, J=8.8 Hz, 1 H), 7.69 (d, J=2.0 Hz, 1 H), 7.66 (d, J=8.4 Hz, 1 H), 7.49 (m, 2 H), 7.26 (d, J=8.0 Hz, 1H), 7.09 (d, J=2.0 Hz, 1 H), 5.19 (s, 1 H), 4.61 (m, 2 H), 3.46 (t, J=6.0 Hz, 2 H), 2.74 (s, 3 H), 0.91 (s, 9 H). LCMS-ESI$^+$ (m/z): [M+H]$^+$ calcd for $C_{30}H_{29}N_4O_4$: 509.21. found: 509.26.

EXAMPLE 72

(S)-2-tert-butoxy-2-4R)-5-(2,3-dihydropyrano[4,3,2-de]quinolin-7-yl)-7-methyl-2-(pyrimidin-5-yl)quinolin-6-yl)acetic acid (72).

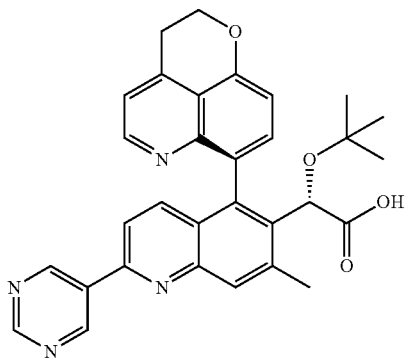

(S)-2-tert-butoxy-2-((R)-5-(2,3-dihydropyrano[4,3,2-de]quinolin-7-yl)-7-methyl-2-(pyrimidin-5-yl)quinolin-6-yl)acetic acid (S)-2-tert-Butoxy-2-((R)-5-(2,3-dihydropyrano[4,3,2-de]quinolin-7-yl)-7-methyl-2-(pyrimidin-5-yl)quinolin-6-yl)acetic acid (72) was prepared using the procedure to prepare (S)-2-tert-butoxy-2-((R)-5-(2,3-dihydropyrano[4,3,2-de]quinolin-7-yl)-7-methyl-2-(1H-pyrazol-5-yl)quinolin-6-yl)acetic acid of Example 71 except that pyrimidin-5-ylboronic acid was used instead of 1H-pyrazol-5-ylboronic acid and the final reaction was stirred 1 hour. $^1$H-NMR: 400 MHz, ($CD_3CN$) δ: 9.43 (s, 2 H), 9.19 (s, 1 H), 8.63 (d, J=4.8 Hz, 1 H), 8.08 (s, 1 H), 7.76 (d, J=8.8 Hz, 1 H), 7.71 (d, J=8.8 Hz, 1 H), 7.50 (d, J=5.2 Hz, 1 H), 7.44 (d, J=8.4 Hz, 1 H), 7.29 (d, J=8 Hz, 1 H), 5.22 (s, 1 H), 4.62 (m, 2 H), 3.48 (t, J=5.6 Hz, 2 H), 2.75 (s, 3 H), 094 (s, LCMS-ESI⁺ (m/z): [M+H]⁺ calcd for $C_{31}H_{29}N_4O_4$: 521.21. found: 521.18.

EXAMPLE 73

(S)-2-tert-butoxy-2-(5-(4-chlorophenyl)-7-methyl-2-(pyridin-4-yl)quinolin-6-yl)acetic acid (73).

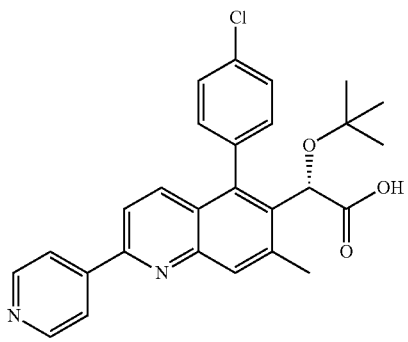

(S)-2-tert-butoxy-2-(5-(4-chlorophenyl)-7-methyl-2-(pyridin-4-yl)quinolin-6-yl)acetic acid (S)-2-tert-Butoxy-2-(5-(4-chlorophenyl)-7-methyl-2-(pyridin-4-yl)quinolin-6-yl)acetic acid (73) was prepared following the procedure used for (S)-2-tert-butoxy-2-(5-(4-chlorophenyl)-7-methyl-2-(1H-pyrazol-5-yl)quinolin-6-yl)acetic acid of Example 70 except that pyridin-4-ylboronic acid was used instead of 1H-pyrazol-5-ylboronic acid and in the final step the reaction was stirred for 3 hours.

¹H-NMR: 400 MHz, (CD₃CN) δ: 8.84 (s, 2 H), 8.46 (d, J=5.6 Hz, 2 H), 8.03 (s, 1 H), 7.98 (d, J=9.2 Hz, 1 H), 7.87 (d, J=8.8 Hz, 1 H), 7.60 (m, 3 H), 7.37 (d, J=8 Hz, 1 H), 5.27 (s, 1 H), 2.66 (s, 3 H), 0.99 (s, 9 H). LCMS-ESI⁺ (m/z): [M+H]⁺ calcd for $C_{27}H_{25}ClN_2O_3$: 461.16. found: 461.64.

EXAMPLE 74

(S)-2-tert-butoxy-2-(5-(4-chlorophenyl)-7-methyl-2-(pyridin-3-yl)quinolin-6-yl)acetic acid (74).

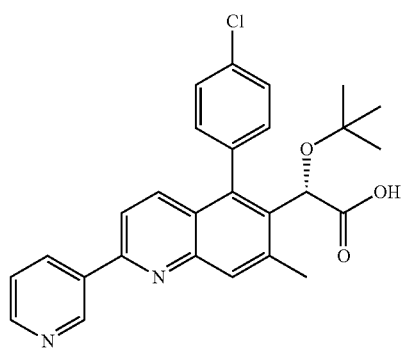

(S)-2-tert-butoxy-2-(5-(4-chlorophenyl)-7-methyl-2-(pyridin-3-yl)quinolin-6-yl)acetic acid (S)-2-tert-Butoxy-2-(5-(4-chlorophenyl)-7-methyl-2-(pyridin-3-yl)quinolin-6-yl)acetic acid (74) was prepared following the procedure for (S)-2-tert-butoxy-2-(5-(4-chlorophenyl)-7-methyl-2-(pyridin-4-yl)quinolin-6-yl)acetic acid of Example 73 except that pyridin-3-ylboronic acid was used instead of pyridin-4-ylboronic acid. ¹H-NMR: 400 MHz, (CD₃CN) δ: 9.49 (s, 1 H), 8.94 (d, J=8.4 Hz, 1 H), 8.79 (s, 1 H), 7.91 (m, 2H), 7.80 (Abq, J=26.2, 8.8 Hz, 2 H), 7.58 (m, 3 H), 7.34 (m, 1 H), 5.25 (s, 1 H), 2.61 (s, 3H), 0.97 (s, 9 H). LCMS-ESI⁺ (m/z): [M+H]⁺ calcd for $C_{27}H_{26}ClN_2O_3$: 461.16. found: 461.00.

EXAMPLE 75

(S)-2-tert-Butoxy-2-((R)-5-(2,3-dihydropyrano[4,3,2-de]quinolin-7-yl)-7-methyl-2-(pyridin-4-yl)quinolin-6-yl)acetic acid (75).

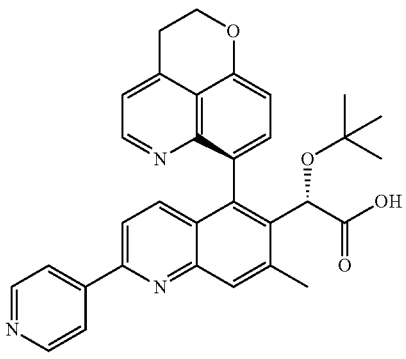

(S)-2-tert-butoxy-2-((R)-5-(2,3-dihydropyrano[4,3,2-de]quinolin-7-yl)-7-methyl-2-(pyridin-4-yl)quinolin-6-yl)acetic acid (S)-2-tert-Butoxy-2-((R)-5-(2,3-dihydropyrano[4,3,2-de]quinolin-7-yl)-7-methyl-2-(pyridin-4-yl)quinolin-6-yl)acetic acid (75) was prepared following the procedure for (S)-2-tert-butoxy-2-((R)-5-(2,3-dihydropyrano[4,3,2-de]quinolin-7-yl)-7-methyl-2-(1H-pyrazol-5-yl)quinolin-6-yl)acetic acid of Example 71 except that pyridin-4-ylboronic acid was used instead of 1H-pyrazol-5-ylboronic acid and the final reaction was stirred for 1 hour. ¹H-NMR: 400 MHz, (CD₃CN) δ: 8.82 (br s, 2 H), 8.63 (d, J=4.4 Hz, 1 H), 8.48 (d, J=5.2 Hz, 2 H), 8.10 (s, 1 H), 7.85 (d, J=8.8 Hz, 1 H), 7.64 (d, J=8 Hz, 1 H), 7.48 (d, J=8.8 Hz, 1 H), 7.45 (d, J=5.2 Hz, 1 H), 7.25 (d, J=8 Hz, 1 H), 5.24 (s, 1 H), 4.60 (m, 2 H), 3.44 (t, J=6 Hz, 2 H), 2.75 (s, 3 H), 0.92 (s, 9 H). LCMS-ESI+ (m/z): [M+H]+ calcd for $C_{32}H_{30}N_3O_4$: 520.22. found: 520.22.

EXAMPLE 76

(S)-2-tert-butoxy-2-(5-(4-chlorophenyl)-7-methyl-2-(thiazol-4-yl)quinolin-6-yl)acetic acid (76).

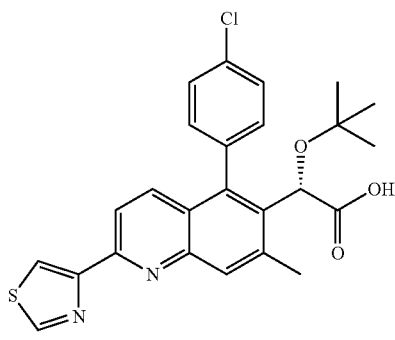

(S)-2-tert-butoxy-2-(5-(4-chlorophenyl)-7-methyl-2-(thiazol-4-yl)quinolin-6-yl)acetic acid (S)-2-tert-Butoxy-2-(5-(4-chlorophenyl)-7-methyl-2-(thiazol-4-yl)quinolin-6-yl)acetic acid (76) was prepared following the procedure for (S)-2-tert-butoxy-2-(5-(4-chlorophenyl)-7-methyl-2-(1H-pyrazol-5-yl)quinolin-6-yl) acetic acid of Example 70 except that thiazol-4-ylboronic acid was used instead of 1H-pyrazol-5-ylboronic acid and the in the final step the reaction was stirred for 1.5 hours. $^1$H-NMR: 400 MHz, (CD$_3$CN) δ: 9.07 (d, J=2.0 Hz, 1 H), 8.58 (d, J=2.0 Hz, 1 H), 8.17 (d, J=9.2 Hz, 1 H), 8.02 (s, 1 H), 7.93 (d, J=9.2 Hz, 1 H), 7.59 (m, 3 H), 7.35 (d, J=7.6 Hz, 1 H), 5.25 (s, 1H), 2.64 (s, 3 H), 0.98 (s, 9 H).

LCMS-ESI+ (m/z): [M+H]+ calcd for $C_{25}H_{24}ClN_2O_3S$: 467.11. found: 467.49.

EXAMPLE 77

(S)-2-tert-butoxy-2-(5-(4-chlorophenyl)-7-methyl-2-(1H-pyrazol-4-yl)quinolin-6-yl)acetic acid (77).

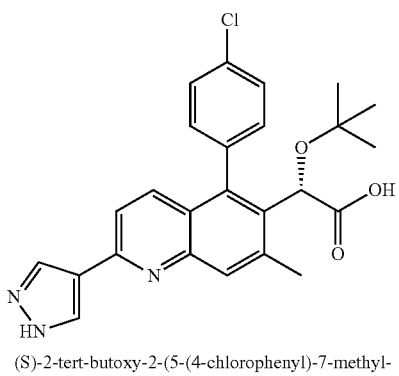

(S)-2-tert-butoxy-2-(5-(4-chlorophenyl)-7-methyl-2-(1H-pyrazol-4-yl)quinolin-6-yl)acetic acid (S)-2-tert-Butoxy-2-(5-(4-chlorophenyl)-7-methyl-2-(1H-pyrazol-4-yl)quinolin-6-yl)acetic acid (77) was prepared following the procedure for (S)-2-tert-butoxy-2-(5-(4-chlorophenyl)-7-methyl-2-(1H-pyrazol-5-yl)quinolin-6-yl) acetic acid of Example 70 except that 4-(4,4,5,5-tetramethyl-1,3,2-dioxaborolan-2-yl)-1H-pyrazole was used instead of 1H-pyrazol-5-ylboronic acid and the in the final step the reaction was stirred for 1 hour. $^1$H-NMR: 400 MHz, (CD$_3$CN) δ: 8.45 (s, 2 H), 8.08 (s, 1 H), 7.89 (d, J=8.8 Hz, 1 H), 7.73 9 (d, J=8.8 Hz, 1 H), 7.59 (m, 3 H), 7.34 (d, J=7.2 Hz, 1H), 5.22 (s, 1 H), 2.63 (s, 3 H), 0.97 (s, 9 H). LCMS-ESI+ (m/z): [M+H]+ calcd for $C_{25}H_{25}ClN_3O_3$: 450.15. found: 450.53.

EXAMPLE 78

(S)-2-tert-Butoxy-2-((R)-5-(2,3-dihydropyrano[4,3, 2-de]quinolin-7-yl)-7-methyl-2-(1H-pyrazol-4-yl) quinolin-6-yl)acetic acid (78).

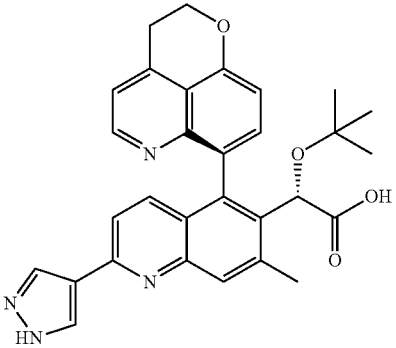

(S)-2-tert-butoxy-2-((R)-5-(2,3-dihydropyrano[4,3,2-de]quinolin-7-yl)-7-methyl-2-(1H-pyrazol-4-yl)quinolin-6-yl)acetic acid (S)-2-tert-Butoxy-2-((R)-5-(2,3-dihydropyrano[4,3,2-de] quinolin-7-yl)-7-methyl-2-(1H-pyrazol-4-yl)quinolin-6-yl) acetic acid (78) was prepared following the procedure for (S)-2-tert-butoxy-2-((R)-5-(2,3-dihydropyrano[4,3,2-de] quinolin-7-yl)-7-methyl-2-(pyrimidin-5-yl)quinolin-6-yl) acetic acid of Example 71 except that 4-(4,4,5,5-tetramethyl-1,3,2-dioxaborolan-2-yl)-1H-pyrazole was used instead of 1H-pyrazol-5-ylboronic acid. $^1$H-NMR: 400 MHz, (CD$_3$CN) δ: 8.64 (d, J=5.2 Hz, 1 H), 8.50 (br s, 2 H), 8.23 (s, 1 H), 7.61 (m, 3 H), 7.45 (d, J=5.2 Hz, 1 H), 7.24 (d, J=8.0 Hz, 1H), 5.20 (s, 1 H), 4.60 (m, 2 H), 3.44 (t, J=6.0 Hz, 2 H), 2.74 (s, 3 H), 0.89 (s, 9 H).

LCMS-ESI+ (m/z): [M+H]+ calcd for $C_{30}H_{29}N_4O_4$: 509.21. found: 509.07.

EXAMPLE 79

(S)-2-tert-butoxy-2-(5-(4-chlorophenyl)-7-methyl-2-(pyridin-2-yl)quinolin-6-yl)acetic acid (79).

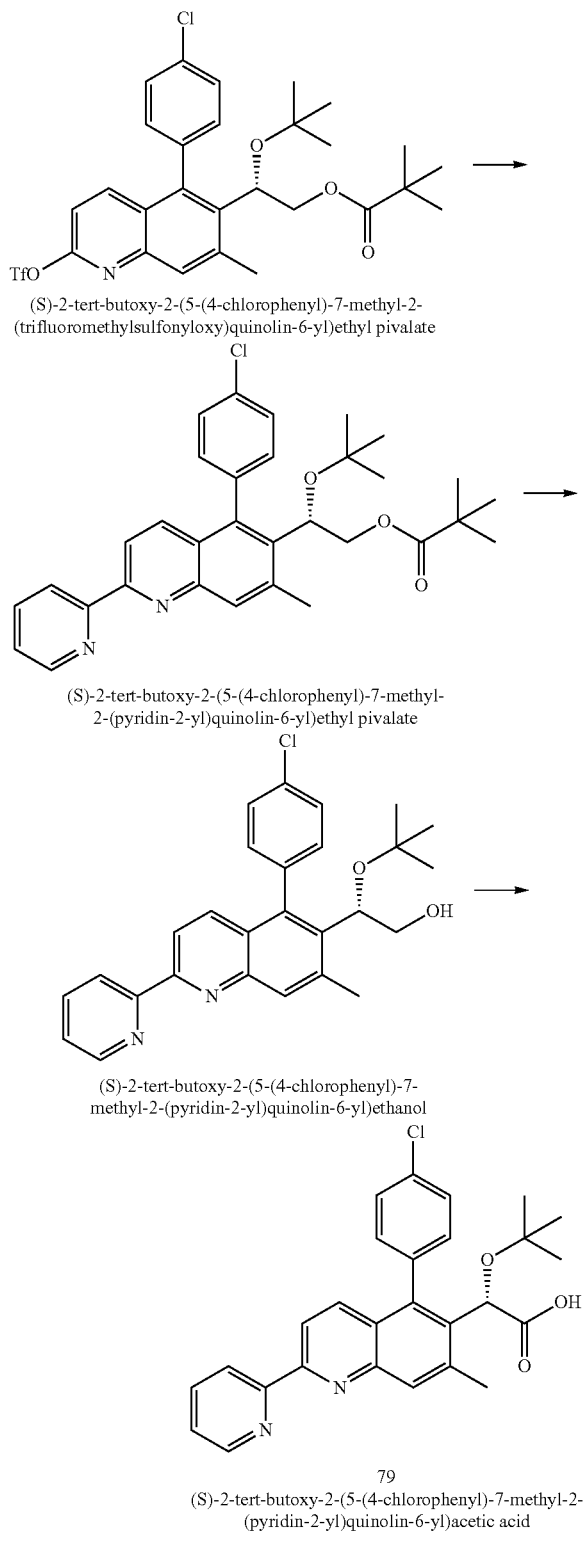

Preparation of (S)-2-tert-butoxy-2-(5-(4-chlorophenyl)-7-methyl-2-(pyridin-2-yl)quinolin-6-yl)ethyl pivalate: To a solution of (S)-2-tert-butoxy-2-(5-(4-chlorophenyl)-7-methyl-2-(trifluoromethylsulfonyloxy)quinolin-6-yl)ethyl pivalate (compound of Example 26; 50 mg, 0.08 mmol) in 1,2 dimethoxyethane (1 mL) was added 2-(tributylstannyl)pyridine (0.040 mL, 0.125 mmol) and Pd(PPh$_3$)$_4$ and the reaction mixture was degassed with argon for 5 minutes. The reaction was heated to 110° C. in a microwave reactor for 20 minutes. The crude reaction mixture was absorbed onto silica gel and purified by flash column chromatography (silica gel, ethyl acetate/hexanes) to give a clear oil (45.2 mg). LCMS-ESI$^+$ (m/z): [M+H]$^+$ calcd for $C_{32}H_{36}ClN_2O_3$: 531.23. found: 531.68.

Preparation of (S)-2-tert-butoxy-2-(5-(4-chlorophenyl)-7-methyl-2-(pyridin-2-yl)quinolin-6-yl)ethanol: To a solution of (S)-2-tert-butoxy-2-(5-(4-chlorophenyl)-7-methyl-2-(pyridin-2-yl)quinolin-6-yl)ethyl pivalate (45.2 mg, 0.085 mmol) in tetrahydrofuran and methanol (5:1, 1 mL) was added 1 M sodium hydroxide (2 mL) and the reaction was heated to 45° C. overnight. The reaction was cooled to room temperature, diluted with water and extracted with ethyl acetate. The organic layer was washed with brine, dried over sodium sulfate and concentrated. The crude extract was co-evaporated two times with acetonitrile to give a clear oil (33.8 mg). LCMS-ESI$^+$ (m/z): [M+H]$^+$ calcd for $C_{27}H_{28}ClN_2O_2$: 447.18. found: 447.72.

Preparation of (S)-2-tert-butoxy-2-(5-(4-chlorophenyl)-7-methyl-2-(pyridin-2-yl)quinolin-6-yl)acetic acid (79): To a solution of (S)-2-tert-butoxy-2-(5-(4-chlorophenyl)-7-methyl-2-(pyridin-2-yl)quinolin-6-yl)ethanol (33.8 mg, 0.076 mmol) in wet acetonitrile at 0° C. was added 0.4 M CrO$_3$/H$_5$IO$_6$ (1.13 mL, 0.454 mmol) and the reaction was stirred at 0° C. for 2 hours. The reaction was quenched with 1 M NaH$_2$PO$_4$·2H$_2$O and extracted with ethyl acetate. The organic layer was concentrated and purified by reverse phase HPLC (Gemini, 10-70% ACN/H$_2$O+0.1% TFA) and the desired product was lyophilized to give a white amorphous powder (5.1 mg). $^1$H-NMR: 400 MHz, (CD$_3$CN): 8.77 (d, J=4.4 Hz, 1 H), 8.62 (d, J=8.0 Hz, 1 H), 8.31 (d, J=8.8 Hz, 1 H), 8.15 (t, J=7.0 Hz, 1 H), 8.01 (s, 1 H), 7.86 (d, J=8.8 Hz, 1 H), 7.59 (m, 4 H), 7.36 (d, J=8.4 Hz, 1 H), 5.26 (s, 1 H), 2.65 (s, 3 H), 0.98 (s, 9 H).

LCMS-ESI$^+$ (m/z): [M+H]$^+$ calcd for $C_{27}H_{26}ClN_2O_3$: 461.16. found: 461.91.

EXAMPLE 80

(S)-2-tert-Butoxy-2-((R)-5-(2,3-dihydropyrano[4,3,2-de]quinolin-7-yl)-7-methyl-2-(pyridin-2-yl)quinolin-6-yl)acetic acid (80).

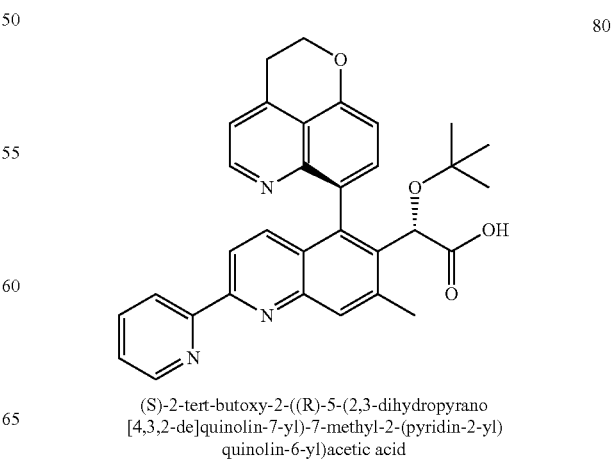

(S)-2-tert-butoxy-2-((R)-5-(2,3-dihydropyrano[4,3,2-de]quinolin-7-yl)-7-methyl-2-(pyridin-2-yl)quinolin-6-yl)acetic acid (S)-2-tert-Butoxy-2-((R)-5-(2,3-dihydropyrano[4,3,2-de]quinolin-7-yl)-7-methyl-2-(pyridin-2-yl)quinolin-6-yl)acetic acid (80) was prepared following the procedure for (S)-2-tert-butoxy-2-(5-(4-chlorophenyl)-7-methyl-2-(pyridin-2-yl)quinolin-6-yl)acetic acid of Example 79 except that (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate was used instead of (S)-2-tert-butoxy-2-(5-(4-chlorophenyl)-7-methyl-2-(trifluoromethylsulfonyloxy)quinolin-6-yl)ethyl pivalate, a catalytic amount of lithium chloride was used during the first step and the final step was stirred for 1 hour. $^1$H-NMR: 400 MHz, (CD$_3$CN) δ: 8.72 (d, J=4.4 Hz, 1 H), 8.63 (m, 2 H), 8.23 (d, J=8.8 Hz, 1 H), 8.11 (s, 1 H), 8.07 (t, J=7.6 Hz, 1H), 7.70 (d, H=8.0 Hz, 1 H), 7.54 (t, J=4.8 Hz, 1 H), 7.50 (d, J=4.8 Hz, 1 H), 7.47 (d, J=9.2 Hz, 1 H), 7.28 (d, J=8 Hz, 1 H), 5.22 (s, 1 H), 4.62 (m, 2 H), 3.47 (t, J=6.0, 2H), 2.75 (s, 3 H), 0.92 (s, 9 H). LCMS-ESI$^+$ (m/z): [M+11]$^+$ calcd for C$_{32}$H$_{30}$N$_3$O$_4$: 520.22. found: 520.23.

EXAMPLE 81

(S)-2-tert-butoxy-2-((R)-5-(2,3-dihydropyrano[4,3,2-de]quinolin-7-yl)-7-methyl-2-(pyridin-3-yl)quinolin-6-yl)acetic acid (81).

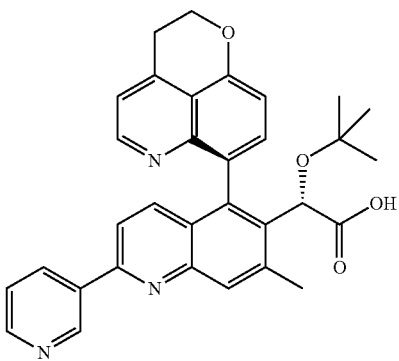

(S)-2-tert-butoxy-2-((R)-5-(2,3-dihydropyrano[4,3,2-de]quinolin-7-yl)-7-methyl-2-(pyridin-3-yl)quinolin-6-yl)acetic acid (S)-2-tert-Butoxy-2-((R)-5-(2,3-dihydropyrano[4,3,2-de]quinolin-7-yl)-7-methyl-2-(pyridin-3-yl)quinolin-6-yl)acetic acid (81) was prepared following the procedure use for (S)-2-tert-butoxy-2-((R)-5-(2,3-dihydropyrano[4,3,2-de]quinolin-7-yl)-7-methyl-2-(1H-pyrazol-5-yl)quinolin-6-yl)acetic acid of Example 71 except that pyridin-3-ylboronic acid was used instead of 1H-pyrazol-5-ylboronic acid. $^1$H-NMR: 400 MHz, (CD$_3$CN) δ: 8.73 (d, J=7.4 Hz, 1 H), 8.60 (d, J=5.2 Hz, 1 H), 8.58 (m, 1 H), 8.38 (br s, 1 H), 7.68 (m, 3 H), 7.51 (m, 2 H), 7.40 (d, J=8.8 Hz, 1 H), 7.25 (d, J=8.0 Hz, 1 H), 5.05 (s, 1 H), 4.55 (m, 2 H), 3.43 (t, J=6.0 Hz, 2 H), 2.62 (s, 3 H), 0.88 (s, 9 H). LCMS-ESI$^+$ (m/z): [M+H]$^+$ calcd for C$_{32}$H$_{30}$N$_3$O$_4$: 520.22. found: 520.22.

EXAMPLE 82

(S)-2-tert-Butoxy-2-(5-(4-chlorophenyl)-7-methyl-2-(1-methyl-1H-imidazol-5-yl)quinolin-6-yl)acetic acid (82).

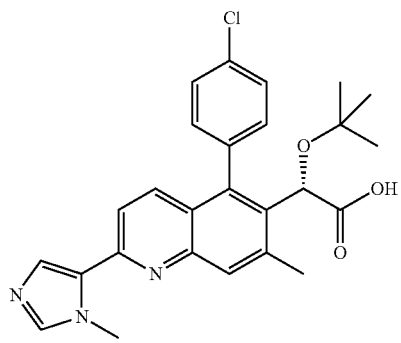

(S)-2-tert-butoxy-2-(5-(4-chlorophenyl)-7-methyl-2-(1-methyl-1H-imidazol-5-yl)quinolin-6-yl)acetic acid (S)-2-tert-Butoxy-2-(5-(4-chlorophenyl)-7-methyl-2-(1-methyl-1H-imidazol-5-yl)quinolin-6-yl)acetic acid (82) was prepared following the procedure for (S)-2-tert-butoxy-2-(5-(4-chlorophenyl)-7-methyl-2-(pyridin-2-yl)quinolin-6-yl)acetic acid of Example 79 except that 1-methyl-5-(tributylstannyl)-1H-imidazole was used instead of 2-(tributylstannyl)pyridine, a catalytic amount of lithium chloride was used in the first step and the final reaction was stirred for 3 hours. $^1$H-NMR: 400 MHz, (CD$_3$CN) δ: 8.47 (s, 1 H), 7.91 (s, 1 H), 7.85 (s, 1 H), 7.66 (d, J=8.8 Hz, 1 H), 7.58 (s, 2 H), 7.54 (t, J=8.0 Hz, 2 H), 7.31 (d, J=8.4 Hz, 1 H), 5.22 (s, 1 H), 4.27 (s, 3 H), 2.61 (s, 3 H), 0.96 (s, 9H). LCMS-ESI$^+$ (m/z): [M+H]$^+$ calcd for C$_{26}$H$_{27}$ClN$_3$O$_3$: 464.17. found: 464.51.

EXAMPLE 83

(S)-2-tert-Butoxy-2-((R)-5-(2,3-dihydropyrano[4,3,2-de]quinolin-7-yl)-7-methyl-2-(1-methyl-1H-imidazol-5-yl)quinolin-6-yl)acetic acid (83).

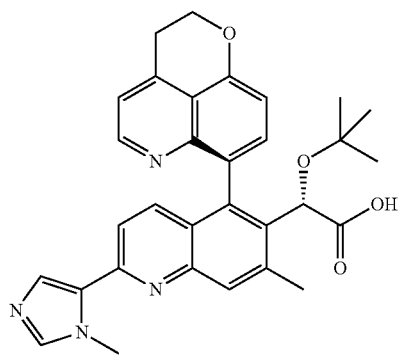

(S)-2-tert-butoxy-2-((R)-5-(2,3-dihydropyrano[4,3,2-de]quinolin-7-yl)-7-methyl-2-(1-methyl-1H-imidazol-5-yl)quinolin-6-yl)acetic acid (S)-2-tert-Butoxy-2-((R)-5-(2,3-dihydropyrano[4,3,2-de]quinolin-7-yl)-7-methyl-2-(1-methyl-1H-imidazol-5-yl)quinolin-6-yl)acetic acid (83) was prepared following the procedure for (S)-2-tert-butoxy-2-((R)-5-(2,3-dihydropyrano[4,3,2-de]quinolin-7-yl)-7-methyl-2-(pyridin-2-yl)quinolin-6-yl)acetic acid of Example 80 except that 1-methyl-5-(tributylstannyl)-1H-imidazole was used instead of 2-(tributylstannyl)pyridine, the first reaction was run for 25 minutes and using a catalytic amount of lithium chloride, and the second step was stirred at room temperature over the weekend instead of overnight at 45° C. $^1$H-NMR: 400 MHz, (CD$_3$CN) δ: 8.66 (d, J=4.8 Hz, 1 H), 8.34 (s, 1 H), 8.02 (s, 1 H), 7.62 (d, J=8.0 Hz, 1 H), 7.53 (s, 1 H), 7.47 (d, J=5.2 Hz, 1 H), 7.38 (s, 2 H), 7.24 (d, J=7.6 Hz, 1 H), 5.14 (s, 1 H), 4.59 (m, 2 H), 4.27 (s, 3 H), 3.45 (t, J=5.6 Hz, 2 H), 2.74 (s, 3 H), 0.92 (s, 9 H). LCMS-ESI$^F$ (m/z): [M+H]$^+$ calcd for C$_{31}$H$_{31}$N$_4$O$_4$: 523.23. found: 523.28.

EXAMPLE 84

(S)-2-tert-Butoxy-2-((R)-5-(2,3-dihydropyrano[4,3,2-de]quinolin-7-yl)-7-methyl-2-(1-methyl-1H-imidazol-2-yl)quinolin-6-yl)acetic acid (84).

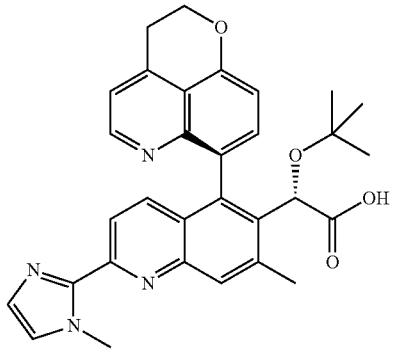

(S)-2-tert-butoxy-2-((R)-5-(2,3-dihydropyrano[4,3,2-de]quinolin-7-yl)-7-methyl-2-(1-methyl-1H-imidazol-2-yl)quinolin-6-yl)acetic acid (S)-2-tert-Butoxy-2-((R)-5-(2,3-dihydropyrano[4,3,2-de]quinolin-7-yl)-7-methyl-2-(1-methyl-1H-imidazol-2-yl)quinolin-6-yl)acetic acid (84) was prepared following the procedure for (S)-2-tert-butoxy-2-((R)-5-(2,3-dihydropyrano[4,3,2-de]quinolin-7-yl)-7-methyl-2-(pyridin-2-yl)quinolin-6-yl)acetic acid of Example 80 except using 1-methyl-2-(tributylstannyl)-1H-imidazole instead of 2-(tributylstannyl)pyridine, using a catalytic amount of lithium chloride in the first step, and the second step was run at room temperature over the weekend instead of at 45° C. overnight. $^1$H-NMR: 400 MHz, (CD$_3$CN). δ: 8.63 (d, J=4.8 Hz, 1 H), 8.12 (s, 1 H), 7.92 (d, J=8.8 Hz, 1 H), 7.64 (d, J=7.6 Hz, 1 H), 7.47 (m, 4 H), 7.25 (d, J=8.0 Hz, 1H), 5.25 (s, 1 H), 4.60 (m, 2 H), 4.30 (s, 3 H), 3.45 (t, J=5.6 Hz, 2 H), 2.75 (s, 3 H), 0.92 (s, 9 H). LCMS-ESI$^+$ (m/z): [M+H]$^+$ calcd for C$_{31}$H$_{31}$N$_4$O$_4$: 523.23. found: 523.12.

EXAMPLE 85

(S)-2-tert-butoxy-2-((R)-5-(2,3-dihydropyrano[4,3,2-de]quinolin-7-yl)-7-methyl-2-(1-methyl-1H-imidazol-4-yl)quinolin-6-yl)acetic acid (85).

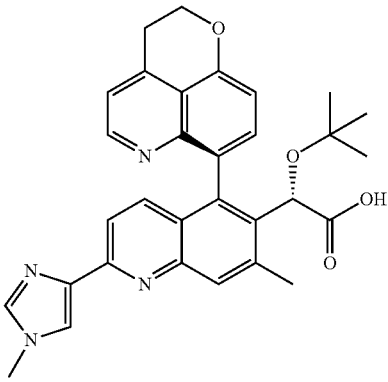

(S)-2-tert-butoxy-2-((R)-5-(2,3-dihydropyrano[4,3,2-de]quinolin-7-yl)-7-methyl-2-(1-methyl-1H-imidazol-4-yl)quinolin-6-yl)acetic acid (S)-2-tert-Butoxy-2-((R)-5-(2,3-dihydropyrano[4,3,2-de]quinolin-7-yl)-7-methyl-2-(1-methyl-1H-imidazol-4-yl)quinolin-6-yl)acetic acid (85) was prepared following the procedure for (S)-2-tert-butoxy-2-((R)-5-(2,3-dihydropyrano[4,3,2-de]quinolin-7-yl)-7-methyl-2-(pyridin-2-yl)quinolin-6-yl)acetic acid of Example 80 except that 1-methyl-4-(tributylstannyl)-1H-imidazole was used instead of 2-(tributylstannyl)pyridine, and a catalytic amount of lithium chloride was used in the first step as well as being heated for 25 minutes. The second step was run at room temperature over the weekend, followed by at 45° C. for four hours. $^1$H-NMR: 400 MHz, (CD$_3$CN) δ: 8.64 (d, J=4.8 Hz, 1 H), 8.35 (s, 1 H), 7.99 (s, 1 H), 7.90 (s, 1 H), 7.58 (d, J=8.0 Hz, 1 H), 7.47 (m, 2 H), 7.36 (d, J=8.8 Hz, 1 H), 7.22 (d, J=8.0 Hz, 1H), 5.17 (s, 1 H), 4.61 (m, 2 H), 3.85 (s, 3 H), 3.46 (t, J=6.0 Hz, 2 H), 2.67 (s, 3 H), 0.88 (s, 9 H). LCMS-ESI$^+$ (m/z): [M+H]$^+$ calcd for C$_{31}$H$_{31}$N$_4$O$_4$: 523.23. found: 523.28.

EXAMPLE 86

(S)-2-tert-butoxy-2-(5-(4-chlorophenyl)-7-methyl-2-(1-methyl-1H-imidazol-4-yl)quinolin-6-yl)acetic acid (86).

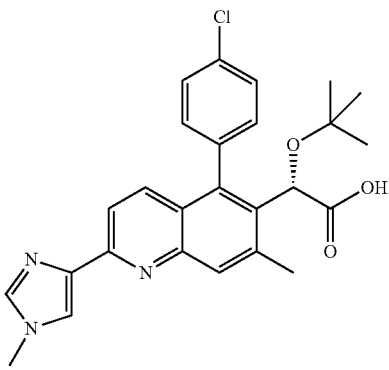

(S)-2-tert-butoxy-2-(5-(4-chlorophenyl)-7-methyl-2-(1-methyl-1H-imidazol-4-yl)quinolin-6-yl)acetic acid (S)-2-tert-Butoxy-2-(5-(4-chlorophenyl)-7-methyl-2-(1-methyl-1H-imidazol-4-yl)quinolin-6-yl)acetic acid (86) was prepared following the procedure for (S)-2-tert-butoxy-2-(5-(4-chlorophenyl)-7-methyl-2-(pyridin-2-yl)quinolin-6-yl)acetic acid of Example 79 except that 1-methyl-4-(tributylstannyl)-1H-imidazole was used instead of 2-(tributylstannyl)pyridine, a catalytic amount of lithium chloride was used in the first step, as well as being heated for 25 minutes instead of 20 minutes. In the final step the reaction was stirred for 4 hours.

$^1$H-NMR: 400 MHz, (CD$_3$CN) δ: 8.34 (s, 1 H), 8.04 (s, 1 H), 7.74 (s, 1 H), 7.55 (m, 5 H), 7.25 (d, J=8.0 Hz, 1 H), 5.16 (s, 1 H), 3.87 (s, 3 H), 2.52 (s, 3 H), 0.93 (s, 9 H).

LCMS-ESI$^+$ (m/z): [M+H]$^+$ calcd for C$_{26}$H$_{27}$ClN$_3$O$_3$: 464.17. found: 464.48.

EXAMPLE 87

(S)-2-tert-Butoxy-2-(5-(4-chlorophenyl)-7-methyl-2-(pyrimidin-5-yl)quinolin-6-yl)acetic acid: (87).

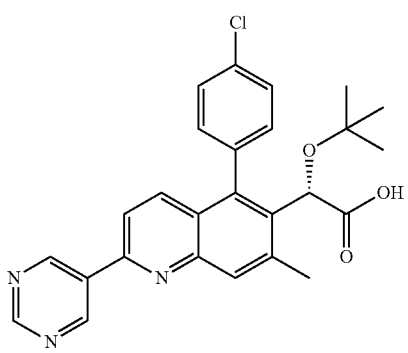

(S)-2-tert-butoxy-2-(5-(4-chlorophenyl)-7-methyl-2-(pyrimidin-5-yl)quinolin-6-yl)acetic acid (S)-2-tert-Butoxy-2-(5-(4-chlorophenyl)-7-methyl-2-(pyrimidin-5-yl)quinolin-6-yl)acetic acid (87) was prepared following the procedure used for (S)-2-tert-butoxy-2-(5-(4-chlorophenyl)-7-methyl-2-(1H-pyrazol-5-yl)quinolin-6-yl)acetic acid of Example 70 except that pyrimidin-5-ylboronic acid was used instead of 1H-pyrazol-5-ylboronic acid.

$^1$H-NMR: 400 MHz, (CD$_3$CN) δ: 9.52 (br s, 2 H), 9.26 (s, 1 H), 8.00 (s, 1H), 7.90 (d, J=8.8 Hz, 1 H), 7.83 (d, J=9.2 Hz, 1 H), 7.60 (m, 3 H), 7.37 (d, J=7.6 Hz, 1 H), 5.27 (s, 1 H), 2.65 9s, 3 H), 0.99 (s, 9 H). LCMS-ESI$^+$ (m/z): [M+H]$^+$ calcd for C$_{26}$H$_{25}$ClN$_3$O$_3$: 462.15. found: 462.45.

EXAMPLE 88

(S)-2-tert-butoxy-2-((R)-5-(2,3-dihydropyrano[4,3,2-de]quinolin-7-yl)-7-methyl-2-(pyridazin-4-yl)quinolin-6-yl)acetic acid (88).

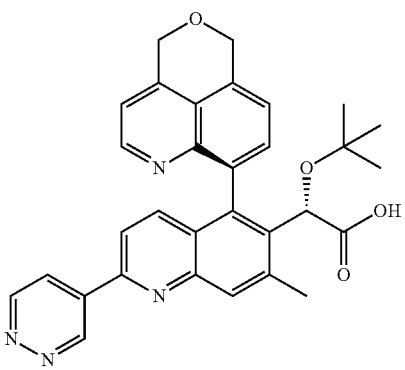

(S)-2-tert-butoxy-2-((R)-5-(2,3-dihydropyrano[4,3,2-de]quinolin-7-yl)-7-methyl-2-(pyridazin-4-yl)quinolin-6-yl)acetic acid (S)-2-tert-Butoxy-2-((R)-5-(2,3-dihydropyrano[4,3,2-de]quinolin-7-yl)-7-methyl-2-(pyridazin-4-yl)quinolin-6-yl)acetic acid (88) was prepared following the procedure for (S)-2-tert-butoxy-2-((R)-5-(2,3-dihydropyrano[4,3,2-de]quinolin-7-yl)-7-methyl-2-(pyridin-2-yl)quinolin-6-yl)acetic acid of Example 80 except that 4-(tributylstannyl)pyridazine was used instead of 2-(tributylstannyl)pyridine. The first step was run with a catalytic amount of lithium chloride, and the last step required an additional 1 mL of 0.4 M CrO$_3$/H$_5$IO$_6$ and three drops of water for completion. $^1$H-NMR: 400 MHz, (CD$_3$CN)S: 9.80 (br s, 1 H), 9.24 (br s, 1 H), 8.67 (d, J=4.8 Hz, 1 H), 8.25 (s, 1 H), 8.05 (s, 1 H), 7.83 (d, J=8.8 Hz, 1 H), 7.75 (d, J=8.0 Hz, 1 H), 7.58 (d, J=4.4 Hz, 1 H), 7.48 (d, J=8.8 Hz, 1 H), 7.33 (d, J=8.4 Hz, 1 H), 5.22 (s, 1 H), 4.64 (m, 2H), 3.52 (t, J=5.6 Hz, 2 H), 2.76 (s, 3 H), 0.94 (s, 9 H).

LCMS-ESI$^+$ (m/z): [M+H]$^+$ calcd for C$_{31}$H$_{29}$N$_4$O$_4$: 521.21. found: 521.18.

EXAMPLE 89

(S)-2-tert-Butoxy-2-((R)-5-(5-chloro-3,4-dihydro-2H-benzo[b][1,4]oxazin-6-yl)-2,7-dimethylquinolin-6-yl)acetic acid (89).

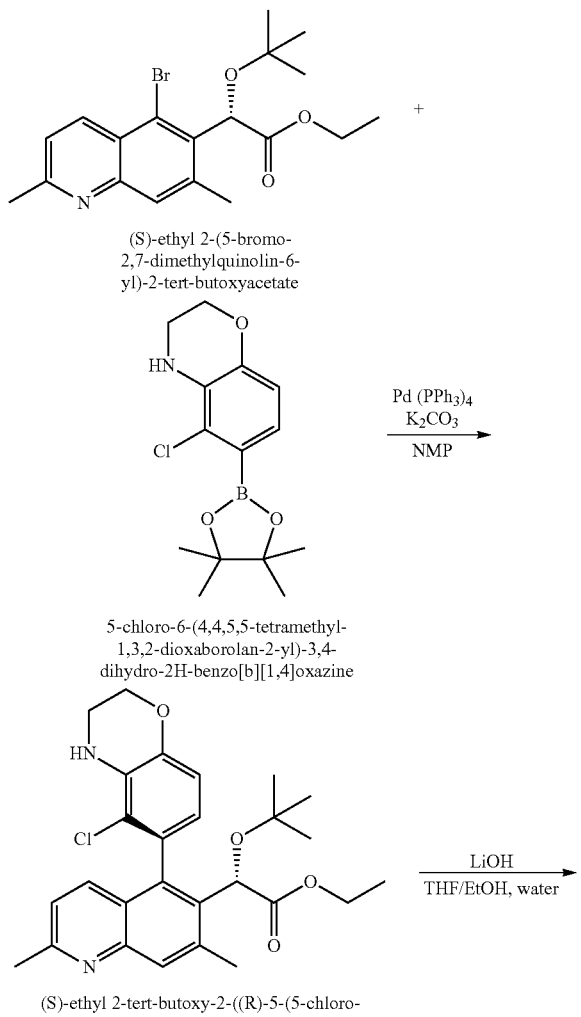

Preparation of (S)-ethyl 2-tert-butoxy-2-((R)-5-(5-chloro-3,4-dihydro-2H-benzo[b][1,4]oxazin-6-yl)-2,7-dimethylquinolin-6-yl)acetate: To a solution of (S)-ethyl 2-(5-bromo-2,7-dimethylquinolin-6-yl)-2-tert-butoxyacetate (5H) (50 mg, 0.126 mmol) and 5-chloro-6-(4,4,5,5-tetramethyl-1,3,2-dioxaborolan-2-yl)-3,4-dihydro-2H-benzo[b][1,4]oxazine (74 mg, 0.252 mmol) in 1-methyl-2-pyrrolidinone was added 2 M potassium carbonate (0.252 mL, 0.504 mmol) and Pd(PPh$_3$)$_4$ (15 mg, 0.013 mmol) and the reaction was degassed with argon for 5 minutes. The reaction was heated to 110° C. for 30 minutes in a microwave reactor. The crude reaction was absorbed onto silica and purified by flash column chromatography (silica gel, ethyl acetate/hexanes) to give a yellow oil (44 mg). LCMS-ESI$^+$ (m/z): [M+H]$^+$ calcd for $C_{27}H_{32}ClN_2O_4$: 483.20; found: 483.93.

Preparation of (S)-2-tert-butoxy-2-((R)-5-(5-chloro-3,4-dihydro-2H-benzo[b][1,4]oxazin-6-yl)-2,7-dimethylquinolin-6-yl)acetic acid (89): To a solution of (S)-ethyl 2-tert-butoxy-2-((R)-5-(5-chloro-3,4-dihydro-2H-benzo[b][1,4]oxazin-6-yl)-2,7-dimethylquinolin-6-yl)acetate (44 mg, 0.092 mmol) in tetrahydrofuran:ethanol:water (2:2:1, 3 mL) was added lithium hydroxide (11 mg, 0.459 mmol) and the reaction was heated to 45° C. overnight. The crude material was purified by reverse phase HPLC (Gemini, 10-48% ACN/H$_2$O+0.1% TFA) and the desired product was lyophilized to give a yellow powder (3.8 mg). $^1$H-NMR: 400 MHz, (CD$_3$CN) δ: 8.22 (s, 1 H), 7.99 (d, J=8.8 Hz, 1 H), 7.50 (d, J=8.8 Hz, 1 H), 6.81 (d, J=8.0 Hz, 1 H), 6.40 (d, J=8.0 Hz, 1 H), 5.35 (s, 1 H), 4.27 (m, 2 H), 3.50 (t, J=4.2 Hz, 2 H), 2.87 (s, 3 H), 2.80 (s, 3 H), 1.10 (s, 9 H). LCMS-ESI$^+$ (m/z): [M+H]$^+$ calcd for $C_{25}H_{28}ClN_2O_4$: 455.17. found: 455.51.

EXAMPLE 90

(S)-2-tert-butoxy-2-(5-(4-chlorophenyl)-2-isopropyl-7-methylquinolin-6-yl)acetic acid (90).

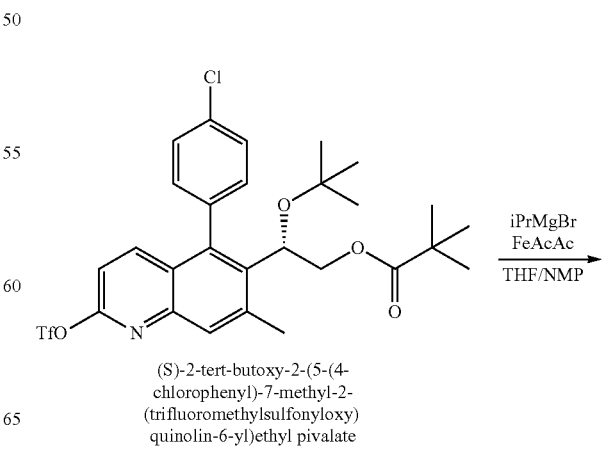

(S)-2-tert-butoxy-2-(5-(4-chlorophenyl)-7-methyl-2-(trifluoromethylsulfonyloxy)quinolin-6-yl)ethyl pivalate

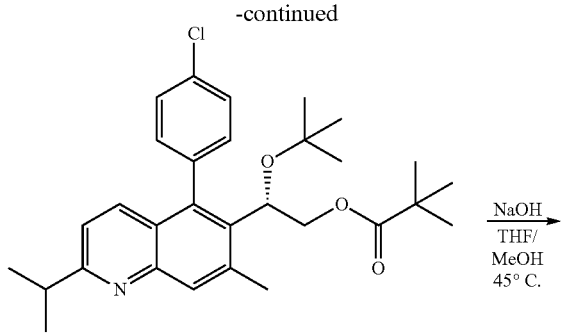

(S)-2-tert-butoxy-2-(5-(4-chlorophenyl)-2-isopropyl-7-methylquinolin-6-yl)ethyl pivalate

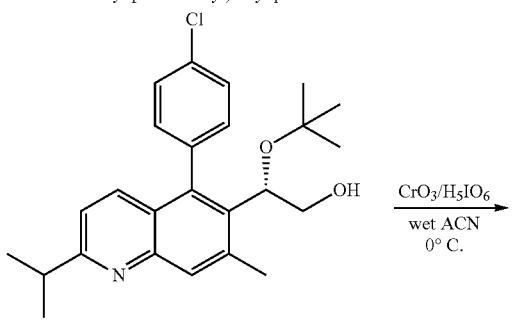

(S)-2-tert-butoxy-2-(5-(4-chlorophenyl)-2-isopropyl-7-methylquinolin-6-yl)ethanol

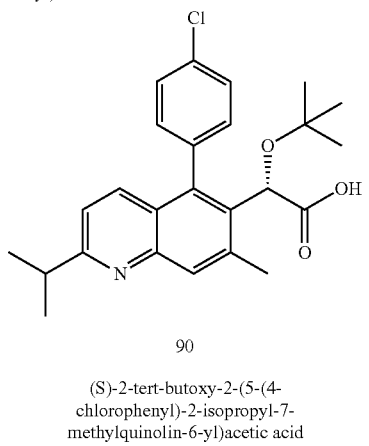

90

(S)-2-tert-butoxy-2-(5-(4-chlorophenyl)-2-isopropyl-7-methylquinolin-6-yl)acetic acid Preparation of (S)-2-tert-butoxy-2-(5-(4-chlorophenyl)-2-isopropyl-7-methylquinolin-6-yl)ethyl pivalate: To a solution of (S)-2-tert-butoxy-2-(5-(4-chlorophenyl)-7-methyl-2-(trifluoromethylsulfonyloxy)quinolin-6-yl)ethyl pivalate (compound of Example 26) (200 mg, 0.33 mmol) and iron (III) acetylacetonate (6 mg, 0.017 mmol) in anhydrous tetrahydrofuran/1-methyl-2-pyrrolidinone (5 mL/0.5 mL) at 0° C. was added 2.9 M in tetrahydrofuran isopropylmagnesium bromide (0.149 mL, 0.431 mmol) drop wise. The reaction was let warm to room temperature over three hours, quenched with water and extracted with ethyl acetate and concentrated. The crude reaction was purified by flash column chromatography (silica gel, ethyl acetate/hexanes) to give a yellow oil (77 mg). LCMS-ESI$^+$ (m/z): [M+H]$^+$ calcd for $C_{30}H_{39}ClNO_3$: 496.25. found: 496.83.

Preparation of (S)-2-tert-butoxy-2-(5-(4-chlorophenyl)-2-isopropyl-7-methylquinolin-6-yl)ethanol: To a solution of (S)-2-tert-butoxy-2-(5-(4-chlorophenyl)-2-isopropyl-7-methylquinolin-6-yl)ethyl pivalate (77 mg, 0.156 mmol) in tetrahydrofuran/methanol (2:1, 1 mL) was added 1 M sodium hydroxide (2 mL) and the reaction was heated to 45° C. overnight. The reaction mixture was cooled to room temperature and diluted with water, extracted with ethyl acetate and washed with brine. The organic layer was then dried over sodium sulfate and concentrated, followed by co-evaporation with acetonitrile to give a clear oil (62 mg). LCMS-ESI$^+$ (m/z): [M+H]$^+$ calcd for $C_{25}H_{31}ClNO_2$: 412.20. found: 412.96.

Preparation of (S)-2-tert-butoxy-2-(5-(4-chlorophenyl)-2-isopropyl-7-methylquinolin-6-yl)acetic acid (90): To a solution of (S)-2-tert-butoxy-2-(5-(4-chlorophenyl)-2-isopropyl-7-methylquinolin-6-yl)ethanol (62 mg, 0.149 mmol) in wet acetonitrile at 0° C. was added 0.4 M $CrO_3/H_5IO_6$ (2.24 mL, 0.897 mmol) drop wise and stirred at 0° C. for 3 hours. Reaction was quenched with 2 M $NaH_2PO_4·2H_2O$ and purified by reverse phase HPLC (Gemini, 15-56% ACN/$H_2O$+ 0.1% TFA) and the desired product lyophilized to give a white powder (38 mg).

$^1$H-NMR: 400 MHz, (CD$_3$CN) δ: 8.21 (s, 1 H), 8.12 (d, J=9.2 Hz, 1 H), 7.60 (m, 4 H), 7.33 (d, J=7.6 Hz, 1 H), 5.25 (s, 1 H), 3.57 (dq, J=6.8, 6.4 Hz, 1 H), 2.68 (s, 3 H), 1.42 (d, J=6.8 Hz, 3 H), 1.41 (d, J=6.4 Hz, 3 H), 0.97 (s, 9 H).

LCMS-ESI (m/z): [M+H]$^+$ calcd for $C_{25}H_{29}ClNO_3$: 426.18. found: 426.78.

EXAMPLE 91

(S)-2-tert-Butoxy-2-(5-(4-chlorophenyl)-2-(1H-imidazol-1-yl)-7-methylquinolin-6-yl)acetic acid (91).

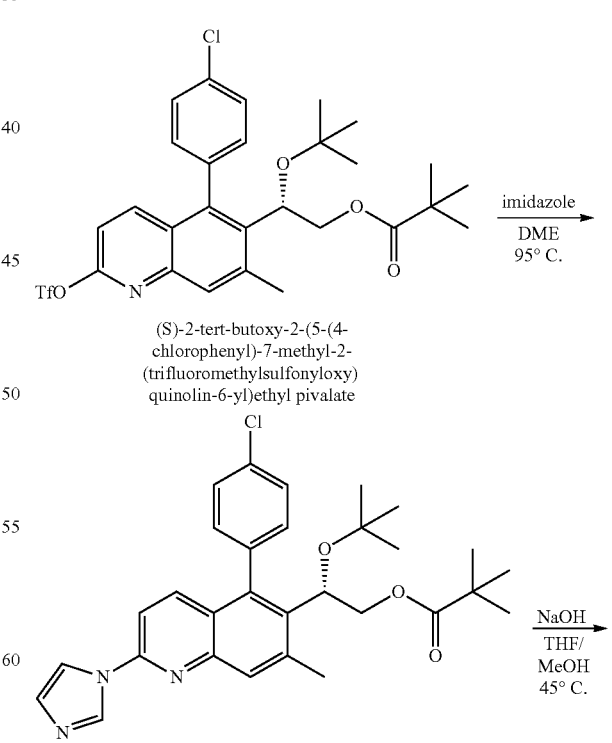

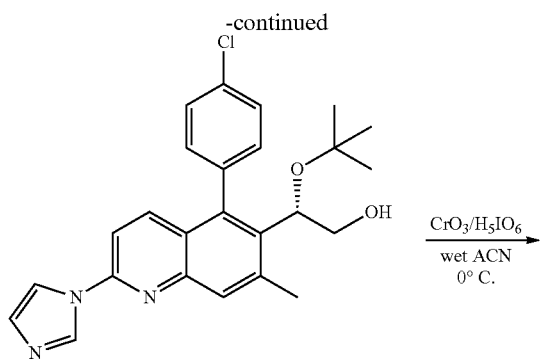

(S)-2-tert-butoxy-2-(5-(4-chlorophenyl)-2-(1H-imidazol-1-yl)-7-methylquinolin-6-yl)ethanol

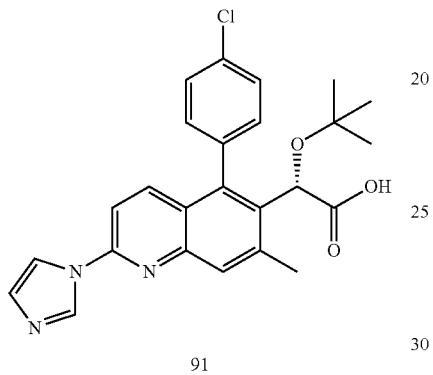

91

(S)-2-tert-butoxy-2-(5-(4-chlorophenyl)-2-(1H-imidazol-1-yl)-7-methylquinolin-6-yl)acetic acid Preparation of (S)-2-tert-butoxy-2-(5-(4-chlorophenyl)-2-(1H-imidazol-1-yl)-7-methylquinolin-6-yl)ethyl pivalate: To a solution of (S)-2-tert-butoxy-2-(5-(4-chlorophenyl)-7-methyl-2-(trifluoromethylsulfonyloxy)quinolin-6-yl)ethyl pivalate (compound of Example 26) (200 mg, 0.332 mmol) in 1,2-dimethoxyethane was added imidazole (226 mg, 3.32 mmol) and the reaction was sealed and heated to 95° C. overnight. The crude reaction mixture was absorbed onto silica gel and purified by flash column chromatography (silica gel, ethyl acetate/hexanes) to give a yellow oil (33.2 mg). LCMS-ESI$^+$ (m/z): [M+H]$^+$ calcd for C$_{30}$H$_{35}$ClN$_3$O$_3$: 520.23. found: 520.35.

Preparation of (S)-2-tert-butoxy-2-(5-(4-chlorophenyl)-2-(1H-imidazol-1-yl)-7-methylquinolin-6-yl)ethanol: To a solution of (S)-2-tert-butoxy-2-(5-(4-chlorophenyl)-2-(1H-imidazol-1-yl)-7-methylquinolin-6-yl)ethyl pivalate (39.2 mg, 0.075 mmol) in tetrahydrofuran and methanol (5:1, 1 mL) was added 1 M sodium hydroxide (2 mL) and the reaction was heated to 45° C. overnight. The reaction was cooled to room temperature, diluted with water and extracted with ethyl acetate. The organic layer was washed with brine, dried over sodium sulfate and concentrated. The crude extract was co-evaporated two times with acetonitrile to give a clear white oil (32.1 mg). LCMS-ER$^+$ (m/z): [M+H]$^+$ calcd for C$_{25}$H$_{27}$ClN$_3$O$_2$: 436.17. found: 436.86.

Preparation of (S)-2-tert-butoxy-2-(5-(4-chlorophenyl)-2-(1H-imidazol-1-yl)-7-methylquinolin-6-yl)acetic acid (91): To a solution of (S)-2-tert-butoxy-2-(5-(4-chlorophenyl)-2-(1H-imidazol-1-yl)-7-methylquinolin-6-yl)ethanol (32.1 mg, 0.074 mmol) in wet acetonitrile at 0° C. was added 0.4 M CrO$_3$/H$_5$IO$_6$ (1.1 mL, 0.442 mmol) and the reaction was stirred at 0° C. for three hours. The reaction was quenched with 1 M NaH$_2$PO$_4$2H$_2$O and extracted with ethyl acetate. The organic layer was concentrated and purified by reverse phase HPLC (Gemini, 10-55% ACN/H$_2$O+0.1% TFA) and the desired product lyophilized to give a white amorphous powder (11.1 mg).

$^1$H-NMR: 400 MHz, (CD$_3$CN) δ: 9.15 (s, 1 H), 8.13 (s, 1 H), 7.87 (m, 2 H), 7.58 (m, 4H), 7.51 (s, 1 H), 7.33 (d, J=8 Hz, 1 H), 5.24 (s, 1 H), 2.62 (s, 3 H), 0.97 (s, 9 H).

LCMS-ESI$^+$ (m/z): [M+H]$^+$ calcd for C$_{25}$H$_{25}$ClN$_3$O$_3$: 450.15. found: 450.59.

EXAMPLE 92

(S)-2-tert-butoxy-2-((R)-5-(2,3-dihydropyrano[4,3,2-de]quinolin-7-yl)-2-(isobutyl(methyl)amino)-7-methylquinolin-6-yl)acetic acid (92).

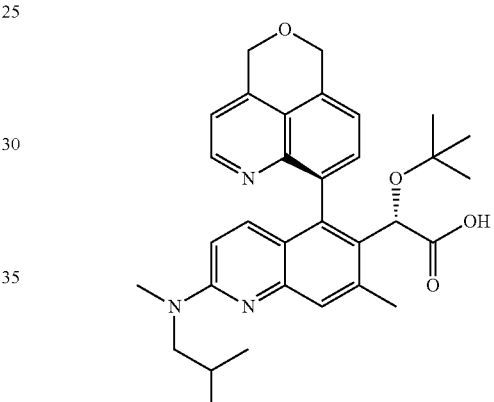

92

(S)-2-tert-butoxy-2-((R)-5-(2,3-dihydropyrano[4,3,2-de]quinolin-7-yl)-2-(isobutyl(methyl)amino)-7-methylquinolin-6-yl)acetic acid (S)-2-tert-Butoxy-2-((R)-5-(2,3-dihydropyrano[4,3,2-de]quinolin-7-yl)-2-(isobutyl(methypamino)-7-methylquinolin-6-yl)acetic acid (92) was prepared following the procedure for (S)-2-tert-butoxy-2-(5-(4-chlorophenyl)-2-(1H-imidazol-1-yl)-7-methylquinolin-6-yl)acetic acid of Example 91 except that (S)-2-tert-butoxy-2-((R)-5-(2,3-dihydropyrano[4,3,2-de]quinolin-7-yl)-7-methyl-2-(trifluoromethylsulfonyloxy)quinolin-6-yl)ethyl pivalate was used instead of (S)-2-tert-butoxy-2-(5-(4-chlorophenyl)-7-methyl-2-(trifluoromethylsulfonyloxy)quinolin-6-yl)ethyl pivalate and N,2-dimethylpropan-1-amine was used instead of imidazole. $^1$H-NMR: 400 MHz, (CD$_3$CN) δ: 8.65 (d, J=4.8 Hz, 1 H), 7.96 (s, 1 H), 7.52 (d, J=7.6 Hz, 1 H), 7.41 (d, J=4.8 Hz, 1 H), 7.26 (d, J=10.0 Hz, 1 H), 7.18 (d, J=7.6 Hz, 1 H), 6.89 (d, J=9.6 Hz, 1 H), 5.12 (s, 1 H), 4.57 (m, 2 H), 3.48 (m, 2 H), 3.40 (t, J=5.2 Hz, 2H), 3.34 (s, 3 H), 2.68 (s, 3 H), 2.09 (m, 1 H), 0.93 (m, 6 H), 0.86 (s, 9 H).

LCMS-ESI$^+$ (m/z): [M+H]$^+$ calcd for C$_{32}$H$_{38}$N$_3$O$_4$: 528.28. found: 528.34.

EXAMPLE 93

(S)-2-tert-Butoxy-2-((R)-5-(2,3-dihydropyrano[4,3,2-de]quinolin-7-yl)-2-(ethyl(methyl)amino)-7-methylquinolin-6-yl)acetic acid (93).

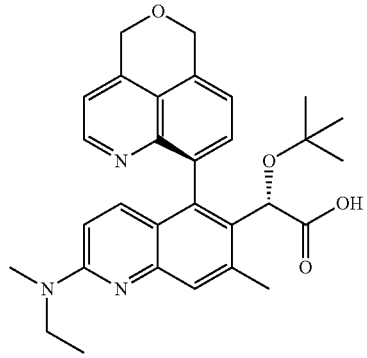

(S)-2-tert-butoxy-2-((R)-5-(2,3-dihydropyrano[4,3,2-de]quinolin-7-yl)-2-(ethyl(methyl)amino)-7-methylquinolin-6-yl)acetic acid (S)-2-tert-Butoxy-2-((R)-5-(2,3-dihydropyrano[4,3,2-de]quinolin-7-yl)-2-(ethyl(methypamino)-7-methylquinolin-6-yl)acetic acid (93) was prepared following the procedure for (S)-2-tert-butoxy-2-((R)-5-(2,3-dihydropyrano[4,3,2-de]quinolin-7-yl)-2-(isobutyl(methyl)amino)-7-methylquinolin-6-yl)acetic acid of Example 92 except that N-ethyl-N-methylamine was used instead of N,2-dimethylpropan-1-amine. $^1$H-NMR: 400 MHz, (CD$_3$CN) δ: 8.64 (d, J=4.4 Hz, 1 H), 7.96 (s, 1 H), 7.51 (d, J=7.6 Hz, 1 H), 7.39 (d, J=4.8 Hz, 1 H), 7.25 (d, J=9.6 Hz, 1 H), 7.17 (d, J=8.0 Hz, 1 H), 6.84 (d, J=9.6 Hz, 1 H), 5.11 (s, 1 H), 4.57 (m, 2 H), 3.71 (m, 2 H), 3.40 (t, J=5.6 Hz, 2H), 3.31 (s, HI), 2.66 (s, 3 H), 1.23 (t, J=7.2 Hz, 3 H), 0.85 (s, 9 H). LCMS-ESI$^+$ (m/z): [M+H]$^+$ calcd for C$_{30}$H$_{34}$N$_3$O$_4$: 500.25. found: 500.32.

EXAMPLE 94

(S)-2-tert-butoxy-2-((R)-5-(2,3-dihydropyrano[4,3,2-de]quinolin-7-yl)-7-methyl-2-(pyrrolidin-1-yl)quinolin-6-yl)acetic acid (94).

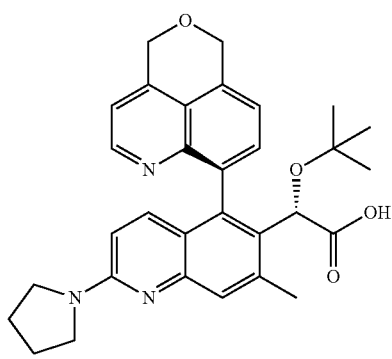

(S)-2-tert-butoxy-2-((R)-5-(2,3-dihydropyrano[4,3,2-de]quinolin-7-yl)-7-methyl-2-(pyrrolidin-1-yl)quinolin-6-yl)acetic acid (S)-2-tert-Butoxy-2-((R)-5-(2,3-dihydropyrano[4,3,2-de]quinolin-7-yl)-7-methyl-2-(pyrrolidin-1-yl)quinolin-6-yl) acetic acid (94) was prepared following the procedure for (S)-2-tert-butoxy-2-((R)-5-(2,3-dihydropyrano[4,3,2-de]quinolin-7-yl)-2-(isobutyl(methyl)amino)-7-methylquinolin-6-yl)acetic acid in of Example 92 except that pyrrolidine was used instead of N,2-dimethylpropan-1-amine. $^1$H-NMR: 400 MHz, (CD$_3$CN) δ: 8.64 (d, 4.8 Hz, 1 H), 7.91 (s, 1 H), 7.52 (d, J=7.2 Hz, 1 H), 7.39 (d, J=4.4 Hz, 1 H), 7.24 (d, J=10.0 Hz, 1 H), 7.17 (d, J=8.0 Hz, 1 H), 6.71 (d, J=10.0 Hz, 1 H), 5.11 (s, 1 H), 4.57 (m, 2 H), 3.74 (m, 2 H), 3.60 (m, 2 H), 3.40 (t, J=6.0 Hz, 2 H), 2.66 (s, 3H), 2.09 (m, 4 H), 0.85 (s, 9 H). LCMS-ESI$^+$ (m/z): [M+H]$^+$ calcd for C$_{31}$H$_{34}$N$_3$O$_4$: 512.25. found: 512.18.

EXAMPLE 95

(S)-2-((R)-2-(azetidin-1-yl)-5-(2,3-dihydropyrano[4,3,2-de] quinolin-7-yl)-7-methylquinolin-6-yl)-2-tert-butoxyacetic acid (95).

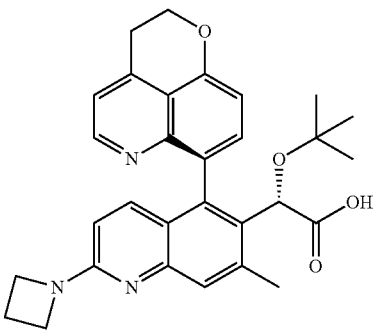

(S)-2-((R)-2-(azetidin-1-yl)-5-(2,3-dihydropyrano[4,3,2-de]quinolin-7-yl)-7-methylquinolin-6-yl)-2-tert-butoxyacetic acid (S)-2-((R)-2-(Azetidin-1-yl)-5-(2,3-dihydropyrano[4,3,2-de] quinolin-7-yl)-7-methylquinolin-6-yl)-2-tert-butoxyacetic acid (95) was prepared following the procedure for (S)-2-tert-butoxy-2-((R)-5-(2,3-dihydropyrano[4,3,2-de]quinolin-7-yl)-2-(isobutyl(methypamino)-7-methylquinolin-6-yl) acetic acid of Example 92 except that azetidine was used instead of N,2-dimethylpropan-1-amine.

$^1$H-NMR: 400 MHz, (CD$_3$CN) δ: 8.63 (d, (J=4.4 Hz, 1 H), 7.77 (s, 1 H), 7.50 (m, 1 H), 7.38 (d, 4.4 Hz, 1 H), 7.19 (d, J=10.4 Hz, 1 H), 7.16 (d, 8.0 Hz, 1 H), 6.41 (d, 10.0 Hz, 1H), 5.10 (s, 1 H), 4.56 (m, 2 H), 4.40 (m, 4 H), 3.39 (t, J=6.4 Hz, 2 H), 2.65 (s, 3 H), 2.51 (p, J=7.6 Hz, 2 H), 0.85 (s, 9 H). LCMS-ESI$^+$ (m/z): [M+H]$^+$ calcd for C$_{30}$H$_{32}$N$_3$O$_4$: 498.23. found: 498.14.

EXAMPLE 96

(S)-2-tert-butoxy-2-((R)-5-(2,3-dihydropyrano[4,3,2-de]quinolin-7-yl)-2-(dimethylamino)-7-methylquinolin-6-yl)acetic acid (96).

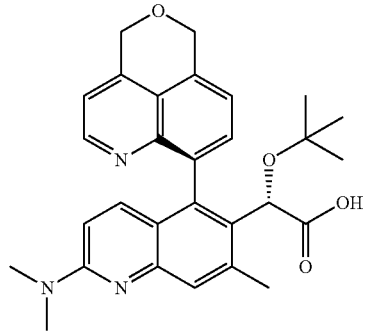

(S)-2-tert-butoxy-2-((R)-5-(2,3-dihydropyrano[4,3,2-de]quinolin-7-yl)-2-(dimethylamino)-7-methylquinolin-6-yl)acetic acid (S)-2-tert-Butoxy-2-((R)-5-(2,3-dihydropyrano[4,3,2-de]quinolin-7-yl)-2-(dimethylamino)-7-methylquinolin-6-yl)acetic acid (96) was prepared following the procedure for (S)-2-tert-butoxy-2-((R)-5-(2,3-dihydropyrano[4,3,2-de]quinolin-7-yl)-2-(isobutyl(methypamino)-7-methylquinolin-6-yl)acetic acid of Example 92 except that dimethylamine was used instead of N,2-dimethylpropan-1-amine.

$^1$H-NMR: 400 MHz, (CD$_3$CN) δ: 8.63 (d, J=4.8 Hz, 1 H), 7.96 (s, 1 H), 7.52 (d, J=7.6 Hz, 1 H), 7.39 (d, J=4.4 Hz, 1 H), 7.26 (d, J=9.6 Hz, 1 H), 7.17 (d, J=7.6 Hz, 1 H), 6.83 (d, J=10.4 Hz, 1 H), 5.12 (s, 1 H), 4.57 (m, 2 H), 3.39 (t, J=6.8 Hz, 2 H), 3.32 (s, 6H), 2.66 (s, 3 H), 0.86 (s, 9 H). LCMS-ESI$^+$ (m/z): [M+H]$^+$ calcd for C$_{29}$H$_{32}$N$_3$O$_4$: 486.23. found: 486.25.

EXAMPLE 97

(S)-2-tert-Butoxy-2-((R)-5-(2,3-dihydropyrano[4,3,2-de]quinolin-7-yl)-7-methyl-2-oxo-1,2-dihydroquinolin-6-yl)acetic acid (97).

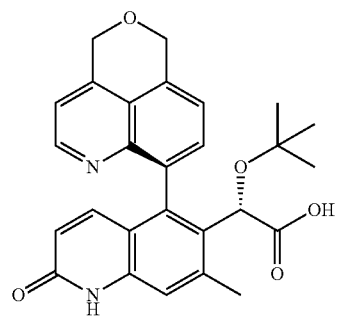

(S)-2-tert-butoxy-2-((R)-5-(2,3-dihydropyrano[4,3,2-de]quinolin-7-yl)-7-methyl-2-oxo-1,2-dihydroquinolin-6-yl)acetic acid Preparation of (S)-2-tert-butoxy-2-((R)-5-(2,3-dihydropyrano[4,3,2-de]quinolin-7-yl)-7-methyl-2-oxo-1,2-dihydroquinolin-6-yl)acetic acid (97): Compound 97 was isolated as a side product of the synthesis of (S)-2-tert-butoxy-2-((R)-5-(2,3-dihydropyrano[4,3,2-de]quinolin-7-yl)-2-(1H-imidazol-1-yl)-7-methylquinolin-6-yl)acetic acid (compound 98 of Example 98). $^1$H-NMR: 400 MHz, (CD$_3$CN) δ: 8.69 (d, J=5.2 Hz, 1 H), 7.63 (d, J=8.0 Hz, 1 H), 7.54 (d, J=4.8 Hz, 1 H), 7.26 (d, J=4.0 Hz, 1 H), 7.24 (s, 1 H), 6.87 (d, J=9.6 Hz, 1 H), 6.19 (J=9.6 Hz, 1 H), 5.03 (s, 1 H), 4.59 (m, 2 H), 3.47 (t, J=5.6 Hz, 2 H), 2.59 (s, 3 H), 0.87 (s, 9 H). LCMS-ESI$^+$ (m/z):

[M+H]$^+$ calcd for C$_{27}$H$_{27}$N$_2$O$_5$: 459.51. found: 459.20.

EXAMPLE 98

(S)-2-tert-butoxy-2-((R)-5-(2,3-dihydropyrano[4,3,2-de]quinolin-7-yl)-2-(1H-imidazol-1-yl)-7-methylquinolin-6-yl)acetic acid (98).

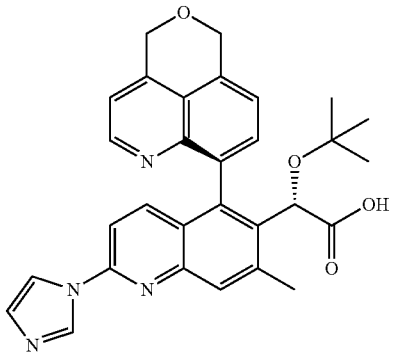

(S)-2-tert-butoxy-2-((R)-5-(2,3-dihydropyrano[4,3,2-de]quinolin-7-yl)-2-(1H-imidazol-1-yl)-7-methylquinolin-6-yl)acetic acid (S)-2-tert-Butoxy-2-((R)-5-(2,3-dihydropyrano[4,3,2-de]quinolin-7-yl)-2-(1H-imidazol-1-yl)-7-methylquinolin-6-yl)acetic acid (98) was prepared following the procedure for (S)-2-tert-butoxy-2-((R)-5-(2,3-dihydropyrano[4,3,2-de]quinolin-7-yl)-2-(isobutyl(methypamino)-7-methylquinolin-6-yl)acetic acid of Example 92 except that imidazole was used instead of N,2-dimethylpropan-1-amine and the last step had an additional 6 equivalents of 0.4 CrO$_3$/H$_5$IO$_6$ added 2 hours into the reaction and was then stirred an additional 3 hours. $^1$H-NMR: 400 MHz, (CD$_3$CN) δ: 9.16 (s, 1 H), 8.63 (d, J=4.4 Hz, 1 H), 8.12 (s, 1 H), 7.98 (s, 1 H), 7.59 (d, J=14.8 Hz, 1 H), 7.53 (m, 3 H), 7.42 (d, J=4.8 Hz, 1 H), 5.22 (s, 1 H), 4.59

(m, 2 H), 3.43 (t, J=6.0 Hz, 2 H), 2.74 (s, 3H), 0.91 (s, 9 H). LCMS-ESI+ (m/z): [M+H]+ calcd for $C_{30}H_{29}N_4O_4$: 509.21. found: 509.14.

EXAMPLE 99

(S)-2-tert-butoxy-2-((R)-2-(difluoromethyl)-5-(2,3-dihydropyrano[4,3,2-de]quinolin-7-yl)-7-methylquinolin-6-yl)acetic acid (99).

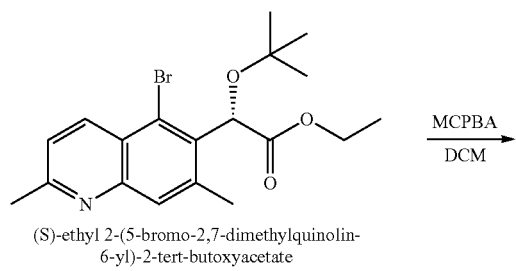

(S)-ethyl 2-(5-bromo-2,7-dimethylquinolin-6-yl)-2-tert-butoxyacetate

MCPBA
DCM

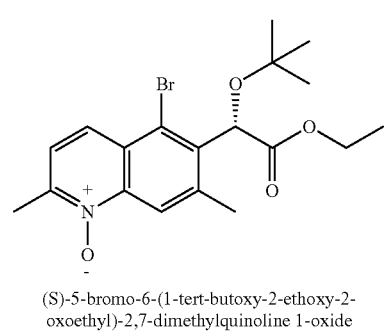

(S)-5-bromo-6-(1-tert-butoxy-2-ethoxy-2-oxoethyl)-2,7-dimethylquinoline 1-oxide 1. acetic acid
   acetic anhydride
2. 6M KOH
   THF

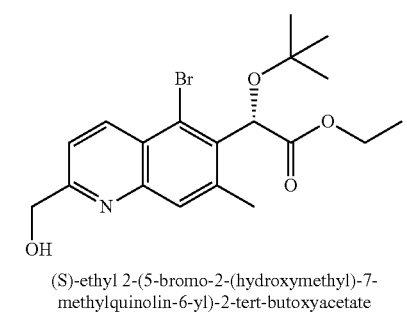

(S)-ethyl 2-(5-bromo-2-(hydroxymethyl)-7-methylquinolin-6-yl)-2-tert-butoxyacetate Dess-Martin
DCM

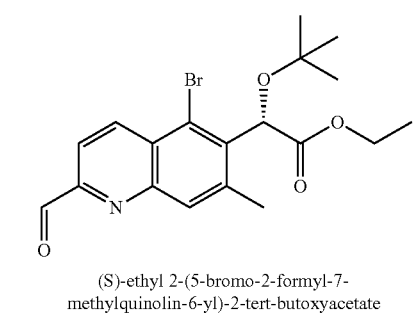

(S)-ethyl 2-(5-bromo-2-formyl-7-methylquinolin-6-yl)-2-tert-butoxyacetate

FluoLead
DCM

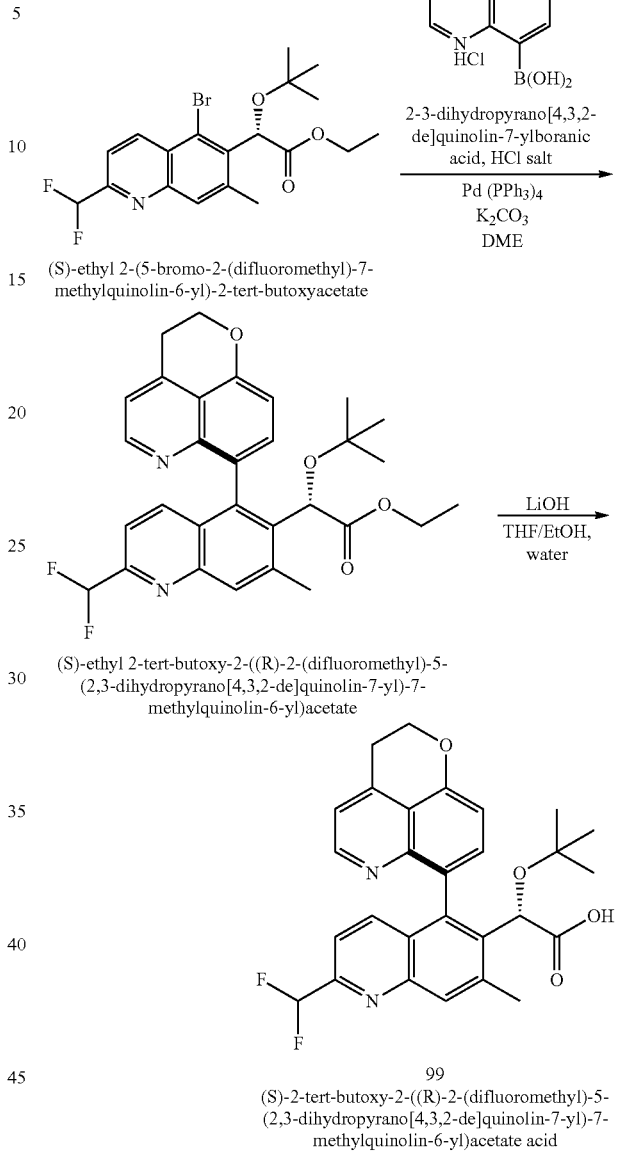

Preparation of (S)-5-bromo-6-(1-tert-butoxy-2-ethoxy-2-oxoethyl)-2,7-dimethylquinoline 1-oxide: To a solution of (S)-ethyl 2-(5-bromo-2,7-dimethylquinolin-6-yl)-2-tert-butoxyacetate (5H) (500 mg, 1.27 mmol) in dichloromethane (13 mL) at 0° C. was added 3-chloroperoxybenzoic acid (269 mg, 77%, 1.21 mmol) and the reaction mixture was allowed to slowly warm to room temperature over 3 hours. The reaction mixture was partitioned between ethyl acetate and water and the organic layer was concentrated and purified by flash column chromatography (silica gel, ethyl acetate/hexanes and methanol/ethyl acetate) to give a yellow oil (497 mg, 95%). LCMS-ESI+ (m/z): [M]+ calcd for $C_{19}H_{24}13rNO_4$: 410.3; found: 410.8.

Preparation of (S)-ethyl 2-(5-bromo-2-(hydroxymethyl)-7-methylquinolin-6-yl)-2-tert-butoxyacetate: A solution of S)-5-bromo-6-(1-tert-butoxy-2-ethoxy-2-oxoethyl)-2,7-dimethylquinoline 1-oxide (497 mg, 1.21 mmol) in acetic acid (12 mL) was heated at 80° C. for 15 minutes. To the solution was added acetic anhydride (1.37 mL, 14.5 mmol) and the resulting solution was heated at 110° C. for 2 hours. The reaction mixture was cooled to 50° C. and methanol (6 mL) was added and stirred for 1 hour. The reaction was cooled to room temperature and concentrated. The resultant oil was taken up in tetrahydrofuran (20 mL) to which was added 6 M potassium hydroxide (20 mL) and stirred for 1 hour. The product was extracted with ethyl acetate and the organic layer was concentrated and purified by flash column chromatography (silica gel, ethyl acetate/hexanes) to give a yellow oil (366 mg, 74%). LCMS-ESI$^+$ (m/z):

[M+H]$^+$ calcd for $C_{19}H_{25}BrNO_4$: 411.3. found: 410.7.

Preparation of (S)-ethyl 2-(5-bromo-2-formyl-7-methylquinolin-6-yl)-2-tert-butoxyacetate: To a solution of (S)-ethyl 2-(5-bromo-2-(hydroxymethyl)-7-methylquinolin-6-yl)-2-tert-butoxyacetate (200 mg, 0.49 mmol) in anhydrous dichloromethane (13 mL) at 0° C. was added Dess-Martin periodinane (248 mg, 0.58 mmol) and the reaction mixture was stirred for 1 hour. Reaction mixture was partitioned between dichloromethane and water and organic layer was concentrated and purified by flash column chromatography (silica gel, ethyl acetate/hexanes) to give a white solid (160 mg, 80%). LCMS-ESI$^+$ (m/z): [M+H]$^+$ calcd for $C_{19}H_{23}BrNO_4$: 408.07. found: 408.88, 410.14

Preparation of (S)-ethyl 2-(5-bromo-2-(difluoromethyl)-7-methylquinolin-6-yl)-2-tert-butoxyacetate: To a solution of Fluolead (392 mg, 1.57 mmol) in anhydrous dichloromethane (2 mL) at 0° C. was added (S)-ethyl 2-(5-bromo-2-formyl-7-methylquinolin-6-yl)-2-tert-butoxyacetate (160 mg, 0.39 mmol) as a solution in anhydrous dichloromethane (2 mL) and the reaction mixture was allowed to slowly warm to room temperature overnight. The reaction mixture was quenched with 0.5 M sodium hydroxide (10 mL), stirred 1 hour, and then partitioned between dichloromethane and 0.5 M sodium hydroxide and organic layer was concentrated and purified by flash column chromatography (silica gel, ethyl acetate/hexanes) to give a white solid (137 mg, 81%). LCMS-ESI$^+$ (m/z): [M+H]$^+$ calcd for $C_{19}H_{23}BrNO_4$: 430.08. found: 430.61, 431.85.

Preparation of (S)-ethyl 2-tert-butoxy-2-((R)-2-(difluoromethyl)-5-(2,3-dihydropyrano[4,3,2-de]quinolin-7-yl)-7-methylquinolin-6-yl)acetate: To a solution of (S)-ethyl 2-(5-bromo-2-(difluoromethyl)-7-methylquinolin-6-yl)-2-tert-butoxyacetate (70 mg, 0.16 mmol) in 1,2-dimethoxyethane (2 mL) was added 2,3-dihydropyrano[4,3,2-de]quinolin-7-yl-boronic acid, HCl salt (82 mg, 0.325 mmol), 2 M potassium carbonate (0.326 mL, 0.65 mmol) and Pd(PPh$_3$)$_4$ (19 mg, 0.016 mmol). The reaction mixture was sparged with argon for 5 minutes and then heated in microwave at 100° C. for 40 minutes. The reaction mixture was absorbed onto silica and purified by flash column chromatography (silica gel, ethyl acetate/hexanes) to give a brown film (35 mg, 41%). LCMS-ESI$^+$ (m/z): [M+H]$^+$ calcd for $C_{30}H_{31}F_2N_2O_4$: 521.22. found: 521.20.

Preparation of (S)-2-tert-butoxy-2-((R)-2-(difluoromethyl)-5-(2,3-dihydropyrano[4,3,2-de]quinolin-7-yl)-7-methylquinolin-6-yl)acetic acid (99): To a solution of (S)-ethyl 2-tert-butoxy-2-((R)-2-(difluoromethyl)-5-(2,3-dihydropyrano[4,3,2-de]quinolin-7-yl)-7-methylquinolin-6-ypacetate (35 mg, 0.07 mmol) in 1:1 tetrahydrofuran and ethanol (2.4 mL) was added lithium hydroxide (8 mg, 0.34 mmol) in 0.6 mL of water. The reaction was heated to 45° C. overnight. The reaction mixture was purified by reverse phase HPLC (Gemini, 15 to 55% ACN/H$_2$O+0.1% TFA) and the desired product was lyophilized to give a yellow powder (15.9 mg).
$^1$H-NMR: 400 MHz, (CD$_3$CN): 8.63 (d, J=4.8 Hz, 1 H), 8.10 (s, 1 H), 7.71 (d, J=8 Hz, 1 H), 7.54 (d, J=5.2 Hz, 1 H), 7.48 (s, 2 H), 7.30 (d, J=8 Hz, 1 H), 6.83 (t, J$_{H-F}$=55.2 Hz, 1 H), 5.22 (s, 1 H), 4.61 (m, 2 H), 3.49 (t, J=6 Hz, 2 H), 2.75 (s, 3 H), 0.91 (s, 9H). LCMS-ESI$^+$ (m/z): [M+H]$^+$ calcd for $C_{28}H_{27}F_2N_2O_4$: 493.19. found: 493.12.

EXAMPLE 100

(S)-2-tert-butoxy-2-(5-(4-chlorophenyl)-2-(difluoromethyl)-7-methylquinolin-6-yl)acetic acid (100).

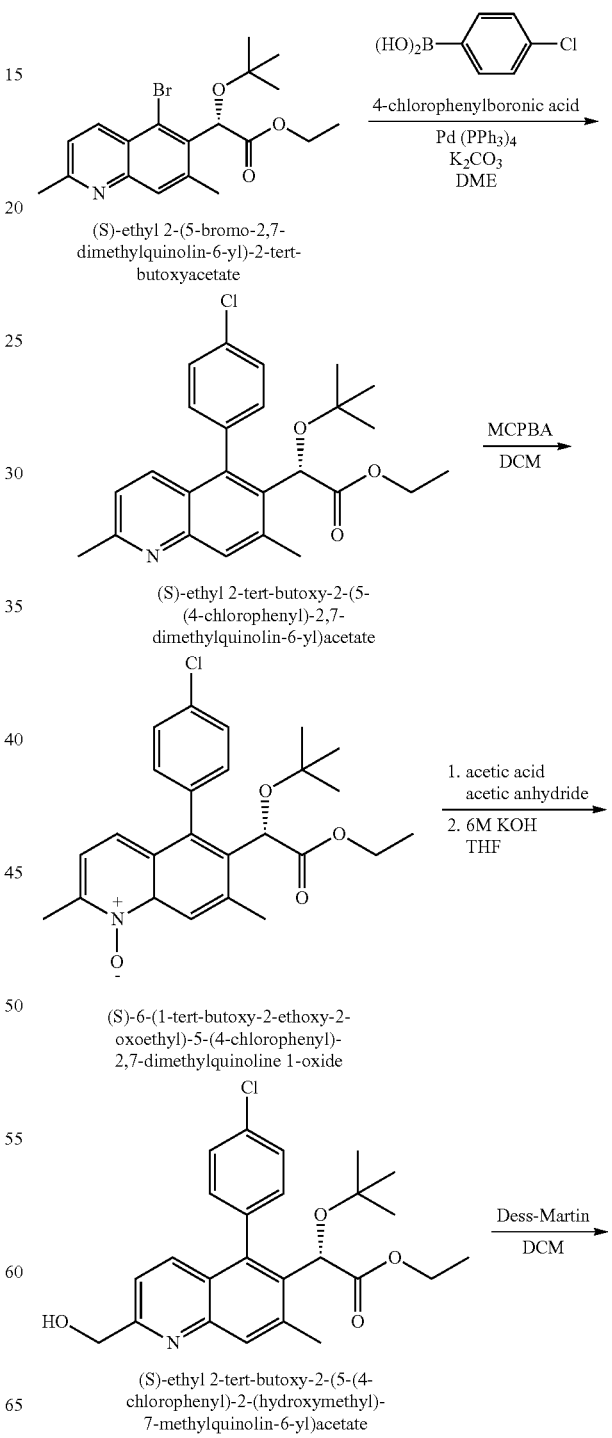

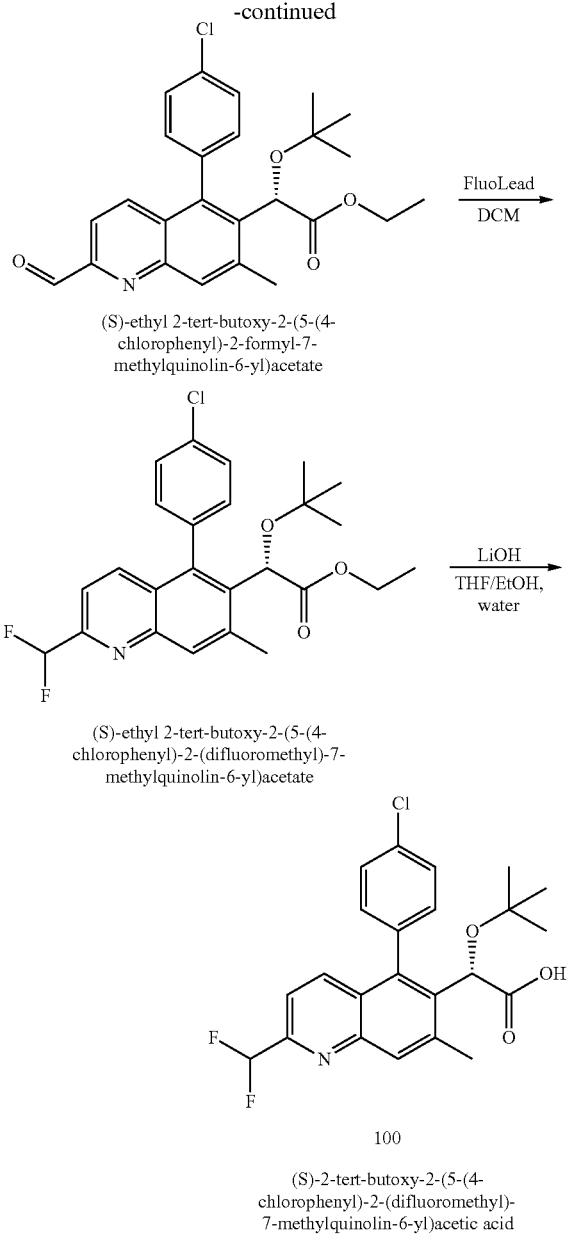

(S)-ethyl 2-tert-butoxy-2-(5-(4-chlorophenyl)-2-formyl-7-methylquinolin-6-yl)acetate (S)-ethyl 2-tert-butoxy-2-(5-(4-chlorophenyl)-2-(difluoromethyl)-7-methylquinolin-6-yl)acetate

100

(S)-2-tert-butoxy-2-(5-(4-chlorophenyl)-2-(difluoromethyl)-7-methylquinolin-6-yl)acetic acid Preparation of (S)-ethyl 2-tert-butoxy-2-(5-(4-chlorophenyl)-2,7-dimethylquinolin-6-yl)acetate: To a solution of (S)-ethyl 2-(5-bromo-2,7-dimethylquinolin-6-yl)-2-tert-butoxyacetate (5H) (500 mg, 1.27 mmol) and 4-chlorophenylboronic acid (238 mg, 1.52 mmol) in 1,2-dimethoxyethane (8 mL) was added Pd(PPh$_3$)$_4$ (147 mg, 0.13 mmol) and 2 M potassium carbonate (1.91 mL). The reaction was degassed for 15 minutes with argon and then heated to 110° C. for 20 minutes in a microwave reactor. The crude reaction was absorbed onto silica and purified by flash column chromatography (silica gel, ethyl acetate/hexanes) to give a pink foam (489 mg). LCMS-ESI$^+$ (m/z): [M+H]$^+$ calcd for C$_{25}$H$_{29}$ClNO$_3$: 426.18; found: 426.75.

Preparation of (S)-6-(1-tert-butoxy-2-ethoxy-2-oxoethyl)-5-(4-chlorophenyl)-2,7-dimethylquinoline 1-oxide: To a solution of (S)-ethyl 2-tert-butoxy-2-(5-(4-chlorophenyl)-2,7-dimethylquinolin-6-yl)acetate (489 mg, 1.15 mmol) in anhydrous dichloromethane at 0° C. was added 3-chloroperoxybenzoic acid (243 mg, 77%, 1.09 mmol) and the reaction was stirred for 3 h. The crude reaction was absorbed onto silica gel and purified by flash column chromatography (silica gel, ethyl acetate/hexanes, methanol/ethyl acetate) to give a white foam (261 mg). LCMS-ESI$^+$ (m/z): [M+H]$^+$ calcd for C$_{25}$H$_{29}$ClNO$_4$: 442.17. found: 442.88.

Preparation of (S)-ethyl 2-tert-butoxy-2-(5-(4-chlorophenyl)-2-(hydroxymethyl)-7-methylquinolin-6-ypacetate: A solution of (S)-6-(1-tert-butoxy-2-ethoxy-2-oxoethyl)-5-(4-chlorophenyl)-2,7-dimethylquinoline 1-oxide (261 mg, 0.59 mmol) in acetic acid (6 mL) was heated to 80° C. for 15 minutes. To the solution was added acetic anhydride (0.67 mL, 7.09 mmol) and the resulting solution was heated at 110° C. for 2 hours. The reaction mixture was cooled to 50° C. and 3 mL of methanol was added and stirred for 1 hour. The reaction was cooled to room temperature and concentrated. The resultant oil was taken up in tetrahydrofuran and 6 M potassium hydroxide was added to adjust to pH 12 and stirred for 3 hours. The mixture was then diluted with water and extracted with ethyl acetate and concentrated. The product was purified by flash column chromatography (silica gel, ethyl acetate/hexanes) to give a clear oil (213 mg).

LCMS-ESI$^+$ (m/z): [M+H]$^+$ calcd for C$_{25}$H$_{29}$ClNO$_4$: 442.17. found: 442.69.

Preparation of (S)-ethyl 2-tert-butoxy-2-(5-(4-chlorophenyl)-2-formyl-7-methylquinolin-6-ypacetate: To a solution of (S)-ethyl 2-tert-butoxy-2-(5-(4-chlorophenyl)-2-(hydroxymethyl)-7-methylquinolin-6-ypacetate (160 mg, 0.36 mmol) in anhydrous dichloromethane at 0° C. was added Dess-Martin periodinane (184 mg, 0.43 mmol) and the reaction was stirred for 1 hour at 0° C. The reaction was quenched with water, extracted with dichloromethane and concentrated. The crude product was purified by flash column chromatography (silica gel, ethyl acetate/hexanes) to give a clear oil (139 mg). LCMS-ESI$^+$ (m/z): [M+H]$^+$ calcd for C$_{25}$H$_{27}$ClNO$_4$: 440.16. found: 440.55.

Preparation of (S)-ethyl 2-tert-butoxy-2-(5-(4-chlorophenyl)-2-(difluoromethyl)-7-methylquinolin-6-ypacetate: To a solution of (S)-ethyl 2-tert-butoxy-2-(5-(4-chlorophenyl)-2-formyl-7-methylquinolin-6-ypacetate (139 mg, 0.32 mmol) in anhydrous dichloromethane (3 mL) at 0° C. was added Fluolead (174 mg, 0.695 mmol) and the reaction was stirred for ½ hour at 0° C. and then allowed to warm to room temperature overnight. The reaction was quenched with 0.5 M sodium hydroxide and stirred for 1 hour. The crude product was extracted with dichloromethane, concentrated and purified by flash column chromatography (silica gel, ethyl acetate/hexanes) to give a clear oil (111 mg). LCMS-ESI$^+$ (m/z): [M+H]$^+$ calcd for C$_{25}$H$_{27}$ClF$_2$NO$_3$: 462.16. found: 462.54.

Preparation of (S)-2-tert-butoxy-2-(5-(4-chlorophenyl)-2-(difluoromethyl)-7-methylquinolin-6-yl)acetic acid (100): To a solution of (S)-ethyl 2-tert-butoxy-2-(5-(4-chlorophenyl)-2-(difluoromethyl)-7-methylquinolin-6-ypacetate (111 mg, 0.24 mmol) in tetrahydrofuran:ethanol:water (2:2:1, 3 mL) was added lithium hydroxide (29 mg, 1.2 mmol) and the reaction was heated to 45° C. overnight. The crude product was purified by reverse phase HPLC (Gemini, 20-29% ACN/H$_2$O+0.1% TFA) and the desired product was lyophilized to give a white powder (77.5 mg).

$^1$H-NMR: 400 MHz, (CD$_3$CN) δ: 7.97 (s, 1 H), 7.87 (d, J=8.8 Hz, 1 H), 7.59 (m, 4 H), 7.35 (d, J=7.6 Hz, 1 H), 6.84 (t, J$_{H-F}$=55.2 Hz, 1 H), 5.26 (s, 1 H), 2.64 (s, 3 H), 0.97 (s, 9H).
$^{19}$F-NMR: 377 MHz, (CD$_3$CN) δ: −116.71 (dd, J=62.02, 55.42 Hz).

LCMS-ESI⁺ (m/z): [M+H]⁺ calcd for $C_{23}H_{23}ClF_2NO_3$: 434.88. found: 434.47.

EXAMPLE 101

(S)-2-(1-(2-(((9H-Fluoren-9-yl)methoxy)carbonylamino)ethyl)-5-(4-chlorophenyl)-7-methyl-2-oxo-1,2-dihydroquinolin-6-yl)-2-tert-butoxyacetic acid (101).

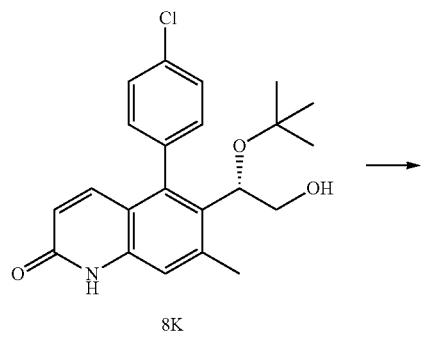

8K (S)-6-(1-tert-butoxy-2-hydroxyethyl)-5-(4-chlorophenyl)-7-methylquinolin-2(1H)-one

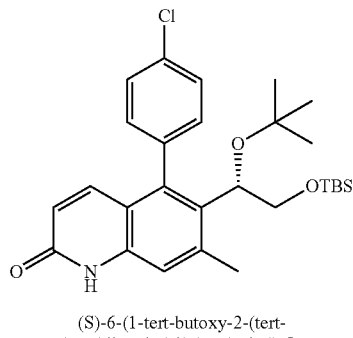

(S)-6-(1-tert-butoxy-2-(tert-butyldimethylsilyloxy)ethyl)-5-(4-chlorophenyl)-7-methylquinolin-2(1H)-one

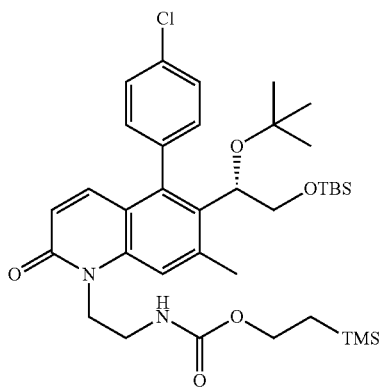

(S)-2-(trimethylsilyl)ethyl 2-(6-(1-tert-butoxy-2-(tert-butyldimethylsilyloxy)ethyl)-5-(4-chlorophenyl)-7-methyl-2-oxoquinolin-1(2H)-yl)ethylcarbamate

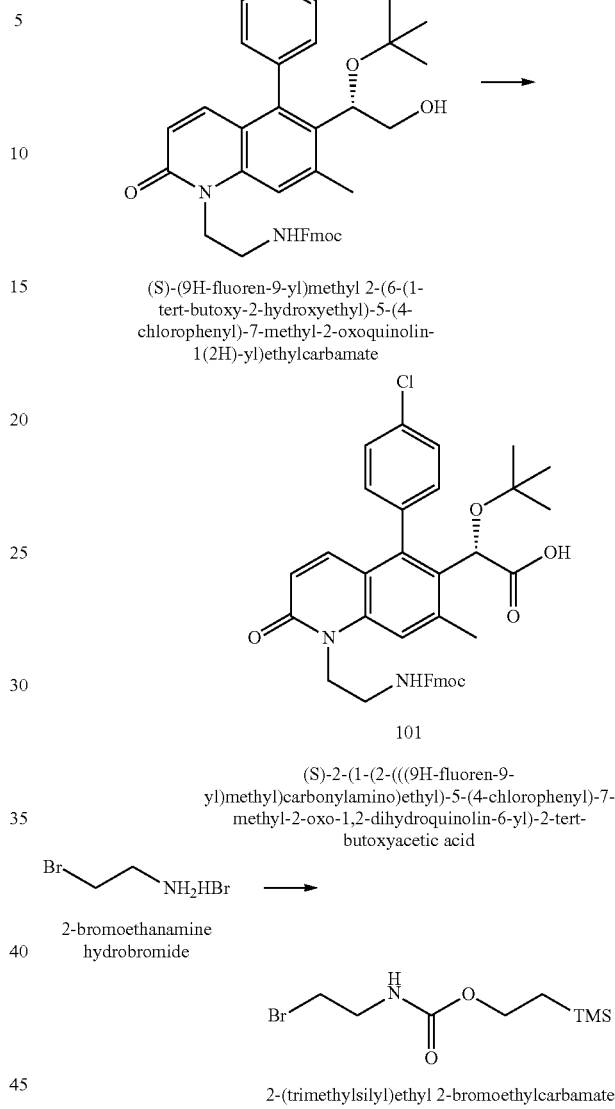

(S)-(9H-fluoren-9-yl)methyl 2-(6-(1-tert-butoxy-2-hydroxyethyl)-5-(4-chlorophenyl)-7-methyl-2-oxoquinolin-1(2H)-yl)ethylcarbamate

101

(S)-2-(1-(2-(((9H-fluoren-9-yl)methyl)carbonylamino)ethyl)-5-(4-chlorophenyl)-7-methyl-2-oxo-1,2-dihydroquinolin-6-yl)-2-tert-butoxyacetic acid 2-bromoethanamine hydrobromide 2-(trimethylsilyl)ethyl 2-bromoethylcarbamate Preparation of (S)-6-(1-tert-butoxy-2-(tert-butyldimethylsilyloxy)ethyl)-5-(4-chlorophenyl)-7-methylquinolin-2(1H)-one: To a solution of (S)-6-(1-tert-butoxy-2-hydroxyethyl)-5-(4-chlorophenyl)-7-methylquinolin-2(1H)-one (8K) (0.5175 g, 1.34 mmol) in DMF (5.0 mL), was added imidazole (0.204 g, 4.02 mmol), followed by tert-butyldimethylsilyl chloride (0.243 g, 1.61 mmol) at 0° C. The reaction mixture was warmed to room temperature overnight. Additional imidazole (0.2 g) and tert-butyldimethylsilyl chloride (0.30 g) were added and the mixture stirred for another 2 hours. The reaction mixture was the diluted with ethyl acetate, washed with 5% lithium chloride solution (2×), brine, dried (MgSO₄), filtered, concentrated and purified by flash column chromatography (silica gel, 20 to 60% ethyl acetate/hexanes) to give a yellow foam (0.500 g). LCMS-ESI⁺ (m/z): calcd for $C_{28}H_{39}ClNO_3Si$: 501.1; found: 500.3, 502.2.

Preparation of (S)-2-(trimethylsilyl)ethyl 2-(6-(1-tert-butoxy-2-(tert-butyldimethylsilyloxy)ethyl)-5-(4-chlorophenyl)-7-methyl-2-oxoquinolin-1(2H)-yl)ethylcarbamate: To a solution of (S)-6-(1-tert-butoxy-2-(tert-butyldimethylsilyloxy)ethyl)-5-(4-chlorophenyl)-7-methylquinolin-2(1H)-one (0.4061 g, 0.812 mmol) in DMF (8.0 mL) was added potassium tert-butoxide (0.137 g, 1.22 mmol) and the mixture stirred for 30 minutes. A solution of 2-(trimethylsilyl)ethyl 2-bromoethylcarbamate (0.327 g, 1.22 mmol) in DMF (1 mL) was added and the reaction mixture was allowed to slowly warm to room temperature overnight. The reaction mixture was cooled to 0° C., potassium tert-butoxide (0.200 g) was added and the resulting reaction mixture was stirred for 30 minutes. A solution of 2-(trimethylsilyl)ethyl 2-bromoethylcarbamate (0.5 g) in DMF (1 mL) was added and the reaction mixture was warmed to room temperature overnight. Reaction mixture was diluted with ethyl acetate and washed with 5% lithium chloride solution (2×), brine, dried (MgSO$_4$), filtered, concentrated and purified by flash column chromatography (silica gel, 10 to 50% ethyl acetate/hexanes) to give desired product a yellow foam (0.2725 g). Some O-alkylation side-product was also observed.

LCMS-ESI$^+$ (m/z): [M+H]$^+$ calcd for $C_{36}H_{56}ClN_2O_5Si_2$: 688.5. found: 687.1, 689.1.

Preparation of (S)-(9H-fluoren-9-yl)methyl 2-(6-(1-tert-butoxy-2-hydroxyethyl)-5-(4-chlorophenyl)-7-methyl-2-oxoquinolin-1(2H)-yl)ethylcarbamate: To a solution of (S)-2-(trimethylsilyl)ethyl 2-(6-(1-tert-butoxy-2-(tert-butyldimethylsilyloxy)ethyl)-5-(4-chlorophenyl)-7-methyl-2-oxoquinolin-1(2H)-yl)ethylcarbamate (0.456 g, 0.663 mmol) in THF (6.6 mL) at 0° C. was added 1 M TBAF in THF (1.99 mL, 1.99 mmol) and reaction mixture was warmed to room temperature overnight. Reaction mixture was cooled to 0° C., additional 1 M TBAF in THF (1.0 mL, 1.0 mmol) was added and warmed to room temperature over 8 hours. Reaction mixture was cooled to 0° C., saturated sodium bicarbonate solution (1.0 mL) and 9-fluorenylmethoxycarbonyl chloride (0.257 g, 0.995 mmol) were added. Reaction mixture was vigorously stirred overnight at room temperature, diluted with ethyl acetate, washed with brine, dried (MgSO$_4$), filtered, concentrated and purified by flash column chromatography (silica gel, 30 to 70% ethyl acetate/hexanes) to give a white foam (0.389 g). LCMS-ESI$^+$ (m/z): [M+H]$^+$ calcd for $C_{39}H_{40}ClN_2O_5$: 652.2. found: 651.2, 652.2, 653.2.

Preparation of (S)-2-(1-(2-(((9H-fluoren-9-ylmethoxy)carbonylamino)ethyl)-5-(4-chlorophenyl)-7-methyl-2-oxo-1,2-dihydroquinolin-6-yl)-2-tert-butoxyacetic acid (101): To a solution of (S)-(9H-fluoren-9-yl)methyl 2-(6-(1-tert-butoxy-2-hydroxyethyl)-5-(4-chlorophenyl)-7-methyl-2-oxoquinolin-1(2H)-yl)ethylcarbamate (0.3443 g, 0.529 mmol) in dichloromethane (5.0 mL) was added Dess-Martin periodinane (0.449 g, 1.06 mmol). Reaction mixture was allowed to warm to room temperature over 1.5 hours, quenched with sodium thiosulfate solution and extracted with ethyl acetate. Organic layer was washed with brine, dried (MgSO$_4$), filtered, concentrated and used in next step without further purification. LCMS-ESI$^+$ (m/z): [M+H]$^+$ calcd for $C_{39}H_{38}ClN_2O_5$: 650.2. found: 649.1, 650.1.

To a solution of the above residue in acetonitrile (5.0 mL) and 1 M NaH$_2$PO$_4$ buffer (5.0 mL) was added 80% sodium chlorite (0.44 g, 1.587 mmol). Reaction mixture was stirred for 1.5 hours, diluted with water and ethyl acetate. The pH was adjusted to -pH 5 with 1 N HCl solution and organic layer was washed with brine, dried (MgSO$_4$), filtered, concentrated and purified by flash column chromatography (silica gel, 0 to 10% methanol/dichloromethane) to give a yellow powder (0.1943 g).

$^1$H NMR (400 MHz, CD$_3$OD) δ 7.78 (d, J=7.6 Hz, 2 H), 7.71 (s, 1 H), 7.63 (dd, J=6.4, 6.4 Hz, 2 H), 7.57-7.51 (m, 3 H), 7.41-7.28 (m, 5 H), 7.22 (d, J=7.2 Hz, 1 H), 6.47 (d, J=10 Hz, 1 H), 5.02 (s, 1 H), 4.49 (dd, J=8.4, 8.4 Hz, 2 H), 4.36-4.28 (m, 2 H), 4.15 (dd, J=7.2, 7.2 Hz, 1 H), 3.51-3.48 (m, 2 H), 2.64 (s, 3 H), 0.92 (s, 9 H).

LCMS-ESI$^+$ (m/z): [M+H]$^+$ calcd for $C_{39}H_{38}ClN_2O_6$: 666.2. found: 665.1, 666.1.

Preparation of 2-(trimethylsilyl)ethyl 2-bromoethylcarbamate: Trimethylsilylethyl chloroformate was prepared according to Sekine et al, *Lett. Org. Chem.* 2004, 1, 179-182. To a mixture of 2-bromoethylamine hydrobromide (1.0 g, 4.88 mmol) in THF (20 mL) was added saturated sodium bicarbonate solution, followed by crude trimethylsilylethyl chloroformate (8.8 g, 14.64 mmol). Reaction mixture was stirred overnight at room temperature, concentrated and portioned between ethyl acetate and saturated sodium bicarbonate solution. Aqueous layer was extracted with ethyl acetate (2x) and combined organic layer was dried (MgSO$_4$), filtered, concentrated and purified by flash column chromatography (silica gel, 0 to 20% ethyl acetate/hexanes) to give a colorless oil (1.321 g).

$^1$H-NMR: 400 MHz, (CD$_3$Cl) δ: 4.14 (dd, J=8.4, 8.4 Hz, 2 H), 3.74-3.69 (m, 2 H), 3.55 (dd, J=5.6, 5.6 Hz, 2 H), 3.44 (dd, J=5.6, 5.6 Hz, 2 H), 0.99-0.92 (m, 2 H), -0.008 (s, 9H).

EXAMPLE 102

(S)-2-tert-butoxy-2-((R)-5-(2,3-dihydrobenzo[de]chromen-7-yl)-2,7-dimethylquinolin-6-yl)acetic acid (102A) and (S)-2-tert-butoxy-2-((S)-5-(2,3-dihydrobenzo[de]chromen-7-yl)-2,7-dimethylquinolin-6-yl)acetic acid (102B).

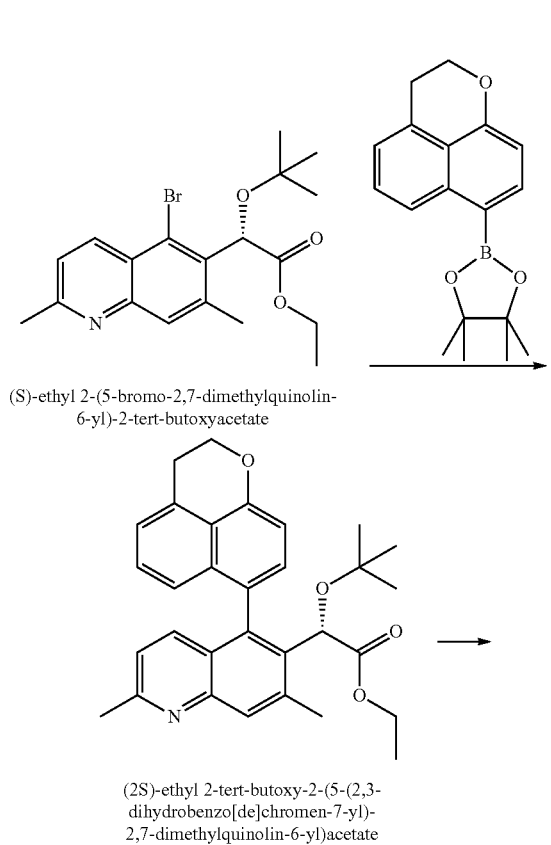

(S)-ethyl 2-(5-bromo-2,7-dimethylquinolin-6-yl)-2-tert-butoxyacetate (2S)-ethyl 2-tert-butoxy-2-(5-(2,3-dihydrobenzo[de]chromen-7-yl)-2,7-dimethylquinolin-6-yl)acetate

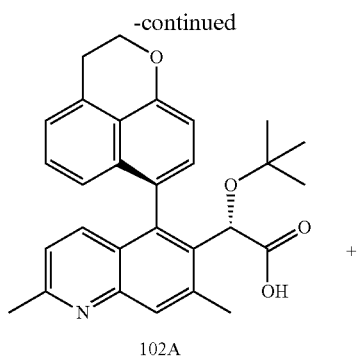

102A (S)-2-tert-butoxy-2-((R)-5-(2,3-dihydrobenzo[de]chromen-7-yl)-2,7-dimethylquinolin-6-yl)acetic acid

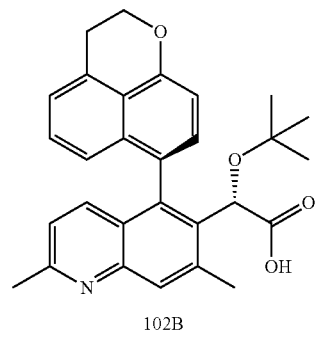

102B (S)-2-tert-butoxy-2-((S)-5-(2,3-dihydrobenzo[de]chromen-7-yl)-2,7-dimethylquinolin-6-yl)acetic acid Preparation of (2S)-ethyl 2-tert-butoxy-2-(5-(2,3-dihydrobenzo[de]chromen-7-yl)-2,7-dimethylquinolin-6-yl)acetate: In a 5-10 mL microwave vial, (S)-ethyl 2-(5-bromo-2,7-dimethylquinolin-6-yl)-2-tert-butoxyacetate (5H) (82.4 mg, 0.21 mmol) was dissolved in 4.0 mL of DMA. To this was added 2-(2,3-dihydrobenzo[de]chromen-7-yl)-4,4,5,5-tetramethyl-1,3,2-dioxaborolane (110 mg, 0.37 mmol), Pd(PPh$_3$)$_4$ (24.2 mg, 0.021 mmol) and 225 µL of 2 M K$_2$CO$_3$, the reaction vessel sealed and heated thermally at 80° C. for 4 hours. The mixture was diluted 400% with EtOAc, washed with 5% LiCl (4×8 mL), saturated NH$_4$Cl and brine. After drying with sodium sulfate, the extracts were concentrated in vacuo and chromatographed on silica gel using EtOAc in Heptane to give rise to desired product (42.4 mg, 0.088 mmol). LCMS-ESI$^+$ (m/z): [M+H]$^+$ calcd for C$_{31}$H$_{34}$NO$_4$: 483.6. Found: 484.47, 485.49.

Preparation of (S)-2-tert-butoxy-2-((R)-5-(2,3-dihydrobenzo[de]chromen-7-yl)-2,7-dimethylquinolin-6-yl)acetic acid (102A) and (S)-2-tert-butoxy-2-((S)-5-(2,3-dihydrobenzo[de]chromen-7-yl)-2,7-dimethylquinolin-6-yl) acetic acid (102B): To a 3:1:1 (v/v/v) THF-MeOH—H$_2$O solution (10 mL) of (2S)-ethyl 2-tert-butoxy-2-(5-(2,3-dihydrobenzo[de]chromen-7-yl)-2,7-dimethylquinolin-6-yl)acetate (42.4 mg, 0.088 mmol) was added LiOH (170 mg, 4.05 mmol) and the reaction allowed to stir overnight at 23° C. Hydrolysis was incomplete, so NaOH (~200 mg) was added and the mixture stirred an additional 90 min at 23° C. The reaction was diluted 400% with EtOAc, washed with brine and dried with sodium sulfate. Concentration in vacuo followed by PREP HPLC purification gave rise to two atropisomer mixtures.

The first eluting atropisomer mixture was found to be 95:5 (ratio determined by NMR) mixture of (S)-2-tert-butoxy-2-((R)-5-(2,3-dihydrobenzo[de]chromen-7-yl)-2,7-dimethylquinolin-6-yl)acetic acid (102A) as the major constituent and (S)-2-tert-butoxy-2-((S)-5-(2,3-dihydrobenzo[de]chromen-7-yl)-2,7-dimethylquinolin-6-yl)acetic acid as the impurity. $^1$H-NMR: 400 MHz, (CD$_3$OD): δ: 8.02 (s, 1 H); 7.94 (d, J=9.2 Hz, 1 H); 7.56 (d, J=8.8 Hz, 1 H); 7.31 (d, J=7.6 Hz, 1 H); 7.26-7.20 (m, 2 H); 70.07 (d, J=8.0 Hz, 1 H); 7.02 (d, J=7.6 Hz, 1 H); 5.20 (s, 1 H); 4.55-4.48 (m, 2 H); 2.92 (s, 3 H); 2.86 (s, 3 H); 1.04 (s, 9 H). LCMS-ESI$^+$ (m/z): [M+H]$^+$ calcd for C$_{29}$H$_{30}$NO$_4$: 456.5;

Found: 456.44.

The other atropisomer, (S)-2-tert-butoxy-2-((S)-5-(2,3-dihydrobenzo[de]chromen-7-yl)-2,7-dimethylquinolin-6-yl) acetic acid (102B), eluted later and was obtained as a 2.61:1 (ratio determined by NMR) mixture as the major constituent with (S)-2-tert-butoxy-2-((R)-5-(2,3-dihydrobenzo[de]chromen-7-yl)-2,7-dimethylquinolin-6-yl)acetic acid as the impurity. $^1$H-NMR: 400 MHz, (CD$_3$OD): δ: 7.99 (s, 1 H); 7.89 (d, J=8.4 Hz, 1 H); 7.66 (d, J=8.0 Hz, 1 H); 7.52 (d, J=8.8 Hz, 1 H); 7.24-7.20 (m, 2 H); 7.13 (d, J=8.0 Hz, 1 H); 6.81 (d, J=8.0 Hz, 1 H); 5.32 (s, 1 H); 4.53-4.51 (m, 2 H); 2.91 (2, 3H); 2.82 (s, 3 H); 0.73 (s, 9 H). LCMS-ESI$^+$ (m/z): [M+H]$^+$ calcd for C$_{29}$H$_{30}$NO$_4$: 456.5. Found: 456.44.

EXAMPLE 103

(2S)-2-tert-butoxy-2-(2,7-dimethyl-5-(3,5,6,7-tetrahydro-2H-[1,4]oxazino[2,3,4-ij]quinolin-8-yl)quinolin-6-yl)acetic acid (103)

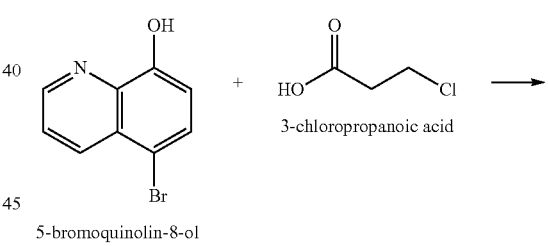

5-bromoquinolin-8-ol    3-chloropropanoic acid

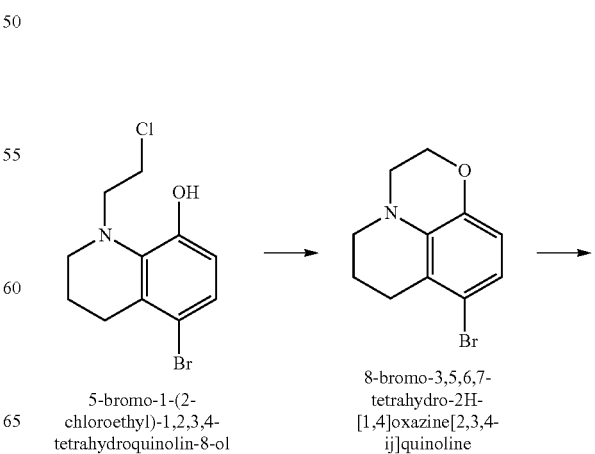

5-bromo-1-(2-chloroethyl)-1,2,3,4-tetrahydroquinolin-8-ol    8-bromo-3,5,6,7-tetrahydro-2H-[1,4]oxazine[2,3,4-ij]quinoline

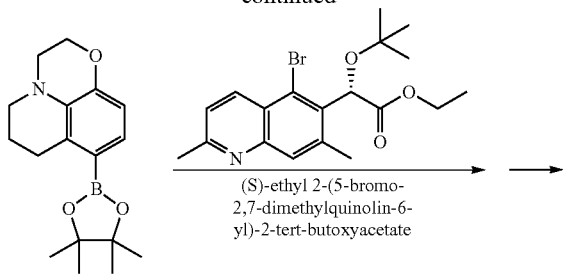

8-(4,4,5,6-tetramethyl-1,3,2-dioxaborolan-2-yl)-3,5,6,7-tetrahydro-2H-[1,4]oxazino[2,3,4-ij]quinoline (S)-ethyl 2-(5-bromo-2,7-dimethylquinolin-6-yl)-2-tert-butoxyacetate

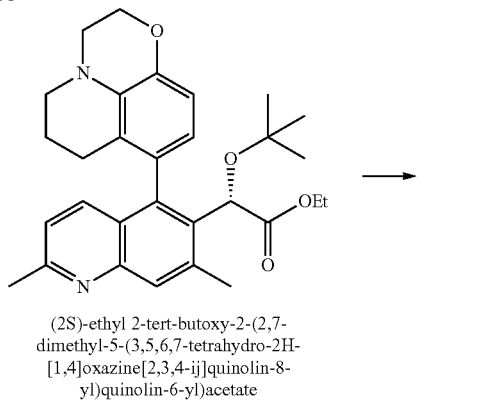

(2S)-ethyl 2-tert-butoxy-2-(2,7-dimethyl-5-(3,5,6,7-tetrahydro-2H-[1,4]oxazine[2,3,4-ij]quinolin-8-yl)quinolin-6-yl)acetate

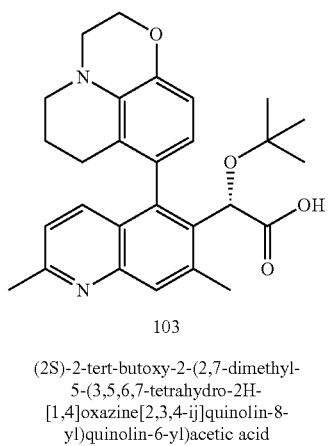 [SMILES: Cc1ccc2c(-c3ccc4c5c3CCCN5CCO4)c([C@H](OC(C)(C)C)C(=O)O)c(C)cc2n1]

103

(2S)-2-tert-butoxy-2-(2,7-dimethyl-5-(3,5,6,7-tetrahydro-2H-[1,4]oxazine[2,3,4-ij]quinolin-8-yl)quinolin-6-yl)acetic acid Preparation of 5-bromo-1-(2-chloroethyl)-1,2,3,4-tetrahydroquinolin-8-ol: In a round bottom flask, 3-chloropropanoic acid (8.44 g, 89.3 mmol, 20 eq.) was added to 5-bromoquinolin-8-ol (1 g, 4.46 mmol, 1 eq.) in 15 mL THF at 0° C. NaBH$_4$ (759 mg, 20 mmol, 4.5 eq.) was added portionwise in 50 minutes at 0° C. The reaction was stirred at 0° C. for 30 minutes then heated to 80° C. for 2 hours. The reaction was cooled down. Reaction mixture was diluted with ethyl acetate and washed with brine, dried (MgSO$_4$), filtered, concentrated to give 5-bromo-1-(2-chloroethyl)-1,2,3,4-tetrahydroquinolin-8-ol crude. LCMS-ESI$^+$ (m/z): [M+H]$^+$ calcd for C$_{11}$H$_{14}$BrClNO: 291.58. found: 292.0.

Preparation of 8-bromo-3,5,6,7-tetrahydro-2H-[1,4]oxazino[2,3,4-ij]quinoline: The above reaction crude was dissolved in 20 mL MeOH. 50 mL 2 N NaOH aqueous solution was added. The reaction was stirred at room temperature for 2 days. The reaction mixture was filtered. The filtrate was concentrated and diluted with ethyl acetate and washed with brine, purified by flash column chromatography (silica gel, 0 to 20% ethyl acetate/hexanes) to 8-bromo-3,5,6,7-tetrahydro-2H-[1,4]oxazino[2,3,4-ij]quinoline as a pale solid (374 mg, 33%). LCMS-ESI$^+$ (m/z): [M+H]$^+$ calcd for C$_{11}$H$_{13}$BrNO: 255.12. found: 255.41.

Preparation of 8-(4,4,5,5-tetramethyl-1,3,2-dioxaborolan-2-yl)-3,5,6,7-tetrahydro-2H-[1,4]oxazino[2,3,4-ij]quinoline: In a round bottom flask was charged with 8-bromo-3,5,6,7-tetrahydro-2H-[1,4]oxazino[2,3,4-ij]quinoline (104 mg, 0.409 mmol, 1 eq.), 4,4,4',4',5,5,5',5'-octamethyl-2,2'-bi(1,3,2-dioxaborolane) (208 mg, 0.818 mmol, 2 eq.), Pd(dppf)Cl$_2$ (33 mg, 10%) and KOAc (201 mg, 5 eq.) in 3 mL dioxane. The reaction was heated at 80° C. under Ar overnight. The reaction was cooled down and diluted with ethyl acetate and washed with brine, purified by flash column chromatography (silica gel, 0 to 20% ethyl acetate/hexanes) to 8-(4,4,5,5-tetramethyl-1,3,2-dioxaborolan-2-yl)-3,5,6,7-tetrahydro-2H-[1,4]oxazino[2,3,4-ij]quinoline as a pale solid (146 mg, 100%). LCMS-ESI$^+$ (m/z): [M+H]$^+$ calcd for C$_{17}$H$_{25}$BNO$_3$: 302.19; found: 302.2.

Preparation of (2S)-ethyl 2-tert-butoxy-2-(2,7-dimethyl-5-(3,5,6,7-tetrahydro-2H-[1,4]oxazino[2,3,4-ij]quinolin-8-yl)quinolin-6-yl)acetate: A Smith process vial was charged with (S)-ethyl 2-(5-bromo-2,7-dimethylquinolin-6-yl)-2-tert-butoxyacetate (52 mg, 0.133 mmol, 1 eq.), 8-(4,4,5,5-tetramethyl-1,3,2-dioxaborolan-2-yl)-3,5,6,7-tetrahydro-2H-[1,4]oxazino[2,3,4-ij]quinoline (48 mg, 0.159 mmol.), Pd(PPh$_3$)$_4$ (15 mg, 10%) and flushed with nitrogen. Dimethoxyethane (1.6 mL) and 2 M K$_2$CO$_3$ (0.24 mL, 0.48 mmol) was added. The reaction was heated in oil bath at 80° C. for 5 hours. The reaction mixture was diluted with ethyl acetate and washed with brine, dried (MgSO$_4$), filtered, concentrated and purified by flash column chromatography (silica gel, 0 to 20% ethyl acetate/hexanes) to give (2S)-ethyl 2-tert-butoxy-2-(2,7-dimethyl-5-(3,5,6,7-tetrahydro-2H-[1,4]oxazino[2,3,4-ij]quinolin-8-yl)quinolin-6-yl)acetate as atropisomer mixture (39 mg, 60%). LCMS-ESI$^+$: calcd for C$_{30}$H$_{37}$N$_2$O$_4$: 489.52 (M+H$^+$). Found: 489.3.

Preparation of (2S)-2-tert-butoxy-2-(2,7-dimethyl-5-(3,5,6,7-tetrahydro-2H-[1,4]oxazino[2,3,4-ij]quinolin-8-yl)quinolin-6-yl)acetic acid (103): A solution of (2S)-ethyl 2-tert-butoxy-2-(2,7-dimethyl-5-(3,5,6,7-tetrahydro-2H-[1,4]oxazino[2,3,4-ij]quinolin-8-yl)quinolin-6-ypacetate (39 mg) and 2 M sodium hydroxide (0.8 mL) in tetrahydrofuran (0.5 mL) and ethanol (2 mL) was heated at 60° C. for 8 hours. Reaction mixture was diluted with ethyl acetate and washed with brine. The aqueous layer was back-extracted with ethyl acetate and the combined organic layer was dried (MgSO$_4$), filtered, concentrated and purified by reverse phase HPLC (Gemini, 5 to 100% ACN/H$_2$O+0.1% TFA). Product lyophilized to give an orange color powder (18 mg).

$^1$H-NMR: 400 MHz, (CD$_3$OD): δ 8.31, 8.20 (d, d, 1 H), 7.92, 7.88 (s, s, 1 H), 7.70-7.67 (m, 1 H), 6.74 (m, 1 H), 6.42 (m, 1 H), 5.42, 5.37 (s, s, 1 H), 4.37 (m, 2 H), 3.33 (m, 2 H), 3.14 (m, 2 H), 2.96 (s, 3 H), 2.81, 2.78 (s, s, 3 H), 2.40 (m, 1 H), 1.96-1.78 (m, 3 H), 1.17, 1.04 (s, s, 9 H). LCMS-ESI$^+$: calcd for C$_{28}$H$_{33}$N$_2$O$_4$: 461.56 (M+H$^+$). Found: 461.3.

EXAMPLE 104

Compounds 104 and 105

Compounds 104 and 105 were prepared by similar methods as shown in the above Examples.

| Compound Number | Compound | Parent MW | Measured mass |
|---|---|---|---|
| 104 | 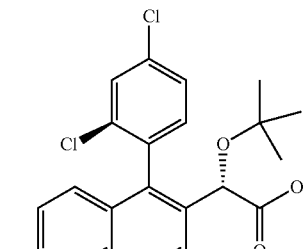 | 432.35 | 432.1/434.1 |
| 105 | 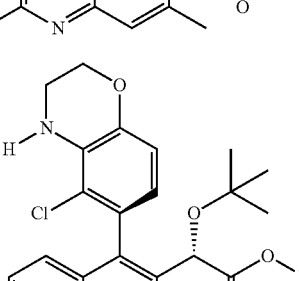 | 454.95 | 455.6 |

EXAMPLE 105

(S)-2-tert-Butoxy-2-((R)-5-(2,3-dihydropyrano[4,3,2-de]quinolin-7-yl)-7-methyl-2-(3-methylpyridin-2-yl)quinolin-6-yl)acetic acid (106)

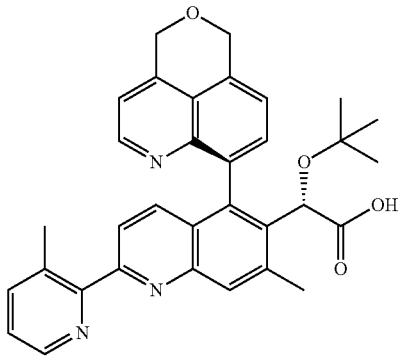

(S)-2-tert-butoxy-2-((R)-5-(2,3-dihydropyrano[4,3,2-de]quinolin-7-yl)-7-methyl-2-(3-methylpyridin-2-yl)quinolin-6-yl)acetic acid (S)-2-tert-Butoxy-2-((R)-5-(2,3-dihydropyrano[4,3,2-de]quinolin-7-yl)-7-methyl-2-(3-methylpyridin-2-yl)quinolin-6-yl)acetic acid (106) was prepared following the procedure for (S)-2-tert-butoxy-2-((R)-5-(2,3-dihydropyrano[4,3,2-de]quinolin-7-yl)-7-methyl-2-(pyridin-2-yl)quinolin-6-yl)acetic acid of Example 80 except that 2-(dibutyl(pentypstannyl)-3-methylpyridine and a catalytic amount of copper iodide was added to the first reaction. $^1$H-NMR: 400 MHz, (CD$_3$CN) δ: 8.63 (d, J=4.8 Hz, 1 H), 8.57 (d, J=4.8 Hz, 1 H), 8.08 (s, 1 H), 7.90 (d, J=7.6 Hz, 1 H), 7.76 (d, J=8.8 Hz, 1 H), 7.67 (d, J=8.0 Hz, 1 H), 7.48-7.43 (m, 3 H), 5.25 (s, 1 H), 4.62-4.56 (m, 2 H), 3.44 (t, J=6.2 Hz, 2 H), 2.74 (s, 3 H), 2.64 (s, 3 H), 0.93 (s, 9 H). LCMS-ESI$^+$ (m/z): [M+H]$^+$ calcd for C$_{33}$H$_{32}$N$_3$O$_4$: 534.23. found: 534.27.

EXAMPLE 106

(S)-2-tert-Butoxy-2-((R)-5-(2,3-dihydropyrano[4,3,2-de]quinolin-7-yl)-7-methyl-2-(4-methylpyridin-3-yl)quinolin-6-yl)acetic acid (107)

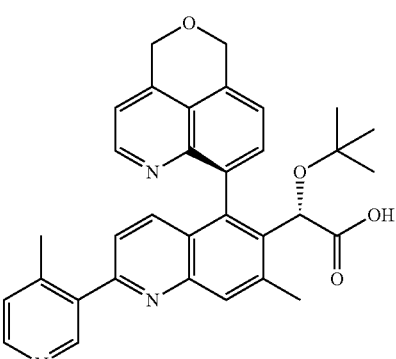

(S)-2-tert-butoxy-2-((R)-5-(2,3-dihydropyrano[4,3,2-de]quinolin-7-yl)-7-methyl-2-(4-methylpyridin-3-yl)quinolin-6-yl)acetic acid (S)-2-tert-Butoxy-2-((R)-5-(2,3-dihydropyrano[4,3,2-de]quinolin-7-yl)-7-methyl-2-(4-methylpyridin-3-yl)quinolin-6-yl)acetic acid (107) was prepared similarly to (S)-2-tert-butoxy-2-((R)-5-(2,3-dihydropyrano[4,3,2-de]quinolin-7-yl)-7-methyl-2-(3-methylpyridin-2-yDquinolin-6-yl)acetic acid of Example 105 using 3-(dibutyl(pentypstannyl)-4-methylpyridine instead of 2-(dibutyl(pentyl)stannyl)-3-methylpyridine. $^1$H-NMR: 400 MHz, (CD$_3$CN) δ: 8.71 (s, 1 H), 8.64-8.60 (m, 2 H), 8.05 (s, 1 H), 7.78 (d, J=6.0 Hz, 1 H), 7.68 (d, J=8.0 Hz, 1 H), 7.49-7.42 (m, 3 H), 7.27 (d, J=8.0 Hz, 1 H), 5.25 (s, 1 H), 4.63-4.59 (m, 2 H), 3.46 (t, J=6.0 Hz, 2 H), 2.74 (s, 3 H), 2.63 (s, 3 H), 0.94 (s, 9 H). LCMS-ESI⁺ (m/z): [M+H]⁺ calcd for $C_{33}H_{32}N_3O_4$: 534.23; found: 534.34.

EXAMPLE 107

(S)-2-tert-Butoxy-2-(2-(difluoromethyl)-7-methyl-5-(spiro[2.5]oct-5-en-6-yl)quinolin-6-yl)acetic acid (108)

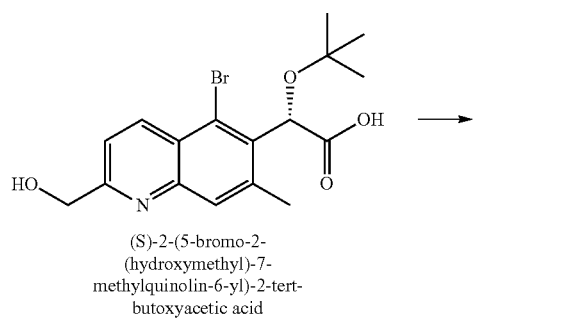

(S)-2-(5-bromo-2-(hydroxymethyl)-7-methylquinolin-6-yl)-2-tert-butoxyacetic acid

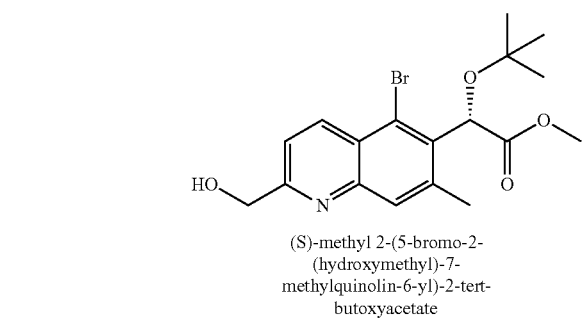

(S)-methyl 2-(5-bromo-2-(hydroxymethyl)-7-methylquinolin-6-yl)-2-tert-butoxyacetate

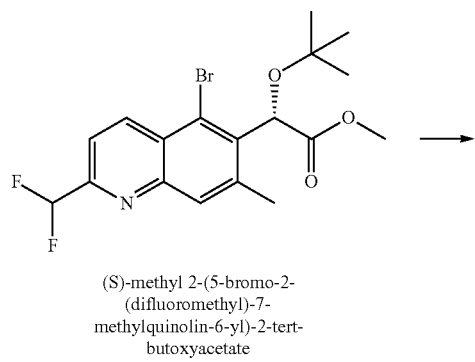

(S)-methyl 2-(5-bromo-2-(difluoromethyl)-7-methylquinolin-6-yl)-2-tert-butoxyacetate

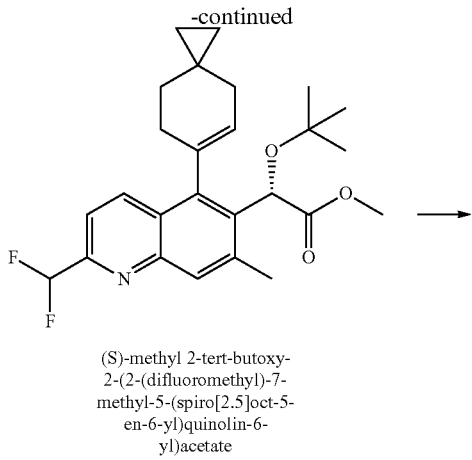

(S)-methyl 2-tert-butoxy-2-(2-(difluoromethyl)-7-methyl-5-(spiro[2.5]oct-5-en-6-yl)quinolin-6-yl)acetate

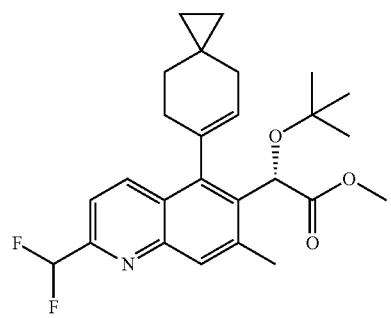

108

(S)-2-tert-butoxy-2-(2-(difluoromethyl)-7-methyl-5-(spiro[2.5]oct-5-en-6-yl)quinolin-6-yl)acetic acid Preparation of (S)-2-(5-bromo-2-(hydroxymethyl)-7-methylquinolin-6-yl)-2-tert-butoxyacetic acid: (S)-2-(5-Bromo-2-(hydroxymethyl)-7-methylquinolin-6-yl)-2-tert-butoxyacetic acid was isolated as a side product of the reaction forming (S)-ethyl 2-(5-bromo-2-(difluoromethyl)-7-methylquinolin-6-yl)-2-tert-butoxyacetate from Example 99. LCMS-ESI⁺ (m/z): [M+H]⁺ calcd $C_{17}H_{21}BrNO_4$: 382.06. found: 382.72.

Preparation of (S)-methyl 2-(5-bromo-2-(hydroxymethyl)-7-methylquinolin-6-yl)-2-tert-butoxyacetate: To a solution of (S)-2-(5-bromo-2-(hydroxymethyl)-7-methylquinolin-6-yl)-2-tert-butoxyacetic acid (3.6 g, 9.4 mmol) in anhydrous dichloromethane and methanol (1:1, 20 mL) was added (trimethylsilyl)diazomethane (2 M in hexanes, 5.17 mL, 10.34 mmol) and the reaction was stirred at room temperature for three hours. An additional 2 mL of (trimethylsilyl)diazomethane was added and stirred for 2 hours, followed by an additional 1 mL of (trimethylsilyl)diazomethane for 1 hour, then 1 mL of (trimethylsilyl)diazomethane added and let go overnight. An additional 3.5 mL of (trimethylsilyl)diazomethane were added and stirred for 1 hour. The reaction was quenched with 30 mL of acetic acid and then stirred 15 minutes. The reaction was concentrated under reduced pressure and then absorbed onto silica. The crude reaction was purified by flash column chromatography (silica gel, ethyl acetate/hexanes) to give a yellow foam (2.37 g). LCMS-ESI⁺ (m/z): [M+H]⁺ calcd $C_{18}H_{23}BrNO_4$: 396.07. found: 396.71.

Preparation of (S)-methyl 2-(5-bromo-2-(difluoromethyl)-7-methylquinolin-6-yl)-2-tert-butoxyacetate: Prepared similarly to (S)-ethyl 2-(5-bromo-2-(difluoromethyl)-7-methylquinolin-6-yl)-2-tert-butoxyacetate of Example 99 using (S)-methyl 2-(5-bromo-2-(hydroxymethyl)-7-methylquinolin-6-yl)-2-tert-butoxyacetate instead of (S)-ethyl 2-(5-bromo-2-(hydroxymethyl)-7-methylquinolin-6-yl)-2-tert-butoxyacetate. LCMS-ESI$^+$ (m/z): [M+H]$^+$ calcd $C_{18}H_{21}$I rF$_2$NO$_3$: 416.06. found: 416.75.

Preparation of (S)-methyl 2-tert-butoxy-2-(2-(difluoromethyl)-7-methyl-5-(spiro[2.5]oct-5-en-6-yl)quinolin-6-yl)acetate: To a solution of (S)-methyl 2-(5-bromo-2-(difluoromethyl)-7-methylquinolin-6-yl)-2-tert-butoxyacetate (50 mg, 0.12 mmol) in tetrahydrofuran and water (1 mL and 0.1 mL) was added 4,4,5,5-tetramethyl-2-(spiro[2.5]oct-5-en-6-yl)-1,3,2-dioxaborolane (42 mg, 0.18 mmol), potassium phosphate (84 mg, 0.36 mmol) and (2-dicyclohexylphosphino-2',6'-dimethoxy-1,1'-biphenyl)[2-(2-aminoethylphenyl)]palladium(II) chloride methyl-t-butyl ether adduct, (SPhos) palladium(II) phenethylamine chloride (8.1 mg, 0.012 mmol). The reaction was heated in a microwave reactor at 110° C. for 30 minutes and then absorbed onto silica. The crude reaction was purified by flash column chromatography (silica gel, ethyl acetate/hexanes) to give a clear white oil (44.7 mg). LCMS-ESI$^+$ (m/z): [M+H]$^+$ calcd $C_{26}H_{32}F_2NO_3$: 444.23. found: 444.54.

Preparation of (S)-2-tert-butoxy-2-(2-(difluoromethyl)-7-methyl-5-(spiro[2.5]oct-5-en-6-yl)quinolin-6-yl)acetic acid (108): To a solution of (S)-methyl 2-tert-butoxy-2-(2-(difluoromethyl)-7-methyl-5-(spiro[2.5]oct-5-en-6-yl)quinolin-6-yl)acetate (44.7 mg, 0.101 mmol) in tetrahydrofuran:methanol:water (2:2:1, 2 mL) was added lithium hydroxide (12 mg, 0.504 mmol) and the reaction was heated to 50° C. overnight. The reaction was diluted with acetonitrile and purified by reverse phase HPLC (Gemini, 15 to 95 ACN/H$_2$O+0.1% TFA) and the desired product was lyophilized to give a white powder (29.2 mg). $^1$H-NMR: 400 MHz, (CD$_3$CN) δ: 8.49 (d, J=8.8 Hz, 1 H), 7.85 (s, 1 H), 7.69 (d, J=8.4 Hz, 1 H), 6.84 (t, =55.2 Hz, 1 H), 5.93 (s, 1 H), 5.68 (s, 1 H), 2.67 (m, 1 H), 2.62 (s, 3 H), 2.46 (m, 1 H), 2.28-2.24 (m, 2 H), 1.66 (m, 2 H), 1.23 (s, 9 H), 0.54-0.40 (m, 4 H). LCMS-ESI$^+$ (m/z): [M+H]$^+$ calcd for $C_{25}H_{30}F_2NO_3$: 430.21. found: 430.32.

EXAMPLE 108

(S)-2-tert-butoxy-2-((R)-2-(cyclopropylmethoxy)-5-(2,3-dihydropyrano[4,3,2-de]quinolin-7-yl)-7-methylquinolin-6-yl)acetic acid (109).

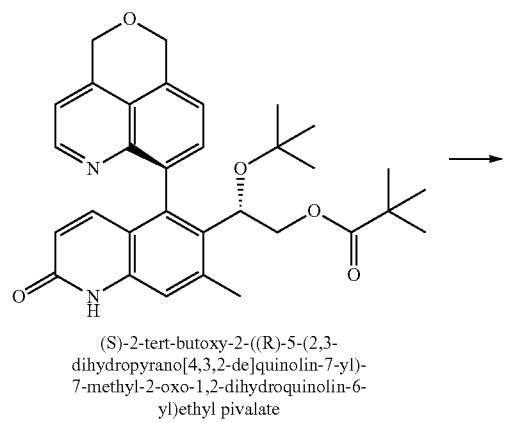

(S)-2-tert-butoxy-2-((R)-5-(2,3-dihydropyrano[4,3,2-de]quinolin-7-yl)-7-methyl-2-oxo-1,2-dihydroquinolin-6-yl)ethyl pivalate

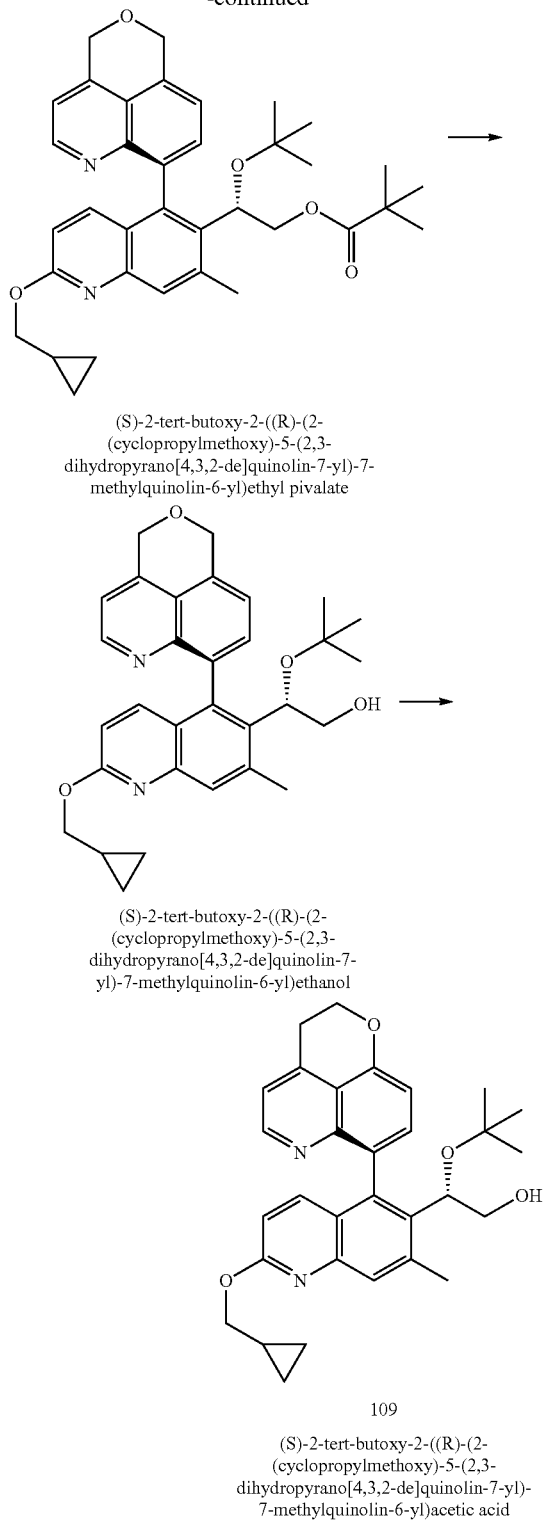

(S)-2-tert-butoxy-2-((R)-(2-(cyclopropylmethoxy)-5-(2,3-dihydropyrano[4,3,2-de]quinolin-7-yl)-7-methylquinolin-6-yl)ethyl pivalate (S)-2-tert-butoxy-2-((R)-(2-(cyclopropylmethoxy)-5-(2,3-dihydropyrano[4,3,2-de]quinolin-7-yl)-7-methylquinolin-6-yl)ethanol

109

(S)-2-tert-butoxy-2-((R)-(2-(cyclopropylmethoxy)-5-(2,3-dihydropyrano[4,3,2-de]quinolin-7-yl)-7-methylquinolin-6-yl)acetic acid Preparation of (S)-2-tert-butoxy-2-((R)-2-(cyclopropylmethoxy)-5-(2,3-dihydropyrano[4,3,2-de]quinolin-7-yl)-7-methylquinolin-6-yl)ethyl pivalate: To a solution of (S)-2-tert-butoxy-2-((R)-5-(2,3-dihydropyrano[4,3,2-de]quinolin-7-yl)-7-methyl-2-oxo-1,2-dihydroquinolin-6-yl)ethyl pivalate (100 mg, 0.189 mmol) and silver carbonate (156 mg, 0.567 mmol) in benzene:dichloroethane (1:1, 1 mL) was added (bromomethyl)cyclopropane (0.037 mL, 0.38 mmol) and the reaction was heated at 45° C. overnight. The crude reaction was purified by flash column chromatography (silica gel, ethyl acetate/hexanes) to give a brown oil (65.8 mg). LCMS-ESI⁺ (m/z): [M+H]⁺ calcd for $C_{36}H_{43}N_2O_5$: 583.31. found: 583.67.

Preparation of (S)-2-tert-butoxy-2-((R)-2-(cyclopropylmethoxy)-5-(2,3-dihydropyrano[4,3,2-de]quinolin-7-yl)-7-methylquinolin-6-yl)ethanol: To a solution of (S)-2-tert-butoxy-2-((R)-2-(cyclopropylmethoxy)-5-(2,3-dihydropyrano[4,3,2-de]quinolin-7-yl)-7-methylquinolin-6-yl)ethyl pivalate (65.8 mg, 0.113 mmol) in tetrahydrofuran:methanol (5:1, 3 mL) was added 1 M sodium hydroxide (3 mL) and the reaction was heated at 45° C. overnight. The reaction was diluted with water, extracted with ethyl acetate, washed with brine and dried over sodium sulfate. The solution was concentrated and then co-evaporated 2 times with acetonitrile to give a brown oil (55 mg). LCMS-ESI⁺ (m/z): [M+H]⁺ calcd for $C_{31}H_{35}N_2O_4$: 499.25. found: 499.54.

Preparation of (S)-2-tert-butoxy-2-((R)-2-(cyclopropylmethoxy)-5-(2,3-dihydropyrano[4,3,2-de]quinolin-7-yl)-7-methylquinolin-6-yl)acetic acid (109): To a solution of (S)-2-tert-butoxy-2-((R)-2-(cyclopropylmethoxy)-5-(2,3-dihydropyrano[4,3,2-de]quinolin-7-yl)-7-methylquinolin-6-yl)ethanol (55 mg, 0.11 mmol) in wet acetonitrile (2 mL) was added $CrO_3/H_5IO_6$ (0.4 M, 1.65 mL, 0.662 mmol) at 0° C. The reaction was stirred for 3 hours and then diluted with methanol. The crude material was purified by reverse phase HPLC (Gemini, 15 to 65% ACN/$H_2O$=0.1% TFA) and the desired product was lyophilized to give a yellow powder (18.1 mg). ¹H-NMR: 400 MHz, ($CD_3CN$) δ: 8.58 (d, J=5.2 Hz, 1 H), 7.76 (s, 1 H), 7.71 (d, J=8.0 Hz, 1 H), 7.55 (d, J=5.2 Hz, 1 H), 7.30 (d, J=8.0 Hz, 1 H), 7.13 (d, J=9.2 Hz, 1 H), 6.67 (d, J=8.8 Hz, 1 H), 5.14 (s, 1 H), 4.64-4.58 (m, 2 H), 4.28 (d, J=6.8 Hz, 2 H), 3.49 (t, J=5.6 Hz, 2 H), 2.67 (s, 3 H), 1.33-1.28 (m, 1 H), 0.91 (s, 9 H), 0.60-0.57 (m, 2 H), 0.40-0.37 (m, 2 H). LCMS-ESI⁺ (m/z): [M+H]⁺ calcd for $C_{31}H_{33}N_2O_5$: 513.23. found: 513.31.

EXAMPLE 109

(S)-2-tert-Butoxy-2-((R)-5-(2,3-dihydropyrano[4,3,2-de]quinolin-7-yl)-7-methyl-2-(trifluoromethyl)quinolin-6-yl)acetic acid (110)

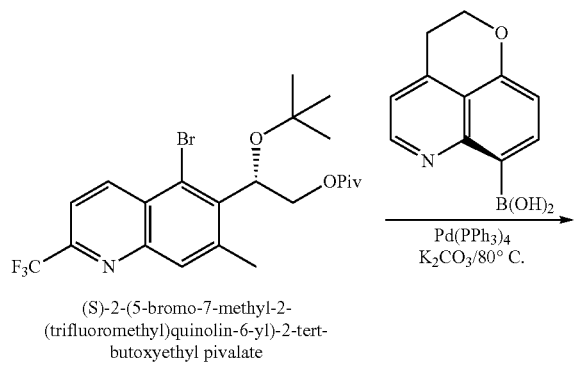

(S)-2-(5-bromo-7-methyl-2-(trifluoromethyl)quinolin-6-yl)-2-tert-butoxyethyl pivalate

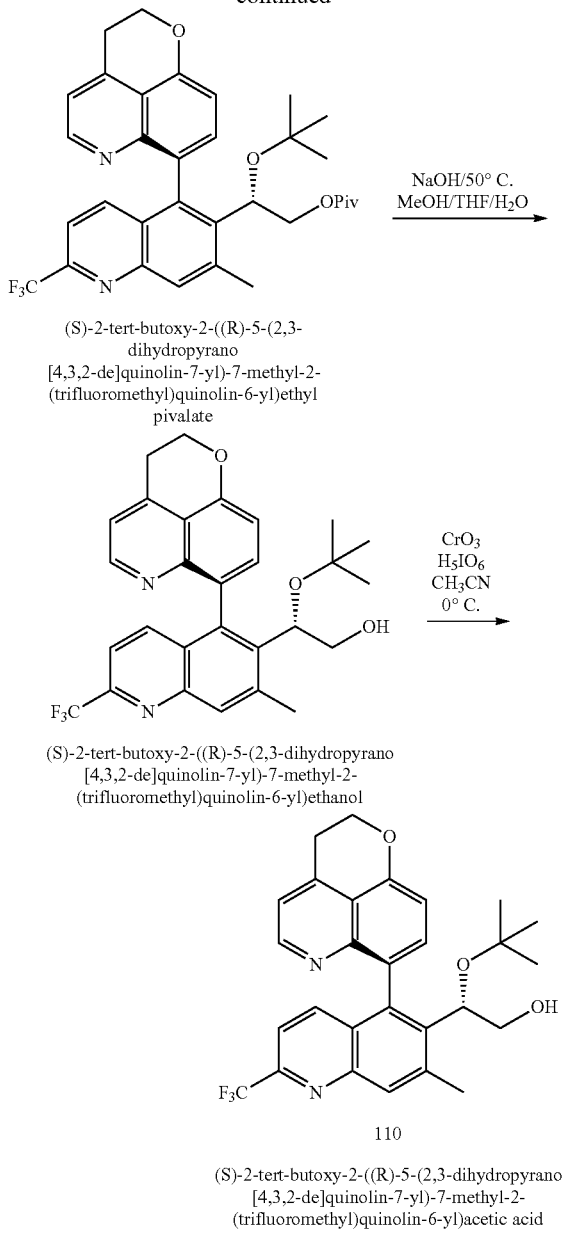

(S)-2-tert-butoxy-2-((R)-5-(2,3-dihydropyrano[4,3,2-de]quinolin-7-yl)-7-methyl-2-(trifluoromethyl)quinolin-6-yl)ethyl pivalate (S)-2-tert-butoxy-2-((R)-5-(2,3-dihydropyrano[4,3,2-de]quinolin-7-yl)-7-methyl-2-(trifluoromethyl)quinolin-6-yl)ethanol

110

(S)-2-tert-butoxy-2-((R)-5-(2,3-dihydropyrano[4,3,2-de]quinolin-7-yl)-7-methyl-2-(trifluoromethyl)quinolin-6-yl)acetic acid Preparation of (S)-2-tert-butoxy-2-((R)-5-(2,3-dihydropyrano[4,3,2-de]quinolin-7-yl)-7-methyl-2-(trifluoromethyl)quinolin-6-yl)ethyl pivalate: (S)-2-tert-Butoxy-2-((R)-5-(2,3-dihydropyrano[4,3,2-de]quinolin-7-yl)-7-methyl-2-(trifluoromethyl)quinolin-6-yl)ethyl pivalate (72 mg) was prepared in a similar manner as compound (S)-2-tert-butoxy-2-(5-(4-chlorophenyl)-7-methyl-2-(trifluoromethyl)quinolin-6-yl)ethyl pivalate (7H) of example 7J except using 2,3-dihydropyrano[4,3,2-de]quinolin-7-ylboronic acid hydrochloride instead of 4-chlorophenylboronic acid. LCMS-ESI⁺ (m/z): [M+H]⁺ calc'd for $C_{33}H_{36}F_3N_2O_4$: 581.2; Found: 581.1.

Preparation of (S)-2-tert-butoxy-2-((R)-5-(2,3-dihydropyrano[4,3,2-de]quinolin-7-yl)-7-methyl-2-(trifluoromethyl)quinolin-6-yl)ethanol: (S)-2-tert-Butoxy-2-((R)-5-(2,3-dihydropyrano[4,3,2-de]quinolin-7-yl)-7-methyl-2-(trifluoromethyl)quinolin-6-yl)ethanol (60 mg) was prepared in a similar manner as compound (S)-2-tert-butoxy-2-(5-(4-chlorophenyl)-7-methyl-2-(trifluoromethyl)quinolin-6-yl)ethanol (7I) of example 7J except using (S)-2-tert-butoxy-2-((R)-5-(2,3-dihydropyrano[4,3,2-de]quinolin-7-yl)-7-methyl-2-(trifluoromethyl)quinolin-6-yl)ethyl pivalate instead of (S)-2-tert-butoxy-2-(5-(4-chlorophenyl)-7-methyl-2-(trifluoromethyl)quinolin-6-yl)ethyl pivalate (7II).

LCMS-ESI$^+$ (m/z): [M+H]$^+$ calc'd for $C_{28}H_{28}F_3N_2O_3$: 497.2. Found: 497.0.

Preparation of (S)-2-tert-butoxy-2-((R)-5-(2,3-dihydropyrano[4,3,2-de]quinolin-7-yl)-7-methyl-2-(trifluoromethyl)quinolin-6-yl)acetic acid (110): (S)-2-tert-Butoxy-2-((R)-5-(2,3-dihydropyrano[4,3,2-de]quinolin-7-yl)-7-methyl-2-(trifluoromethyl)quinolin-6-yl)acetic acid was prepared in a similar manner as compound (S)-2-tert-Butoxy-2-(5-(4-chlorophenyl)-7-methyl-2-(trifluoromethyl)quinolin-6-yl)acetic acid (7J) of example 7J except using (S)-2-tert-butoxy-2-((R)-5-(2,3-dihydropyrano[4,3,2-de]quinolin-7-yl)-7-methyl-2-(trifluoromethyl)quinolin-6-yl)ethanol instead of (S)-2-tert-butoxy-2-(5-(4-chlorophenyl)-7-methyl-2-(trifluoromethyl)quinolin-6-yl)ethanol (7I). $^1$H-NMR 400 MHz, (CD$_3$OD) 8.70 (d, J=5.5 Hz, 1 H), 8.26 (s, 1 H), 7.87 (d, J=8.2 Hz, 1 H), 7.80 (d, J=5.5 Hz, 1 H), 7.70 (d, J=9.0 Hz, 1 H), 7.63 (d, J=8.4 Hz, 1 H), 7.46 (d, J=7.8 Hz, 1 H), 5.28 (s, 1 H), 4.74 (m, 2 H), 3.66 (t, J=5.5 Hz, 2 H), 2.88 (s, 3 H), 0.95 (s, 9 H); LCMS-ESI$^+$ (m/z): [M+H]$^+$ calc'd for $C_{28}H_{26}F_3N_2O_4$: 511.20. Found: 511.10.

EXAMPLE 110

(S)-2-((R)-2-Acetyl-5-(2,3-dihydropyrano[4,3,2-de]quinolin-7-yl)-7-methylquinolin-6-yl)-2-tert-butoxyacetic acid (111)

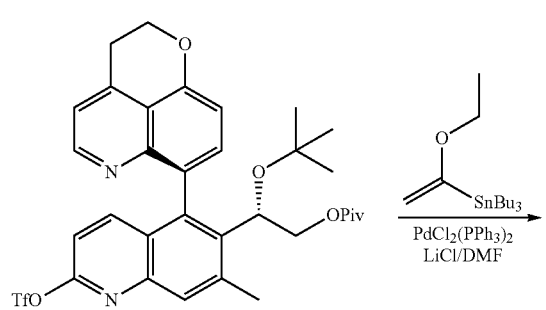

(S)-2-tert-butoxy-2-((R)-5-(2,3-dihydro pyrano[4,3,2-de]quinolin-7-yl)-7-methyl-2-(trifluoromethylsulfonyloxy)quinolin-6-yl)ethyl pivalate

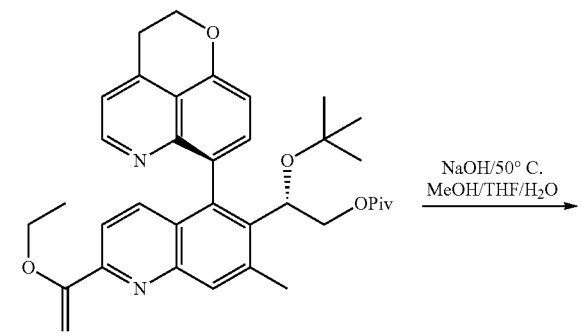

(S)-2-tert-butoxy-2-((R)-5-(2,3-dihydro pyrano[4,3,2-de]quinolin-7-yl)-2-(1-ethoxyvinyl)-7-methylquinolin-6-yl)ethyl pivalate

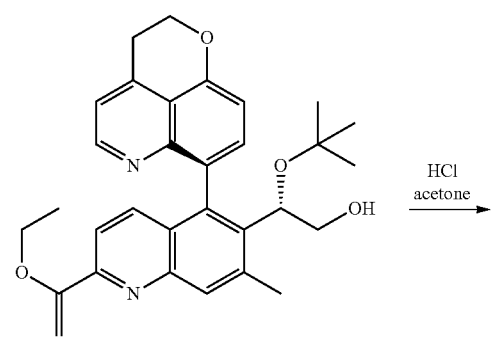

(S)-2-tert-butoxy-2-((R)-5-(2,3-dihydro pyrano[4,3,2-de]quinolin-7-yl)-2-(1-ethoxyvinyl)-7-methylquinolin-6-yl)ethanol

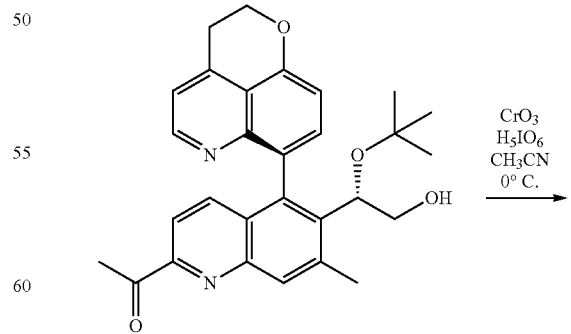

1-((R)-6-((S)-1-tert-butoxy-2-hydroxyethyl)-5-(2,3-dihydropyrano[4,3,2-de]quinolin-7-yl)-7-methylquinolin-2-yl)ethanone

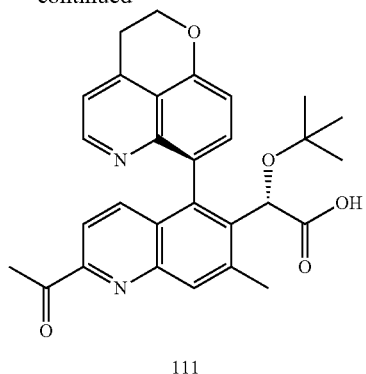

111

(S)-2-((R)-2-acetyl-5-(2,3-dihydro
pyrano[4,3,2-de]quinolin-7-yl)-7-
methylquinolin-6-yl)-2-tert-
butoxyacetic acid Preparation of (S)-2-tert-butoxy-2-((R)-5-(2,3-dihydropyrano[4,3,2-de] quinolin-7-yl)-2-(1-ethoxyvinyl)-7-methylquinolin-6-yl)ethyl pivalate: (S)-2-tert-Butoxy-2-((R)-5-(2,3-dihydropyrano[4,3,2-de] quinolin-7-yl)-2-(1-ethoxyvinyl)-7-methylquinolin-6-yl)ethyl pivalate (46 mg) was prepared in a similar manner as 5-bromo-7-methyl-6-vinylquinoline (8E) of example 8L except using (S)-2-tert-butoxy-2-((R)-5-(2,3-dihydropyrano[4,3,2-de]quinolin-7-yl)-7-methyl-2-(trifluoromethylsulfonyloxy) quinolin-6-yl) ethyl pivalate and tributyl(1-ethoxyvinyl)stannane instead of 5-bromo-7-methylquinolin-6-yl trifluoromethanesulfonate (8D) and tributyl(vinyl)stannane.

LCMS-ESI$^+$ (m/z): [M+H]$^+$ calc'd for $C_{36}H_{43}N_2O_5$: 583.30. Found: 583.30.

Preparation of (S)-2-tert-butoxy-2-((R)-5-(2,3-dihydropyrano[4,3,2-de]quinolin-7-yl)-2-(1-ethoxyvinyl)-7-methylquinolin-6-yl)ethanol: (S)-2-tert-Butoxy-2-((R)-5-(2,3-dihydropyrano[4,3,2-de]quinolin-7-yl)-2-(1-ethoxyvinyl)-7-methylquinolin-6-yl)ethanol (16 mg) was prepared in a similar manner as compound (S)-2-tert-butoxy-2-(5-(4-chlorophenyl)-7-methyl-2-(trifluoromethyl)quinolin-6-yl)ethanol (71) of example 7J except using (S)-2-tert-butoxy-2-((R)-5-(2,3-dihydropyrano[4,3,2-de]quinolin-7-yl)-2-(1-ethoxyvinyl)-7-methylquinolin-6-yl)ethyl pivalate instead of (S)-2-tert-butoxy-2-(5-(4-chlorophenyl)-7-methyl-2-(trifluoromethyl)quinolin-6-yl)ethyl pivalate (7H). LCMS-ESI$^+$ (m/z): [M+H]$^+$ calc'd for $C_{31}H_{35}N_2O_4$: 499.31. Found: 499.30.

Preparation of 1-((R)-6-((S)-1-tert-butoxy-2-hydroxyethyl)-5-(2,3-dihydropyrano[4,3,2-de]quinolin-7-yl)-7-methylquinolin-2-yl)ethanone: (S)-2-tert-Butoxy-2-((R)-5-(2,3-dihydropyrano[4,3,2-de]quinolin-7-yl)-2-(1-ethoxyvinyl)-7-methylquinolin-6-yl)ethanol (16 mg) was dissolved in acetone (1.6 ml), and aqueous hydrochloric acid (2 N, 0.16 ml) was added. The mixture was stirred for 12 hours, and diluted with dichloromethane. The organic solution was washed with water and brine, and dried over sodium sulfate. Concentration and purification with flash column chromatography (silica gel, hexane/EtOAc) gave 1-((R)-6-((S)-1-tert-butoxy-2-hydroxyethyl)-5-(2,3-dihydropyrano[4,3,2-de]quinolin-7-yl)-7-methylquinolin-2-yl)ethanone (15 mg). LCMS-ESI$^+$ (m/z): [M+H]$^+$ calc'd for $C_{29}H_{31}N_2O_4$: 471.2. Found: 471.1.

Preparation of (S)-2-((R)-2-acetyl-5-(2,3-dihydropyrano[4,3,2-de]quinolin-7-yl)-7-methylquinolin-6-yl)-2-tert-butoxyacetic acid (111): (S)-2-((R)-2-Acetyl-5-(2,3-dihydropyrano[4,3,2-de]quinolin-7-yl)-7-methylquinolin-6-yl)-2-tert-butoxyacetic acid (7.2 mg) was prepared in a similar manner as compound (S)-2-tert-Butoxy-2-(5-(4-chlorophenyl)-7-methyl-2-(trifluoromethyl)quinolin-6-yl)acetic acid (7J) of example 7J except using 1-((R)-6-((S)-1-tert-butoxy-2-hydroxyethyl)-5-(2,3-dihydropyrano[4,3,2-de]quinolin-7-yl)-7-methylquinolin-2-yl)ethanone instead of (S)-2-tert-butoxy-2-(5-(4-chlorophenyl)-7-methyl-2-(trifluoromethyl) quinolin-6-yl)ethanol (7I). $^1$H-NMR 400 MHz (CD$_3$OD) δ 8.69 (d, J=6.3 Hz, 1 H), 8.29 (s, 1 H), 7.89-7.79 (m, 3 H), 7.53 (d, J=9.0 Hz, 1 H), 7.45 (d, J=8.2 Hz, 1 H), 5.28 (s, 1 H), 4.70 (m, 2H), 3.66 (t, J=5.5 Hz, 2 H), 2.86 (s, 3 H), 2.82 (s, 3 H), 0.95 (s, 9 H); LCMS-ESI$^+$ (m/z): [M+H]$^+$ calc'd for $C_{29}H_{29}N_2O_5$: 485.2. Found: 485.1; LCMS-ESI$^+$ (m/z): [M−H]$^+$ calc'd for $C_{29}H_{27}N_2O_5$: 483.2. Found: 483.2.

EXAMPLE 111

(2S)-2-tert-Butoxy-2-((5 R)-5-(2,3-dihydropyrano[4,3,2-de] quinolin-7-yl)-2-(1-hydroxyethyl)-7-methylquinolin-6-yl)acetic acid (112)

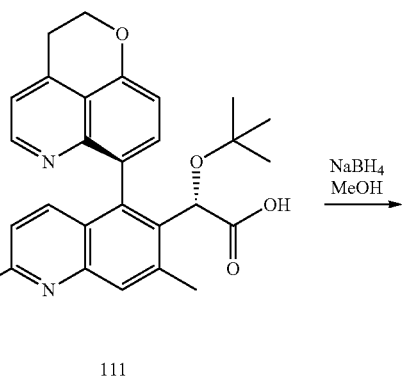

111

(S)-2-((R)-2-acetyl-5-(2,3-dihydro
pyrano[4,3,2-de]quinolin-7-yl)-7-
methylquinolin-6-yl)-2-tert-
butoxyacetic acid

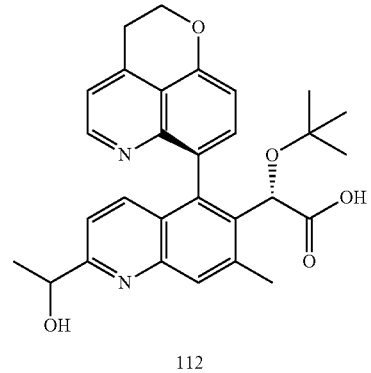

112

(2S)-2-tert-butoxy-2-((5R)-5-
(2,3-dihydro
pyrano[4,3,2-de]quinolin-7-yl)-2-
(1-hydroxyethyl)-7-
methylquinolin-6-yl)acetic acid Preparation of (2S)-2-tert-Butoxy-2-((5R)-5-(2,3-dihydropyrano[4,3,2-de]quinolin-7-yl)-2-(1-hydroxyethyl)-7-methylquinolin-6-yl)acetic acid (112): To the solution of (S)-2-((R)-2-acetyl-5-(2,3-dihydropyrano[4,3,2-de]quinolin-7- yl)-7-methylquinolin-6-yl)-2-tert-butoxyacetic acid (4.4 mg) im methanol (0.2 ml) at 0° C. was added sodium borohydride (1 mg). The mixture was warmed to 25° C. and stirred for one hour. The mixture was quenched with water, and methanol was removed under reduced pressure. Filtration and purification by reverse phase HPLC (0.1% TFA/CH$_3$CN-0.1% TFA/H$_2$O) gave (2S)-2-tert-butoxy-2-((5R)-5-(2,3-dihydropyrano[4,3,2-de]quinolin-7-yl)-2-(1-hydroxyethyl)-7-methylquinolin-6-yl)acetic acid (112) (0.5 mg). $^1$H-NMR 400 MHz (CD$_3$OD) δ 8.64 (d, J=5.2 Hz, 1 H), 8.25 (s, 1 H), 7.90-7.87 (m, 1 H), 7.74 (m, 1 H), 7.66-7.60 (m, 2 H), 7.36-7.34 (m, 1 H), 5.26 (s, 1 H), 5.20 (m, 1 H), 4.66 (m, 2 H), 3.55 (m, 2 H), 2.89 (s, 3 H), 1.60 (m, 3 H), 0.92 (s, 9 H); LCMS-ESI$^+$ (m/z): [M+H]$^+$ calc'd for C$_{29}$H$_{31}$N$_2$O$_5$: 487.2. Found: 487.2.

EXAMPLE 112

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. The compound of of formula Ih, or a pharmaceutically acceptable salt thereof:

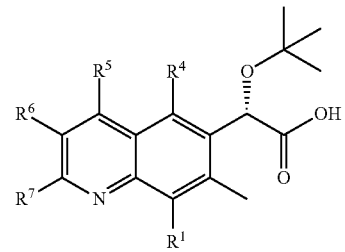

Ih wherein:
R$^1$ is R$^{1a}$ or R$^{1b}$;
R$^4$ is R$^{4a}$;
R$^5$ is R$^{5a}$ or R$^{5b}$;
R$^6$ is R$^{6a}$ or R$^{6b}$;
R$^7$ is R$^{7a}$ or R$^{7b}$;
R$^{1a}$ is selected from the group consisting of:
 a) H, halo, (C$_1$-C$_6$)alkyl and (C$_1$-C$_6$)haloalkyl;
 b) (C$_2$-C$_6$)alkenyl, (C$_2$-C$_6$)alkynyl, (C$_3$-C$_7$)cycloalkyl, nitro, cyano, (C$_6$-C$_{20}$)aryl, heterocycle and heteroaryl;
 c) —C(=O)—R$^{11}$, —C(=O)—O—R$^{11}$, —O—R$^{11}$, —S—R$^{11}$, —SO$_2$—R$^{11}$, —(C$_1$-C$_6$)alkyl-R$^{11}$, —(C$_1$-C$_6$)alkyl-C(=O)—R$^{11}$, —(C$_1$-C$_6$)alkyl-C(=O)—O—R$^{11}$, —(C$_1$-C$_6$)alkyl-O—R$^{11}$, —(C$_1$-C$_6$)alkyl-S—R$^{11}$, —(C$_1$-C$_6$)alkyl-S(O)—R$^{11}$ and —(C$_1$-C$_6$)alkyl-SO$_2$—R$^{11}$, wherein each R$^{11}$ is independently selected from the group consisting of H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, (C$_6$-C$_{20}$)aryl, heterocycle and heteroaryl; and d) —N(R⁹)R¹⁰, —C(=O)—N(R⁹)R¹⁰, —O—C(=O)—N(R⁹)R¹⁰, —SO₂—N(R⁹)R¹⁰, —(C₁-C₆)alkyl-N(R⁹)R¹⁰, —(C₁-C₆)alkyl-C(=O)—N(R⁹)R¹⁰, —(C₁-C₆)alkyl-O—C(=O)—N(R⁹)R¹⁰ and —(C₁-C₆)alkyl-SO₂—N(R⁹)R¹⁰, wherein each R¹⁰ is independently selected from the group consisting of R¹¹, —(C₁-C₆)alkyl-R¹¹, —SO₂—R¹¹, —C(=O)—R¹¹, —C(=O)OR¹¹ and —C(=O)N(R⁹)R¹¹, each R⁹ is independently selected from the group consisting of H, (C₁-C₆)alkyl and (C₃-C₇)cycloalkyl, and wherein each R¹¹ is independently selected from the group consisting of H, (C₁-C₆)alkyl, (C₂-C₆)alkenyl, (C₂-C₆)alkynyl, (C₁-C₆)haloalkyl, (C₃-C₇)cycloalkyl, (C₆-C₂₀)aryl, heterocycle and heteroaryl, and wherein any (C₆-C₂₀)aryl, heterocycle or heteroaryl of R¹ᵃ is optionally independently substituted with 1 to 3 Z¹⁰ groups;

R¹ᵇ is selected from the group consisting of:
a) —(C₁-C₆)alkyl-O—(C₁-C₆)alkyl-(C₃-C₇)carbocycle, —(C₁-C₆)alkyl-S—(C₁-C₆)alkyl-(C₃-C₇)carbocycle, —(C₁-C₆)alkyl-S(O)—(C₁-C₆)alkyl-(C₃-C₇)carbocycle, —(C₁-C₆)alkyl-SO₂—(C₁-C₆)alkyl-(C₃-C₇)carbocycle, —(C₁-C₆)alkyl-SO₂—(C₁-C₆)alkyl-Z¹³, —C(O)—(C₁-C₆)alkyl-Z¹³, —O—(C₁-C₆)alkyl-Z¹³, —S—(C₁-C₆)alkyl-Z¹³, —S(O)—(C₁-C₆)alkyl-Z¹³, —SO₂—(C₁-C₆)alkyl-Z¹³, —(C₁-C₆)alkyl-Z¹⁴, —(C₁-C₆)alkyl-C(O)—(C₁-C₆)alkyl-Z¹³, —(C₁-C₆)alkyl-C(O)—O—(C₁-C₆)alkyl-Z¹³, —(C₁-C₆)alkyl-O—(C₁-C₆)alkyl-Z¹³, —(C₁-C₆)alkyl-S—(C₁-C₆)alkyl-Z¹³, —(C₂-C₆)alkenyl-(C₁-C₆)haloalkyl, —(C₂-C₆)alkynyl-(C₁-C₆)haloalkyl, —(C₃-C₇)halocarbocycle, —NRₐSO₂NRcRd, —NRₐSO₂O(C₃-C₇)carbocycle, —NRₐSO₂O(C₆-C₂₀)aryl, —(C₂-C₆)alkenyl-(C₃-C₇)carbocycle, —(C₂-C₆)alkenyl-(C₆-C₂₀)aryl, —(C₂-C₆)alkenyl-heteroaryl, —(C₂-C₆)alkenyl-heterocycle, —(C₂-C₆)alkynyl-(C₃-C₇)carbocycle, —(C₂-C₆)alkynyl-(C₆-C₂₀)aryl, —(C₂-C₆)alkynyl-heteroaryl —(C₂-C₆)alkynyl-heterocycle, —(C₃-C₇)carbocycle-Z¹ and -halo(C₁-C₆)alkyl-Z³, wherein each (C₁-C₆)alkyl, (C₁-C₆)haloalkyl, (C₃-C₇)carbocycle, (C₃-C₇)halocarbocycle, (C₂-C₆)alkenyl, (C₂-C₆)alkynyl, (C₆-C₂₀)aryl, heterocycle and heteroaryl, either alone or as part of a group, is optionally independently substituted with 1 to 5 Z¹ groups;
b) spiro-bicyclic carbocycle, fused-bicyclic carbocycle and bridged-bicyclic carbocycle, wherein each spiro-bicyclic carbocycle, fused-bicyclic carbocycle and bridged-bicyclic carbocycle is optionally independently substituted with 1 to 5 Z¹ groups, wherein two Z¹ groups together with the atom or atoms to which they are attached optionally form a (C₃-C₇)carbocycle or heterocycle, wherein the (C₃-C₇)carbocycle or heterocycle is optionally independently substituted with 1 to 5 Z¹ groups;
c) (C₁-C₆)alkyl, wherein (C₁-C₆)alkyl is independently substituted with 1 to 5 Z² groups and optionally independently substituted with 1 to 5 Z¹ groups;
d) —X(C₁-C₆)alkyl, —X(C₁-C₆)haloalkyl, —X(C₂-C₆)alkenyl, —X(C₂-C₆)alkynyl and —X(C₃-C₇)carbocycle, wherein each X(C₁-C₆)alkyl and X(C₁-C₆)haloalkyl is independently substituted with 1 to 5 Z³ groups and optionally independently substituted with 1 to 5 Z¹ groups, and wherein each X(C₂-C₆)alkenyl, X(C₂-C₆)alkynyl and X(C₃-C₇)carbocycle is independently substituted with 1 to 5 Z⁴ groups and optionally independently substituted with 1 to 5 Z¹ groups;
e) (C₆-C₂₀)aryl, heteroaryl, heterocycle, —X(C₆-C₂₀)aryl, —Xheteroaryl and —Xheterocycle, wherein each (C₆-C₂₀)aryl, heteroaryl and heterocycle, either alone or as part of a group, is independently substituted with 1 to 5 Z⁵ groups and optionally independently substituted with 1 to 5 Z¹ groups;
f) (C₁-C₆)haloalkyl, (C₃-C₇)carbocycle, (C₂-C₆)alkenyl, and (C₂-C₆)alkynyl, wherein each (C₁-C₆)haloalkyl, (C₃-C₇)carbocycle, (C₂-C₆)alkenyl and (C₂-C₆)alkynyl is independently substituted with 1 to 5 Z⁶ groups and optionally independently substituted with 1 to 5 Z¹ groups; and
g) —NRₑRf, —C(O)NRₑRf, —OC(O)NRₑRf, —SO₂NRₑRf, —(C₁-C₆)alkyl-NRₑRf, —(C₁-C₆)alkylC(O)—NRₑRf, —(C₁-C₆)alkyl-O—C(O)—NRₑRf and —(C₁-C₆)alkyl-SO₂NRₑRf, wherein each (C₁-C₆)alkyl, as part of a group, is optionally independently substituted with 1 to 5 Z¹ groups, R⁴ᵃ is selected from the group consisting of:

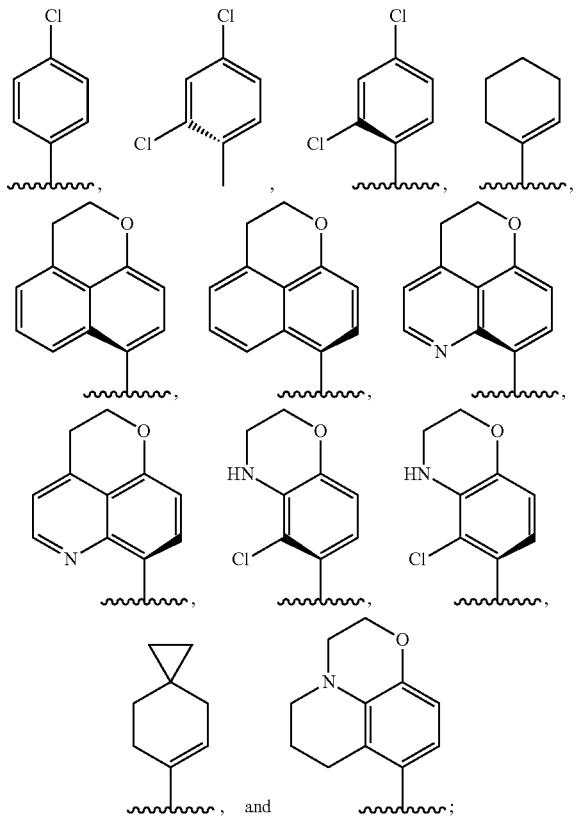

R⁵ᵃ is selected from the group consisting of:
a) halo, nitro and cyano;
b) R¹¹, —C(=O)—R¹¹, —C(=O)—O—R¹¹, —O—R¹¹, —S—R¹¹, —S(O)—R¹¹, —SO₂—R¹¹, —(C₁-C₆)alkyl-R¹¹, —(C₁-C₆)alkyl-C(=O)—R¹¹, —(C₁-C₆)alkyl-C(=O)—O—R¹¹, —(C₁-C₆)alkyl-O—R¹¹, —(C₁-C₆)alkyl-S—R¹¹, —(C₁-C₆)alkyl-S(O)—R¹¹ and —(C₁-C₆)alkyl-SO₂—R¹¹, wherein each R¹¹ is independently selected from the group consisting of H, (C₁-C₆)alkyl, (C₂-C₆)alkenyl, (C₂-

$C_6$)alkynyl, ($C_1$-$C_6$)haloalkyl, ($C_3$-$C_7$)cycloalkyl, ($C_6$-$C_{20}$)aryl, heterocycle and heteroaryl, wherein each ($C_6$-$C_{20}$)aryl, heterocycle and heteroaryl is optionally independently substituted with 1 to 3 $Z^{11}$ groups;
c) —N($R^9$)$R^{10}$, —C(=O)—N($R^9$)$R^{10}$, —O—C(=O)—N($R^9$)$R^{10}$, —SO$_2$—N($R^9$)$R^{10}$, —($C_1$-$C_6$)alkyl-N($R^9$)$R^{10}$, —($C_1$-$C_6$)alkyl-C(=O)—N($R^9$)$R^{10}$ —($C_1$-$C_6$)alkyl-O—C(=O)—N($R^9$)$R^{10}$, and —($C_1$-$C_6$)alkyl-SO$_2$—N($R^9$)$R^{10}$, wherein each $R^{10}$ is independently selected from the group consisting of $R^{11}$, —($C_1$-$C_6$)alkyl-$R^{11}$, SO$_2$—$R^{11}$, —C(=O)—$R^{11}$, —C(=O)O$R^{11}$ and —C(=O)N($R^9$)$R^{11}$, each $R^9$ is independently selected from the group consisting of H, ($C_1$-$C_6$)alkyl and ($C_3$-$C_7$)cycloalkyl, and wherein each $R^{11}$ is independently selected from the group consisting of H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, ($C_6$-$C_{20}$)aryl, heterocycle and heteroaryl;

$R^{5b}$ is selected from the group consisting of:
a) —($C_1$-$C_6$)alkyl-O—($C_1$-$C_6$)alkyl-($C_3$-$C_7$)carbocycle, —($C_1$-$C_6$)alkyl-S—($C_1$-$C_6$)alkyl-($C_3$-$C_7$)carbocycle, —($C_1$-$C_6$)alkylS(O)—($C_1$-$C_6$)alkyl-($C_3$-$C_6$)carbocycle, —($C_1$-$C_6$)alkylSO$_2$($C_1$-$C_6$)alkyl-($C_3$-$C_7$)carbocycle, —($C_2$-$C_6$)alkenyl-($C_1$-$C_6$)haloalkyl, —($C_2$-$C_6$)alkynyl-($C_1$-$C_6$)haloalkyl, —($C_3$-$C_7$)halocarbocycle, —NR$_a$SO$_2$NR$_c$R$_d$, —NR$_a$SO$_2$O($C_3$-$C_7$)carbocycle, —NR$_a$SO$_2$O($C_6$-$C_{20}$)aryl, —($C_2$-$C_6$)alkenyl-($C_3$-$C_7$)carbocycle, —($C_2$-$C_6$)alkenyl-($C_6$-$C_{20}$)aryl, —($C_2$-$C_6$)alkenyl-heteroaryl, —($C_2$-$C_6$)alkenyl-heterocycle, —($C_2$-$C_6$)alkynyl-($C_3$-$C_7$)carbocycle, —($C_2$-$C_6$)alkynyl-($C_6$-$C_{20}$)aryl, —($C_2$-$C_6$)alkynyl-heteroaryl, —($C_2$-$C_6$)alkynyl-heterocycle, —($C_3$-$C_7$)carbocycle-$Z^1$ and -halo($C_1$-$C_6$)alkyl-$Z^3$, wherein each ($C_1$-$C_6$)alkyl, ($C_1$-$C_6$)haloalkyl, ($C_3$-$C_7$)carbocycle, ($C_3$-$C_7$)halocarbocycle, ($C_2$-$C_6$)alkenyl, ($C_2$-$C_6$)alkynyl, ($C_6$-$C_{20}$)aryl, heterocycle and heteroaryl, either alone or as part of a group, is optionally independently substituted with 1 to 5 $Z^1$ groups;
spiro-bicyclic carbocycle, fused-bicyclic carbocycle and bridged-bicyclic carbocycle, wherein each spiro-bicyclic carbocycle, fused-bicyclic carbocycle and bridged-bicyclic carbocycle is optionally independently substituted with 1 to 5 Z groups, wherein two $Z^1$ groups together with the atom or atoms to which they are attached optionally form a ($C_3$-$C_7$)carbocycle or heterocycle, wherein the ($C_3$-$C_7$)carbocycle or heterocycle is optionally independently substituted with 1 to 5 $Z^1$ groups;
c) ($C_1$-$C_6$)alkyl, wherein ($C_1$-$C_6$)alkyl is independently substituted with 1 to 5 $Z^2$ groups and optionally independently substituted with 1 to 5 $Z^1$ groups;
d) —X($C_1$-$C_6$)alkyl, —X($C_1$-$C_6$)haloalkyl, —X($C_2$-$C_6$)alkenyl, —X($C_2$-$C_6$)alkynyl and —X($C_3$-$C_7$)carbocycle, wherein each X($C_1$-$C_6$)alkyl and X($C_1$-$C_6$)haloalkyl is independently substituted with 1 to 5 $Z^3$ groups and optionally independently substituted with 1 to 5 $Z^1$ groups, and wherein each X($C_2$-$C_6$)alkenyl, X($C_2$-$C_6$)alkynyl and X($C_3$-$C_7$)carhocycle is independently substituted with 1 to 5 $Z^4$ groups and optionally independently substituted with 1 to 5 $Z^1$ groups;
e) ($C_6$-$C_{20}$)aryl, heteroaryl, heterocycle, —X($C_6$-$C_{20}$)aryl, —Xheteroaryl and —Xheterocycle, wherein each ($C_6$-$C_{20}$)aryl, heteroaryl and heterocycle, either alone or as part of a group, is independently substituted with 1 to 5 $Z^5$ groups and optionally independently substituted with 1 to 5 $Z^1$ groups;
f) ($C_1$-$C_6$)haloalkyl, ($C_3$-$C_7$)carbocycle, ($C_2$-$C_6$)alkenyl, and ($C_2$-$C_6$)alkynyl, wherein each ($C_1$-$C_6$)haloalkyl, ($C_3$-$C_7$)carbocycle, ($C_2$-$C_6$)alkenyl and ($C_2$-$C_6$)alkynyl is independently substituted with 1 to 5 $Z^6$ groups and optionally independently substituted with 1 to 5 $Z^1$ groups; and
g) —NR$_e$R$_f$, —C(O)NR$_e$R$_f$, —OC(O)NR$_e$R$_f$, —SO$_2$NR$_e$R$_f$, —($C_1$-$C_6$)alkyl-NR$_e$R$_f$, —($C_1$-$C_6$)alkylC(O)—NR$_e$R$_f$, —($C_1$-$C_6$)alkyl-O—C(O)—NR$_e$R$_f$ and —($C_1$-$C_6$)alkyl —SO$_2$NR$_e$R$_f$, wherein each ($C_1$-$C_6$)alkyl, as part of a group, is optionally independently substituted with 1 to 5 $Z^1$ groups;

$R^{6a}$ is selected from the group consisting of:
a) H, halo, ($C_1$-$C_6$)alkyl, and ($C_1$-$C_6$)haloalkyl;
b) ($C_2$-$C_6$)alkenyl, ($C_2$-$C_6$)alkynyl, ($C_3$-$C_7$)cycloalkyl, nitro, cyano, ($C_6$-$C_{20}$)aryl, heterocycle and heteroaryl;
c) —C(=O)—$R^{11}$, —C(=O)—O—$R^{11}$, —O—$R^{11}$, —S—$R^{11}$, —S(O)—$R^{11}$, —SO$_2$—$R^{11}$, —($C_1$-$C_6$)alkyl-$R^{11}$, —($C_1$-$C_6$)alkyl-C(=O)—$R^{11}$, —($C_1$-$C_6$)alkyl-C(=O)—O—$R^{11}$, —($C_1$-$C_6$)alkyl-O—$R^{11}$, —($C_1$-$C_6$)alkyl-S—$R^{11}$, —($C_1$-$C_6$)alkyl-S(O)—$R^{11}$ and —($C_1$-$C_6$)alkyl-SO$_2$—$R^{11}$ wherein each $R^{11}$ is independently selected from the group consisting of H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, ($C_6$-$C_{20}$)aryl, heterocycle and heteroaryl; and
d) —N($R^9$)$R^{10}$, —C(=O)—N($R^9$)$R^{10}$, —O—C(=O)—N($R^9$)$R^{10}$, —SO$_2$—N($R^9$)$R^{10}$, —($C_1$-$C_6$)alkyl-N($R^9$)$R^{10}$, —($C_1$-$C_6$)alkyl-C(=O)—N($R^9$)$R^{10}$, —($C_1$-$C_6$)alkyl-O—C(=O)—N($R^9$)$R^{10}$ and —($C_1$-$C_6$)alkyl-SO$_2$—N($R^9$)$R^{10}$, wherein each $R^{10}$ is independently selected from the group consisting of $R^{11}$, —($C_1$-$C_6$)alkyl-$R^{11}$, —SO$_2$—$R^{11}$, —C(=O)—$R^{11}$, —C(=O)O$R^{11}$ and —C(=O)N($R^9$)$R^{11}$, each $R^9$ is independently selected from the group consisting of H, ($C_1$-$C_6$)alkyl and ($C_3$-$C_7$)cycloalkyl, and wherein each $R^{11}$ is independently selected from the group consisting of H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, ($C_6$-$C_{20}$)aryl, heterocycle and heteroaryl;
and wherein any ($C_6$-$C_{20}$)aryl, heterocycle or heteroaryl of $R^{6a}$ is optionally independently substituted with 1 to 3 $Z^{10}$ groups $R^{6b}$ is selected from the group consisting of:
a) —($C_1$-$C_6$)alkyl-O—($C_1$-$C_6$)alkyl-($C_3$-$C_7$)carbocycle, —($C_1$-$C_6$)alkyl-S—($C_1$-$C_6$)alkyl-($C_3$-$C_7$)carbocycle, —($C_1$-$C_6$)alkyl-S(O)—($C_1$-$C_6$)alkyl-($C_3$-$C_7$)carbocycle, —($C_1$-$C_6$)alkyl-SO$_2$—($C_1$-$C_6$)alkyl-($C_3$-$C_7$)carbocycle, —($C_2$-$C_6$)alkenyl-($C_1$-$C_6$)haloalkyl, —($C_2$-$C_6$)alkynyl-($C_1$-$C_6$)haloalkyl, -halo($C_3$-$C_7$)carbocycle, —NR$_a$SO$_2$NR$_c$R$_d$, —NR$_a$SO$_2$O($C_3$-$C_7$)carbocycle, —NR$_a$SO$_2$O($C_6$-$C_{20}$)ary, —($C_2$-$C_6$)alkenyl-($C_3$-$C_7$)carbocycle, —($C_2$-$C_6$)alkenyl-($C_6$-$C_{20}$)aryl, —($C_2$-$C_6$)alkenyl-heteroaryl, —($C_2$-$C_6$)alkenyl-heterocycle, —($C_2$-$C_6$)alkynyl-($C_3$-$C_7$)carbocycle, —($C_2$-$C_6$)alkynyl-($C_6$-$C_{20}$)aryl, —($C_2$-$C_6$)alkynyl-heteroaryl, —($C_2$-$C_6$)alkynyl-heterocycle, —($C_3$-$C_7$)carbocycle-$Z^1$ and -halo($C_1$-$C_6$)alkyl-$Z^3$, wherein each ($C_1$-$C_6$)alkyl, ($C_1$-$C_6$)haloalkyl, ($C_3$-$C_7$)carbocycle, ($C_2$-$C_6$)alkenyl, ($C_2$-$C_6$)alkynyl, ($C_6$-$C_{20}$)aryl, heterocycle and heteroaryl, either alone or as part of a group, is optionally independently substituted with 1 to 5 $Z^1$ groups;

b) spiro-bicyclic carbocycle, fused-bicyclic carbocycle and bridged-bicyclic carbocycle, wherein each spiro-bicyclic carbocycle, fused-bicyclic carbocycle and bridged-bicyclic carbocycle is optionally independently substituted with 1 to 5 $Z^1$ groups, wherein two $Z^1$ groups together with the atom or atoms to which they are attached optionally form a carbocycle or heterocycle wherein the carbocycle or heterocycle is optionally independently substituted with 1 to 5 $Z^1$ groups;

c) $(C_1-C_6)$alkyl, wherein $(C_1-C_6)$alkyl is independently substituted with 1 to 5 $Z^2$ groups and optionally independently substituted with 1 to 5 $Z^1$ groups;

d) —$X(C_1-C_6)$alkyl, —$X(C_1-C_6)$haloalkyl, —$X(C_2-C_6)$alkenyl, —$X(C_2-C_6)$alkynyl and —$X(C_3-C_7)$carbocycle, wherein each $X(C_1-C_6)$alkyl and $X(C_1-C_6)$haloalkyl is independently substituted with 1 to 5 $Z^3$ groups and optionally independently substituted with 1 to 5 $Z^1$ groups, and wherein each $X(C_2-C_6)$alkenyl, $X(C_2-C_6)$alkynyl and $X(C_3-C_7)$carbocycle is independently substituted with 1 to 5 $Z^4$ groups and optionally independently substituted with 1 to 5 $Z^1$ groups;

e) $(C_6-C_{20})$aryl, heteroaryl, heterocycle, —$X(C_6-C_{20})$aryl, —Xheteroaryl and —Xheterocycle, wherein each $(C_6-C_{20})$aryl, heteroaryl and heterocycle, either alone or as part of a group, is independently substituted with 1 to 5 $Z^5$ groups and optionally independently substituted with 1 to 5 $Z^1$ groups;

f) $(C_1-C_6)$haloalkyl, $(C_3-C_7)$carbocycle, $(C_2-C_6)$alkenyl, and $(C_2-C_6)$alkynyl, wherein each $(C_1-C_6)$haloalkyl, $(C_3-C_7)$carbocycle, $(C_2-C_6)$alkenyl and $(C_2-C_6)$alkynyl is independently substituted with 1 to 5 $Z^6$ groups and optionally independently substituted with 1 to 5 $Z^1$ groups; and g) —$NR_eR_f$, —$C(O)NR_eR_f$, —$OC(O)NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—C(O)—$NR_eR_f$ and —$(C_1-C_6)$alkyl-$SO_2NR_eR_f$ wherein each $(C_1-C_6)$alkyl, as part of a group, is optionally independently substituted with 1 to 5 $Z^1$ groups;

$R^{7a}$ is selected from the group consisting of:

a) H, halo, $(C_1-C_6)$alkyl and $(C_1-C_6)$haloalkyl;

b) $(C_2-C_6)$alkenyl, $(C_2-C_6)$alkynyl, $(C_3-C_7)$cycloalkyl, nitro, cyano, $(C_6-C_{20})$aryl, heterocycle and heteroaryl;

c) —C(=O)—$R^{11}$, —C(=O)—O—$R^{11}$, —O—$R^{11}$, —S—$R^{11}$, —S(O)$_2$—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-SO$_2$—$R^{11}$, wherein each $R^{11}$ is independently selected from the group consisting of H, $(C_1-C_6)$alkyl, $(C_2-C_6)$alkenyl, $(C_2-C_6)$alkynyl, $(C_1-C_6)$haloalkyl, $(C_3-C_7)$cycloalkyl, $(C_6-C_{20})$aryl, heterocycle and heteroaryl; and d) —N(R$^9$)R$^{10}$, —C(=O)—N(R$^9$)R$^{10}$, —O—C(=O)—N(R$^9$)R$^{10}$, —SO$_2$—N(R$^9$)R$^{10}$, —$(C_1-C_6)$alkyl-N(R$^9$)R$^{10}$, —$(C_1-C_6)$alkyl-C(=O)—N(R$^9$)R$^{10}$, —$(C_1-C_6)$alkyl-O—C(=O)—N(R$^9$)R$^{10}$ and —$(C_1-C_6)$alkyl-SO$_2$—N(R$^9$)R$^{10}$, wherein each R$^{10}$) is independently selected from the group consisting of R$^{11}$, —$(C_1-C_6)$alkyl-R$^{11}$, —SO$_2$—R$^{11}$, —C(=O)OR$^{11}$ and —C(=O)N(R$^9$)R$^{11}$, each R$^9$ is independently selected from the group consisting of H, $(C_1-C_6)$alkyl and $(C_3-C_7)$cycloalkyl, and wherein each R$^{11}$ is independently selected from the group consisting of H, $(C_1-C_6)$alkyl, $(C_2-C_6)$alkenyl, $(C_2-C_6)$alkynyl, $(C_1-C_6)$haloalkyl, $(C_3-C_7)$cycloalkyl, $(C_6-C_{20})$aryl, heterocycle and heteroaryl, and wherein any $(C_6-C_{20})$aryl, heterocycle or heteroaryl of $R^{7a}$ is optionally independently substituted with 1 to 3 $Z^{10}$ groups;

$R^{7b}$ is selected from the group consisting of:

a) —$(C_1-C_6)$alkyl-SO$_2$—$(C_1-C_6)$alkyl-$Z^{13}$, —C(O)—$(C_1-C_6)$alkyl-$Z^{13}$, —O—$(C_1-C_6)$alkyl-$Z^{13}$, —S—$(C_1-C_6)$alkyl-$Z^{13}$, —S(O)—$(C_1-C_6)$alkyl-$Z^{13}$, —SO$_2$—$(C_1-C_6)$alkyl-$Z^{13}$, —$(C_1-C_6)$alkyl-$Z^{14}$, —$(C_1-C_6)$alkyl-C(O)—$(C_1-C_6)$alkyl-$Z^{13}$, —$(C_1-C_6)$alkyl-C(O)—O$(C_1-C_6)$alkyl-$Z^{13}$, —$(C_1-C_6)$alkyl-O—$(C_1-C_6)$alkyl-$Z^{13}$, —$(C_1-C_6)$alkyl-S—$(C_1-C_6)$alkyl-$Z^{13}$, —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkyl-S(O)—$(C_1-C_6)$alkyl-$(C_3-C_7)$carbocycle, —$(C_1-C_6)$alkyl-SO$_2$—$(C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, —$(C_3-C_7)$halocarbocycle, —$NR_aSO_2NR_cR_d$, —$NR_aSO_2O(C_3-C_7)$carbocycle, —$NR_aSO_2O(C_6-C_{20})$aryl, —$(C_2-C_6)$alkenyl-$(C_3-C_7)$carbocycle, —$(C_2-C_6)$alkenyl-$(C_6-C_{20})$aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-$(C_6-C_{20})$aryl, —$(C_2-C_6)$alkynyl-heteroaryl, —$(C_2-C_6)$alkynyl-heterocycle, —$(C_3-C_7)$carbocycle-$Z^1$ and -halo$(C_1-C_6)$alkyl-$Z^3$, wherein each $(C_1-C_6)$alkyl, $(C_1-C_6)$haloalkyl, $(C_3-C_7)$carbocycle, $(C_3-C_7)$halocarbocycle, $(C_2-C_6)$alkenyl, $(C_2-C_6)$alkynyl, $(C_6-C_{20})$aryl, heterocycle and heteroaryl, either alone or as part of a group, is optionally independently substituted with 1 to 5 $Z^1$ groups;

b) spiro-bicyclic carbocycle, fused-bicyclic carbocycle and bridged-bicyclic carbocycle, wherein each spire-bicyclic carbocycle, fused-bicyclic carbocycle and bridged-bicyclic carbocycle is optionally independently substituted with 1 to 5 $Z^1$ groups, wherein two $Z^1$ groups together with the atom or atoms to which they are attached optionally form a $(C_3-C_7)$carbocycle or heterocycle, wherein the $(C_3-C_7)$carbocycle or heterocycle is optionally independently substituted with 1 to 5 $Z^1$ groups;

c) $(C_1-C_6)$alkyl, wherein $(C_1-C_6)$alkyl is independently substituted with 1 to 5 $Z^2$ groups and optionally independently substituted with 1 to 5 $Z^1$ groups;

d) —$X(C_1-C_6)$alkyl, —$X(C_1-C_6)$haloalkyl, —$X(C_2-C_6)$alkenyl, —$X(C_2-C_6)$alkynyl and —$X(C_3-C_7)$carbocycle, wherein each $X(C_1-C_6)$alkyl and $X(C_1-C_6)$haloalkyl is independently substituted with 1 to 5 $Z^3$ groups and optionally independently substituted with 1 to 5 $Z^1$ groups, and wherein each $X(C_2-C_6)$alkenyl, $X(C_2-C_6)$alkynyl and $X(C_3-C_7)$carbocycle is independently substituted with 1 to 5 $Z^4$ groups and optionally independently substituted with 1 to 5 $Z^1$ groups;

e) $(C_6-C_{20})$aryl, heteroaryl, heterocycle, —$X(C_6-C_{20})$aryl, —Xheteroaryl and —Xheteroaryl, wherein each $(C_6-C_{20})$aryl, heteroaryl and heterocycle, either alone or as part of a group, is independently substituted with 1 to 5 $Z^5$ groups and optionally independently substituted with 1 to 5 $Z^1$ groups;

f) $(C_1-C_6)$haloalkyl, $(C_3-C_7)$carbocycle, $(C_2-C_6)$alkenyl and $(C_2-C_6)$alkynyl, wherein each $(C_1-C_6)$haloalkyl, $(C_3-C_7)$carbocycle, $(C_2-C_6)$alkenyl and $(C_2-C_6)$alkynyl is independently substituted with 1 to 5 $Z^6$ groups and optionally independently substituted with 1 to 5 $Z^1$ groups; and g) —$NR_eR_f$, —$C(O)NR_eR_f$, —$OC(O)NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—C(O)—$NR_eR_f$, and —$(C_1-C_6)$alkyl-$SO_2NR_eR_f$, wherein each $(C_1-C_6)$alkyl is optionally independently substituted with 1 to 5 $Z^1$ groups;

or any of $R^{5a}$ and $R^{6a}$ or $R^{6a}$ and $R^{7a}$, together with the atoms to which they are attached form a 5 or 6-membered carbocycle or a 4, 5, 6 or 7-membered heterocycle, wherein the 5 or 6-membered carbocycle or the 4, 5, 6 or 7-membered heterocycle is optionally independently substituted with 1 to 3 substituents selected from the group consisting of halo, $(C_1-C_6)$alkyl, $(C_2-C_6)$alkenyl, $(C_1-C_6)$haloalkyl, $(C_3-C_7)$cycloalkyl, —OH, —O$(C_1-C_6)$alkyl, —SH, —S$(C_1-C_6)$alkyl, —$NH_2$, —NH$(C_1-C_6)$alkyl and —N$((C_1-C_6)$alkyl$)_2$;

or any of $R^5$ and $R^6$ or $R^6$ and $R^7$, together with the atoms to which they are attached form a 5 or 6-membered carbocycle or a 4, 5, 6 or 7-membered heterocycle, wherein each 5 or 6-membered carbocycle or 4, 5, 6 or 7-membered heterocycle is independently substituted with 1 to 3 $Z^7$ or $Z^6$ groups, wherein when two $Z^7$ groups are on same atom the two $Z^7$ groups together with the atom to which they are attached optionally form a $(C_3-C_7)$carbocycle or 4, 5 or 6-membered heterocycle;

X is independently selected from the group consisting of O, —C(O)—, —C(O)O—, —S—, —S(O)—, —$SO_2$, —$(C_1-C_6)$alkylO—, —$(C_1-C_6)$alkylC(O)—, —$(C_1-C_6)$alkylC(O)O—, —$(C_1-C_6)$alkylS—, —$(C_1-C_6)$alkylS(O)— and —$(C_1-C_6)$alkylSO$_2$—;

each $Z^1$ is independently selected from the group consisting of halo, —$NO_2$, —OH, =$NOR_a$, —SH, —CN, —$(C_1-C_6)$alkyl, —$(C_2-C_6)$alkenyl, —$(C_2-C_6)$alkynyl, —$(C_1-C_6)$haloalkyl, —$(C_3-C_7)$carbocycle, —$(C_3-C_7)$halocarbocycle, —$(C_6-C_{20})$aryl, -heteroaryl, -heterocycle, —O$(C_1-C_6)$alkyl, —O$(C_2-C_6)$alkenyl, —O$(C_2-C_6)$alkynyl, —O$(C_1-C_6)$haloalkyl, —O$(C_3-C_7)$carbocycle, —O$(C_3-C_7)$halocarbocycle, —O$(C_6-C_{20})$aryl, —Oheteroaryl, —Oheterocycle, —S$(C_1-C_6)$alkyl, —S$(C_2-C_6)$alkenyl, —S$(C_2-C_6)$alkynyl, —S$(C_1-C_6)$haloalkyl, —S$(C_3-C_7)$carbocycle, —S$(C_3-C_7)$halocarbocycle, —S$(C_6-C_{20})$aryl, —Sheteroaryl, —Sheterocycle, —S(O)$(C_1-C_6)$alkyl, —S(O)$(C_2-C_6)$alkenyl, —S(O)$(C_2-C_6)$alkynyl, —S(O)$(C_1-C_6)$haloalkyl, —S(O) $(C_3-C_7)$carbocycle, —S(O)$(C_3-C_7)$halocarbocycle, —$SO_2$ $(C_1-C_6)$alkyl, —S(O)$(C_6-C_{20})$aryl, —S(O)carbocycle, —S(O)heteroaryl, —S(O)heterocycle, —$SO_2(C_2-C_6)$alkenyl, —$SO_2(C_2-C_6)$alkynyl, —$SO_2(C_1-C_6)$haloalkyl, —$SO_2(C_3-C_7)$carbocycle, —$SO_2(C_3-C_7)$halocarbocycle, —$SO_2(C_6-C_{20})$aryl, —$SO_2$heteroaryl, —$SO_2$heterocycle, —$SO_2NR_cR_d$, —$NR_aR_d$, —$NR_aC(O)R_a$, —$NR_aC(O)OR_a$, —$NR_aC(O)NR_cR_d$, —$NR_aSO_2R_b$, —$NR_aSO_2NR_cR_d$, —$NR_aSO_2O(C_3-C_7)$carbocycle, —$NR_aSO_2O(C_6-C_{20})$aryl, —$OS(O)_2R_a$, —$C(O)R_a$, —$C(O)OR_b$, —$C(O)NR_cR_d$, and —$OC(O)NR_cR_d$, wherein any $(C_1-C_6)$alkyl, $(C_1-C_6)$haloalkyl, $(C_2-C_6)$alkenyl, $(C_2-C_6)$alkynyl, —$(C_3-C_7)$halocarbocycle, $(C_3-C_7)$carbocycle, $(C_3-C_7)$halocarbocycle, $(C_6-C_{20})$aryl, heteroaryl and heterocycle of $Z^1$, either alone or as part of a group, is optionally independently substituted with 1 to 5 halogen, —OH, —$OR_b$, —CN, —$NR_aC(O)_2R_b$, heteroaryl, heterocycle, —Oheteroaryl, —Oheterocycle, —NHheteroaryl, —NHheterocycle, or —$S(O)_2NR_cR_d$;

each $Z^2$ is independently selected from the group consisting of —$NO_2$, —CN, spiro-heterocycle, bridged-heterocycle, spiro-bicyclic carbocycle, bridged-bicyclic carbocycle, $NR_aSO_2(C_3-C_7)$carbocycle, —$NR_aSO_2(C_6-C_{20})$aryl, —$NR_aSO_2$heteroaryl, —$NR_aSO_2NR_cR_d$, —$NR_aSO_2O(C_3-C_7)$carbocycle and —$NR_aSO_2O(C_6-C_{20})$aryl, each $Z^3$ is independently selected from the group consisting of —$NO_2$, —CN, —OH, oxo, =$NOR_a$, thioxo, —$(C_6-C_{20})$aryl, -heterocycle, -heteroaryl, —$(C_3-C_7)$carbocycle, —$(C_3-C_7)$halocarbocycle, —O$(C_1-C_6)$alkyl, —O$(C_3-C_7)$carbocycle, —Ohalo$(C_3-C_7)$carbocycle, —O$(C_6-C_{20})$aryl, —Oheterocycle, —Oheteroaryl, —S$(C_1-C_6)$alkyl, —S$(C_3-C_7)$carbocycle, —S$(C_3-C_7)$halocarbocycle, —S$(C_6-C_{20})$aryl, —Sheterocycle, —Sheteroaryl, —S(O)$(C_1-C_6)$alkyl, —S(O)$(C_3-C_7)$carbocycle, —S(O) $(C_3-C_7)$halocarbocycle, —S(O)$(C_6-C_{20})$aryl, —S(O)heterocycle, —S(O)heteroaryl, —$SO_2(C_1-C_6)$alkyl, —SO$(C_3-C_7)$carbocycle, —$SO_2(C_3-C_7)$halocarbocycle, $SO_2(C_6-C_{20})$aryl, —$SO_2$heterocycle, —$SO_2$heteroaryl, —$NR_aR_b$, —$NR_aC(O)R_b$, —$C(O)NR_cR_d$, —$SO_2NR_cR_d$, —$NR_aSO_2NR_cR_d$, —$NR_aSO_2O(C_3-C_7)$carbocycle and —$NR_aSO_2O(C_6-C_{20})$aryl;

each $Z^4$ is independently selected from the group consisting of halogen, —$(C_1-C_6)$alkyl, $(C_3-C_7)$carbocycle, -halo$(C_1-C_6)$alkyl, —$NO_2$, —CN, —OH, oxo, =$NOR_a$, thioxo, —$(C_6-C_{20})$aryl, -heterocycle, -heteroaryl, —$(C_3-C_7)$halocarbocycle, —O$(C_1-C_6)$alkyl, —O$(C_3-C_7)$carbocycle, —O$(C_3-C_7)$halocarbocycle, —O$(C_6-C_{20})$aryl, —Oheterocycle, —Oheteroaryl, —S$(C_1-C_6)$alkyl, —S$(C_3-C_7)$carbocycle, —S$(C_3-C_7)$halocarbocycle, —S$(C_6-C_{20})$aryl, —Sheterocycle, —Sheteroaryl, —S(O)$(C_1-C_6)$alkyl, —S(O)$(C_3-C_7)$carbocycle, —S(O)$(C_3-C_7)$halocarbocycle, —S(O)$(C_6-C_{20})$aryl, —S(O)heterocycle, —S(O)heteroaryl, —$SO_2$ $(C_1-C_6)$alkyl, —$SO_2(C_3-C_7)$carbocycle, —$SO_2(C_3-C_7)$halocarbocycle, $SO_2(C_6-C_{20})$aryl, —$SO_2$heterocycle, —$SO_2$heteroaryl, —$NR_aR_b$, —$NR_aC(O)R_a$, —$C(O)NR_cR_d$, —$SO_2NR_cR_d$, —$NR_a$ $SO_2NR_cR_d$, —$NR_aSO_2O(C_3-C_7)$carbocyole and —$NR_aSO_2O(C_6-C_{20})$aryl;

each $Z^5$ is independently selected from the group consisting of —$NO_2$, —CN, —$NR_aSO_2NR_cR_d$, —$NR_aSO_2O(C_3-C_7)$carbocycle, —$NR_aSO_2O(C_6-C_{20})$aryl, —$NR_aSO_2(C_1-C_6)$alkyl, —$NR_aSO_2(C_2-C_6)$alkenyl, —$NR_aSO_2(C_2-C_6)$alkynyl, —$NR_aSO_2(C_3-C_7)$carbocycle, —$NR_aSO_2(C_3-C_7)$halocarbocycle, —$NR_aSO_2(C_6-C_{20})$aryl, —$NR_aSO_2$heteroaryl, —$NR_aSO_2$heterocycle, —$NR_aC(O)$alkyl, —$NR_aC(O)$alkenyl, —$NR_aC(O)$alkynyl, —$NR_aC(O)(C_3-C_7)$carbocycle, —$NR_aC(O)(C_3-C_7)$halocarbocycle, —$NR_aC(O)(C_6-C_{20})$aryl, —$NR_aC(O)$heteroaryl, —$NR_aC(O)$heterocycle, $NR_aC(O)NR_cR_d$ and $NR_aC(O)OR_b$;

each $Z^6$ is independently selected from the group consisting of —$NO_2$, —CN, —$NR_aR_a$, $NR_aC(O)R_b$, —$C(O)NR_cR_d$, —$(C_3-C_7)$halocarbocycle, —$(C_6-C_{20})$aryl, -heteroaryl, -heterocycle, —O$(C_6-C_{20})$aryl, —Oheteroaryl, —Oheterocycle, —O$(C_3-C_7)$halocarbocycle, —O$(C_1-C_6)$alkyl, —O$(C_1-C_6)$alkyl-O—$(C_1-C_6)$alkyl, —O$(C_3-C_7)$carbocycle, —Ohalo$(C_1-C_6)$alkyl, —S$(C_6-C_{20})$aryl, —Sheteroaryl, —Sheterocycle, —S$(C_3-C_7)$halocarbocycle, —S$(C_1-C_6)$alkyl, —S$(C_3-C_7)$carbocycle, —S$(C_1-C_6)$haloalkyl, —S(O)$(C_6-C_{20})$aryl, —S(O)heteroaryl, —S(O)heterocycle, —S(O)$(C_3-C_7)$halocarbocycle, —S(O)$(C_1-C_6)$alkyl, —S(O)$(C_3-C_7)$carbocycle, —S(O)halo$(C_1-C_6)$alkyl, —$S(O)_2$(C6-C20)aryl, —$SO_2$heteroaryl, —$SO_2$heterocycle, —$SO_2$ ($C_1$-$C_6$)alkyl, —$SO_2$halo($C_1$-$C_6$)alkyl, —$SO_2$($C_3$-$C_7$)carbocycle, —$SO_2$($C_3$-$C_7$)halocarbocycle —$SO_2NR_cR_d$, —$NR_aSO_2$($C_3$-$C_7$)halocarbocycle, —$NR_aSO_2$($C_6$-$C_{20}$)aryl, —$NR_aSO_2$heteroaryl, —$NR_aSO_2NR_cR_d$, —$NR_aSO_2O$($C_3$-$C_7$)carbocycle and —$NR_aSO_2O$($C_6$-$C_{20}$)aryl;

each $Z^7$ is independently selected from the group consisting of —$NO_2$, =$NOR_a$, —CN, —$C_1$-$C_6$)alkyl-$Z^{12}$, —($C_2$-$C_6$)alkehyl-$Z^{12}$, —($C_2$-$C_6$)alkenylOH, —($C_2$-$C_6$)alkynyl-$Z^{12}$, —($C_2$-$C_6$)alkynyl-OH, —($C_1$-$C_6$)haloalkyl-$Z^{12}$, —($C_1$-$C_6$)haloalkylOH, —($C_3$-$C_7$)carbocycle-$Z^{12}$, —($C_3$-$C_7$)carbocycleOH, —($C_3$-$C_7$)halocarbocycle, —($C_1$-$C_6$)alkyl$NR_cR_d$, —($C_1$-$C_6$)alkyl$NR_aC(O)R_a$, —($C_1$-$C_6$)alkyl$NR_aSO_2R_a$, —($C_6$-$C_{20}$)aryl, -heteroaryl, -heterocycle, —O($C_1$-$C_6$)alkyl-$Z^{12}$, —O($C_2$-$C_6$)alkenyl, —O($C_2$-$C_6$)alkynyl, —O($C_1$-$C_6$)haloalkyl, —O($C_3$-$C_7$)carbocycle, —O($C_3$-$C_7$)halocarbooycle, —O($C_6$-$C_{20}$)aryl, —O($C_1$-$C_6$)alkyl$NR_cR_d$, —O($C_1$-$C_6$)alkyl$NR_aC(O)R_a$, —O($C_1$-$C_6$)alkyl$NR_aSO_2R_a$, —Oheteroaryl, —Oheterocycle, —S($C_1$-$C_6$)alkyl-$Z^{12}$, —S($C_2$-$C_6$)alkenyl, —S($C_2$-$C_6$)alkynyl, —S($C_1$-$C_6$)haloalkyl, —S($C_3$-$C_7$)carbocycle, —S($C_3$-$C_7$)halocarbocycle, —S($C_1$-$C_6$)alkyl$NR_cR_d$, —S($C_1$-$C_6$)alkyl$NR_aC(O)R_a$, —S($C_1$-$C_6$)alkyl$NR_aSO_2R_a$, —S($C_6$-$C_{20}$)aryl, —Sheteroaryl, —Sheterocycle, —S(O)($C_1$-$C_6$)alkyl, —S(O)($C_2$-$C_6$)alkenyl, —S(O)($C_2$-$C_6$)alkynyl, —S(O)($C_1$-$C_6$)haloalkyl, —S(O)($C_3$-$C_7$)carbocycle, —S(O)($C_3$-$C_7$)halocarbocycle, —$SO_2$($C_1$-$C_6$)alkyl, —S(O)($C_1$-$C_6$)alkyl$NR_cR_d$, —S(O)($C_1$-$C_6$)alkyl$NR_aC(O)R_a$, —S(O)($C_1$-$C_6$)alkyl$NR_aSO_2R_a$, —S(O)($C_6$-$C_{20}$)aryl, —S(O)heteroaryl, —S(O)heterocycle, —$SO_2$($C_1$-$C_6$)alkyl, —$SO_2$($C_2$-$C_6$)alkenyl, —$SO_2$($C_2$-$C_6$)alkynyl, —$SO_2$($C_1$-$C_6$)haloalkyl, —$SO_2$($C_3$-$C_7$)carbocycle, —$SO_2$($C_3$-$C_7$)halocarbocycle, —$SO_2$($C_6$-$C_{20}$)aryl, —$SO_2$heteroaryl, —$SO_2$heterocycle, —$SO_2$($C_1$-$C_6$)alkyl$NR_cR_d$, —$SO_2$($C_1$-$C_6$)alkyl$NR_aC(O)R_a$, —$SO_2$($C_1$-$C_6$)alkyl$NR_aSO_2R_a$, —$SO_2NR_cR_d$, —$NR_aC(O)OR_b$, —$NR_aC(O)NR_cR_d$ —$NR_aSO_2R_b$, —$NR_aSO_2NR_cR_d$, —$NR_aSO_2O$($C_3$-$C_7$)carbocycle, —$NR_aSO_2O$($C_6$-$C_{20}$)aryl, —$OS(O)_2R_a$, —$C(O)NR_cR_d$, and —$OC(O)NR_cR_d$, wherein any ($C_1$-$C_6$)alkyl, ($C_1$-$C_6$)haloalkyl, ($C_2$-$C_6$)alkenyl, ($C_2$-$C_6$)alkynyl, ($C_3$-$C_7$)carbocycle, ($C_3$-$C_7$)halocarbocycle, ($C_6$-$C_{20}$)aryl, heteroaryl and heterocycle of $Z^7$, either alone or as part of a group, is optionally independently substituted with 1 to 5 halogen, —OH, —$OR_b$, —CN, —$NR_aC(O)_2R_b$, -heteroaryl, -heterocycle, —Oheteroaryl, —Oheterocycle, —NHheteroaryl, —NHheterocycle, or —$S(O)_2NR_cR_d$;

each $Z^8$ is independently selected from the group consisting of —$NO_2$ and —CN;

each $Z^9$ is independently selected from the group consisting of —($C_1$-$C_6$)alkyl and —O($C_1$-$C_6$)alkyl;

each $Z^{11}$ is independently selected from the group consisting of $Z^{10}$, —C(=O)—$NH_2$, —C(=O)—NH($C_1$-$C_4$)alkyl, —C(=O)—N(($C_1$-$C_4$)alkyl)$_2$, —C(=O)—($C_6$-$C_{20}$)aryl, —C(=O)-heterocycle and —C(=O)-heteroaryl;

each $Z^{10}$ is independently selected from the group consisting of:
i) halo, oxo, thioxo, ($C_2$-$C_6$)alkenyl, ($C_1$-$C_6$)haloalkyl, ($C_3$-$C_7$)cycloalkyl, ($C_3$-$C_7$)cycloalkyl-($C_1$-$C_6$)alkyl-, —OH, —O($C_1$-$C_6$)alkyl, —O($C_1$-$C_6$)haloalkyl, —SH, —S($C_1$-$C_6$)alkyl, —SO($C_1$-$C_6$)alkyl, —$SO_2$($C_1$-$C_6$)alkyl, —$NH_2$, —NH($C_1$-$C_6$)alkyl and —N(($C_1$-$C_6$)alkyl)$_2$;

ii) ($C_1$-$C_6$)alkyl optionally independently substituted with —OH, —O—($C_1$-$C_6$)haloalkyl, or —O—($C_1$-$C_6$)alkyl; and iii) ($C_6$-$C_{20}$)aryl, heterocycle and heteroaryl, which each ($C_6$-$C_{20}$)aryl, heterocycle and heteroaryl is optionally independently substituted with halo, ($C_1$-$C_6$)alkyl or COOH;

each $Z^{12}$ is independently selected from the group consisting of —$NO_2$, =$NOR_a$, thioxo, —($C_6$-$C_{20}$)aryl, -heterocycle, -heteroaryl, —($C_3$-$C_7$)halocarbocycle, —($C_3$-$C_7$)carbocycle, —O($C_3$-$C_7$)carbocycle, —Ohalo($C_3$-$C_7$)carbocycle, —O($C_6$-$C_{20}$)aryl, —Oheterocycle, —Oheteroaryl, —S($C_1$-$C_6$)alkyl, —S($C_3$-$C_7$)carbocycle, —Shalo($C_3$-$C_7$)carbocycle, —S($C_6$-$C_{20}$)aryl, —Sheterocycle, —Sheteroaryl, —S(O)($C_1$-$C_6$)alkyl, —S(O)($C_3$-$C_7$)carbocycle, —S(O)halo($C_3$-$C_7$)carbocycle, —S(O) ($C_6$-$C_{20}$)aryl, —S(O)heterocycle, —S(O)heteroaryl, —$SO_2$($C_1$-$C_6$)alkyl, —$SO_2$($C_3$-$C_7$)carbocycle, —$SO_2$($C_3$-$C_7$)halocarbocycle, $SO_2$($C_6$-$C_{20}$)aryl, —$SO_2$heterocycle, —$SO_2$heteroaryl, —$NR_aR_a$, —$NR_aC(O)R_b$, —$C(O)NR_cR_d$, —$SO_2NR_cR_d$, —$NR_aSO_2NR_cR_d$, —$NR_aSO_2O$($C_3$-$C_7$)carbocycle and —$NR_aSO_2O$($C_6$-$C_{20}$)aryl;

each $Z^{13}$ is independently selected from the group consisting of —$NO_2$, —OH, =$NOR_a$, —SH, —CN, —($C_3$-$C_7$)halocarbocycle, —O($C_1$-$C_6$)alkyl, —O($C_2$-$C_6$)alkenyl, —O($C_2$-$C_6$)alkynl, —O($C_1$-$C_6$)haloalkyl, —O($C_3$-$C_7$)carbocycle, —O($C_3$-$C_7$)halocarbocycle, —O($C_6$-$C_{20}$)aryl, —Oheteroaryl, —Oheterocycle, —S($C_1$-$C_6$)alkyl, —S($C_2$-$C_6$)alkenyl, —S($C_2$-$C_6$)alkynyl, —S($C_1$-$C_6$)haloalkyl, —S($C_3$-$C_7$)carbocycle, —S($C_3$-$C_7$)halocarbocycle, —S($C_6$-$C_{20}$)aryl, —Sheteroaryl, —Sheterocycle, —S(O)($C_1$-$C_6$)alkyl, —S(O)($C_2$-$C_6$)alkenyl, —S(O)($C_2$-$C_6$)alkynyl, —S(O)($C_1$-$C_6$)haloalkyl, —S(O)($C_3$-$C_7$)carbocycle, —S(O)($C_3$-$C_7$)halocarbocycle, —S(O)($C_6$-$C_{23}$)aryl, —S(O)heteroaryl, —S(O)heterocycle, —$SO_2$($C_1$-$C_6$)alkyl, —$SO_2$($C_2$-$C_6$)alkenyl, —$SO_2$($C_2$-$C_6$)alkynyl, —$SO_2$($C_1$-$C_6$)haloalkyl, —$SO_2$($C_3$-$C_7$)carbocycle, —$SO_2$($C_3$-$C_7$)halocarborycle, —$SO_2$($C_6$-$C_{20}$)aryl, —$SO_2$heteroaryl, —$SO_2$heterocycle, —$SO_2NR_cR_d$, —$NR_cR_d$, —$NR_aC(O)R_a$, —$NR_aC(O)OR_b$, —$NR_aC(O)NR_cR_d$ —$NR_aSO_2R_b$, —$NR_aSO_2NR_cR_d$, —$NR_aSO_2O$($C_3$-$C_7$)carbocycle, —$NR_aSO_2O$($C_6$-$C_{20}$)aryl, —$OS(O)_2R_a$, —$C(O)R_a$, —$C(O)OR_b$, —$C(O)NR_cR_d$, and —$OC(O)NR_cR_c$ wherein any ($C_1$-$C_6$)alkyl, ($C_1$-$C_6$)haloalkyl, ($C_2$-$C_6$)alkenyi, ($C_2$-$C_6$)alkynyl, ($C_3$-$C_7$)carbocycle, ($C_3$-$C_7$)halooarbocycle, ($C_6$-$C_{20}$)aryl, heteroaryl and heterocycle of $Z^{13}$, either alone or as part of a group, is optionally independently substituted with 1 to 5 halogen, —OH, —$OR_b$, —CN, —$NR_aC(O)_2R_b$, -heteroaryi, -heterocycle, —Oheteroaryl, —Oheterocycle, —NHheteroaryl, —NHheterocycle, or —$S(O)_2NR_cR_d$;

each $Z^{14}$ is independently selected from the group consisting of —$NO_2$, =$NOR_a$, —CN, —($C_3$-$C_7$)halocarbocycle, —O($C_3$-$C_7$)halocarbocycle, —S($C_3$-$C_7$)halocarbocycle, —S(O)($C_3$-$C_7$)halocarbocycle, —$SO_2$($C_3$-$C_7$)halocarbocycle, —$NR_aSO_2NR_cR_d$, —$NR_aSO_2O$($C_3$-$C_7$)halocarbocycle, —$NR_aSO_2O$($C_6$-$C_{20}$)aryl and —$OS(O)_2R_a$, wherein any —($C_3$-$C_7$)halocarbocycle of $Z^{14}$, either alone or as part of a group, is optionally independently substituted with 1 to 5 halogen, —OH, —$OR_b$, —CN, —$NR_aC(O)_2R_b$, -heteroaryl, -heterocycle, —Oheteroaryl, —Oheterocycle, —NHheteroaryl, —NHheterocycle, or —$S(O)_2NR_cR_d$;

each $R_a$ is independently H, ($C_1$-$C_6$)alkyl, —($C_2$-$C_6$)alkenyl, —($C_2$-$C_6$)alkynyl, ($C_3$-$C_7$)carbocycle, heterocycle, (C$_6$-C$_{20}$)aryl, (C$_6$-C$_{20}$)aryl(C$_1$-C$_6$)alkyl-, heteroaryl or heteroaryl(C$_1$-C$_6$)alkyl-, wherein any (C$_1$-C$_6$)alkyl, (C$_2$-C$_6$)alkenyl, (C$_2$-C$_6$)alkynyl, (C$_3$-C$_7$)carbocycle, heterocycle, (C$_6$-C$_{20}$)aryl, or heteroaryl of R$_a$, either alone or as part of a group, is optionally independently substituted by 1 to 5 halogen, OH or cyano;

each R$_b$ is independently —(C$_1$-C$_6$)alkyl, —(C$_2$-C$_6$)alkenyl, —(C$_2$-C$_6$)alkynyl, (C$_3$-C$_7$)carbocycle, heterocycle, (C$_6$-C$_{20}$)aryl, (C$_6$-C$_{20}$)aryl(C$_1$-C$_6$)alkyl-, heteroaryl or heteroaryl(C$_1$-C$_6$)alkyl-; wherein any (C$_1$-C$_6$)alkyl, —(C$_2$-C$_6$)alkenyl, —(C$_2$-C$_6$)alkynyl, (C$_3$-C$_7$)carbocycle, heterocycle, (C$_6$-C$_{20}$)aryl, or heteroaryl of R$_b$, either alone or as part of a group, is optionally independently substituted by 1 to 5 halogen, OH or cyano;

R$_c$ and R$_d$ are each independently selected from the group consisting of H, (C$_1$-C$_6$)alkyl, (C$_2$-C$_6$)alkenyl, (C$_2$-C$_6$)alkynyl, (C$_3$-C$_7$)carbocycle, (C$_6$-C$_{20}$)aryl, (C$_6$-C$_{20}$)aryl(C$_1$-C$_6$)alkyl-, heterocycle, heteroaryl and heteroaryl(C$_1$-C$_6$)alkyl-, wherein any (C$_1$-C$_6$)alkyl, —(C$_2$-C$_6$)alkenyl, —(C$_2$-C$_6$)alkynyl, (C$_3$-C$_7$)carbocycle, heterocycle, (C$_6$-C$_{20}$)aryl and heteroaryl of R$_c$ or R$_d$, either alone or as part of a group, is optionally independently substituted by 1 to 5 halogen, OH or cyano; or R$_c$ and R$_d$ together with the nitrogen to which they are attached form a heterocycle, wherein any heterocycle of R$_c$ and R$_d$ together with the nitrogen to which they are attached is optionally independently substituted by 1 to 5 halogen, OH or cyano;

each R$_e$ is independently selected from the group consisting of —OR$_a$ (C$_1$-C$_6$)alkyl and (C$_3$-C$_7$)carbocycle, wherein each (C$_1$-C$_6$)alkyl and (C$_3$-C$_7$)carbocycle is independently substituted by 1 to 5 Z$^6$ and optionally independently substituted with 1 to 5 Z$^1$, —(C$_2$-C$_6$)haloalkyl, —(C$_2$-C$_6$)alkenyl and —(C$_2$-C$_6$)alkynyl, wherein each —(C$_2$-C$_6$)haloalkyl, —(C$_2$-C$_6$)alkenyl and —(C$_2$-C$_6$)alkynyl is optionally independently substituted with 1 to 5 Z$^1$; and (C$_6$-C$_{20}$)aryl, heterocycle and heteroaryl wherein each (C$_6$-C$_{20}$)aryl, heterocycle and heteroaryl is independently substituted by 1 to 5 Z$^5$ ;

each R$_f$ is independently selected from the group consisting of —R$_g$, —OR$_a$, —(C$_1$-C$_6$)alkyl-Z$^6$, —SO$_2$R$_g$, —C(O)R$_g$, C(O)OR$_g$ and —C(O)NR$_e$R$_g$; and each R$_g$ is independently selected from the group consisting of H, —OR$_a$, (C$_1$-C$_6$)alkyl, (C$_3$-C$_7$)carbocycle (C$_1$-C$_6$)haloalkyl, (C$_2$-C$_6$)alkenyl, (C$_2$-C$_6$)alkynyl, (C$_6$-C$_{20}$)aryl, heterocycle and heteroaryl, wherein any (C$_1$-C$_6$)alkyl, (C$_3$-C$_7$)carbocycle —(C$_1$-C$_6$)haloalkyl, (C$_2$-C$_6$)alkenyl, (C$_2$-C$_6$)alkynyl, (C$_6$-C$_{20}$)aryl, heterocycle and heteroaryl of R$_g$ is optionally independently substituted with 1 to 5 Z$_1$ groups;

wherein each heteroaryl has 1 to 6 carbon atoms and 1 to 4 heteroatoms selected from the group consisting of oxygen, nitrogen and sulfur, and each heterocycle has 1 to 6 carbon atoms and 1 to 3 heteroatoms selected from the group consisting of oxygen, nitrogen and sulfur.

2. The compound of claim 1, or a pharmaceutically acceptable salt thereof, wherein R$^1$ is H.

3. The compound of claim 1, or a pharmaceutically acceptable salt thereof, wherein R$^6$is H.

4. The compound of claim 1, or a pharmaceutically acceptable salt thereof, wherein R$^5$ is H or (C$_1$-C$_6$)alkyl.

5. The compound of claim 1, or a pharmaceutically acceptable salt thereof, which is a compound of formula Ik:

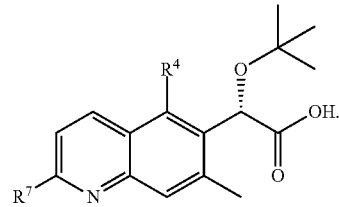

Ik

6. The compound of claim 1, or a pharmaceutically acceptable salt thereof, wherein:

R$^7$ is R$^{7a}$ or R$^{7b}$;

R$^{7a}$ is selected from the group consisting of:
a) H, halo, (C$_1$-C$_6$)alkyl and (C$_1$-C$_6$)haloalkyl;
b) (C$_2$-C$_6$)alkenyl, (C$_2$-C$_6$)alkynyl, (C$_3$-C$_7$)cycloalkyl, nitro, cyano, (C$_6$-C$_{20}$)aryl, heterocycle and heteroaryl;
c) —C(=O)—R$^{11}$, —C(=O)—O—R$^{11}$, —O—R$^{11}$, —S—R$^{11}$, —(C$_1$-C$_6$)alkyl-R$^{11}$, —(C$_1$-C$_6$)alkyl-C(=O)—R$^{11}$, —(C$_1$-C$_6$)alkyl-C(=O)—O—R$^{11}$, —(C$_1$-C$_6$)alkyl-O—R$^{11}$, and —(C$_1$-C$_6$)alkyl-S—R$^{11}$, wherein each R$^{11}$ is independently selected from the group consisting of H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, (C$_6$-C$_{20}$)aryl, heterocycle and heteroaryl; and
d) —N(R$^9$)R$^{10}$, —C(=O)—N(R$^9$)R$^{10}$, —O—C(=O)—N(R$^9$)R$^{10}$ , —(C$_1$-C$_6$) alkyl-N(R$^9$)R$^{10}$, —(C$_1$-C$_6$)alkyl-C(=O)—N(R$^9$)R$^{10}$, and —(C$_1$-C$_6$) alkyl-O—C(=O)—N(R$^9$)R$^{10}$, wherein each R$^9$ is independently selected from the group consisting of H, (C$_1$-C$_6$)alkyl and (C$_3$-C$_7$)cycloalkyl, each R$^{10}$ is independently selected from the group consisting of R$^{11}$, —(C$_1$-C$_6$)alkyl-R$^{11}$, —C(=O)—R$^{11}$, and —C(=O)OR$^{11}$, and wherein each R$^{11}$ is independently selected from the group consisting of H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, (C$_6$-C$_{20}$)aryl, heterocycle and heteroaryl, and wherein any (C$_6$-C$_{20}$)aryl, heterocycle or heteroaryl of R$^{7a}$ is optionally independently substituted with 1 to 3 Z$^{10}$ groups;

R$^{7b}$ is selected from the group consisting of:
a) —(C$_2$-C$_6$)alkynyl-(C$_3$-C$_7$)carbocycle and —(C$_2$-C$_6$)alkynyl-(C$_6$-C$_{20}$)aryl, wherein each (C$_3$-C$_7$)carbocycle, (C$_2$-C$_6$)alkynyl, and (C$_6$-C$_{20}$)aryl, either alone or as part of a group, is optionally independently substituted with 1 to 5 Z$^1$ groups;
d) —X(C$_1$-C$_6$)alkyl and —X(C$_1$-C$_6$)haloalkyl, wherein each —X(C$_1$-C$_6$)alkyl and —X(C$_1$-C$_6$)haloalkyl is independently substituted with 1 to 5 Z$^3$ groups and optionally independently substituted with 1 to 5 Z$^3$ groups;
f) (C$_1$-C$_6$)haloalkyl, (C$_3$-C$_7$)carbocycle, (C$_2$-C$_6$)alkenyl and (C$_2$-C$_6$)alkynyl, wherein each (C$_1$-C$_6$)haloalkyl, (C$_3$-C$_7$)carbocycle, (C$_2$-C$_6$)alkenyl and (C$_2$-C$_6$)alkynyl is independently substituted with 1 to 5 Z$^6$ groups and optionally independently substituted with 1 to 5 Z$^1$ groups; and
g) —NR$_e$R$_f$, —C(O)NR$_e$R$_f$, —OC(O)NR$_e$R$_f$, —(C$_1$-C$_6$)alkyl-NR$_e$R$_f$, —(C$_1$-C$_6$)alkylC(O)—NR$_e$R$_f$, and —(C$_1$-C$_6$)alkyl-O—C(O)—NR$_e$R$_f$, wherein each (C$_1$-C$_6$)alkyl is optionally independently substituted with 1 to 5 Z$^1$ groups;

X is O;

each Z is independently selected from the group consisting of halo and —($C_1$-$C_6$)alkyl;

each $Z^3$ is independently selected from the group consisting of —($C_6$-$C_{20}$)aryl and ($C_3$-$C_7$)carbocycle;

each $Z^{11}$ is independently $Z^{10}$;

each $Z^{10}$) is independently selected from the group consisting of halo and ($C_1$-$C_6$)alkyl;

each $R_e$ is independently ($C_1$-$C_6$)alkyl independently substituted with 1 to 5 $Z^6$;

each $Z^6$ is independently selected from the group consisting of —($C_6$-$C_{20}$)aryl, -heteroaryl, -heterocycle, and —O($C_1$-$C_6$)alkyl-O—($C_1$-$C_6$)alkyl; and each $R_f$ is H.

7. The compound of claim 1, or a pharmaceutically acceptable salt thereof, wherein:

$R^7$ is $R^{7a}$ or $R^{7b}$;

$R^{7a}$ is selected from the group consisting of:
a) H, ($C_1$-$C_6$)alkyl and ($C_1$-$C_6$)haloalkyl;
b) ($C_2$-$C_6$)alkenyl, ($C_2$-$C_6$)alkynyl, ($C_3$-$C_7$)cycloalkyl, ($C_6$-$C_{20}$)aryl, heterocycle and heteroaryl;
c) —C(=O)—$R^{11}$, —C(=O)—O—$R^{11}$, —O—$R^{11}$, —($C_1$-$C_6$)alkyl-$R^{11}$, and —($C_1$-$C_6$)alkyl-O—$R^{11}$, wherein each $R^{11}$ is independently selected from the group consisting of H, ($C_1$-$C_6$)alkyl, ($C_3$-$C_7$)cycloalkyl, ($C_6$-$C_{20}$)aryl, and heterocycle; and
d) —N($R^9$)$R^{10}$, —C(=O)—N($R^9$)$R^{10}$, and —($C_1$-$C_6$)alkyl-N($R^9$)$R^{10}$, wherein each $R^9$ is independently selected from the group consisting of H, ($C_1$-$C_6$)alkyl and ($C_3$-$C_7$)cycloalkyl, each $R^{10}$ is independently selected from the group consisting of $R^{11}$ and —($C_1$-$C_6$)alkyl-$R^{11}$, and wherein each $R^{11}$ is independently selected from the group consisting of H, ($C_1$-$C_6$)alkyl, ($C_3$-$C_7$)cycloalkyl, ($C_6$-$C_{20}$)aryl, heterocycle and heteroaryl, and wherein any ($C_6$-$C_{20}$)aryl, heterocycle or heteroaryl of $R^{7a}$ is optionally independently substituted with 1 to 2 $Z^{10}$ groups;

$R^{7b}$ is selected from the group consisting of:
a) —($C_2$-$C_6$)alkynyl-($C_3$-$C_7$)carbocycle and —($C_2$-$C_6$)alkynyl-($C_6$-$C_{20}$)aryl;
b) —X($C_1$-$C_6$)alkyl, wherein —X($C_1$-$C_6$)alkyl is substituted with 1 $Z^3$ group;
c) ($C_2$-$C_6$)alkynyl substituted with 1 $Z^6$ group; and
d) —N$R_e R_f$;

X is O;

each $Z^1$ is independently selected from the group consisting of halo and —($C_1$-$C_6$)alkyl;

each $Z^3$ is independently selected from the group consisting of —($C_6$-$C_{20}$)aryl and ($C_3$-$C_7$)carbocycle;

each $Z^{11}$ is independently $Z^{10}$;

each $Z^{10}$ is independently selected from the group consisting of halo and ($C_1$-$C_6$)alkyl;

each $R_e$ is independently ($C_1$-$C_6$)alkyl independently substituted with 1 $Z^6$;

each $Z^6$ is independently selected from the group consisting of —($C_6$-$C_{20}$)aryl, -heteroaryl, -heterocycle, and —O($C_1$-$C_6$)alkyl-O—($C_1$-$C_6$)alkyl, and each $R_f$ is H.

8. The compound of claim 1, or a pharmaceutically acceptable salt thereof, wherein $R^4$ is:

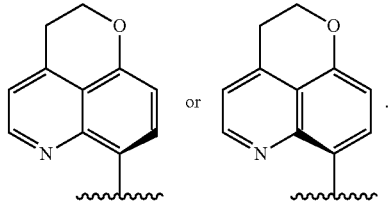

9. The compound of claim 1, or a pharmaceutically acceptable salt thereof, wherein $R^7$ is selected from the group consisting of:
a) H, halo, ($C_1$-$C_6$)alkyl and ($C_1$-$C_6$)haloalkyl;
b) ($C_2$-$C_6$)alkenyl, ($C_2$-$C_6$)alkynyl, ($C_3$-$C_7$)cycloalkyl, nitro, cyano, ($C_6$-$C_{20}$)aryl, heterocycle and heteroaryl, wherein anyeach ($C_6$-$C_{20}$)aryl, heterocycle or heteroaryl is optionally independently substituted with 1 to 3 $Z^{10}$ groups;
c) —C(=O)—$R^{11}$, —C(=O)—O—$R^{11}$, —O—$R^{11}$, —S—$R^{11}$, —S(O)—$R^{11}$, —SO$_2$—$R^{11}$, —($C_1$-$C_6$)alkyl-$R^{11}$, —($C_1$-$C_6$)alkyl-C(=O)—$R^{11}$, —($C_1$-$C_6$)alkyl-C(=O)—O—$R^{11}$, —($C_1$-$C_6$)alkyl-O—$R^{11}$, —($C_1$-$C_6$)alkyl-S—$R^{11}$, —($C_1$-$C_6$)alkyl-S(O)—$R^{11}$ and —($C_1$-$C_6$)alkyl-SO$_2$—$R^{11}$, wherein each $R^{11}$ is independently selected from the group consisting of H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, ($C_6$-$C_{20}$)aryl, heterocycle and heteroaryl, wherein anyeach ($C_6$-$C_{20}$)aryl, heterocycle or heteroaryl is optionally independently substituted with 1 to 3 $Z^{10}$ groups;
d) —N($R^9$)$R^{10}$, —C(=O)—N($R^9$)$R^{10}$, —O—C(=O)—N($R^9$)$R^{10}$, SO$_2$—N($R^9$)$R^{10}$, —($C_1$-$C_6$)alkyl-N($R^9$)$R^{10}$, —($C_1$-$C_6$)alkyl-C(=O)—N($R^9$)$R^{10}$, —($C_1$-$C_6$)alkyl-O—C(=O)—N($R^9$)$R^{10}$ and —($C_1$-$C_6$)alkyl-SO$_2$—N($R^9$)$R^{10}$, wherein each $R^9$ is independently selected from H, ($C_1$-$C_6$)alkyl and ($C_3$-$C_7$)cycloalkyl, and each $R^{10}$ is independently selected from the group consisting of $R^{11}$, —($C_1$-$C_6$)alkyl-$R^{11}$, —SO$_2$—$R^{11}$, —C(=O)—$R^{11}$, —C(=O)O$R^{11}$ and —C(=O)N($R^9$)$R^{11}$, each $R^9$ is independently selected from the group consisting of H, ($C_1$-$C_6$)alkyl and ($C_3$-$C_7$)cycloalkyl, and wherein each $R^{11}$ is independently selected from the group consisting of H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, ($C_6$-$C_{20}$)aryl, heterocycle and hetercaryl, wherein anyeach ($C_6$-$C_{20}$)aryl, heterocycle or heteroaryl is optionally independently substituted with 1 to 3 $Z^{10}$ groups;
e) —($C_1$-$C_6$)alkyl-SO$_2$—($C_1$-$C_6$)alkyl-$Z^{13}$, —C(O)—($C_1$-$C_6$)alkyl-$Z^{13}$, —O—($C_1$-$C_6$)alkyl-$Z^{13}$, —S—($C_1$-$C_6$)alkyl-$Z^{13}$, —S(O)—($C_1$-$C_6$)alkyl-$Z^{13}$, —SO$_2$—($C_1$-$C_6$)alkyl-$Z^{13}$, —($C_1$-$C_6$)alkyl-$Z^{14}$, —($C_1$-$C_6$)alkyl-C(O)—($C_1$-$C_6$)alkyl-$Z^{13}$, —($C_1$-$C_6$)alkyl-C(O)—O($C_1$-$C_6$)alkyl-$Z^{13}$, —($C_1$-$C_6$)alkyl-O—($C_1$-$C_6$)alkyl-$Z^{13}$, —($C_1$-$C_6$)alkyl-S—($C_1$-$C_6$)alkyl-$Z^{13}$, —($C_1$-$C_6$)alkyl-O—($C_1$-$C_6$)alkyl-($C_3$-$C_7$)carbocycle, —($C_1$-$C_6$)alkyl-S—($C_1$-$C_6$)alkyl-($C_3$-$C_7$)carbocycle, —($C_1$-$C_6$)alkyl-S(O)—($C_1$-$C_6$)alkyl-($C_3$-$C_7$)carbocycle, —($C_1$-$C_6$)alkyl-SO$_2$—($C_1$-$C_6$)alkyl-($C_3$-$C_7$)carbocycle, —($C_2$-$C_6$)alkenyl-($C_1$-$C_6$)haloalkyl, —($C_2$-$C_6$)alkynyl-($C_1$-$C_6$)haloalkyl, —($C_3$-$C_7$)halocarbocycle, -NR$_a$SO$_2$NR$_c$R,$_d$, —NR$_a$SO$_2$O($C_3$-$C_7$)carbocycle, —NR$_a$SO$_2$O($C_6$-$C_{20}$)aryl, —($C_2$-$C_6$)alkenyl-($C_3$-$C_7$)carbocycle, —($C_2$-$C_6$)alkenyl-($C_6$-$C_{20}$)aryl, —($C_2$-$C_6$)alkenyl-heteroaryl, —($C_2$-$C_6$)alkenyl-heterocycle, —($C_2$-$C_6$)alkynyl-($C_3$-$C_7$)carbocycle, —($C_2$-$C_6$)alkynyl-($C_6$-$C_{20}$)aryl, —($C_2$-$C_6$)alkynyl-heteroaryl, —($C_2$-$C_6$)alkynyl-heterocycle, —($C_3$-$C_7$)carbocycle-$Z^1$ and -halo($C_1$-$C_6$)alkyl-$Z^3$, wherein each ($C_1$-$C_6$)alkyl, ($C_1$-$C_6$)haloalkyl, ($C_3$-$C_7$)carbocycle, ($C_2$-$C_6$)alkenyl, ($C_2$-$C_6$)alkynyl, ($C_6$-$C_{20}$)aryl, heterocycle, and heteroaryl, either alone or as a group, is optionally independently substituted with 1 to 5 $Z^1$ groups;

f) —X($C_1$-$C_6$)alkyl, X($C_1$-$C_6$)haloalkyl, X($C_2$-$C_6$)alkenyl, —X($C_2$-$C_6$)alkynyl and —X($C_3$-$C_7$)carbocycle, wherein anyeach X($C_1$-$C_6$)alkyl and X($C_1$-$C_6$)haloalkyl is independently substituted with 1 to 5 $Z^3$ groups and optionally independently substituted with 1 to 5 $Z^1$ groups, and wherein anyeach X($C_2$-$C_6$)alkenyl, —X($C_2$-$C_6$)alkynyl and —X($C_3$-$C_7$)carbocycle is independently substituted with 1 to 5 $Z^4$ groups and optionally independently substituted with 1 to 5 $Z^1$ groups;

g) ($C_1$-$C_6$)alkyl, wherein ($C_1$-$C_6$)alkyl is independently substituted with 1 to 5 $Z^2$ groups and optionally independently substituted with 1 to 5 $Z^1$ groups;

h) ($C_6$-$C_{20}$)aryl, heteroaryl, heterocycle, —X($C_6$-$C_{20}$)aryl, —Xheteroaryl and —Xheterocycle, wherein anyeach ($C_6$-$C_{20}$)aryl, heteroaryl and heterocycle, either alone or as part of a group, is independently substituted with 1 to 5 $Z^5$ groups and optionally independently substituted with 1 to 5 $Z^1$ groups;

i) ($C_1$-C6)haloalkyl, ($C_3$-$C_7$)carbocycle, ($C_2$-$C_6$)alkenyl and ($C_2$-$C_6$)alkynyl, wherein each ($C_1$-$C_6$)haloalkyl, ($C_3$-$C_7$)carbocycle, ($C_2$-$C_6$)alkenyl and ($C_2$-$C_6$)alkynyl are eachis independently substituted with 1 to 5 $Z^6$ groups and optionally independently substituted with 1 to 5 $Z^1$ groups; and j) —$NR_eR_f$, —C(O)$NR_eR_f$, —OC(O)$NR_eR_f$, —$SO_2NR_eR_f$, —($C_1$-$C_6$)alkyl-$NR_eR_f$, —($C_1$-$C_6$)alkylC(O)—$NR_eR_f$, —($C_1$-$C_6$)alkyl-O—C(O)—$NR_eR_f$ and —($C_1$-$C_6$)alkyl-$SO_2NR_eR_f$, wherein each ($C_1$-$C_6$)alkyl is optionally independently substituted with 1 to 5 $Z^1$ groups.

10. The compound of claim 1, or a pharmaceutically acceptable salt thereof, wherein $R^7$ is selected from the group consisting of:
a) H, ($C_1$-$C_6$)alkyl and ($C_1$-$C_6$)haloalkyl;
b) ($C_2$-$C_6$)alkenyl, ($C_2$-$C_6$)alkynyl, ($C_3$-$C_7$)cycloalkyl, ($C_6$-$C_{20}$)aryl, heterocycle and heteroaryl, wherein anyeach ($C_6$-$C_{20}$)aryl, heterocycle or heteroaryl is optionally independently substituted with 1 to 3 $Z^{10}$ groups;
c) —C(=O)—O—$R^{11}$, —O—$R^{11}$, —($C_1$-$C_6$)alkyl-$R^{11}$ and —($C_1$-$C_6$)alkyl-O—$R^{11}$, wherein each $R^{11}$ is independently selected from the group consisting of H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, ($C_6$-$C_{20}$)aryl, heterocycle and heteroaryl, wherein each ($C_6$-$C_{20}$)aryl, heterocycle or heteroaryl is optionally independently substituted with 1 to 3 $Z^{10}$ groups;
d) —N($R^9$)$R^{10}$, —C(=O)—N($R^9$)$R^{10}$, —($C_1$-$C_6$)alkyl-N($R^9$)$R^{10}$, wherein each $R^9$ is independently selected from H, ($C_1$-$C_6$)alkyl and ($C_3$-$C_7$)cycloalkyl, and each $R^{10}$ is independently selected from the group consisting of $R^{11}$, —($C_1$-$C_6$)alkyl-$R^{11}$, $SO_2$ $R^{11}$, —C(=O)—$R^{11}$, —C(=O)O$R^{11}$ and —C(=O)N($R^9$)$R^{11}$, each $R^9$ is independently selected from the group consisting of H, ($C_1$-$C_6$)alkyl and ($C_3$-$C_7$)cycloalkyl, and wherein each $R^{11}$ is independently selected from the group consisting of H, ($C_1$ $C_6$)alkyl, ($C_2$-$C_6$)alkenyl, ($C_2$-$C_6$)alkynyl, ($C_1$-$C_6$)haloalkyl, ($C_3$-$C_7$)cycloalkyl, ($C_6$-$C_{20}$)aryl, heterocycle and heteroaryl, wherein anyeach ($C_6$-$C_{20}$)aryl, heterocycle or heteroaryl is optionally independently substituted with 1 to 3 $Z^{10}$ groups;

e) —($C_2$-$C_6$)alkynyl-($C_3$-$C_7$)carbocycle and —($C_2$-$C_6$)alkynyl-($C_6$-$C_{20}$)aryl, wherein anyeach —($C_2$-$C_6$)alkynyl-($C_3$-$C_7$)carbocycle and —($C_2$-$C_6$)alkynyl-($C_6$-$C_{20}$)aryl is optionally independently substituted with 1 to 5 $Z^1$ groups;
f) —X($C_1$-$C_6$)alkyl, wherein —X($C_1$-$C_6$)alkyl is independently substituted with 1 to 5 $Z^3$ groups and optionally independently substituted with 1 to 5 $Z^1$ groups, and wherein X is O;
g) ($C_1$-$C_6$)alkyl, wherein ($C_1$-$C_6$)alkyl is independently substituted with 1 to 5 $Z^2$ groups and optionally independently substituted with 1 to 5 $Z^1$ groups;
h) ($C_6$-$C_{20}$)aryl, heteroaryl and heterocycle, wherein anyeach ($C_6$-$C_{20}$)aryl, heteroaryl and heterocycle is independently substituted with 1 to 5 $Z^5$ groups and optionally independently substituted with 1 to 5 $Z^1$ groups;
i) ($C_1$-$C_6$)haloalkyl, ($C_3$-$C_7$)carbocycle, ($C_2$-$C_6$)alkenyl and ($C_2$-$C_6$)alkynyl, wherein anyeach ($C_1$-$C_6$)haloalkyl, ($C_3$-$C_7$)carbocycle, ($C_2$-$C_6$)alkenyl and ($C_2$-$C_6$)alkynyl is independently substituted with 1 to 5 $Z^6$ groups and optionally independently substituted with 1 to 5 $Z^1$ groups; and
j) —$NR_eR_f$, —C(O)$NR_eR_f$ and —($C_1$-$C_6$)alkyl-$NR_eR_f$, wherein —($C_1$-$C_6$)alkyl-$NR_eR_f$ is optionally independently substituted with 1 to 5 $Z^1$ groups.

11. The compound of claim 1, or a pharmaceutically acceptable salt thereof, wherein $R^7$ is selected from the group consisting of:
a) H, ($C_1$-$C_6$)alkyl and ($C_1$-$C_6$)haloalkyl;
b) ($C_2$-$C_6$)alkynyl and ($C_6$-$C_{20}$)aryl, wherein each ($C_6$-$C_{20}$)aryl is optionally independently substituted with 1 to 3 $Z^{10}$ groups;
c) ($C_1$-$C_6$)alkyl, wherein ($C_1$-$C_6$)alkyl is independently substituted with 1 to 5 $Z^2$ groups and optionally independently substituted with 1 to 5 $Z^1$ groups;
d) ($C_6$-$C_{20}$)aryl, wherein ($C_6$-$C_{20}$)aryl is independently substituted with 1 to 5 $Z^5$ groups and optionally independently substituted with 1 to 5 $Z^1$ groups; and
e) ($C_1$-$C_6$)haloalkyl, wherein ($C_1$-$C_6$)haloalkyl is independently substituted with 1 to 5 $Z^6$ groups and optionally independently substituted with 1 to 5 $Z^1$ groups.

12. The compound of claim 1, or a pharmaceutically acceptable salt thereof, wherein $R^7$ is selected from the group consisting of:
a) ($C_1$-$C_6$)haloalkyl; and
b) ($C_1$-$C_6$.)haloalkyl, wherein ($C_1$-$C_6$)haloalkyl is independently substituted with 1 to 5 $Z^6$ groups and optionally independently substituted with 1 to 5 $Z^1$ groups.

13. The compound of claim 1, or a pharmaceutically acceptable salt thereof, wherein $R^7$ is:

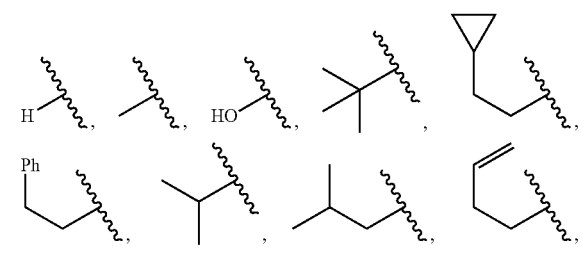

-continued
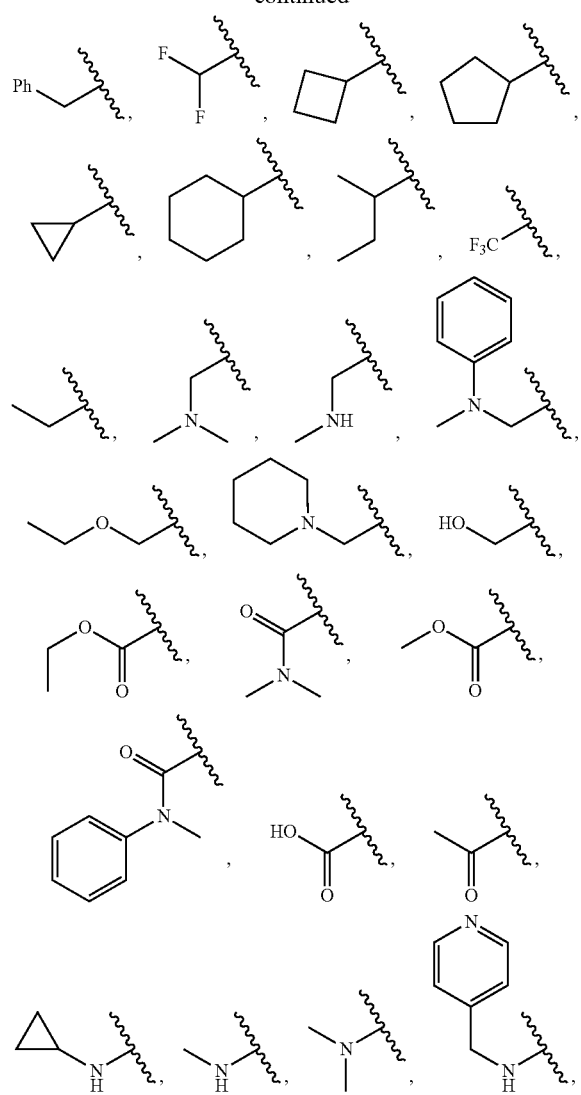
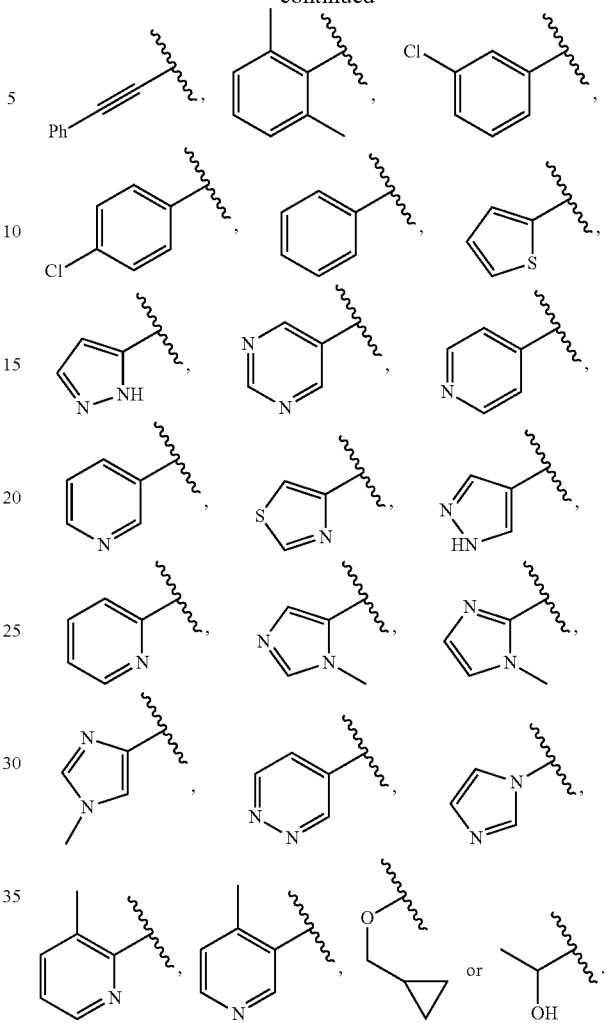
14. The compound of claim 1, or a pharmaceutically acceptable salt thereof, selected from the group consisting of:
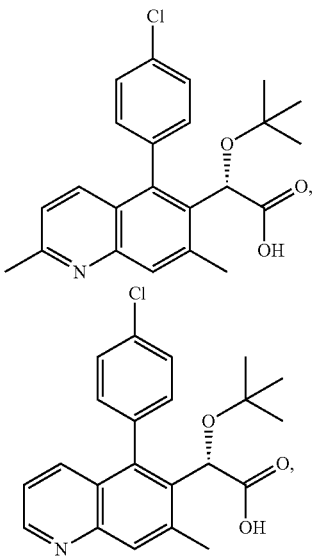

309
-continued
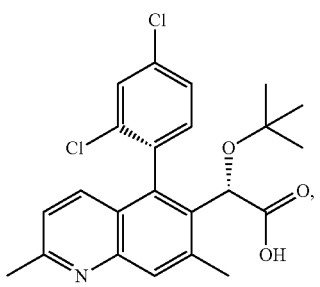
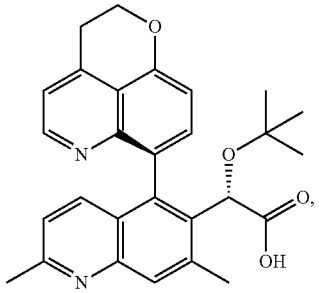
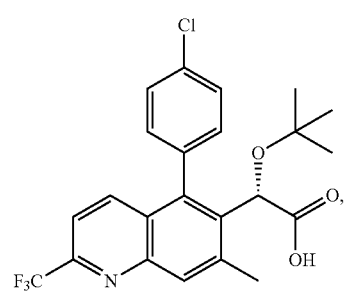
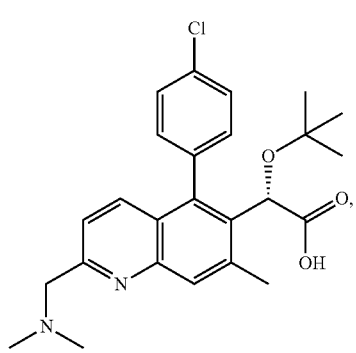
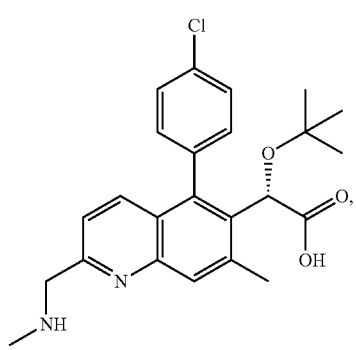
310
-continued
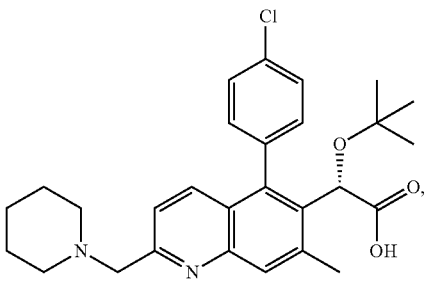
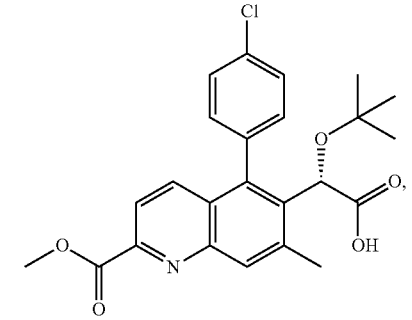
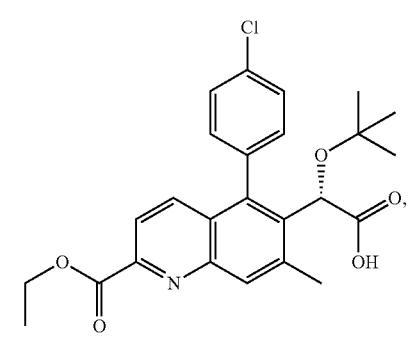
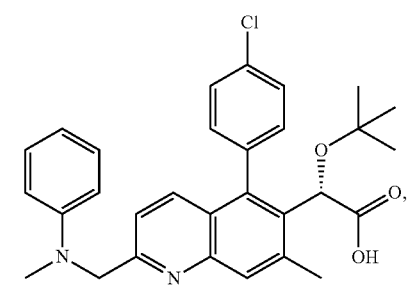
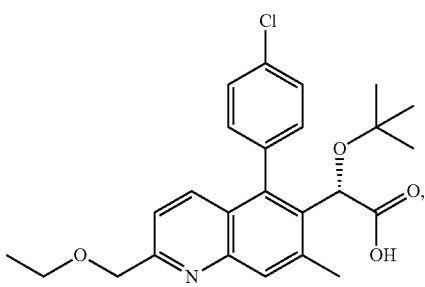

311
-continued
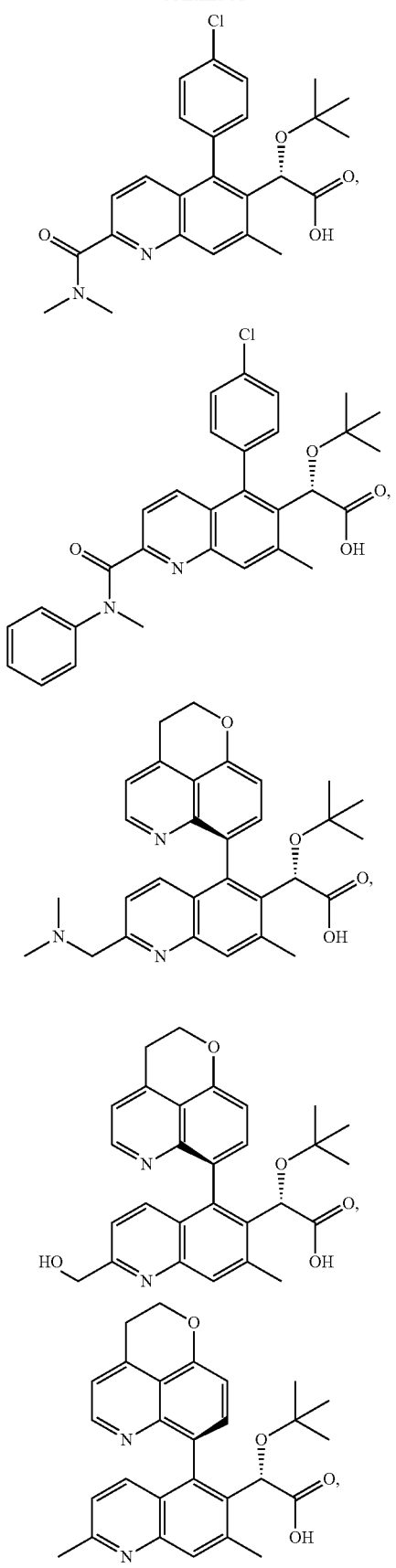
312
-continued
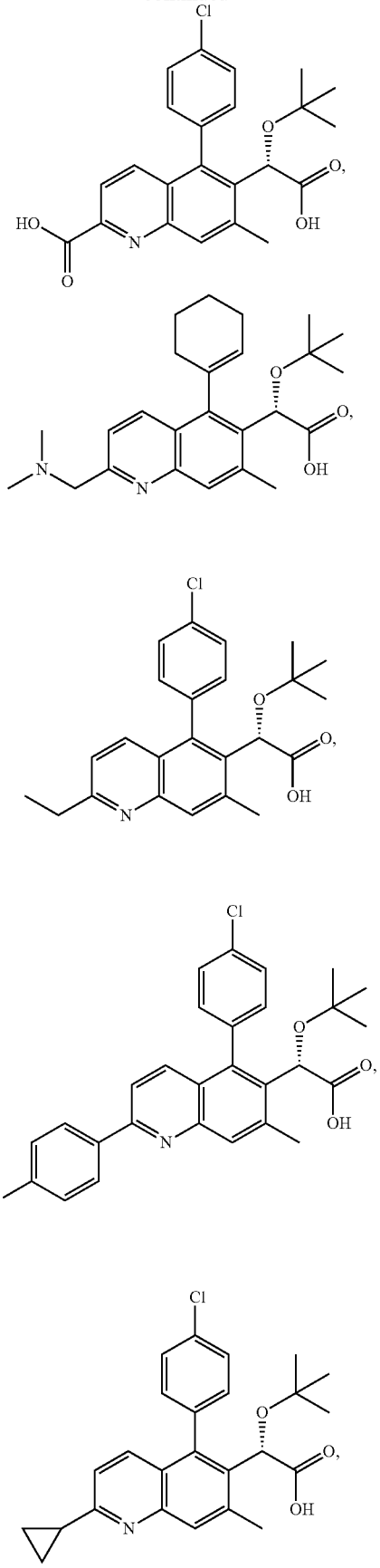

313
-continued
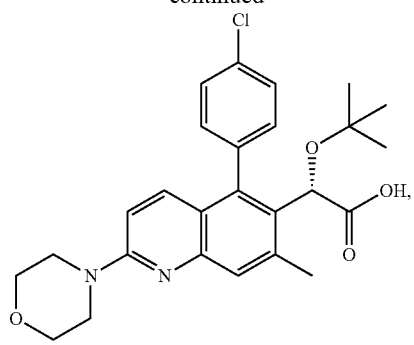
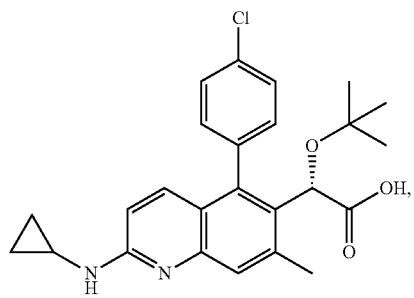
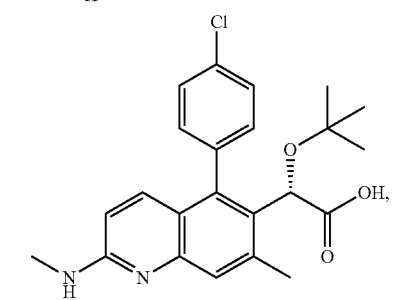
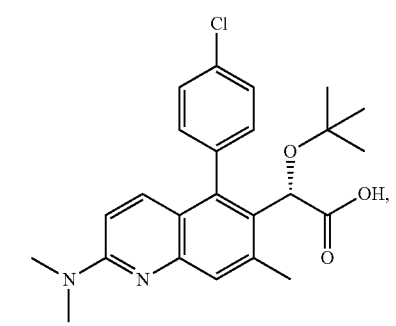
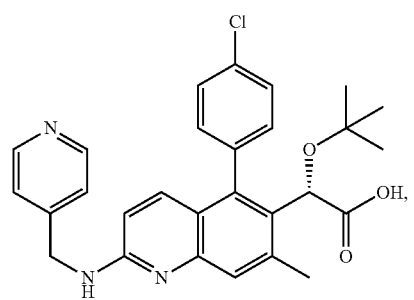
314
-continued
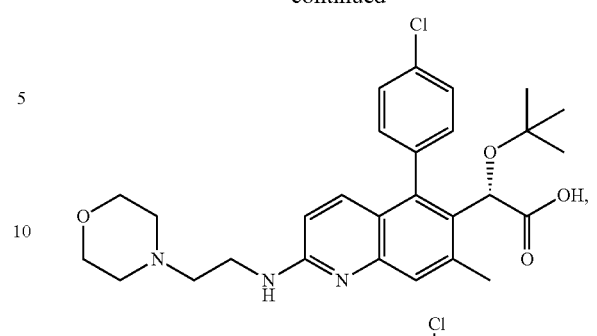
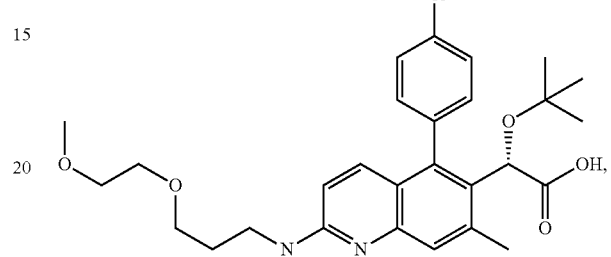
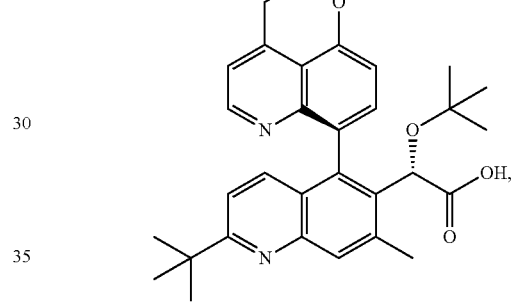
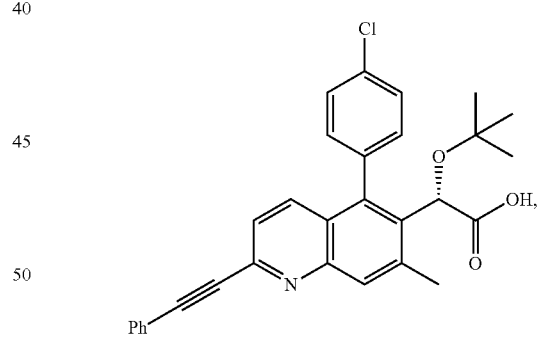
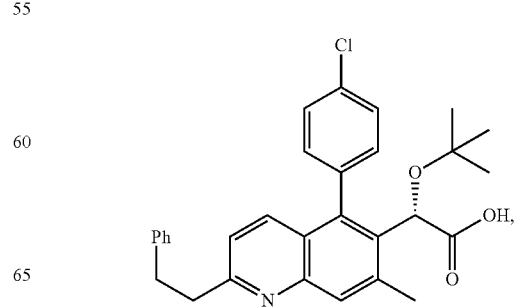

315
-continued
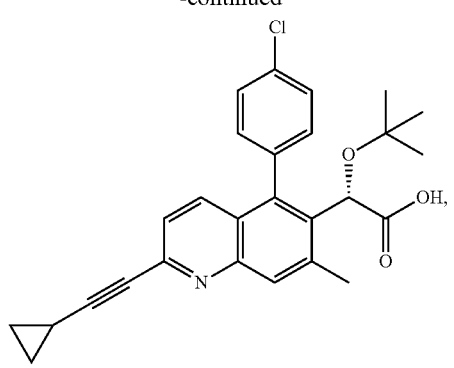
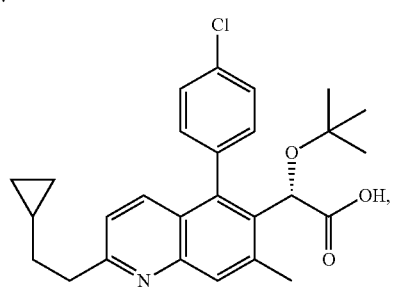
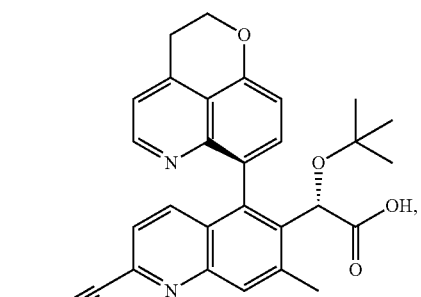
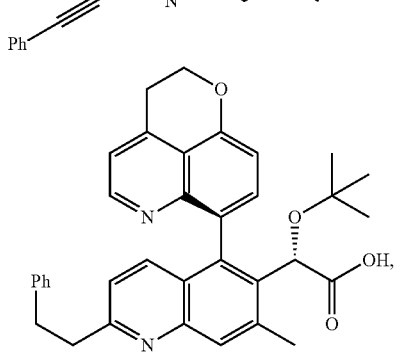
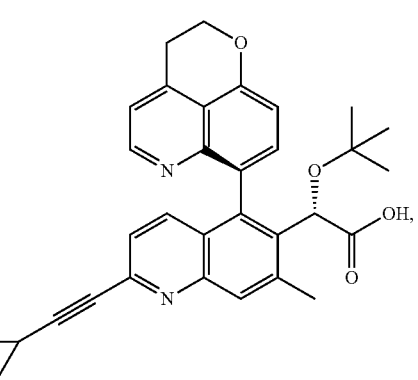
316
-continued
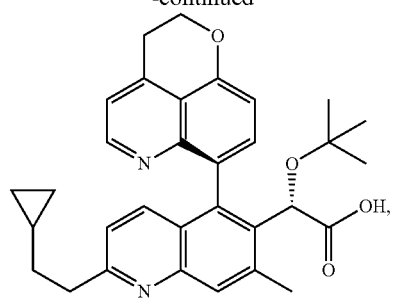
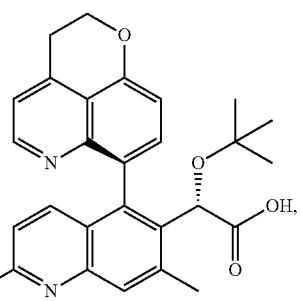
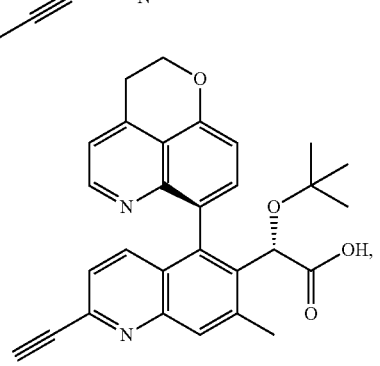
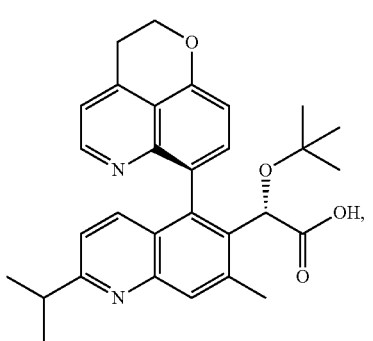
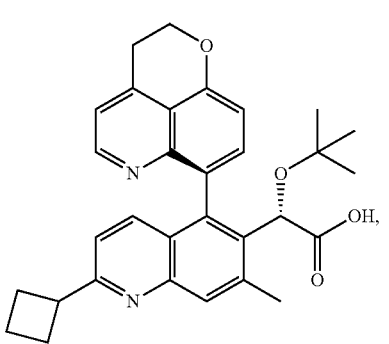

317
-continued
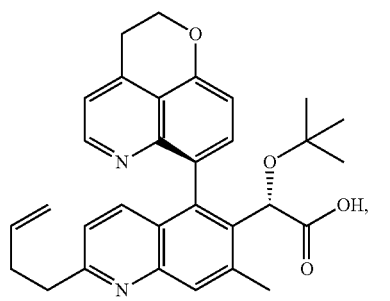
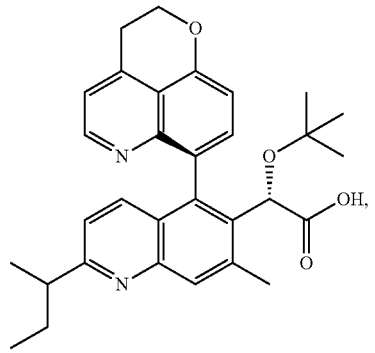
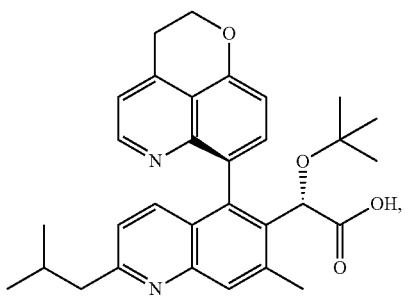
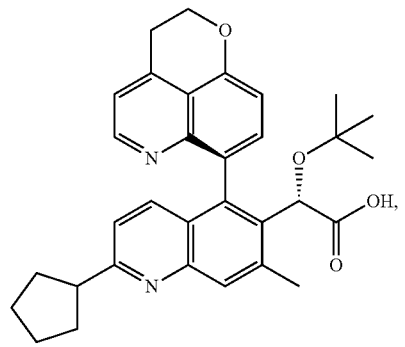
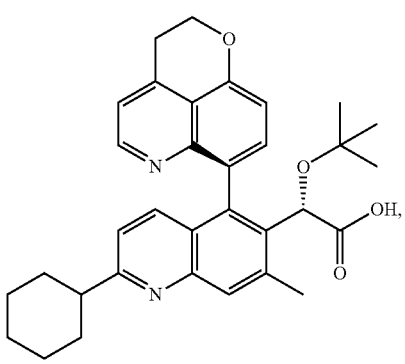
318
-continued
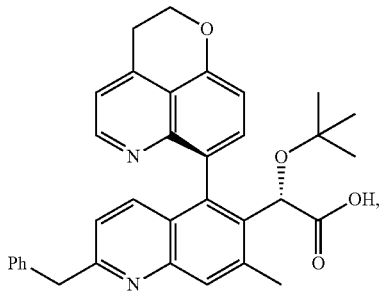
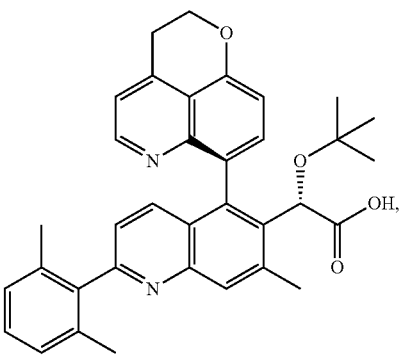
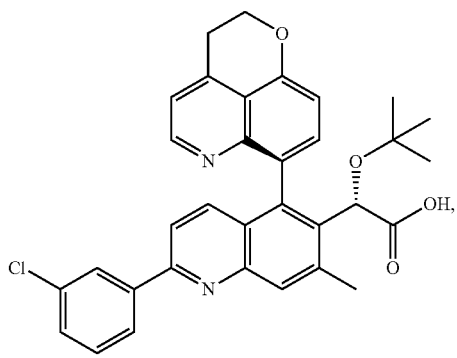
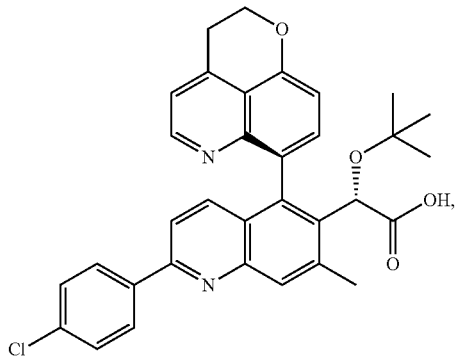
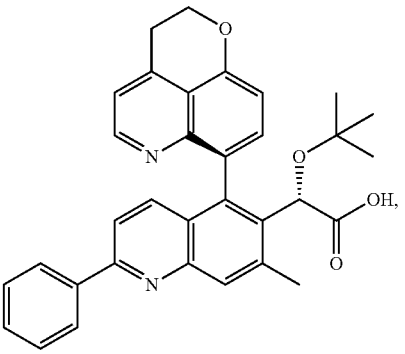

319
-continued
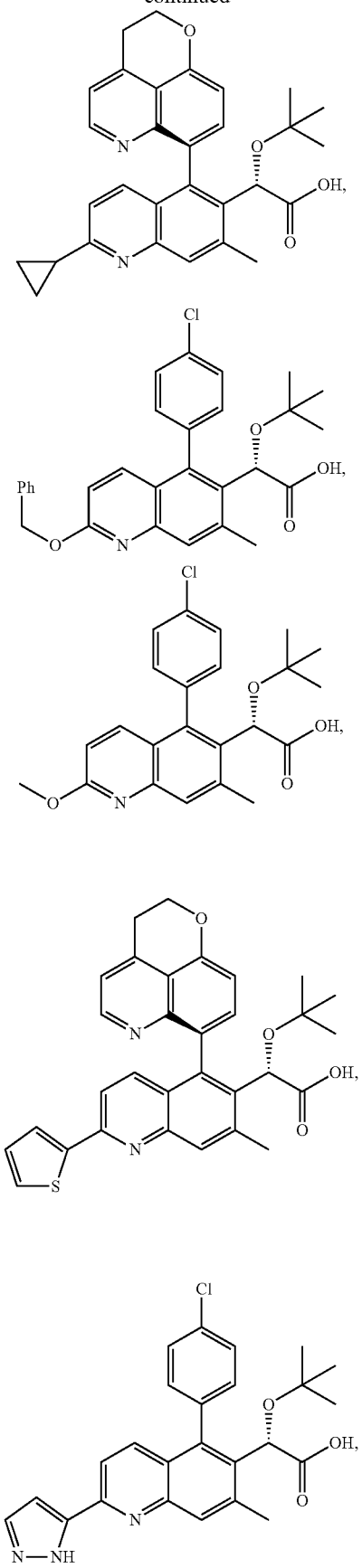
320
-continued
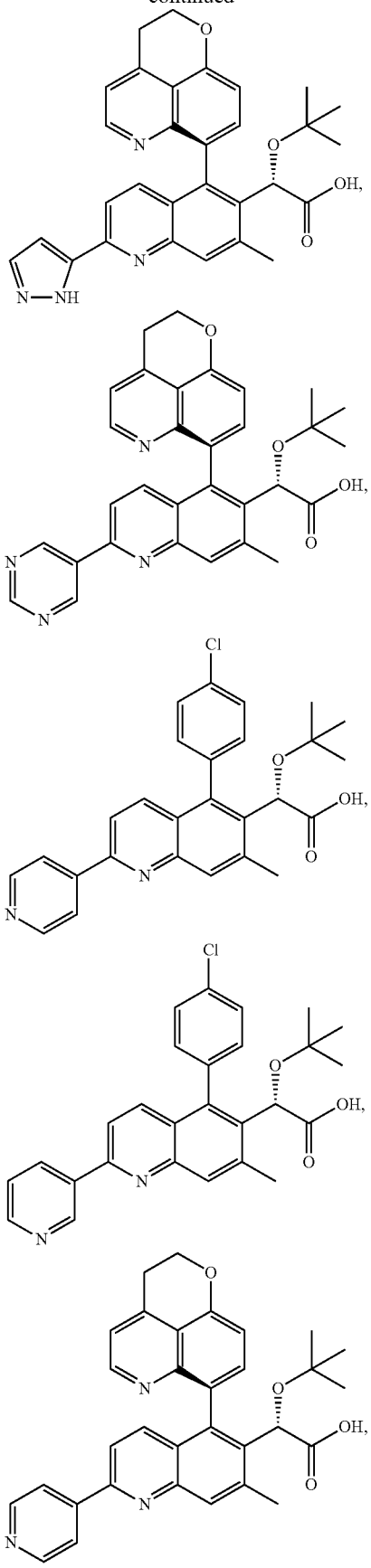

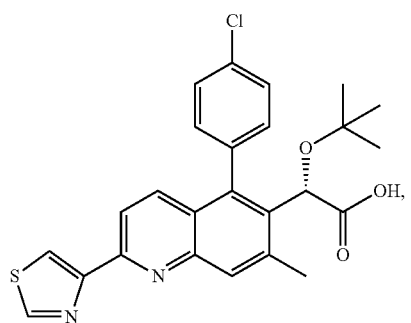
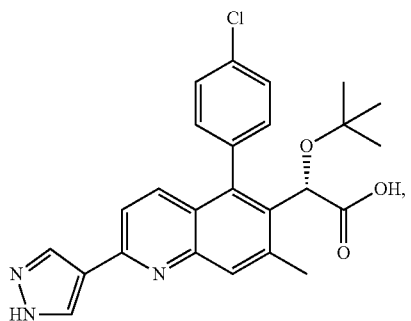
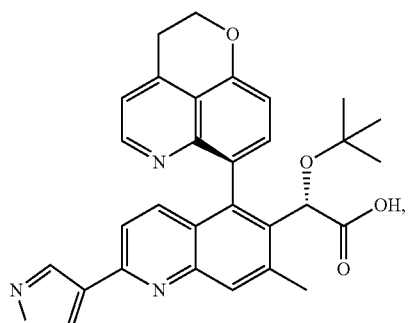
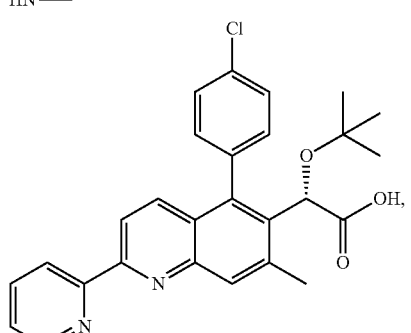
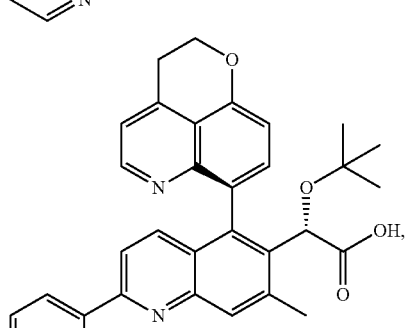
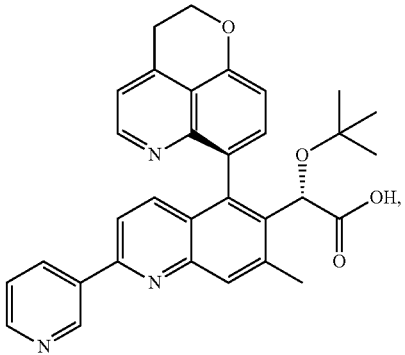
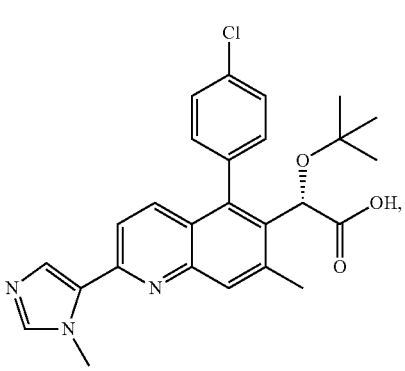
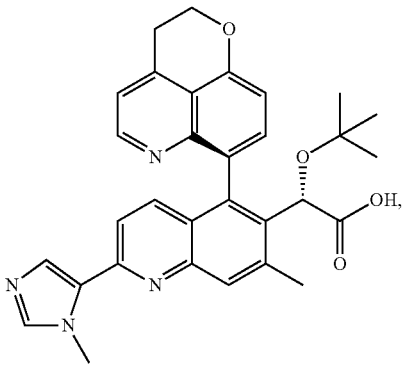
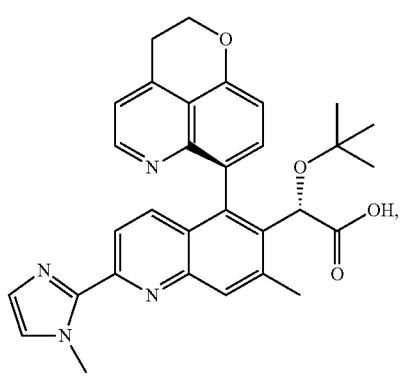

323
-continued
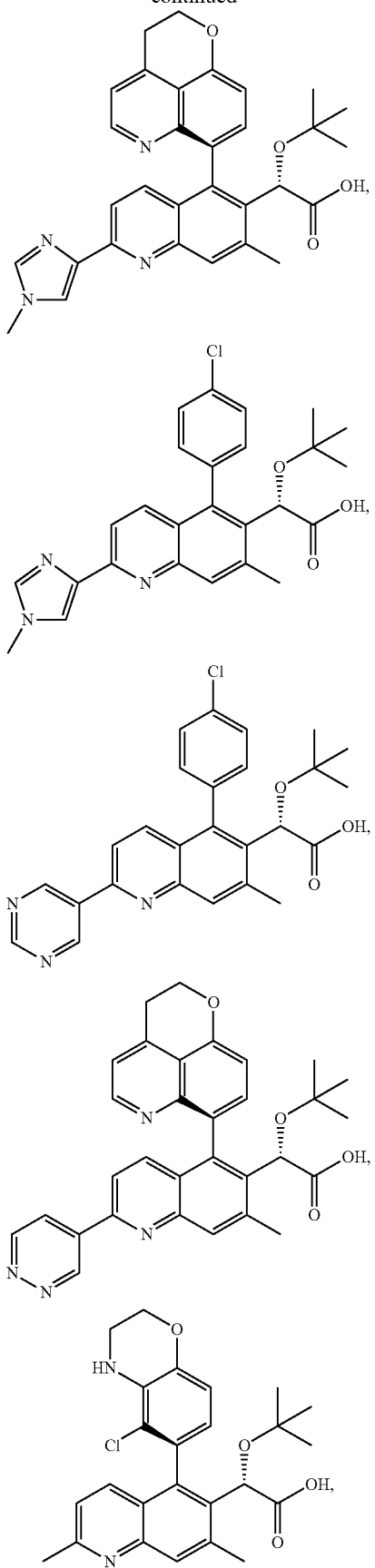
324
-continued
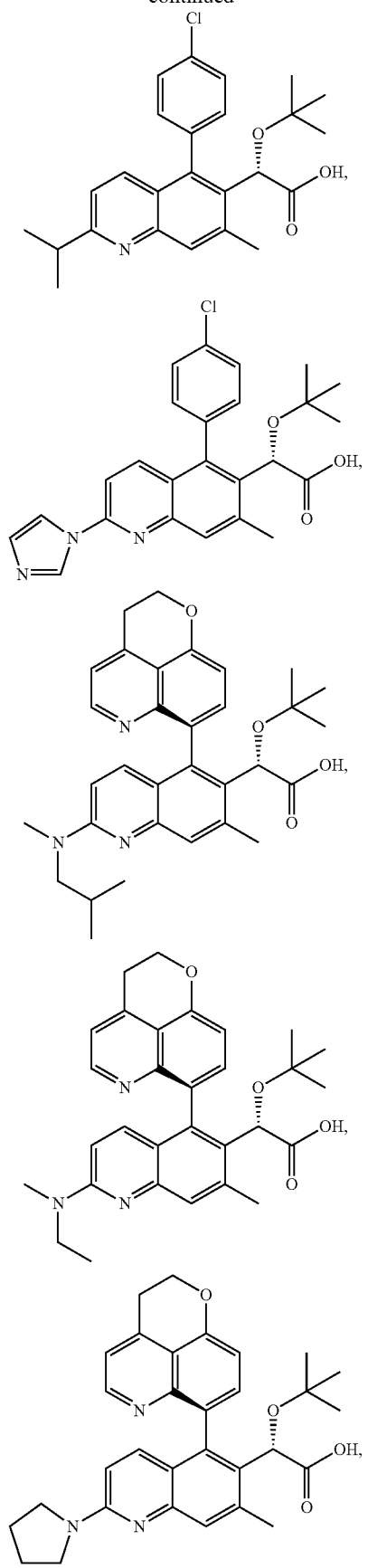

325
-continued
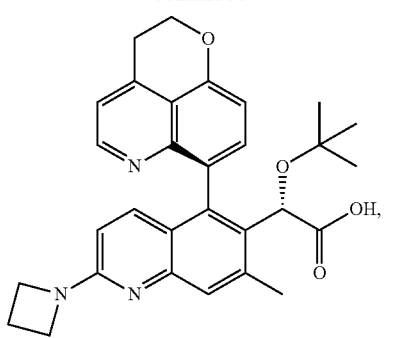
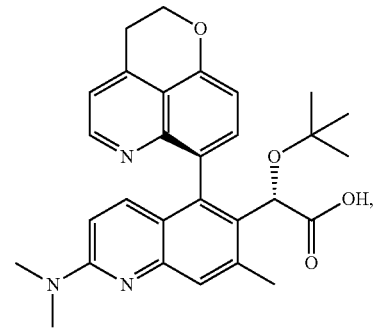
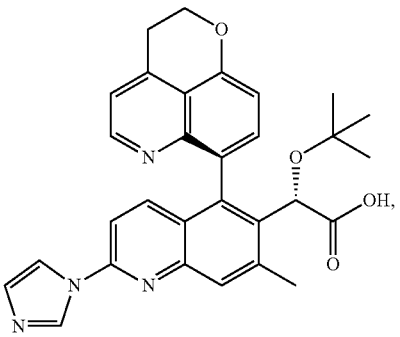
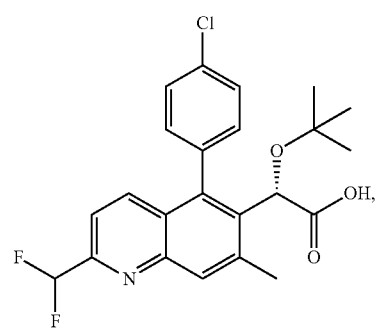
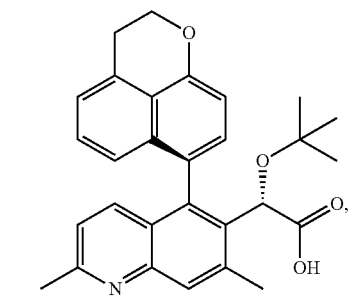
326
-continued
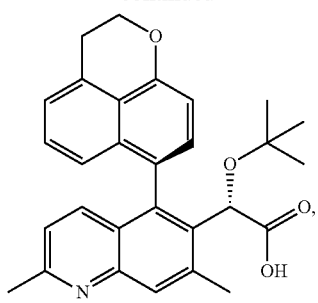
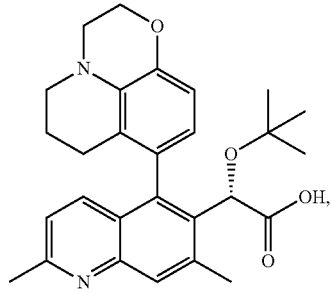
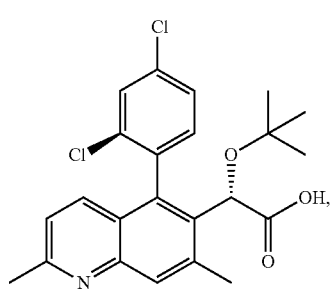
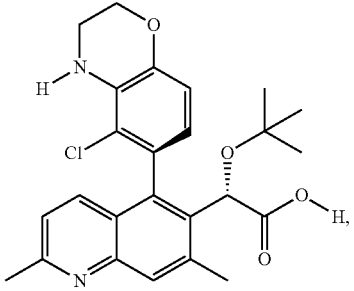
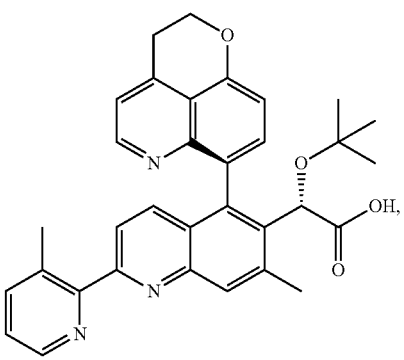

327
-continued
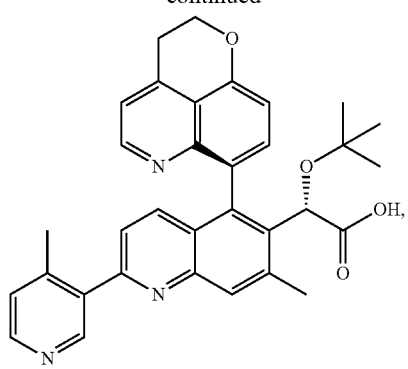
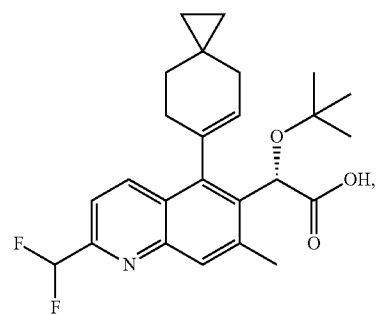
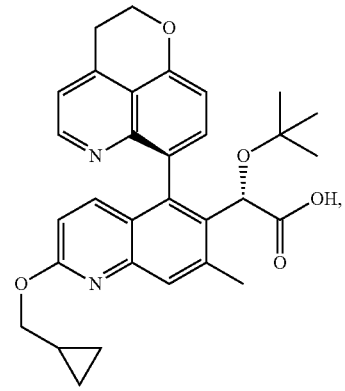
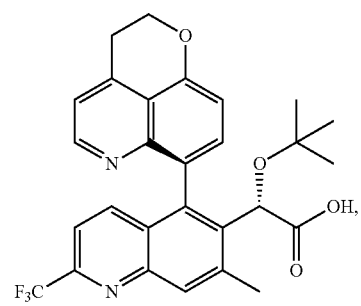
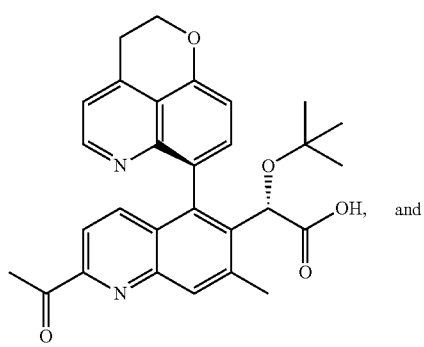
and
328
-continued
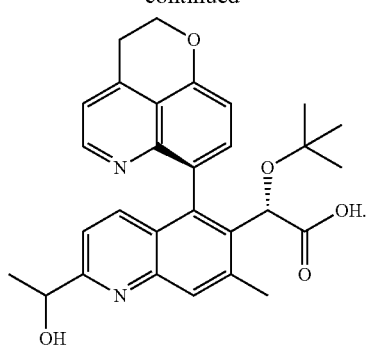
15. A pharmaceutical composition comprising a compound of formula I as described in claim 1, or a pharmaceutically acceptable salt thereof, in combination with a pharmaceutically acceptable carrier.
16. A compound, or a pharmaceutically acceptable salt thereof, selected from the group consisting of:
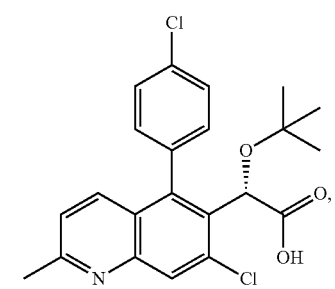
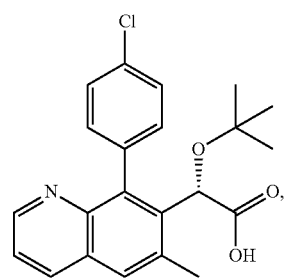
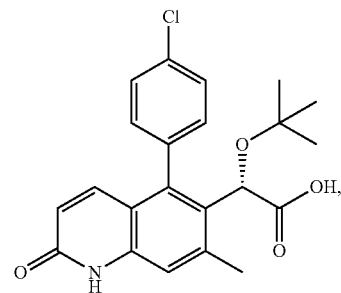

329
-continued
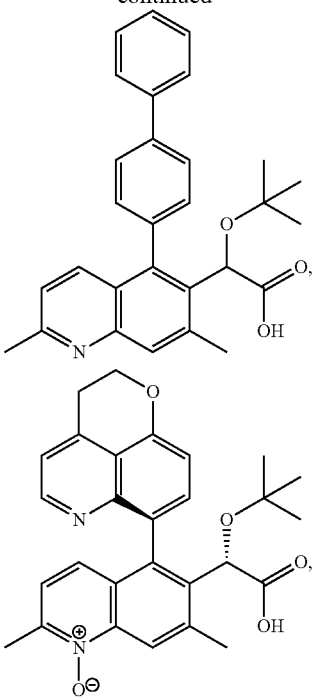
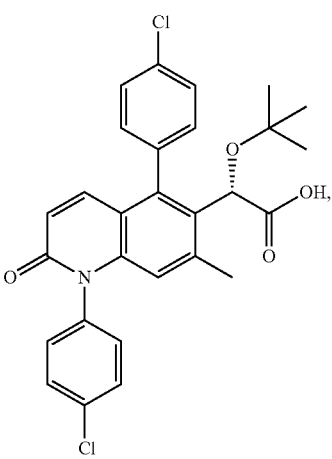
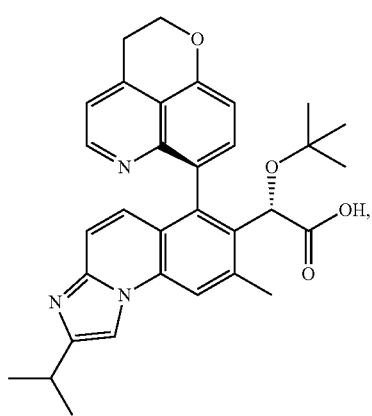
330
-continued
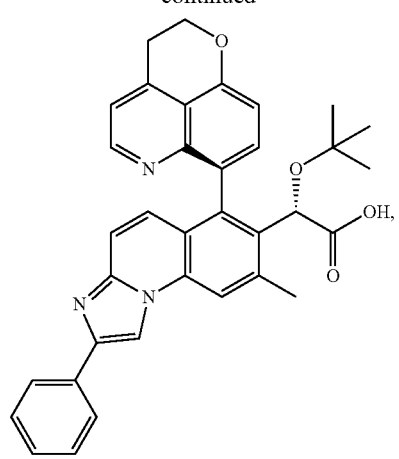
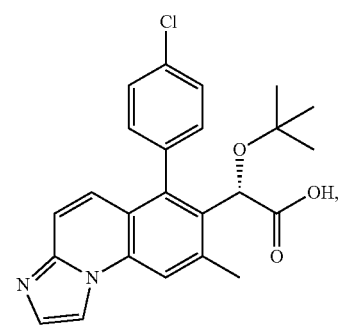
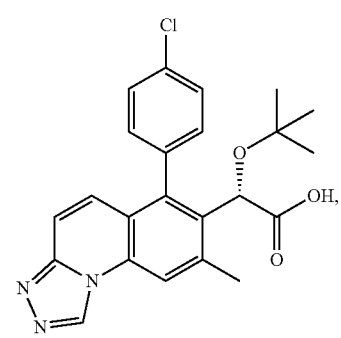
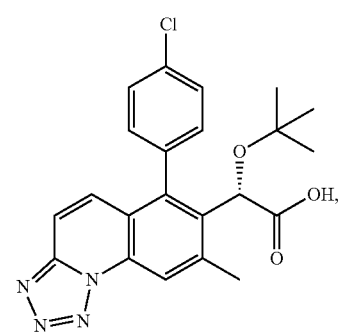

331
-continued
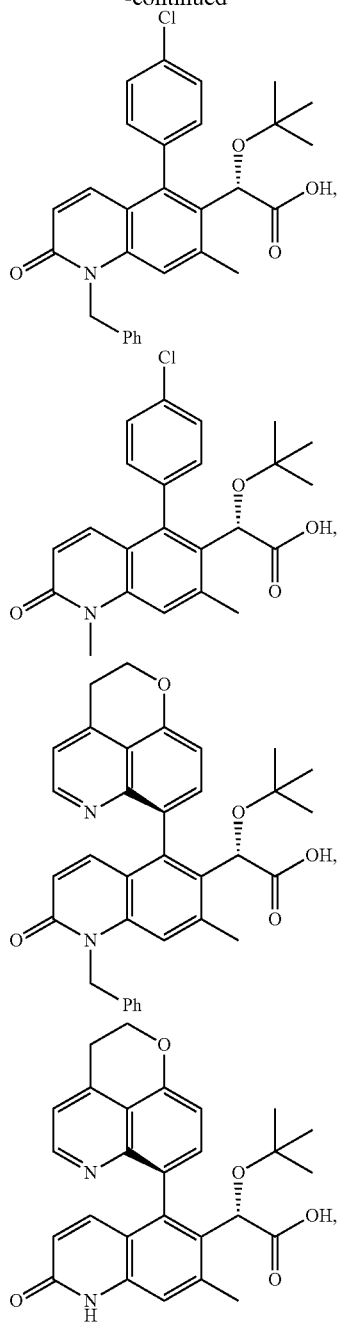
332
-continued
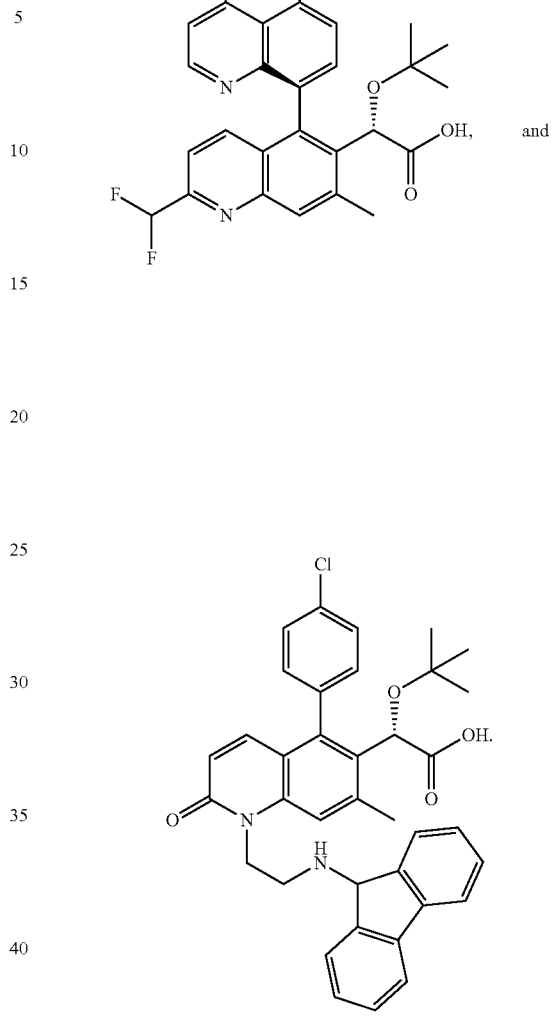
17. A method of inhibiting the proliferation of the HIV virus, inhibiting AIDS or delaying the onset of AIDS or ARC symptoms in a human comprising administering a compound of formula I as described in claim 1, or a pharmaceutically acceptable salt thereof to the human.
* * * * *